US007429609B2

(12) United States Patent
Ohi et al.

(10) Patent No.: US 7,429,609 B2
(45) Date of Patent: Sep. 30, 2008

(54) PYRAZOLE COMPOUND AND MEDICINAL COMPOSITION CONTAINING THE SAME

(75) Inventors: Norihito Ohi, Ibaraki (JP); Nobuaki Sato, Ibaraki (JP); Motohiro Soejima, Ibaraki (JP); Takashi Doko, Ibaraki (JP); Taro Terauchi, Ibaraki (JP); Yoshimitsu Naoe, Ibaraki (JP); Takafumi Motoki, Ibaraki (JP)

(73) Assignee: Eisai R & D Management Co., Ltd., Tokyo (JP)

( * ) Notice: Subject to any disclaimer, the term of this patent is extended or adjusted under 35 U.S.C. 154(b) by 83 days.

(21) Appl. No.: 10/509,795

(22) PCT Filed: May 29, 2003

(86) PCT No.: PCT/JP03/06777

§ 371 (c)(1),
(2), (4) Date: Feb. 25, 2005

(87) PCT Pub. No.: WO03/101968

PCT Pub. Date: Dec. 11, 2003

(65) Prior Publication Data

US 2005/0261339 A1 Nov. 24, 2005

(30) Foreign Application Priority Data

May 31, 2002 (JP) ............................ 2002-158467
Jan. 6, 2003 (JP) ............................ 2003-000153

(51) Int. Cl.
*A61K 31/416* (2006.01)
*C07D 231/56* (2006.01)

(52) U.S. Cl. .................................... 514/406; 548/361.5

(58) Field of Classification Search ............. 548/361.1; 514/406

See application file for complete search history.

(56) References Cited

U.S. PATENT DOCUMENTS

| | | | | | |
|---|---|---|---|---|---|
| 3,705,175 | A * | 12/1972 | Gorog et al. | ................ | 544/371 |
| 3,755,332 | A * | 8/1973 | Wasley et al. | ............... | 546/160 |
| 6,897,231 | B2 | 5/2005 | Bhagwat et al. | | |
| 2002/0103229 | A1 | 8/2002 | Bhagwat et al. | | |
| 2004/0009968 | A1 | 1/2004 | Binch et al. | | |

FOREIGN PATENT DOCUMENTS

| | | | |
|---|---|---|---|
| DE | 1168437 | * | 4/1964 |
| DE | 1266763 | * | 4/1968 |
| EP | 239191 | A1 | 9/1987 |
| EP | 594001 | A1 | 4/1994 |
| EP | 1 110 957 | A1 | 6/2001 |
| JP | 50157363 | * | 12/1975 |
| JP | 1-190681 | A | 7/1989 |
| SU | 1147712 | A1 | 3/1985 |
| WO | WO-98/52948 | A1 | 11/1998 |
| WO | WO-99/07705 | A1 | 2/1999 |
| WO | WO-99/20624 | A1 | 4/1999 |
| WO | WO-00/35906 | A2 | 6/2000 |
| WO | WO-00/35909 | A1 | 6/2000 |
| WO | WO-00/35921 | A1 | 6/2000 |
| WO | WO-00/56710 | A1 | 9/2000 |
| WO | WO-00/64872 | A1 | 11/2000 |
| WO | WO-00/75118 | A1 | 12/2000 |
| WO | WO-01/12609 | A1 | 2/2001 |
| WO | WO-01/12621 | A1 | 2/2001 |
| WO | WO-01/23378 | A1 | 4/2001 |
| WO | WO-01/23379 | A1 | 4/2001 |
| WO | WO-01/23382 | A1 | 4/2001 |
| WO | WO 0153268 | A2 * | 7/2001 |
| WO | WO-01/91749 | A1 | 12/2001 |
| WO | WO-02/10137 | A2 | 2/2002 |
| WO | WO 02010137 | A2 * | 2/2002 |
| WO | WO-02/083648 | A1 | 10/2002 |
| WO | WO 03064397 | A1 * | 8/2003 |

OTHER PUBLICATIONS

Ortoleva, G. Gazzetta Chimica Italiana (1908), 37(2), 71-82.*
Patridge et al. Abstract from Journal of the Chemical Society 1964, 3663-9.*

(Continued)

*Primary Examiner*—Rebecca L Anderson
*Assistant Examiner*—Jason M Nolan
(74) *Attorney, Agent, or Firm*—Birch, Stewart, Kolasch & Birch, LLP

(57) ABSTRACT

The present invention provides a novel compound having an excellent JNK inhibitory effect. That is, it provides a compound represented by the following formula, a salt thereof or a hydrate of them.

(I)

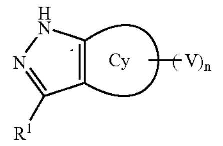

Wherein $R^1$ designates —$(CO)_h$—$(NR^a)_j$—$(CR^b{=}CR^c)_k$—Ar (wherein $R^a$, $R^b$ and $R^c$ each independently designate a hydrogen atom, a halogen atom, hydroxyl group, an optionally substituted $C_{1-6}$ alkyl group or the like;

Cy designates a 5- or 6-membered heteroaryl; and

V each independently designate the formula -L-X—Y (wherein L designates a single bond, an optionally substituted $C_{1-6}$ alkylene group or the like; X designates a single bond or the formula -A- (wherein A designates $NR^2$, O, CO, S, SO or $SO_2$) and so on; and Y designates a hydrogen atom, a halogen atom, nitro group or the like).

6 Claims, No Drawings

OTHER PUBLICATIONS

Burmistrov et al. Abstract from Khimiya Geterosiklicheskikh Soedinenii 1973, 2, 249-51.*
Simon et al. Justus Liebigs Annalen der Chemie 1966, 697, 17-41. (the CAS abstract and structures is provided).*
O'Neill, L. A.J. Nature Reviews Drug Discovery 2006, 1-15.*
Piozzi et al. Gazzetta Chimica Italiana 1965, 95(7), 814-24.*
Burmistrov et al. Khimiya Geterotsiklicheskikh Soedinenii 1973, 2, 249-51.*
Claverie et al. Farmaco, Edizione Scientifica 1973, 28(7), 523-7.*
Krishnan et al. J. Heterocyclic Chem. 1988, 25(2), 447-52.*
Kyriakis et al,; "The stress-activated protein kinase subfamily of c-Jun kinases"; Letter to Nature, vol. 369, pp. 156-160, 1994.
Xia et al.; "Opposing Effects of ERK and JNK-p38 MAP Kinases on Apoptosis"; Science, vol. 270, pp. 1326-1331, 1995.
Pulverer et al.; "Phosphorylation of c-*jun* mediated by MAP kinases"; Letters to Nature, vol. 353, pp. 670-674, 1991.
Gupta et al.; "Selective interaction of JNK protein kinase isoforms with transcription factors"; The Embo Journal, vol. 15, No. 11, pp. 2760-2770, 1996.
Mohlt et al.; "p49$^{3F12}$ Kinase: A Novel MAP Kinase Expressed in a Subset of Neurons in the Human Nervous System"; Neuron, vol. 14, pp. 67-78, 1995.
Kuan et al.; "The Jnk1 and Jnk2 Protein Kinases Are Required for Regional Specific Apoptosis during Early Brain Development"; Neuron, vol. 22, pp. 667-676, 1999.
Sabapathy et al.; c-Jun $NH_2$-Terminal Kinase (JNK)1 and JNK2 Have Similar and Stage-dependent Roles in Regulating T Cell Apoptosis and Proliferation; J. Exp. Med., vol, 193, No. 3, pp. 317-328, 2001.
Hirosumi et al.; "A central role for JNK in obesity and insulin resistance"; Nature, vol. 420, pp. 333-336, 2002.
Yang et al.; "Absence of excitotoxicity-Induced apoptosis in the hippocampus of mice lacking the Jnk3 gene"; Letters to Nature, vol. 389, pp. 865-870, 1997.
Ham et al.; "A c-Jun Dominant Negative Mutant Protects Sympathetic Neurons against Programmed Cell Death"; Neuron, vol. 14, pp. 927-939, 1995.
Watson et al.; "Phosphorylation of c-Jun Is Necessary for Apoptosis Induced by Survival Signal Withdrawal in Cerebellar Granule Neurons"; The Journal of Neuroscience, vol. 18, pp. 751-762, 1998.
Yuan et al.; "Apoptosis in the nervous system"; Nature, vol. 407, pp. 802-809, 2000.
Xia et al.; "Gene transfer of the JNK interacting protein-1 protects dopaminergic neurons in the MPTP model of Parkinson's disease"; PNAS, vol. 98, No. 18, pp. 10433-10438, 2001.
Savage et al.; "Activation of c-Jun N-Terminal Kinase and p38 in an Alzheimer's Disease Model is Associated with Amyloid Deposition"; The Journal of Neuroscience, vol. 22, pp. 3376-3385, 2002.
Zhu et al.; "Activation and redistribution of c-Jun N-Terminal kinase/stress activated protein kinase in degenerating neurons in Alzheimer's disease"; Journal of Neurochemistry, vol. 76, pp. 435-441, 2001.
Bonni et al.; "Cell Survival Promoted by the Ras-MAPK Signaling Pathway by Transcription-Dependent and -Independent Mechanisms"; Science, vol. 286, pp. 1358-1362, 1999.
Han et al.; "BDNF Protects the Neonatal Brain from Hypoxic-Ischemic Injury In Vivo via the ERK Pathway"; The Journal of Neuroscience, vol. 20, pp. 5775-5781, 2000.
Abdel-Aziz El-Taweel et al., Alexandria Journal of Pharmaceutical Sciences, (1998), 12(1), 11-15.
Ghozlan, S.A.S. et al., Egyptian Journal of Pharmaceutical Sciences, (1992), 33(5-6), 859-67.
Marei, Mohamed Gaber, Bulletin of the Chemical Society of Japan, (1993), 66(4), 1172-5.
Rusinov, V.L. et al., Khimiya Geterotsiklicheskikh Soedinenii, (1992), (11), 1560-4.
Marei, Mohamed Gaber, Afinidad, (1993), 50(443), 55-8.
Radinov. R. et al., Journal of Molecular Structure, (1987), 158, 99-108.
Cecchi, L. et al., Farmaco, Edizione Scientifica, (1983), 38(1), 24-8.
Cecchi, L. et al., Farmaco, Edizione Scientifica, (1982), 37(2), 116-22.
Joshi, K. et al., Journal of Heterocyclic Chemistry, (1979), 16(6), 1141-5.
Kocevar, M. et al., Journal of Heterocyclic Chemistry, (1978), 15(7), 1175-84.
Charbonnier et al., *Journal of Molecular Structure*, vol. 158, pp. 109-125 (1987).
Huff, *Journal of Medicinal Chemistry*, vol. 34, No. 8, pp. 2305-2314 (1991).
FDA mulls drug to slow late-stage Alzheimer's [online], [retrieved on Sep. 23, 2003]. Retrieved from the Internet, URL http://ww.cnn.com/2003/HEALTH/conditions/09/24/alzheimers.drug.ap/index.html.

* cited by examiner

PYRAZOLE COMPOUND AND MEDICINAL COMPOSITION CONTAINING THE SAME

TECHNICAL FIELD

The present invention relates to a novel pyrazole compound having an excellent inhibitory effect on protein kinases, in particular, JNK c-Jun amino-terminal kinase.

PRIOR ART

Mitogen-activated protein kinase (hereinafter, referred to as "MAPK") signaling cascades are generally found in from yeast to human, and play a very important role in intracellular signal transduction pathways. As MAPK-related kinases in mammalian cells, in particular, three kinds of kinases are well known: extracellular signal-regulation kinase (ERK), p38 and c-Jun amino-terminal kinase (JNK; or also called as SAPK (=stress-activated protein kinase)). SAPK is a homologue of JNK found in rat, and its isoform group is known to have amino acid sequences of 90% or more homologous to the corresponding isoform group of JNK (Nature, 369, 156, 1994). In recent years, a number of activators involved with MAPK have been identified, which have demonstrated that pathways respectively activating ERK, p38 and JNK have different roles in terms of function. In particular, the JNK pathway is considered to be one of valuable intracellular signaling pathways from medical and pharmaceutical viewpoints because of the following reasons. JNK is activated, for example, by cytokines such as tumor necrosis factor α (TNF-α) or interleukin-1 (IL-1), or cell stresses such as heat shock, ultraviolet ray (UV), X-ray and the like, and is considered to be an important signal transduction pathway inducing not only cellular proliferation and differentiation but also apoptosis (cell death) [Science, 270, 1326, 1995.] JNK was initially discovered as a protein which phosphorylates Ser63 and Ser73 located at N-terminal of c-Jun (Nature, 353, 670, 1991), however, at present, JNK is known to phosphorylate a number of transcription factors such as ATF-2 and Elk-1 and regulate their activities (EMBO J., 15, 2760, 1996.) There are three kinds of JNKs: JNK1, JNK2 and JNK3. While JNK1 and JNK2 are expressed in most of tissues, JNK3 is expressed at high level especially in brain (Neuron, 14, 67, 1995; Neuron, 22, 667, 1999.) Analysis of JNK1 or JNK2 knockout mouse demonstrated that these JNKs have an important role in differentiation and activation of T cell (J. Exp. Med., 193, 317, 2001). Also, analysis of JNK1 knockout mouse suggested the importance of JNK1 in onset of metabolic disorders such as insulin resistance caused by obesity and type II diabetes (Nature, 420, 333, 2002). On the other hand, other report described that JNK3 knockout mouse showed resistance against seizure induced by kainic acid which is an excitatory amino acid receptor agonist, and that the apoptosis which would be observed subsequently in hippocampal neurons in normal mouse was not observed while in JNK3 knockout mouse (Nature 389, 865, 1997.) Since previous research using cultured neurons has proved the necessity of phosphorylation of c-Jun for induction of apoptosis by removal of neurotrophic factor (Neuron 14, 927, 1995; J. Neurosci. 18, 751, 1998), JNK seems to play an important role in inducing apoptosis of neurons. As for neurodegenerative diseases such as Alzheimer disease and Parkinson disease, importance of apoptosis in the process of neurodegeneration has been noticed (Nature 407, 802, 2000), and investigation using model animals of these diseases (Proc Natl Acad Sci USA, 98, 10433, 2001; J. Neurosci. 22, 3376, 2002) and analysis using postmortem brain of patient (Neuron, 14, 67, 1995; J. Neurochem., 76, 435, 2001) have accumulated the results suggesting the possibility of involvement of JNK in neurodegeneration in Alzheimer's disease and Parkinson's disease.

The following are known reports with regard to substances of low molecular weight having JNK inhibitory effect.

(1) Compounds having anti-inflammatory effect represented by the formula ($I^1$) and the compound represented by the formula ($I^{1a}$) as a concrete embodiment (WO00/00491).

($I^1$)

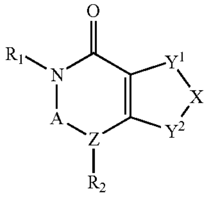

($I^{1a}$)

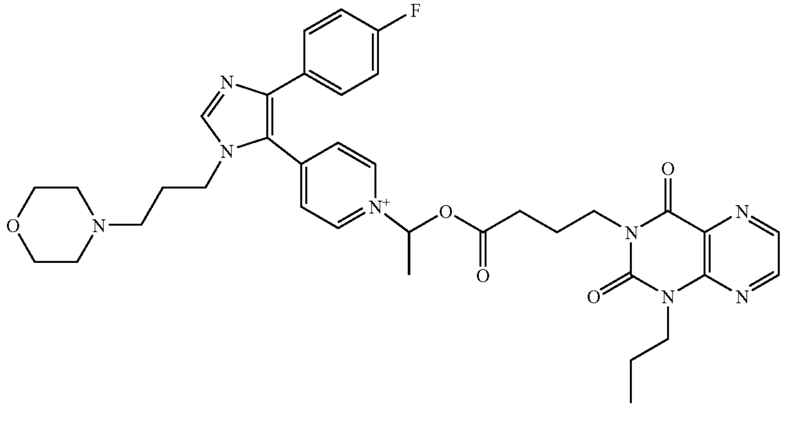

(2) 4-Allyloxyindole compounds represented by the formula $(I^2)$ and the compound represented by the formula $(I^{2a})$ as a concrete embodiment (WO00/35909).

$(I^2)$

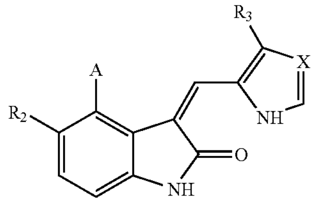

$(I^{2a})$

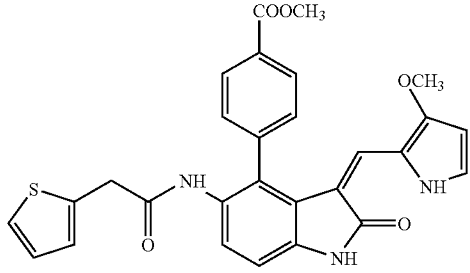

(3) 4,5-Pyrazinoxyindole compounds represented by the formula $(I^3)$ and the compound represented by the formula $(I^{3a})$ as a concrete embodiment (WO00/35921).

$(I^3)$

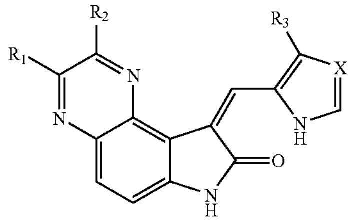

$(I^{3a})$

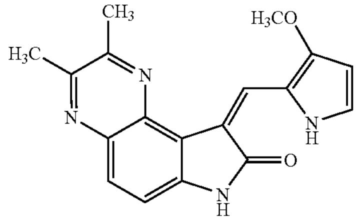

(4) Compounds represented by the formula $(I^4)$ and the compound represented by the formula $(I^{4a})$ as a concrete embodiment (WO00/64872).

$(I^4)$

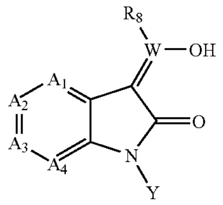

-continued $(I^{4a})$

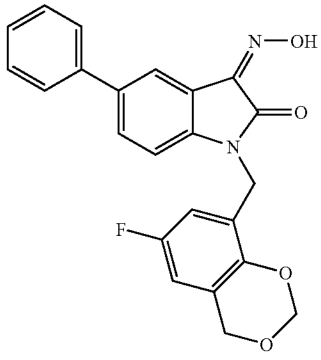

(5) Oxyindole derivatives represented by the formula $(I^5)$ and the compound represented by the formula $(I^{5a})$ as a concrete embodiment (WO00/35906).

$(I^5)$

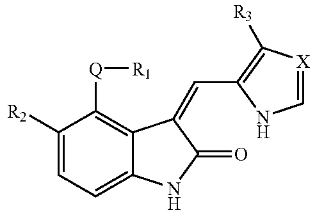

$(I^{5a})$

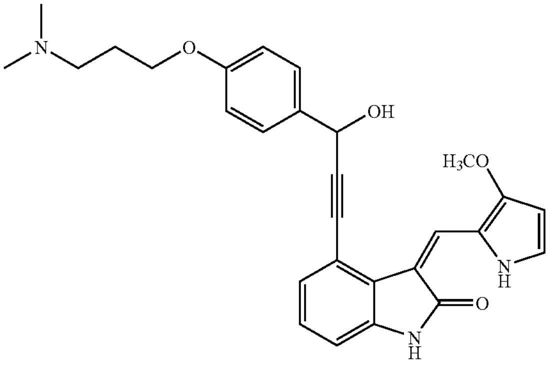

(6) Compounds represented by the formula $(I^6)$ having JNK inhibitory effect and the compound represented by the formula $(I^{6a})$ as a concrete embodiment (WO00/75118).

$(I^6)$

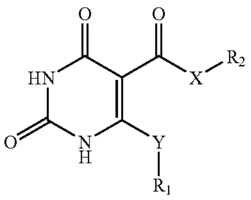

-continued (I6a)

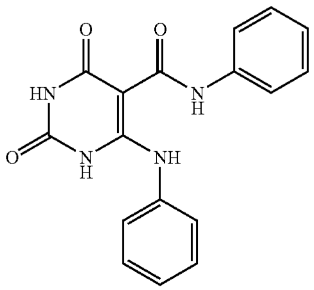

(7) Compounds represented by the formula ($I^7$) having a JNK inhibitory effect and the compound represented by the formula ($I^{7a}$) as a concrete embodiment (WO01/12609).

($I^7$)

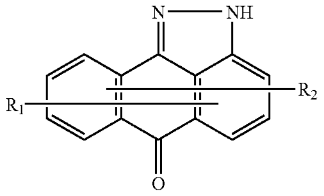

-continued ($I^{7a}$)

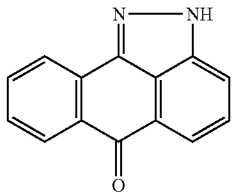

(8) Compounds represented by the formula ($I^8$) having JNK inhibitory effect and the compound represented by the formula ($I^{8a}$) as a concrete embodiment (WO01/12621).

($I^8$)

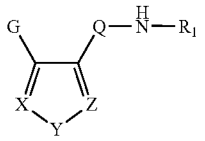

($I^{8a}$)

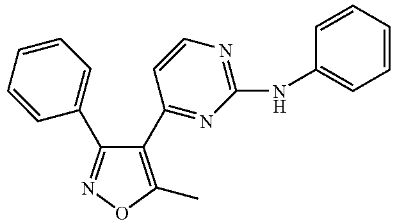

(9) Sulfonamide derivatives represented by the formula ($I^9$) and the compound represented by the formulae ($I^{9a}$) ($I^{9b}$) ($I^{9c}$) as concrete embodiments (WO01/23378, WO01/23379, WO01/23382).

($I^9$)

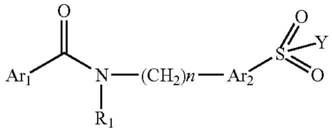

($I^{9a}$)

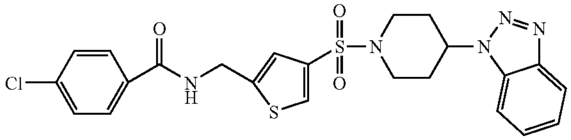

($I^{9b}$)

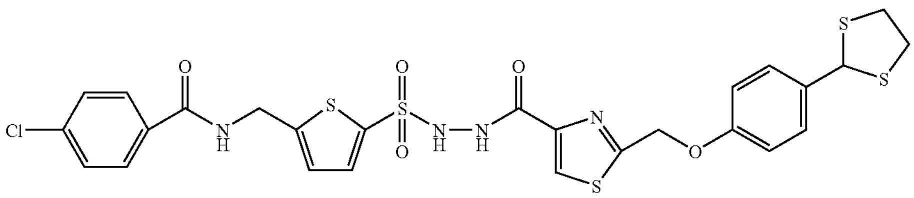

($I^{9c}$)

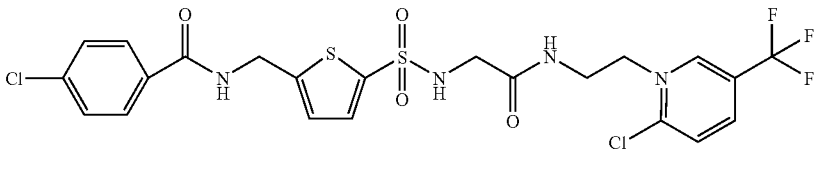

(10) Compounds represented by the formula ($I^{10}$) having JNK inhibitory effect and the compound represented by the formula ($I^{10a}$) as a concrete embodiment (EP01/110957)

($I^{10}$)

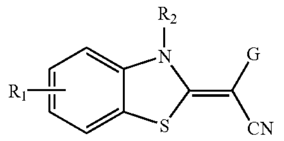

($I^{10a}$)

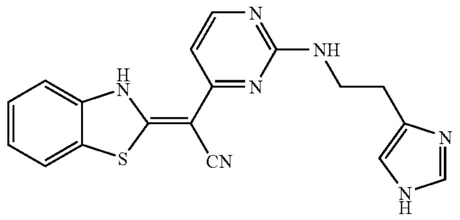

(11) Compounds represented by the formula ($I^{11}$) having JNK inhibitory effect and the compound represented by the formula ($I^{11a}$) as a concrete embodiment (WO01/91749)

($I^{11}$)

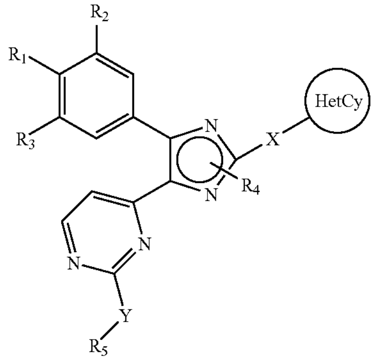

($I^{11a}$)

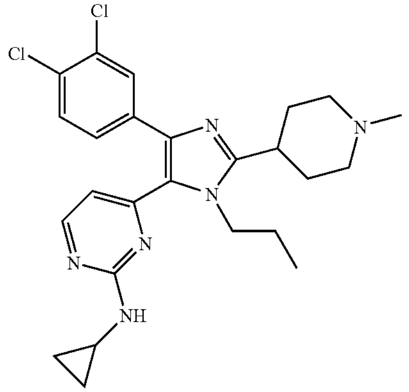

On the other hand, compounds having pyrazole skeleton are found only in the report below.

(12) Compounds represented by the formula ($I^{12}$) having JNK inhibitory effect and the compound represented by the formula ($I^{12a}$) as a concrete embodiment (WO02/10137).

($I^{12}$)

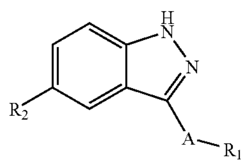

($I^{12a}$)

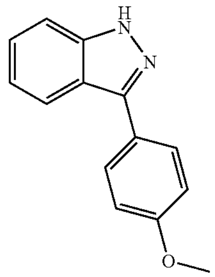

As described above, JNK pathway is noticed as one of important mechanisms involved in activation of various cells and regulation of immuno cells by cytokines, or in apoptosis of neurons induced by various kinds of stress signals. Therefore, compounds having inhibitory effect on JNK pathway, especially on JNK protein kinase can be expected to be useful as therapeutic drugs for a variety of immunological diseases, inflammatory diseases, metabolic diseases, neurodegenerative diseases. On the other hand, ERK which belongs to MAPK to which JNK also belongs is known to play an important role in signal transduction of growth factors and neurotrophic factors, and especially in neurons, ERK is deeply concerned with survival and maintenance of neurons accomplished by neurotrophic factors such as Brain-derived neurotrophic factor (BDNF) and the like (Science, 286, 1358, 1999; J. Neurosci., 20, 5775, 2000.) This suggests the possibility of the ERK inhibitory effect to cancel out the useful effect which the compounds having inhibitory effect on JNK protein kinase are liable to exhibit, e.g., protective effect on neurons, so that a need for discovery of JNK-selective compounds not having ERK inhibitory effect exists. However, such excellent compounds having selective inhibitory effect on JNK protein kinase, while satisfying the points of pharmacological effect, dosage, safety and the like required for pharmaceutics have not been found yet.

DISCLOSURE OF THE INVENTION

As a result of strenuous effort and vigorous research in consideration of the above circumstances, inventors of the present invention finally found a novel pyrazole compound having a JNK inhibitory effect.

That is, the present invention relates to:

1) a compound represented by the formula (I), a salt thereof or a hydrate of them:

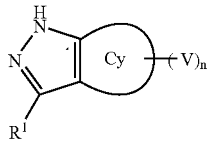

(I)

(wherein, $R^1$ designates a group represented by the formula —$(CO)_h$—$(NR^a)_j$—$(CR^b{=}CR^c)_k$—Ar (wherein $R^a$, $R^b$ and $R^c$ each independently designate a hydrogen atom, halogen atom, hydroxyl group, an optionally substituted $C_{1-6}$ alkyl group, an optionally substituted $C_{2-6}$ alkenyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group; Ar designates an optionally substituted $C_{6-14}$ aryl group or an optionally substituted 5- to 14-membered heteroaryl group; and h, j and k each independently designate 0 or 1);

Cy designates a 5- to 6-membered heteroaryl group;

V designates a group represented by the formula -L-X-Y (wherein, L designates a single bond, an optionally substituted $C_{1-6}$ alkylene group, an optionally substituted $C_{2-6}$ alkenylene group or an optionally substituted $C_{2-6}$ alkynylene group;

X designates a single bond, or a group represented by —$NR^7$—, —O—, —CO—, —S—, —SO—, —$SO_2$—, —CO—$NR^8$-Z-, —C(O)O—, —$NR^8$—CO-Z-, —$NR^8$—C(O)O—, —$NR^8$—S—, —$NR^8$—SO—, —$NR^8$—$SO_2$-Z-, —$NR^9$—CO—$NR^{10}$—, —$NR^9$—CS—$NR^{10}$—, —$S(O)_m$—$NR^{11}$-Z-, —C(=$NR^{12}$)—$NR^{13}$-, —OC(O)—, —OC(O)—$NR^{14}$— or —$CH_2$—$NR^8$—$COR^7$— (wherein $R^7$, $R^8$, $R^9$, $R^{10}$, $R^{11}$, $R^{12}$, $R^{13}$ and $R^{14}$ each independently designate a hydrogen atom, halogen atom, hydroxyl group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$cycloalkyl group, an optionally substituted $C_{3-8}$ cycloalkenyl group, an optionally substituted 4- to 14-membered non-heteroaryl group, an optionally substituted $C_{6-14}$ aryl group or an optionally substituted 5- to 14-membered heteroaryl group, Z designates a single bond or an optionally substituted $C_{1-6}$ alkylene group, and m designates 0, 1 or 2);

Y designates any one group selected from the group consisting of a hydrogen atom, halogen atom, nitro group, hydroxyl group, cyano group, carboxyl group or an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{3-8}$ cycloalkenyl group, an optionally substituted 4- to 14-membered non-aromatic heterocyclic group, an optionally substituted $C_{6-14}$ aryl group, an optionally substituted 5- to 14-membered heteroaryl group, an optionally substituted amino group and a group represented by the formula —W—$R^{15}$ (wherein W designates CO or $SO_2$; $R^{15}$ designates an optionally substituted $C_{1-6}$ alkyl group, an optionally substituted amino group, an optionally substituted $C_{6-14}$ aryl group or an optionally substituted 5- to 14-membered heteroaryl group)); and n designates 0, 1, 2, 3 or 4, and when n is 2 or more, plural Vs each independently designate -L-X—Y as defined above);

2) the compound according to 1), a salt thereof or a hydrate of them, wherein Cy forms a 5-membered heteroaryl group;

3) the compound according to 1), a salt thereof or a hydrate of them, wherein Cy forms a thiophene ring;

4) the compound according to 1), a salt thereof or a hydrate of them, wherein in the formula (I), the structure of moiety consisting of Cy and the pyrazole ring adjoining to the Cy is 1H-thieno[2,3-c]pyrazole;

5) a compound represented by the formula (II), a salt thereof or a hydrate of them:

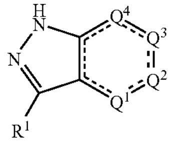

(II)

wherein, $Q^1$ to $Q^4$ each independently designate —$NV^1$—, —$CV^2$=, —N=, —N(→O)= or —CO—, and at least one of $Q^1$ to $Q^4$ designates —$NV^1$— or —N=, —N(→O)=; and $R^1$ designates a group represented by the formula —$(CO)_h$—$(NR^a)_j$—$(CR^b{=}CR^c)_k$—Ar (wherein $R^a$, $R^b$ and $R^c$ each independently designate a hydrogen atom, halogen atom, hydroxyl group, an optionally substituted $C_{1-6}$ alkyl group, an optionally substituted $C_{2-6}$ alkenyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group; Ar designates an optionally substituted $C_{6-14}$ aryl group or an optionally substituted 5- to 14-membered heteroaryl group; and h, j and k each independently designate 0 or 1), $V^1$ and $V^2$ each independently designate a group represented by the formula -L-X-Y (wherein, L designates a single bond, an optionally substituted $C_{1-6}$ alkylene group, an optionally substituted $C_{2-6}$ alkenylene group or an optionally substituted $C_{2-6}$ alkynylene group;

X designates a single bond, or a group represented by —$NR^7$-, —O—, —CO—, —S—, —SO—, —$SO_2$—, —CO—$NR^8$-Z-, —C(O)O—, —$NR^8$—CO-Z-, —$NR^8$—C(O)O—, —$NR^8$—S—, —$NR^8$—SO—, —$NR^8$—$SO_2$-Z-, —$NR^9$—CO—$NR^{10}$—, —$NR^9$—CS—$NR^{10}$—, —$S(O)_m$—$NR^{11}$-Z-, —C(=$NR^{12}$)—$NR^{13}$—, —OC(O)—, —OC(O)—$NR^{14}$— or —$CH_2$—$NR^8$—$COR^7$— (wherein $R^7$, $R^8$, $R^9$, $R^{10}$, $R^{11}$, $R^{12}$, $R^{13}$ and $R^{14}$ each independently designate a hydrogen atom, halogen atom, hydroxyl group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$cycloalkyl group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group, Z designates a single bond or an optionally substituted $C_{1-6}$ alkylene group, and m designates 0, 1 or 2); and Y designates any one group selected from the group consisting of a hydrogen atom, halogen atom, nitro group, hydroxyl group, cyano group, carboxyl group or an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{3-8}$ cycloalkenyl group, an optionally substituted 4-to 14-membered non-aromatic heterocyclic group, an optionally substituted $C_{6-14}$ aryl group, an optionally substituted 5- to 14-membered heteroaryl group, an optionally substituted amino group and a group represented by the formula —W—$R^{15}$ (wherein W designates CO or $SO_2$; and $R^{15}$ designates an optionally substituted $C_{1-6}$ alkyl group, an optionally substituted amino group, an optionally substituted $C_{6-14}$ aryl group or an optionally substituted 5- to 14-membered heteroaryl group);

6) the compound according to 5), a salt thereof or a hydrate of them, wherein among $Q^1$ to $Q^4$, either one is —N═, and the others are —$CV^2$═;

7) the compound according to 5), a salt thereof or a hydrate of them, wherein among $Q^1$ to $Q^4$, either one of $Q^1$, $Q^3$ and $Q^4$ is —N═, and the others are —$CV^2$═;

8) the compound according to 6), a salt thereof or a hydrate of them, wherein $Q^1$ is —N═;

9) the compound according to 6), a salt thereof or a hydrate of them, wherein $Q^2$ is —N═;

10) the compound according to 6), a salt thereof or a hydrate of them, wherein $Q^3$ is —N═;

11) the compound according to 6), a salt thereof or a hydrate of them, wherein $Q^4$ is —N═;

12) the compound according to 5), a salt thereof or a hydrate of them, wherein among $Q^1$ to $Q^4$, either two are —N═, and the others are —$CV^2$═;

13) the compound according to 12), a salt thereof or a hydrate of them, wherein among $Q^1$ to $Q^4$, either two of $Q_1$, $Q_3$ and $Q_4$ are —N═, and the others are —$CV^2$═, 14) the compound according to any one of 5) to 13), a salt thereof or a hydrate of them, wherein when either of $Q^1$, $Q^3$ and $Q^4$ is —$CV^2$═, the —$CV^2$═ in $Q^1$, $Q^3$ or $Q^4$, is —CH═;

15) the compound according to 5), a salt thereof or a hydrate of them, wherein among $Q^1$ to $Q^4$, either three are —N═, and the other is —$CV^2$═;

16) the compound according to 15), a salt thereof or a hydrate of them, wherein $Q^1$, $Q^3$ and $Q^4$ are —N═;

17) the compound according to 5), a salt thereof or a hydrate of them, wherein among $Q^1$ to $Q^4$, at least one is —CO—;

18) the compound according to 5), a slat thereof or a hydrate of them, wherein $Q^1$ is —CO—, $Q^2$ is —$NV^1$—, and $Q^3$ and $Q^4$ are —$CV^2$═;

19) the compound according to 5), a slat thereof or a hydrate of them, wherein $Q^3$ is —CO—, $Q^2$ is —$NV^1$—, and $Q^1$ and $Q^4$ are —$CV^2$═;

20) a compound represented by the formula (III), a salt thereof or a hydrate of them:

(III)

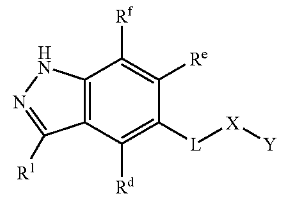

wherein $R^1$ designates a group represented by the formula —$(CO)_h$—$(NR^a)_j$—$(CR^b$═$CR^c)_k$—Ar (wherein $R^a$, $R^b$ and $R^c$ each independently designate a hydrogen atom, halogen atom, hydroxyl group, an optionally substituted $C_{1-6}$ alkyl group, an optionally substituted $C_{2-6}$ alkenyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group; Ar designates an optionally substituted $C_{6-14}$ aryl group or an optionally substituted 5- to 14-membered heteroaryl group; and h, j and k each independently designate 0 or 1, provided that when h and j are 0, k is 1);

$R^d$, $R^e$ and $R^f$ each independently designate a hydrogen atom, halogen atom, hydroxyl group, cyano group, nitro group, carboxyl group, an optionally substituted $C_{1-6}$ alkyl group, an optionally substituted $C_{1-6}$ alkoxy group, an optionally substituted $C_{2-7}$ acyl group, —CO—$NR^{2a}R^{2b}$, —$NR^{2b}$CO—$R^{2a}$ or —$NR^{2a}R^{2b}$ (wherein $R^{2a}$ and $R^{2b}$ each independently designate a hydrogen atom or an optionally substituted $C_{1-6}$ alkyl group);

L designates a single bond, an optionally substituted $C_{1-6}$ alkylene group, an optionally substituted $C_{2-6}$ alkenylene group or an optionally substituted $C_{2-6}$ alkynylene group;

X designates a single bond, or a group represented by —$NR^7$-, —O—, —CO—, —S—, —SO—, —$SO_2$—, —CO—$NR^8$-Z-, —C(O)O—, —$NR^8$—CO-Z-, —$NR^8$—C(O)O—, —$NR^8$—S—, —$NR^8$—SO—, —$NR^8$—$SO_2$-Z-, —$NR^9$—CO—$NR^{10}$—, —$NR^9$—CS—$NR^{10}$—, —$S(O)_m$—$NR^{11}$-Z-, —C(═$NR^{12}$)—$NR^{13}$—, —OC(O)—, —OC(O)—$NR^{14}$— or —$CH_2$—$NR^8$—$COR^7$— (wherein $R^7$, $R^8$, $R^9$, $R^{10}$, $R^{11}$, $R^{12}$, $R^{13}$ and $R^{14}$ each independently designate a hydrogen atom, halogen atom, hydroxyl group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$cycloalkyl group, an optionally substituted $C_{3-8}$cycloalkenyl group, an optionally substituted 4-to 14-membered non-aromatic heterocyclic group, an optionally substituted $C_{6-14}$ aryl group or an optionally substituted 5- to 14-membered heteroaryl group, Z designates a single bond or an optionally substituted $C_{1-6}$ alkylene group, and m designates 0, 1 or 2); and Y designates anyone group selected from the group consisting of a hydrogen atom, halogen atom, nitro group, hydroxyl group, cyano group, carboxyl group or an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{3-8}$ cycloalkenyl group, an optionally substituted 4- to 14-membered non-aromatic heterocyclic group, an optionally substituted $C_{6-14}$ aryl group, an optionally substituted 5- to 14-membered heteroaryl group, an optionally substituted amino group and a group represented by the formula —W—$R^{15}$ (wherein W designates CO or $SO_2$; and $R^{15}$ designates an optionally substituted $C_{1-6}$ alkyl group, an optionally substituted amino group, an optionally substituted $C_{6-14}$ aryl group or an optionally substituted 5- to 14-membered heteroaryl group);

21) the compound according to 20), a salt thereof or a hydrate of them, wherein at least one of $R^d$, $R^e$ and $R^f$ is not a hydrogen atom;

22) the compound according to 20), a salt threof or a hydrate of them, wherein either one of $R^d$, $R^e$ and $R^f$ is a halogen atom or an optionally substituted $C_{1-6}$ alkoxy group;

23) the compound according to any one of 20) to 22), a salt thereof or a hydrate of them, wherein at least one of $R^b$ and $R^c$ is not a hydrogen atom, and L is a single bond, an optionally substituted $C_{2-6}$ alkenylene group or an optionally substituted $C_{2-6}$ alkynylene group, provided that, when L is a single bond, the case where X is a single bond, and Y is an optionally substituted $C_{1-6}$ alkyl group, an optionally substituted $C_{3-8}$ cycloalkyl group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group is excluded;

24) the compound according to any one of 1) to 22), a salt thereof or a hydrate of them, wherein at least either h or j is 1;

25) the compound according to any one of 1) to 22), a salt thereof or a hydrate of them, wherein h and j are 0, and k is 1;

26) the compound according to any one of 1) to 19), a salt thereof or a hydrate of them, wherein h, j and k are 0;

27) the compound according to any one of 24) and 25), a salt thereof or a hydrate of them, wherein $R^b$ and/or $R^c$ are(is) a hydrogen atom;

28) the compound according to 27), a salt thereof or a hydrate of them, wherein $R^b$ and $R^c$ are a hydrogen atom;

29) the compound according to any one of 1) to 28), a salt thereof or a hydrate of them, wherein Ar is a $C_{6-14}$ aryl group or a 5-to 14-membered heteroaryl group, and Ar is a group which may be substituted with 1 to 3 group(s) selected from the following substituent group (a):

<Substituent group a> the group consisting of (1) each optionally substituted (a) $C_{1-6}$ alkyl groups, (b) $C_{1-6}$ alkoxy groups, (c) $C_{1-7}$ acyl groups, (d) amide group, (e) amino group, (f) $C_{3-8}$ cycloalkyl groups, (2) halogen atom, (3) hydroxyl group, (4) nitro group, (5) cyano group, and (6) carboxyl group;

30) the compound according to 29), a salt thereof or a hydrate of them, wherein Ar is a phenyl group, naphthyl group or a 5- to 10-membered heteroaryl group, and Ar is a group optionally substituted with 1 to 3 group(s) selected from Substituent group a described in 29);

31) the compound according to 29), a salt thereof or a hydrate of them, wherein Ar is a phenyl group, 2-naphthyl group, pyridyl group, 2-thienyl group, 2-furyl group, 2-benzofuryl group, 2-quinolyl group or 2-benzothienyl group, and Ar is a group optionally substituted with 1 to 3 group(s) selected from Substituent group a described in 29);

32) the compound according to 29), a salt thereof or a hydrate of them, wherein Ar is a phenyl group, pyridyl group, 2-thienyl group or 2-furyl group, and Ar is a group optionally substituted with 1 to 3 group(s) selected from Substituent group a described in 29);

33) the compound according to 29), a salt thereof or a hydrate of them, wherein Ar is a 2-naphthyl group, 2-benzofuryl group, 2-quinolyl group or 2-benzothienyl group, and Ar is a group optionally substituted with 1 to 3 group(s) selected from Substituent group a described in 29);

34) the compound according to any one of 29) to 33), a salt thereof or a hydrate of them, wherein Substituent group a is the group consisting of (1) $C_{1-6}$ alkyl groups each optionally substituted with 1 to 3 group(s) selected from the group consisting of a halogen atom, hydroxyl group and cyano group, (2) $C_{1-6}$ alkoxy groups optionally substituted with 1 to 3 group(s) selected from the group consisting of a halogen atom, hydroxyl group and cyano group, (3) halogen atom, (4) hydroxyl group, (5) cyano group, and (6) $C_{1-7}$ acyl groups;

35) the compound according to any one of 29) to 33), a salt thereof or a hydrate of them, wherein Substituent group a is a halogen atom;

36) the compound according to any one of 1) to 35), a salt thereof or a hydrate of them, wherein L is a single bond or methylene group;

37) the compound according to 36), a salt thereof or a hydrate of them, wherein L is a single bond;

38) the compound according to any one of 1) to 37), a salt thereof or a hydrate of them, wherein X is a group represented by —CO—$NR^8$-Z-, —$NR^8$—CO-Z- or —$NR^8$—$SO_2$-Z- (wherein $R^8$ and Z have the same meanings as defined for $R^8$ and Z in 1));

39) the compound according to 38), a salt thereof or a hydrate of them, wherein $R^8$ is a hydrogen atom;

40) the compound according to 38), a salt thereof or a hydrate of them, wherein X is a group represented by —CO—NH—$(CH_2)_t$— (wherein t designates 0 or 1);

41) the compound according to 38), a salt thereof or a hydrate of them, wherein X is a group represented by —NH—CO—$(CH_2)_t$— (wherein t designates 0 or 1);

42) the compound according to any one of 1) to 37), a salt thereof or a hydrate of them, wherein X is a single bond;

43) the compound according to any one of 1) to 42), a salt thereof or a hydrate of them, wherein Y is a $C_{1-6}$ alkyl group, a $C_{6-14}$ aryl group, a $C_{1-6}$ alkoxy group, a $C_{3-8}$ cycloalkyl group, a 4- to 14-membered non-aromatic heterocyclic group or a 5- to 14-membered heteroaryl group, and Y is a group optionally substituted with 1 to 3 group(s) selected from the following Substituent group a2:

<Substituent group a2> the group consisting of (1) each optionally substituted (a) $C_{1-6}$ alkyl groups, (b) $C_{2-6}$ alkenyl groups, (c) $C_{2-6}$ alkynyl groups, (d) $C_{1-6}$ alkoxy groups, (e) $C_{2-7}$ acyl groups, (f) amide group, (g) amino group, (h) $C_{3-8}$cycloalkyl groups, (i) $C_{3-8}$ cycloalkenyl groups, (j) $C_{6-14}$ aryl groups, (k) 5- to 14-membered heteroaryl groups, (1) $C_{6-14}$ aryloxy groups, and (m) 4-to 14-membered non-aromatic heterocyclic groups, (2) halogen atom, (3) hydroxyl group, (4) nitro group, (5) cyano group, and (6) carboxyl group;

44) the compound according to 43), a salt thereof or a hydrate of them, wherein Y is a $C_{3-8}$ cycloalkyl group, phenyl group, a 5- or 6-membered non-aromatic heterocyclic group, or a 5- or 6-membered heteroaryl group, and Y is a group optionally substituted with 1 to 3 group(s) selected from Substituent group a2 described in 43);

45) the compound according to any one of 1) to 42), a salt thereof or a hydrate of them, wherein Y is a furyl group, thienyl group, pyrrolyl group, phenyl group, pyridyl group, $C_{3-8}$ cycloalkyl group, tetrahydrofuran-yl group, tetrahydrothiophene-yl group, pyrrolidinyl group, tetrahydrofuran-2-on-yl group, pyrrolidine-2-on-yl group or a group represented by the formula:

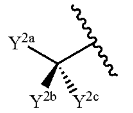

(wherein $Y^{2a}$ designates a group represented by —$CONH_2$ or —$CH_2OH$, $Y^{2b}$ and $Y^{2c}$ each independently designate a hydrogen atom, an optionally substituted phenyl group or an optionally substituted $C_{1-6}$ alkyl group), and Y is a group optionally substituted with 1 to 3 group(s) selected from Substituent group a2 described in 43);

46) the compound according to 43), a salt thereof or a hydrate of them, wherein Y is a furyl group or thienyl group, and Y is a group optionally substituted with 1 to 3 group(s) selected from Substituent group a2 described in 43);

47) the compound according to any one of 43) to 46), a salt thereof or a hydrate of them, wherein Substituent group a2 is the group consisting of (1) (a) $C_{1-6}$ alkyl groups, (b) $C_{1-6}$ alkoxy groups, (c) $C_{1-7}$ acyl groups, (d) amide group, (e) amino group, (f) $C_{3-8}$ cycloalkyl groups, each of which may be substituted with 1 to 3 group(s) selected from the following Substituent group b2, (2) halogen atom, (3) hydroxyl group, (4) nitro group, (5) cyano group, and (6) carboxyl group, and <Substituent group b2>is the group consisting of $C_{1-6}$ alkyl groups, halogen atom, hydroxyl group, nitro group, cyano group and carboxyl group;

48) the compound according to any one of 43) to 46), a salt thereof or a hydrate of them, wherein Substituent group a2 is the group consisting of (1) $C_{1-6}$ alkoxy groups, (2) halogen atoms and (3) cyano groups;

49) the compound according to any one of 20) to 35), a salt thereof or a hydrate of them, wherein L and X are a single bond, Y is a 5- to 6-membered heteroaryl group, and Y is a group optionally substituted with 1 to 3 group(s) selected from Substituent group a2 described in 43);

50) a pharmaceutical composition comprising the compound according to any one of 1) to 49), a salt thereof or a hydrate of them, and a pharmaceutically acceptable carrier;

51) a c-Jun amino-terminal kinase (JNKs) inhibitor comprising the compound according to any one of 1) to 49), a salt thereof or a hydrate of them;

52) a c-Jun amino-terminal kinase 1 (JNK 1), c-Jun amino-terminal kinase 2 (JNK 2) and/or c-Jun amino-terminal kinase 3 (JNK 3) inhibitor, comprising the compound according to any one of 1) to 49), a salt thereof or a hydrate of them;

53) an agent for treating or preventing immunological diseases, inflammatory diseases or metabolic disorders, which comprises the compound according to any one of 1) to 49), a salt thereof or a hydrate of them;

54) an agent for treating or preventing neurodegenerative diseases, which comprises the compound according to any one of 1) to 49), a salt thereof or a hydrate of them;

55) an agent for treating or preventing Alzheimer's disease, Parkinson's disease, Huntington's chorea, amyotrophic lateral sclerosis, multiple sclerosis or spinocerebellar degeneration, which comprises the compound according to any one of 1) to 49), a salt thereof or a hydrate of them;

56) use of the compound according to any one of 1) to 49), a salt thereof or a hydrate of them for prevention or treatment of immunological diseases, inflammatory diseases, metabolic disorders and/or neurodegenerative diseases;

57) use of the compound according to any one of 1) to 49), a salt thereof or a hydrate of them, for producing an agent for treating or preventing a disease based on JNK action against which inhibition of a c-Jun amino-terminal kinase (JNK) is effective for prevention or treatment, immunological diseases, inflammatory diseases, metabolic disorders or neurodegenerative diseases;

58) the use according to 57), wherein the disease is Alzheimer's disease, Parkinson's disease, Huntington's chorea, amyotrophic lateral sclerosis, multiple sclerosis or spinocerebellar degeneration;

59) a method for treating or preventing a disease based on JNK 3 action against which inhibition of a c-Jun amino-terminal kinase 3 (JNK 3) is effective for prevention or treatment, immunological diseases, inflammatory diseases, metablic disorders and/or neurodegenerative diseases, which comprises administering a pharmacologically effective amount of the compound according to any one of 1) to 49), a salt thereof or a hydrate of them to a patient;

60) a method for treating or preventing a disease based on JNK action against which inhibition of a c-Jun amino-terminal kinase (JNK) is effective for prevention or treatment, immunological diseases, inflammatory diseases, metablic disorders or neurodegenerative diseases, which comprises administering a pharmacologically effective amount of the compound according to any one of 1) to 49), a salt thereof or a hydrate of them to a patient; and 61) the method according to 60), wherein the disease is Alzheimer's disease, Parkinson's disease, Huntington's chorea, amyotrophic lateral sclerosis, multiple sclerosis or spinocerebellar degeneration.

In the following, definition for symbols, terms and the like used in the present specification will be provided for detailed explanation of the present invention.

The term "and/or" used herein intends to embrace both cases of "and" and "or".

The term "JNK" used herein refers to enzymes that phosphorylates N-terminal region of c-Jun protein, and examples of which include JNK1, JNK2, JNK3 and the like. There are three kinds of JNKs: JNK1, JNK2 and JNK3. While JNK1 and JNK2 are expressed in most of tissues, JNK3 is expressed at high level especially in brain (Neuron, 14, 67, 1995; Neuron, 22, 667, 1999.)

The term "neurodegenerative diseases" used herein comprehends all diseases that are generally categorized in neurodegenerative diseases in the medical field, and concrete examples of which include, but not limited to, chronic neurodegenerative diseases such as subarachnoid hemorrhage, cerebrovascular disorder acute stage, head injury, spinal cord injury, neuropathy due to low oxygen and low blood sugar, Alzheimer's disease, Parkinson' s disease, Huntington's chorea, amyotrophic lateral sclerosis, epilepsy, hepatic encephalopathy, peripheral neuropathy, Parkinson syndrome, exanthematous paralysis, pain, neuralgia, schizophrenia, depression, anxiety, drug dependence, nausea, emesis, urination disorder, visual disorder due to glaucoma, hearing disorder due to antibiotics, alimentary intoxication, multiple sclerosis or spinocerebellar degeneration, and acute neurodegenerative diseases.

The term "immunological diseases" or "inflammatory diseases" used herein comprehends all diseases that are generally categorized in immunological diseases in the medical field, and concrete examples of which include, but not limited to, sepsis, chronic articular rheumatism, osteoarthritis, gout, psoriasis, psoriatic arthropathy, bronchitis, chronic obstructive pulmonary disease, cyst nature fibroid lung, insulin dependent type I diabetes mellitus, autoimmune thyroiditis, Crohn's disease, colitis ulcerosa, atopic dermatitis, asthma, allergic rhinitis, hepatitis, systemic lupus erythematodes, acute and chronic allograft rejection after organ transplantation, graft-versus-host disease, eczema, hives, myasthenia gravis, acquired immunodeficiency syndrome, idiopathic thrombocytopenic purpura, glomerulonephritis and the like.

The term "metabolic disorders" used herein refers to diseases caused by metabolic disorder of sugar and lipid, and examples of which include diabetes mellitus, diabetic complication, hypercholesterolemia, hyperlipemia, obesity, syndrome X and the like.

In the present description, a particular structural formula may represent certain isomers, and the present invention comprehends all isomers and mixture of isomers such as geometrical isomers, optical isomers based on an asymmetric carbon, stereoisomers and tautomers occurring due to the particular structure of the compound, but they are not conveniently limited by the description of the above formula, and may be either one isomer or mixture thereof. Therefore, optical isomers and racemic bodies may exist because of an asymmetric carbon in a molecule, however the present invention includes both cases without particularly limited. There is also the case that crystal polymorphs occur, and such crystal polymorphs may exist singly or in mixture without any limitation. The compound (I) or compound (III) or its salt according to the present invention may be anhydride or hydrate, both of which are involved in the scope of claims of the present specification. Metabolites occurring by biodegradation of the compound (I) according to the present invention, and prodrugs of the compound (I) according to the present invention and its salt are also involved in the scope of claims of the present specification.

The "halogen atom" used herein include, for example, a fluorine atom, chlorine atom, bromine atom iodine atom and the like atoms, fluorine atom and chlorine atom are preferred, and fluorine atom is more preferred.

The term "$C_{1-6}$ alkyl group" used herein refers to linear or branched alkyl groups having 1 to 6 carbon atom(s), and concrete examples of which include a methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like, methyl group, ethyl group, n-propyl group, iso-propyl group, n-butyl group, iso-butyl group, sec-butyl group, tert-butyl group, n-pentyl group and the like are more preferred.

The term "$C_{2-6}$ alkenyl group" used herein refers to linear or branched alkenyl groups having 2 to 6 carbons, and concrete examples of which include a vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group, 1,6-hexadienyl group and the like.

The term "$C_{2-6}$ alkynyl group" used herein refers to linear or branched alkynyl groups having 2 to 6 carbons, and concrete examples of which include an ethynyl group, 1-propynyl group, 2-propynyl group, 1-butynyl group, 2-butynyl group, 3-butynyl group, 3-methyl-1-propynyl group, 1-ethynyl-2 propynyl group, 2-methyl-3-propynyl group, 1-pentynyl group, 1-hexynyl group, 1,3-hexane-diynyl group, 1,6-hexane-diynyl group, and the like.

The term "$C_{1-6}$alkylene group" used herein refers to bivalent groups derived by removing one hydrogen atom at any position from the above defined "$C_{1-6}$ alkyl group", and concrete examples of which include a methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group, hexamethylene group and the like, with methylene group and 1,2-ethylene group being preferred.

The term "$C_{2-6}$ alkenylene group" used herein refers to bivalent groups derived by removing one hydrogen atom from the above defined "$C_{2-6}$ alkenyl group", and concrete examples of which include a vinylene group, propenylene group, butenylene group, pentenylene group, hexenylene group and the like, with vinylene group, propenylene group, butenylene group and pentenylene group being preferred and vinylene group, propenylene group and butenylene group more preferred, and 1,2-vinylene group and 1,3-propenylene group further preferred.

The term "$C_{2-6}$ alkynylene group" used herein refers to bivalent groups derived by removing one hydrogen atom from the above defined "$C_{2-6}$ alkynyl group", and concrete examples of which include an ethynylene group, propynylene group, butynylene group, pentynylene group, hexynylene group and the like, ethynylene group, propynylene group, butynylene group and pentynylene group are preferred, ethynylene group, propynylene group and butynylene group are more preferred, ethynylene group and propynylene group are still preferred, and ethynylene group is most preferred.

The term "$C_{3-8}$ cycloalkyl group" used herein refers to cyclic aliphatic hydrocarbon groups of from 3 to 8 carbons, and concrete examples of which include a cyclopropyl group, cyclobutyl group, cyclopentyl group, cyclohexyl group, cycloheptyl group, cyclooctyl group and the like, and cyclopropyl group and cyclobutyl group are preferred.

The term "$C_{3-8}$ cycloalkenyl group" used herein refers to $C_{3-8}$ cycloalkenyl groups having 3 to 8 carbon atoms, and examples of which include cyclopentene-3-yl, cyclohexene-1-yl, cyclohexene-3-yl and the like.

The term "$C_{1-6}$ alkoxy group" used herein refers to oxy groups to which the above-defined "$C_{1-6}$ alkyl group" is bound, and examples of which include methoxy group, ethoxy group, N-propoxy group, iso-propoxy group, sec-propoxy group, N-butoxy group, iso-butoxy group, sec-butoxy group, tert-butoxy group, N-pentyloxy group, iso-pentyloxy group, sec-pentyloxy group, N-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 1,3-dimethylbutoxy group, 2-methylpentoxy group, 3-methylpentoxy group, hexyloxy group and the like, methoxy group, ethoxy group, n-propoxy group and iso-propoxy group, sec-propoxy group are preferred, and methoxy group and ethoxy group are more preferred.

The term "$C_{2-6}$ alkenyloxy group" used herein refers to oxy groups to which the above-defined "$C_{2-6}$ alkenyl group" is bound.

The term "$C_{2-6}$ alkenylthio group" used herein refers to thio groups to which the above-defined "$C_{2-6}$ alkenyl group" is bound.

The term "$C_{1-6}$ alkoxycarbonyl group" used herein refers to carbonyl groups to which the above-defined "$C_{1-6}$ alkoxy group" is bound, and concrete examples of which include a methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group, tert-butoxycarbonyl group and the like.

The term "$C_{2-7}$ acyl group" used herein refers to carbonyl groups to which the above-defined "$C_{1-6}$ alkyl group" is bound, and examples of which include an acetyl group, propionyl group, butylyl group, isobutylyl group, valeryl group, isovaleryl group, pivaloyl group and the like.

Concrete examples of "$C_{1-6}$ alkylcarbamoyl group" used herein include a methylcarbamoyl group, ethylcarbamoyl group, N-propylcarbamoyl group, iso-propylcarbamoyl group, N-butylcarbamoyl group, iso-butylcarbamoyl group, sec-butylcarbamoyl group, tert-butylcarbamoyl group, N-pentylcarbamoyl group, 1,1-dimethylpropylcarbamoyl group, 1,2-dimethylpropylcarbamoyl group, 2,2-dimethylpropylcarbamoyl group, 1-ethylpropylcarbamoyl group, 2-ethylpropylcarbamoyl group, N-hexylcarbamoyl group, 1-methyl-2-ethylpropylcarbamoyl group, 1-ethyl-2-methylpropylcarbamoyl group, 1,1,2-trimethylpropylcarbamoyl group, 1-propylpropylcarbamoyl group, 1-methylbutylcarbamoyl group, 2-methylbutylcarbamoyl group, 1,1-dimethylbutylcarbamoyl group, 1,2-dimethylbutylcarbamoyl group, 2,2-dimethylbutylcarbamoyl group, 1,3-dimethylbutylcarbamoyl group, 2,3-dimethylbutylcarbamoyl group, 2-ethylbutylcarbamoyl group, 2-methylpentylcarbamoyl group, 3-methylpentylcarbamoyl group and the like.

The term "$C_{1-6}$ alkylcarbonyloxy group" used herein refers to oxy groups to which the above-defined "$C_{2-7}$ acyl group" is bound, andconcreteexamplesofwhichincludeamethylcarbonyloxy group, ethylcarbonyloxy group, N-propylcarbonyloxy group, iso-propylcarbonyloxy group, N-butylcarbonyloxy group, iso-butylcarbonyloxy group, sec-butylcarbonyloxy group, tert-butylcarbonyloxy group, N-pentylcarbonyloxy group, 1,1-dimethylpropylcarbonyloxy group, 1,2-dimethylpropylcarbonyloxy group, 2,2-dimethylpropylcarbonyloxy group, 1-ethylpropylcarbonyloxy group, 2-ethylpropylcarbonyloxy group, N-hexylcarbonyloxy group, 1-methyl-2-ethylpropylcarbonyloxy group, 1-ethyl-2-methylpropylcarbonyloxy group, 1,1,2-trimethylpropylcarbonyloxy group, 1-propylpropylcarbonyloxy group, 1-methylbutylcarbonyloxy group, 2-methylbutylcarbonyloxy group, 1,1-dimethylbutylcarbonyloxy group, 1,2-dimethylbutylcarbonyloxy group, 2,2-dimethylbutylcarbonyloxy group, 1,3-dimethylbutylcarbonyloxy group, 2,3-dimethylbutylcarbonyloxy group, 2-ethylbutylcarbonyloxy group, 2-methylpentylcarbonyloxy group, 3-methylpentylcarbonyloxy group and the like.

The term "$C_{1-6}$ alkylsulfonyl group" used herein refers to sulfonyl groups to which the above-defined "$C_{1-6}$ alkyl group" is bound, and concrete examples of which include a methylsulfonyl group, ethylsulfonyl group, N-propylsulfonyl group, iso-propylsulfonyl group, N-butylsulfonyl group, iso-butylsulfonyl group, sec-butylsulfonyl group, tert-butylsulfonyl group, N-pentylsulfonyl group, 1,1-dimethylpropylsulfonyl group, 1,2-dimethylpropylsulfonyl group, 2,2-dimethylpropylsulfonyl group, 1-ethylpropylsulfonyl group, 2-ethylpropylsulfonyl group, N-hexylsulfonyl group, 1-methyl-2-ethylpropylsulfonyl group, 1-ethyl-2-methylpropylsulfonyl group, 1,1,2-trimethylpropylsulfonyl group, 1-propylpropylsulfonyl group, 1-methylbutylsulfonyl group, 2-methylbutylsulfonyl group, 1,1-dimethylbutylsulfonyl group, 1,2-dimethylbutylsulfonyl group, 2,2-dimethylbutylsulfonyl group, 1,3-dimethylbutylsulfonyl group, 2,3-dimethylbutylsulfonyl group, 2-ethylbutylsulfonyl group, 2-methylpentylsulfonyl group, 3-methylpentylsulfonyl group and the like.

The term "$C_{1-6}$ alkylsulfinyl group" used herein refers to sulfinyl groups to which the above-defined "$C_{1-6}$ alkyl group" is bound, and concrete examples of which include a methylsulfinyl group, ethylsulfinyl group, N-propylsulfinyl group, iso-propylsulfinyl group, N-butylsulfinyl group, iso-butylsulfinyl group, sec-butylsulfinyl group, tert-butylsulfinyl group, N-pentylsulfinyl group, 1,1-dimethylpropylsulfinyl group, 1,2-dimethylpropylsulfinyl group, 2,2-dimethylpropylsulfinyl group, 1-ethylpropylsulfinyl group, 2-ethylpropylsulfinyl group, N-hexylsulfinyl group, 1-methyl-2-ethylpropylsulfinyl group, 1-ethyl-2-methylpropylsulfinyl group, 1,1,2-trimethylpropylsulfinyl group, 1-propylpropylsulfinyl group, 1-methylbutylsulfinyl group, 2-methylbutylsulfinyl group, 1,1-dimethylbutylsulfinyl group, 1,2-dimethylbutylsulfinyl group, 2,2-dimethylbutylsulfinyl group, 1,3-dimethylbutylsulfinyl group, 2,3-dimethylbutylsulfinyl group, 2-ethylbutylsulfinyl group, 2-methylpentylsulfinyl group, 3-methylpentylsulfinyl group and the like.

The term "$C_{1-6}$ alkylthio group" used herein refers to thio groups to which the above-defined "$C_{1-6}$ alkyl group" is bound, and examples of which include a methylthio group, ethylthio group, N-propylthio group, iso-propylthio group, N-butylthio group, iso-butylthio group, sec-butylthio group, tert-butylthio group, N-pentylthio group, 1,1-dimethylpropylthio group, 1,2-dimethylpropylthio group, 2,2-dimethylpropylthio group, 1-ethylpropylthio group, 2-ethylpropylthio group, N-hexylthio group, 1-methyl-2-ethylpropylthio group, 1-ethyl-2-methylpropylthio group, 1,1,2-trimethylpropylthio group, 1-propylpropylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group, 3-methylpentylthio group and the like.

The term "$C_{6-14}$ aryl group" used herein refers to aryl groups of from 6 to 14 carbon atoms, which include a monocyclic group and condensed rings such as bicyclic group and tricyclic group. Concrete examples of such group include a phenyl group, indanyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, benzocyclooctenyl group and the like. In the "$C_{6-14}$ aryl group", phenyl group, 1-naphthyl group or 2-naphthyl group is preferred, and phenyl group, indanyl group or 2-naphthyl group is more preferred.

The term "$C_{6-14}$ aryloxy group" used herein refers to oxy groups to which the above-defined "$C_{6-14}$ aryl group" is bound.

The term "5- to 14-membered heteroaryl group" used herein refers to monocyclic, bicyclic or tricyclic, 5- to 14-membered heteroaryl groups containing one or more hetero atom selected from the group consisting of a nitrogen atom, sulfur atom and oxygen atom. Concrete examples of such group include 1) nitrogen-containing heteroaryl groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthyridinyl group, quinoxalyl group, quinazolinyl group, cinnolinyl group, pteridinyl group, imidazotriazinyl group, pyrazino pyridazinyl group, acridinyl group, phenanthridinyl group, carbazolyl group, carbazolinyl group, pyrimidinyl group, phenanthrolinyl group, phenacynyl group, imidazopyridinyl group, imidazopyrimidinyl group, pyrazolopyridinyl group, pyrazolopyridinyl group and the like; 2) sulfur-containing heteroaryl groups such as thienyl group, benzothienyl group and the like; 3) oxygen-containing heteroaryl groups such as furyl group, pyranyl group, benzofuryl group, isobenzofuryl group and the like; 4) heteroaryl groups containing two or more different hetero atoms such as thiazolyl group, isothiazolyl group, benzothiazolyl group, benzthiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group, pyridoxadinyl group and the like.

The term "4- to 14-membered non-aromatic heterocyclic group" used herein refers to non-aromatic heterocyclic groups having the following features:

1) the number of atoms constituting the ring of the cyclic group is from 4 to 14;
2) at least one hetero atom is contained in the atoms constituting the ring of the cyclic group;
3) the ring may contain 1 to 3 carbonyl group(s);
4) monocyclic, bicyclicortricyclic. Concrete examples of such group include pyrrolidyl group, pyrrolyl group, piperidyl group, pyperazyl group, imidazolyl group, pyrazolidyl group, imidazolidyl group, morphoryl group, tetrahydrofuryl group, tetrahydropyranyl group, aziridinyl group, oxylanyl group, oxathiolanyl group and the like. Such non-aromatic heterocyclic groups also include groups derived from pyridine ring and non aromatic condensed rings (for example, groups derived from phthalimide ring, succinimide ring or the like), and pyrrolidyl group, pyrrolyl group, piperidyl group, pyperazyl group, imidazolyl group, pyrazolidyl group, imidazolidyl group, morphoryl group, tetrahydrofuryl group, tetrahydropyranyl group, aziridinyl group, oxylanyl group, oxathiolanyl group and the like are preferred.

The term "5- to 10-membered heteroaryl group" used herein refers to monocyclic or bicyclic heteroaryl groups in which the ring of the cyclic group is made up of 5 to 10 atoms and at least one hetero atom(s) is (are) contained in the atoms constituting the ring of the cyclic group. Examples of such group include 1) nitrogen-containing heteroaryl groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizyl group, phthalazyl group, naphthyridinyl group, quinoxalyl group, quinazolinyl group, cinnolinyl group, pteridinyl group, imidazotriazinyl group, pyrazino pyridazinyl group, imidazopyridinyl group, imidazopyrimidinyl group, pyrazolopyridinyl group, pyrazolopyridinyl group and the like; 2) sulfur-containing heteroaryl groups such as thienyl group, benzothienyl group and the like; 3) oxygen-containing heteroaryl groups such as furyl group, pyranyl group, benzofuryl group, isobenzofuryl group and the like; 4) heteroaryl groups containing two or more different hetero atoms such as thiazolyl group, isothiazolyl group, benzothiazolyl group, benzthiadiazolyl group, isoxazolyl group, furazanyl group, oxazolyl group, isoxazoyl group, benzoxazolyl group, oxadiazolyl group, pyrazolooxazolyl group, imidazothiazolyl group, thienofuranyl group, furopyrrolyl group, pyridoxadinyl group and the like.

Among these, pyrrolyl group, furyl group, thienyl group, pyridyl group, benzothienyl group, benzofuryl group, indolyl group, benzlyl group and indazolyl group are preferred, and furyl group, thienyl group, benzothienyl group and benzofuryl group are more preferred.

The term "5- to 6-membered heteroaryl" used herein refers to monocyclic heteroaryl group in which the ring of the cyclic group is made up of 5 to 6 atoms and at least one hetero atom(s) is (are) contained in the atoms constituting the ring of the cyclic group. Examples of such group include pyrrolyl group, imidazolyl group, pyrazolyl group, 1,2,3-triazolyl group, pyridyl group, pyridazyl group and pyrimidinyl group, pyrazinyl group, triazinyl group, furyl group, thienyl group, thiazolyl group, oxazolyl group, isooxazolyl group and the like, and "heteroaryl" used herein contains an optionally substituted pyridonyl group on a nitrogen atom. Among these, pyrrolyl group, pyridyl group, piridonyl group, pyridazinyl group, pyrimidinyl group, pyrazinyl group, triazinyl group, furyl group or thienyl group is preferred.

The term "5-membered heteroaryl" used herein refers to 5-membered heteroaryl groups containing at least one heteroatom selected from the group consisting of a nitrogen atom, sulfur atom and oxygen atom. Examples of such group include pyrrolyl group, imidazolyl group, pyrazolyl group, 1,2,3-triazolyl group, furyl group, thienyl group, oxazolyl group, isooxazolyl group and the like, furyl group or thienyl group being preferred, and thienyl group more preferred.

The term "5- to 6-membered non-aromatic heterocycle" used herein refers to 5- or 6-membered heterocyclic groups containing at least one heteroatom selected from the group consisting of a nitrogen atom, sulphur atom and oxygen atom. Concrete examples of such group include piperidyl group, piperazyl group, morpholyl group, thiomorpholyl group, tetrahydro-2-pyron-yl group, tetrahydropyran-yl group, tetrahydrothiopyran-yl group, pyperidine-2-on-yl group, tetrahydrofuran-yl group, tetrahydrothiophene-yl group, pyrrolidinyl group, tetrahydrofuran-2-on-yl group or pyrrolidine-2-on-yl group. In the above "5- or 6-membered non-aromatic heterocycle", piperidyl group, piperazyl group, morpholyl group, thiomorpholyl group, tetrahydro-2-pyron-yl group, tetrahydropyran-yl group, tetrahydrothiopyran-yl group and pyperidine-2-on-yl group are preferred.

The term "amino group" used herein comprehends primary amines represented by the formula —$NH_2$, as well as secondary amines in which a hydrogen atom is substituted with other substituent (for example, $C_{1-6}$ alkyl group and the like) and tertiary amines in which two hydrogen atoms are substituted. In the cases of tertiary amines, two substituents may be bound with each other, to form a 4- to 8-membered ring (for example, piperidine ring, piperazine ring, morpholine ring or the like).

The term "amide group" used herein comprehends groups represented by —CO—$NH_2$, as well as secondary or tertiary amides in which hydrogen atom is substituted with $C_{1-6}$ alkyl group or the like as described in the definition for "amino group". The term "amide group" also involves amide groups forming a ring such as lactam.

The term "furyl group" used herein refers to 2-furyl group or 3-furyl group, with 2-furyl group being preferred.

The term "thienyl group" used herein refers to 2-thienyl group or 3-thienyl group, with 2-thienyl group being preferred.

The term "pyrrolyl group" used herein refers to 1-pyrrolyl group, 2-pyrrolyl group or 3-pyrrolyl group, with 2-pyrrolyl group being preferred.

The term "tetrahydrofuran-yl group" used herein refers to tetrahydrofuran-2-yl group or tetrahydrofuran-3-yl group, with tetrahydrofuran-2-yl group being preferred.

The term "tetrahydrothiophene-yl group" used herein refers to tetrahydrothiophene-2-yl group or tetrahydrothiophene-3-yl group, with tetrahydrothiophene-2-yl group being preferred.

The term "pyrrolidinyl group" used herein refers to 1-pyrrolidinyl group, 2-pyrrolidinyl group or 3-pyrrolidinyl group, with 2-pyrrolidinyl group being preferred.

The term "tetrahydrofuran-2-on-yl group" used herein refers to tetrahydrofuran-2-on-3-yl group, tetrahydrofuran-2-on-4-yl group or tetrahydrofuran-2-on-5-yl group, with tetrahydrofuran-2-on-5-yl group being preferred.

The term "pyrrolidine-2-on-yl group" used herein refers to pyrrolidine-2-on-1-yl group, pyrrolidine-2-on-3-yl group, pyrrolidine-2-on-4-yl group or pyrrolidine-2-on-5-yl group, and pyrrolidine-2-on-5-yl group is preferred.

The term "quinolyl group" used herein refers to monovalent groups derived by removing any one of hydrogen atoms from a quinoline ring, and concrete examples of which include 2-quinolyl group, 3-quinolyl group, 4-quinolyl group, 5-quinolyl group, 6-quinolyl group, 7-quinolyl group and 8-quinolyl group, and 2-quinolyl group is preferred.

In the groups represented by the formula:

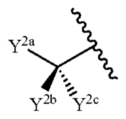

(wherein $Y^{2a}$, $Y^{2b}$ and $Y^{2c}$ have the same meaning as defined above), preferred examples include the groups represented by the formula:

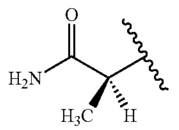

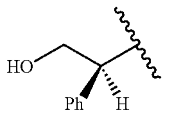

or

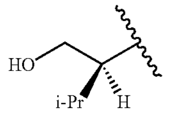

The term "optionally substituted" used herein is synonymous with the expression "a site at which substitution is possible may have one or plural substituent (s) in arbitrary combination".

Typical examples of substituent involved in "optionally substituted" include:

(1) halogen atoms;

(for example, fluorine atom, chlorine atom, bromine atom, iodine atom and the like);

(2) hydroxyl groups;

(3) cyano groups;

(4) nitro groups;

(5) carboxyl groups;

(6) amino groups;

(7) $C_{1-6}$ alkyl groups (for example, methyl group, ethyl group, N-propyl group, iso-propyl group, N-butyl group, tert-butyl group, N-pentyl group, 1,1-dimethyipropyl group, 1,2-dimethylpropyl group, 2,2-dimethylpropyl group, 1-ethylpropyl group, 2-ethylpropyl group, N-hexyl group and the like);

(8) $C_{2-6}$ alkenyl groups (for example, vinyl group, allyl group, 1-propenyl group, 2-propenyl group, isopropenyl group, 2-methyl-1-propenyl group, 3-methyl-1-propenyl group and the like);

(9) $C_{2-6}$ alkynyl groups (for example, ethynyl group, 1-propynyl group, 2-propynyl group, 1-butynyl group, 2-butynyl group, 3-butynyl group, 3-methyl-1-propynyl group, 1-ethynyl-2propynyl group, 2-methyl-3-propynyl group and the like);

(10) $C_{3-8}$ cycloalkyl groups (for example, cyclopropyl group, cyclobutyl group, cyclopentyl group, cyclohexyl group, cycloheptyl group, cyclooctyl group and the like);

(11) $C_{3-8}$ cycloalkenyl groups (for example, cyclopropene-1-yl, cyclopropene-3-yl, cyclobutene-1-yl, cyclobutene-3-yl, 1,3-cyclobutadiene-1-yl, cyclopentene-1-yl, cyclopentene-3-yl, cyclopentene-4-yl, 1,3-cyclopentadiene-1-yl, 1,3-cyclopentadiene-2-yl, 1,3-cyclopentadiene-5-yl, cyclohexene-1-yl, cyclohexene-3-yl, cyclohexene-4-yl, 1,3-cyclohexadiene-1-yl, 1,3-cyclohexadiene-2-yl, 1,3-cyclohexadiene-5-yl, 1,4-cyclohexadiene-3-yl, 1,4-cyclohexadiene-1-yl and the like);

(12) $C_{1-6}$ alkoxy groups (for example, methoxy group, ethoxy group, N-propoxy group, iso-propoxy group, sec-propoxy group, N-butoxy group, iso-butoxy group, sec-butoxy group, tert-butoxy group, N-pentyloxy group, iso-pentyloxy group, sec-pentyloxy group, N-hexoxy group, iso-hexoxy group, 1,1-dimethyipropyloxy group, 1,2-dimethylpropoxy group, 2,2-dimethyipropyloxy group and the like);

(13) $C_{1-6}$ alkenyloxy groups (for example, vinyloxy group, allyloxy group, 1-propenyloxy group, 2-propenyloxy group, isopropenyloxy group, 2-methyl-1-propenyloxy group, 3-methyl-1-propenyloxy group, 2-methyl-2-propenyloxy group, 3-methyl-2-propenyloxy group, 1-butenyloxy group, 2-butenyloxy group, 3-butenyloxy group, 1-pentenyloxy group, 1-hexenyloxy group, 1,3-hexadienyloxy group, 1,6-hexadienyloxy group and the like);

(14) $C_{1-6}$ alkylthio groups (for example, methylthio group, ethylthio group, N-propylthio group, iso-propylthio group, N-butylthio group, iso-butylthio group, sec-butylthio group, tert-butylthio group, N-pentylthio group, 1,1-dimethylpropylthio group, 1,2-dimethylpropylthio group, 2,2-dimethylpropylthio group, 1-ethylpropylthio group, 2-ethylpropylthio group, N-hexylthio group, 1-methyl-2-ethylpropylthio group, and the like);

(15) $C_{1-6}$ alkenylthio groups (for example, vinylthio group, allylthio group, 1-propenylthio group, 2-propenylthio group, isopropenylthio group, 2-methyl-1-propenylthio group, 3-methyl-1-propenylthio group, 2-methyl-2-propenylthio group, 3-methyl-2-propenylthio group, 1-butenylthio group, 2-butenylthio group, 3-butenylthio group, 1-pentenylthio group, 1-hexenylthio group, 1,3-hexane dienylthio group, 1,6-hexane dienylthio group, and the like);

(16) $C_{1-14}$ aryloxy groups (for example, phenyloxy group and the like);

(17) $C_{2-7}$ acyl groups (for example, acetyl group, propionyl group, butyroyl group and the like);

(18) $C_{6-14}$ aryl groups (for example, phenyl group, 1-naphthyl group, 2-naphthyl group, and the like);

(19) 4- to 14-membered heterocyclic groups (for example, 1) pyrrolidyl group, pyrrolilyl group, piperidyl group, pyperazyl group, imidazolyl group, pyrazolidyl group, imidazolidyl group, morphoryl group, tetrahydrofuryl group, tetrahydropyranyl group, aziridinyl group, oxylanyl group and oxathiolanyl group;

2) groups derived from pyrrolidone ring;

3) groups derived from condensed rings such as phthalimide ring and succinimide group, and the like);

(20) 5- to 14-membered heteroaryl groups (for example, pyrrolyl group, pyridyl group, pyridazinyl group, pyrimidyl group, pyrazinyl group, imidazolyl group, benzimidazolyl group, indolyl group, indazolyl group, quinolyl group, isoquinolyl group, thienyl group, benzothienyl group, furyl group, pyranyl group, benzofuryl group, thiazolyl group, benzothiazolyl group and the like);

(21) amide group,

(22) sulfonyl groups having $C_{1-6}$ aliphatic hydrocarbon groups as substituent;

(23) sulfonamide groups,

(24) $C_{1-6}$ alkylcarbamoyl groups,

(25) $C_{1-6}$ alkoxycarbonyl groups,

(26) $C_{1-6}$ alkylcarbonyloxy groups,

(27) $C_{1-6}$ alkylsulfonyl groups,

(28) $C_{1-6}$ alkylsulfinyl groups,

(29) formyl group,

(30) the formula:

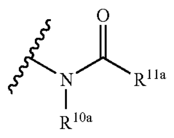

(wherein $R^{10a}$ and $R^{11a}$ each independently designate a hydrogen atom or $C_{1-6}$ alkyl group)

(31) the formula:

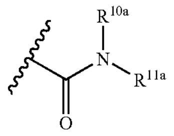

(wherein $R^{10a}$ and $R^{11a}$ each independently designate a hydrogen atom or $C_{1-6}$ alkyl group)

(32) the formula:

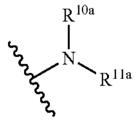

(wherein $R^{10a}$ and $R^{11a}$ each independently designate a hydrogen atom or $C_{1-6}$ alkyl group) and the like groups, and the term "optionally substituted" used herein means that the compound may have 1 to 4 substituent(s) selected from the above substituent groups.

In the above (6) to (23) listing available substituents for "optionally substituted", amino group, $C_{1-6}$ alkyl groups, $C_{2-6}$ alkenyl groups, $C_{2-6}$ alkynyl groups, $C_{3-8}$ cycloalkyl groups, $C_{3-8}$cycloalkenyl groups, $C_{1-6}$alkoxy groups, $C_{1-6}$alkenyloxy groups, $C_{1-6}$ alkylthio groups, $C_{1-6}$ alkenylthio groups, $C_{1-14}$ allyloxy groups, $C_{2-7}$ acyl groups, $C_{6-14}$ aryl groups, 4- to 14-membered non-aromatic hydrocarbon cyclic groups or 5- to 14-membered heteroaryl groups, amide groups, sulfonyl groups having $C_{1-6}$ aliphatic hydrocarbon groups as substituent or sulfonamide groups may be further optionally substituted with 1 to 4 group(s) selected from the group consisting of:

(a) halogen atoms, (b) hydroxyl group, (C) cyano group, (d) nitro group, (e) carboxyl group, (f) amino group, (g) $C_{1-6}$ alkyl groups, (h) $C_{2-6}$ alkenyl groups, (i) $C_{2-6}$ alkynyl groups, (j) $C_{3-8}$ cycloalkyl groups, (k) $C_{3-8}$ cycloalkenyl groups, (l) $C_{1-6}$ alkoxy groups, (m) $C_{1-6}$ alkenyloxy groups, (n) $C_{1-6}$ alkylthio groups, (o) $C_{1-6}$ alkenylthio groups, (p) $C_{1-14}$ allyloxy groups, (q) $C_{2-7}$ acyl groups, (r) $C_{6-14}$ aryl groups, (s) 4- to 14-membered non-aromatic hydrocarbon-cyclic groups, (t) 5- to 14-membered heteroaryl groups, (u) amide group, (v) sulfonyl groups having $C_{1-6}$aliphatic hydrocarbon groups as substituent, and (w) sulfonamide groups as described in (1) to (23).

Preferred examples of substituents for "optionally substituted" include:

(a-1) halogen atoms, (a-2) hydroxyl group, (a-3) nitrile group, (a-4) $C_{1-6}$ alkyl groups, $C_{2-6}$ alkenyl groups, $C_{2-6}$ alkynyl groups, $C_{3-8}$ cycloalkyl groups and $C_{1-6}$ alkoxy groups each optionally substituted with 1 to 3 halogen atom(s) or hydroxyl group, (a-5) $C_{6-10}$ aryl groups.

(a-6) 5- to 14-membered heteroaryl groups, (a-7) 5- to 14-membered heterocyclic groups, (a-8) carboxyl group, (a-9) trifluoromethyl group, (a-10) $C_{1-6}$ alkylcarbamoyl groups, (a-11) $C_{1-6}$ alkoxycarbonyl groups, (a-12) $C_{2-7}$ acyl groups, (a-13) $C_{1-6}$ alkylcarbonyloxy groups, (a-14) $C_{1-6}$ alkylsulfonyl groups, (a-15) $C_{1-6}$ alkylsulfinyl groups, (a-16) $C_{1-6}$ alkylthio groups, (a-17) nitro group, (a-18) formyl group, (a-19) the formula:

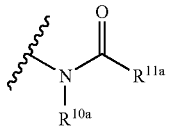

(wherein $R^{10a}$ and $R^{11a}$ each independently designate a hydrogen atom or $C_{1-6}$ alkyl group), (a-20) the formula:

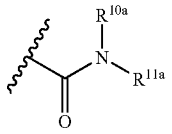

(wherein $R^{10a}$ and $R^{11a}$ each independently designate a hydrogen atom or $C_{1-6}$ alkyl group), (a-21) the formula:

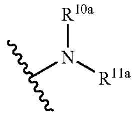

(wherein $R^{10a}$ and $R^{11a}$ each independently designate a hydrogen atom or $C_{1-6}$ alkyl group) and the like substituents.

More preferred examples of substituents for "optionally substituted" include:

(a-1) halogen atom, (a-2) hydroxyl group, (a-3) nitrile group, (a-4) $C_{1-6}$ alkyl groups, $C_{3-8}$ cycloalkyl groups and $C_{1-6}$ alkoxy groups each optionally substituted with 1 to 3 halogen atom(s) or hydroxyl group, (a-17) nitro group, and the groups represented by (a-19) the formula:

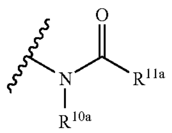

(wherein $R^{10a}$ and $R^{11a}$ each independently designate a hydrogen atom or $C_{1-6}$ alkyl group), and (a-20) the formula:

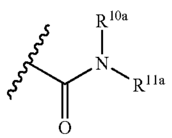

(wherein $R^{10a}$ and $R^{11a}$ each independently designate a hydrogen atom or $C_{1-6}$ alkyl group).

More preferred examples of substituents for "optionally substituted" include halogen atoms, nitrile group, $C_{1-6}$ alkyl groups, $C_{3-8}$ cycloalkyl groups, $C_{1-6}$ alkoxy groups and trifluoromethyl groups.

More preferred examples of substituents for "optionally substituted" include a fluorine atom, cyclopropyl group, trifluoromethyl group, methoxy group or the like.

When the number of substituent is 2 or more in "optionally substituted" used herein, the substituents may be bound with each other to form a ring. For example, when referring to "optionally substituted phenyl group", piperonyl group and the like are included.

In the compounds represented by the formula (I) in accordance with the present invention, Cy is 5- to 6-membered heteroaryl, preferably 5-membered heteroaryl, more preferably a thiophene ring, and most preferably such that structure of a moiety consisting of the Cy and the pyrazole ring adjoining the Cy forms 1H-thieno[2,3-C]pyrazole.

In the compounds represented by the formula (I) according to the present invention, n is 0, 1, 2, 3 or 4, and preferably 1 or 2.

In the compounds represented by the formula (II), $Q^1$ to $Q^4$ each independently designate —$NV^1$-, —$CV^2$═, —N═, —N(→O)═ or —CO—, and at least one of $Q^1$ to $Q^4$ is —$NV^1$— or —N═, —N(→O)═, namely containing a nitrogen atom on the ring, and it is preferred that only one of $Q^1$ to $Q^4$ is —$NV^1$— or —N═, —N(→O)═, and —N═ is more preferable in the substituents of —$NV^1$— or —N═, —N(→O)═. Furthermore, it is preferred that either one of $Q^1$, $Q^3$ or $Q^4$ is —$NV^1$— or —N═, —N(→O)═, especially —N═.

In the compounds represented by the formula (III) according to the present invention, $R^d$, $R^e$ or $R^f$ each independently designate a hydrogen atom, halogen atom, hydroxyl group, cyano group, nitro group, carboxyl group, optionally substituted $C_{1-6}$ alkyl group, optionally substituted $C_{1-6}$ alkoxy group, optionally substituted $C_{2-7}$ acyl group, —CO—$NR^{2a}R^{2b}$, —$NR^{2b}$CO—$R^{2a}$ or —$NR^{2a}R^{2b}$ (wherein $R^{2a}$ and $R^{2b}$ each independently designate a hydrogen atom or an optionally substituted $C_{1-6}$ alkyl group), and it is preferable that at least one of $R^d$, $R^e$ and $R^f$ is not a hydrogen atom, and only one of $R^d$, $R^e$ and $R^f$ is not a hydrogen atom. That is at least one or more of $R^d$, $R^e$ and $R^f$ is (are) preferably a substituent other than hydrogen atom, and it is more preferred that either two of $R^d$, $R^e$ and $R^f$ are hydrogen atoms while the other one is a substituent other than hydrogen atom. When expresses as "other than hydrogen atom", a halogen atom, hydroxyl group or optionally substituted alkoxy group is a preferred substituent, and a fluorine atom or methoxy group is a more preferred substituent.

In the compounds represented by the formulae (I) to (III) according to the present invention, $R^1$ is a group represented by the formula —$(CO)^h$—$(NR^a)_j$—$(CR^b$═$CR^c)_k$—Ar (wherein $R^a$, $R^b$ and $R^c$ each independently designate a hydrogen atoms halogen atom, hydroxyl group, optionally substituted $C_{1-6}$ alkyl group, optionally substituted $C_{2-6}$ alkenyl group, optionally substituted $C_{1-6}$ alkoxy group, optionally substituted $C_{2-6}$ alkenyloxy group, optionally substituted $C_{1-6}$ alkylthio group, optionally substituted $C_{2-6}$ alkenylthio group, optionally substituted $C_{3-8}$ cycloalkenyl group, optionally substituted 4-to 14-membered non-aromatic heterocyclic group, optionally substituted $C_{6-14}$ aryl group or optionally substituted 5- to 14-membered heteroaryl group, Ar designates an optionally substituted $C_{6-14}$ aryl group or optionally substituted 5- to 14-membered heteroaryl group, h, j and k each independently designate 0 or 1), and it is preferred that h and j are 0, and it is more preferred that h and j are 0 and k is 1.

In the compounds represented by the formulae (I) to (III) according to the present invention, $R^a$, $R^b$ and $R^c$ each independently designate a hydrogen atom, halogen atom, hydroxyl group, optionally substituted $C_{1-6}$ alkyl group, optionally substituted $C_{2-6}$alkenyl group, optionally substituted $C_{1-6}$ alkoxy group, optionally substituted $C_{2-6}$ alkenyloxy group, optionally substituted $C_{1-6}$ alkylthio group, optionally substituted $C_{2-6}$ alkenylthio group, optionally substituted $C_{3-8}$ cycloalkenyl group, optionally substituted 4- to 14-membered non-aromatic heterocyclic group, optionally substituted $C_{6-14}$ aryl group or optionally substituted 5- to 14-membered heteroaryl group, preferably a hydrogen atom, halogen atom, hydroxyl group, optionally substituted $C_{1-6}$ alkyl group, optionally substituted $C_{2-6}$ alkenyl group or optionally substituted $C_{1-6}$ alkoxy group, and more preferably a hydrogen atom or halogen atom.

In the compound represented by the formulae (I) to (III) according to the present invention, Ar is an optionally substituted $C_{6-14}$ aryl group or optionally substituted 5- to 14-membered heteroaryl group, preferably an optionally substituted benzene ring, optionally substituted naphthalene ring, optionally substituted thiophene ring or optionally substituted pyridine group.

In the compounds represented by formulae (I) to (III) according to the present invention, L is a single bond, optionally substituted $C_{1-6}$ alkylene group, optionally substituted $C_{2-6}$ alkenylene group or optionally substituted $C_{2-6}$ alkynylene group, preferably a single bond or optionally substituted $C_{1-6}$ alkylene group, and more preferably a single bond, methylene group or ethylene group.

In the compounds represented by the formulae (I) to (III) according to the present invention, X designates a single bond or a group represented by $-NR^7$-, —O—, —CO—, —S—, —SO—, $-SO_2-$, $-CO-NR^8$-Z-, —C(O)O—, $-NR^8-$CO-Z-, $-NR^8-C(O)O-$, $-NR^8-S-$, $-NR^8-SO-$, $-NR^8-SO_2$-Z-, $-NR^9-CO-NR^{10}-$, $-NR^9-CS-NR^{10}-$, $-S(O)_m-NR^{11}$-Z-, $-C(=NR^{12})-NR^{13}-$, —OC(O)—, $-OC(O)-NR^{14}-$ or $-CH_2-NR^8-COR^7-$ (wherein $R^7$, $R^8$, $R^9$, $R^{10}$, $R^{11}$, $R^{12}$, $R^{13}$ and $R^{14}$ each independently designate a hydrogen atom, halogen atom, hydroxyl group, optionally substituted $C_{1-6}$ alkyl group, optionally substituted $C_{2-6}$ alkenyl group, optionally substituted $C_{2-6}$ alkynyl group, optionally substituted $C_{1-6}$ alkoxy group, optionally substituted $C_{2-6}$ alkenyloxy group, optionally substituted $C_{1-6}$ alkylthio group, optionally substituted $C_{2-6}$ alkenylthio group, optionally substituted $C_{3-8}$ cycloalkyl group, optionally substituted $C_{3-8}$ cycloalkenyl group, optionally substituted 4- to 14-membered non-aromatic heterocyclic group, optionally substituted $C_{6-14}$ aryl group or optionally substituted 5-to 14-membered heteroaryl group, Z designates a single bond or optionally substituted $C_{1-6}$ alkylene group, m designates 0, 1 or 2), and preferably a single bond, $-CO-NR^8$-Z-, or $-NR^8-$CO-Z-.

In the compounds represented by the formulae (I) to (III) according to the present invention, Y is selected from the group consisting of a hydrogen atom, halogen atom, nitro group, hydroxyl group, cyano group, carboxyl group or optionally substituted $C_{1-6}$ alkyl group, optionally substituted $C_{2-6}$ alkenyl group, optionally substituted $C_{2-6}$ alkynyl group, optionally substituted C1-6 alkoxy group, optionally substituted $C_{3-8}$ cycloalkyl group, optionally substituted $C_{3-8}$ cycloalkenyl group, optionally substituted 4- to 14-membered non-aromatic heterocyclic group, optionally substituted $C_{6-14}$ aryl group, optionally substituted 5- to 14-membered heteroaryl group, optionally substituted amino group and group represented by the formula $-W-R^{15}$ wherein W designates CO or $SO_2$; $R^{15}$ designates an optionally substituted $C_{1-6}$ alkyl group, optionally substituted amino group, optionally substituted $C_{6-14}$ aryl group or optionally substituted 5- to 14-membered heteroaryl group), preferably an optionally substituted 5- to 14-membered heteroaryl group, and more preferably 5-to 6-membered heteroaryl group. Furthermore, when Y is $-W-R^{15}$, W is CO, while when $R^{15}$ is optionally substituted $C_{1-6}$ alkyl group, preferred is an optionally substituted amino group.

In the compounds represented by the formulae (I) to (III) according to the present invention, $R^7$, $R^8$, $R^9$, $R^{10}$, $R^{11}$, $R^{12}$, $R^{13}$ and $R^{14}$ each independently designate a hydrogen atom, halogen atom, hydroxyl group, optionally substituted $C_{1-6}$ alkyl group, optionally substituted $C_{2-6}$ alkenyl group, optionally substituted $C_{2-6}$alkynyl group, optionally substituted $C_{1-6}$alkoxy group, optionally substituted $C_{2-6}$ alkenyloxy group, optionally substituted $C_{1-6}$ alkylthio group, optionally substituted $C_{2-6}$ alkenylthio group, optionally substituted $C_{3-8}$ cycloalkyl group, optionally substituted $C_{3-8}$ cycloalkenyl group, optionally substituted 4- to 14-membered non-aromatic heterocyclic group, optionally substituted $C_{6-14}$ aryl group or optionally substituted 5-to 14-membered heteroaryl group, and preferably hydrogen atom or optionally substituted $C_{1-6}$ alkyl group.

Now, general methods for synthesizing the compounds represented by the formulae (I) to (III) according to the present invention will be described. It goes without saying that in the following general synthesis methods, exemplification based on the above formula (I) also applies to the formulae (II) and (III) unless otherwise noticed. In particular, as for the method of introducing the substituent $R^1$ as described later, it obviously applies to the formulae (II) and (III).

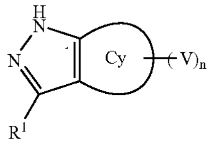

(I)

A typical production method of condensed pyrazole compound represented by the formula (I) according to the present invention will be described below. It is to be noted that "Cy" used in the reaction schemes of Production methods 1 to 80 has the same meaning as defined above. $R^1$, $Q^1$, $Q^2$, $Q^3$, $Q^4$ and V each have the same meaning as defined above. "V" indicated as a reagent in schemes of the Production methods provided below may exists alone or associated with an appropriate leaving group. The symbol "n" designates 0, 1, 2, 3 or 4. $T^1$ means a hydrogen atom, bromine atom or iodine atom. $T^2$ means a halogen atom, preferably fluorine atom. $T^3$ means a chlorine atom, bromine atom or iodine atom, preferably bromine atom or iodine atom. Pro and $Pro^1$ each designate a protective group. J, $J^1$ and $J^2$ each independently designate, but not limited to, an alkyl group or may together form a ring. $V^1$ and $V^2$ each have the same meaning as defined for V.

Production method 1

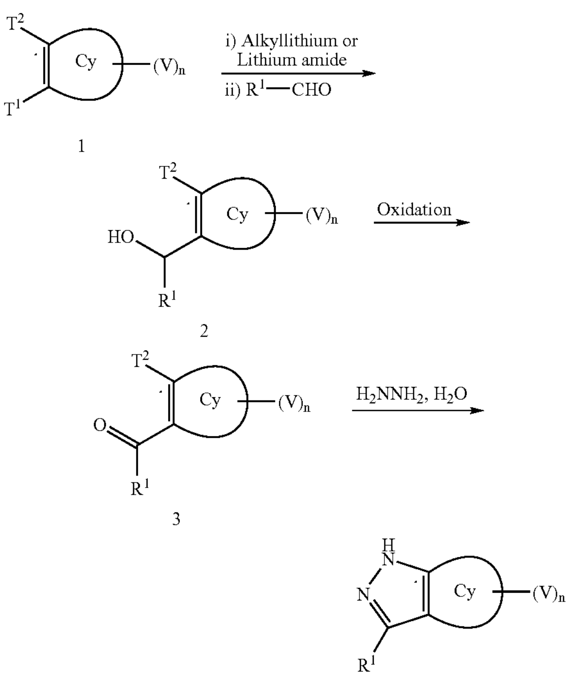

1 2 3 (I)

Compound (I) can be produced by converting aromatic ring compound 1 into a metal aryl with the use of alkyl lithium, lithium amide or the like, reacting the metal aryl with aryl aldehyde to render it alcohol 2, oxidizing alcohol 2 into ketone 3, and then subjecting ketone 3 to cyclization of indazole ring with the use of hydrazine. As the alkyl lithium to be used for converting aromatic ring compound 1 into a metal aryl, for example, N-butyllithium, sec-butyllithium, tert-butyllithium, phenyl lithium and the like are used. Additives such as diazabicyclo[2.2.0]octane, N,N,N',N'-tetramethylethylenediamine, hexamethylphosphoramide and the like may also be added as is necessary. Further, as the lithium amide, for example, lithium diisopropylamide, lithium 2,2,6,6-tetramethylpiperidide and the like are used. As the solvent, any solvents can be used insofar as they are not concerned with the reaction, and preferred examples of such solvent include, but are not limited to, ether-based solvents such as diethyl ether, tetrahydrofuran or dioxane, dimethoxyethane, and the like, as well as benzene, toluene and the like. The reaction temperature is from −78° C. to room temperature. As the oxidizing reagent for oxidizing the alcohol of compound 2, for example, manganese dioxide, sulfur trioxide-pyridine complex, N-methylmorpholine-N-oxide, various kinds of chromic acid oxidizing reagents and the like can be used, and also Swern oxidation, Moffat oxidation and the like may be applied. As the solvent, any solvent can be used insofar as they are not concerned with the reaction, and examples of such solvent include hydrocarbon halides such as dichloromethane, chloroform and the like, as well as other ethyl acetate, acetonitrile, dimethyl sulfoxide, N,N-dimethylformamide and the like. The reaction temperature is usually from −78° C. to reflux temperature of the solvent. The reaction of cyclizing compound 3 with the use of hydrazine monohydrate may be carried out either in the absence of solvent or in the presence of solvent. Any solvents can be used insofar as they are not concerned with the reaction, and examples of such solvent include, but are not limited to, ether solvents such as diethyl ether, tetrahydrofuran, dioxane or dimethoxyethane, alcohol solvents such as methanol, ethanol or propanol, as well as pyridine, dimethyl sulfoxide, benzene, toluene and so on. The use amount of hydrazine monohydrate is from 2 to 20 equivalents with respect to the material. The reaction temperature is usually from 0° C. to reflux temperature of the solvent.

Production method 2

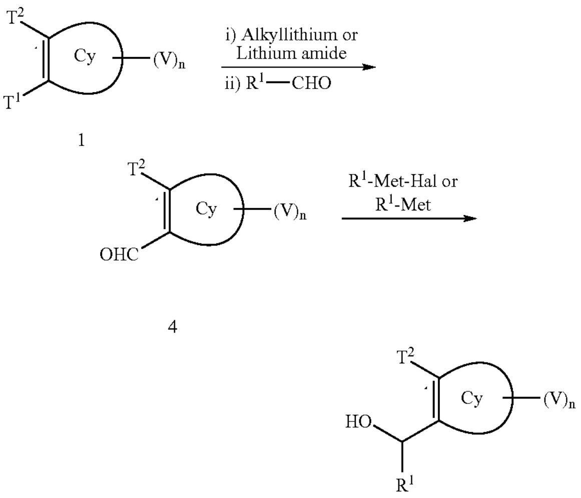

1 4 2

Compound 2 can also be produced in accordance with Production method 2. Aromatic ring compound 1 is made into a metal aryl in accordance with Production method 1, which is then reacted with formylation agent, to thereby produce compound 4. Examples of formylation agent include N,N-dimethylformamide, N-formylpiperidine, methylphenylformamide and so on. As the reaction solvent, any solvents can be used insofar as they are not concerned with the reaction, and examples of which include, but are not limited to, ether solvents such as diethyl ether, tetrahydrofuran, dioxane, dimethoxyethane and the like, as well as benzene, toluene and the like. The reaction temperature is from −78° C. to room temperature. Compound 2 can be produced by making a metal aryl or metal halogenoaryl to react on compound 4. The metal aryl or metal halogenoaryl can be readily prepared, for example, by converting halogenoaryl into aryl lithium or metal halogenoaryl by using alkyl lithium, magnesium, zinc and the like. As the alkyl lithium, for example, N-butyllithium, sec-butyllithium, tert-butyllithium, phenyl lithium and the like can be used, and N,N,N',N'-tetramethylethylenediamine, hexamethylphosphoramide and the like additives may be used as necessary. As the reaction solvent, any solvents can be used insofar as they are not concerned with the reaction, and examples of such solvent include, but are not limited to, ether solvents such as diethyl ether, tetrahydrofuran, dioxane, dimethoxyethane and the like, as well as benzene, toluene and the like. The reaction temperature is from −78° C. to room temperature.

Production method 3

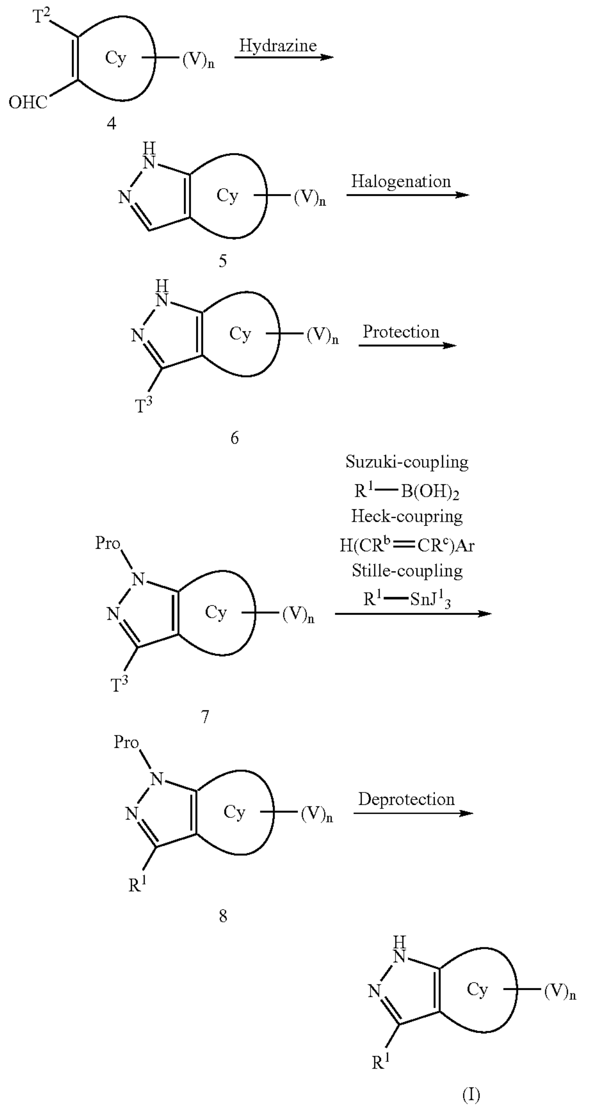

Compound (I) can be produced by cyclizing compound 4 in accordance with Production method 1 using hydrazine to render indazole compound 5, halogenating 3-position of compound 5 to render it compound 6, protecting 1-position of pyrazole of compound 6 to render it composition 7, and then introducing a substituent into 3-position by coupling reaction, followed by deprotection at 1-position. The $R^1$ which may be introduced by coupling reaction has the same meaning as defined above, and the case where h=j=0 is preferred. Compound 8 wherein an aromatic ring is directly bonded to 3-position of pyrazole can be produced by Suzuki coupling with aryl boronic acid or by Stille reaction with aryl trialkyl tin or the like. Furthermore, in particular, compound 8 having styrene (h=j=0, k=1) at 3-position can also be produced by coupling based on Heck reaction in which styrene is reacted on compound 7, besides the Suzuki coupling. The method for producing 3-styrene compound 8 is described in Production methods 35 to 40 below. As a halogenation reagent for 3-position, for example, N-bromosuccinimide, N-iodosuccinimide, N-chlorosuccinimide, bromine, iodine and the like are used, and radical initiators such as 2,2'-azodiisobutyronitrile or benzoyl peroxide or bases such as sodium hydroxide may be added as necessary. The use amount of the halogenation reagent is from 1.05 to 1.2 equivalents with respect to the material. As the solvent, any solvents can be used insofar as they are not concerned with the reaction, and examples of such solvent include, but are not limited to, hydrocarbon halides such as dichloromethane, chloroform, carbon tetrachloride and the like, as well as ethyl acetate, acetonitrile, dimethyl sulfoxide, N,N-dimethylformamide and so on. The reaction temperature is usually from room temperature to reflux temperature of the solvent.

Examples of the protective group at 1-position include tert-butoxycarbonyl group, p-toluenesulfonyl group, trityl group, methoxymethyl group and the like. Introduction of tert-butoxycarbonyl group and p-toluenesulfonyl group can be achieved by letting compound 6 and di-tert-butyldicarbonate or p-toluenesulfonyl chloride react with each other in the presence of a base. Preferred examples of the base include, but are not limited to, triethylamine, 4-N,N-dimethylaminopyridine and the like. As the solvent, any solvents can be used insofar as they are not concerned with the reaction, and examples of such solvent include, but are not limited to, ether solvents such as diethyl ether, tetrahydrofuran, dioxane or dimethoxyethane, hydrocarbon halides such as dichloromethane or chloroform, as well as ethyl acetate, acetonitrile, dimethyl sulfoxide, dimethylformamide and so on. The reaction temperature is usually from 0° C. to reflux temperature of the solvent.

Introduction of trityl group and methoxymethyl group can be achieved by letting compound 6 and chlorotriphenylmethane or chloromethylmethyl ether react with each other in the presence of a base. Preferred examples of the base include, but are not limited to, sodium hydride, potassium tert-butoxide, lithium diisopropylamide, potassium carbonate, sodium hydroxide and the like. As the solvent, any solvents can be used insofar as they are not concerned with the reaction, and examples of such solvent include, but are not limited to, ether solvents such as diethyl ether, tetrahydrofuran, dioxane or dimethoxyethane, as well as ethyl acetate, acetonitrile, dimethyl sulfoxide, dimethylformamide and so on. The reaction temperature is from −20° C. to reflux temperature of the solvent.

Aromatic olefins used for Heck reaction and aryl boronic acids used for Suzuki coupling are commercially available, or may readily be prepared in a conventional manner if not commercially available. Aryl boronic acid can be prepared by converting a halogenoaryl into an aryl lithium or metal halogenoaryl with the use of a alkyl lithium, magnesium, zinc and the like, and letting the aryl lithium or metal halogenoaryl react with a trialkyl borate to render it a boric acid ester, followed by hydrolysis. Examples of the alkyl lithium include N-butyllithium, sec-butyllithium, tert-butyllithium, phenyl lithium and the like, and additives such as N,N,N',N'-tetramethylethylenediamine or hexamethylphosphoramide may be added as is necessary. The hydrolysis following the reaction between aryl lithium and trialkyl borate to obtain ester borate may be carried out by adding water, or by using an acid such as hydrochloric acid, sulfuric acid. As the solvent, any solvents can be used insofar as they are not concerned with the reaction, and preferred examples of such solvent include, but are not limited to, ether solvents such as diethyl ether, tetrahydrofuran, dioxane or dimethoxyethane. The reaction temperature is from −78° C. to room temperature. Aromatic olefins can be prepared by letting an aryl aldehyde and methylphosphonium ylide react with each other. For example, methyltriphenylphosphonium salt is treated with a base to make it methylphophonium ylide, which is then reacted with an aryl aldehyde in the same system, to thereby produce aromatic olefins. Examples of the base include potassium tert-butoxide, sodium methoxide, sodium hydride, potassium carbonate, sodium hydroxide and the like. Examples of the solvent include, but are not limited to, ether solvents such as diethyl ether, tetrahydrofuran or dioxane, hydrocarbon halides such as dichloromethane, chloroform, as well as toluene and the like. The reaction temperature is from −20° C. to reflux temperature of the solvent.

The use amount of aryl boronic acid used for Suzuki coupling or aromatic olefins used for Heck reaction is from 1 to 3 equivalent(s) with respect to the material. Examples of the base include, but are not limited to, aqueous sodium hydroxide, aqueous potassium hydroxide and the like. As the solvent, any solvents can be used insofar as they are not concerned with the reaction, and examples of such solvent include, but are not limited to, alcohol solvents such as methanol or ethanol, ether solvents such as diethyl ether, tetrahydrofuran, dioxane or dimethoxyethane. The reaction temperature is room temperature or reflux temperature of the solvent. Deprotection of the methoxymethyl group is generally achieved by acid treatment, however, when an aminal which is incompletely-deprotected by acid treatment remains, treatment with ammonia water is carried out to achieve the deprotection.

Production method 4

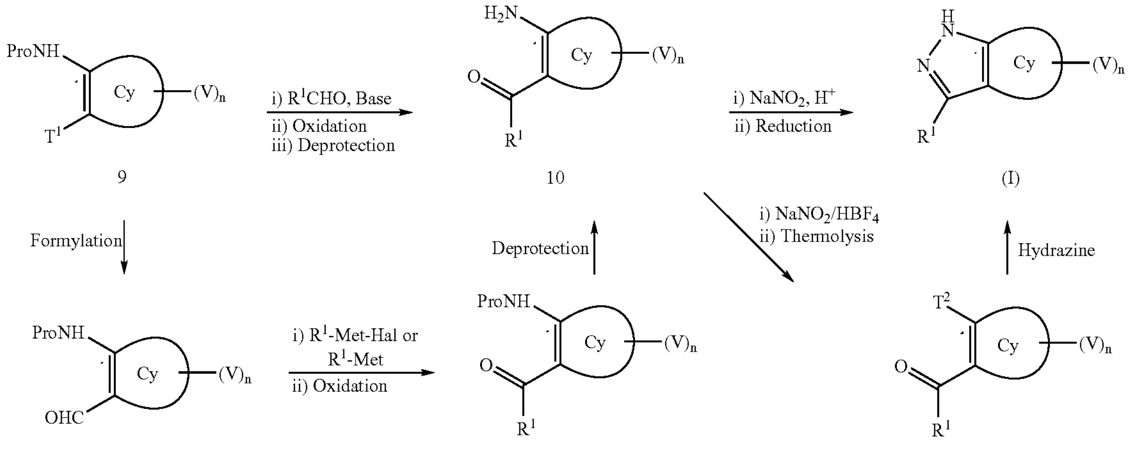

9 10 (I) 11 12 3 catalyst to be used include, palladium acetate(II), dichlorobistriphenylphosphine palladium(II), tetrakis(triphenylphosphine)palladium (0) and the like. The use amount of catalyst is about 5% by mole with respect to the material. As is necessary, phosphine ligand, twice in mole of catalyst of a phosphine ligand, for example, tri-tert-butylphosphine, 2-(di-tert-butylphosphino)biphenyl, 2-(dicyclohexylphosphino)biphenyl, triphenyl phosphine and the like may be added. Examples of the base to be used include sodium hydrogen carbonate, sodium carbonate, potassium carbonate, cesium carbonate, potassium fluoride and the like. As the solvent to be used, any solvents can be used insofar as they do not inhibit the reaction, and examples of such solvent include, but are not limited to, dimethylformamide, N-methylpyrrolidone, tetrahydrofuran, dioxane, diethylene glycol dimethyl ether, toluene and the like. The reaction temperature is usually from room temperature to reflux temperature of the solvent.

Deprotection of a tert-butoxycarbonyl group and a trityl group can be readily achieved by acid. Examples of the acid include hydrochloric acid, sulfuric acid, trifluoroacetic acid and the like. As is necessary, radical scavengers such as thiophenol or tri-iso-propylsilane may be added. As the solvent, any solvents can be used insofar as they are not concerned with the reaction, and examples of such solvent include, but are not limited to, hydrocarbon halides such as dichloromethane or chloroform, alcohol solvents such as methanol or ethanol, as well as anisole and the like. The reaction temperature is −20° C. or reflux temperature of the solvent. Deprotection of the tert-butoxycarbonyl group and p-toluenesulfonyl group can be readily achieved by a base.

Compound (I) can be produced in the following manner: oxidation of an alcohol which is obtained by metallizing α-position adjoining to the amino group suitably protected by treating compound 9 with a base and nucleophilically adding to analdehyde, and deprotection of the amino group are successively conducted to thereby obtain aminoketone 10; and then aminoketone 10 is diazotizated and reduced so as to be closed into a pyrazole.

As the protective group for amino group, any groups may be used insofar as they are base-resistant, and preferred examples of such protective group include, but are not limited to, a tert-butoxycarbonyl group, benzyloxycarbonyl group, methoxymethyl group and the like. Conversion of compound 9 into a metal aryl is basically conducted in the manner as described in Production method 1, however, in this case 2 or more equivalents of base is required. Oxidation of alcohol can be achieved in the manner as described in Production method 1. Deprotection of amino group from tert-butoxycarbonyl group, benzyloxycarbonyl group, methoxymethyl group and the like can be readily achieved by acid treatment. The acid to be used is as same as those recited in Production method 3, and as for the benzyloxycarbonyl group and the like, for example, may be deprotected under the condition of catalytic reduction or the like.

In the case where compound 10 cannot be derived directly from compound 9 for such a reason that aromatic aldehyde is relatively difficult to avail, the ortho position of the protected amino group is formylated to obtain 11, to which a metal aryl, a metal halogenoaryl or the like is nucleophilically added, followed by deprotection of amino group, to thereby obtain compound 10. The condition for formylation is as described in Production method 2.

Conversion of compound 10 into diazonium salt is achieved by letting nitrite esters such as sodium nitrite ester or isoamyl nitrite ester act in the presence of acid. As the reaction solvent, for example, alcohol solvents such as methanol, ethanol, water and the like are used, as the acid, hydrochloric acid, sulfuric acid, acetic acid and the like can be used. The reaction temperature is usually around 0° C.

Reduction of diazonium salt and subsequent ring closing of indazole ring are achieved by letting tin chloride (II), copper chloride (II) or the like reducing agent act in the presence of acid, to thereby obtain hydrazine which is an intermediate, and the use amounts of these are usually from 1 to 10 equivalent(s) with respect the starting material. Generally, compound (I) is obtained as a result of spontaneous ring closing associated with dehydration within the system. As the reaction solvent, for example, alcohol solvents such as methanol or ethanol, as well as hydrochloric acid, sulfuric acid, acetic acid and the like can be used. The reaction temperature is usually from 0° C. to reflux temperature of the solvent.

As an alternative method, an amino group is substituted with a suitable halogen atom to make compound 3, which is then made cyclic in the manner as described in Production method 1 using hydrazine, thereby obtaining compound (I). Preferred example of the halogen atom is, but are not limited to, a fluorine atom. As a concrete method, Baltz-Schiemann reaction can be recited, and by conducting this reaction, it is possible to derive fluoro ketone 3. Baltz-Schiemann reaction is achieved in the following manner: a nitrite ester such as sodium nitrite ester or isoamyl nitrite ester is caused to act on compound 10 in the presence of tetrafluoroboric acid so as to convert compound 10 into a diazonium tetrafluoroborate salt, followed by thermal decomposition or photodegradation. The nitrite ester or nitrite salt used for diazotization is usually in the amount of from 1 to 2 equivalent(s) with respect to the material, and the reaction temperature is preferably and usually 0° C. or less. Besides tetrafluoroboric acid, hexafluorophosphoric acid, hexafluorosilicic acid, hexafluoroantimonic acid and the like may be used. After separating the azonium salt, the thermal decomposition may be achieved by dilution in barium sulfate, barium fluoride and the like, or may be achieved by heating in an organic solvent such as acetone or hexane. In the case where separation of diazonium salt is difficult, the thermal decomposition may be conducted while adding a copper salt such as copper chloride or copper powder in the solution.

Production method 5

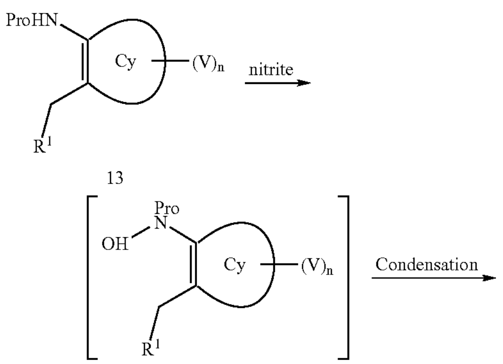

-continued

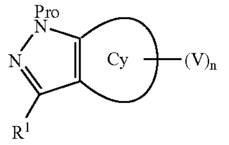

8

Alternatively, Compound 13 may be produced in the manner as described in Production method 5. Herein, $R^1$ are as defined, however, this also achieved in the case where $R^1$ is a methyl group as is a hydrogen atom. The protective group recited herein preferably designates an amino group or carbamoyl group although such protective group may be absent. That is, starting from a precursor, compound 13 wherein an amino group or its equivalent functional group and an active methyl group or an active methylene group are adjacent with each other on the aromatic ring, the amino group or its equivalent functional group is made into nitroso compound using a nitrite salt or nitrite ester, going through the reaction intermediate as described above, and then the intramolecular dehydration condensation with the adjoining active methyl group or methylene group in the presence of a suitable acid or base in the reaction system is carried out, to thereby lead pyrazole ring compound 8. As the reagent used for conversion into nitroso, nitrite salts or nitrite esters can be exemplified. Examples of nitrite esters include, but are not limited to, isoamyl nitrite ester and t-butyl nitrite ester, and examples of nitrite salts include sodium nitrite ester, potassium nitrite ester and the like. In particular, when a nitrite salt is used, a phase transfer catalyst such as crown ether may be used together. The use of the nitrite salt or nitrite ester is from 1 to 10 equivalent(s) with respect to the material. As the amino group or its equivalent functional group, amino groups such as acetamide are preferred without limitation, and in such a case, acetic anhydride is used as a solvent or present together in most general cases. General examples of the condensing reagent and base include, but are not limited to, sodium acetate and potassium acetate, and the use amount is usually from 1 to 10 equivalent (s). As the reaction solvent, any solvents besides acetic anhydrous can be used insofar as they are not concerned with the reaction, however, by conducting the reaction in, for example, but are not limited to, hydrocarbon solvents such as benzene, toluene or xylene, halogen solvents such as chloroform or 1,2-dichloroethane, dioxane, glacial acetic acid, as well as acidic solvents such as hydrochloric acid or sulfuric acid, it is possible to complete the condensation. The reaction temperature is from 0° C. to reflux temperature of the solvent.

In the following, concrete Production method of the compound represented by the general formula (II) including the Production method for side chain moiety, however it is to be noted that the Production method is not limited thereto.

From Production method 6 to Production method 12, Q designates a nitrogen atom, and at least one atom other than Q among atoms existing on the aromatic ring in which Q is involved designates —CH═. In this case, Q is a generic designation for $Q^1$ to $Q^4$ in the above general formula (II) and means either 1, 2 or 3 from $Q^1$ to $Q^4$.

Production method 6

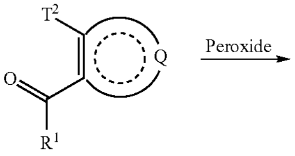

14

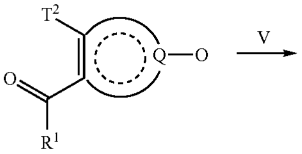

15

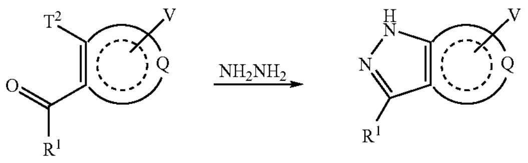

16 (II)-a

After treating Halogenoketone compound 14 obtained by using Production method 1 and so on with a peroxide to lead it into N oxide 15, a various kinds of reagents are caused to act on N-oxide 15, to thereby obtain compound 16 wherein a substituent is introduced onto a carbon atom around which no substitution occurs and hence generally having predominant orientation. As the functional group which can be introduced by using N-oxide as a starting material, a cyano group, halogen group, acyloxy group, alkoxy group and the like can be exemplified. The obtained compound 16 is made cyclic in accordance with Production method 1 using hydrazine, to thereby produce compound (II)-a.

In the method for leading compound 14 into N-oxide, for example, peroxides such as m-chloroperbenzoic acid, benzoyl peroxide or hydrogen peroxide are used, and the use amount of peroxide is from 1 to 10 equivalent(s) with respect to the material. As the solvent, any solvents can be used insofar as they are not concerned with the reaction, and examples of such solvent include, but are not limited to, halogen solvents such as dichloromethane, chloroform or 1,2-dichloroethane, hydrocarbon solvents such as benzene and toluene, as well as water, acetic acid and the like. The reaction temperature is usually from 0° C. to reflux temperature of the solvent.

As shown in J. Org. Chem. 1983, 48, 1375, for example, the method of cyanizing the adjoining carbon atom by using N-oxide is achieved by causing the cyanizing reagent directly to act or causing the cyanizing reagent to act in the presence of acid chloride. Examples of reagent for direct cyanation include sodium prussiate, potassium prussiate, trimethylsilyl cyanide, diethylcyano phosphate and the like, and bases such as triethylamine or 1,8-diazabicyclo[5.4.0]unde-7-cene may be present together in the reaction system. It is also possible to practice the above reaction with the cyanizing reagent in the presence of acid chloride, and examples of such acid chloride include benzoyl chloride, N,N-dimethyl, carbamoyl chloride and the like. As the solvent, any solvents can be used insofar as they are not concerned with the reaction, and examples of which include, but are not limited to, halogen solvents such as dichloromethane, chloroform, 1,2-dichloroethane and the like, and polar solvents such as acetonitrile, N,N-dimethylformamide or dimethyl sulfoxide, dimethylsulfuric acid and the like. The use amounts of cyanizing reagent, base and acid chloride are from 1 to 10 equivalent(s) with respect to the material. The reaction temperature is usually from room temperature to reflux temperature of the solvent.

Examples of the reagent for halogenating the adjoining carbon atom by using N-oxide include, phosphorus oxychloride, phosphorus oxybromide, benzoyl chloride, p-toluene sulfonyl chloride, ethyl chloroformate, trifluoromethanesulfonyl chloride, thionyl chloride and the like. The reaction may be carried out in the presence or absence of solvent, and as such a solvent any solvents can be used insofar as they are not concerned with the reaction, and examples of such solvent include, but are not limited to, halogen solvents such as dichloromethane, chloroform or 1,2-dichloroethane, hydrocarbon solvents such as benzene or toluene, ether solvents such as tetrahydrofuran, N,N-dimethylformamide and the like. The use amount of the solvent is from an equivalent with respect to the material to solvent amount. When the substrate is unstable to acid, a base such as triethylamine may coexist in the reaction system. The reaction temperature is usually from room temperature to reflux temperature of the solvent.

As the reagent for acyloxylation of the adjoining carbon atom of N-oxide, carboxylic anhydrides are usually used. The use amount is from an equivalent with respect to the material to solvent amount. The reaction temperature is usually from room temperature to reflux temperature of the solvent.

Alkoxylation of the adjoining carbon atom of N-oxide can be achieved by causing ethyl chloroformate, p-toluenesulfonyl chloride or the like to act in the presence of a base in alcohol. The use amount is from 1 to 10 equivalent(s) with respect to the material. As the base, metal alkoxides, triethylamine and the like are used, and the use amount is from 1 to 2 equivalent(s) with respect to the material. As the solvent, any solvents can be used without particular limitation insofar as they are not concerned with the reaction, however, it is general to conduct the reaction in a solvent of alcohol which corresponds to the alkoxy group intended to be introduced. The reaction temperature is usually from room temperature to reflux temperature of the solvent.

Production method 7

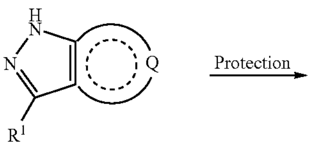

17

-continued

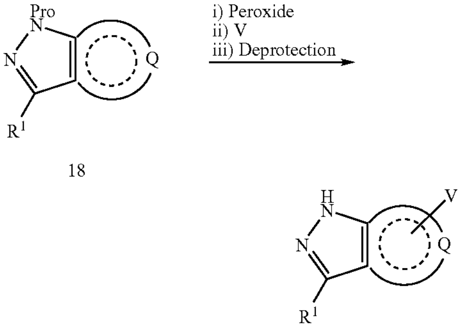

18

(II)-a

Introduction of functional group using the similar manner as described in Production method 6 is also applicable to the nitrogen-containing condensed pyrazole compound 17. That is, after oxidizing a desired nitrogen atom Q and leading into N-oxide by protecting the pyrazole ring of compound 17 and letting a peroxide act on compound 18, various kinds of reagents are made to act on the N-oxide so as to introduce a substituent into an adjoining carbon atom having predominant orientation. Then deprotection is conducted to produce Compound (II)-a.

Protection and Deprotection of a nitrogen-containing condensed pyrazole ring are achieved in the manner as described in Production method 3. The process of protection and deprotection of pyrazole ring may be eliminated from Production method, however, it is preferred to employ the process in consideration of yield and versatility.

Production method 8

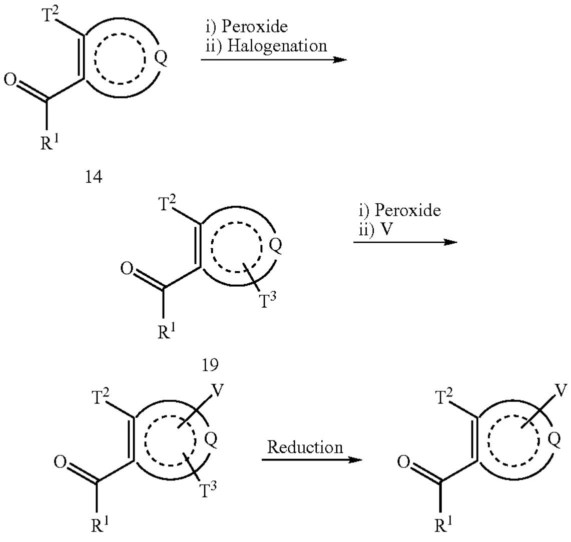

14

19

20

16

In the reaction between N-oxide and various kinds of reagents as described in Production method 6, when it is difficult to directly introduce a functional group other than halogens into a carbon atom at a desired position because of orientation of the reaction regent, the functional group may be indirectly introduced to the desired position as is described in Production method 8. That is, as an alternative method of Production method 6, first compound 19 wherein a carbon atom at a position of predominant orientation is substituted with a halogen is obtained by halogenating N-oxide, then compound 20 wherein a functional group is introduced to a desired position in the similar manner as described in Production method 6 is obtained, and then compound 20 is dehalogenated by reduction, to afford objective intermediate 16. Compound 16 is then made cyclic with hydrazine in accordance with Production method 1, to there by obtain Compound (II). As the halogen $T^3$, chlorine, bromine, iodine which are easy to leave can be exemplified, with chlorine and bromine being preferred for which commercially available phosphorous oxychloride, phosphorous oxybromide and the like can be used.

As the method for reducing the halogen group introduced into compound 20 to lead compound 16, for example, hydrogenation using palladium-carbon, palladium hydride-carbon, platinum oxide, Raney nickel and the like catalyst, or the condition of zinc-acetic acid, copper-acetic acid and the like are used. As other conditions, the condition of hydrazine, palladium-carbon and the like are also known. As the solvent for hydrogenation, any solvents can be used insofar as they do not inhibit the reaction, and examples of such solvent include, but are not limited to, alcohol solvents such as methanol, ethanol, halogen solvents such as dichloromethane and chloroform, ether solvents such as tetrahydrofuran or diethyl ether, as well as ethyl acetate, dimethylformamide, toluene and the like. The use amount of catalyst for hydrogenation is from 5% to 20% by weight with respect to the material. The pressure of hydrogen is usually atmospheric pressure to 5 atm. The reaction temperature is usually from room temperature to reflux temperature of the solvent. In the catalytic reduction, more gentle reaction can be achieved in the presence of a base, such as for example, sodium hydroxide, potassium hydroxide, triethylamine and the like. The reaction temperature is usually from room temperature to reflux temperature of the solvent. As the solvent for Zinc-acetic acid, copper-acetic acid and the like, glacial acetic acid or hydrous acetic acid and the like are used, and the use amount of metal is from 3 to 10 equivalents with respect to the material. The reaction temperature is usually reflux temperature of the solvent.

Production method 9

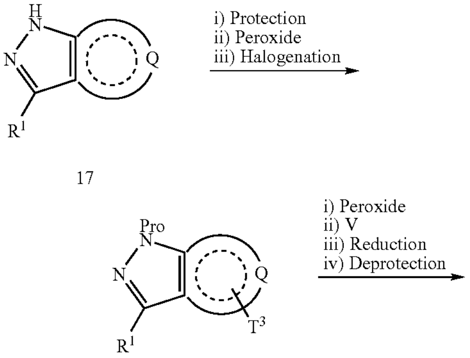

17

21

-continued

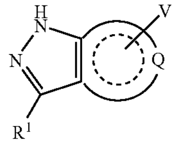

(II)-a

In the similar manner as described in Production method 8, when it is difficult to directly introduce a functional group other than halogens into a carbon atom at a desired position because of orientation of the reaction regent acting on N-oxide, the similar way as described in Production method 8 can be generally applied to nitrogen-containing condensed pyrazole compounds. That is, after oxidizing compound 17 with a peroxide while protecting 1-position of pyrazole of compound 17 to lead N-oxide, the N-oxide is halogenated, thereby producing compound 21 of predominant orientation. Next, compound 21 is treated again with a peroxide and allowed to react with a suitable reagent so as to introduce a substituent to a carbon atom at a more desirable position, followed by dehalogenation and deprotection, to thereby produce Compound (II)-a. Protection and deprotection of compound 17 can be achieved in the manner as described in Production method 3.

Production method 10

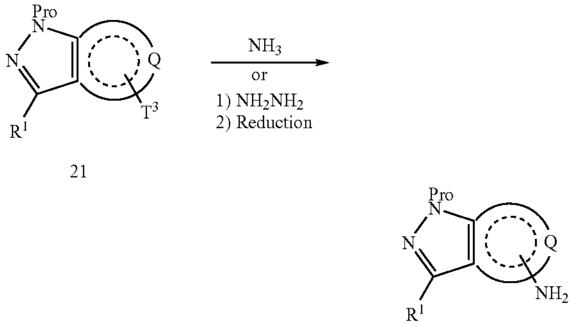

21

22

As described in Production method 8 and the like, in the case where the substitution position of the halogen atom which is introduced by causing a halogenation reagent such as phosphorus oxychloride to react on N-oxide is ortho- or para- position of the nitrogen atom constituting the ring, by letting amines to act, it is possible to readily substitute the halogen atom to obtain aniline 22. Aniline 22 can be converted into either primary, secondary or tertiary amine without limitation, and preferably to a primary amine. For introducing a primary amine, a variety of methods are applicable, for example, a method of causing imino chloride to act on the hydrazine and conducting catalytic reduction to lead an amine; a method of introducing an amine by using liquid ammonia or concentrated aqueous ammonia; or a method of causing potassium phthalimide to act and then introducing amine by hydrolysis using hydrazine or the like. Using the above reaction, it is possible to convert halide 21 into aniline 22.

The reaction with hydrazine is conducted, for example in alcohol solvents such as methanol or ethanol, and various kinds of solvents such as toluene, benzene, tetrahydrofuran or dioxane. The use amount of hydrazine is usually from 1 to solvent amount. The reaction temperature is usually from room temperature to reflux temperature of the solvent. In the method for catalytic reaction, Raney nickel is generally and often used. As the reaction solvent, hydrous alcohol solvents and the like are exemplifies. Amination using ammonia can be readily achieved by causing a large excess of ammonia to act. The reaction may be carried out after diluting with alcohol solvents such as methanol or with water, or liquid ammonia may be directly caused to act. The reaction may be carried out in a sealed tube for some cases. The reaction temperature is usually from −78° C. to reflux temperature of the solvent. The use amount of potassium phthalimide is usually from 1 to 2 equivalent(s), and as the reaction solvent, any solvents insofar as they are not concerned with the reaction can be used, and preferred examples of such solvent include, but are not limited to, N,N-dimethylformamide, acetonitrile, dimethyl sulfoxide, pyridine, tetrahydrofuran, dioxane or the like, as well as alcohols such as methanol or ethanol. The reaction system may contain a base, and examples of such base include triethylamine, diisopropylethylamine, pyridine and the like. The reaction temperature is usually from room temperature to reflux temperature of the solvent. Deprotection of phthaloyl group thus introduced can be practiced generally in strong base or reduction condition, and examples of which include hydrazine, sodium sulfide, sodium boron hydride and the like. Preferably, the deprotection is achieved by causing hydrazine to act in ethanol at room temperature. The use amount is from 1 equivalent to solvent amount with respect to the material.

Production method 11

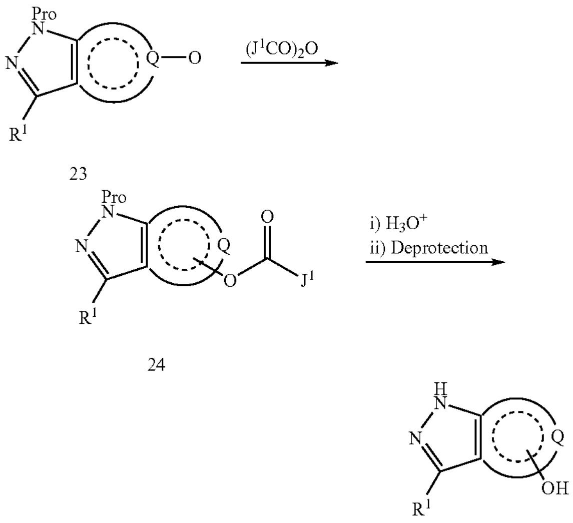

23

24

(II)-b

N-oxide 23 produced in Production method 7 or the like can be led to compound 24 by letting an acid anhydride act on N-oxide as is exemplified in Production method 6, followed by acyloxylation. In the case where the substitution position of the introduced acyloxy group is ortho- or para- position of the nitrogen atom constituting the ring, it is readily hydrolyzed to be led to pyridone compound (II)-b. As the hydrolyzing reagent, hydrochloric acid, sulfuric acid, p-toluenesulfonic acid, as well as alkalis such as sodium hydroxide, potassium hydroxide or potassium carbonate are exemplified, and the hydrolysis can be readily achieved in aqueous solutions, hydrous alcohol solvents and the like. The reaction temperature is usually from room temperature to reflux temperature of the solvent.

equivalent(s). As the solvent, any solvents can be used insofar as they are not concerned with the reaction, and examples of such solvent include, but are not limited to, halogen solvents such as dichloromethane, chloroform or 1,2-dichloroethane, Production method 12

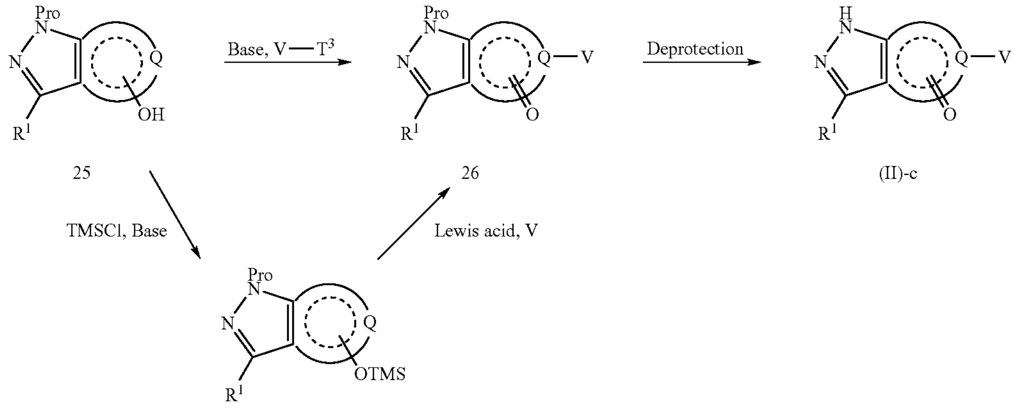

25 26 (II)-c 27

In the case where the substitution position of the hydroxyl group introduced by Production method 11 or the like is ortho- or para- position of the nitrogen atom constituting the ring, by letting a variety of halides on compound 25 in the presence of a base, it is possible to obtain compound 26 wherein a substituent is introduced to the nitrogen atom. As the base to be used, sodium hydride, potassium carbonate, cesium carbonate and the like are exemplified, and the use amount is usually from 1 to 2 equivalent(s). Examples of the halide to be used include, but are not limited to, bromides and iodides, and the use amount thereof is usually from 1 to 3 equivalent(s) with respect to the material. The halides which may be aliphatic or aromatic halides optionally have a suitable functional group. In the case of aromatic halides, iodides are especially preferred, and by adding a metal catalyst such as copper iodide in the presence of a base, it is possible to achieve excellent result. The use amount of metal catalyst is usually from a catalyst amount to 1 equivalent. In the cases of aralkyl halides, allyl halides and the like which are highly reactive, a salt such as sodium iodide is used together instead of base. As the solvent, any solvents can be used insofar as they are not concerned with the reaction, and examples of such solvent include, but are not limited to, halogen solvents such as dichloromethane, chloroform or 1,2-dichloroethane, hydrocarbon solvents such as benzene or toluene, ether solvents such as tetrahydrofuran, and polar solvents such as N,N-dimethylformamide or acetonitrile. The reaction temperature is usually from room temperature to reflux temperature of the solvent.

By reacting a silylation reagent such as trimethylsilyl chloride with compound 25 in the presence of a base, it is possible to obtain compound 27 in which a hydroxyl group is silylated. Examples of the base to be used include, but are not limited to, N-butyllithium, sec-butyllithium, tert-butyllithium, phenyl lithium, triethylamine, potassium carbonate and the like, and the use amount is from 1 to 2 equivalent (s). Examples of silylation reagent include, trimethylsilyl chloride and trimethylsilyl trifluoroacetate, trimethylsilyl trifluoromethanesulfonate and the like, and the use amount is from 1 to 2 hydrocarbon solvents such as benzene or toluene, and ether solvents such as tetrahydrofuran. The reaction temperature is from −78° C. to reflux temperature of the solvent.

It is possible to enable compound 27 to act as a nucleophile by introduction of trimethylsilyl group or the like. As a result of this, compound 27 nucleophilically reacts with a variety of reagents V in the presence of a Lewis acid, to form a corresponding adduct 26. Examples of the reagent that is reactive with compound 27 having such a property include, but are not limited to, Michael receptors such as epoxide, aldehyde, ketone or conjugate enone, and the use amount is from 1 to 2 equivalent(s) with respect to the material. Examples of the Lewis acid include, but are not limited to, aluminum chloride, boron trifluoride-diethyl ether complex and the like, and the use amount is from 1 to 2 equivalent(s). As the solvent, any solvents can be used insofar as they are not concerned with the reaction, and examples of such solvent include, but are not limited to, halogen solvents such as dichloromethane, chloroform or 1,2-dichloroethane, hydrocarbon solvents such as benzene or toluene, and ether solvents such as tetrahydrofuran. The reaction temperature is from −78° C. to reflux temperature of the solvent.

Deprotection of the protective group in compound 26 is carried out in the similar manner as described in Production method 3, whereby corresponding (II)-C is obtained.

The compounds embraced in the general formula (I) or (II) include a group of compounds which are readily produced by a production method other than the production method using the above-exemplified production process, which is specific to the forming condensed pyrazole ring. Now, production methods which are useful for production of specific heterocycle are exemplified in Production method 13 to Production method 19. As for synthesis of this group of compounds, it goes without saying that these compounds may be produced by using the above-described production method and the production method is not limited to the following production methods.

Production method 13

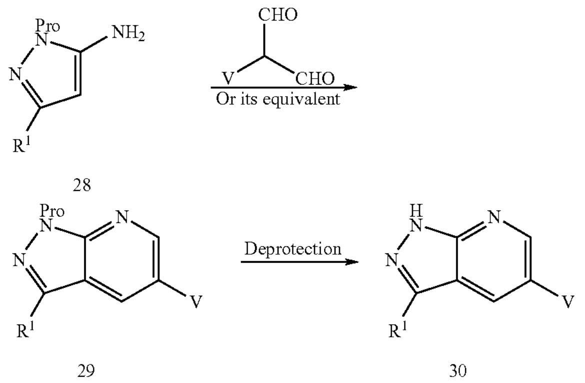

28 29 30

In $Q^1$ to $Q^4$ in general formula (II), 1H-pyrazolo[3,4-b] pyridines wherein only $Q^4$ is —N= can be synthesized in the manner as described, for example, in Production method 13. In general, by letting malonaldehyde or its equivalent act on 5-amino-1H-pyrazoles 28 in accordance with the known method (Synthesis. 1987, 1124), it is possible to form 1H-pyrazolo [3,4-b]pyridine ring 29. In this condensing reaction, when malonaldehyde or its equivalent has a suitable functional group, direct introduction of the substituent into the 5-position of the nitrogen-containing pyrazole ring by condensation is possible. As the equivalent of malonaldehyde having a suitable functional group, but are not limited to, sodium 2-cyano-3,3-dimethoxy-1-propenolate is preferably exemplified, and using this, it is possible to synthesize 1H-pyrazolo[3,4-b]pyridine ring 29 wherein a nitrile group is introduced into 5-position. Similarly by using sodium 2-nitromalonaldehyde, it is possible to produce 1H-pyrazolo[3,4-b]pyridine ring 29 wherein a nitrile group is introduced into 5-position. As the solvent for condensation reaction, any solvents are used insofar as they do not inhibit the reaction, and examples of such solvent include, but are not limited to, alcohol solvents such as methanol or ethanol, water and the like. The reaction may be carried out in the presence of an acid for neutralizing alkaline or in an acidic solvent, and as the reaction solvent, acetic acid, hydrochloric acid, sulfuric acid and the like can be exemplified. The use amount of malonaldehyde or its equivalent is usually from 1 to 3 equivalent (s) with respect to the material, and the reaction temperature is usually from room temperature to reflux temperature of the solvent.

By deprotecting compound 29, it is possible to produce compound 30. As the protective group, any groups can be used insofar as they do not influence on the reaction, and examples of such group include, but are not limited to, a benzyl group, benzyloxycarbonyl group, methoxymethyl group, tert-butoxycarbonyl group, trityl group and the like.

Deprotection of benzyloxycarbonyl group, methoxymethyl group, tert-butoxycarbonyl group and trityl group can be achieved in accordance with Production method 3.

Deprotection of benzyl group can be achieved, for example, by the method of letting a Lewis acid act, the method of acidically hydrolyzing, as well as the method of using active hydrogen such as the case of catalytic reduction. As a special example, it is known that heating in pyridine hydrochloride achieves deprotection. As the catalyst for catalytic reduction, palladium-carbon, platinum oxide and the like are used as is described in Production method 8, but other cases use sodium hydride or the like as active hydrogen species. As a Lewis acid, aluminum chloride is preferably used in the amount of from 1 to 10 equivalent(s). As the reaction solvent, any solvents can be used insofar as they are not concerned with the reaction, and examples of such solvent include, but are not limited to, halogen solvents such as dichloromethane or chloroform, benzene and the like. The reaction temperature is from room temperature to reflux temperature of the solvent. As the reagent used for the purpose of acidic deprotection, various chromic acids, permanganic acid, cerium ammonium sulfate, selenium dioxide and the like are exemplified, and various chromic acids and permanganic acid are generally caused to act in an acidic solvent. As the reaction solvent, for example, sulfuric acid, acetic acid, hydrochloric acid, water, acetonitrile, acetone or the like is used singly. Alternatively, by using a phase transfer catalyst, the reaction is conducted in a double phase reaction system made up of an organic solvent such as dichloromethane or an acidic solution containing an oxidizing reagent. The oxidizing reagent is used in an amount of 1 to 5 equivalent(s) with respect to the material, and the reaction temperature is usually from room temperature to reflux temperature of the solvent.

Production method 14

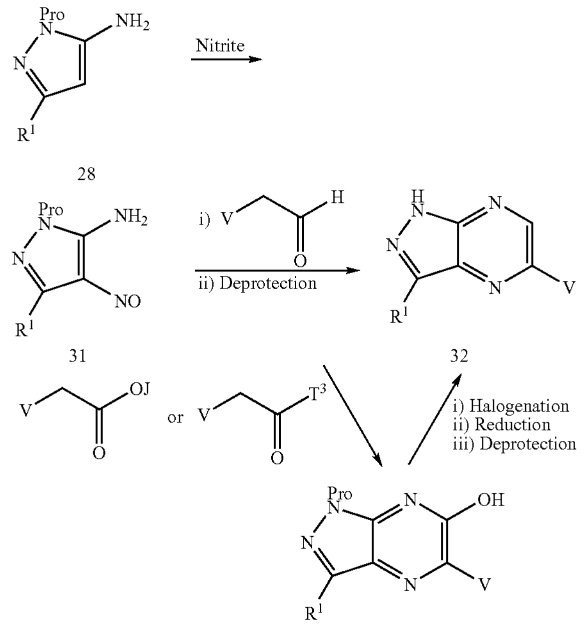

28 31 32 33

In $Q^1$ to $Q^4$ in the general formula (II), 1H-pyrazolo[3,4-b]pyrazines wherein $Q^1$ and $Q^4$ are —N= can be synthesized in the manner as described in Production method 14. After leading 5-amino-1H-pyrazoles 28 represented by Production method 13 into nitroso compound 31, a carbonyl compound whose a position is substituted is condensed in accordance with the known method (J. Chem. Thechnol. Biotechnol. 1990, 49 (4), 311-320 or the like), to thereby form 1H-pyrazolo[3,4-b]pyrazine ring 32. Preferred examples of the reagent having a suitable substituent include, but are not limited to, cyanoacetic acid or its ester, cyanoacetoaldehyde, malonic halide half ester and the like.

By intermolecular dehydration condensation between compound 31 and the above reaction reagent, amides or imines having an active methylene can be obtained. By treating these amides or imines having an active methylene with a suitable base, the formed anion is dehydration-condensed with the nitroso group in the molecule, with the result that compound 32 is obtained. Depending on the reagent to be condensed and reaction condition, a hydroxyl compound as is compound 33 is sometimes separated, however, by halogenation and reduction of the hydroxyl group so as to remove the hydroxyl group, it can be led into compound 32.

Generally, nitroso reaction is achieved by letting a nitrite ester or a nitrite salt act on a substrate in an acidic solvent. As the reaction solvent, a strong acid such as diluted hydrochloric acid, as well as a mixture thereof with an alcohol such as ethanol can be used. Examples of the nitrite salt or nitrite ester to be used include sodium nitrite ester, sodium nitrite ester, isoamyl nitrite ester and the like, and the use amount is from 1 to 3 equivalent(s) with respect to the material. The reaction temperature is usually around 0° C.

As the solvent for intermolecular condensation reaction, any solvents can be used insofar as they do not inhibit the reaction, and examples of such solvent include, but are not limited to, alcohol solvents such as methanol or ethanol, ether solvents such as 1,2-dimethoxyethane or tetrahydrofuran, N,N-dimethylformamide and the like. The solvent may contain a base for neutralizing the acid occurring in the system as is necessary, or by containing an excess base, intramolecular condensation can be achieved concurrently in one pot.

As the solvent for intramolecular condensation reaction, any solvents can be used insofar as they do not inhibit the reaction, and examples of such solvent include, but are not limited to, alcohol solvents such as methanol or ethanol, ether solvents such as 1,2-dimethoxyethane or tetrahydrofuran, N,N-dimethylformamide, water and the like, containing a base. As the base to be used, metal alkoxide, sodium acetate, sodium hydride, tert-butoxy potassium and the like are exemplified, and the use amount is from 1 to 3 equivalent(s) with respect to the material. As other reaction solvents, the reaction may be conducted in a basic solvent of either one of pyridine, triethylamine, picoline and the like.

The use amount of reagent used for condensation of cyanoacetic acid ester, cyanoacetoaldehyde and the like is usually from 1 to 3 equivalent(s), and the reaction temperature is usually from room temperature to reflux temperature of the solvent.

As the halogenation reagent for compound 33, phosphorus oxychloride, phosphorus oxybromide, phosphorous pentachloride, dichlorophenylphosphine and the like can be exemplified. The use amount is usually from 1 to 5 equivalent(s) with respect to the material, and as the reaction solvent, hydrocarbon solvents such as benzene or toluene, N,N-dimethylformamide and the like are used, however, phosphorus oxychloride, for example may be used in absence of solvent. The reaction temperature is usually from room temperature to reflux temperature of the solvent. Next, in accordance with Production method 9 or the like, the halogen group is reduced and deprotected, to obtain compound 32.

Production method 15

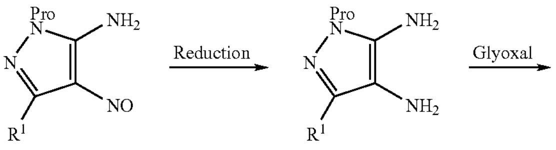

31 34

-continued

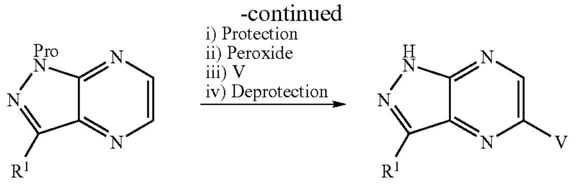

35 32

1H-pyrazolo[3,4-b]pyrazine ring compound 32 can also be produced in accordance with Production method 15 as well as Production method 14. That is, considering that after reducing nitroso compound 31 described in Production method 14 into diamine 34, a substituent is selectively introduced to 5-position of a pyrazolopyrazine ring, in accordance with the known method (Farmaco. Ed. Sci. 1982, 37, 116 or the like), preferably a glyoxal equivalent is made to act, to thereby obtain compound 35. Introduction of substituent into compound 35 can be achieved in the manner as described in Production method 7. As the method of reducing a nitroso group, for example, hydrogenation using palladium-carbon, palladium hydroxide-carbon, platinum oxide, Raney nickel and the like as a catalyst, or the condition of zinc-acetic acid, copper-acetic acid or the like is used. Also other conditions such as hydrazine or palladium carbon are known. As the solvent for hydrogenation, any solvents are used insofar as they do not inhibit the reaction, and the examples of such solvent include, but are not limited to, alcohol solvents such as methanol or ethanol, halogen solvents such as dichloromethane or chloroform, ether solvents such as tetrahydrofuran or diethyl ether, as well as ethyl acetate, dimethylformamide, toluene and the like. The use amount of the catalyst for hydrogenation is 5% to 20% by weight with respect to the material. The pressure of hydrogen is usually from atmospheric pressure to 5 atm. The reaction temperature is usually from room temperature to reflux temperature of the solvent.

Production method 16

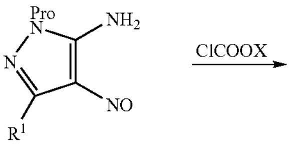

31

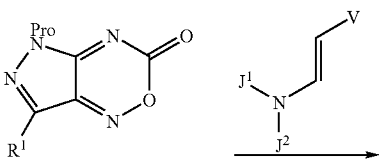

36

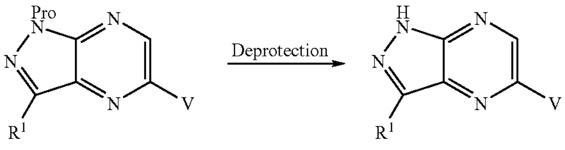

37 32

1H-pyrazolo[3,4-b]pyrazine ring compound 32 may be produced in accordance with Production method 16 as is the known method (J. Org. Chem. 1993, 58(22), 6155-6157). After treating compound 31 with chloroformic acid ester or the like to render it a cyclic compound 36, various kinds of enamine is caused to act, to thereby obtain pyrazolopyrazine ring 37 wherein a substituent is selectively introduced to 5-position. Then compound 37 is deprotected in accordance with Production method 3 or the like, thereby obtaining compound 32.

Production method 17

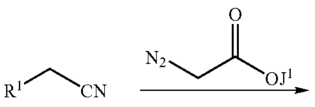

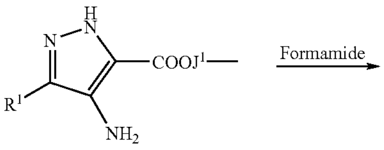

38

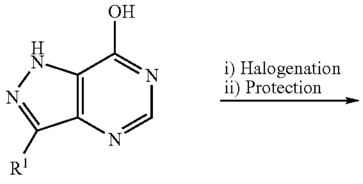

39

-continued

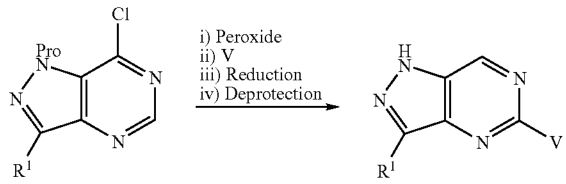

40 41

1H-pyrazolo[4,3-d]pyrimidine ring 41 can be synthesized by a variety of ring-closing reactions, and preferably it can be synthesized according to Production method 17. That is, starting from 4-amino-1H-pyrazole-2-yl carboxylic acid ester 38 obtained by the known method (Farmaco, Ed. Sci 1984, 39(7), 618), formamide is caused to act in the known manner (Chem. Pharm, Bull. 1983, 31, 1228) to obtain 1H-pyrazolo[4,3-d]pyrimidine-7-ol 39, and then the alcohol is removed and a substituent is introduced to 5-position in the manner as described in the above Production method 14. That is, following halogenation of compound 39 in accordance with Production method 14, pyrazole is protected in accordance with Production method 3 to produce compound 40. Then a substituent is introduced to 5-position in the method as described in Production method 7 or the like, followed by dehalogenation by reduction and deprotection, to thereby produce the objective compound 41. As the solvent for the condensation reaction with formamide, any solvents can be used insofar as they are not concerned with the reaction, and examples of such solvent include, but are not limited to, alcohol solvents such as ethanol, ether solvents such as tetrahydrofuran or diethyl ether, and hydrocarbon solvents such as benzene or toluene. The use amount of formamide is from 1 equivalent with respect to the material to solvent amount, and the reaction temperature is from room temperature to reflux temperature of the solvent.

Production method 18

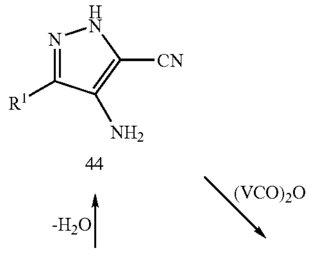

44

-continued

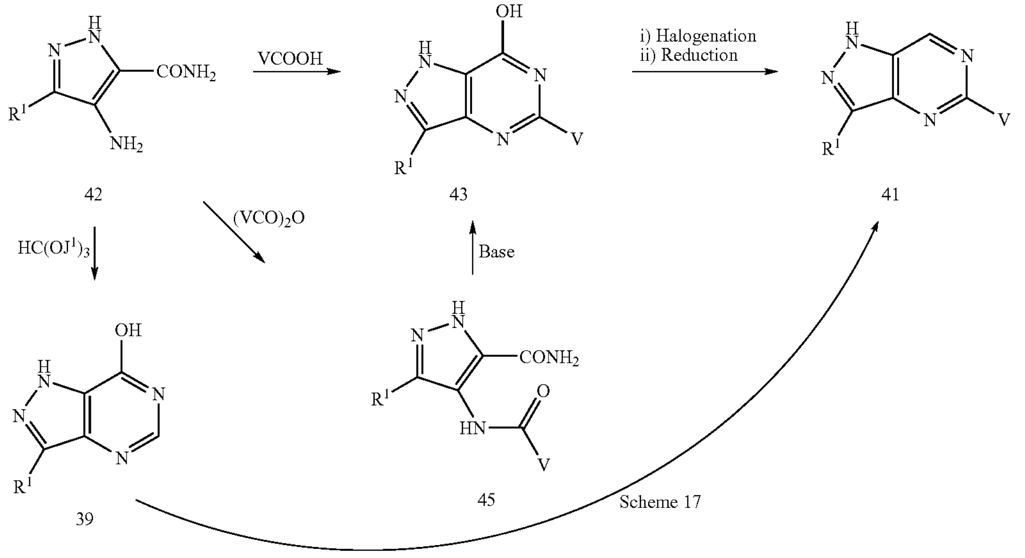

42 43 41 39 45

Scheme 17

As other construction methods for 1H-pyrazolo[4,3-d]pyrimidine ring compound 41, various kinds of pyrazole analogs can be selected for a starting material as described in Production method 18. As a compound which is analogous to 4-amino-1H-pyrazole-2-yl carboxylic acid ester 38 shown in Production method 17, compound 42 synthesized by the known method (Bioorg. Med. Chem, Lett. 2000, 17(10), 1983-1986) and the like can be preferably exemplified.

Compound 42 is a useful intermediate for constructing a ring by various kinds of cyclization reactions as is shown in Production method 18. For example, by condensing compound 42 by action of formic acid or alkyl orthoformate by way or a known method (Phrmazie, 1996, 51(12), 983-984), it is possible to obtain 1H-pyrazolo[4,3-d]pyrimidine-7-ol derivative 43 or compound 39. Furthermore, from compound 39, by successively conducting halogenation, protection, peroxidation, actions of various reagents to N-oxide, reduction and deprotection in accordance with the above-mentioned Production method 17, it is possible to produce compound 41 wherein a functional group is introduced to 5-position.

In accordance with the known method (J. Med. Chem. 1988, 31, 454), compound 44 which is easily obtained from compound 42 by dehydration may be condensed with a suitable carboxylic acid anhydride so as to introduce a functional group to 5-position.

Similarly, compound 42 may be condensed with various kinds of carboxylic acid derivatives, to produce cyclic compound 43. As a condensing reagent to be acted on 42, acid chlorides and acid anhydrides are preferably used. Depending on the reagent to be used, cyclization proceeds stepwise through intermediate 45. With regard to condensation ring-forming reaction as described above, reference is made to the known method (Heterocycles. 2000, 53(12), 2643-2652) for detail. It can be obtained by halogenating and reducing 1H-pyrazolo[4,3-d]pyrimidine-7-ol 43 in which 5-position is substituted by condensation in accordance with Production method 14.

Production method 19

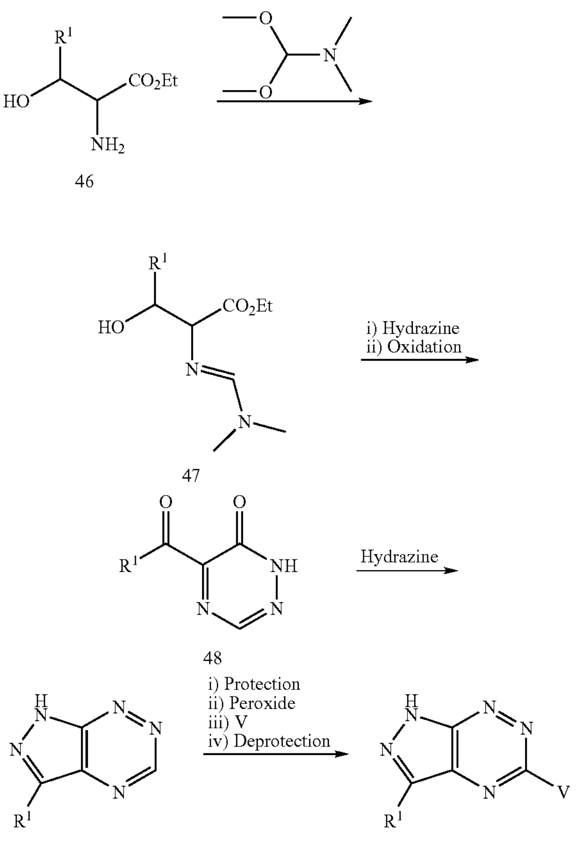

46 47 48 49 50

1H-pyrazolo[4,3-e][1,2,4]triazine ring compound 50 can be readily constructed (synthesized) by using, for example, serine derivative 46 as a starting material. In accordance with a regular method, an amino group of compound 46 is turned to dimethylaminomethylidene, a formyl equivalent such as compound 47 is introduced, and then compound 47 is treated with hydrazine in accordance with the known method (J. Het. Chem. 1985, 22(2), 409), whereby 6-hydroxytriazine ring is constructed. Subsequently, the resultant compound is oxidized by using the method of Production method 1 or the like, to produce compound 48, which is again treated with hydrazine in accordance with the known method (Pharmazie, 1984, 39(7), 504), thereby constructing 1H-pyrazolo[4,3-e][1,2,4] triazine ring compound 49. Subsequently, a side chain moiety is introduced in the manner as described in Production method 7 or the like, to produce compound 50.

The followings are concrete production examples for the compounds represented by the general formula (I)-A including production methods for the side chain moiety, however, it is to be understood that production methods are not limited thereto. The general formula (I)-A represents a compound in which Cy is a 5-membered heteroaryl among the compounds represented by general formula (I). In this formula, $U^1$ to $U^3$ each independently designate —O—, —$NV^1$—, —SV—, —CV═, —N═ or —CO—, and at least one of $U^1$ to $U^3$ designates —O—, —$NV^1$-, —SV— or —N═and U designates —OH, —$NH_2$ or —SH.

Production methods 20 to 22 describe for the case where $U^1$ at 4-position is a hetero atom.

Production method 20

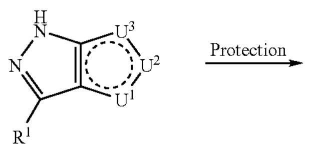

51

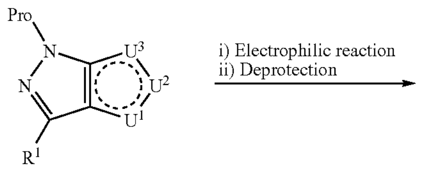

52

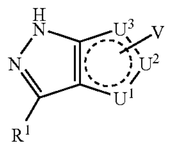

(I)-A-1

In the case where $U^1$ is a hetero atom and at least one of $U^2$ and $U^3$ is —CH═ in the general formula (I)-A, by introducing a variety of functional groups into a position corresponding to $U^2$ or $U^3$ of compound 52 obtainable by protecting 1-position of compound 51 by way of electrophilic substitution reaction using the orientation, followed by deprotection, it is possible to produce Compound (I)-A-1. As the functional group which may be introduced by way of electrophilic substitution reaction, halogen groups, sulfon groups, nitro group, acyl groups and the like can be exemplified.

Halogenation can be achieved in accordance with Production method 3.

As a sulfonation method, a reaction in the presence of proton such as sulfuric acid, a condition using pyridine sulfur trioxide where there are no protons and the like are used. The use amount of sulfonation reagent is from 1.05 to 1.2 equivalent(s) with respect to the material. The reaction may be conducted in the absence of solvent or in the presence of solvent. As the solvent, any solvents can be used insofar as they are not concerned with the reaction, and examples of such solvent include, but are not limited to, hydrocarbon halides such as dichloromethane, chloroform or carbon tetrachloride. The reaction temperature is usually from room temperature to reflux temperature of the solvent.

As a nitration method, concentrated nitric acid, fuming nitric acid, mixed acid of nitric acid and sulfuric acid, mixture of sodium nitrate or potassium nitrate and sulfuric acid, acetyl nitrate, trifluoroacetyl nitrate, as well as nitronium salts such as nitronium trifluoromethanesulfonate or nitronium tetrafluoroborate and the like are used. The use amount of nitration reagent is from 1.05 equivalents with respect to the material to solvent amount. The reaction may be conducted in the absence of solvent or in the presence of solvent. As the solvent, any solvents can be used insofar as they are not concerned with the reaction, and examples of such solvent include, but are not limited to, hydrocarbon halides such as dichloromethane, chloroform or carbon tetrachloride, hydrocarbons such as hexane or pentane, and when a nitronium salt is used, sulfolane or acetonitrile can be used. The reaction temperature is usually from −20° C. to reflux temperature of the solvent.

As an acylation method, Friedel-Crafts reaction is preferably used.

In the case where $U^1$ is a NH group, the group maybe protected with a suitable protective group in the similar manner as described for protection of 1-position, and then deprotected in the final step. Protection and deprotection of 1-poition is achieved in the manner as described in Production method 3.

Production method 21

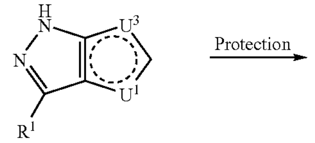

53

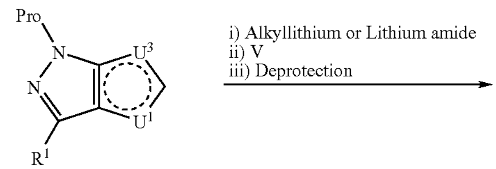

54

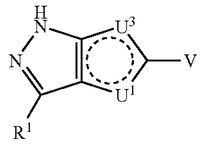

(I)-A-2

Compound (I)-A-2 in which a substituent is introduced to the position corresponding to $U^2$ can be produced by protecting 1-position of pyrazole of compound 53 wherein $U^2$ is —CH═ to obtain compound 54, and converting compound 54 into a metal aryl with the use of alkyl lithium, lithium amide or the like, introducing a substituent V in accordance with the Production method 6, and then conducting deprotection. As the functional group which may be introduced, halogen groups, formyl group, acyl groups, azido group, amino group and the like are exemplified.

Compound (I)-A-2 is produced in the following manner. After converting compound 54 into a metal aryl in accordance with Production method 1, the resultant metal aryl is reacted with a variety of reagents, followed by deprotection. As the variety of reagents, the following reagents can be exemplified. Examples of halogenation reagent include iodine, N-iodosuccinimide, bromine, N-bromosuccinimide and the like. Examples of formylation reagent include N,N-dimethylformamide, N-formylpiperidine, methylphenylformamide and the like. Examples of azidation reagent include azidomethyltrimethylsilane, toluenesulfonyl azide and the like.

Protection and deprotection of 1-position of pyrazole ring are achieved in the manner as described in Production method 3.

Production method 22

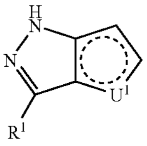

55 i) Protection
ii) Alkyllithium or Lithium amide
iii) Halogenation

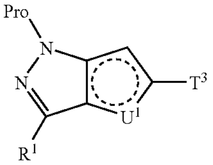

56 i) Electrophilic reaction
ii) Reduction
iii) Deprotection

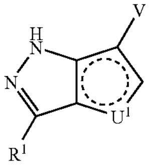

(I)-A-3

In the Production method 20, when $U^2$ and $U^3$ are —CH═, and hence it is difficult to selectively introduce a substituent by way of electrophilic substitution reaction using orientation to $U^3$, first 1-position of pyrazole of compound 55 is protected in the similar manner as described in Production method 21, which is then converted into a metal aryl with the use of alkyl lithium, lithium amide or the like, and then halogenated by action of a halogenation reagent to obtain compound 56 wherein $U^2$ is halogenated; and then a substituent is introduced to $U^3$ by electrophilic substitution reaction, followed by a sequence of reduction and deprotection, whereby Compound (I)-A-3 is obtained.

Protection and deprotection of 1-position are achieved in the manner as described in Production method 3.

Production methods 23 to 24 describe the case where $U^2$ at 5-position is a hetero atom.

Production method 23

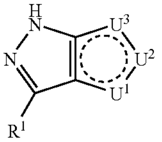

57

Protection

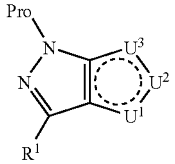

58 i) Electrophilic reaction
ii) Deprotection

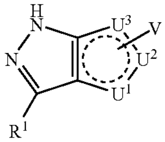

(I)-A-4

In the case where $U^2$ is a hetero atom, and at least one of $U^1$ and $U^3$ is —CH═, in accordance with the method described in Production method 20, it is possible to produce Compound (I)-A-4 having a substituent at $U^1$ or $U^3$ from compound 58 which is obtained by protecting 1-position of compound 57.

Production method 24

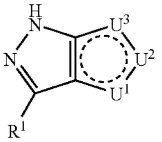

57

Protection

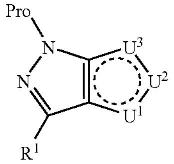

58 i) Alkyllithium or Lithium amide
ii) V
iii) Deprotection

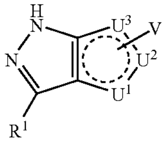

(I)-A-4

Compound (I)-A-4 having a substituent at $U^1$ or $U^3$ can also be produced in the manner as described in Production method 21.

Production methods 25 to 27 describe the case where $U^3$ at 6-position is a hetero atom.

Production method 25

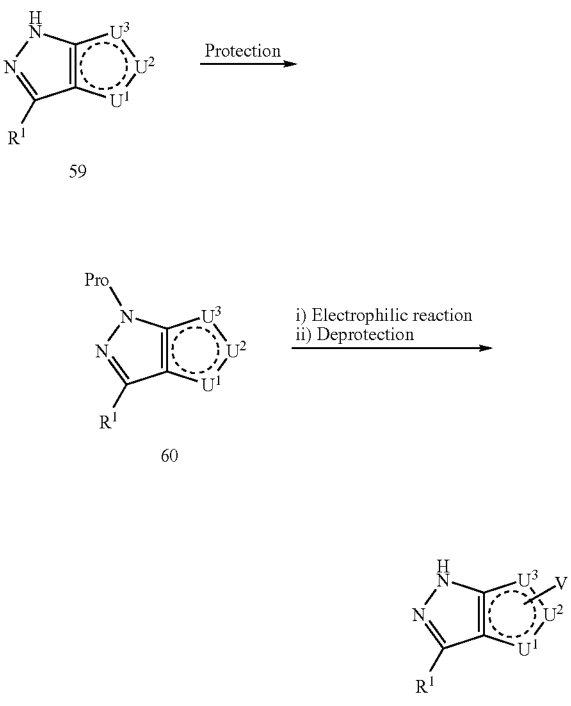

59

60

(I)-A-5

In the case where $U^3$ is a hetero atom and at least one of $U^1$ and $U^2$ is —CH═, it is possible to produce Compound (I)-A-5 into which a substituent is introduced at $U^1$ or $U^2$ in the manner as described in Production method 20.

Production method 26

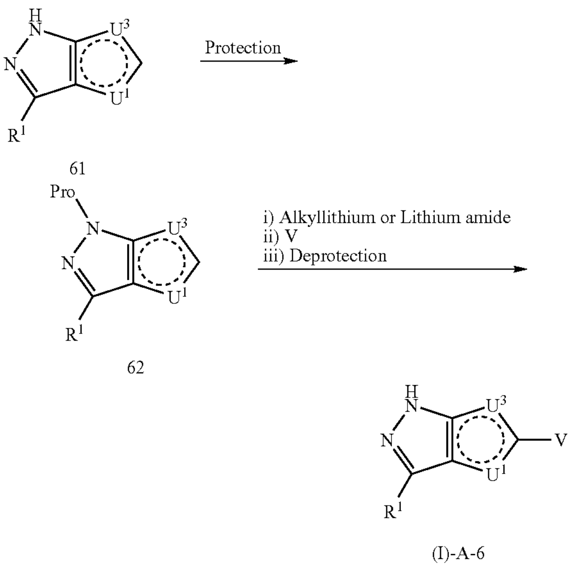

61

62

(I)-A-6

Compound (I)-A-6 in which a substituent is introduced to the position corresponding to $U^2$ can be produced in the manner as described in Production method 21.

Production method 27

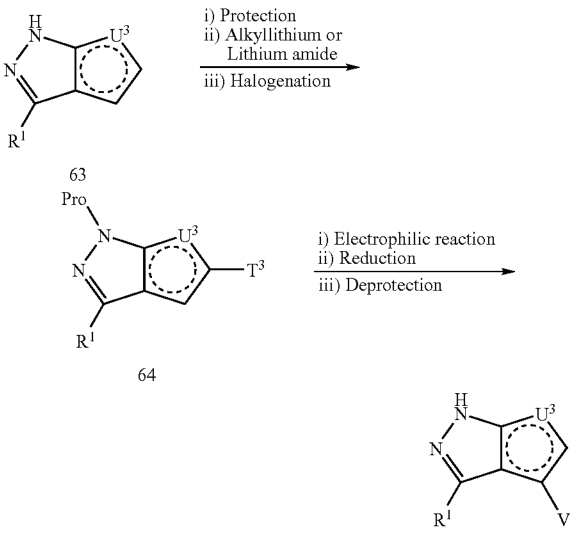

63

64

(I)-A-7

In the case where $U^1$ and $U^2$ are —CH═ and hence it is difficult to selectively introduce a substituent by way of electrophilic substitution reaction using orientation to $U^1$ in Production method 24, Compound (I)-A-7 can be produced in the similar manner as described in Production method 22 while protecting 1-position of pyrazole of compound 63 in the similar manner as Production method 25.

Production method 28

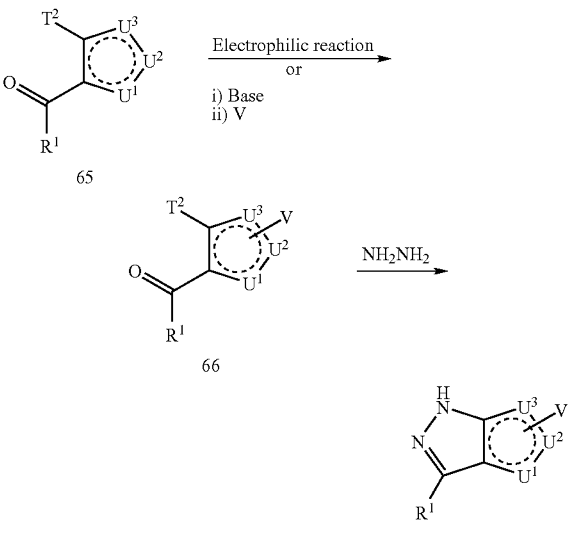

65

66

(I)-A

Methods which are similar to Production methods 20 to 27 may also be generally applied before ring-closing of pyrazole ring. That is, after introducing a substituent V to into compound 65, the pyrazole ring is closed with hydrazine monohydrate, to thereby produce Compound (I)-A. Cyclization reaction of hydrazine monohydrate can be achieved in accordance with Production method 1.

Production method 29

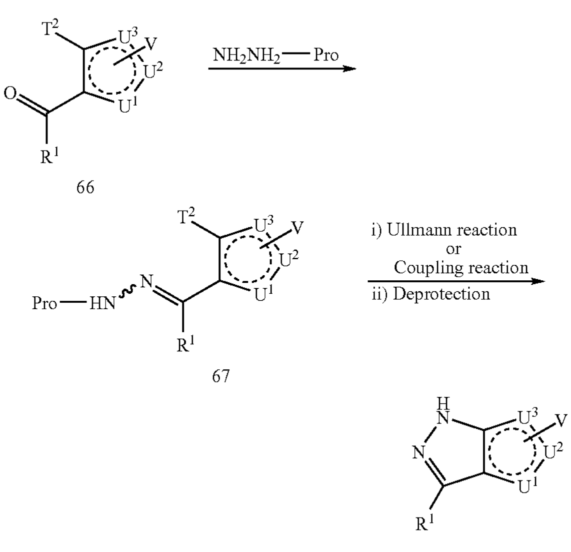

66

67

(I)-A

In the case where it is difficult to practice Production method 28 in accordance with Production method 1, first compound 67 is separated, which is then cyclized by Ullmann reaction using a copper reagent or coupling reaction using a palladium catalyst, to thereby produce Compound (I)-A.

Hydrazine may be reacted with compound 66 without being protected, however, hydrazide which is protected with an acetyl group or the like is preferably used. This reaction may be conducted in the absence of solvent or in the presence of solvent. As the solvent, any solvents can be used insofar as they are not concerned with the reaction, and examples of such solvent include, but are not limited to, ether solvents such as diethyl ether, tetrahydrofuran, dioxane or dimethoxyethane, alcohol solvents such as methanol, ethanol or propanol, as well as pyridine, dimethyl sulfoxide, benzene, toluene and the like. The use amount of hydrazine or hydrazide is from 2 to 20 equivalents with respect to the material. The reaction temperature is usually from 0° C. to reflux temperature of the solvent.

As the copper reagent to be used in Ullmann reaction, copper, copper chloride, copper bromide, copper iodide, copper oxide and the like can be exemplified. The use amount is from a catalyst amount to 2 equivalents with respect to the material. Examples of the base to be used include, but are not limited to, potassium carbonate, sodium carbonate, potassium acetate, sodium acetate and the like. The reaction may be conducted in the absence of solvent or in the presence of solvent. As the solvent, any solvents can be used insofar as they are not concerned with the reaction, and examples of such solvent include, but are not limited to, toluene, nitrobenzene, diphenyl ether, dimethylformamide, dioxane and the like. The reaction temperature is usually from room temperature to reflux temperature of the solvent.

Examples of the palladium catalyst to be used when the reaction is achieved by coupling reaction include, but are not limited to, tris(dibenzylideneacetone)dipalladium, palladium acetate and the like. As a ligand, 2,2'-bis(diphenylphosphino)-1,1'-naphtyl, 1,1'-bis(diphenylphosphino) ferrocene, tri(tert-butyl) phosphine or the like is used in the amount of 1 to 3 equivalent(s) to the catalyst. As the base, sodium tert-butoxide, potassium tert-butoxide, cesium carbonate and the like are preferred. As the solvent, any solvents can be used insofar as they are not concerned with the reaction, and preferred examples of such solvent include, but are not limited to, dimethylformamide, tetrahydrofuran, dioxane, diethyleneglycol dimethyl ether, toluene, xylene and the like. The reaction temperature is usually from room temperature to reflux temperature of the solvent.

Protection and deprotection of 1-position of pyrazole are achieved in the manner as described in Production method 3.

Production method 30

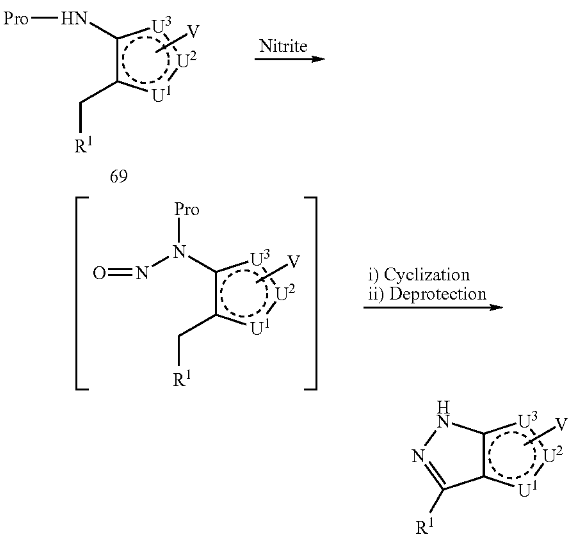

69

(I)-A

Synthesis of Compound (I)-A is also achieved by the method in accordance with Production method 5. That is, using compound 69 wherein an amino group or its equivalent functional group and an active methyl group or active methylene group are adjacent with each other on the aromatic ring, as a precursor, the amino group or its equivalent functional group is converted to a nitroso group using nitrite salt or nitrite ester. This reaction intermediate is then subjected to intramolecular dehydrating condensation with the adjacent active methyl group or methylene group in the presence of a suitable acid or base, to thereby construct a pyrazole ring. Finally, deprotection is conducted, to produce Compound (I)-A.

Protection and deprotection of 1-position of pyrazole are achieved in the manner as described in Production method 3.

The compounds embraced in the general formula (I)-A include other compounds which are readily produced by a production method other than the production method using the above-exemplified production process, which is specific to the forming condensed pyrazole ring. Now, production methods which are useful for production of specific heterocycle are exemplified in Production method 31 to Production method 34. As for synthesis of these group of compounds, it goes without saying that these compounds may be produced by using the above-described production method and the production method is not limited to the following production methods.

Production method 31

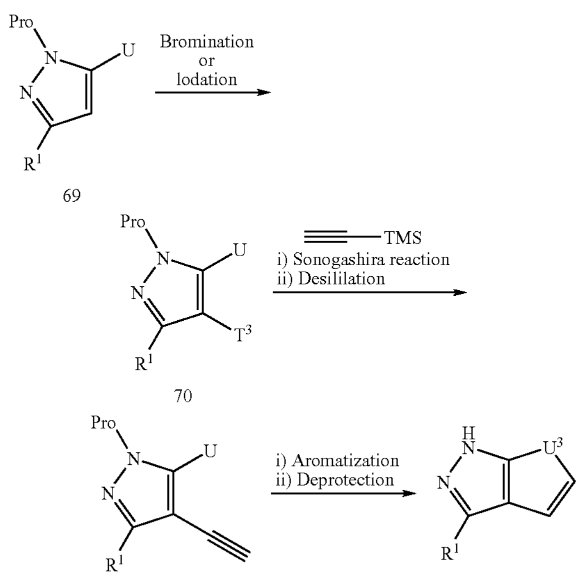

69 70 71 72

Compound 72 can be produced in the following manner: compound 69 which is easily in accordance with the known methods (U=hydroxyl group: for example, *J. Org. Chem.* 1992, 57 5680-5686., U=thiol group: for example, *J. Heterocycle. Chem.* 1990, 27 567., U=amino group: for example, *Synthesis* 1987, 1124.) is iodized or brominated at 4-position of pyrazole to obtain compound 70; trimethylsilyl acetylene is coupled to this compound 70 by Sonogashira coupling and detrimethylsilylation is conducted to obtain compound 71; and then compound 71 is aromatized and deprotected.

By halogenating 4-position of compound 69 in accordance with Production method 1, it is possible to produce compound 70. As the halogen atom to be substituted, iodine or bromine is preferred.

Trimethylsilyl acetylene used for Sonogashira coupling is commercially available one. The use amount of trimethylsilyl acetylene is from 1 to 3 equivalent (s) with respect to the material. Examples of catalyst to be used include, but are not limited to, palladium acetate (II), dichlorobistriphenyl phosphine palladium (II), tetrakis(triphenylphosphine)palladium (0) and the like. The use amount of catalyst is about 0.1% by mole with respect to the material. As is necessary, it is possible to add an equivalent or twice the catalyst amount of an additive, for example, copper iodide (I), triphenylphosphine and the like. Examples of the base to be used include, but are not limited to, triethylamine, diisopropylamine, piperidine and the like. As the solvent, any solvents can be used insofar as they do not inhibit the reaction, and preferred examples of such solvent include, but are not limited to, dimethylformamide, tetrahydrofuran, dioxane, diethyleneglycol dimethyl ether, toluene, xylene and the like. The reaction temperature is usually from room temperature to reflux temperature of the solvent.

Detrimethylsilylation can be readily achieved using fluorine anion or acid. As the fluorine anion, tetrabutylammonium fluoride, hydrogen fluoride, potassium fluoride, cesium fluoride and the like can be used. As the solvent, any solvents can be used insofar as they are not concerned with the reaction, and examples of such solvent include, but are not limited to, hydrocarbon halides such as dichloromethane or chloroform, alcohol solvents such as methanol or ethanol, as well as water, diethyl ether, tetrahydrofuran, dioxane, toluene and the like. The reaction temperature is from −20° C. to reflux temperature of the solvent. As the acid, hydrochloric acid, sulfuric acid, trifluoroacetic acid and the like are used. As the solvent, any solvents can be used insofar as they are not concerned with the reaction, and examples of such solvent include, but are not limited to, hydrocarbon halides such as dichloromethane or chloroform, alcohol solvents such as methanol or ethanol, diethyl ether, tetrahydrofuran and the like. The reaction temperature is −20° C. or reflux temperature of the solvent.

Aromatization is achieved in the similar condition as that of Sonogashira coupling.

In the case where U is a nitrogen atom, the nitrogen atom may be protected with a suitable protective group in the similar manner as is protection of 1-position, and finally protected. Protection and deprotection of 1-position of pyrazole and U are achieved in the manner as described in Production method 3.

Production method 32

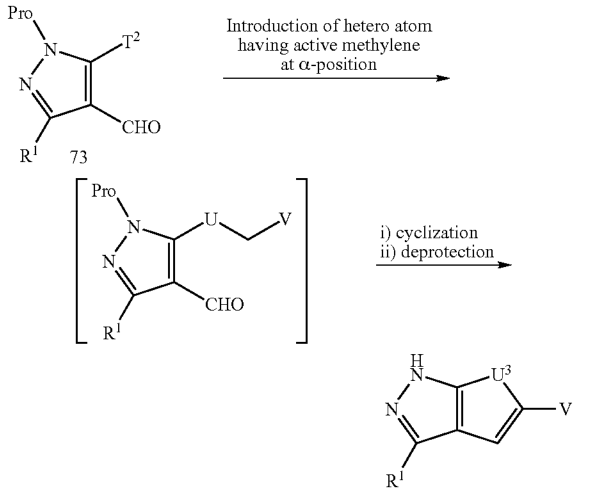

73 74

Compound 74, which already has a substituent introduced to $U^2$ of compound 72 before subjected to cyclization can be readily produced by introducing a hetero group having an active methylene at α-position into 5(3)-position of compound 73 which is readily synthesized in accordance with the known method (for example, *Synlett.* 2000, 8, 1115-1118.), followed by cyclization.

As a reagent for introducing a hetero atom having α active methylene into compound 73, t-butoxycarbonyl glycine, thioglycolic acid or its ester, thioglyconitrile, glycolic acid or its ester, glyconitrile and the like can be exemplified. Examples of the base to be used include, but are not limited to, sodium hydroxide, potassium hydroxide, sodium alkoxide, potassium alkoxide and the like. As the solvent, any solvents can be used insofar as they are not concerned with the reaction, and preferred examples of such solvent include, but are not limited to, alcohols such as methanol, ethanol, isopropanol or tert-butanol. The reaction temperature is from room temperature to reflux temperature of the solvent.

In the case where U is an amino group, the amino group may be protected with a suitable protective group in the similar manner as is protection of 1-position, and protected in the final step. Protection and deprotection of 1-position of pyrazole and U are achieved in the manner as described in Production method 3.

Production method 33

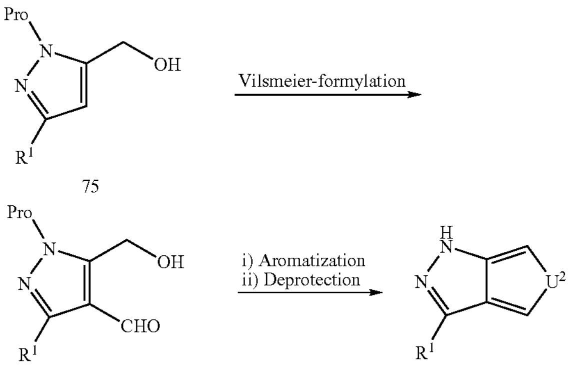

75 76 77

Compound 77 can be produced in the following manner: 4-position of pyrazole of compound 75 which is easily synthesized in the documentarily known method (for example, *J. Heterocycle. Chem.* 1982, 19, 117.) is formylated by Vilsmeier reaction to render compound 76; and then compound 76 is aromatized and deprotected.

Vilsmeier reaction is achieved by a methylene iminium compound formed of phosphorus oxychloride and formamide, and as the formamide, N,N-dimethylformamide is preferred. The use amount of phosphorus oxychloride is from 1 to 2 equivalent(s) with respect to a starting material, and the use amount of N,N-dimethylformamide is from 1 equivalent with respect to the material to solvent amount. As the solvent, any solvents can be used without particular limitation insofar as the are not concerned with the reaction, and no solvent or N,N-dimethylformamide used as the formamide is preferred. The reaction temperature is usually from 0° C. to reflux temperature of the solvent.

As the method for aromatization, a documentarily known method can be used. For example, Lewis acids such as boron trifluoride-diethyl ether complex is used for the case of furan ring (for example, *Synth. Commun.* 1999, 29, 729-747.), protonic acids such as trifluoroacetic acid or p-toluenesulfonic acid (for example, *J. Org. Chem.* 1998, 63, 2909-2917.) and the like can be used depending on the type of the hetero atom. In the case of a thiophene ring, the method of converting a hydroxyl group to a thiol group by means of Lawesson reagent (for example, *J. Org. Chem.* 1998, 63, 2909-2917.), the method of conducting ring-closing after bromination of hydroxyl group (for example, *J. Heterocycle. Chem.* 1998, 35, 71-75.) and the like can be used. Bromination of hydroxyl group can be achieved with phosphorous tribromide, 48% hydrobromic acid and the like. In the case of a pyrrole ring, a method of oxidizing hydroxyl group to aldehyde to obtain dialdehyde, and then closing the ring (for example, *Tetrahedron,* 1979, 35, 1433.), and the method of making the diol obtained by reduction of formyl group into a dibromide compound, and then closing the ring (for example, *Synthesis,* 1975, 252.) and the like can be used. Oxidation of hydroxyl group into aldehyde can be achieved using manganese dioxide or the like. Reduction of formyl group into alcohol can be achieved by sodium borohydride or the like, and dibromination of diol can be achieved by phosphorous tribromide, 48% hydrobromic acid and the like.

Protection and deprotection of 1-position of pyrazole can be achieved in the manner as described in Production method 3.

Production method 34

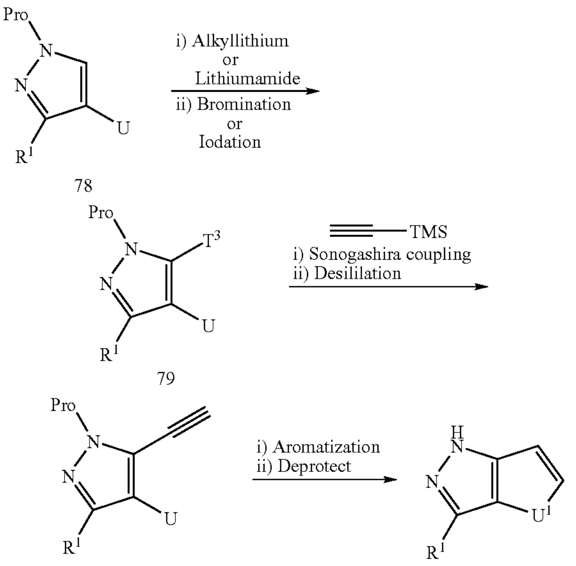

78 79 80 81

Compound 81 can be produced by using compound 78 readily synthesized in the known manner (U=hydroxyl group: for example, *J. Chem. SOC., Perkin Trans.*, 1985, 81., U=amino group: for example, *J. Am. Chem. Soc.* 1950, 72, 2978.) as a starting material. More specifically, 5(3) position of pyrazole of compound 78 is turned to a metal aryl by means of alkyl lithium, lithium amide or the like, followed by iodization or bromination to obtain compound 79, to which trimethylsilyl acetylene is coupled by Sonogashira coupling. Then detrimethylsilylation is conducted and the resultant compound 80 is aromatized and deprotected, whereby compound 81 is produced. In the case where U is a thiol group, after converting the amino group into diazonium using sodium nitrite ester or the like byway of the known method (*Org. Synth.* 1955, III, 809.) or the like, the resultant compound is treated with potassium O-ethyl dithiocarbonate or the like, whereby compound 81 is produced. Alternatively, compound 81 may be produced using a known method (*J. Heterocycle. Chem.* 1991, 28, 41.) or the like, by introducing a thiol group after halogenating 4-position of pyrazole with N-iodosuccinimide, N-bromosuccinimide or the like.

Conversion of compound 78 into a metal aryl and subsequent iodization or bromination are conducted in accordance with Production method 1, and conversion from compound 79 to compound 80, that is, Sonogashira coupling and subsequent detrimethylsilylation are conducted in accordance with Production method 31. Also, protection and deprotection of 1-position of pyrazole are achieved in the manner described in Production method 3.

In the general synthesis methods exemplified in Production method 35 to Production method 44 below, $R^1$ has the same meaning as the formula —$(CO)_h$—$(NR^a)_j$—$(CR^b{=}CR^c)_k$—Ar in the general formula (I). These general synthesis methods are given as detailed description for conversion of $R^1$ moiety, and the present invention is not limited to the exemplified Production methods. Therefore, a process of introduction and conversion of V may be included in any reaction route, and protecting apyrazole ring in a desired production, step will not influence on the process.

Protection method 35

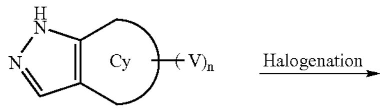

82

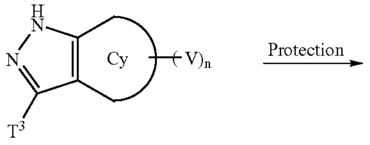

83

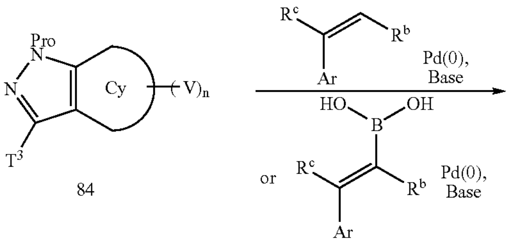

84

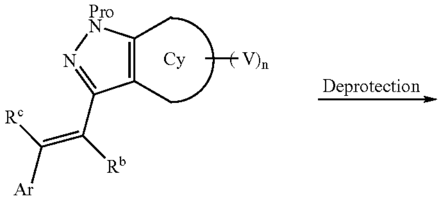

85

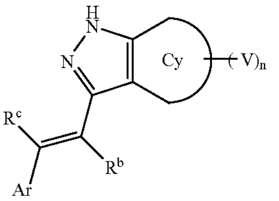

(I)-a

The compound (I)-a represented by (h=j=0, k=1) in the general formula (I) can be produced after converting compound 82 into compound 84 by halogenating 3-position of compound 82 while protecting 1-position, compound 85 is obtained by Heck reaction or Suzuki reaction, followed by deprotection.

3-position of compound 82 is halogenated in the manner as described in Production method 3, whereby compound 83 is obtained. As a protective group for 1-position of pyrazole in compound 83, tert-butoxycarbonyl group, trityl group and the like are preferred without limitation, and compound 83 can be led to compound 84 in accordance with Production method 3.

By conducting Heck reaction or Suzuki coupling on compound 84 in the manner as described in Production method 3, it is possible to produce compound 85.

Deprotection of compound 85 readily proceeds by acid treatment in accordance with Production method 3, whereby compound (I)-a is produced.

Production method 36

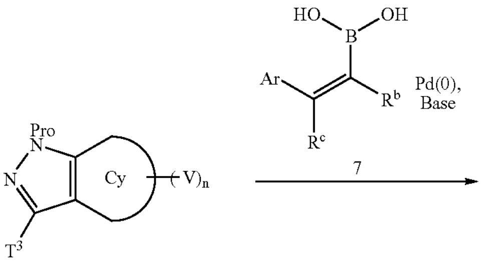

84

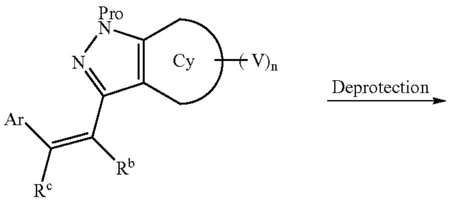

86

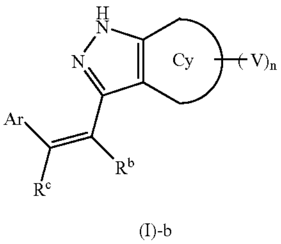

(I)-b

Compound (I)-b wherein positional relationship between Ar and pyrazole is “cis” which is different from (I)-a can be produced by using a boronic acid which corresponds to a position isomer different from the boronic acid used in Production method 35. Starting from compound 84 and through compound 86, (I)-b can be produced in the similar manner as described in Production method 35.

Production method 37

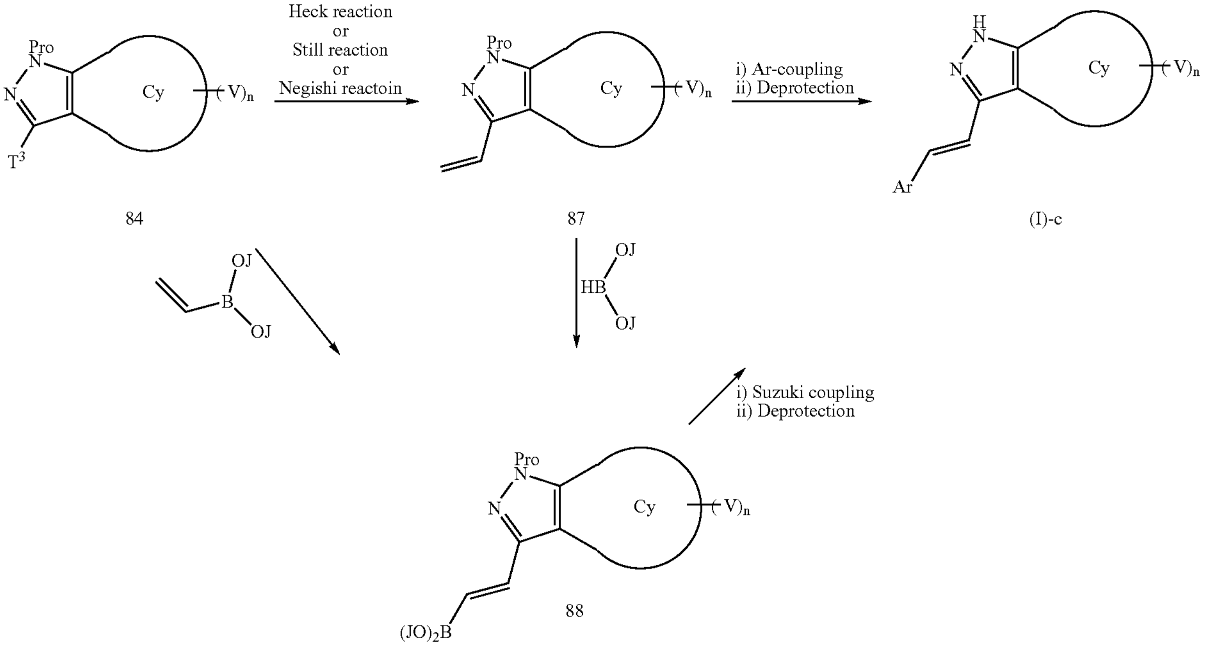

84 87 (I)-c 88

With regard to (I)-c represented by (h=j=0, k=1, $R^b$=$R^c$=H) in the general formula (I), it is possible to construct the $R^1$ moiety stepwise in the methods described in Production methods 35 and 36. That is, after introducing a vinyl unit and a vinylboronic acid unit into compound 84, aromatic ring coupling and deprotection are conducted in accordance with the Production method 3, whereby II)-c is produced.

Introduction of a vinyl group into compound 84 can be achieved, for example, by Stille reaction, Negishi reaction or Heck reaction. As avinylation reagent, commercially available reagent is purchased and commercially unavailable reagents are prepared in a commonly used method. As the reaction reagent, vinyl trialkyl tin for Stille reaction, vinyl zinc halide for Negishi reaction, and ethylene gas for Heck reaction can be used. As a reagent other than the above, vinyltrialkoxysilane, vinyltrialkylsilane and the like can be exemplified.

Production of compound 88 into which vinyl boronic acid or vinylboronic acid ester unit is introduced can be achieved, for example, by Heck reaction with respect to compound 84. As the reaction reagent, vinylboronic acid pinacol ester or the like is exemplified without limitation.

With respect to compound 87, an aromatic ring can be introduced by Suzuki coupling with aryl boronic acid, Heck reaction with aryl halide, and Stille reaction with aryltrialkyl tin. With respect to compound 88, an aromatic ring can be introduced by Suzuki coupling with aryl halide.

As a Pd catalyst used in these coupling reactions, for example, tris(dibenzylideneacetone)dipalladium (0), reagents described in Production method 3 and the like are used without limitation, and a suitable phosphine ligand as described in Production method 3 may coexist. The condition for coupling reaction is achieved in accordance with Production method 3.

Furthermore, production of compound 88 into which vinylboronic acid unit is introduced can be achieved also by addition reaction of borane with respect to compound 87 in the presence of a rhodium or iridium catalyst. Examples of such reagent include, but are not limited to, chloro(1,5-cyclooctadiene) rhodium (I) dimer and pinacol borane.

Production method 38

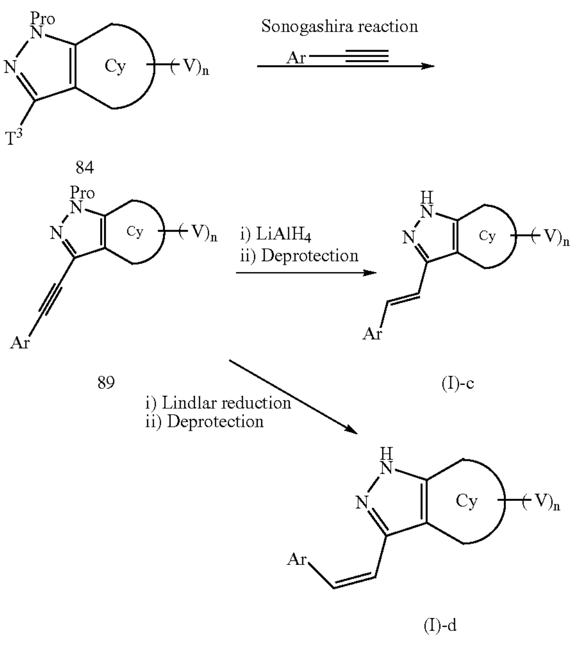

84 89 (I)-c (I)-d (I)-c and (I)-d represented by (h=j=0, k=1,$R^b$=$R^c$=H) in the general formula (I) can be produced by converting compound 84 into alkynyl compound 89 by Sonogashira reaction, and reducing compound 89 to olefin.

The acetylene derivative used for Sonogashira reaction is readily prepared by conducting Sonogashira reaction using commercially available aryl halide and trimethylsilyl acetylene, and removing the trimethylsilyl group by an acid. It is possible to produce compound 89 from compound 84 in the manner as described in Production method 31.

In reduction from alkyne compound 89 to olefin, it is possible to control the generation ratio of position isomers by selecting a variety of reducing agents. As is exemplified in Production method 38, by reducing compound 89 using lithium aluminum hydride, Lindlar catalyst and the like under different conditions, it is possible to obtain trans (I)-c and cis (I)-d olefins as main products in the respective conditions. By deprotection in accordance with Production method 3, (I)-c and (I)-d can be obtained.

Production method 39

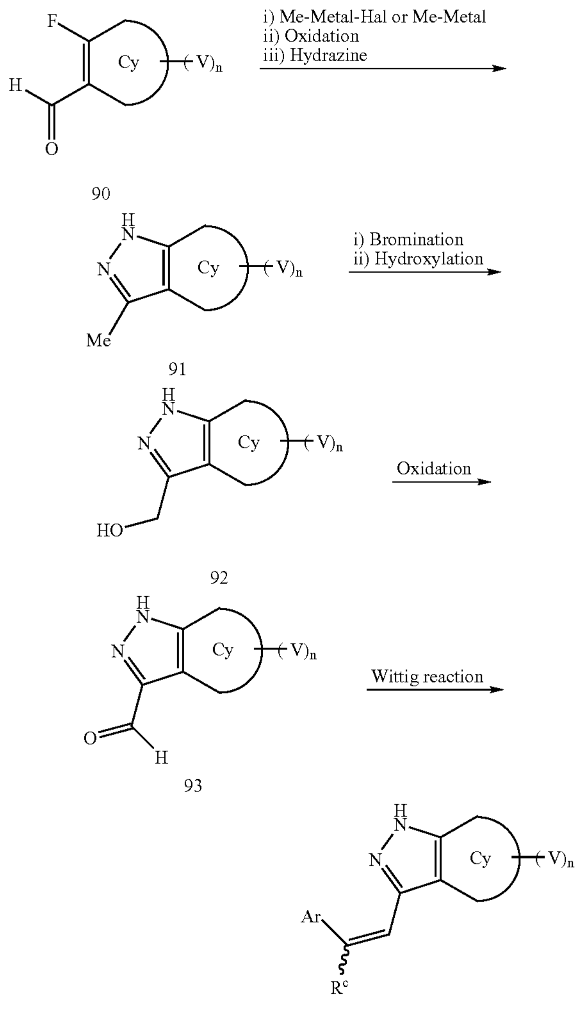

90

91

92

93

(I)-e (I)-e represented by (h=j=0, k=1, $R^b$=H) in the general formula (I) can be produced by converting aldehyde 90 into pyrazole 91, then converting a methyl group at 3-position into a methyl alcohol and then into a formyl group, and then conducting Wittig reaction. Conversion of aldehyde 90 to pyrazole 91 can be achieved, for example, by causing methyl metal such as methyl lithium or methyl magnesium to act on aldehyde 90, oxidizing the resultant alcohol in accordance with Production method 1, and then causing hydrazine to act.

Conversion from compound 91 to compound 92 can be achieved, for example, by introduction of a halogen, followed by hydrolysis by treatment with a base. Introduction of halogen can be conducted in the similar manner as described in Production method 3, and as is necessary, pyrazole may be protected. Conversion of halogen compound to alcohol 92 maybe direct conversion using, for example, sodium hydroxide, potassium hydroxide and the like, however, it is also possible to obtain compound 92 by first converting into an acetate by action of sodium acetate, potassium acetate or the like, and then hydrolyzing the acetate sodium hydroxide, potassium hydroxide or the like. Also, it is possible to produce compound 93 by oxidizing the methyl group at 3-position of pyrazole of compound 91 with a suitable oxidizing reagent to an aldehyde.

Oxidation from alcohol compound 92 to aldehyde 93 can be conducted in accordance with Production method 1. Wittig reaction of compound 93 can be achieved by reaction between compound 93 and phosphonium ylide. The phosphonium ylide can be readily synthesized by letting a commercially available alkyl halide or the like react with triphenylphosphine in an ether solvent to render a phosphonium salt, which is then treated with a base such as sodium hydride, sodium hydroxide, potassium carbonate or metal alkoxide. As the reaction solvent for Wittig reaction of compound 93, for example, ether solvents such as diethyl ether or tetrahydrofuran, hydrocarbon halides such as dichloromethane or chloroform, hydrocarbon solvents such as benzene or toluene, alcohol solvents such as methanol, as well as N,N-dimethylformamide and the like are used. The use amount of the base is usually from 1 to 3 equivalent(s) with respect to the material. The reaction temperature is from 0° C. to reflux temperature of the solvent.

Production method 40

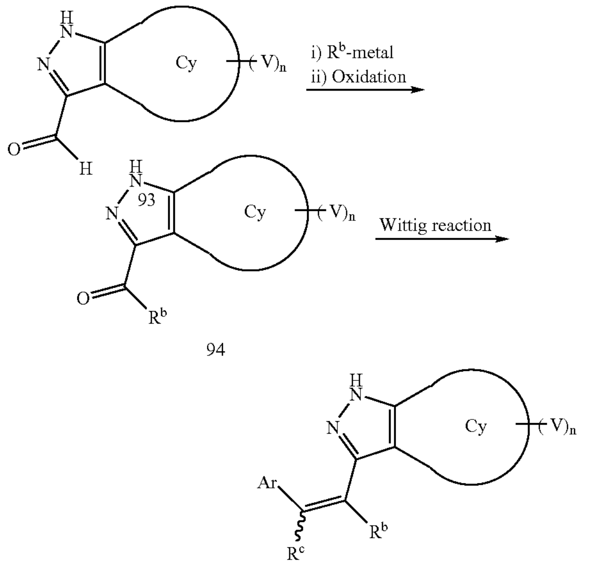

93

94

(I)-f

Compound (I)-f represented by (h=j=0, k=1) in the general formula (I) is obtained by letting a metal reagent such as alkyl lithium or aryl lithium act on aldehyde 93 to convert it an alcohol, oxidizing the resultant alcohol to ketone 94 in accordance with Production method 1, and then subjecting the ketone 94 to Wittig reaction in the similar manner as described in Production method 39.

Production method 41

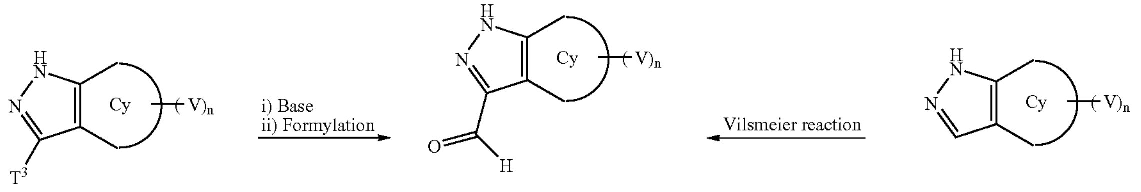

83 93 82

Compound 93 which is a starting material for synthesis in Production method 39, Production method 40 or the like can be produced, for example, by lithionating 1-position of halogen compound 83 with N-butyllithium or phenyl lithium, lithionating a halogen at 3-position with sec-butyllithium or tert-butyllithium, and then letting the resultant compound react with N,N-dimethylformamide, N-formylpiperidine, methylphenylformamide or the like. The amount of N-butyllithium or phenyl lithium is from 1 to 2 equivalent(s) with respect to the material. The amount of sec-butyllithium or tert-butyllithium is from 1 to 2 equivalent(s) with respect to the material. The amount of formylation reagent such as N,N-dimethylformamide is from 1 to 5 equivalent(s) with respect to the material. The reaction solvent is preferably ether solvents such as diethyl ether or tetrahydrofuran. The reaction temperature is from −78° C. to room temperature. The reaction may be conducted after protecting pyrazole in the similar manner as described in Production method 1 as is necessary. In this case, the use amount of lithionating reagent is from theoretical amount to 2 equivalent(s).

Formyl compound 93 may be produced by subjecting compound 82 to Vilsmeier reaction in the similar manner as described in Production method 33.

Production method 42

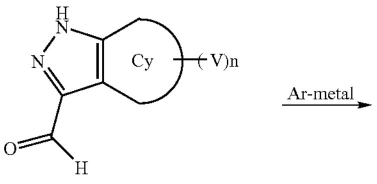

93

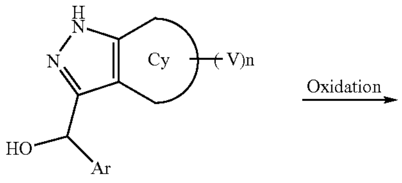

95

-continued

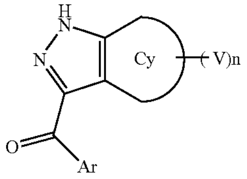

(I)-g

Compound (I)-g represented by (h=1,j=k=0) in the above general formula (I) can be produced by letting compound 93 and metal aryl or metal halogenoaryl react in accordance with Production method 1 to make alcohol 95, and oxidizing the alcohol to ketone in accordance with Production method 1.

Compound (I)-g may also be produced by introducing a suitable protective group to 1-position of compound 93, executing the above Production method, and the conducting deprotection.

Production method 43

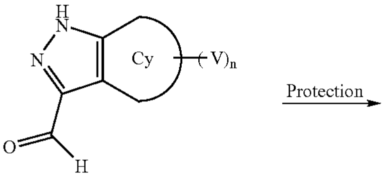

93

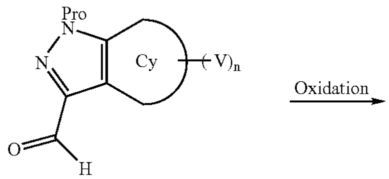

96

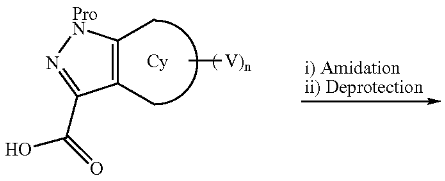

97

-continued

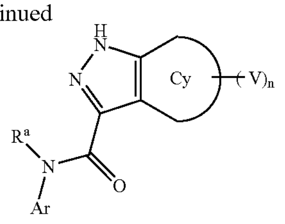

(I)-h

Compound (I)-h represented by (h=j=1, k=0) in the above general formula (I) can be produced by protecting 1-position of compound 93, oxidizing formyl group to convert into carboxylic acid 97, and then successively conducting amidation and deprotection.

Introduction of protective group into 1-position of compound 93 can be conducted in accordance with Production method 3. As the oxidizing reagent for oxidizing compound 96 into carboxylic acid 97, Jones reagent, pyridinium dichromate, sodium chlorite can be exemplified. As the solvent, any solvents can be used insofar as they are not concerned with the reaction, and examples of such solvent include hydrocarbon halides such as dichloromethane or chloroform, as well as ethyl acetate, N,N-dimethylformamide, dimethyl sulfoxide and the like. The reaction temperature is from 0° C. to reflux temperature of the solvent.

Amidation of carboxylic acid 97 can be achieved in accordance with Production method 47. Also amidation of carboxylic acid 97 can be achieved by converting carboxylic acid 97 into an acid chloride using thionyl chloride, oxalyl chloride and the like, and then subjecting the acid chloride to Schotten-Baumann reaction with an amine in the presence of a base such as triethylamine, diisopropylethylamine, pyridine and the like.

The protective group at 1-position is deprotected in accordance with Production method 3, whereby (I)-h is produced.

Production method 44

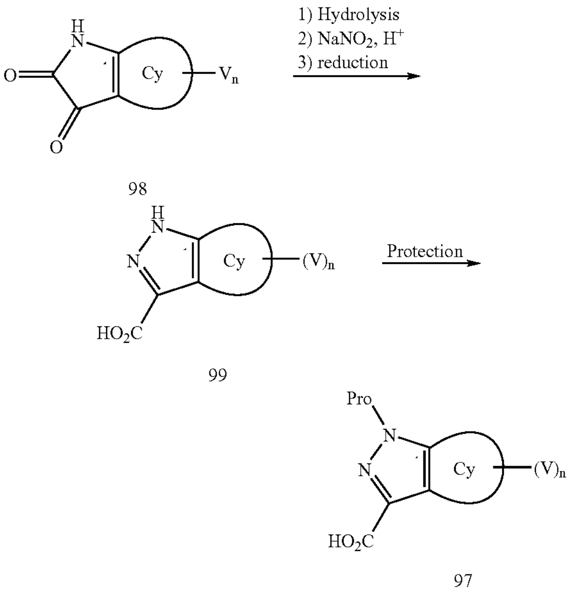

98

99

97

Carboxylic acid 97 produced in Production method 43 can also be produced by hydrolyzing compound 98, and introducing a protective group at 1-postion after diazotization and reduction.

For hydrolysis of compound 98, for example, an aqueous solution of sodium hydroxide, an aqueous solution of potassium hydroxide and the like is used. The reaction for converting into diazonium salt is achieved by reaction with a nitrite ester such as sodium nitrite ester or isoamyl nitrite ester in the presence of an acid. As the reaction solvent, for example, alcohol solvents such as methanol or ethanol, water and the like are used, and as the acid, hydrochloric acid, sulfuric acid, acetic acid and the like are can be used. The reaction temperature is usually around 0° C.

Reduction of diazonium salt and subsequent ring-closing of the indazole ring can be achieved by action of a reducing reagent, such as tin chloride (II) or copper chloride (II), for example in the presence of an acid, and the use amount of these reagent is usually from 1 to 10 equivalent(s) with respect to the material. In general, the ring-closing occurs spontaneously in the reaction system accompanied with dehydration, and thereby compound 99 is obtained. As the reaction solvent, for example, alcohol solvents such as methanol or ethanol, as well as hydrochloric acid, sulfuric acid, acetic acid and the like can be used. The reaction temperature is usually from 0° C. to reflux temperature of the solvent.

Introduction of protective group into 1-position of compound 99 can be achieved in accordance with Production method 3. Also compound 97 can be produced by hydrolysis of ester under a usual condition after converting a carboxylic acid into an ester in a usually-used condition, and introducing a protective group into 1-position as is necessary.

The following production methods are concrete description for typical functional group conversion after formation of condensed pyrazole rings represented by the general formulae (I) (II) and (III). It is to be noted that following production methods may also be employed in production steps before formation of pyrazole ring rather than after formation of condensed pyrazole ring, and commercially available starting materials and intermediates originally having suitable functional groups may be used. Diversity of functional groups to be introduced is not limited to the methods exemplified in Production methods.

Production method 45

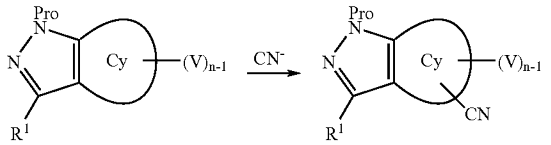

100

101

In general, aryl halide can be converted into a cyano group by means of a cyanizing reagent. As the halogen atom $T^3$, a chlorine atom, bromine atom and iodine atom are recited, with a bromine atom or iodine atom being desired. In the case where the substitution position of halogen atom corresponds to ortho-position or para-position of a nitrogen atom forming the aromatic ring, the halogen may be a chlorine atom. Although a protective group for pyrazole ring is sometimes unnecessary, it is usually preferable to have a protective group. As the cyanization reagent to act on compound 100, zinc cyanide, lithium cyanide, sodium cyanide, potassium cyanide and the like are exemplified, and the cyanization is achieved by using a transition metal catalyst such as tetrakis (triphenylphosphine) palladium, tris(dibenzylideneacetone) dipalladium, dichlorobis(triphenylphosphine)palladium, palladium diacetate and the like, and adding a catalyst amount of a copper iodide or a phosphine ligand such triphenylphosphine and 1,1'-bis(diphenylphosphino) ferrocene as is necessary for promoting the reaction. As the solvent to be used, dimethylformamide, N-methylpyrrolidone, propionnitrile, acetonitrile and the like are preferred. The reaction temperature is preferably in the range from 80° C. to 150° C. Furthermore, nitrile 101 may also be produced by letting copper cyanide and compound 100 react in a solvent such as dimethylformamide or N-methylpyrrolidone at a temperature ranging from 140° C. to 200° C.

Production method 46

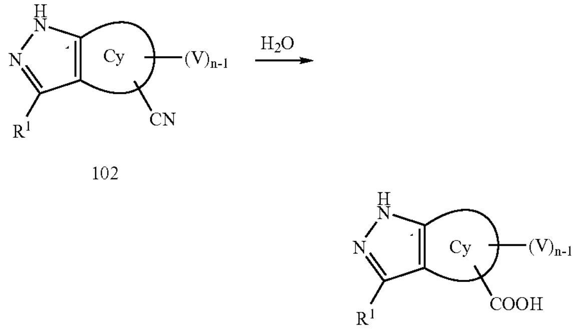

102

103

Hydrolysis of nitrile of compound 102 which is readily produced by deprotection of compound 101 or the like can be achieved by using an acid or alkaline. As the acid, hydrochloric acid, hydrous sulfuric acid and the like can be recited. Although the reaction may be conducted in the absence of solvent, when a solvent is used, for example, methanol, ethanol, propanol and the like alcohol solvents, as well as acetic acid and the like can be used. The reaction temperature is usually from room temperature to reflux temperature of the solvent. As the alkaline, for example, sodium hydroxide, potassium hydroxide and the like can be used. As the solvent, the reaction may be conducted just in alkaline water, however, when a solvent is used, for example, methanol, ethanol, propanol and the like alcohol solvents, dioxane and the like can be used. The reaction temperature is usually from room temperature to reflux temperature of the solvent. In this production method, when compound 101 having tert-butoxycarbonyl group, trityl group or the like, for example, as a protective group at 1-position is subjected to the similar hydrolysis condition, deprotection generally occurs to generate 103.

Production method 47

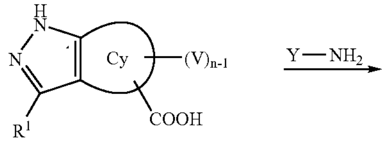

103

-continued

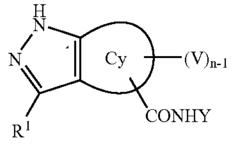

104

Amidation of carboxylic acid 103 can be achieved by mixing amine and a condensing reagent. As the condensing reagent, for example, dicyclohexylcarbodiimide, diisopropylcarbodiimide, 1-ethyl-3-(3-dimethylaminopropyl)carbodiimide, 1-ethyl-3-(3-dimethylaminopropyl)carbodiimide hydrochloride and the like can be used. As is necessary, 1-hydroxybenzotriazole, N-hydroxysuccinimide and the like may be added. As the solvent, any solvents can be used insofar as they are not concerned with the reaction, and examples of such solvent include halogen solvents such as dichloromethane or chloroform, ether solvents such as ether or tetrahydrofuran, as well as ethyl acetate, N,N-dimethylformamide, N-methylpyrrolidone, toluene and the like. The reaction temperature is usually from 0° C. to reflux temperature of the solvent.

Compound 104 may be produced by introducing a suitable protective group into 1-position of compound 103, executing the above Production method, and then conducting deprotection.

Production method 48

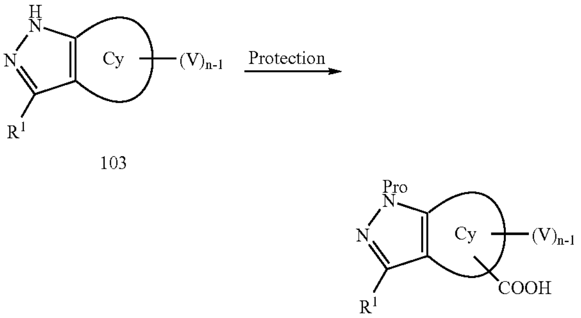

103

105

For converting a carboxyl group of compound 103 into other functional groups such as amino group, for example, by Curtius rearrangement, it is preferred to introduce a protective group into the pyrazole ring as shown in Production method 48 as is necessary, thereby converting into compound 105. A variety of protective groups described in the Production method 3 can be used, and a trityl group or the like is preferred. Any bases can be used as the base, and sodium hydride or the like is preferred. The use amount is from 2 to 3 equivalents. As the reagent, tritylchloride is preferably used in the amount of from 1 to 2 equivalent (s). As the solvent, any solvents can be used insofar as they are not concerned with the reaction, and preferred examples of such solvent include, but are not limited to, ether solvents such as tetrahydrofuran or dioxane, N,N-dimethylformamide and the like. The reaction temperature is usually ice-cooled temperature to reflux temperature of the solvent.

Production method 49

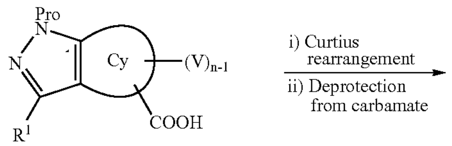

105

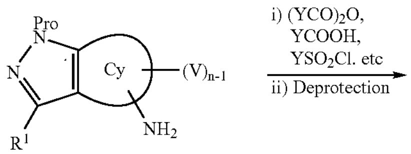

106

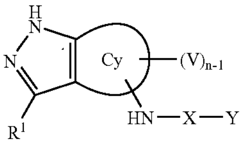

107

After converting a carboxyl group of condensed pyrazole ring compound 105 into a carbamate by Curtius rearrangement, the carbamate is removed, to thereby obtain compound 106. Curtius rearrangement of compound 105 can be achieved, for example, by making an isocyanate using diphenylphosphorylazide and an amine such as triethylamine or diisopropylethylamine, and letting the resultant isocyanate react with an alcohol; or making an acid chloride using thionyl chloride, oxalyl chloride or the like, converting the resultant acid chloride into an isocyanate using lithium azide, sodium azide, potassium azide and the like, and letting the resultant isocyanate react with an alcohol. Preferred examples of the alcohol include, but are not limited to, benzyl alcohol or tert-butanol. As the solvent, any solvents can be used insofar as they are not concerned with the reaction, and examples of which include, but are not limited to, toluene, benzene, tetrahydrofuran, dioxane and the like. Alternatively, the reaction may be conducted using a solvent amount of an alcohol such as tert-butanol. Usually the reaction temperature is from room temperature to reflux temperature of the solvent. Deprotection of carbamate, for example, deprotection of tert-butoxycarbonyl group is readily achieved by means of acid in accordance with Production method 3. Deprotection of benzyloxycarbonyl group is readily achieved by hydrogen addition.

Amidation of amine 106 can be achieved by mixing a carboxylic acid and a condensing reagent. The condensation condition is as described in Production method 47.

In the case where compound 106 is a nitrogen-containing aromatic amine, specifically, amidation of compound 22 or the like can be achieved by the method using the condensing reagent as described above, and preferably by a method of letting acid chloride or acid anhydride react in the presence of a base. Examples of the base include, but are not limited to, triethylamine, diisopropylethylamine, pyridine and the like. As the solvent, any solvent can be used insofar as they are not concerned with the reaction, and examples of such solvent include halogen solvents such as dichloromethane or chloroform, ether solvents such as ether or tetrahydrofuran, as well as ethyl acetate, toluene and the like. The reaction temperature is usually from −78° C. to reflux temperature of the solvent. For amidation of nitrogen-containing aromatic amine, dehydration condensation using triphenylphosphine and bromotrichloromethane is also possible.

Production method 50

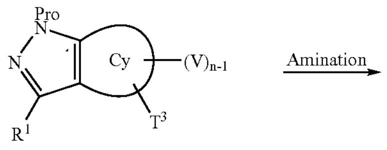

100

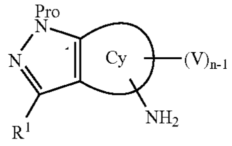

106

In general, aryl halide can be converted into an amino group by coupling reaction using a palladium catalyst. As the halogen atom $T^3$ in compound 100, bromine atom and iodine atom are represented, with bromine or iodine atom having high reactivity being preferred. Also in an aromatic ring wherein substitution position of halogen atom is ortho-position or para-position of the nitrogen atom constituting the ring, $T^3$ may be a chlorine atom. Furthermore, the protective group of pyrazole ring is sometimes unnecessary, however, it is usually preferred to have a protective group.

As a palladium catalyst used for amination of compound 100, for example, tris(dibenzylideneacetone)dipalladium, palladium diacetate and the like are used, as the phosphine ligand, 2,2'-bis(diphenylphosphino)-1,1'-naphthyl, 1,1'-bis (diphenylphosphino) ferrocene, tri(tert-butyl)phosphine and the like are used, and as the base, sodium tert-butoxide, potassium tert-butoxide, cesium carbonate and the like are used. As an ammonia equivalent, benzophenoneimine is preferred without limitation. As the acid used for hydrolysis of the resultant imine compound, diluted hydrochloric acid, diluted sulfuric acid and the like can be used without limitation. As the solvent, any solvents can be used insofar as they are not concerned with the reaction, and examples of such solvent include, but are not limited to, toluene, tetrahydrofuran, dioxane, dimethoxyethane and the like. Usually the reaction temperature is from room temperature to 120° C. As a result of this, it is possible to produce amine 106.

Production method 51

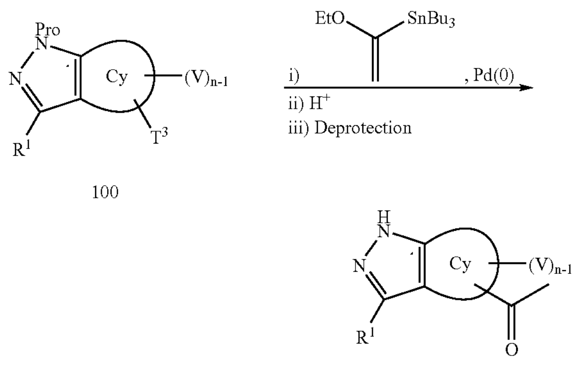

100

108

In general, it is possible to readily introduce a variety of functional groups into aryl halide by coupling using Pd(0) For example, as exemplified in Production method 51, it is possible to introduce an acyl group by coupling, to thereby obtain corresponding acyl compound 108. As the halogen atom $T^3$, chlorine atom, bromine atom and iodine atom are recited, with bromine or iodine atom being desired. Furthermore, in an aromatic ring wherein substitution position of halogen atom is ortho-position or para-position of the nitrogen atom constituting the ring, $T^3$ may be a chlorine atom. Furthermore, the protective group of pyrazole ring is sometimes unnecessary, however, it is usually preferred to have a protective group. As the method for introducing an acetyl group, Stille coupling using tributyl(1-ethoxyvinyl)tin can be recited. As the tin reagent, commercially available one was purchased. The use amount of tributyl(1-ethoxyvinyl)tin is from 1 to 3 equivalent (s) with respect to the material. As the catalyst to be used, for example, tetrakis(triphenylphosphine)palladium (0) and the like is preferred without limitation. The use amount of catalyst is about 5% by mole with respect to the material. As the solvent, any solvents can be used insofar as they do not inhibit the reaction, and examples of such solvent include, but are not limited to, tetrahydrofuran, dioxane, N,N-dimethylformamide, diethyleneglycol dimethyl ether, toluene, xylene and the like. The reaction temperature is usually from room temperature to reflux temperature of the solvent. The vinyl ether which is obtainable as an intermediate is readily hydrolyzed with acid, to be led to a ketone. As such an acid, diluted hydrochloric acid or the like is preferred without limitation. Depending on the condition, deprotection may be conducted as exemplified in Production method. It is also possible that N-bromosuccinimide is caused to act instead of the acid to be acted on vinyl ether, thereby introducing a bromomethylketone unit.

Production method 52

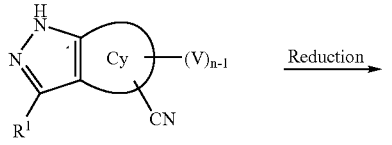

102

-continued

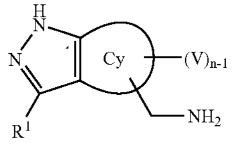

109

As another way to conversion with respect to substituent V, for example, as exemplified in Production method 52, a cyano group of compound 102 may be reduced so as to convert to aralkyl amine 109. Although a protective group is not particularly required, the reaction may be conducted for compounds having protective groups introduced therein.

As the reducing reagent of cyano group, for example, sodium borohydride, lithium aluminum hydride, aluminum hydride and the like are recited. As is necessary, additives such as aluminum trichloride, boron trifluoride, cobalt chloride, Raney nickel and the like may be added. As the solvent, any solvents can be used insofar as they are not concerned with the reaction, and examples of such solvent include, but are not limited to, alcohol solvents such as methanol or ethanol, ether solvents such as diethyl ether, tetrahydrofuran, dioxane, dimethoxyethane and the like. The reaction temperature is usually from −78° C. to reflux temperature of the solvent.

Production method 53

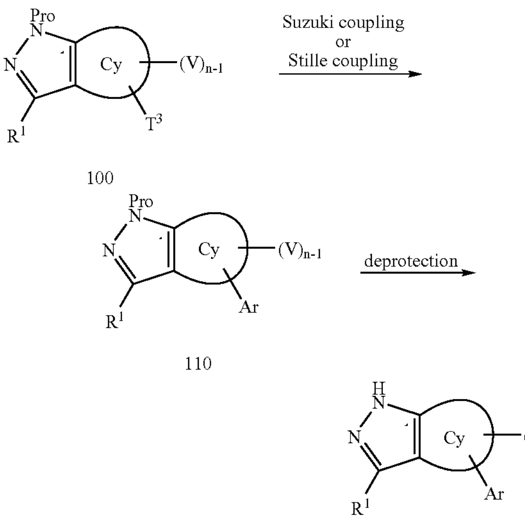

100

110

111

Compound 111 can be produced by subjecting compound 100 to Suzuki coupling or Stille coupling, followed by deprotection. Furthermore, although the protective group of pyrazole ring is sometimes unnecessary, it is usually preferred to have a protective group.

The aryl bronic acid used for Suzuki coupling or aryl trialkyl tin used for Stille coupling is commercially available, or readily prepared in accordance with Production method 3 if not commercially available. The use amount of aryl boronic acid used for coupling reaction, or aryl trialkyl tin is from 1 to 3 equivalent(s) with respect to the material. As the solvent to be used, for example, palladium acetate (II), dichlorobistriphenyl phosphine palladium (II), tetrakis(triphenylphosphine) palladium(0) and the like can be exemplified. The use amount of catalyst is about 5% by mole with respect to the material. As is necessary, twice as much as catalyst by mole of phosphine ligand, for example, tri-tert-butylphosphine, 2-(di-tert-butylphosphino)biphenyl, 2-(dicyclohexylphosphino)biphenyl, triphenyl phosphine and the like may be added. As the base to be used, sodium hydrogen carbonate, sodium carbonate, potassium carbonate, cesium carbonate, potassium fluoride and the like can be recited. As the solvent, any solvents can be used insofar as they do not inhibit the reaction, and examples of such solvent include, but are not limited to, N,N-dimethylformamide, N-methylpyrrolidone, tetrahydrofuran, dioxane, diethyleneglycol dimethyl ether, toluene and the like. The reaction temperature is usually from room temperature to reflux temperature of the solvent.

Deprotection of compound 110 is conducted in accordance with Production method 3.

Production method 54

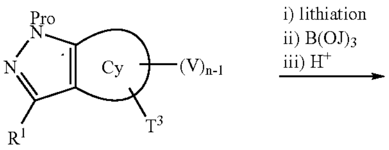

100

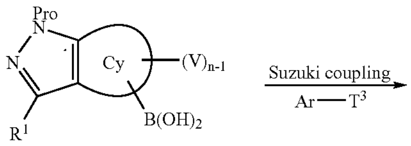

112

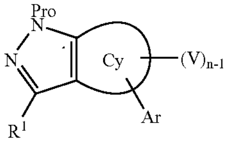

110

Compound 110 obtained by Production method 53 can also be produced by converting compound 100 into a boronic acid, and conducting Suzuki coupling.

Boronic acid 112 can be obtained by converting compound 100 into aryl lithium, letting the aryl lithium react with trialkyl borate to lead a borate ester, and then hydrolyzing the borate ester. As the alkyl lithium for converting compound 100 into aryl lithium, for example, N-butyllithium, sec-butyllithium, tert-butyllithium, phenyl lithium and the like are used, and additives such as N,N,N',N'-tetramethylethylenediamine or hexamethylphosphoramide may be added as necessary. Hydrolysis after making borate ester by letting aryl lithium and trialkyl borate react with each other may be achieved by adding water or using an acid such as hydrochloric acid of sulfuric acid. As the solvent, any solvents can be used insofar as they are not concerned with the reaction, and preferred examples of such solvent include, but are not limited to, diethyl ether, tetrahydrofuran, dioxane, dimethoxyethane and the like ether solvents. The reaction temperature is from −78° C. to room temperature.

Compound 110 can be produced by coupling boronic acid 112 and aryl halide or aryl sulfonates by Suzuki coupling in accordance with Production method 53.

Production method 55

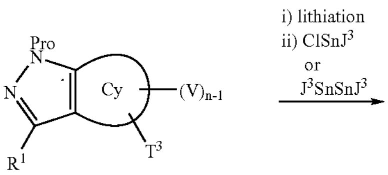

100

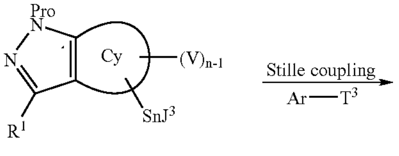

113

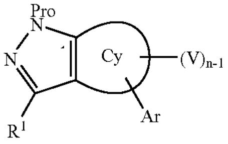

110

Compound 110 obtained by Production method 53 may be produced by converting compound 100 into tin compound 113, and then conducting Stille coupling.

Tin compound 113 can be produced by converting compound 100 into aryl lithium in accordance with Production method 54, and then letting the aryl lithium react with chlorotrialkyl tin or hexaalkyl ditin.

Compound 110 can be produced by Stille coupling between tin compound 113 and aryl halide or aryl sulfonates in accordance with Production method 53.

Production method 56

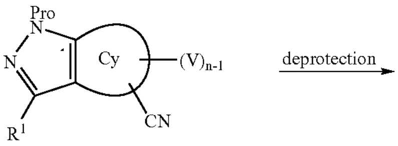

101

-continued

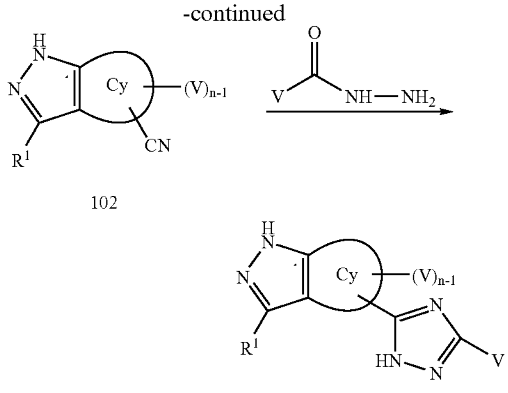

102

114

Compound 114 can be produced by letting compound 101 produced in Production method 45 to react with hydrazide after deprotecting the same.

Deprotection of compound 101 is conducted in accordance with Production method 3.

The hydrazide used for the reaction with compound 102 is purchased if commercially available, or can be readily prepared if not commercially available. Compound 102 can also be produced by amide condensing a carboxylic acid and a mono-protected hydrazine, and then conducting deprotection. As the reaction solvent, any solvents can be used insofar as they are not concerned with the reaction, and examples of such solvent include, but are not limited to, ethanol, toluene, xylene, dimethylformamide, N-methylpyrrolidone, diphenyl ether and the like. The reaction temperature is usually from room temperature to reflux temperature of the solvent.

Production method 57

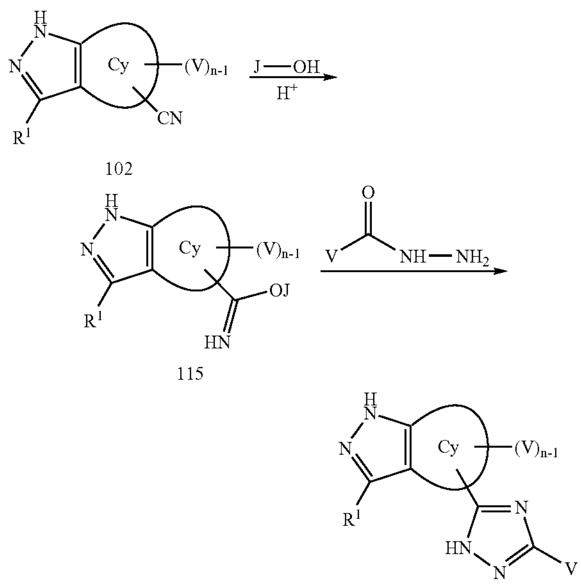

102

115

114 compound 114 produced by Production method 56 can also be produced by converting compound 102 into an imidate, then reacting the imidate with hydrazide.

As the acid used for converting compound 102 into imidate 115, hydrogen chloride, hydrogen bromide, sulfuric acid and the like can be exemplified. As the alcohol, methanol, ethanol and the like are preferred without limitation. As the solvent, any solvents can be used without limitation insofar as they are not concerned with the reaction, and dichloromethane, 1,4-dioxane, diethyl ether, toluene or the like is used, or alternatively the alcohol to be reacted may be used as a solvent. The reaction temperature is usually from room temperature to reflux temperature of the solvent.

From compound 115 and hydrazide, it is possible to produce compound 114. A base may be added if necessary. As the base to be used, triethylamine, diisopropylethylamine, potassium carbonate and the like can be recited. As the solvent, any solvents can be used insofar as they are not concerned with the reaction, and preferred examples of such solvent include, but are not limited to, methanol, ethanol, tetrahydrofuran, toluene, 1,4-dioxane, dimethylformamide and the like. The reaction temperature is usually from room temperature to reflux temperature of the solvent.

Production method 58

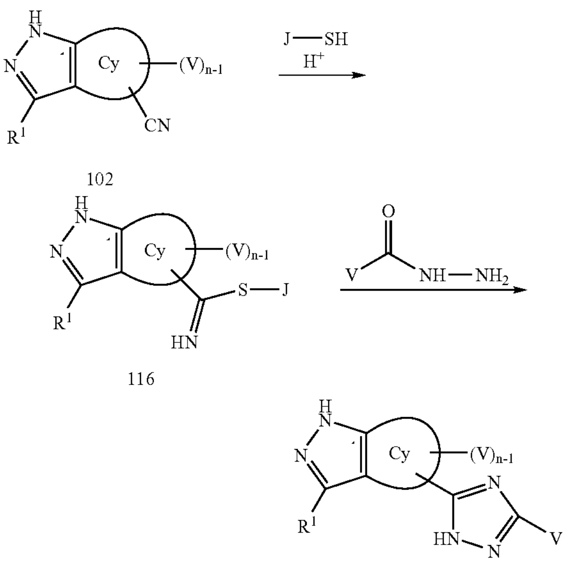

102

116

114

Compound 114 produced by Production method 56 can also be produced by converting compound 102 into a thioimidate and then letting the thioimidate react with hydrazide.

Thioimidate 116 can be produced by adding a thiol to compound 102 in the presence of an acid catalyst. As the acid to be used, hydrogen chloride, hydrogen bromide, sulfuric acid and the like can be recited. As the thiol to be used, for example, ethanethiol, propanethiol, thiophenol and the like can be recited without limitation. As the solvent, any solvents can be used insofar as they are not concerned with the reaction, and examples of such solvent include, but are not limited to, ethanol, dichloromethane, toluene, diethyl ether, dioxane, dimethoxyethane and the like. The reaction temperature is usually from room temperature to reflux temperature of the solvent.

In accordance with Production method 57, by letting compound 116 react with hydrazide, compound 114 can be produced.

Production method 59

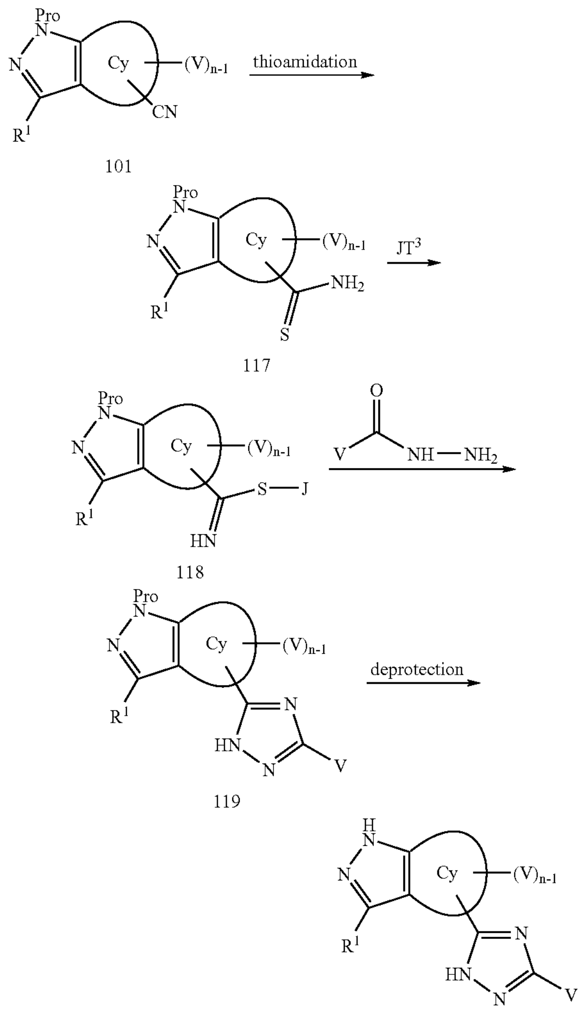

101

117

118

119

114

Compound 114 produced by Production method 56 can be produced by converting compound 101 produced by Production method 45 into thioamide 117, letting thioamide 117 to react with alkyl halide to render it thioimidate 118, then letting the thioimidate 118 react with hydrazide, and conducting deprotection.

Thioamidation of compound 101 is conducted using the condition which is usually employed, for example, using hydrogen sulfide and a base. In this case, as the base, triethylamine, diisopropylethylamine or the like is used, and as the solvent, any solvents can be used insofar as they are not concerned with the reaction, and examples of such solvent include, but are not limited to, methanol, ethanol, pyridine and the like. The reaction temperature is from room temperature to reflux temperature of the solvent.

As the alkyl halide to be used for thiomidation of thioamide 117, methyl iodide or the like is preferred without limitation. As the solvent, any solvents can be used insofar as they are not concerned with the reaction, and examples of such solvent include, but are not limited to, dichloromethane, acetonitrile, toluene, tetrahydrofuran, 1,4-dioxane, dimethylformamide and the like. The reaction temperature is from room temperature to reflux temperature of the solvent.

In accordance with Production method 58, thioimidate 118 and hydrazide are reacted, followed by deprotection in accordance with Production method 3, to thereby produce compound 114.

Production method 60

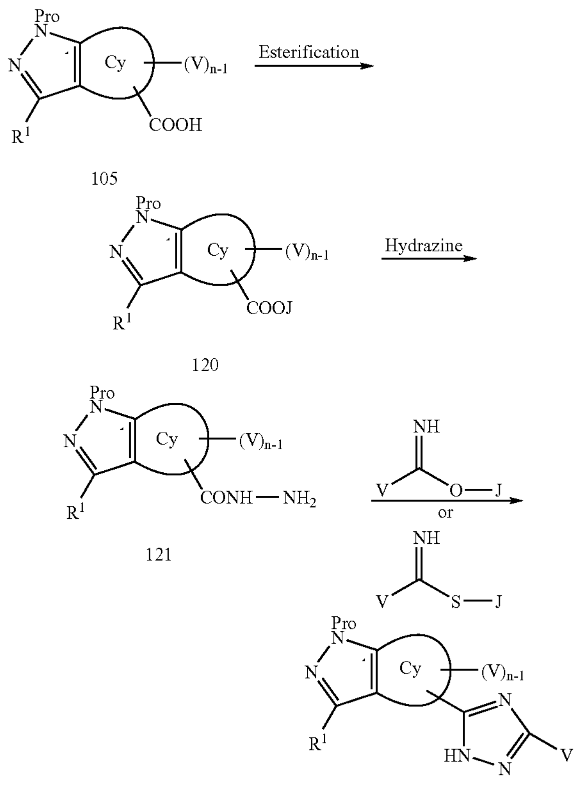

105

120

121

119

Compound 119 produced by Production method 59 can be produced by esterifying compound 105 produced by Production method 48, letting the resultant ester react with hydrazine to render it hydrazide, and letting the hydrazide react with imidate or thioimidate.

Esterification of compound 105 can be achieved, for example, by dehydration reaction with alcohol using an acid catalyst, dehydration reaction with alcohol using a condensing reagent, and reaction using diazomethane. For example, in the case where a sulfuric acid is used as the acid catalyst, methanol, ethanol or the like is preferably used as the alcohol. And the solvent is preferably the alcohol to be used. The reaction temperature is usually from 0° C. to reflux temperature of the solvent. As the reaction solvent in the case of using diazomethane, for example, diethyl ether, methanol, tetrahydrofuran or the like is used, and the reaction temperature is usually from 0° C. to room temperature.

As the solvent to be used for reaction between ester 120 and hydrazine, any solvents can be used insofar as they are not concerned with the reaction, and examples of such solvent include, but are not limited to, ethanol, 1,4-dioxane, toluene, N-methylpyrrolidone, N,N-dimethylformamide and the like. The reaction temperature is from room temperature to reflux temperature of the solvent.

As the solvent to be used in the reaction between hydrazide 121 and imidate or thioimidate, any solvents can be used insofar as they are not concerned with the reaction, and examples of such solvent include, but are not limited to, ethanol, 1,4-dioxane, dichloromethane, toluene, N-methylpyrrolidone, N,N-dimethylformamide and the like, and if necessary, a base such as triethylamine, potassium carbonate or the like may be added. The reaction temperature is from room temperature to reflux temperature of the solvent. The imidate to be used is purchased if commercially available, or can be produced, for example, by causing nitrile to react with an alcohol such as ethanol in the presence of an acid such as hydrogen chloride if not commercially available. The thioimidate to be used is purchased if commercially available, or can be produced, for example, by causing thioamide to react with an alkyl halide or causing a nitrile to react with ethanethiol or thiophenol in the presence of an acid such as hydrogen chloride if not commercially available.

Production method 61

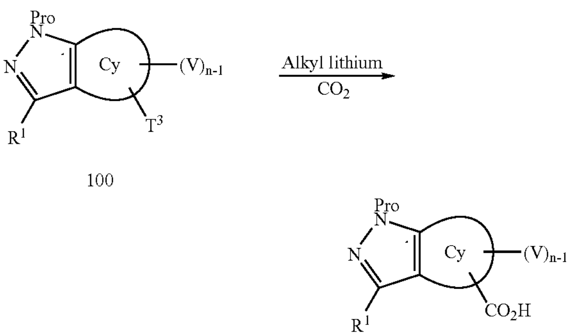

100

105

Carboxylic acid 105 produced by Production method 48 can also be produced by converting compound 100 into an aryl lithium in the manner as described in Production method 54, and the letting the aryl lithium react with carbon dioxide.

Production method 62

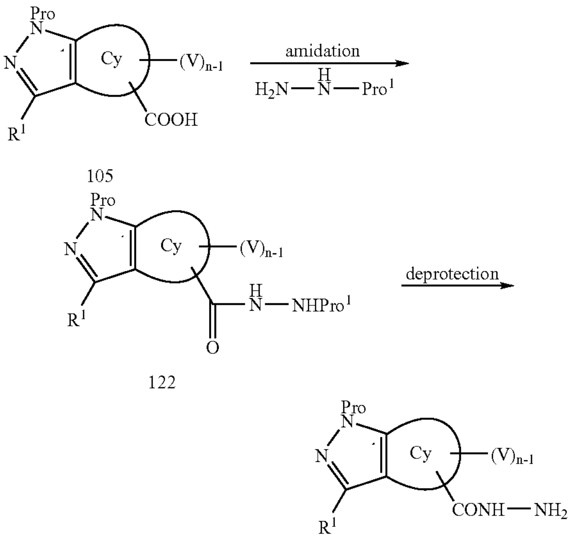

105

122

121

Hydrazide 121 produced by Production method 60 can also be produced by amide-condensing carboxylic acid 105 produced by Production method 48 and a mono-protected hydrazine, and then conducting deprotection.

Amidation of carboxylic acid 105 can be achieved by mixing a mono-protected hydrazine and a condensing reagent in accordance with Production method 47. As a protective group of mono-protected hydrazine, for example, tert-butyloxycarbonyl group, benzyloxycarbonyl group and the like can be recited.

As the condition for deprotecting compound 122, in the case of tert-butyloxycarbonyl group, deprotection can be readily achieved by using an acid in accordance with Production method 3. Similarly, in the case of benzyloxycarbonyl group, deprotection can be easily achieved by catalytic hydrogen reduction.

Production method 63

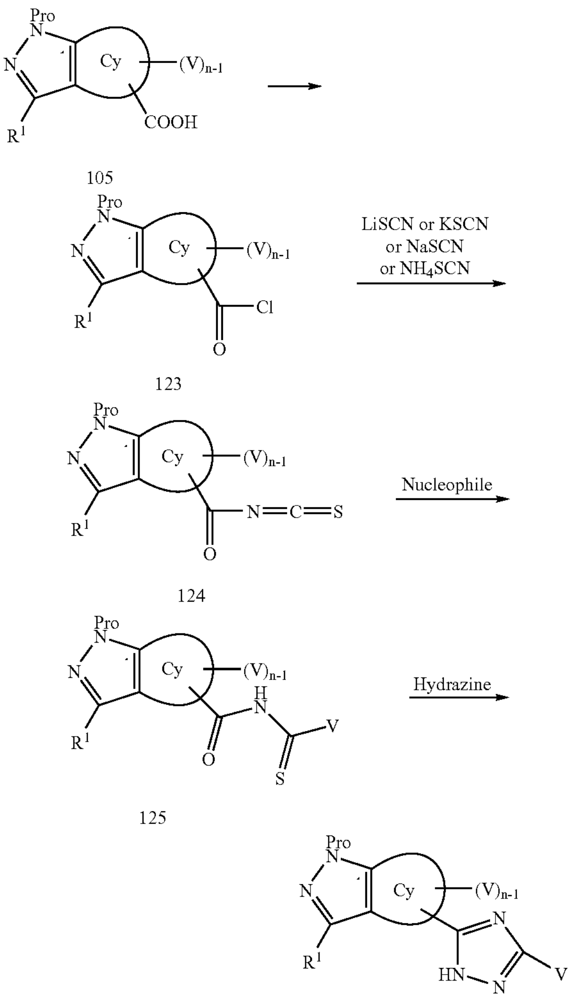

105

123

124

125

119

Compound 119 produced by Production method 59 can also be produced by converting carboxylic acid produced 105 by Production method 48 into an acid chloride, letting the acid chloride react with a thiocyanate salt, letting the resultant compound 124 react with a nucleophilic reagent to render it compound 125, and then letting compound 125 react with hydrazine.

As the method for producing acid chloride 123 from carboxylic acid 105, usual condition is employed, and for example, thionyl chloride or oxalyl chloride is used, and as if necessary, a small amount of N,N-dimethylformamide is added. As the solvent, any solvents can be used insofar as they do not inhibit the reaction, and examples of such solvent include, but are not limited to, dichloromethane, toluene, tetrahydrofuran, 1,4-dioxane and the like. Also the reaction may be conducted in the absence of solvent. The reaction temperature is usually from 0° C. to reflux temperature of the solvent.

As the solvent used in producing compound 124 from acid chloride 123 and thiocyanate salt, any solvents can be used insofar as they do not inhibit the reaction, and examples of such solvent include, but are not limited to, toluene, acetonitrile, pyridine and the like. The reaction temperature is usually from 0° C. to reflux temperature of the solvent.

As the nucleophilic reagent used in producing compound 125 from compound 124, alcohol and amine, alkyl lithium, Grignard reagent and the like can be recited. As the solvent to be used when the nucleophilic reagent is alcohol or amine, any solvents can be used insofar as they do not inhibit the reaction, and examples of such solvent include, but are not limited to, toluene, acetonitrile, pyridine and tetrahydrofuran. The reaction temperature is usually from 0° C. to reflux temperature of the solvent. Also the reaction may conducted in the absence of solvent. As the solvent to be used when the nucleophilic reagent is alkyl lithium or Grignard reagent, any solvents can be used insofar as they do not inhibit the reaction, and examples of such solvent include, but are not limited to, diethyl ether, tetrahydrofuran, dimethoxyethane and the like. The reaction temperature is usually from −78° C. to room temperature.

As the solvent to be used in the reaction between compound 125 and hydrazine, any solvents can be used insofar as they do not inhibit the reaction, and examples of such solvent include, but are not limited to, ethanol, methanol, pyridine, toluene, tetrahydrofuran and the like. The reaction temperature is usually from room temperature to reflux temperature of the solvent.

Production method 64

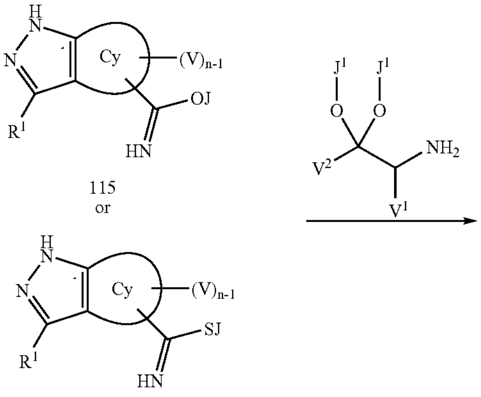

115 or

116

-continued

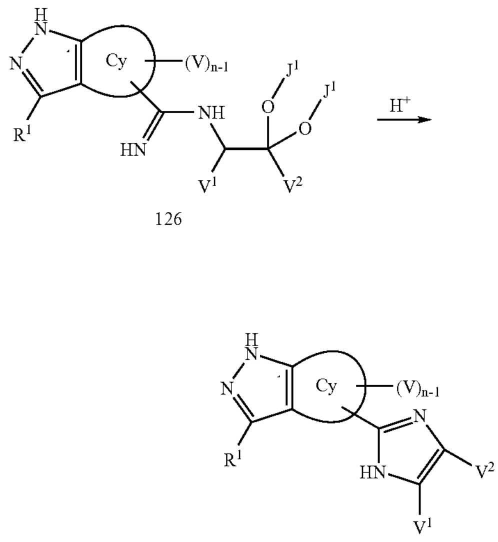

126

127

Compound 127 can be produced by letting α-aminoacetal or α-aminoketal react on imidate 115 produced by Production method 57 or thioimidate 116 produced by Production method 58 to render it 126, and conducting acid treatment on 126.

As the solvent to be used in producing compound 126 from compound 115 or 116, any solvents can be used insofar as they do not inhibit the reaction, and examples of such solvent include, but are not limited to, methanol, ethanol, acetic acid, dimethoxyethane, dimethylformamide and the like, and if necessary, a base such as triethylamine, diisopropylethylamine, potassium carbonate or the like may be added. The reaction temperature is usually from room temperature to reflux temperature of the solvent.

As the acid used in acid treatment for compound 126, for example, hydrochloric acid, sulfuric acid, acetic acid, para-toluenesulfonic acid and the like can be recited. As the reaction solvent, for example, methanol, ethanol, acetic acid, 1,2-dimethoxyethane, N,N-dimethylformamide and the like can be recited. The reaction temperature is usually from room temperature to reflux temperature of the solvent.

Production method 65

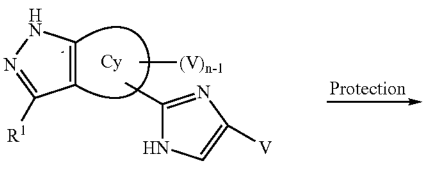

128

-continued

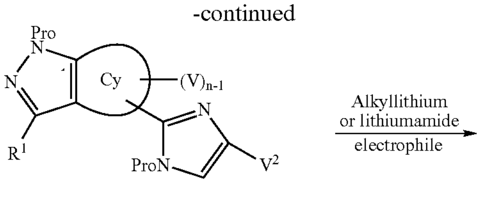

129

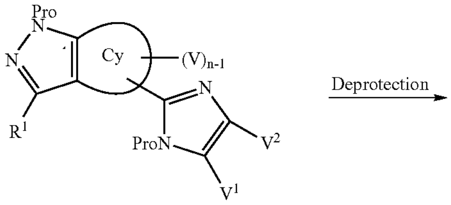

130

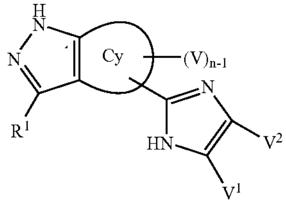

127

Compound 127 produced by Production method 64 can also be produced by introducing a protective group to compound 128 (compound in which $V^1$ is a hydrogen atom in compound 127), lithionating the imidazole and letting an electrophilic reagent act on the lithio compound, and then conducting deprotection.

As the protective group to be introduced into compound 128, for example, p-toluenesulfonyl group, dimethylsulfamoyl group, methoxymethyl group and the like can be recited. Introduction of p-toluenesulfonyl group and dimethylsulfamoyl group and methoxymethyl group can be achieved by letting compound 128 react with p-toluenesulfonyl chloride or dimethylsulfamoyl chloride or chloromethylmethyl ether in the presence of a base. Preferred examples of the base include, but are not limited to, triethylamine, 4-N,N-dimethylamionopyridine, sodium hydroxide, sodium hydride, potassium tert-butoxide, potassium carbonate and the like. As the solvent, any solvents can be used insofar as they are not concerned with the reaction, and examples of such solvent include, but are not limited to, ether solvents such as diethyl ether, tetrahydrofuran, dioxane or dimethoxyethane, hydrocarbon halides such as dichloromethane or chloroform, as well as pyridine, acetonitrile, dimethyl sulfoxide, dimethylformamide, toluene and the like. The reaction temperature is usually from 0° C. to reflux temperature of the solvent.

As the alkyl lithium for litionation of compound 129, for example, N-butyllithium, sec-butyllithium, tert-butyllithium, as well as phenyl lithium is used, and if necessary, an additive such as N,N,N',N'-tetramethylethylenediamine, hexamethylphosphoramide and the like may be added. As the lithium amide, for example, lithium diisopropylamide, lithium 2,2,6,6-tetramethylpiperidide or the like is used. As the electrophilic reagent to be used, for example, alkyl halide, aldehyde, isocyanate and the like can be recited. As the solvent, any solvents can be used insofar as they are not concerned with the reaction, and examples of such solvent include, but are not limited to, ether solvents such as diethyl ether, tetrahydrofuran, dioxane or dimethoxyethane, as well as benzene, toluene and the like. The reaction temperature is from −78° C. to room temperature.

Deprotection of p-toluenesulfonyl group and dimethylsulfamoyl group is readily achieved by means of a base. As the base, sodium hydroxide water, potassium hydroxide water and the like can be recited without limitation. As the solvent, any solvents can be used insofar as they are not concerned with the reaction, and examples of such solvent include, but are not limited to, alcohol solvents such as methanol or ethanol, and ether solvents such as diethylether, tetrahydrofuran or dioxane, dimethoxyethane. The reaction temperature is room temperature or reflux temperature of the solvent. Deprotection of methoxymethyl group can be achieved by treating the remaining aminal with ammonia water after acid treatment. Deprotection of dimethylsulfamoyl group can be readily achieved by an acid. As the acid, hydrochloric acid, sulfuric acid, hydrobromic acid, perhydrochloric acid and the like can be recited. As the reaction solvent, any limitation insofar as they are not concerned with the reaction, and examples of such solvent include methanol, ethanol, water, dioxane and dimethoxyethane. The reaction temperature is room temperature or reflux temperature of the solvent.

Production method 66

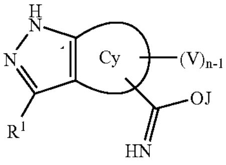

115 or

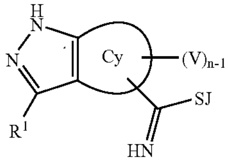

116

$NH_3$

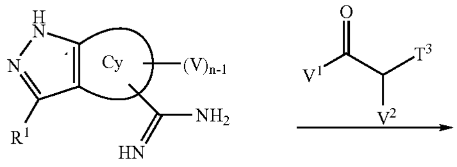

131

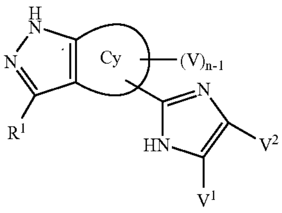

127

Compound 127 produced by Production method 64 can also be produced by letting imidate 115 produced by Production method 57 or thioimidate 116 produced by Production method 58 react with ammonia to render it amidine 131, and then letting amidine 131 react with α-haloketone.

As the solvent to be used in producing 131 from compound 115 or compound 116, any solvents can be used insofar as they are not concerned with the reaction, and examples of such solvent include, but are not limited to, methanol, ethanol, propanol, water, dioxane, dimethoxyethane and tetrahydrofuran. The reaction temperature is room temperature or reflux temperature of the solvent.

By letting amidine 131 and a-haloketone in the presence of a base, it is possible to produce 127. As the base to be used, for example, triethylamine, dimethylaminopyridine, sodium hydroxide, potassium carbonate, potassium tert-butoxide and the like can be recited. As the solvent, any solvents can be used insofar as they are not concerned with the reaction, and examples of such solvent include, but are not limited to, methanol, ethanol, dioxane, tetrahydrofuran, toluene, pyridine and N,N-dimethylformamide. The reaction temperature is usually from room temperature to reflux temperature of the solvent.

Production method 67

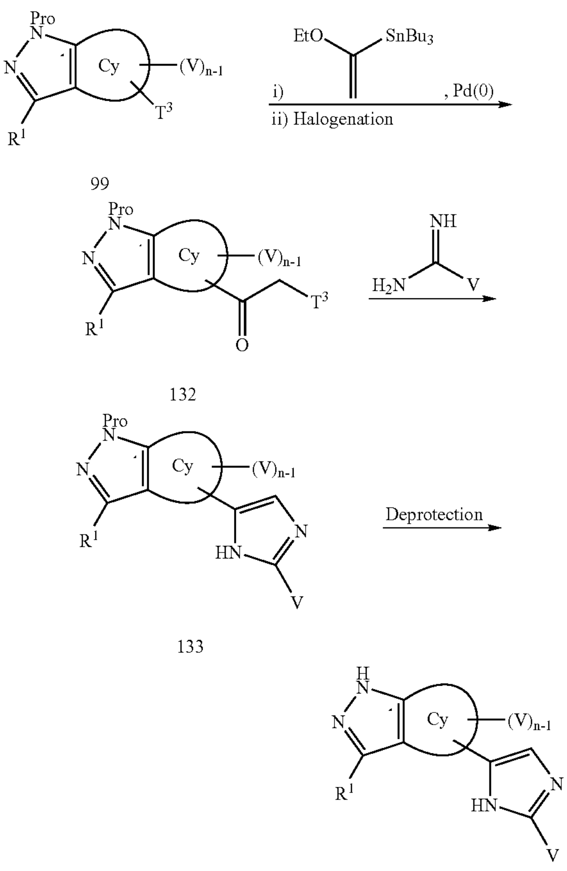

99

132

133

134

Compound 134 can be produced by letting α-haloketone 132 produced by Production method 51 react with amidine, and then conducting deprotection.

By letting compound 132 and amidine react with each other in the presence of a base, it is possible to produce compound 133. As the base to be used, for example, triethylamine, dimethylaminopyridine, sodium hydroxide, potassium carbonate, potassium tert-butoxide and the like can be recited. As the solvent, any solvents can be used insofar as they are not concerned with the reaction, and examples of such solvent include, but are not limited to, methanol, ethanol, dioxane, tetrahydrofuran, toluene, pyridine and N,N-dimethylformamide. The reaction temperature is usually from room temperature to reflux temperature of the solvent.

Deprotection of compound 133 is conducted in accordance with Production method 3.

Production method 68

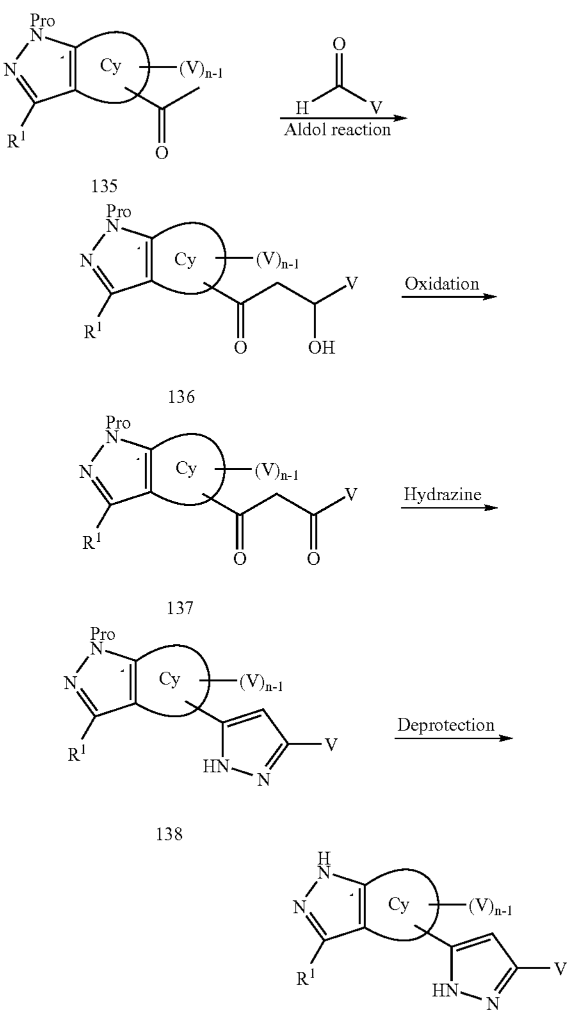

135

136

137

138

139

Compound 139 can be produced by converting compound 135 produced as an intermediate in Production method 51 into diketone 137 by aldol reaction and subsequent oxidation reaction, then constructing a pyrazole ring by using hydrazine, and conducting deprotection.

As the base to be used in the aldol reaction for compound 135, for example, sodium hydroxide, sodium methoxide, lithium hexamethyldisilazide, lithium diisopropylamide and the like can be recited. As the solvent, any solvents can be used insofar as they are not concerned with the reaction, and examples of such solvent include, but are not limited to, diethyl ether, tetrahydrofuran, dimethoxyethane, toluene and dioxane. The reaction temperature is usually from 0° C. to reflux temperature of the solvent.

As the oxidizing reagent to be used in the oxidation reaction for compound 136, for example, sulfur trioxide-pyridine complex, N-methylmorpholine-N-oxide, a variety of chromic acid oxidizing reagents and the like can be used, and also the oxidization may be achieved by Swern oxidation, Moffat oxidation and the like. As the solvent, any solvents can be used insofar as they are not concerned with the reaction, and examples of such solvent include hydrocarbon halides such as dichloromethane or chloroform, as well as ethyl acetate, acetonitrile, dimethyl sulfoxide, dimethylformamide and the like. The reaction temperature is usually from −78° C. to reflux temperature of the solvent.

As the reaction solvent used for the reaction between compound 137 and hydrazine, any solvents can be used insofar as they do not inhibit the reaction, and examples of such solvent include, but are not limited to, methanol, ethanol, tetrahydrofuran, dioxane, pyridine and acetic acid. The reaction temperature is usually from room temperature to reflux temperature of the solvent.

Deprotection of compound 138 is conducted in accordance with Production method 3.

Production method 69

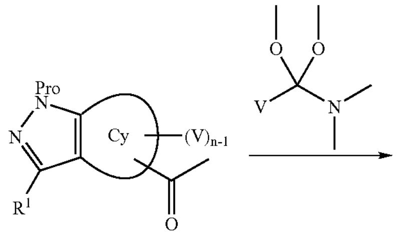

135

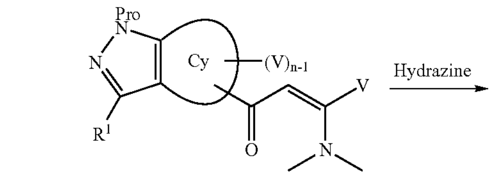

140

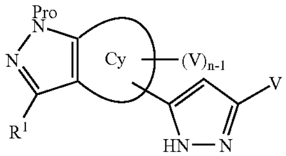

138

Compound 138 produced by Production method 68 can also be produced by converting compound 135 which is produced as an intermediate in Production method 51 into enamine 140, and then letting enamine 140 react with hydrazine.

Enamine 140 can be produced by letting compound 135 and dimethylamide-dimethylacetal react with each other. As the reaction solvent, any solvents can be used insofar as they do not inhibit the reaction, and examples of such solvent include, but are not limited to, methanol, ethanol, toluene and dimethylformamide. The reaction temperature is usually from room temperature to reflux temperature of the solvent.

As the reaction solvent to be used in the reaction between enamine 140 and hydrazine, any solvents can be used insofar as they do not inhibit the reaction, and examples of such solvent include, but are not limited to, methanol, ethanol, tetrahydrofuran, dioxane, pyridine and acetic acid. The reaction temperature is usually from room temperature to reflux temperature of the solvent.

Production method 70

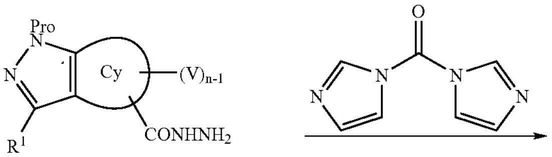

121

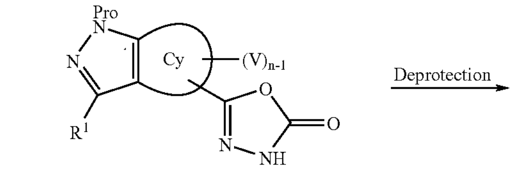

141

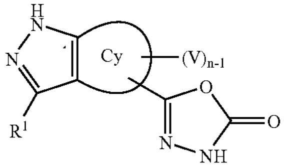

142

Compound 142 can be produced by letting hydrazide 121 produced by Production method 60 react with carbonyldiimidazole, and then conducting deprotection.

As the reaction solvent used in the reaction between hydrazide 121 and carbonyldiimidazole, any solvents can be used insofar as they do not inhibit the reaction, and examples of such solvent include, but are not limited to, tetrahydrofuran, dimethoxyethane and dimethylformamide. The reaction temperature is usually from room temperature to reflux temperature of the solvent.

Deprotection of compound 141 is conducted in accordance with Production method 3.

Production method 71

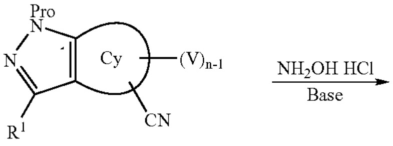

101

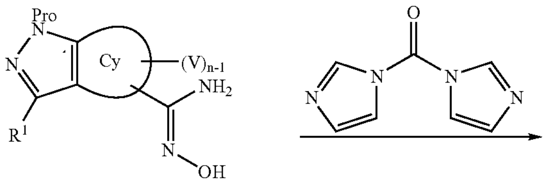

143

-continued

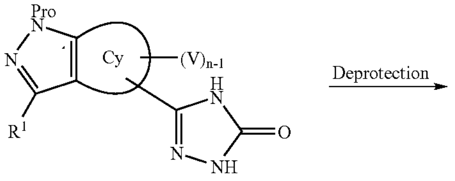

144

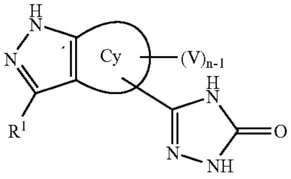

145

Compound 145 can be produced by letting compound 101 produced by Production method 45 react with hydroxyammonium chloride in the presence of a base, to render it compound 143, letting compound 143 react with carbonyldiimidazole, and the conducting deprotection.

As the base to be used in production of compound 143, for example, triethylamine, potassium carbonate, sodium hydroxide and the like can be recited. As the solvent, any solvents can be used insofar as they are not concerned with the reaction, and examples of such solvent include, but are not limited to, methanol, ethanol, propanol, dioxane and N,N-dimethylformamide. The reaction temperature is room temperature or reflux temperature of the solvent.

As the solvent to be used in the reaction between compound 143 and carbonyldiimidazole, any solvents can be used insofar as they do not inhibit the reaction, and examples of such solvent include, but are not limited to, tetrahydrofuran, dimethoxyethane and dimethylformamide. The reaction temperature is usually from room temperature to reflux temperature of the solvent.

Deprotection of compound 144 is conducted in accordance with Production method 3.

Production method 72

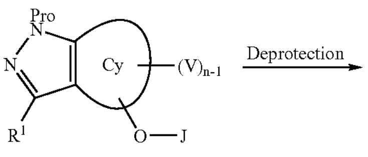

146

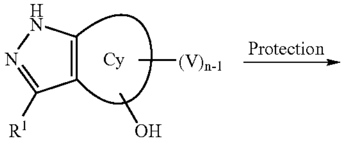

147

-continued

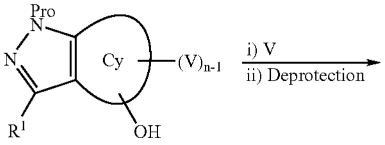

148

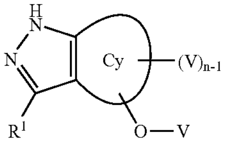

149

Compound 149 can be produced by selectively protecting 1-position after deprotecting compound 146 to make compound 148, introducing a substituent into a phenol group, and the removing the protective group. J in compound 146 is preferably a methyl group.

Deprotection of compound 146 is readily achieved by means of Lewis acid, alkaline metal salt of thio, acid and the like. As the Lewis acid, boron tribromide, aluminum trichloride and the like are used, as the alkaline salt of thiol, sodium salts of ethanethiol or thiophenol and the like are used, and as the acid, trifluoroacetic acid, hydrobromic acid and the like are used. As the solvent, any solvents can be used insofar as they are not concerned with the reaction, and examples of such solvent include, but are not limited to, hydrocarbon halides such as dichloromethane, chloroform or carbon tetrachloride, as well as ethyl acetate, acetonitrile, dimethyl sulfoxide, N, N-dimethylformamide and the like. The reaction temperature is −20° C. or reflux temperature of the solvent.

The subsequent selective protection of 1-position is achieved in the manner as described in Production method 3. Introduction of alkyl group into compound 148 can be achieved by reaction with a halide in the presence of a base. As the base to be used, sodium hydride, potassium carbonate, cesium carbonate and the like are recited, and the use amount thereof is usually fro 1 to 2 equivalent(s). As the halide to be used, bromides and iodides are preferred without limitation, and the use amount thereof is usually from 1 to 3 equivalent(s) with respect to the material. As the halide, both aliphatic halides and aromatic halides can be employed and they may have suitable functional groups. As for aromatic halides, iodides are particularly preferred, and by adding a metal catalyst such as copper iodide in the presence of a base, an excellent result is achieved. The use amount of metal catalyst is usually from catalyst amount to 1 equivalent. In the cases of highly-reactive aralkyl halides or aryl halides, the reaction can be achieved by using a salt such as sodium iodide instead of the base. As the reaction solvent, any solvents can be used insofar as they are not concerned with the reaction, and examples of such solvent include, but are not limited to, halogen solvents such as dichloromethane, chloroform or 1,2-dichloroethane, hydrocarbon solvents such as benzene or toluene, ether solvents such as tetrahydrofuran, and polar solvents such as N,N-dimethylformamide or acetonitrile. The reaction temperature is usually from room temperature to reflux temperature of the solvent.

Furthermore, compound 148 can be converted into an ester by reaction with acid chloride or acid anhydride in the presence of a base. As the base, triethylamine, diisopropylethylamine, pyridine and the like can be recited without limitation. As the solvent, any solvents can be used insofar as they are not concerned with the reaction, and examples of such solvent include halogen solvents such as dichloromethane or chloroform, ether solvents such as ether or tetrahydrofuran, as well as ethyl acetate, toluene and the like. The reaction temperature is usually from −78° C. to reflux temperature of the solvent. Furthermore, compound 148 can also be esterified by mixing a carboxylic acid and a condensing reagent. As the condensing reagent, for example, dicyclohexylcarbodiimide, diisopropylcarbodiimide, 1-ethyl-3-(3-dimethylaminopropyl) carbodiimide, 1-ethyl-3-(3-dimethylaminopropyl)carbodiimide hydrochloride and the like can be recited. 1-Hydroxybenzotriazole, N-hydroxysuccinimide and the like may be added where appropriate. As the solvent, any solvents can be used insofar as they are not concerned with the reaction, and examples of such solvent include halogen solvents such as dichloromethane or chloroform, ether solvents such as ether or tetrahydrofuran, as well as ethyl acetate, dimethylformamide, toluene and the like. The reaction temperature is usually from room temperature to reflux temperature of the solvent. Furthermore, compound 148 may be converted into an ester by reaction with a carboxylic acid under the condition of an acid catalyst. As the acid, hydrochloric acid, sulfuric acid, trifluoroacetic acid and the like are exemplified. As the solvent, any solvents can be used insofar as they are not concerned with the reaction, and examples of such solvent include, but are not limited to, halogen solvents such as dichloromethane, chloroform or 1,2-dichloroethane, hydrocarbon solvents such as benzene or toluene, ether solvents such as tetrahydrofuran, and polar solvents such as N,N-dimethylformamide or acetonitrile. The reaction temperature is usually from room temperature to reflux temperature of the solvent.

By deprotecting 1-position in the manner as described in Production method 3, it is possible to produce compound 149.

Production method 73

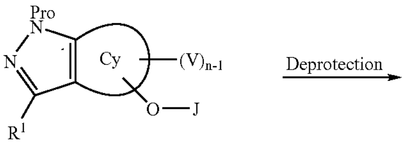

146

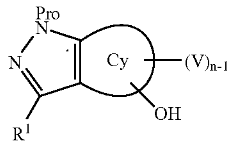

148

Compound 148 obtained by Production method 72 can also be produced by selectively deprotecting compound 146.

For selective deprotection of compound 146, for example, Lewis acids such as boron tribromide or aluminum trichloride, alkaline metal salts such as sodium salts of ethanethiol or thiophenol, and acids such as trifluoroacetic acid or hydrobromic acid are used, and alkaline metal salts of thiol are preferably used. As the solvent, any solvents can be used insofar as they are not concerned with the reaction, and examples of such solvent include, but are not limited to, hydrocarbon halides such as dichloromethane, chloroform and carbon tetrachloride, as well as ethyl acetate, acetonitrile, dimethyl sulfoxide, N,N-dimethylformamide and the like. The reaction temperature is −20° C. or reflux temperature of the solvent.

Production method 74

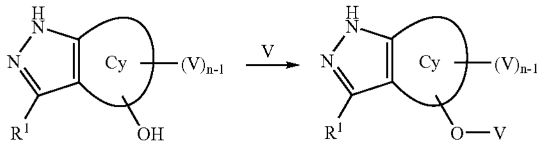

147 149

Compound 149 can also be produced by letting compound 147 react with halide, carboxylic acid, acid chloride or acid anhydride in the similar manner as described in Production method 72.

Production method 75

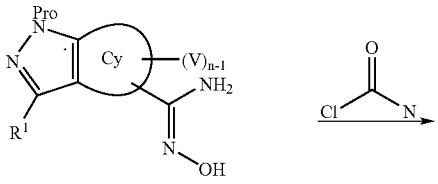

143

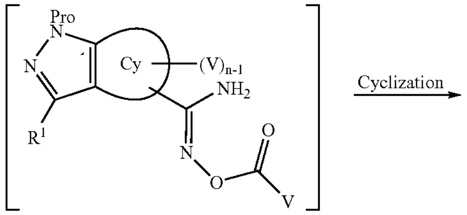

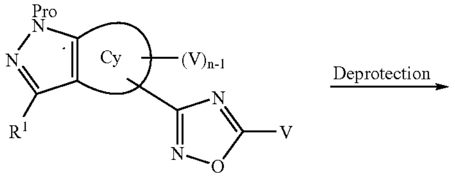

150

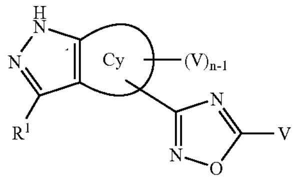

151

Compound 151 can be produced by letting compound 143 produced by Production method 71 react with an acid chloride, allowing dehydrating-cyclization to render compound 150, and then conducting deprotection.

In producing compound 150 from compound 143, a base may be added. As the base to be used, for example, triethylamine, pyridine, sodium hydride and the like are recited. As the reaction solvent, any solvents can be used insofar as they are not concerned with the reaction, and examples of such solvent include, but are not limited to, tetrahydrofuran, dimethoxyethane and N,N-dimethylformamide. The reaction temperature is room temperature or reflux temperature of the solvent. A corresponding acid anhydride or ester may be used instead of the acid chloride used for acylation.

Deprotection of compound 150 is conducted in accordance with Production method 3.

Production method 76

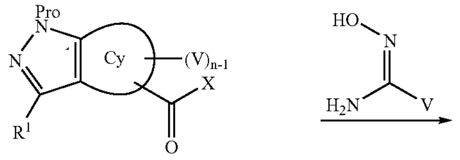

152
X = Cl, OMe

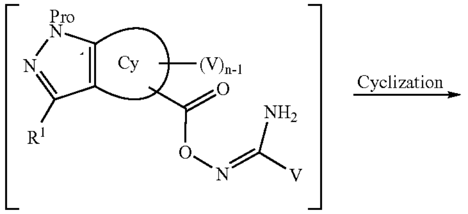

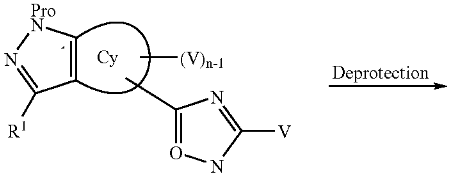

153

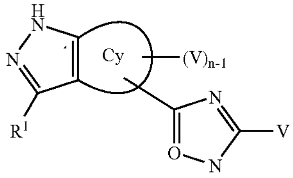

154

Compound 154 can be produced by letting compound 152 react with amidoxime, allowing dehydrating-cyclization to render compound 153, and then conducting deprotection.

In producing compound 153 from compound 152, a base may be added. As the base to be used, for example, triethylamine, pyridine, sodium hydride and the like can be recited. As the reaction solvent, any solvents can be used insofar as they are not concerned with the reaction, and examples of such solvent include, but are not limited to, tetrahydrofuran, dimethoxyethane and N,N-dimethylformamide. The reaction temperature is room temperature or reflux temperature of the solvent.

Deprotection of compound 153 is conducted in accordance with Production method 3.

Production method 77

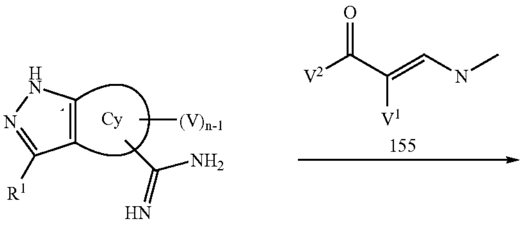

155

131

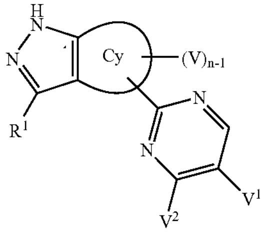

156

Compound 156 can be produced by reacting compound 131 produced by Production method 66 and compound 155.

In the reaction between amidine 131 and compound 155, a base is used as necessary. As the base, triethylamine, diisopropylethylamine, potassium carbonate and the like are recited. As the solvent, any solvents can be used insofar as they are not concerned with the reaction, and preferred examples of such solvent include, but are not limited to, methanol, ethanol, pyridine, acetic acid, tetrahydrofuran, toluene, 1,4-dioxane, N,N-dimethylformamide and the like. The reaction temperature is usually from room temperature to reflux temperature of solvent.

Production method 78

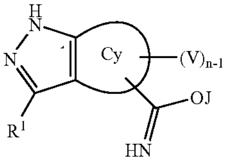

115
or

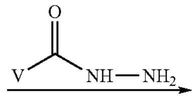

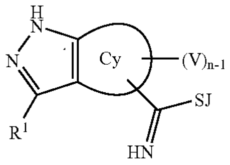

116

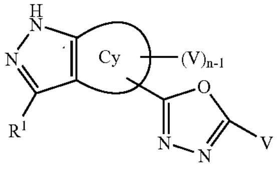

157

Compound 157 can be produced by reacting imidate 115 produced by Production method 57 orthioimidate 116 produced by Production method 58 with hydrazide in the absence of a base. As the reaction solvent, any solvents can be used insofar as they are not concerned with the reaction, and preferred examples of such solvent include, but are not limited to, methanol, ethanol, propanol, butanol, tetrahydrofuran, toluene, 1,4-dioxane, dimethylformamide, pyridine and the like. The reaction temperature is usually from room temperature to reflux temperature of solvent.

Production method 79

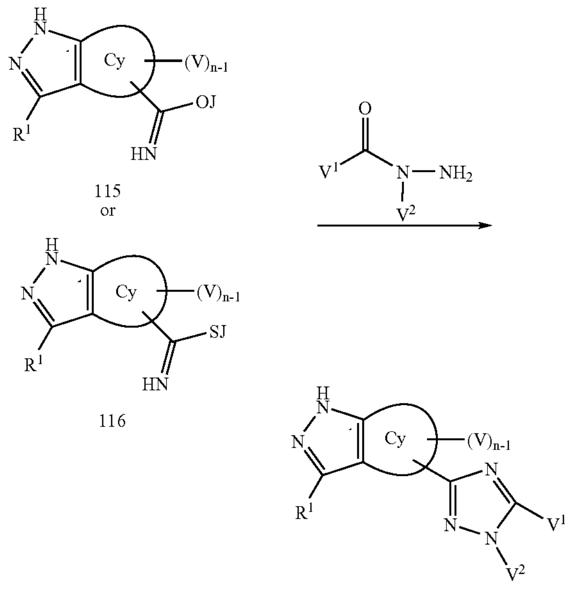

115 or

116

158

Compound 158 can be produced by reacting imidate 115 produced by Production method 57 or thioimidate 116 produced by Production method 58 with hydrazide in accordance with the method described in Production method 57 for producing compound 114.

Production method 80

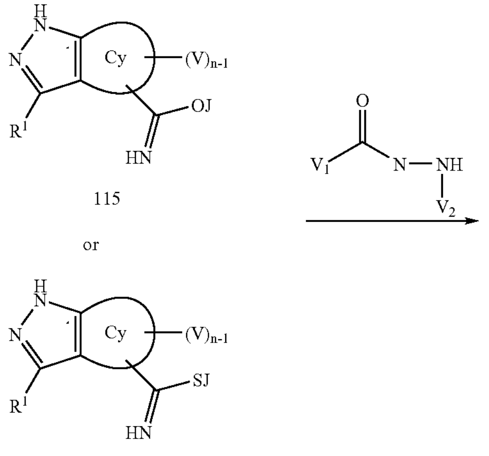

115 or

116

-continued

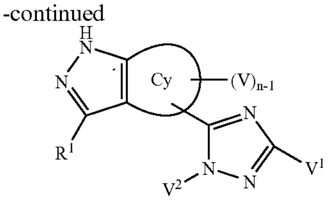

159

Compound 159 can be produced by reacting imidate 115 produced by Production method 57 orthioimidate 116 produced by Production method 58 with hydrazide in accordance with the method described in Production method 57 for producing compound 114.

The “salt” used herein refers to any pharmaceutically acceptable salts that form salts with compounds in accordance with the present invention and are, and preferably, but are not limited to, hydrohalic acid salts (for example, hydrofluoric acid salts, hydrochloric acid salts, hydrobromic acid salts, hydroiodic acid salts and the like), inorganic acid salts (for example, sulfuric acid salts, nitric acid salts, perchloric acid salts, phosphoric acid salts, carbonic acid salts, bicarbonic acid salts and the like), organic carboxylic acid salts (for example, acetic acid salts, maleic acid salts, tartaric acid salts, fumaric acid salts, citric acid salts and the like), organic sulfonic acid salts (for example, methanesulfonic acid salts, ethanesulfonic acid salts, benzenesulfonic acid salts, toluenesulfonic acid salts, camphorsulfonic acid salts and the like), amino acid salts (for example, aspartic acid salts, glutamic acid salts and the like), quaternary amine salts, alkaline metal salts (for example, sodium salts, potassium salts and the like), alkaline earth metal salts (magnesium salts, potassium salts and the like) and the like, and more preferably hydrochloric acid salts, sulfuric acid salts, methanesulfonic acid salts, acetic acid salts and the like.

The compounds represented by the above formulae (I) to (III) or their salts or hydrates thereof in accordance with the present invention can be formulated in conventional methods, and examples of preferred dosage forms include tablet, powder, fine grain agent, granule, coating tablet, encapsulated formulation, syrup, troche, inhalant, suppository, injection, ointment, eye ointment agent, eye drop, nasal drop, ear drops, cataplasm, lotion and the like. In preparation, commonly used excipient, binder, disintegrator, lubricant, colorant, flavoring agent, as well as stabilizer, emulsifying agent, absorption promoter, surfactant, pH modifier, antiseptics, anti-oxidant and the like can be used as necessary, and preparation is achieved by means of conventional methods while blending components that are generally used as raw materials of pharmaceutical formulation. Examples of the above components include: (1) animal and vegetable oils such as soybean oil, beef tallow or synthesis glyceride; (2) hydrocarbons such as liquid paraffin, squalane or solid paraffin; (3) ester oils such as octyldodecyl myristate or isopropylmyristate; (4) higher alcohols such as ceto-stearyl alcohol or behenyl alcohol; (5) silicon resin; (6) silicon oil; (7) surfactants such as polyoxyethylene fatty acid esters, sorbitan fatty acid esters, glycerine fatty acid esters, polyoxyethylene sorbitan fatty acid esters, polyoxyethylene hardened castor oil or polyoxyethylene polyoxypropylene block copolymer; (8) water-soluble polymers such as hydroxyethyl cellulose, polyacrylic acid, carboxy vinyl polymer, polyethylene glycol, polyvinylpyrrolidone or methyl cellulose; (9) lower alcohols such as ethanol or isopropanol; (10) polyols such as glycerin, propylene glycol, dipropylene glycol or sorbitol; (11) sugars such as glucose or sucrose; (12) inorganic powders such as silicic anhydride, aluminum silicate magnesium or aluminum silicate; and (13) purified water.

1) Examples of excipients include lactose, corn starch, saccharose, glucose, mannitol, sorbit, crystalline cellulose, silicon dioxide and the like; 2) examples of binders include polyvinyl alcohol, polyvinyl ether, methyl cellulose, ethyl cellulose, gum Arabic, gum tragacanth, gelatine, shellac, hydroxypropylcellulose, hydroxypropyl methylcellulose, polyvinylpyrrolidone, polypropylene glycol polyoxyethylene block polymer, meglumine, calcium citrate, dextrin, pectin and the like; 3) examples of disintegrators include starch, agar, gelatin powder, crystalline cellulose, calcium carbonate, sodium hydrogen carbonate, calcium citrate, dextrin, pectin, carboxymethylcellulose calcium and the like; 4) examples of lubricants include magnesium stearate, talc, polyethylene glycol, silica, consolidation vegetable oil and the like; 5) examples of colorants include those accepted to be added to pharmaceuticals; 6) examples of flavoring agents include cocoa powder, menthol, aroma powder, mentha oil, borneol, cassia bark and the like; and 7) examples of anti-oxidants include ascorbic acid, α-tocopherol and the like that are accepted to be added to pharmaceuticals.

1) As to oral formulations, after blending the compound or its pharmaceutically acceptable salt according to the present invention and an excipient, as well as a binder, disintegrator, lubricant, colorant, flavoring agent and the like as necessary, the mixture is formed into powder, fine grain agent, granule, tablet, coating tablet, encapsulated formulation and the like. 2) In the cases of tablets and granules, it is allowable to appropriately coat with sugar, gelatin and other materials if necessary. 3) Liquid agents such as syrup, injection formulation or eye drop may produced by blending the compound according to the present invention or a pharmaceutically acceptable salt thereof with pH regulating agents, resolvents, tonicity agents, etc., optionally together with dissolution aids, stabilizers, buffer agents, suspending agents, antioxidants etc. and processing the resultant blends into preparations by the conventional methods. Such liquid agents may be lyophilized and injection may be subcutaneously or intramuscularly administered. Preferred examples of suspending agents include methyl cellulose, polysolvate 80, hydroxymethyl cellulose, gum Arabic, tragacanth powder, carboxymethylcellulose sodium, polyoxyethylene sorbitanmonolaurate and the like; preferred examples of dissolution aids include polyoxyethylene hardened castor oil, polysolvate 80, nicotinamide, polyoxyethylene sorbitanmonolaurate and the like; preferred examples of stabilizers include sodium sulfite, sodium metasulfite, ether and the like; and preferred examples of preservatives include methyl paraoxybenzoate, ethyl paraoxybenzoate, sorbic acid, phenol, cresol, chlorocresol and the like. 4) In the cases of External preparations, may be produced by the conventional methods without limitation. As the bases, use can be made of various materials commonly used in drugs, quasidrugs, cosmetics, etc. Particular examples of the base materials include animal and vegetable oils, mineral oils, ester oils, waxes, higher alcohols, fatty acids, silicone oils, surfactants, phospholipids, alcohols, polyhydric alcohols, water-soluble polymers, clay minerals and purified water. If needed, it is possible to further add pH regulating agents, antioxidants, chelating agents, antiseptics, fungicides, coloring agents, perfumes, etc. If necessary, it is also possible to further add other ingredients capable of inducing differentiation, blood flow accelerators, bactericides, antiinflammatory agents, cell activators, vitamins, amino acids, humectants, keratolytic agents, etc.

The dosage amount of the pharmaceutical according to the present invention differs depending on the severity of symptom, age, sex, bodyweight, dosage form, type of the salt, sensitivity to drug, particular type of the disease, and the like, and generally, these compounds are administered to an adult in a dose of about 30 μg to 1,000 mg, preferably from 100 μg to 500 mg and Stille preferably from 100 μg to 100 mg, per day once or several times a day. In the case of injection, generally about 1 μg/kg to 3,000 μg/kg, and preferably about 3 μg/kg to 1,000 μg/kg is administered.

In accordance with the present invention, novel indazole compounds are provided. The compounds (I) to (III) or their salts according to the present invention have excellent selective inhibiting effect on c-Jun amino terminal kinase (JNK), especially on JNK 3. Therefore, the compounds (I) to (III) or their salts and pharmaceutical compositions containing the same are useful as therapeutic agents or preventive agents for immunological diseases, inflammatory disease, metabolic diseases and/or neurodegenerative diseases, and particularly useful as therapeutic agents or preventive agents for acute neurodegenerative diseases (for example, cerebrovascular disorder acute stage, head injury, spinal cord injury, neuropathy due to low oxygen, neuropathy low blood sugar and the like), chronic neurodegenerative diseases (for example, Alzheimer's disease, Parkinson's disease, Huntington's chorea, amyotrophic lateral sclerosis, multiple sclerosis, spinocerebellar degeneration and the like), epilepsy, hepatic encephalopathy, peripheral neuropathy, Parkinson syndrome, exanthematous paralysis, pain, neuralgia, infectious encephalomyelitis, cerebrovascular dementia, dementia or neurosis due to meningitis and the like.

EXAMPLES

Any Production examples, Examples and Test examples provided below are merely illustrative, and compounds according to the present invention are not restricted by the following concrete examples. Those skilled in the art can conduct the present invention to the utmost while making various modifications within the scope of claims associated with the present description as well as the Examples provided below, and all such modifications are involved in the boundary of the present description.

Production Example 1

(3-Fluorophenyl)-(3-fluoropyridin-2-yl)-methanol

Under nitrogen atmosphere, a solution of 9.75 g of diazabicyclo[2.2.0]octane in 150 mL of dehydrated diethyl ether was cooled to −40° C., added with 56 mL of 1.56 M n-butyllithium in hexane, and stirred at −20° C. for 1 hour. The solution was cooled to-60° C., added dropwise with 6.9 mL of 3-fluoropyridine, stirred at −60° C. for 1 hour, and added with 9.2 mL of 3-fluorobenzaldehyde. After stirring for 1 hour, aqueous ammonium chloride and ethyl acetate were successively added, and the mixture was recovered to room temperature. The organic layer was extracted, washed with water, and then dried over anhydrous magnesium sulfate. The solvent was evaporated, and the resulting crude product was purified and separated by silica gel column chromatography (ethyl acetate:hexane=1:4), to give 12.6 g of the title compound as colorless needle crystals.

$^1$H-NMR (400 MHz, $CDCl_3$) δ 5.26 (1H, d, J=6.8 Hz), 5.98 (1H, d, J=6.8 Hz), 6.95 (1H, dt, J=2.4, 8.4 Hz), 7.10 (1H, bd, J=9.8 Hz), 7.20 (1H, bd, J=8.4 Hz), 7.29 (1H, dt, J=5.5, 8.4 Hz), 7.30 (1H, dd, J=4.9, 8.8 Hz), 8.39 (1H, dt, J=1.2, 8.8 Hz), 8.42 (1H, d, J=1.2, 4.9 Hz).

Production Example 2

(3-Fluorophenyl)-(3-fluoropyridin-2-yl)-methanone

A mixed solution of 12.6 g of (3-fluorophenyl)-(3-fluoropyridin-2-yl)-methanol obtained by Production example 1 in 30 mL dichloromethane and 30 mL toluene was added with 10.0 g of activated manganese dioxide, and heated under reflux for 8 hours. After completion of the reaction, manganese dioxide was filtered off through Celite, and the solvent was evaporated, to give 12.1 g of the title compound as a pale yellow oil.

$^1$H-NMR (400 MHz, $CDCl_3$) δ 7.32 (1H, ddt, J=1.4, 2.8, 7.9 Hz), 7.47 (1H, dt, J=5.3, 7.9 Hz), 7.54 (1H, dd, J=4.5, 9.0 Hz), 7.61 (1H, dt, J=1.4, 9.0 Hz), 7.66 (1H, ddd, J=1.4, 2.8, 9.2 Hz), 7.72 (1H, dt, J=1.4, 7.9 Hz), 8.54 (1H, dt, J=1.4, 4.5 Hz).

Example 3

3-(3-Fluorophenyl)-1H-pyrazolo[4,3-b]pyridine 1.5 g of (3-fluorophenyl)-(3-fluoropyridin-2-yl)-methanone was dissolved in 5 mL of methanol, added with 1.0 mL of hydrazine monohydrate, and heated at 80° C. for 4 hours. The reaction solution was added with water, and extracted with ethyl acetate. The organic layer was washed successively with water and saturated brine, and dried over anhydrous magnesium sulfate. The solvent was distilled off, and the residue was purified and separated by silica gel column chromatography (ethyl acetate:n-hexane=1:4), to afford 240 mg of the title compound as a colorless powder.

$^1$H-NMR (400 MHz, DMSO-$D_6$) δ 7.21 (1H, dt, J=2.4, 8.0 Hz), 7.44 (1H, dd, J=4.1, 8.6 Hz), 7.55 (1H, dt, J=6.0, 8.0 Hz), 8.07 (1H, dd, J=1.5, 8.6 Hz), 8.30 (1H, dd, J=2.4, 10.9 Hz), 8.35 (1H, d, J=8.0 Hz), 8.64 (1H, dd, J=1.5, 4.1 Hz), 13.47-13.53 (1H, bs).

Production Example 4

(3-Fluoro-1-oxypyridin-2-yl)-(3-fluorophenyl)-methanone 3.0 g of (3-fluorophenyl)-(3-fluoropyridin-2-yl)-methanone obtained by Production example 2 was dissolved in 30 mL of chloroform, added with 3.6 g of 3-chloro perbenzoic acid under ice-cooling, and the reaction solution was heated under reflux for 6 hours. After completion of the reaction, aqueous sodium hydrogen carbonate was added, extracted with ethyl acetate, and the organic layer was washed with water and dried over anhydrous magnesium sulfate. The solvent was evaporated, and the resulting residue was purified and separated by silica gel column chromatography (ethyl acetate: methanol=19:1), to afford 2.1 g of the title compound as colorless needle crystals.

$^1$H-NMR (400 MHz, $CDCl_3$) δ 7.21 (1H, ddd, J=0.7, 6.7, 8.9 Hz), 7.35 (1H, ddt, J=1.2, 2.6, 8.0 Hz), 7.40 (1H, dt, J=6.7, 8.9 Hz), 7.49 (1H, dt, J=5.4, 8.0 Hz), 7.58 (1H, ddd, J=1.2, 2.6, 8.9 Hz), 7.62 (1H, dt, J=1.2, 8.0 Hz), 8.14 (1H, dt, J=0.7, 6.7 Hz).

Production Example 5

5-Fluoro-6-(3-fluorobenzoyl)-pyridine-2-carbonitrile

To 20 mL of a solution of 2.1 g of (3-fluoro-1-oxypyridin-2-yl)-(3-fluorophenyl)-methanone obtained by Production example 4 in acetonitrile were added 6.0 mL of trimethylsilylcyanide and 1.7 mL of dimethylcarbamoyl chloride, and heated under reflux for 8 hours. After completion of the reaction was added aqueous sodium hydrogen carbonate and extracted with ethyl acetate, and the organic layer was washed with water, and dried over anhydrous magnesium sulfate. The solvent was evaporated, and the resulting residue was purified and separated by silica gel column chromatography (ethyl acetate:n-hexane=1:9), to afford 1.0 g of a crude product of the title compound as a colorless oil.

Example 6

3-(3-Fluorophenyl)-1H-pyrazolo[4,3-b]pyridine-5-carbonitrile

From 1.0 g of crude 5-fluoro-6-(3-fluorobenzoyl)-pyridine-2-carbonitrile, 280 mg of the title compound was obtained as a pale yellow powder in accordance with Production example 3.

$^1$H-NMR (400 MHz, DMSO-$D_6$) δ 7.28 (1H, dt, J=2.4, 8.0 Hz), 7.61 (1H, dt, J=6.4, 8.0 Hz), 7.98 (1H, dt, J=8.5 Hz), 8.16 (1H, dd, J=2.4, 10.6 Hz), 8.28 (1H, d, J=8.0 Hz), 8.32 (1H, d, J=8.5 Hz), 13.95-14.20 (1H, bs).

Example 7

3-(3-Fluorophenyl)-1H-pyrazolo[4,3-b]pyridine-5-carboxylic acid 140 mg of 3-(3-fluorophenyl)-1H-pyrazolo[4,3-b]-pyridine-5-carbonitrile was added to a mixed solution of 1 mL water, 1 mL concentrated sulfuric acid and 1 mL glacial acetic acid, and heated under 100° C. for 3 hours. The reaction solution was added with 25 mL of ice-cooled water, neutralized with sodium hydrogen carbonate, and the precipitated crystals were collected by filtration. The crystals collected by filtration were washed with cold water, and dried under reduced pressure, to give 150 mg of a crude product of the title compound as a colorless powder.

$^1$H-NMR (400 MHz, DMSO-$D_6$) δ 7.17 (1H, dt, J=2.8, 8.1 Hz), 7.52 (1H, dt, J=6.8, 8.1 Hz), 7.89 (1H, d, J=9.0 Hz), 7.95 (1H, d, J=9.0 Hz), 8.38 (1H, d, J=8.1 Hz), 8.40 (1H, bd, J=11.3 Hz).

Production Example 8

(3-Fluoropyridin-2-yl)-(naphthalen-2-yl)-methanol

In the manner as described in Production example 1 while using 5.2 mL of 3-fluoropyridine and 10.2 g of 2-naphthaldehyde as starting materials, 3.8 g of the title compound was obtained as pale yellow needle crystals.

$^1$H-NMR (400 MHz, $CDCl_3$) δ 5.34 (1H, d, J=6.8 Hz), 6.17 (1H, d, J=6.8 Hz), 7.29 (1H, dd, J=4.9, 8.6 Hz), 7.36 (1H, dt, J=1.0, 8.6 Hz), 7.42-7.50 (3H, m), 7.77-7.84 (1H, m), 7.79 (1H, d, J=8.5 Hz), 7.83 (1H, d, J=8.5 Hz), 7.88 (1H, s), 8.45 (1H, dt, J=1.0, 4.9 Hz)

Production Example 9

(3-Fluoropyridin-2-yl)-(naphthalen-2-yl)-methanone

From 3.8 g of (3-fluoropyridine2-yl)-(naphthalene-2-yl)-methanol, 3.4 g of the title compound was obtained as colorless needle crystals in accordance with Production example 2.

$^1$H-NMR (400 MHz, $CDCl_3$) δ 7.54 (1H, dt, J=1.3, 7.4 Hz), 7.55 (1H, dd, J=4.6, 8.8 Hz), 7.62 (1H, dt, J=1.3, 8.8 Hz), 7.64 (1H, dt, J=1.3, 7.4 Hz), 7.90 (1H, bd, J=7.4 Hz), 7.91 (1H, bd, J=7.4 Hz), 7.94 (1H, d, J=8.6 Hz), 8.07 (1H, dd, J=1.5, 8.6 Hz), 8.36 (1H, d, J=1.5 Hz), 8.58 (1H, dt, J=1.3, 4.6 Hz).

Example 10

3-(Naphthalen-2-yl)-1H-pyrazolo[4,3-b]pyridine

From 1.2 g of (3-fluoropyridin-2-yl)-(naphthalen-2-yl)-methanone, 460 mg of the title compound was obtained as colorless needle crystals in the same manner as described in Production example 3.

$^1$H-NMR (400 MHz, DMSO-$D_6$) δ 7.44 (1H, dd, J=4.1, 8.8 Hz), 7.53 (1H, t, J=8.5 Hz), 7.55 (1H, t, J=8.5 Hz), 7.84 (1H, bd, J=8.8 Hz), 8.03 (2H, d, J=8.5 Hz), 8.09 (1H, dd, J=0.6, 8.8 Hz), 8.57 (1H, dd, J=1.8, 8.8 Hz), 8.69 (1H, dd, J=0.6, 4.1 Hz), 9.17 (1H, d, J=1.8 Hz).

Production Example 11

(3-Fluoro-1-oxypyridin-2-yl)-naphthalen-2-yl-methanone

From 1.5 g of (3-fluoropyridin-2-yl)-(naphthalen-2-yl)-methanone obtained by Production example 9, 0.8 g of the title compound was obtained as colorless needle crystals in accordance with Production example 4.

$^1$H-NMR (400 MHz, $CDCl_3$) δ 7.24 (1H, ddd, J=0.8, 6.5, 8.8 Hz), 7.41 (1H, dt, J=6.5, 8.8 Hz), 7.55 (1H, dt, J=1.4, 7.4 Hz), 7.63 (1H, dt, J=1.4, 7.4 Hz), 7.89 (1H, bd, J=7.4 Hz), 7.91 (1H, bd, J=7.4 Hz), 7.95 (1H, d, J=8.8 Hz), 8.01 (1H, dd, J=1.5, 8.8 Hz), 8.18 (1H, dt, J=0.8, 6.5 Hz), 8.27 (1H, d, J=1.5 Hz).

Production Example 12

5-Fluoro-6-(naphthalene-2-carbonyl)-pyridine-2-carbonitrile

From 780 mg of (3-fluoro-1-oxypyridin-2-yl)-naphthalen-2-yl-methanone obtained by Production example 11, 550 mg of a crude product of the title compound was obtained as a pale yellow oil in the same manner as described in Production example 5.

$^1$H-NMR (400 MHz, $CDCl_3$) δ 7.49 (1H, dd, J=8.1, 9.5 Hz), 7.52-7.57 (2H, m), 7.57 (1H, dd, J=2.0, 8.8 Hz), 7.77 (1H, dd, J=3.3, 8.1 Hz), 7.82-7.86 (1H, m), 7.85 (1H, d, J=8.8 Hz), 7.89-7.93 (1H, m), 8.13 (1H, d, J=2.0 Hz).

Production Example 13

3-(Naphthalen-2-yl)-1-trityl-1H-pyrazolo[4,3-b]pyridine

From 440 mg of 3-(naphthalen-2-yl)-1H-pyrazolo[4,3-b]pyridine, 800 mg of the title compound was obtained as a colorless powder in accordance with Production example 22.

$^1$H-NMR (400 MHz, $CDCl_3$) δ 6.66 (1H, dd, J=1.1, 8.8 Hz), 6.95 (1H, dd, J=4.2, 8.8 Hz), 7.25-7.34 (15H, m), 7.43-7.51 (2H, m), 7.83 (1H, dd, J=2.3, 7.9 Hz), 7.88 (1H, d, J=8.5 Hz), 8.00 (1H, dd, J=2.3, 7.9 Hz), 8.42 (1H, dd, J=2.0, 8.5 Hz), 8.62 (1H, dd, J=1.1, 4.2 Hz), 9.18 (1H, d, J=2.0 Hz).

Production Example 14

3-(Naphthalen-2-yl)-1-trityl-1H-pyrazolo[4,3-b]pyridine-4-oxide

From 800 mg of 3-(naphthalen-2-yl)-1-trityl-1H-pyrazolo[4,3-b]pyridine, 500 mg of the title compound was obtained as colorless crystals in the same manner as described in Production example 4.

$^1$H-NMR (400 MHz, DMSO-$D_6$) δ 6.36 (1H, d, J=8.6 Hz), 7.10 (1H, dd, J=5.8, 8.6 Hz), 7.24 (6H, bd, J=6.9 Hz), 7.30-7.40 (9H,m), 7.50-7.55 (2H,m), 7.90 (1H, d, J=8.6 Hz), 7.90-7.94 (2H,m), 7.99 (1H, dd, J=1.9, 8.6 Hz), 8.13 (1H, d, J=5.8 Hz), 8.60 (1H, d, J=1.9 Hz).

Production Example 15

3-(Naphthalen-2-yl)-1-trityl-1H-pyrazolo[4,3-b]pyridine-5-carbonitrile

From 480 mg of 3-naphthalen-2-yl-1-trityl-1H-pyrazolo[4,3-b]pyridine-4-oxide, 380 mg of the title compound was obtained as pale yellow crystals in the same manner as described in Production example 5.

$^1$H-NMR (400 MHz, DMSO-$D_6$) δ 6.89 (1H, d, J=9.1 Hz), 7.23-7.28 (6H,m), 7.33-7.42 (9H,m), 7.54-7.59 (2H,m), 7.77 (1H, d, J=9.1 Hz), 7.92-7.97 (1H,m), 8.02-8.07 (1H,m), 8.04 (1H, d, J=8.7 Hz), 8.25 (1H, dd, J=1.8, 8.7 Hz), 8.97 (1H, d, J=1.8 Hz).

Example 16

3-(Naphthalen-2-yl)-1H-pyrazolo[4,3-b]pyridine-5-carbonitrile

To 10 mL of a solution containing 360 mg of 3-naphthalen-2-yl-1-trityl-1H-pyrazolo[4,3-b]pyridine-5-carbonitrile obtained by Production example 15 in dichloromethane, 3 mL of trifluoroacetic acid was added at room temperature and stirred for 2 hours. The reaction solution was added with aqueous sodium hydrogen carbonate, extracted with ethyl acetate, washed with water, and dried over magnesium sulfate. After evaporating, the residue was purified and separated by silica gel column chromatography (ethyl acetate:n-hexane=3:1), to afford 180 mg of the title compound as a colorless powder.

$^1$H-NMR (400 MHz, DMSO-$D_6$) δ 7.53-7.60 (2H, m), 7.94-7.99 (1H, m), 8.00 (1H, d, J=8.6 Hz), 8.05-8.10 (1H, m), 8.08 (1H, d, J=8.6 Hz), 8.33 (1H, d, J=8.6 Hz), 8.51 (1H, dd, J=1.3, 8.6 Hz), 9.02 (1H, d, J=1.3 Hz), 14.02-14.13 (1H, bs).

The title compound was also synthesized in an alternative method as described below.

Using 550 mg of crude 5-fluoro-6-(naphthalene-2-carbonyl)-pyridine-2-carbonitrile obtained by Production example 12 as a starting material, 3 mg of the title compound was obtained in the method similar to Production example 3.

Example 17

3-(Naphthalen-2-yl)-1H-pyrazolo[4,3-b]pyridine-5-carboxylic acid

From 180 mg of 3-(naphthalen-2-yl)-1H-pyrazolo[4,3-b]pyridine-5-carbonitrile obtained by Example 16, 150 mg of the title compound was obtained as a colorless powder in the same manner as described in Example 7.

$^1$H-NMR (400 MHz, DMSO-$D_6$) δ 7.51-7.59 (2H, m), 7.95 (1H, bd, J=7.9 Hz), 8.03 (1H, bd, J=7.9 Hz), 8.06 (1H, d, J=8.6 Hz), 8.12 (1H, d, J=8.6 Hz), 8.20 (1H, d, J=8.6 Hz), 8.63 (1H, dd, J=1.6, 8.6 Hz), 9.18 (1H, d, J=1.6 Hz), 13.12-13.27 (1H, bs), 13.81 (1H, s).

Production Example 18

(3-Fluorophenyl)-(3-fluoropyridin-4-yl)-methanol

Under nitrogen atmosphere, a solution of 6.1 mL of diisopropylamine in 100 ml of dehydrated tetrahydrofuran was cooled to −70° C., added with 28 mL of 1.56 M n-butyllithium in hexane, and stirred at 0° C. for 15 minutes. After cooling to −70° C., 3.4 mL of 3-fluoropyridine was added dropwise, stirred at the same temperature for 4 hours, and then added dropwise with 4.8 mL of 3-fluorobenzaldehyde. After stirring for 1 hour, aqueous ammonium chloride and ethyl acetate were successively added, and the reaction solution was recovered to room temperature. The organic layer was extracted, washed with water, and dried over anhydrous magnesium sulfate. The solvent was evaporated, and the resulting residue was recrystallized from diisopropyl ether, to afford 7.1 g of the title compound as colorless cubic crystals.

$^1$H-NMR (400 MHz, $CDCl_3$) δ 2.70-3.10 (1H, bs), 6.13 (1H, s), 7.00 (1H, ddd, J=0.9, 1.7, 8.3 Hz), 7.13 (1H, dt, J=1.7, 9.2 Hz), 7.18 (1H, dt, J=0.9, 8.3 Hz), 7.32 (1H, dt, J=5.8, 8.3 Hz), 7.57 (1H, t, J=5.5 Hz), 8.37 (1H, d, J=1.4 Hz), 8.43 (1H, d, J=5.5 Hz).

Production Example 19

(3-Fluorophenyl)-(3-fluoropyridin-4-yl)-methanone

From 3.5 g of (3-fluorophenyl)-(3-fluoropyridin-4-yl)-methanol, 3.5 g of the title compound was obtained as colorless needle crystals in accordance with Production example 2.

$^1$H-NMR (400 MHz, $CDCl_3$) δ 7.37 (1H, bt, J=7.8 Hz), 7.43 (1H, t, J=5.4 Hz), 7.50 (1H, dt, J=5.4, 7.8 Hz), 7.54-7.60 (2H, m), 8.62 (1H, dd, J=1.1, 4.8 Hz), 8.66 (1H, d, J=1.1 Hz).

Production Example 20

(3-fluoro-1-oxypyridin-4-yl)-(3-fluorophenyl)-methanone

From 1.8 g of (3-fluorophenyl)-(3-fluoropyridine-4-yl)-methanone, 1.65 g of the title compound was obtained as colorless needle crystals in accordance with Production example 4.

$^1$H-NMR (400 MHz, $CDCl_3$) δ 7.37 (1H, ddt, J=1.2, 2.5, 8.1 Hz), 7.48-7,59 (4H, m), 8.13 (1H, ddd, J=1.0, 1.5, 6.8 Hz), 8.20 (1H, dt, J=1.5, 5.3 Hz).

Example 21

3-(3-Fluorophenyl)-1H-pyrazolo[3,4-c]pyridine

From 2.0 g of (3-fluorophenyl)-(3-fluoropyridin-4-yl)-methanone obtained by Production example 19, 490 mg of the title compound was obtained as colorless powder in accordance with Production example 3.

$^1$H-NMR (400 MHz, DMSO-$D_6$) δ 7.26 (1H, dt, J=2.6, 8.2 Hz), 7.58 (1H, dt, J=6.6, 8.2 Hz), 7.78 (1H, dd, J=2.6, 10.4 Hz), 7.89 (1H, d, J=8.2 Hz), 8.10 (1H, dd, J=1.2, 5.9 Hz), 8.31 (1H, d, J=5.9 Hz), 9.10 (1H, d, J=1.2 Hz).

Production Example 22

3-(3-fluorophenyl)-1-trityl-1H-pyrazolo[3,4-c]pyridine

To a solution of 2.43 g of 3-(3-fluorophenyl)-1H-pyrazolo[3,4-c]pyridine produced in Production example 21 in 10 mL of N,N-dimethylformamide was added 80 mg of ice-cooled 60% sodium hydride (oily). After stirring 30 minutes, 500 mg of chlorotriphenylmethane was added and stirred at room temperature for 1 hour. The reaction solution was added with water, extracted with ethyl acetate, dried over anhydrous sodium sulfate, and the solvent was evaporated. The residue was added with diisopropyl ether and filtered, to afford 560 mg of the title compound as a colorless powder.

$^1$H-NMR (400 MHz, $CDCl_3$) δ 7.20-7.24 (6H, m), 7.26 (1H, dt, J=2.5, 8.1 Hz), 7.30-7.40 (9H, m), 7.55 (1H, dt, J=6.4, 8.1 Hz), 7.64 (1H, ddd, J=1.4, 2.5, 10.0 Hz), 7.74 (1H, d, J=1.4 Hz), 7.78 (1H, dt, J=1.4, 8.1 Hz), 8.13 (1H, dd, J=1.4, 5.7 Hz), 8.24 (1H, d, J=5.7 Hz).

Production Example 23

3-(3-Fluorophenyl)-1-trityl-1H-pyrazolo[3,4,-c]pyridine-6-oxide

From 300 mg of 3-(3-fluorophenyl)-1-trityl-1H-pyrazolo[3,4-c]pyridine, 285 mg of the title compound was obtained as a colorless powder in the same manner as described in Production example 4.

$^1$H-NMR (400 MHz, $CDCl_3$) δ 7.01 (1H, d, J=1.4 Hz), 7.18-7.24 (6H, m), 7.28 (1H, dt, J=2.5, 8.0 Hz), 7.33-7.42 (9H, m), 7.55 (1H, dt, J=6.0, 8.0 Hz), 7.61 (1H, ddd, J=1.4, 2.5, 10.1 Hz), 7.72 (1H, dt, J=1.4, 8.0 Hz), 7.91 (1H, dd, J=1.4, 7.1 Hz), 8.14 (1H, d, J=7.1 Hz).

Production Example 24

3-(3-Fluorophenyl)-1-trityl-1H-pyrazolo[3,4-c]pyridine-7-carbonitrile

From 200 mg of 3-(3-fluorophenyl)-1-trityl-1H-pyrazolo[3,4,-c]pyridine-6-oxide, 150 mg of the title compound was obtained as a colorless powder in accordance with Production example 5.

$^1$H-NMR (400 MHz, $CDCl_3$) δ 7.15-7.21 (6H, m), 7.28-7.39 (10H, m), 7.57 (1H, dt, J=6.4, 8.0 Hz), 7.59 (1H, ddd, J=1.3, 2.5, 10.7 Hz), 7.72 (1H, dt, J=1.3, 8.0 Hz), 8.52 (1H, d, J=5.7 Hz), 8.60 (1H, d, J=5.7 Hz).

Production Example 25

(3-Fluoropyridin-4-yl)-(naphthalen-2-yl)-methanol

Using 5.2 mL of 3-fluoropyridine and 10.2 g of 2-naphthaldehyde as starting materials, 17.0 g of the title compound was obtained as a colorless powder in the same manner as described in Production example 18.

$^1$H-NMR (400 MHz, $CDCl_3$) δ 2.89 (1H, s), 6.27 (1H, s), 7.44-7.51 (3H, m), 7.64 (1H, t, J=5.7 Hz), 7.80-7.85 (3H, m), 7.87 (1H, bs), 8.35 (1H, d, J=2.0 Hz), 8.42 (1H, dt, J=1.0, 4.9 Hz).

Production Example 26

(3-Fluoropyridin-4-yl)-(naphthalen-2-yl)-methanone

From 17.0 g of (3-fluoropyridin-4-yl)-(naphthalen-2-yl)-methanol, 15.1 g of the title compound was obtained as colorless needle crystals in accordance with Production example 2.

$^1$H-NMR (400 MHz, $CDCl_3$) δ 7.49 (1H, dd, J=4.6, 5.5 Hz), 7.58 (1H, dt, J=1.3, 7.4 Hz), 7.66 (1H, dt, J=1.3, 7.4 Hz), 7.93 (2H, bd, J=7.4 Hz), 7.97 (1H, d, J=8.9 Hz), 8.01 (1H, dd, J=1.5, 8.9 Hz), 8.22 (1H, bd, J=1.5 Hz), 8.64 (1H, dd, J=1.3, 4.6 Hz), 8.68 (1H, d, J=1.3 Hz).

Production Example 27

(3-Fluoro-1-oxypyridin-4-yl)-(naphthalen-2-yl)-methanone

From 1.5 g of (3-fluoropyridin-4-yl)-naphthalen-2-yl-methanone, 1.3 g of the title compound was obtained as a colorless powder in accordance with Production example 4.

$^1$H-NMR (400 MHz, $CDCl_3$) δ 7.60 (1H, dd, J=6.8, 7.8 Hz), 7.61 (1H, dt, J=1.5, 7.5 Hz), 7.68 (1H, dt, J=1.5, 7.5 Hz), 7.93 (1H, bd, J=7.5 Hz), 7.95 (1H, bd, J=7.5 Hz), 7.97 (1H, d, J=8.8 Hz), 7.98 (1H, d, J=8.8 Hz), 8.17 (1H, ddd, J=0.6, 1.8, 6.8 Hz), 8.25 (1H, dd, J=1.8, 5.0 Hz), 8.26 (1H, s).

Production Example 28

(2-Chloro-5-fluoropyridin-4-yl)-(naphthalen-2-yl)-methanone

A solution containing 1.4 g of (3-fluoro-1-oxypyridin-4-yl)-(naphthalen-2-yl)-methanone obtained by Production example 27 in 10 mL of phosphorus oxychloride was heated under nitrogen atmosphere at 80° C. for 1.5 hours. The reaction solution was allowed to cool to room temperature, and the excess phosphorus oxychloride was distilled off under reduced pressure. The resulting residue was then added with aqueous sodium hydrogen carbonate, extracted with ethyl acetate, and the organic layer was washed with water and dried over anhydrous magnesium sulfate. The solvent was evaporated, and the resulting residue was purified and separated by silica gel column chromatography (ethyl acetate:n-hexane=19:1), to afford 680 mg of the title compound as colorless needle crystals and 550 mg of (2-chloro-3-fluoropyridin-4-yl)-naphthalen-2-yl-methanone described in Production example 29 described below as colorless needle crystals.

$^1$H-NMR (400 MHz, $CDCl_3$) δ 7.50 (1H, d, J=4.6 Hz), 7.60 (1H, t, J=7.5 Hz), 7.68 (1H, t, J=7.5 Hz), 7.93 (1H, d, J=7.5 Hz), 7.95 (1H, d, J=7.5 Hz), 7.98 (1H, d, J=9.1 Hz), 7.99 (1H, d, J=9.1 Hz), 8.21 (1H, bs), 8.45 (1H, s).

Production Example 29

(2-Chloro-3-fluoropyridin-4-yl)-(naphthalen-2-yl)-methanone $^1$H-NMR (400 MHz, $CDCl_3$) δ 7.41 (1H, t, J=4.6 Hz), 7.60 (1H, t, J=7.5 Hz), 7.68 (1H, t, J=7.5 Hz), 7.93 (1H, d, J=7.5 Hz), 7.95 (1H, d, J=7.5 Hz), 7.98 (1H, d, J=9.1 Hz), 7.99 (1H, d, J=9.1 Hz), 8.21 (1H, bs), 8.41 (1H, d, J=4.6 Hz).

Production Example 30

2-Benzyl-5-phenyl-2H-pyrazol-3-ylamine 2.9 g of α-cyanoacetophenone and 3.9 g of benzyl hydrazine dihydrochloride were suspended in 50 mL of ethanol. The reaction solution was added with 6.0 ml of triethylamine at room temperature, and heated under reflux for 4 hours. The solvent was evaporated, and the residue was added with water, extracted with ethyl acetate, and dried over anhydrous sodium sulfate. After distilling off the solvent, the residue was purified and separated by silica gel column chromatography (ethyl acetate:n-hexane=1:4), to afford 4.1 g of the title compound as a yellow needle powder.

$^1$H-NMR (400 MHz, $CDCl_3$) δ 3.40 (2H, bs), 5.28 (2H, s), 5.92 (1H, s), 7.22 (2H, d, J=8.0 Hz), 7.28 (2H, t, J=8.0 Hz), 7.32-7.37 (2H, m), 7.38 (2H, t, J=8.0 Hz), 7.77 (2H, d, J=8.0 Hz).

Production Example 31

1-Benzyl-3-phenyl-1H-pyrazolo[3,4-b]pyridine-5-carbonitrile 1.65 g of 2-cyano-3,3-dimethoxy-1-propenolate sodium was suspended in 30 mL of methanol, and the reaction solution was added successively with 2.5 g of 2-benzyl-5-phenyl-2H-pyrazole-3-ylamine obtained by Production example 30 and 1.5 mL of concentrated hydrochloric acid at room temperature, and heated under reflux for 3 hours. The reaction solution was added with aqueous sodium hydrogen carbonate, extracted with ethylacetate, and dried over anhydrous sodium sulfate. After distilling off the solvent, the residue was purified and separated by silica gel column chromatography (ethyl acetate:n-hexane=1:9), to afford 0.8 g of the title compound as a colorless powder.

$^1$H-NMR (400 MHz, $CDCl_3$) δ 5.78 (2H, s), 7.28-7.37 (3H, m), 7.43 (2H, bd, J=7.2 Hz), 7.47 (2H, t, J=7.2 Hz), 7.54 (2H, t, J=7.2 Hz), 7.91 (2H, bd, J=7.2 Hz), 8.66 (1H, d, J=1.9 Hz), 8.78 (1H, d, J=1.9 Hz).

Production Example 32

1-Benzyl-3-phenyl-1H-pyrazolo[3,4-b]pyridine-5-carboxylic acid

Using 600 mg of 1-benzyl-3-phenyl-1H-pyrazolo[3,4-b]pyridine-5-carbonitrile as a starting material, 500 mg of the title compound was obtained as a colorless powder in the same manner as described in Example 7.

$^1$H-NMR (400 MHz, DMSO-$D_6$) δ 5.78 (2H, s), 7.24-7.30 (5H, m), 7.47 (1H, t, J=8.6 Hz), 7.56 (2H, t, J=8.6 Hz), 8.01 (2H, d, J=8.6 Hz), 8.97 (1H, d, J=2.0 Hz), 9.12 (1H, d, J=2.0 Hz).

Production Example 33

1-Benzyl-3-phenyl-1H-pyrazolo[3,4-b]pyridine-5-carboxylic acid Methyl Ester 100 mg of 1-benzyl-3-phenyl-1H-pyrazolo[3,4-b]pyridine-5-carboxylic acid obtained by Example 32 was dissolved in 5 mL of N,N-dimethylformamide, added with 60 mg of potassium carbonate and 30 μl of methyl iodide, and stirred all day and night at room temperature. The residue was added with water, extracted with ethyl acetate, and dried over anhydrous sodium sulfate. After distilling off the solvent, the reaction was crystallized from diisopropyl ether, to afford 100 mg of the title compound as a pale brown powder.

$^1$H-NMR (400 MHz, DMSO-D$_6$) δ 4.00 (3H, s), 5.80 (2H, s), 7.25-7.34 (3H, m), 7.41-7.48 (3H, m), 7.53 (2H, t, J=7.6 Hz), 7.98 (2H, d, J=7.6 Hz), 9.01 (1H, d, J=1.8 Hz), 9.22 (1H, d, J=1.8 Hz).

Example 34

3-Phenyl-1H-pyrazolo[3,4-b]pyridine-5-carboxylic acid 100 mg of 1-benzyl-3-phenyl-1H-pyrazolo[3,4-b]pyridine-5-carboxylic acid obtained by Production example 33 was dissolved in a mixed solvent of 2 mL sulfuric acid/4 mL acetic acid/2 mL water, and added with 300 mg of chromic acid under ice-cooling. The reaction solution was heated at 70° C. for 1 hour, allowed to cool to room temperature, added with sodium hydrogen carbonate, extracted with ethyl acetate, and dried over anhydrous sodium sulfate. After distilling off the solvent, the residue was added with diisopropyl ether, followed by filtration, to afford 60 mg of the title compound as a colorless powder.

$^1$H-NMR (400 MHz, DMSO-D$_6$) δ 7.46 (1H, t, J=7.6 Hz), 7.56 (2H, t, J=7.6 Hz), 8.02 (2H, d, J=7.6 Hz), 8.94 (1H, d, J=2.0 Hz), 9.06 (1H, d, J=2.0 Hz), 13.20-13.35 (1H, bs), 14.18 (1H, s).

Production Example 35

3-(3-Fluorophenyl)-1-trityl-1H-pyrazolo[4,3-b]pyridine

From 220 mg of 3-(3-fluorophenyl)-1H-pyrazolo[4,3-b]pyridine obtained by Production example 3, 460 mg of the title compound was obtained as a colorless powder in accordance with Production example 22.

$^1$H-NMR (400 MHz, CDCl$_3$) δ 6.64 (1H, dd, J=1.8, 8.7 Hz), 6.93 (1H, dd, J=4.6, 8.7 Hz), 7.02 (1H, dt, J=2.5, 8.0 Hz), 7.21-7.26 (6H, m), 7.27-7.33 (9H, m), 7.40 (1H, dt, J=6.4, 8.0 Hz), 8.19 (1H, dd, J=2.5, 10.3 Hz), 8.31 (1H, d, J=8.0 Hz), 8.57 (1H, dd, J=1.8, 4.6 Hz).

Production Example 36

3-(3-Fluorophenyl)-1-trityl-1H-pyrazolo[4,3-b]pyridine-4-oxide

From 480 mg of 3-(3-fluorophenyl)-1-trityl-1H-pyrazolo[4,3-b]pyridine, 250 mg of the title compound was obtained as a colorless powder in the same manner as described in Production example 4.

$^1$H-NMR (400 MHz, CDCl$_3$) δ 6.36 (1H, d, J=8.8 Hz), 7.09 (1H, dd, J=6.2, 8.8 Hz), 7.17-7.24 (6H, m), 7.29-7.39 (10H, m), 7.42 (1H, dt, J=6.2, 8.2 Hz), 7.79 (1H, d, J=8.2 Hz), 7.91 (1H, bd, J=11.3 Hz), 8.13 (1H, d, J=6.2 Hz).

Production Example 37

3-(3-Fluorophenyl)-5-chloro-1-trityl-1H-pyrazolo[4,3-b]pyridine

To 100 mg of 3-(3-fluorophenyl)-1-trityl-1H-pyrazolo[4,3-b]pyridine-4-oxide in toluene was acted phosphorus oxychloride in toluene in the same manner as described in Production example 28, to afford 30 mg of 3-(3-fluorophenyl)-5-chloro-1H-pyrazolo[4,3-b]pyridine described in Example 38 described below as a colorless powder, as well as 60 mg of a crude product of the title compound as a colorless powder.

$^1$H-NMR (400 MHz, CDCl$_3$) δ 6.54 (1H, d, J=8.9 Hz), 6.92 (1H, d, J=8.9 Hz), 7.03 (1H, dt, J=2.5, 8.1 Hz), 7.17-7.23 (6H, m), 7.24-7.35 (9H, m), 7.40 (1H, dt, J=6.0, 8.1 Hz), 8.10 (1H, ddd, J=1.9, 2.5, 10.7 Hz), 8.25 (1H, bd, J=8.1 Hz).

Example 38

3-(3-Fluorophenyl)-5-chloro-1H-pyrazolo[4,3-b]pyridine $^1$H-NMR (400 MHz, CDCl$_3$) δ 7.11 (1H, ddt, J=1.2, 2.8, 8.0 Hz), 7.37 (1H, d, J=8.7 Hz), 7.48 (1H, dt, J=6.0, 8.0 Hz), 7.82 (1H, d, J=8.7 Hz), 8.20 (1H, ddd, J=1.5, 2.8, 10.4 Hz), 8.31 (1H, bd, J=8.0 Hz), 10.20-10.40 (1H, bs).

Example 39

1-[3-(3-Fluorophenyl)-1H-pyrazolo[4,3-b]pyridin-5-yl]ethanone 50 mg of crude 3-(3-fluorophenyl)-5-chloro-1-trityl-1H-pyrazolo[4,3-b]pyridine obtained by Production example 37 and 35 μl of tributyl(1-ethoxyvinyl) tin was dissolved in 2 mL of N,N-dimethylformamide, added with 10 mg of tetrakis (triphenylphosphine)palladium(0), and heated at 100° C. for 15 minutes. After completion of the reaction, the reaction solution was added with water and extracted with ethyl acetate. The organic layer was washed with water, dried over magnesium sulfate, and the solvent was evaporated. The residue was dissolved in a mixed solvent of 10 mL THF-1 mL water, added with 0.5 mL of SN hydrochloric acid and heated at 90° C. for 10 minutes. After completion of the reaction, the reaction solution was added with aqueous sodium hydrogen carbonate and extracted with ethyl acetate. The organic layer was washed with water, dried over magnesium sulfate, and the solvent was evaporated. The residue was dissolved in 3 mL of dichloromethane, added with 0.5 mL of trifluoroacetic acid and stirred at room temperature for 5 minutes. The reaction solution was added with aqueous sodium hydrogen carbonate and extracted with ethyl acetate. The organic layer was washed with water, dried over magnesium sulfate, and the solvent was evaporated. The resulting residue was purified and separated by silica gel column chromatography (ethyl acetate:n-hexane=3:7), to afford 7 mg of the title compound as a colorless powder.

$^1$H-NMR (400 MHz, DMSO-d$_6$) δ 2.78 (3H, s), 7.27 (1H, dt, J=2.6, 7.9 Hz), 7.61 (1H, dt, J=6.3, 7.9 Hz), 8.04 (1H, d, J=8.9 Hz), 8.20 (1H, d, J=8.9 Hz), 8.33 (1H, ddd, J=1.3, 2.6, 10.4 Hz), 8.40 (1H, bd, J=7.9 Hz), 13.82-13.96 (1H, bs).

Production Example 40

[3-(3-Fluorophenyl)-1-trityl-1H-pyrazolo[4,3-b]pyridin-5-yl]acetate 50 mg of 3-(3-fluorophenyl)-1-trityl-1H-pyrazolo[4,3-b]pyridine-4-oxide obtained by Production example 36 was suspended in 2 mL of acetic anhydride, and the reaction solution was heated at 80° C. for 15 minutes. The reaction solution was allowed to cool to room temperature, and the residue obtained by distilling off excess acetic anhydride under reduce pressure was added with aqueous sodium hydrogen carbonate, extracted with ethyl acetate. The organic layer was washed with water, and dried over anhydrous magnesium sulfate. The solvent was evaporated, and the resulting residue was subjected to silica gel column chromatography (ethyl acetate:n-hexane=3:17), to obtain a mixture of the title compound and [3-(3-fluorophenyl)-1-trityl-1H-pyrazolo[4,3-b]pyridin-6-yl]acetate described in Production example 41 which was inseparable from the title compound as a colorless powder. Generated ratio: about 6:4, yield: 62 mg.

$^1$H-NMR (400 MHz, $CDCl_3$) δ 2.38 (3H, s), 6.65 (1H, d, J=9.1 Hz), 6.71 (1H, d, J=9.1 Hz), 7.02 (1H, dt, J=2.7, 8.0 Hz), 7.20-7.28 (6H, m), 7.28-7.34 (9H, m), 7.38 (1H, dt, J=5.8, 8.0 Hz), 8.10 (1H, ddd, J=1.8, 2.7, 10.7 Hz), 8.19 (1H, bd, J=8.0 Hz).

Production Example 41

[3-(3-Fluorophenyl)-1-trityl-1H-pyrazolo[4,3-b]pyridin-6-yl]acetate $^1$H-NMR (400 MHz, $CDCl_3$) δ 2.23 (3H, s), 6.38 (1H, d, J=2.0 Hz), 7.03 (1H, dt, J=2.7, 8.0 Hz), 7.20-7.28 (6H, m), 7.28-7.34 (9H, m), 7.40 (1H, dt, J=5.8, 8.0 Hz), 8.14 (1H, ddd, J=1.8, 2.7, 10.7 Hz), 8.26 (1H, bd, J=8.0 Hz), 8.36 (1H, d, J=2.0 Hz).

Example 42

3-(3-fluorophenyl)-1H-pyrazolo[4,3-b]pyridin-5-ol 62 mg of the mixture of [3-(3-fluorophenyl)-1-trityl-1H-pyrazolo[4,3-b]pyridin-5-yl]acetate and [3-(3-fluorophenyl)-1-trityl-1H-pyrazolo[4,3-b]pyridin-6-yl]acetate obtained by Production example 40 was treated with the method in accordance with Production example 16, and purified and separated by silica gel column chromatography (ethyl acetate:n-hexane=1:1-1:0), to obtain 10 mg of the title compound which is a high-polar component as a colorless powder and 10 mg of [3-(3-fluorophenyl)-1H-pyrazolo[4,3-b]pyridine-6-yl]acetate as described in Example 43 below which is a low-polar component as a colorless powder.

$^1$H-NMR (400 MHz, $CD_3OD$) δ 6.60 (1H, d, J=9.6 Hz), 7.15 (1H, dt, J=2.6, 8.0 Hz), 7.52 (1H, dt, J=5.9, 8.0 Hz), 7.56 (1H, bd, J=10.4 Hz), 7.62 (1H, bd, J=8.0 Hz), 7.88 (1H, d, J=9.6 Hz).

Example 43

[3-(3-Fluorophenyl)-1H-pyrazolo[4,3-b]pyridin-6-yl] acetate $^1$H-NMR (400 MHz, $CD_3OD$) δ 2.38 (3H, s), 7.12 (1H, dt, J=2.7, 8.4 Hz), 7.49 (1H, dt, J=6.1, 8.4 Hz), 7.80 (1H, d, J=2.1 Hz), 8.21 (1H, ddd, J=1.6, 2.7, 10.4 Hz), 8.27 (1H, dd, J=1.6, 8.4 Hz), 8.42 (1H, d, J=2.1 Hz).

Example 44

300 mg of 3-phenyl-1H-pyrazolo[3,4-b]pyridine-5-carboxylic acid obtained by Example 34 was dissolved in 5 mL of N,N-dimethylformamide solution, and each 0.5 mL was poured into 10 test tubes. Each test tube was added successively 130 μl of 1N amine solution in N,N-dimethylformamide, 130 μl of 1N 1-hydroxybenztriazole solution in N,N-dimethylformamide, 48 mg of 1-ethyl-3-(3-dimethylaminopropyl)carbodiimide hydrochloride and 90 μl diisopropylethylamine, subjected to sonication for 10 minutes, and left still all day and night. Each reaction solution was separated and purified by LC-MS [developing solvent: 0.1% trifluoroacetic acid-containing acetonitrile solution: 0.1% trifluoroacetic acid-containing aqueous solution=1:99-100:0/20 min. cycle, flowrate: 20 mL/mim: YMC Combiprep ODS-AM, 20 mmΦ×50 mm(Long)], blown with nitrogen, and the solvent was removed, to afford the following test compounds.

Example 45

3-Phenyl-1H-pyrazolo[3,4-b]pyridine-5-carboxylic acid Cyclopropylamide

MS (ESI)m/z 279 $MH^+$

Example 46

3-Phenyl-1H-pyrazolo[3,4-b]pyridine-5-carboxylic acid (pyridin-2-ylmethyl)-amide MS (ESI)m/z 330 $MH^+$

Example 47

3-Phenyl-1H-pyrazolo[3,4-b]pyridine-5-carboxylic acid (tetrahydrofuran-2-ylmethyl)-amide MS (ESI)m/z 323 $MH^+$

Example 48

3-Phenyl-1H-pyrazolo[3,4-b]pyridine-5-carboxylic acid (furan-2-ylmethyl)-amide MS (ESI)m/z 319 $MH^+$

Example 49

3-Phenyl-1H-pyrazolo[3,4-b]pyridine-5-carboxylic acid (1-methoxymethyl-propyl)-amide MS (ESI)m/z 325 $MH^+$

Example 50

3-Phenyl-1H-pyrazolo[3,4-b]pyridine-5-carboxylic acid (2-acetylamino-ethyl)-amide MS (ESI)m/z 324 $MH^+$

Example 51

3-Phenyl-1H-pyrazolo[3,4-b]pyridine-5-carboxylic acid (2-methylsulfanil-ethyl)-amide MS (ESI)m/z 313 $MH^+$

Example 52

3-Phenyl-1H-pyrazolo[3,4-b]pyridine-5-carboxylic acid (1-hydroxymethyl-3-methylsulfanil-propyl)-amide MS (ESI)m/z 357 $MH^+$

Example 53

3-Phenyl-1H-pyrazolo[3,4-b]pyridine-5-carboxylic acid (1-aza-bicyclo[2,2,2]octo-3-yl)-amide MS (ESI)m/z 348 $MH^+$ Example 54

3-Phenyl-1H-pyrazolo[3,4-b]pyridine-5-carboxylic acid (trans-4-hydroxycyclohexyl)-amide MS (ESI)m/z 337 $MH^+$ Example 55

3-(3-Fluorophenyl)-1H-pyrazolo[4,3-b]pyridine-5-carboxylic acid obtained by Example 7 was condensed with various kinds of amine in the same manner as described in Example 44, to afford the following test compounds.

Example 56

3-(3-Fluorophenyl)-1H-pyrazolo[4,3-b]pyridine-5-carboxylic acid Cyclopropylamide MS (ESI)m/z 297 $MH^+$ Example 57

3-(3-Fluorophenyl)-1H-pyrazolo[4,3-b]pyridine-5-carboxylic acid (furan-2-ylmethyl)-amide MS (ESI)m/z 337 $MH^+$ Example 58

3-(3-Fluorophenyl)-1H-pyrazolo[4,3-b]pyridine-5-carboxylic acid (tetrahydrofuran-2-ylmethyl)-amide MS (ESI)m/z 340 $MH^+$ Example 59

3-(3-Fluorophenyl)-1H-pyrazolo[4,3-b]pyridine-5-carboxylic acid (2-acetylaminoethyl)-amide MS (ESI)m/z 342 $MH^+$ Example 60

3-(3-Fluorophenyl)-1H-pyrazolo[4,3-b]pyridine-5-carboxylic acid (pyridin-2-ylmethyl)-amide MS (ESI)m/z 348 $MH^+$ Example 61

3-(3-Fluorophenyl)-1H-pyrazolo[4,3-b]pyridine-5-carboxylic acid (1-hydroxymethyl-2-methylpropyl)-amide MS (ESI)m/z 343 $MH^+$ Example 62

3-(3-Fluorophenyl)-1H-pyrazolo[4,3-b]pyridine-5-carboxylic acid (1-methoxymethylpropyl)-amide MS (ESI)m/z 343 $MH^+$ Example 63

3-(Naphthalen-2-yl)-1H-pyrazolo[4,3-b]pyridine-5-carboxylic acid obtained by Example 17 was condensed with various kinds of amine in the same manner as described in Example 44, to afford the following test compounds.

Example 64

3-(Naphthalen-2-yl)-1H-pyrazolo[4,3-b]pyridine-5-carboxylic acid cyclopropylamide MS (ESI)m/z 329 $MH^+$ Example 65

3-(Naphthalen-2-yl)-1H-pyrazolo[4,3-b]pyridine-5-carboxylic acid (furan-2-ylmethyl)-amide MS (ESI)m/z 369 $MH^+$ Example 66

3-(Naphthalen-2-yl)-1H-pyrazolo[4,3-b]pyridine-5-carboxylic acid (tetrahydrofuran-2-ylmethyl)-amide MS (ESI)m/z 373 $MH^+$ Example 67

3-(Naphthalen-2-yl)-1H-pyrazolo[4,3-b]pyridine-5-carboxylic acid (2-acetylaminoethyl)-amide MS (ESI)m/z 374 $MH^+$ Example 68

3-(Naphthalen-2-yl)-1H-pyrazolo[4,3-b]pyridine-5-carboxylic acid (pyridin-2-ylmethyl)-amide MS (ESI)m/z 380 $MH^+$ Example 69

3-(Naphthalen-2-yl)-1H-pyrazolo[4,3-b]pyridine-5-carboxylic acid (1-hydroxymethyl-2-methylpropyl)-amide MS (ESI)m/z 375 $MH^+$ Example 70

3-(Naphthalen-2-yl)-1H-pyrazolo[4,3-b]pyridine-5-carboxylic acid (1-methoxymethylpropyl)-amide MS (ESI)m/z 375 $MH^+$ Production Example 71

5-Fluoro-4-(naphthalene-2-carbonyl)pyridine-2-carbonitrile

To a solution of 300 mg of (3-fluoro-1-oxypyridin-4-yl) naphthalen-2-yl-methanone obtained by Production example 27 in 3 mL of acetonitrile were added 0.30 mL of trimethylcyanide and 0.51 mL of dimethylcarbamyl chloride at room temperature, and heated under reflux for a day. The solution was added with water, extracted with ethyl acetate, washed with saturated brine, and then dried over anhydrous magnesium sulfate. The solvent was evaporated, and the resulting crude product was purified and separated by silica gel column chromatography (ethyl acetate:n-hexane=1:3), to afford 11 mg of the title compound as colorless crystals.

$^1$H-NMR (400 MHz, $CDCl_3$) δ 7.60 (1H, ddd, J=0.8, 7.2, 8.0 Hz), 7.68 (1H, ddd, J=0.8, 7.2, 8.0 Hz), 7.88-8.00 (5H, m), 8.15 (1H, s), 8.75 (1H, s).

Production Example 72

3-Fluoro-4-(naphthalene-2-carbonyl)pyridine-2-carbonitrile

From 300 mg of (3-fluoro-1-oxypyridin-4-yl)naphthalen-2-yl-methanone, 230 mg of the title compound was obtained as colorless crystals in accordance with the method of Production example 71.

$^1$H-NMR (400 MHz, $CDCl_3$) δ 7.60 (1H, ddd, J=0.8, 7.2, 8.0 Hz), 7.68 (1H, ddd, J=0.8, 7.2, 8.0 Hz), 7.71 (1H, t, J=4.8 Hz), 7.91 (1H, s), 7.93 (1H, d, J=0.8 Hz), 7.95 (1H, dd, J=1.6, 8.0 Hz), 7.98 (1H, d, J=8.0 Hz), 7.88-8.00 (5H, m), 8.15 (1H, s), 8.73 (1H, dd, 0.8, 4.8 Hz).

Example 73

5-Chloro-3-(naphthalen-2-yl)-1H-pyrazolo[3,4-c]pyridine

A solution of 500 mg of (2-chloro-5-fluoropyridin-4-yl)-(naphthalen-2-yl)-methanone obtained by Production example 28 in 5 mL pyridine was added at room temperature with 0.26 mL of hydrazine monohydrate, and heated under reflux for a day. The reaction solution was evaporated, and the resulting crystals were washed successively with water and ethylacetate, to afford 350 mg of the title compound as pale yellow crystals.

$^1$H-NMR (400 MHz, DMSO-$D_6$) δ 7.54 (1H, td, J=1.6, 7.2 Hz), 7.57 (1H, td, J=1.6, 7.2 Hz), 7.95 (1H, dd, J=1.6, 8.4 Hz), 8.03 (1H, d, J=8.4 Hz), 8.17 (1H, d, J=8.4 Hz), 8.20 (1H, dd, J=1.6, 8.4 Hz), 8.42 (1H, d, J=1.6 Hz), 8.61 (1H, s), 8.95 (1H, d, J=1.6 Hz).

Production Example 74

5-Chloro-3-(naphthalen-2-yl)-1-trityl-1H-pyrazolo[3,4-c]pyridine

To a solution of 320 mg of 5-chloro-3-(naphthalen-2-yl)-1H-pyrazolo[3,4-c]pyridine obtained by Production example 73 in 3 mL of N,N-dimethylformamide was added 55 mg of sodium hydride at room temperature and stirred for 15 minutes at this temperature. Then the solution was added with 335 mg of trityl-chloride at this temperature and stirred for 1 hour at this temperature. Then water was added and diluted with ethyl acetate. After washing the suspension in ethyl acetate twice with saturated aqueous ammonium chloride and once with water, crystals were collected by filtration. The crystals were washed with ethyl acetate, to afford 335 mg of the title compound as colorless crystals.

$^1$H-NMR (400 MHz, DMSO-$D_6$) δ 7.24-7.41 (15H, m), 7.48 (1H, s), 7.51-7.59 (2H, m), 7.92 (1H, d, J=7.2 Hz), 7.96 (1H, d, J=8.8 Hz), 7.99 (1H, d, J=8.8 Hz), 8.15 (1H, d, J=7.2 Hz), 8.46 (1H, s), 8.57 (1H, s).

Example 75

3-(Naphthalen-2-yl)-1H-pyrazolo[3,4-c]pyridine-5-carbonitrile

From 11 mg of 5-fluoro-4-(naphthalen-2-carbonyl)pyridine-2-carbonitrile obtained by Production example 71, 9 mg of the title compound was obtained as colorless crystals in accordance with the method of Production example 3.

$^1$H-NMR (400 MHz, $CD_3OD$) δ 7.51-7.58 (2H, m), 7.90-7.93 (1H, m), 8.02 (1H, d, J=8.8 Hz), 8.04-8.07 (1H, m), 8.15 (1H, dd, J=1.6, 8.4 Hz), 8.51 (1H, s), 8.79 (1H, d, J=1.6 Hz), 9.12 (1H, d, J=1.6 Hz).

Production Example 76

(2-Chlorothiophen-3-yl)naphthalen-2-yl Methanol

Under nitrogen atmosphere, to a solution of 3.2 mL of 1.57 M n-butyllithium in hexane in 7 mL of diethyl ether was added a solution of 1.00 g of 3-bromo-2-chlorothiophene in 8 mL diethyl ether at −78° C., and stirred at this temperature for 1 hour. At the same temperature, 0.87 g of 2-naphthaldehyde was added, stirred for 3 hours while raising the temperature to room temperature, then added with water, extracted with ethylacetate, washed successively with saturated aqueous ammonium chloride and saturated brine, and dried over anhydrous magnesium sulfate. The solvent was evaporated, and the resultant crude product was purified and separated by silica gel column chromatography (ethyl acetate:n-hexane=1:20-1:5), to afford 1.18 g of the title compound as colorless crystals.

$^1$H-NMR (400 MHz, $CDCl_3$) δ 6.19 (1H, d, J=3.6 Hz), 6.95 (1H, d, J=6.0 Hz), 7.05 (1H, dd, J=0.4, 6.0 Hz), 7.43-7.50 (3H, m), 7.78-7.85 (3H, m), 7.91 (1H, d, J=0.4 Hz).

Production Example 77

(2-Chlorothiophen-3-yl)-(naphthalen-2-yl)-methanone

To a solution of 1.18 g of (2-chlorothiophen-3-yl)-(naphthalen-2-yl)-methanol in 12 mL of toluene was added 1.12 g of activated manganese dioxide at room temperature, and after stirring at 50° C. for a day, manganese dioxide was filtered off through Celite. The solvent was distilled off, and the resultant crude product was purified and separated by silica gel column chromatography (ethyl acetate:n-hexane=1:50), to afford 0.61 g of the title compound as a colorless oil.

$^1$H-NMR (400 MHz, $CDCl_3$) δ 7.18 (1H, d, J=6.0 Hz), 7.20 (1H, d, J=6.0 Hz), 7.55 (1H, ddd, J=1.6, 7.2, 8.0 Hz), 7.61 (1H, ddd, J=1.6, 7.2, 8.0 Hz), 7.88-7.95 (3H, m), 7.96 (1H, dd, J=1.6, 8.0 Hz), 8.28 (1H, d, J=0.8 Hz).

Example 78

3-(Naphthalen-2-yl)-1H-thieno[2,3-c]pyrazole

To a solution of 0.61 g of (2-chlorothiophen-3-yl)-(naphthalen-2-yl)-methanone in 6 mL of ethanol was added 0.12 mL of hydrazine monohydrate at room temperature and heated under reflux for 2 days. The reaction solution was diluted with ethyl acetate, and the organic layer washed successively with saturated aqueous ammonium chloride and saturated brine, dried over anhydrous magnesium sulfate, and the solvent was evaporated. The resultant crude product was purified and separated by silica gel column chromatography (ethyl acetate:n-hexane=1:30-1:5), to afford 32 mg of the title compound as colorless crystals.

$^1$H-NMR (400 MHz, DMSO-$D_6$) δ 7.37 (1H, d, J=5.6 Hz), 7.51 (1H, td, J=1.6, 8.0 Hz), 7.55 (1H, td, J=1.6, 8.0 Hz), 7.57 (1H, d, J=5.6 Hz), 7.92 (1H, dd, J=1.6, 8.0 Hz), 7.98-8.09 (3H, m), 8.42 (1H, s).

Production Example 79

1,5-Dibromo-2,4-difluorobenzene

Under ice cooling, a solution of 25.35 g of 1-bromo-2,4-difluorobenzene in 100 mL of concentrated sulfuric acid was added with 25.7 g of N-bromosuccinimide, and stirred for 30 minutes at this temperature and for 2 days at room temperature. After cooling on ice, the reaction solution was added with ice, and extracted with 300 mL of diethyl ether. The organic layer was successively washed with water, saturated aqueous sodium hydrogen carbonate and saturated brine, and then dried over anhydrous magnesium sulfate. The solvent was evaporated, and the resulting crude product was purified and separated by silica gel column chromatography (n-hexane), to afford 34.6 g of the title compound as a colorless oil.

$^1$H-NMR (400 MHz, $CDCl_3$) δ 6.99 (1H, t, J=8.4 Hz), 7.77 (1H, t, J=6.8 Hz)

Production Example 80

5-Bromo-2,4-difluoro-benzaldehyde

Under nitrogen atmosphere and at a temperature of −78° C., a solution of 34.0 g of 1,5-dibromo-2,4-difluorobenzene obtained by Production example 79 in 250 mL of diethyl ether was added with 83 mL of 1.58 M n-butyllithium in n-hexane, and stirred at this temperature for 30 minutes. To the reaction solution, 12 mL of N,N-dimethylformamide was added dropwise, and stirred at this temperature for 30 minutes. The reaction solution was added successively with 20 mL of glacial acetic acid and 300 mL of water, and extracted with diethyl ether. The organic layer was washed successively with 0.2N hydrochloric acid, water, saturated aqueous sodium hydrogen carbonate and saturated brine, and dried over anhydrous magnesium sulfate. The solvent was evaporated, and the resulting crude product was purified and separated by silica gel column chromatography (n-hexane:ethyl acetate=49:1), to afford 21.4 g of the title compound as a pale yellow oil.

$^1$H-NMR (400 MHz, $CDCl_3$) δ 7.03 (1H, dd, J=8.0, 9.6 Hz), 8.11 (1H t, J=7.2 Hz), 10.24 (1H, s).

Production Example 81

2,4-Difluoro-5-formyl-benzonitrile

To a solution of 21.4 g of 5-bromo-2,4-difluoro-benzaldehyde obtained by Production example 80 in 120 mL of N-methyl-2-pyrrolidone, 10.1 g of copper cyanide (I) was added and stirred at 175° C. for 4 hours. After allowing the solution to cool, the reaction solution was added with water and diethyl ether, and the impurities were filtered off through Celite. The organic layer was washed successively with water (×3) and saturated brine, and dried over anhydrous magnesium sulfate. The solvent was evaporated, and the resulting crude product was purified and separated by silica gel column chromatography (n-hexane:ethyl acetate=9:1), to afford 9.87 g of the title compound as pale yellow crystals.

$^1$H-NMR (400 MHz, $CDCl_3$) δ 7.14 (1H, dd, J=8.4, 9.6 Hz), 8.25 (1H t, J=7.2 Hz), 10.27 (1H, s).

Production Example 82

6-Fluoro-1H-indazole-5-carbonitrile 2.50 g of 2,4-difluoro-5-formyl-benzonitrile obtained by Production example 81 was dissolved in 15 mL of pyridine, added with 4.0 mL of hydrazine monohydrate and stirred at room temperature for 2 hours. After evaporating the pyridine, the residue was dissolved in 200 mL of ethyl acetate and 40 mL of tetrahydrofuran, washed successively with 1N hydrochloric acid, water, saturated aqueous sodium hydrogen carbonate and saturated brine, and dried over anhydrous magnesium sulfate. After making the organic layer pass through a silica gel pad (4 cm in diameter×3 cm), the solvent was evaporated, to afford 1.63 g of the title compound as bright yellow crystals.

$^1$H-NMR (400 MHz, DMSO-$D_6$) δ 7.66 (1H, d, J=10.0 Hz), 8.28 (1H, s), 8.51 (1H, d, J=6.0 Hz), 13.68 (1H, s)

Production Example 83

3-Bromo-6-fluoro-1-trityl-1H-indazole-5-carbonitrile

At room temperature, a solution containing 1.25 g of 6-fluoro-1H-indazole-5-carbonitrile obtained by Production example 82 in 12 mL of N,N-dimethylformamide was added with 1.52 g of N-bromosuccinimide and stirred overnight at this temperature. The reaction solution was added to 120 mL of ethyl acetate, and washed successively with semi saturated aqueous sodium hydrogen carbonate, water (twice) and saturated brine, and dried over anhydrous magnesium sulfate. The solvent was evaporated, and the resultant residue was dissolved in 15 mL of N,N-dimethylformamide. Under ice cooling, 2.16 g trityl-chloride and 310 mg of 60% sodium hydride were successively added, and stirred at this temperature for 10 minutes, and further at room temperature for 20 minutes. After adding ice, to the reaction solution was extracted with 120 mL of ethyl acetate. The organic layer was washed successively with water (twice) and saturated brine, and dried over anhydrous magnesium sulfate. After making the organic layer pass through a silica gel pad (4 cm in diameter×3 cm), the solvent was distilled off under reduced pressure, and the resultant crude crystals were recrystallized from ethyl acetate-diisopropyl ether, to afford 1.55 g of the title compound as pale yellow crystals.

$^1$H-NMR (400 MHz, DMSO-$D_6$) δ 6.17 (1H, d, J=10.8 Hz), 7.13-7.22 (6H, m), 7.32-7.42 (9H, m), 8.44 (1H, d, J=6.4 Hz)

Production Example 84

2,4-Difluoro-3-formyl-benzonitrile

Under nitrogen atmosphere and ice cooling, to a solution of 11.1 g of N,N-diisopropylamine in 100 mL of tetrahydrofuran was added 66 mL of 1.6 M n-butyllithium in n-hexane and stirred at this temperature for 20 minutes. After cooling to −78° C., 15 mL of a solution containing 13.9 g of 2,4-difluorobenzonitrile in tetrahydrofuran was added dropwise. After stirring at this temperature for 10 minutes, 8.6 mL of N,N-dimethylformamide was added dropwise and stirred at this temperature for 15 minutes. The reaction solution was added with 20 mL of glacial acetic acid, followed by 200 mL water, and extracted twice with diethyl ether. The organic layer was washed successively with 0.2N hydrochloric acid and saturated brine, and dried over anhydrous magnesium sulfate. The solvent was evaporated, and the resultant crude crystals were triturated with diethyl ether n-hexane, to afford 8.61 g of the title compound as bright yellow crystals.

$^1$H-NMR (400 MHz, DMSO-$D_6$) δ 7.53 (1H, t, J=8.8 Hz), 8.33(1H, ddd, J 6.0, 7.2, 8.8 Hz), 10.17 (1H, s)

Production Example 85

4-Fluoro-1H-indazole-5-carbonitrile 8.55 g of 2,4-difluoro-3-formyl-benzonitrile obtained by Production example 84 was dissolved in 40 mL of tetrahydrofuran and 40 mL of methanol, added with 5.1 mL of hydrazine monohydrate, stirred at room temperature for 3 days, at 50° C. for 3 hours, and at 70° C. for 3 hours. The reaction solution was added with 150 mL of ice water, further with 300 mL of ethyl acetate and 100 mL of tetrahydrofuran, and unnecessary substances were filtered out. The organic layer was washed successively with water and saturated brine, and dried over anhydrous magnesium sulfate. The solvent was evaporated, and the crude product was purified and separated by silica gel column chromatography (ethyl acetate:toluene=1:9-1:4), to afford 509 mg of the title compound as bright yellow crystals. Then the combined fraction with impurities was purified again by silica gel column chromatography (ethyl acetate:n-hexane=1:4-1:0), to obtain 1.80 g of the title compound as bright yellow crystals.

$^1$H-NMR (400 MHz, DMSO-$D_6$) δ 7.58 (1H, d, J=8.8 Hz), 7.70 (1H, dd, J=6.0, 8.8 Hz), 8.45 (1H, s), 13.94 (1H, s)

Production Example 86

4-Fluoro-1H-indazole-5-carboxylic acid Methyl Ester

To 1.65 g of 4-fluoro-1H-indazole-5-carbonitrile obtained by Production example 85, 8 mL of glacial acetic acid, 8 mL of water and 16 mL of concentrated sulfuric acid were added and stirred at 110° C. for 4 hours. After allowing the reaction solution to cool, 150 mL of ice water was added, and the precipitated carboxylic acid was collected by filtration. Under ice cooling, to a solution of the obtained carboxylic acid in N,N-dimethylformamide 12 mL-tetrahydrofuran 40 mL, a solution containing excess diazomethane in diethyl ether was added, and stirred at this temperature for 45 minutes. After distilling off the solvent under reduced pressure, the residue was dissolved in 100 mL of ethyl acetate, washed successively with saturated aqueous sodium hydrogen carbonate, water and saturated brine, and dried over anhydrous magnesium sulfate. The solvent was evaporated, to afford 1.98 g of the title compound as bright yellow crystals.

$^1$H-NMR (400 MHz, DMSO-$D_6$) δ 3.87 (3H, s), 7.45 (1H, d, J=8.8 Hz), 7.82 (1H, dd, J=6.8, 8.8 Hz), 8.36 (1H, s), 13.70 (1H, s)

Production Example 87

3-Bromo-4-fluoro-1H-indazole-5-carboxylic acid Methyl Ester

At room temperature, to a solution of 2.2 g of 4-fluoro-1H-indazole-5-carboxylic acid methyl ester obtained by Production example 86 in 20 mL of N,N-dimethylformamide was added 2.12 g of N-bromosuccinimide and stirred at this temperature for 1 hour. After distilling off the solvent, the residue was added with 120 mL of ethyl acetate, and washed successively with semi-saturated aqueous sodium hydrogen carbonate, water and saturated brine, and dried over anhydrous magnesium sulfate. The solvent was evaporated, to afford 3.0 g of the title compound as bright yellow crystals.

$^1$H-NMR (400 MHz, DMSO-$D_6$) δ 3.88 (3H, s), 7.48 (1H, d, J=8.8 Hz), 7.85 (1H, dd, J=6.4, 8.8 Hz), 14.00 (1H, s)

Production Example 88

3-Bromo-4-fluoro-1-trityl-1H-indazole-5-carboxylic acid Methyl Ester

Under ice cooling, to a solution of 2.99 g of 3-bromo-4-fluoro-1H-indazole-5-carboxylic acid methyl ester obtained by Production example 87 in 30 mL of tetrahydrofuran was added 526 mg of 60% sodium hydride, stirred for 25 minutes, added with 3.21 g of trityl chloride, and stirred at this temperature for 15 minutes and at room temperature for 45 minutes. The reaction solution was cooled again on ice, added with semi-saturated aqueous sodium hydrogen carbonate, and extracted with 100 mL of ethyl acetate. The organic layer was washed successively with water (twice) and saturated brine, and dried over anhydrous magnesium sulfate. The solvent was evaporated, the crude product purified and separated by silica gel column chromatography (ethyl acetate:n-hexane=1:9), and the obtained crude crystals were recrystallized from diisopropyl ether, to afford 1.73 g of the title compound as white needle crystals.

$^1$H-NMR (400 MHz, DMSO-$D_6$) δ 3.83 (3H, s), 6.30 (1H, d, J=8.8 Hz), 7.12-7.20 (6H, m), 7.30-7.40 (9H, m), 7.55 (1H, dd, J=6.8, 8.8 Hz)

Production Example 89

1-Bromo-4-fluoro-2-methoxybenzene 10 g of 2-bromo-5-fluorophenol was dissolved in 105 mL of N,N-dimethylformamide, and added with 10.9 g of potassium carbonate and 4.9 mL of iodomethane under cooling, and stirred at room temperature for 3 hours. The reaction solution was added with water, extracted with diethyl ether, and the resultant organic layer was washed with saturated brine, and dried over magnesium sulfate. The solvent was evaporated, to afford 9.75 g of the title compound as a yellow oil.

$^1$H-NMR (400 MHz, $CDCl_3$) δ 3.88 (3H, s), 6.59 (1H, td, J 8.4, 2.8 Hz), 6.65 (1H, dd, J=10.4, 2.8 Hz), 7.47 (1H, dd, J=8.4, 6.0 Hz)

Production Example 90

5-Bromo-2-fluoro-4-methoxybenzaldehyde 8.4 g of 1-bromo-4-fluoro-2-methoxybenzene obtained by Production example 89 was dissolved in 200 mL of dichloromethane, added under nitrogen atmosphere at 0° C. with 21 mL of titanium tetrachloride and 5.6 mL of dichloromethylmethylether, and stirred at room temperature for 4 hours and 30 minutes. The reaction solution was slowly poured into ice water, and extracted twice with diethyl ether. The organic layer was washed successively with water, saturated aqueous sodium hydrogen carbonate and water, and then dried over magnesium sulfate. The solvent was evaporated, to afford 9.44 g of the title compound as white crystals.

$^1$H-NMR (400 MHz, $CDCl_3$) δ 3.97 (3H, s), 6.67 (1H, d, J=12.0 Hz), 8.05 (1H, d, J=7.6 Hz), 10.15 (1H, s)

Production Example 91

4-Fluoro-5-formyl-2-methoxybenzonitrile 5.33 g of 5-bromo-2-fluoro-4-methoxybenzaldehyde obtained by Production example 90 was dissolved in 73 mL of 1-methyl-2-pyrrolidone, added with 2.46 g of copper cyanide, and stirred at 180° C. for 5 hours and 30 minutes. After allowing to cool, the reaction solution was added with water and diethyl ether, and insoluble substances were filtered off through Celite. The organic layer was washed with water and saturated brine, and dried over magnesium sulfate. The solvent was evaporated, and purified and separated by silica gel column chromatography, to afford 0.983 g of the title compound as pale yellow crystals.

$^1$H-NMR (400 MHz, $CDCl_3$) δ 4.03 (3H, s), 6.76 (1H, d, J=12.0 Hz), 8.14 (1H, d, J=7.2 Hz), 10.17 (1H, s)

Production Example 92

6-Methoxy-1H-indazole-5-carbonitrile 0.983 g of 4-fluoro-5-formyl-2-methoxybenzonitrile obtained by Production example 91 was dissolved in 15 mL of pyridine, and added with 2.66 mL of hydrazine monohydrate. After stirring at 50° C. for 2 hours, the solution was added with water and extracted twice with ethyl acetate. The resultant organic layer was washed with 1N hydrochloric acid, water, saturated aqueous sodium hydrogen carbonate and saturated brine, and dried over magnesium sulfate. The solvent was evaporated, to afford 0.915 g of the title compound as pale yellow crystals.

$^1$H-NMR (400 MHz, $CD_3OD$) δ 3.99 (3H, s), 7.10 (1H, s), 8.06 (1H, s), 8.15 (1H, s)

Production Example 93

3-Bromo-6-methoxy-1H-indazole-5-carbonitrile

To a solution of 0.915 g of 6-methoxy-1H-indazole-5-carbonitrile obtained by Production example 92 in 7.5 mL of N,N-dimethylformamide, 0.986 g of N-bromosuccinimide was added at room temperature, and stirred at this temperature for 1 hour and 30 minutes. The reaction solution was added with ethyl acetate, washed successively with semi-saturated aqueous sodium hydrogen carbonate, water and saturated brine, and dried over anhydrous magnesium sulfate. The solvent was evaporated, to afford 1.2 g of the title compound as yellow crystals.

$^1$H-NMR (400 MHz, $CD_3OD$) δ 4.00 (3H, s), 7.10 (1H, s), 7.97 (1H, s)

Production Example 94

3-Bromo-6-methoxy-1-trityl-1H-indazole-5-carbonitrile

To a solution of 1.2 g of 3-bromo-6-methoxy-1H-indazole-5-carbonitrile obtained by Production example 93 in 50 mL of N,N-dimethylformamide were added 171 mg of sodium hydride and 1.6 g of triphenylmethane chloride under ice cooling, and stirred at this temperature for 1 hour and 30 minutes. The reaction solution was added with water and extracted with ethyl acetate. The organic layer was washed successively with water and saturated brine, dried over anhydrous magnesium sulfate, and the solvent was evaporated, to afford 2.41 g of the title compound as brown crystals.

$^1$H-NMR (400 MHz, $CDCl_3$) δ 3.36 (3H, s), 5.60 (1H, s), 7.14-7.17 (5H, m), 7.24-7.32 (10H, m), 7.81 (1H, s)

Production Example 95

4-Fluoro-2-methoxybenzonitrile 15 g of 1-bromo-4-fluoro-2-methoxybenzene obtained by Production example 89 was dissolved in 150 mL of 1-methyl-2-pyrrolidone, added with 9.9 g of copper cyanide (I), and stirred at 180° C. for 5 hours. After allowing to cool, the reaction solution was poured into 500 mL of 14% ammonia aqueous solution, stirred for 45 minutes, then added with 150 mL of diethyl ether, and stirred for another 10 minutes. After filtering off the insoluble substances through Celite, the solution was extracted with diethyl ether. The organic layer was washed with diluted aqueous ammonia, 5N hydrochloric acid, water and saturated brine, and dried over magnesium sulfate. The solvent was evaporated, to afford 10.1 g of the title compound as white crystals.

$^1$H-NMR (400 MHz, $CDCl_3$) δ 3.93 (3H, s), 6.67-6.74 (2H, m), 7.54 (1H, dd, J=6.0, 8.4 Hz)

Production Example 96

4-Fluoro-3-formyl-2-methoxybenzonitrile

Under nitrogen atmosphere and at −78° C., to a solution of 10.7 g of N,N-diisopropylamine in 150 mL of tetrahydrofuran was added 40 mL of 2.66 M n-butyllithium in n-hexane, stirred at this temperature for 1 hour and 15 minutes, and added dropwise with a solution of 14.5 g of 4-fluoro-2-methoxybenzonitrile obtained by Production example 95 in 50 mL of tetrahydrofuran. After stirring at this temperature for 2 hours, 11.94 g of N-formylpiperidine was added. After stirring at this temperature for 40 minutes, the solution was added with 20 mL of acetic acid at this temperature, added with water at room temperature, and extracted three times with diethyl ether. The organic layer was washed successively with 0.2N hydrochloric acid, water and saturated brine, and dried over anhydrous magnesium sulfate. The solvent was evaporated, and the crude product was purified and separated by silica gel column chromatography, to afford 6.4 g of the title compound 6.4 g as pale yellow crystals.

$^1$H-NMR (400 MHz, $CDCl_3$) δ 4.22 (3H, s), 6.99 (1H, t, J=8.8 Hz), 7.78 (1H, dd, J=5.6, 8.8 Hz), 10.34 (1H, s).

Production Example 97

4-Methoxy-1H-indazole-5-carbonitrile

From 6.4 g of 4-fluoro-3-formyl-2-methoxybenzonitrile, 6.03 g of the title compound was obtained as yellow crystals in accordance with the method of Production example 92.

$^1$H-NMR (400 MHz, DMSO-$D_6$) δ 4.37 (3H, s), 7.20 (1H, d, J=8.8 Hz), 7.45 (1H, d, J=8.8 Hz), 8.57 (1H, s), 13.61 (1H, bs)

Production Example 98

3-Bromo-4-methoxy-1H-indazole-5-carbonitrile

From 72 mg of 4-methoxy-1H-indazole-5-carbonitrile, 69 mg of the title compound was obtained as white crystal in accordance with the method of Production example 93.

$^1$H-NMR (400 MHz, DMSO-$D_6$) δ 4.15 (3H, s), 7.42 (1H, d, J=8.8 Hz), 7.59 (1H, d, J=8.8 Hz), 13.94 (1H, bs)

Production Example 99

3-bromo-4-methoxy-1-trityl-1H-indazole-5-carbonitrile

From 69 mg of 3-bromo-4-methoxy-1H-indazole-5-carbonitrile, 150 mg of the title compound was obtained as a brown oil in accordance with the method of Production example 94.

$^1$H-NMR (400 MHz, $CDCl_3$) δ 4.29 (3H, s), 6.11 (1H, d, J=8.8 Hz), 7.00 (1H, d, J=8.8 Hz), 7.11-7.32 (15H, m)

Example 100

6-Fluoro-3-[(E)-2-(3-fluorophenyl)-vinyl]-1H-indazole-5-carbonitrile

To a solution of 1.35 g of 3-bromo-6-fluoro-1-trityl-1H-indazole-5-carbonitrile obtained by Production example 83 in 9 mL of N,N-dimethylformamide were successively added 685 mg of 3-fluoro-styrene, 167 mg of 2-(di-tert-butylphosphino)biphenyl, 63 mg of palladium acetate (II) and 1.95 mL of triethylamine, and stirred at 80° C. for 2 hours. The solvent was evaporated, to obtain 2.75 g of a crude coupling compound. The obtained crude coupling compound was suspended in 9 mL of dichloromethane, added with 3 mL of trifluoroacetic acid and 0.5 mL triisopropylsilane, and stirred at room temperature for 4 hours. The reaction solution was poured into a stirred and mixed solution of 100 mL saturated aqueous sodium hydrogencarbonate/90 mL ethyl acetate/10 mL tetrahydrofuran. The organic layer was washed successively with saturated aqueous sodium hydrogen carbonate and saturated brine, and dried over anhydrous magnesium sulfate. The solvent was evaporated, the crude product purified and separated by silica gel column chromatography (ethyl acetate:toluene=1:19-1:9), to afford 645 mg of the title compound as bright yellow crystals.

$^1$H-NMR (400 MHz, $CD_3$-OD) δ 7.08 (1H, dt, J=2.0, 8.4 Hz), 7.44 (1H, dt, J=5.6, 7.6 Hz), 7.48 (1H, d, J=9.6 Hz), 7.48-7.54 (2H, m), 7.56 (1H, d, J=16.4 Hz), 7.62 (1H, d, J=16.4 Hz), 8.71 (1H, d, J=6.0 Hz)

Example 101

6-Fluoro-3-[(E)-2-(3-fluorophenyl)-vinyl]-1H-indazole-5-carboxylic acid

To a suspension of 544 mg of 6-fluoro-3-[(E)-2-(3-fluorophenyl)-vinyl]-1H-indazole-5-carbonitrile obtained by Example 100 in 2 mL of acetic acid and 3 mL of water was added 6 mL of concentrated sulfuric acid, and stirred at 110° C. for 12 hours. After allowing to cool, the reaction solution was added with ice, and extracted with a mixed solvent of 200 mL of ethyl acetate and 50 mL of tetrahydrofuran. The organic layer was washed successively with water and saturated brine, and dried over anhydrous magnesium sulfate. The solvent was evaporated, to afford 491 mg of the title compound as pale brown crystals.

$^1$H-NMR (400 MHz, DMSO-$D_6$) δ 7.12 (1H, dt, J=2.0, 8.4 Hz), 7.41 (1H, d, J=11.2 Hz), 7.42 (1H, dt, J=5.6, 7.6 Hz), 7.53 (1H, d, J=16.8 Hz), 7.57 (1H, d, J=8.0 Hz), 7.69 (1H, d, J=10.8 Hz), 7.76 (1H, d, J=16.8 Hz), 8.75 (1H, d, J=, 6.8 Hz), 13.02 (1H, br s), 13.50 (1H, s). Compounds of Examples 102-h to 107-h were synthesized according to the following synthesizing method.

6-Fluoro-3-[(E)-2-(3-fluorophenyl)-vinyl]-1H-indazole-5-carboxylic acid synthesized in Example 101 was dissolved in N,N-dimethylformamide and dispensed into test tubes. Each test tube was added successively with preliminarily prepared 1.5 equivalents of different kind of amine in 1M dimethylformamide solution, 2 equivalents of 1-hydroxybenztriazole monohydrate in 1 M dimethylformamide solution, and 2 equivalents of 1-ethyl-3-(3-dimethylaminopropyl)carbodiimide hydrochloride (=WSC.HCl), and stirred at room temperature overnight. The resultant reaction solution was purified and separated by LC-MS[developing solvent:0.1% trifluoroacetic acid-containing acetonitrile solution:0.1% trifluoroacetic acid-containing aqueous solution=20:80-80:20, 10 min. cycle, flow rate: 30 mL/min., column: Wakopak Combi ODs, 20 mmΦ×50 mm(Long)], to afford the compounds of the following Examples.

Example 102

6-Fluoro-3-[(E)-2-(3-fluorophenyl)-vinyl]-1H-indazole-5-carboxylic acid Cyclopropylamide MS (ESI) m/z 340 $MH^+$ Example 103

6-Fluoro-3-[(E)-2-(3-fluorophenyl)-vinyl]-1H-indazole-5-carboxylic acid (furan-2-ylmethyl)-amide MS (ESI) m/z 380 $MH^+$ Example 104

6-Fluoro-3-[(E)-2-(3-fluorophenyl)-vinyl]-1H-indazole-5-carboxylic acid (tetrahydrofuran-2-ylmethyl)-amide MS (ESI) m/z 384 $MH^+$ Example 105

6-Fluoro-3-[(E)-2-(3-fluorophenyl)-vinyl]-1H-indazole-5-carboxylic acid [(1S)-1-hydroxymethyl-2-methylpropyl]-amide MS (ESI) m/z 386 $MH^+$ Example 106

6-Fluoro-3-[(E)-2-(3-fluorophenyl)-vinyl]-1H-indazole-5-carboxylic acid (pyridine-3-ylmethyl)-amide MS (ESI) m/z 391 $MH^+$ Example 107

6-Fluoro-3-[(E)-2-(3-fluorophenyl)-vinyl]-1H-indazole-5-carboxylic acid [(1S)-1-carbamoyl-ethyl]-amide MS (ESI) m/z 763 2M+$Na^+$ Production Example 108

6-Fluoro-3-[(E)-2-(3-fluorophenyl)-vinyl]-1-trityl-1H-indazole-5-carboxylic acid Under ice cooling, to a solution of 350 mg of 6-fluoro-3-[(E)-2-(3-fluorophenyl)-vinyl]-1H-indazole-5-carboxylic acid obtained by Example 101 in 6 mL of N,N-dimethylformamide was added 103 mg of 60% sodium hydride, stirred for 30 minutes, then added with 390 mg of trityl chloride, and stirred at this temperature for 20 minutes and at room temperature for 1 hour. The reaction solution was added with water and extracted with 80 mL of ethyl acetate. The organic layer was washed successively with water and saturated brine, and dried over anhydrous magnesium sulfate. The solvent was evaporated, and the crude product was purified and separated by silica gel column chromatography (ethylacetate: toluene=1:9), to afford 370 mg of the title compound as bright yellow crystals.

$^1$H-NMR (400 MHz, DMSO-D$_6$) δ 5.95 (1H, d, J=12.4 Hz), 7.05-7.40 (18H, m), 7.50 (1H, d, J=7.6 Hz), 7.66 (1H, d, J=10.4 Hz), 7.68 (1H, d, J=16.4 Hz), 8.72 (1H, d, J=7.2 Hz), 13.16 (1H, br s)

Production Example 109

{6-Fluoro-3-[(E)-2-(3-fluorophenyl)-vinyl]-1-trityl-1H-indazol-5-yl}carbamic acid tert-butyl ester To a suspension of 369 mg of 6-fluoro-3-[(E)-2-(3-fluorophenyl)-vinyl]-1-trityl-1H-indazole-5-carboxylic acid obtained by Production example 108 in 6 mL of toluene were added 69 mg of triethylamine, 0.15 mL of 2-methyl-2-propanol and 187 mg of diphenyl phosphoryl azide, and stirred at 80° C. for 7.5 hours. After adding 10 mL of ethyl acetate to the reaction solution, the organic layer was washed successively with water and saturated brine, and dried over anhydrous magnesium sulfate. The solvent was evaporated, and the crude product purified and separated by silica gel column chromatography (n-hexane:toluene=1:1), to afford 102 mg of the title compound as a white non-crystalline powder.

$^1$H-NMR (400 MHz, DMSO-D$_6$) δ 1.44 (9H, s), 5.99 (1H, d, J=11.6 Hz), 7.11 (1H, dt, J=2.0, 8.0 Hz), 7.16-7.45 (17H, m), 7.50 (1H, d, J=7.6 Hz), 7.56 (1H, d, J=16.8 Hz), 7.63 (1H, d, J=10.4 Hz), 8.21 (1H, d, J=7.6 Hz), 8.86 (1H, s)

Example 110

6-Fluoro-3-[(E)-2-(3-fluorophenyl)-vinyl]-1H-indazol-5-ylamine

A solution of 96 mg of {6-fluoro-3-[(E)-2-(3-fluorophenyl)-vinyl]-1-trityl-1H-indazol-5-yl}carbamic acid obtained by Production example 109 in a solution of tert-butyl ester dissolved in 1 mL of 95% trifluoroacetic acid was stirred at room temperature for 1 hour and 20 minutes. The reaction solution was added with saturated aqueous sodium hydrogen carbonate, and extracted with 20 mL of ethyl acetate. The organic layer was washed successively with saturated aqueous sodium hydrogen carbonate and saturated brine, and dried over anhydrous magnesium sulfate. The solvent was evaporated, the crude product purified and separated by silica gel column chromatography (ethyl acetate:toluene=1:1), to afford 28 mg of the title compound as a bright yellow non-crystalline powder.

$^1$H-NMR (400 MHz, DMSO-D$_6$) δ 4.92 (2H, s), 7.07 (1H, dt, J=2.0, 8.0 Hz), 7.22 (1H, d, J=11.2 Hz), 7.28 (1H, d, J=16.8 Hz), 7.38 (1H, d, J=8.8 Hz), 7.37 (1H, dt, J=6.0, 8.0 Hz), 7.45 (1H, d, J=7.6 Hz), 7.49 (1H, d, J=16.8 Hz), 7.51 (1H, d, J=10.4 Hz), 12.86 (1H, s)

Compounds of Examples 111-114 were synthesized in the following synthesizing method.

6-Fluoro-3-[(E)-2-(3-fluorophenyl)-vinyl]-1H-indazol-5-ylamine synthesized in Example 110 was dissolved in N,N-dimethylformamide and dispensed into test tubes. Each test tube was added successively with preliminarily prepared 1.2 equivalents of different kind of carboxylic acid in 1M dimethylformamide solution, 1.6 equivalents of 1-hydroxybenztriazole monohydrate in 1 M dimethylformamide solution, and 1.6 equivalents of 1-ethyl-3-(3'-dimethylaminopropyl) carbodiimide hydrochloride (═WSC—HCl), and stirred at room temperature for 3 days. The resultant reaction solution was purified and separated by LC-MS[developing solvent: 0.1% trifluoroacetic acid-containing acetonitrile solution: 0.1% trifluoroacetic acid-containing aqueous solution=20:80-80:20, 10 min. cycle, flow rate: 30 mL/min., column: Wako Wakopak Combi ODS, 20 mm Φ×50 mm(Long)], to afford the compounds of the following Examples.

Example 111

Cyclopropane Carboxylic acid{6-fluoro-3-[(E)-2-(3-fluorophenyl)-vinyl]-1H-indazol-5-yl}-amide MS (ESI) m/z 340 MH$^{30}$ Example 112

(2S)-5-oxo-pyrrolidine-2-carboxylic acid{6-fluoro-3-[(E)-2-(3-fluorophenyl)-vinyl]-1H-indazol-5-yl}-amide MS (ESI) m/z 383 MH$^+$ Example 113

N-{6-Fluoro-3-[(E)-2-(3-fluorophenyl)-vinyl]-1H-indazol-5-yl}-2-(thiophen-2-yl)-acetamide MS (ESI) m/z 396 MH$^+$ Example 114

Furan-2-carboxylic acid{6-fluoro-3-[(E)-2-(3-fluorophenyl)-vinyl]-1H-indazol-5-yl}-amide MS (ESI) m/z 366 MH$^+$ Example 115

6-Fluoro-3-[(E)-2-(3-fluorophenyl)-vinyl]-1H-indazole-5-carboxylic acid amide

To a suspension of 89 mg of 6-fluoro-3-[(E)-2-(3-fluorophenyl)-vinyl]-1H-indazole-5-carbonitrile obtained by Example 100 in 0.4 mL of acetic acid and 0.4 mL of water was added 1.2 mL of concentrated sulfuric acid, and stirred at 110° C. for 50 minutes. After allowing to cool, ice was added, and extracted with a mixed solvent of 20 mL of ethyl acetate and 10 mL of tetrahydrofuran. The organic layer was washed successively with water, saturated aqueous sodium hydrogen carbonate and saturated brine, and dried over anhydrous magnesium sulfate. After making the organic layer pass through an alumina pad (2.5 diameter ×2 cm), the solvent was evaporated, to afford 76 mg of the title compound as pale yellow crystals.

$^1$H-NMR (400 MHz, DMSO-D$_6$) δ 7.12 (1H, dt, J=2.0, 8.4 Hz), 7.39 (1H, d, J=10.8 Hz), 7.41 (1H, dt, J=6.0, 8.4 Hz), 7.53 (1H, d, J=16.8 Hz), 7.56 (1H, d, J=8.0 Hz), 7.61 (1H, s), 7.66 (1H, d, J=10.8 Hz), 7.70 (1H, d, J=16.8 Hz), 7.74 (1H, s), 8.50 (1H, d, J=, 6.8 Hz), 13.40 (1H, s)

Production Example 116

(6-Bromo-2,3-difluorophenyl)trimethylsilane

Under nitrogen atmosphere, to a solution of 18.2 mL of N,N-diisopropylamine in 200 mL of tetrahydrofuran was added 66.0 mL of 1.57 M n-butyllithium in hexane at 0° C., and stirred at this temperature for 10 minutes. After cooling to −78° C., a solution containing 20.0 g of 1-bromo-3,4-difluorobenzene in 100 mL of tetrahydrofuran was added dropwise and stirred at this temperature for 30 minutes, stirred at this temperature for 30 minutes, added dropwise with 32.9 mL of chlorotrimethylsilane, and the reaction solution was allowed to warm gradually to room temperature, and stirred for a day. After diluting with water and ethyl acetate, the organic layer was washed with saturated brine, dried over anhydrous magnesium sulfate, and the solvent was evaporated. The crude product was purified and separated by silica gel column chromatography (n-hexane)-, to afford 20.3 g of the title compound as a colorless oil.

$^1$H-NMR (400 MHz, $CDCl_3$) δ 0.47 (9H, s), 6.99 (1H, dt, J=9.6, 8.8 Hz), 7.27 (1H, ddd, J=2.0, 4.0, 8.8 Hz).

Production example 117

5-Bromo-2,3-difluoro-4-trimethylsilanyl Benzaldehyde

Under nitrogen atmosphere, to a solution containing 6.34 mL of N,N-diisopropylamine in 100 mL of tetrahydrofuran, 26.4 mL of 1.57 Mn-butyllithium in hexane was added at 0° C., and stirred at this temperature for 10 minutes. After cooling to −78° C., a solution containing 10.0 g of (6-bromo-2,3-difluorophenyl)trimethylsilane in 100 mL of tetrahydrofuran was added dropwise, stirred at this temperature for 1 hour, then added dropwise with 2.92 mL of N,N-dimethylformamide, allowed to gradually warm to room temperature, and stirred fro 3 hours. After diluting with water and ethyl acetate, the organic layer was washed with saturated brine, dried over anhydrous magnesium sulfate, and the solvent was evaporated. The crude product was purified and separated by silica gel column chromatography (n-hexane), to afford 9.70 g of the title compound as a colorless oil.

$^1$H-NMR (400 MHz, $CDCl_3$) δ 0.50 (9H, s), 7.77 (1H, dd, J=4.8, 2.0 Hz), 10.27 (1H, s).

Production Example 118

5-Bromo-2,3-difluoro Benzaldehyde

To a solution of 18.0 g of 5-bromo-2,3-difluoro-4-trimethylsilanyl benzaldehyde in 20 mL of N,N-dimethylformamide and 2 mL of water was added 1.63 g of cesium fluoride at room temperature, and stirred at this temperature for 1 hour. After diluting with ethyl acetate, the organic layer was washed successively with saturated aqueous ammonium chloride and saturated brine, dried over anhydrous magnesium sulfate, and the solvent was evaporated, to afford 10.26 g of the title compound as a colorless oil.

$^1$H-NMR (400 MHz, $CDCl_3$) δ7.58 (1H, ddd, J=9.2, 6.8, 2.4 Hz), 7.76 (1H, ddd, J=4.8, 2.4, 2.0 Hz), 10.27 (1H, s).

Production Example 119

3,4-Difluoro-5-formylbenzonitrile

To a solution of 10.0 g of 5-bromo-2,3-difluorobenzaldehyde in 40.0 mL of 1-methyl-2-pyrrolidone was added 4.26 g of copper cyanide (I) at room temperature and stirred at 170° C. for 8 hours. Adding ethyl acetate and water, the solution was stirred, and insoluble substances were filtered out through celite. The organic layer of filtrate was washed successively with saturated aqueous ammonium chloride, water and saturated brine, dried over anhydrous magnesium sulfate, and the solvent was evaporated. The crude product was purified and separated by silica gel column chromatography (ethyl acetate:n-hexane=1:20), to afford 2.64 g of the title compound as colorless crystals.

$^1$H-NMR (400 MHz, $CDCl_3$) δ7.72 (1H, ddd, J=9.2, 6.8, 2.0 Hz), 7.98 (1H, dt, J=5.6, 2.0 Hz), 10.32 (1H, s).

Production Example 120

7-Fluoro-1H-indazole-5-carbonitrile

From 2.60 g of 3,4-difluoro-5-formyl benzonitrile, 2.46 g of the title compound was obtained as pale yellow crystals according to the method of Production example 92.

$^1$H-NMR (400 MHz, DMSO-$D_6$) δ7.68 (1H, dd, J=11.2, 0.8 Hz), 8.27 (1H, d, J=0.8 Hz), 8.37 (1H, d, J=3.2 Hz).

Production Example 121

3-Bromo-7-fluoro-1H-indazole-5-carbonitrile

From 2.40 g of 7-fluoro-1H-indazole-5-carbonitrile, 2.91 g of the title compound was obtained as pale red crystals according to the method of Production example 93.

$^1$H-NMR (400 MHz, DMSO-$D_6$) δ7.84 (1H, dd, J=10.8, 0.8 Hz), 8.13 (1H, d, J=0.8 Hz).

Production Example 122

3-Bromo-7-fluoro-1-trityl-1H-indazole-5-carbonitrile

From 2.91 g of 3-bromo-7-fluoro-1H-indazole-5-carbonitrile, 2.08 g of the title compound was obtained as colorless crystals according to the method of Production example 94.

$^1$H-NMR (400 MHz, $CDCl_3$) δ7.01 (1H, dd, J=10.8, 0.8 Hz), 7.09-7.32 (15H, m), 7.82 (1H, d, J=0.8 Hz).

Production Example 123

7-Fluoro-1-trityl-3-vinyl-1H-indazole-5-carbonitrile

Under nitrogen atmosphere, 3.32 g of 3-bromo-7-fluoro-1-trityl-1H-indazole-5-carbonitrile was dissolved in 100 mL of toluene, added with 398 mg of tetrakis(triphenylphosphilne)palladium(0) and 2.50 mL of vinyltributyltin, and stirred at 100° C. for 95 minutes. After cooling to room temperature, 10 g of silica gel was added, the solvent was evaporated, followed by purification by silica gel column chromatography, to afford 2.59 g of the title compound as white crystals.

$^1$H-NMR (400 MHz, $CDCl_3$) δ 5.55 (1H, dd, J=0.8, 11.2 Hz), 6.00 (1H, dd, J=0.8, 18.0 Hz), 6.86-6.97 (2H, m), 7.10-7.30 (15H, m), 8.07 (1H, d, J=1.2 Hz).

Production Example 124

7-Fluoro-3-[(E)-2-(pyridin-3-yl)-vinyl]-1-trityl-1H-indazole-5-carbonitrile

Under nitrogen atmosphere, 2.59 g of 7-fluoro-1-trityl-3-vinyl-1H-indazole-5-carbonitrile was dissolved in 50 mL of acetonitrile, added with 10 mL of triethylamine, 271 mg of palladium acetate (II), 450 mg of 2-(di-tert-butylphosphino) biphenyl and 726 μl of 3-bromo pyridine, and refluxed overnight. The solution was cooled to room temperature, added with 10 g of silica gel, the solvent was evaporated, followed by purification by silica gel column chromatography, to afford 2.00 g of the title compound as yellow crystals.

$^1$H-NMR (400 MHz, DMSO-$D_6$) δ 7.09 (6H, d, J=6.4 Hz), 7.27-7.33 (9H, m), 7.40 (1H, dd, J=4.8, 8.0 Hz), 7.52 (1H, d, J=16.8 Hz), 7.56 (1H, dd, J=1.2, 13.2 Hz), 7.62 (1H, d, J=16.8 Hz), 8.17 (1H, m), 8.48 (1H, dd, J=1.6, 4.8 Hz), 8.84 (1H, d, J=1.2 Hz), 8.87 (1H, d, J=1.6 Hz).

Production Example 125

7-Fluoro-3-[(E)-2-(pyridin-3-yl)-vinyl]-1-trityl-1H-indazole-5-carboxylic acid 3.60 g of 7-fluoro-3-[(E)-2-(pyridin-3-yl)-vinyl]-1-trityl-1H-indazole-5-carbonitrile was dissolved in 500 mL of ethanol, added with 154 g of potassium hydroxide, and stirred at 80° C. overnight. After cooling to room temperature, the solution was adjusted to pH 3 by 5N hydrochloric acid, and extracted with ethyl acetate. The organic layer was washed with water and saturated brine, dried over magnesium sulfate, and the solvent was evaporated. The obtained crude product was purified by silica gel column chromatography, and the resultant dark brown solid was washed with 10 mL of diethyl ether, to afford 3.58 g of the title compound as dark brown crystals.

$^1$H-NMR (400 MHz, DMSO-$D_6$) δ 7.11 (6H, d, J=7.2 Hz), 7.26-7.35 (9H, m), 7.40 (1H, d, J=16.8 Hz), 7.42 (1H, dd, J=1.2, 12.4 Hz), 7.63 (1H, m), 7.85 (1H, d, J=16.8 Hz), 8.47 (1H, m), 8.59 (1H, d, J=5.2 Hz), 8.68 (1H, d, J=1.2 Hz), 9.00 (1H, bs).

Example 126

7-Fluoro-3-[(E)-2-(pyridin-3-yl)-vinyl]-1-trityl-1H-indazole-5-carboxylic acid

By treating 1.00 g of 7-fluoro-3-[(E)-2-(pyridin-3-yl)-vinyl]-1-trityl-1H-indazole-5-carboxylic acid in the manner similar to that described in Example 16, 741 mg of the title compound was obtained as yellow crystals.

$^1$H-NMR (400 MHz, DMSO-$D_6$) δ 7.56 (1H, m), 7.60 (1H, d, J=16.8 Hz), 7.67 (1H, d, J=12.4 Hz), 7.91 (1H, d, J=16.4 Hz), 8.39 (1H, m), 8.55 (1H, d, J=4.8 Hz), 8.66 (1H, S), 8.99 (1H, s).

Example 127

7-Fluoro-3-[(E)-2-(pyridin-3-yl)-vinyl]-1H-indazole-5-carboxylic acid(furan-2-ylmethyl)-amide 376 mg of 7-fluoro-3-[(E)-2-(pyridin-3-yl)-vinyl]-1H-indazole-5-carboxylic acid was dissolved in 10 mL of N,N-dimethylformamide, and added with 903 μl of N,N-diisopropylethylamine, 244 mg of 1-hydroxybenzotriazole monohydrate and 147 μl of furfurylamine, and stirred at room temperature for 10 minutes. The solution was cooled to 0° C., added with 509 mg of 1-ethyl-3-(3-dimethylaminopropyl) carbodiimide hydrochloride, and stirred at room temperature overnight. After diluting with water and ethyl acetate, the organic phase was washed with water and saturated brine, and dried over magnesium sulfate. The solvent was evaporated, and the resultant crude product was purified by silica gel column chromatography, to afford 159 mg of the title compound as yellow crystals.

$^1$H-NMR (400 MHz, DMSO-$D_6$) δ 4.53 (2H, d, J=6.0 Hz), 6.32 (1H, d, J=2.8 Hz), 6.41 (1H, dd, J=2.0, 3.2 Hz), 7.43 (1H, dd, J=4.8, 7.2 Hz), 7.58 (1H, d, J=16.8 Hz), 7.59 (1H, s), 7.71 (1H, d, J=12.0), 7.72 (1H, d, J=16.8 Hz), 8.18 (1H, d, J=8.0 Hz), 8.49 (1H, d, J=4.8 Hz), 8.56 (1H, s), 8.88 (1H, d, J=2.4 Hz), 9.07 (1H, bs).

Example 128

7-Fluoro-3-[(E)-2-(pyridin-3-yl)-vinyl]-1H-indazole-5-carboxylic acid [(1S)-1-hydroxymethyl-2-methyl-propyl]-amide By treating 200 mg of 7-fluoro-3-[(E)-2-(pyridin-3-yl)-vinyl]-1H-indazole-5-carboxylic acid obtained by Example 126 and 94.5 μl L-valinol in accordance with Example 127, 102 mg of the title compound was obtained as white crystals.

$^1$H-NMR (400 MHz, DMSO-$D_6$) δ 0.94 (6H, t, J=6.4 Hz), 1.96 (1H, m), 3.56 (2H, t, J=5.6 Hz), 4.10 (1H, t, J=4.8 Hz), 4.63 (1H, m), 7.43 (1H, dd, J=4.8, 7.2 Hz), 7.51-7.68 (2H, m), 7.74 (1H, d, J=16.8 Hz), 8.05 (1H, m), 8.16 (1H, m), 8.46 (1H, s), 8.48 (1H, s), 8.86 (1H, s).

MS (ESI) m/z 369 $MH^+$

Example 12.9

7-Fluoro-3-[(EZ)-2-(pyridin-3-yl)-vinyl]-1H-indazole-5-carboxylic acid[(1S)-1-carbamoylethyl]-amide By treating 200 mg of 7-fluoro-3-[(E)-2-(pyridin-3-yl)-vinyl]-1H-indazole-5-carboxylic acid obtained by Example 126 and 106 mg of (2S)-2-amino-propioneamide hydrochloride in accordance with Example 127, 132 mg of the title compound was obtained as a mixture of E/Z=3/1.

(E) compound: $^1$H-NMR (400 MHz, DMSO-$D_6$) δ 1.38 (3H, d, J=7.2 Hz), 4.46 (1H, m), 7.44 (1H, dd, J=4.8, 8.0 Hz), 7.58 (1H, d, J=16.8 Hz), 7.70 (1H, d, J=12.4 Hz), 7.74 (1H, d, J=16.4 Hz), 8.18 (1H, d, J=7.6 Hz), 8.48 (1H, dd, J=1.6, 4.4 Hz), 8.51 (1H, s), 8.87 (1H, s).

(Z) compound: $^1$H-NMR (400 MHz, DMSO-$D_6$) δ 1.30 (3H, d, J=7.2 Hz), 4.26 (1H, m), 6.84 (1H, m), 7.06 (1H, d, J=12.8 Hz), 7.32 (1H, dd, J=5.2, 8.0 Hz), 7.92 (1H, d, J=8.4 Hz), 8.06 (1H, s), 8.08 (1H, s), 8.34 (1H, dd, J=1.9, 5.1 Hz), 8.77 (1H, s).

MS (ESI)m/z 354 $MH^+$

Example 130

From 7-fluoro-3-[(E)-2-(pyridin-3-yl)-vinyl]-1H-indazole-5-carboxylic acid obtained by Example 126 and various kinds of amine, compounds of Examples 131-132 were obtained in accordance with the method of Example 102.

Example 131

7-Fluoro-3-[(E)-2-(pyridin-3-yl)-vinyl]-1H-indazole-5-carboxylic acid[(1S)-2-hydroxy-1-phenylethyl]-amide MS (ESI)m/z 403 $MH^+$ Example 132

7-Fluoro-3-[(E)-2-(pyridin-3-yl)-vinyl]-1H-indazole-5-carboxylic acid Cyclopropylamide MS (ESI)m/z 323 $MH^+$ Production Example 133

{7-Fluoro-3-[(E)-2-(pyridin-3-yl)-vinyl]-1-trityl-1H-indazol-5-yl}-carbamic acid tert-butyl ester Under nitrogen atmosphere, 200 mg of 7-fluoro-3-[(E)-2-(pyridin-3-yl)-vinyl]-1-trityl-1H-indazole-5-carboxylic acid obtained by Production example 125 was dissolved in toluene, added with 79.6 μl of triethylamine and 81.8 μl of diphenylphosphoryl azide, and stirred at room temperature for 30 minutes. Then after adding 1 mL of tert-butanol, the reaction solution was heated to 120° C. and stirred for 95 minutes. After cooling to room temperature, 1 g silica gel was added, the solvent was evaporated, and purified by silica gel column chromatography, to afford 121 mg of the title compound as a yellow solid solution.

$^1$H-NMR (400 MHz, DMSO-$D_6$) δ 1.47 (9H, s), 7.10 (6H, d, J=6.8 Hz), 7.23 (1H, d, J=8.0 Hz), 7.25-7.33 (10H, m), 7.39 (1H, dd, J=5.2, 8.0 Hz), 7.51 (1H, d, J=16.8 Hz), 8.03 (1H, s), 8.13 (1H, m), 8.46 (1H, dd, J=1.6, 4.4 Hz), 8.75 (1H, d, J=2.0), 9.44 (1H, bs).

Example 134

7-Fluoro-3-[(E)-2-(pyridin-3-yl)-vinyl]-1H-indazol-5-ylamine

By treating 655 mg of {7-fluoro-3-[(E)-2-(pyridin-3-yl)-vinyl]-1-trityl-1H-indazol-5-yl}-carbamic acid tert-butyl ester by the method in accordance with Example 16, 153 mg of the title compound was obtained as a dark brown solid solution.

$^1$H-NMR (400 MHz, DMSO-$D_6$) δ 5.11 (2H, bs), 6.65 (1H, d, J=13.6 Hz), 6.98 (1H, s), 7.29 (1H, d, J=17.6 Hz), 7.40 (1H, dd, J=5.2, 8.0 Hz), 7.56 (1H, d, J=16.8 Hz), 8.10 (1H, m), 8.44 (1H, dd, J=1.6, 4.8 Hz), 8.79 (1H, s), 13.3 (1H, bs).

Production Example 135

Furan-2-carboxylic acid{7-fluoro-1-(furan-2-carbonyl)-3-[(E)-2-(pyridin-3-yl)-vinyl]-1H-indazole-5-yl}-amide Following amidation using 217 mg of 7-fluoro-3-[(E)-2-(pyridin-3-yl)-vinyl]-1H-indazol-5-ylamine and 286 mg of 2-furancarboxylic acid in accordance with the method of Example 127, purification by LC-MS was carried out, to afford 143 mg of the title compound as yellow crystals.

MS (ESI)m/z 443 $MH^+$

Example 136

Furan-2-carboxylic acid[7-fluoro-3-(2-pyridin-3-yl-vinyl)-1H-indazol-5-yl]-amide 208 mg of furan-2-carboxylic acid{7-fluoro-1-(furan-2-carbonyl)-3-[(E)-2-(pyridin-3-yl)-vinyl]-1H-indazol-5-yl}-amide was suspended in 20 mL ethanol, added with 5 mL of concentrated aqueous ammonia and stirred at room temperature overnight. The reaction solution was added with saturated brine, extracted with ethyl acetate, and the organic phase was washed with saturated brine, and dried over magnesium sulfate. The solvent was evaporated, purified by LC-MS and the obtained crystals were suspended in ethyl acetate, neutralized with saturated aqueous sodium hydrogen carbonate, and the organic phase was washed with water and saturated brine, and dried over magnesium sulfate. The solvent was evaporated, to afford 96.2 mg of the title compound as yellow crystals.

MS (ESI)m/z 349 $MH^+$

Production Example 137

2-[(E)-2-(3-Fluorophenyl)-vinyl]-4,4,5,5-tetramethyl-[1,3,2]dioxaborolane

To a solution of 11 mg of chloro(1,5-cyclooctadiene)-rhodium(I) dimer and 0.61 mL of 4,4,5,5-tetramethyl-[1,3,2]dioxaborolane in 15 mL toluene was added dropwise 1.0 mL of 3-fluorostyrene, and stirred at room temperature for 4 hours. The reaction solution was added with water, and dried over anhydrous magnesium sulfate. The solvent was evaporated, and the resultant crude product was purified and separated by silica gel column chromatography (diethyl ether:n-hexane=1:19), to afford 311 mg of the title compound as a pale yellow oil.

$^1$H-NMR (400 MHz, DMSO-$D_6$) δ 1.25 (12H, s), 6.22 (1H, d, J=18.8 Hz), 7.16 (1H, dt, J=2.4, 8.8 Hz), 7.30 (1H, d, J=18.8 Hz), 7.37-7.52 (3H, m).

Production Example 138

{4-[(E)-2-(4,4,5,5,-tetramethyl-[1,3,2]dioxaborolane-2-yl)-vinyl]-phenyl}-carbamic acid tert-butyl ester From 0.921 g of (4-vinylphenyl)-carbamic acid tert-butyl ester, 0.41 g of the title compound was obtained as white crude crystals in accordance with the method of Production example 137.

$^1$H-NMR (400 MHz, $CDCl_3$) δ 1.30 (12H, s), 1.51 (9H, s), 6.04 (1H, d, J=17.6 Hz), 6.52 (1H, bs), 7.32 (2H, d, J=8.8 Hz), 7.33 (1H, d, J=17.6 Hz), 7.41 (2H, d, J=8.8 Hz).

Production Example 139

2-[(E)-2-(2-Fluorophenyl)-vinyl]-4,4,5,5-tetramethyl-[1,3,2]dioxaborolane

From 5 g of 1-fluoro-2-vinylbenzene, 4.22 g of the title compound was obtained as a yellow oil in accordance with the method of Production example 137.

$^1$H-NMR (400 MHz, $CDCl_3$) δ 1.31 (12H, s), 6.23 (1H, d, J=18.0 Hz), 6.97-7.07 (1H, m), 7.07-7.14 (1H, m), 7.18-7.29 (1H, m), 7.55 (1H, dt, J=2.0, 8.0 Hz), 7.57 (1H, d, J=18.0 Hz).

Production Example 140

6-Fluoro-1H-indazole-5-carboxylic acid methyl ester

From 1.22 g of 6-fluoro-1H-indazole-5-carbonitrile obtained by Production example 82, 1.11 g of the title compound was obtained as ocher crystal in accordance with the method of Production Example 86

$^1$H-NMR (400 MHz, DMSO-D$_6$) δ 3.86 (3H, s), 7.43 (1H, d, J=11.6 Hz), 8.26 (1H, s), 8.44 (1H, d, J=7.2 Hz), 13.43 (1H, s).

Production Example 141

3-Bromo-6-fluoro-1-trityl-1H-indazole-5-carboxylic acid methyl ester

From 1.11 g of 6-fluoro-1H-indazole-5-carboxylic acid methyl ester, 1.38 g of the title compound was obtained as pale red crystal in accordance with Production example 87 and Production example 88.

$^1$H-NMR (400 MHz, DMSO-D$_6$) δ 3.84 (3H, s), 6.04 (1H, d, J=12.0 Hz), 7.12-7.23 (6H, m), 7.30-7.44 (9H, m), 8.12 (1H, d, J=6.8 Hz).

Example 142

6-Fluoro-3-[(E)-2-(thiophen-2-yl)-vinyl]-1H-indazole-5-carboxylic acid methyl ester In accordance with the method of Example 100, from 800 mg of 3-bromo-6-fluoro-1-trityl-1H-indazole-5-carboxylic acid methyl ester and 350 mg of 2-vinylthiophene, were obtained 211 mg of the title (E)-compound as bright yellow crystals and 85 mg of (Z)-compound of Example 143 as bright yellow crystals. (E) compound: $^1$H-NMR (400 MHz, DMSO-D$_6$) δ 3.85 (3H, s), 7.11 (1H, dd, J=3.6, 5.2 Hz), 7.32 (1H, d, J=16.4 Hz), 7.41 (1H, d, J=3.6 Hz), 7.44 (1H, d, J=11.2 Hz), 7.54 (1H, d, J=5.2 Hz), 7.71 (1H, d, J=16.4 Hz), 8.70 (1H, d, J=6.8 Hz), 13.51 (1H, s).

Example 143

6-Fluoro-3-[(Z)-2-(thiophen-2-yl)-vinyl]-1H-indazole-5-carboxylic acid methyl ester (Z) compound: $^1$H-NMR (400 MHz, DMSO-D$_6$) δ 3.85 (3H, s), 6.82 (1H, d, J=12.0 Hz), 7.03 (1H, d, J=12.0 Hz), 7.06 (1H, dd, J=3.6, 5.2 Hz), 7.44 (1H, d, J=11.6 Hz), 7.50 (1H, d, J=5.2 Hz), 7.63 (1H, d, J=3.6 Hz), 8.34 (1H, d, J=6.8 Hz), 13.63 (1H, s).

Example 144

6-Fluoro-3-[(E)-2-(thiophen-2-yl)-vinyl]-1H-indazole-5-carboxylic acid

To a mixed solution of 60 mg of 6-fluoro-3-[(E)-2-(thiophen-2-yl)-vinyl]-1H-indazole-5-carboxylic acid methyl ester obtained by Example 142 in a mixture of 2 mL tetrahydrofuran/0.5 mL methanol was added 0.5 mL of 5N sodium hydroxide aqueous solution, and stirred at 50° C.-55° C. for 6 hours. The reaction solution was made acidic with 1N hydrochloric acid, and extracted with 15 mL of ethyl acetate. The organic layer was washed successively with water and saturated brine, and dried over anhydrous magnesium sulfate. The solvent was evaporated, to afford 53 mg of the title compound as bright yellow crystals.

$^1$H-NMR (400 MHz, DMSO-D$_6$) δ 7.11 (1H, dd, J=3.2, 5.2 Hz), 7.31 (1H, d, J=16.0 Hz), 7.39 (1H, d, J=11.2 Hz), 7.41 (1H, d, J=3.2 Hz), 7.54 (1H, d, J=5.2 Hz), 7.69 (1H, d, J=16.0 Hz), 8.67 (1H, d, J=7.2 Hz), 13.07 (1H, bs), 13.46 (1H, s).

Example 145

In accordance with the method of Example 102, from 6-fluoro-3-[(E)-2-(thiophen-2-yl)-vinyl]-1H-indazole-5-carboxylic acid and various kinds of amine, compounds of Examples 146-151 were obtained.

Example 146

6-Fluoro-3-[(E)-2-(thiophen-2-yl)-vinyl]-1H-indazole-5-carboxylic acid cyclopropylamide MS (ESI) m/z 328 MH$^+$ Example 147

6-Fluoro-3-[(E)-2-(thiophen-2-yl)-vinyl]-1H-indazole-5-carboxylic acid(furan-2-ylmethyl)-amide MS (ESI) m/z 368 MH$^+$ Example 148

6-Fluoro-3-[(E)-2-(thiophen-2-yl)-vinyl]-1H-indazole-5-carboxylic acid[(1S)-(2-hydroxy-1-phenyl-ethyl)]-amide MS (ESI) m/z 408 MH$^+$ Example 149

6-Fluoro-3-[(E)-2-(thiophen-2-yl)-vinyl]-1H-indazole-5-carboxylic acid[(1S)-(1-hydroxymethyl-2-methyl-propyl)]-amide MS (ESI) m/z 374 MH$^+$ Example 150

6-Fluoro-3-[(E)-2-(thiophen-2-yl)-vinyl]-1H-indazole-5-carboxylic acid (pyridin-3-ylmethyl)-amide MS (ESI) m/z 379 MH$^+$ Example 151

6-Fluoro-3-[(E)-2-(thiophen-2-yl)-vinyl]-1H-indazole-5-carboxylic acid[(1S)-(1-carbamoyl-ethyl)]-amide MS (ESI) m/z 359 MH$^+$ Production Example 152

6-Fluoro-3-[(E)-2-(thiophen-2-yl)-vinyl]-1-trityl-1H-indazole-5-carboxylic acid 151 mg of 6-fluoro-3-[(E)-2-(thiophen-2-yl)-vinyl]-1H-indazole-5-carboxylic acid methyl ester obtained by Example 142 was tritylated in the same manner as described in Production example 22, followed by hydrolysis in the same manner as described in Example 144, to afford 320 mg of the title compound as bright yellow crystals.

$^1$H-NMR (400 MHz, DMSO-$D_6$) δ 5.99 (1H, d, J=12.0 Hz), 7.11 (1H, dd, J=3.2, 5.2 Hz), 7.14-7.48 (17H, m), 7.54 (1H, d, J=5.2 Hz), 7.59 (1H, d, J=16.4 Hz), 8.66 (1H, d, J=6.8 Hz), 13.18 (1H, bs)

Production Example 153

{6-Fluoro-3-[(E)-2-(thiophen-2-yl)-vinyl]-1-trityl-1H-indazol-5-yl}-carbamic acid tert-butyl ester From 320 mg of 6-fluoro-3-[(E)-2-thiophen-2-yl-vinyl]-1-trityl-1H-indazole-5-carboxylic acid, 66 mg of the title compound was obtained as orange crystals in the similar method as described in Production example 109.

$^1$H-NMR (400 MHz, DMSO-$D_6$) δ 1.44 (9H, s), 6.00 (1H, d, J=11.6 Hz), 7.09 (1H, dd, J=2.8, 5.6 Hz), 7.14-7.55 (19H, m), 8.15 (1H, d, J=7.6 Hz), 8.85 (1H, s).

Example 154

6-Fluoro-3-[(E)-2-(thiophen-2-yl)-vinyl]-1H-indazol-5-ylamine

From 90 mg of {6-fluoro-3-[(E)-2-(thiophen-2-yl)-vinyl]-1-trityl-1H-indazol-5-yl}-carbamic acid tert-butyl ester, 22 mg of the title compound was obtained as a dark brown powder in the similar method as described in Example 110.

$^1$H-NMR (400 MHz, DMSO-$D_6$) δ 4.94 (2H, s), 7.09 (1H, dd, J=3.6, 5.2 Hz), 7.12 (1H, d, J=16.4 Hz), 7.22 (2H, d, J=10.8 Hz), 7.25 (1H, d, J=3.6 Hz), 7.33 (1H, d, J=8.4 Hz), 7.44 (1H, d, J=16.4 Hz), 7.47 (1H, d, J=5.2 Hz), 12.83 (1H, s).

Example 155

From 6-fluoro-3-[(E)-2-(thiophen-2-yl)-vinyl]-1H-indazol-5-ylamine and various kinds of carboxylic acid, compounds of Examples 156-159 were obtained in accordance with the method of Example 111.

Example 156

Cyclopropane carboxylic acid{6-fluoro-3-[(E)-2-(thiophen-2-yl)-vinyl]-1H-indazol-5-yl}-amide MS (ESI) m/z 328 $MH^+$ Example 157

(2S)-5-Oxo-pyrrolidine-2-carboxylic acid{6-fluoro-3-[(E)-2-(thiophen-2-yl)-vinyl]-1H-indazol-5-yl}-amide MS (ESI) m/z 371 $MH^+$ Example 158

N-{6-Fluoro-3-[(E)-2-(thiophen-2-yl)-vinyl]-1H-indazol-5-yl}-2-(thiophen-2-yl)-acetamide MS (ESI) m/z 384 $MH^+$ Example 159

Furan-2-carboxylic acid{6-fluoro-3-[(E)-2-(thiophen-2-yl)-vinyl]-1H-indazol-5-yl}-amide MS (ESI) m/z 354 $MH^+$ Example 160

6-Fluoro-3-[(E)-2-(naphthalen-2-yl)-vinyl]-1H-indazole-5-carbonitrile

From 1.0 g of 3-bromo-6-fluoro-1-trityl-1H-indazole-5-carbonitrile obtained by Production example 83 and 674 mg of 2-vinylnaphthalene, 590 mg of the title compound was obtained as ocher crystals in accordance with the method of Example 100.

$^1$H-NMR (400 MHz, DMSO-$D_6$) δ 7.47-7.58 (2H, m), 7.67 (1H, d, J=10.0 Hz), 7.72 (1H, d, J=16.8 Hz), 7.83 (1H, d, J=16.4 Hz), 7.93 (2H, d, J=9.2 Hz), 7.96 (1H, d, J=8.8 Hz), 8.01 (1H, d, J=8.4 Hz), 8.20 (1H, s), 9.06 (1H, d, J=6.4 Hz), 13.76 (1H, s).

Example 161

6-Fluoro-3-[(E)-2-(naphthalen-2-yl)-vinyl]-1H-indazole-5-carboxylic acid

To a suspension of 588 mg of 6-fluoro-3-[(E)-2-(naphthalen-2-yl)-vinyl]-1H-indazole-5-carbonitrile in 3 mL of acetic acid and 1 mL of water was added 3 mL of concentrated sulfuric acid, and stirred at 110° C. for 1 hours. After allowing to cool, the reaction solution was added with ice, and extracted with a mixed solvent of 30 mL ethyl acetate/15 mL tetrahydrofuran. The organic layer was washed with saturated brine, and dried over anhydrous magnesium sulfate. The solvent was evaporated, and the resultant crude product was dissolved in 6 mL of 1,4-dioxane, added with 6 mL of 4N lithium hydroxide, and stirred at 120° C. for 15 hours. The reaction solution was made acidic with 5N hydrochloric acid, and then extracted with a mixed solvent of 30 mL ethyl acetate/20 mL tetrahydrofuran. The organic layer was washed successively with water and saturated brine, and dried over anhydrous magnesium sulfate. The solvent was evaporated, to afford 477 mg of the title compound as ocher crystals.

$^1$H-NMR (400 MHz, DMSO-$D_6$) δ 7.41 (1H, d, J=11.6 Hz), 7.48-7.57 (2H, m), 7.70 (1H, d, J=16.4 Hz), 7.82 (1H, d, J=16.4 Hz), 7.92 (1H, d, J=8.8 Hz), 7.94 (2H, d, J=8.8 Hz), 8.05 (1H, d, J=8.4 Hz), 8.17 (1H, s), 8.79 (1H, d, J=7.2 Hz), 13.08 (1H, bs), 13.49 (1H, s).

Example 162

From 6-fluoro-3-[(E)-2-(naphthalen-2-yl)-vinyl]-1H-indazole-5-carboxylic acid and various kinds of amine, compounds of Examples 163-166 were obtained in accordance with the method of Example 102.

Example 163

6-Fluoro-3-[(E)-2-(naphthalen-2-yl)-vinyl]-1H-indazole-5-carboxylic acid cyclopropylamide MS (ESI) m/z 372 $MH^+$ Example 164

6-Fluoro-3-[(E)-2-(naphthalen-2-yl)-vinyl]-1H-indazole-5-carboxylic acid(furan-2-ylmethyl)-amide MS (ESI) m/z 412 $MH^+$ Example 165

6-Fluoro-3-[(E)-2-(naphthalen-2-yl)-vinyl]-1H-indazole-5-carboxylic acid(pyridin-3-ylmethyl)-amide MS (ESI) m/z 423 $MH^+$ Example 166

6-Fluoro-3-[(E)-2-(naphthalen-2-yl)-vinyl]-1H-indazole-5-carboxylic acid[(1S)-(1-carbamoyl-ethyl)]-amide MS (ESI) m/z 403 $MH^+$ Production Example 167

6-Fluoro-3-[(E)-2-(naphthalen-2-yl)-vinyl]-1-trityl-1H-indazole-5-carboxylic acid From 350 mg of 6-fluoro-3-[(E)-2-(naphthalen-2-yl)-vinyl]-1H-indazole-5-carboxylic acid obtained by Example 161, 188 mg of the title compound was obtained as bright yellow non-crystalline powder in accordance with Production example 108.

$^1$H-NMR (400 MHz, DMSO-$D_6$) δ 6.00 (1H, d, J=12.4 Hz), 7.10-7.44 (15H, m), 7.48-7.56 (2H, m), 7.58 (1H, d, J=16.4 Hz), 7.75 (1H, d, J=16.4 Hz), 7.88-7.98 (3H, m), 8.04 (1H, d, J=8.8 Hz), 8.13 (1H, s), 8.79 (1H, d, J=7.2 Hz), 13.19 (1H, bs).

Production Example 168

{6-Fluoro-3-[(E)-2-(naphthalen-2-yl)-vinyl]-1-trityl-1H-indazol-5-yl}-carbamic acid tert-butyl ester From 182 mg of 6-fluoro-3-[(E)-2-(naphthalen-2-yl)-vinyl]-1-trityl-1H-indazole-5-carboxylic acid, 42 mg of the title compound was obtained as a yellow viscous oil in the similar method as described in Production example 109.

$^1$H-NMR (400 MHz, DMSO-$D_6$) δ 1.46 (9H, s), 6.02 (1H, d, J=11.2 Hz), 7.10-7.58 (18H, m), 7.62 (1H, d, J=16.4 Hz), 7.85-7.95 (3H, m), 7.99 (1H, d, J=8.4 Hz), 8.13 (1H, s), 8.26 (1H, d, J=7.2 Hz), 8.88 (1H, s).

Example 169

6-Fluoro-3-[(E)-2-(naphthalen-2-yl)-vinyl]-1H-indazole-5-ylamine

From 42 mg of {6-fluoro-3-[(E)-2-(naphthalen-2-yl)-vinyl]-1-trityl-1H-indazol-5-yl}-carbamic acid tert-butyl ester, 14 mg of the title compound was obtained as ocher crystals in the similar method as described in Example 110.

$^1$H-NMR (400 MHz, DMSO-$D_6$) δ 4.96 (2H, s), 4.23 (1H, d, J=10.0 Hz), 7.40-7.56 (4H, m), 7.57 (1H, d, J=16.8 Hz), 7.85-7.97 (4H, m), 8.04 (1H, s), 12.86 (1H, s).

Example 170

From 6-fluoro-3-[(E)-2-(naphthalen-2-yl)-vinyl]-1H-indazol-5-ylamine and various kinds of carboxylic acid, compounds of Examples 171-173 were obtained in accordance with the method of Example 111.

Example 171

Cyclopropane Carboxylic acid{6-fluoro-3-[(E)-2-(naphthalen-2-yl)-vinyl]-1H-indazol-5-yl}-amide MS (ESI) m/z 372 $MH^+$ Example 172

(2S)-5-Oxo-pyrrolidine-2-carboxylic acid{6-fluoro-3-[(E)-2-(naphthalen-2-yl)-vinyl]-1H-indazol-5-yl}-amide MS (ESI) m/z 415 $MH^+$ Example 173

N-{6-Fluoro-3-[(E)-2-(naphthalen-2-yl)-vinyl]-1H-indazol-5-yl}-2-(thiophen-2-yl)-acetamide MS (ESI) m/z 428 $MH^+$ Production Example 174

6-Fluoro-3-[(E)-2-(3-fluorophenyl)-vinyl]-1-trityl-1H-indazol-5-ylamine

To a solution of 2.95 g of 6-fluoro-3-[(E)-2-(3-fluorophenyl)-vinyl]-1-trityl-1H-indazole-5-carboxylic acid obtained by Production example 108 in 55 mL of N,N-dimethylformamide, 1.58 g of potassium carbonate and 1.50 g of diphenyl phosphoryl azide were added and stirred at room temperature for 30 minutes followed by stirring at 40-50° C. for 2.5 hours. After adding water, the reaction solution was allowed to cool to room temperature, and extracted with 200 mL of ethyl acetate. The organic layer was washed successively with water and saturated brine, and dried over anhydrous magnesium sulfate. The solvent was evaporated, and the resulting crude product was purified and separated by silica gel column chromatography (n-hexane:toluene=1:1-1:2), to afford 1.57 g of the title compound as yellow crystals.

$^1$H-NMR (400 MHz, DMSO-$D_6$) δ 5.00 (2H, s), 5.91 (1H, d, J=12.4 Hz), 7.09 (1H, t, J=8.0 Hz), 7.14-7.48 (19H, m), 7.54 (1H, d, J=10.4 Hz).

Example 175

N-{6-Fluoro-3-[(E)-2-(3-fluorophenyl)-vinyl]-1H-indazol-5-yl}-acetamide 525 mg of 6-fluoro-3-[(E)-2-(3-fluorophenyl)-vinyl]-1-trityl-1H-indazol-5-ylamine and 80 μl of glacial acetic acid were dehydraing-condensed in accordance with Example 127, followed by deprotection in the similar method as described in Example 16, to afford 150 mg of the title compound as bright yellow crystals.

$^1$H-NMR (400 MHz, DMSO-$D_6$) δ 2.11 (3H, s), 7.15 (1H, dt, J=2.4, 8.0 Hz), 7.38-7.48 (3H, m), 7.52 (1H, d, J=8.0 Hz), 7.58-7.66 (2H, m), 8.40 (1H, d, J=7.6 Hz), 9.72 (1H, s), 13.26 (1H, s).

Production Example 176

N-(5-Fluoro-2-methyl-phenyl)-acetamide

To a solution of 5 g of 5-fluoro-2-methylaniline in 30 mL of pyridine was added 4.6 mL of acetic anhydride, and stirred at room temperature for 4 hours. After distilling off the pyridine under reduced pressure, the residue was dissolved in 250 mL of ethyl acetate, and washed successively with water, 1N hydrochloric acid, water, saturated aqueous sodium hydrogen carbonate and saturated brine. The solution was dried over anhydrous magnesium sulfate, allowed to pass though a silica gel pad, and then the solvent was evaporated. The residue was recrystallized from ethyl acetate-diethyl ether, to afford 5.34 g of the title compound as white needle crystals. The mother liquor was further concentrated, and triturated with diethyl ether, to afford 907 mg of the title compound as purple needle crystals.

$^1$H-NMR (400 MHz, $CDCl_3$) δ 2.22 (3H, s), 6.76 (1H, ddd, J=2.0, 7.2, 8.0 Hz), 7.00 (1H, bs), 7.11 (1H, t, J=7.2 Hz), 7.77 (1H, dd, J=2.0, 6.8 Hz).

Production Example 177

N-(5-Fluoro-2-methyl-4-nitrophenyl)-acetamide

To a solution of 5.01 g of N-(5-fluoro-2-methyl-phenyl)-acetamide in 30 mL of concentrated sulfuric acid was added dropwise 2.74 g of 70% nitric acid (d=1.42) while keeping the inner temperature at 3° C. After stirring for 40 minutes at this temperature, the reaction solution was poured dropwise into ice water under stirring. After collecting the precipitated powder by filtration, the powder was dissolved in 100 mL of ethyl acetate, washed successively with saturated aqueous sodium hydrogen carbonate (twice) and saturated brine. After drying over anhydrous magnesium sulfate, the solvent was evaporated. The residue was crystallized from ethanol, to afford 3.68 g of the title compound as yellow needle crystals.

$^1$H-NMR (400 MHz, $CDCl_3$) δ 2.29 (3H, s), 2.32 (3H, s), 7.17 (1H, bs), 7.94 (1H, d, J=8.0 Hz), 8.34 (1H, d, J=13.6 Hz).

Production Example 178

5-Fluoro-2-methyl-4-nitro-phenylamine

A suspension of 3.5 g of N-(5-fluoro-2-methyl-4-nitrophenyl)-acetamide in 5N hydrochloric acid was heated under reflux for 1 hour. After allowing to cool, the solution was neutralized with potassium carbonate, and extracted with 80 mL of ethylacetate. The organic layer was dried over anhydrous magnesium sulfate, allowed to pass through a silica gel pad, and then the solvent was distilled off under reduced pressure, to afford 2.69 g of the title compound as ocher crystals.

$^1$H-NMR (400 MHz, $CDCl_3$) δ 2.16 (3H, s), 4.39 (2H, bs), 6.39 (1H, d, J=12.8 Hz), 7.88 (1H, d, J=8.4 Hz).

Production Example 179

6-Fluoro-5-nitro-1H-indazole

To a suspension of 2 g of 5-fluoro-2-methyl-4-nitro-phenylamine in 50 mL of glacial acetic acid, an aqueous solution of 812 mg of sodium sulfite was added, and stirred at room temperature overnight. The reaction solution was added with 100 mL of water, the precipitated powder filtered out, and the filtrate was concentrated to 50 mL. After extracting with 100 mL of ethyl acetate, the organic layer was washed successively with aqueous sodium hydrogen carbonate, 10% sodium thiosulfate aqueous solution, water and saturated brine, dried over anhydrous magnesium sulfate, and then the solvent was evaporated. The obtained crude crystals were triturated with toluene, to afford 589 mg of the title compound as bright yellow crystals.

$^1$H-NMR (400 MHz, DMSO-$D_6$) δ 7.69 (1H, d, J=11.6 Hz), 8.39 (1H, s), 8.79 (1H, d, J=7.2 Hz), 13.76 (1H, s).

Production Example 180

3-Bromo-6-fluoro-5-nitro-1-trityl-1H-indazole

In accordance with Production example 87 and Production example 88, from 500 mg of 6-fluoro-5-nitro-1H-indazole, 651 mg of the title compound was obtained as pale brown crystals.

$^1$H-NMR (400 MHz, DMSO-$D_6$) δ 6.20 (1H, d, J=12.4 Hz), 7.15-7.23 (6H, m), 7.33-7.43 (9H, m), 8.47 (1H, d, J=7.2 Hz).

Production Example 181

6-Fluoro-3-[(E)-2-(4-fluorophenyl)-vinyl]-5-nitro-1-trityl-1H-indazole

To a solution of 600 mg of 3-bromo-6-fluoro-5-nitro-1-trityl-1H-indazole in 6 mL of N,N-dimethylformamide were successively added 292 mg of 4-fluorostyrene, 71 mg of 2-(di-tert-butylphosphino)biphenyl, 27 mg of palladium acetate (II) and 0.85 mL of triethylamine, and stirred at 80° C. for 6.5 hours. The solvent was evaporated, and the resulting residue was dissolved in 25 mL of ethyl acetate. The organic layer was successively washed with water (twice) and saturated brine, dried over anhydrous magnesium sulfate, and then the solvent was evaporated. The obtained crude crystal was recrystallized from ethyl acetate-diisopropylether, to afford 304 mg of the title compound as bright yellow crystals.

$^1$H-NMR (400 MHz, DMSO-$D_6$) δ 6.12 (1H, d, J=12.8 Hz), 7.15-7.30 (8H, m), 7.32-7.46 (9H, m), 7.47 (1H, d, J=16.4 Hz), 7.63 (1H, d, J=16.4 Hz), 7.81 (1H, dd, J=5.6, 8.4 Hz), 9.16 (1H, d, J=6.8 Hz).

Production Example 182

6-Fluoro-3-[(E)-2-(4-fluorophenyl)-vinyl]-1-trityl-1H-indazol -5-ylamine

To a solution of 290 mg of 6-fluoro-3-[(E)-2-(4-fluorophenyl)-vinyl]-5-nitro-1-trityl-1H-indazole in a mixture of 5 mL N,N-dimethylformamide/9 mL methanol/1 mL water were added 30 mg of ammonium chloride and 150 mg of iron powder, and stirred at 80° C. for 8 hours. After filtering off the insoluble substances through Celite, the solvent was evaporated, and the resultant residue was dissolved in 15 mL of ethyl acetate. The organic layer was washed successively with water, saturated aqueous sodium hydrogen carbonate and saturated brine. After drying over anhydrous magnesium sulfate, the solvent was evaporated, to afford 252 mg of the title compound as pale brown non-crystalline powder.

$^1$H-NMR (400 MHz, DMSO-$D_6$) δ 4.98 (2H, s), 5.91 (1H, d, J=12.0 Hz), 7.14-7.24 (8H, m), 7.25-7.37 (11H, m), 7.40 (1H, d, J=8.8 Hz), 7.69 (1H, dd, J=5.6, 8.8 Hz).

Example 183

6-Fluoro-3-[(E)-2-(4-fluorophenyl)-vinyl]-1-trityl-1H-indazol-5-ylamine synthesized in Production example 182 was dissolved in N,N-dimethylformamide, and dispensed into test tubes. Each test tube was added successively with preliminarily prepared 1.5 equivalents of different kind of carboxylic acid in 1M dimethylformamide solution, 1.5 equivalents of 1-hydroxybenztriazole monohydrate in 1 M dimethylformamide solution, and 1.5 equivalents of 1-ethyl-3-(3-dimethylaminopropyl)carbodiimide hydrochloride (═WSC.HCl), and stirred at room temperature for 6 days. After adding semi-saturated sodium hydrogen carbonate to each test tube, the solution was extracted with ethyl acetate. After distilling off the solvent, the residue was dissolved in 10% trifluoroacetic acid/2% tripropylsilane/dichloromethane and stirred for 6.5 hours. After adding 5% water/methanol to each test tube, the solvent was distilled off. The residue was dissolved in N,N-dimethylformamide, and purified and separated by LC-MS [developing solvent: 0.1% trifluoroacetic acid-containing acetonitrile solution:0.1% trifluoroacetic acid-containing aqueous solution=20:80-80:20, 10 min. cycle, flow rate: 30 mL/min., column: Wako Wakopak Combi ODS, 20 mmΦ×50 mm(Long)], to afford the compounds of Examples 184-188.

Example 184

Cyclopropane Carboxylic acid{6-fluoro-3-[(E)-2-(4-fluorophenyl)-vinyl]-1H-indazol-5-yl}-amide MS (ESI) m/z 340 MH$^+$ Example 185

N-{6-Fluoro-3-[(E)-2-(4-fluorophenyl)-vinyl]-1H-indazol-5-yl}-2-(thiophen-2-yl)-acetamide MS (ESI) m/z 396 MH$^+$ Example 186

N-{6-Fluoro-3-[(E)-2-(4-fluorophenyl)-vinyl]-1H-indazol-5-yl}-acetamide

MS (ESI) m/z 314 MH$^+$

Example 187

N-{6-Fluoro-3-[(E)-2-(4-fluorophenyl)-vinyl]-1H-indazol-5-yl}-3-hydroxy-2,2-dimethyl-propanamide MS (ESI) m/z 372 MH$^+$ Example 188

N-{6-Fluoro-3-[(E)-2-(4-fluorophenyl)-vinyl]-1H-indazol-5-yl}-3-hydroxy-2-phenyl-propanamide MS (ESI) m/z 420 MH$^+$ Example 189

C-{6-Fluoro-3-[(E)-2-(3-fluorophenyl)-vinyl]-1H-indazol-5-yl}-methylamine

To a suspension of 5 mg of lithium aluminum hydride in 1 mL of tetrahydrofuran was added 13 mg of aluminum chloride (III), followed by 9 mg of 6-fluoro-3-[(E)-2-(3-fluorophenyl)-vinyl]-1H-indazole-5-carbonitrile obtained by Example 100, and stirred at room temperature overnight. After adding saturated aqueous ammonium chloride, the reaction solution was added with 15 mL of ethylacetate. The organic layer was washed successively with saturated aqueous sodium hydrogen carbonate (twice) and saturated brine, and dried over anhydrous magnesium sulfate. The solvent was evaporated, and the crude product was purified and separated by silica gel column chromatography (methanol:chloroform=1:9), to afford 3 mg of the title compound as a yellow oil.

$^1$H-NMR (400 MHz, DMSO-$D_6$) δ 3.86 (2H, s), 7.12 (1H, t, J=8.4 Hz), 7.29 (1H, d, J=10.0 Hz), 7.44 (1H, dt, J=6.0, 8.0 Hz), 7.52 (1H, d, J=16.8 Hz), 7,54 (1H, d, J=8.8 Hz), 7.59 (1H, d, J=16.8 Hz), 7.61 (1H, d, J=10.8 Hz), 8.22 (1H, d, J=7.2 Hz), 13.19 (1H, s).

Example 190

N-{6-Fluoro-3-[(E)-2-(3-fluorophenyl)-vinyl]-1H-indazol-5-ylmethyl}-2-methoxy-benzamide From 2.9 mg of C-{6-fluoro-3-[(E)-2-(3-fluorophenyl)-vinyl]-1H-indazol-5-yl}-methylamine, 1.42 mg of the title compound was obtained in accordance with the method of Example 111.

MS (ESI) m/z 420 MH$^+$

Production Example 191

6-Fluoro-1-trityl-3-vinyl-1H-indazole-5-carboxylic acid methyl ester 0.77 g of 3-bromo-6-fluoro-1-trityl-1H-indazole-5-carboxylic acid methyl ester obtained by Production example 141 was treated in the method of Production example 123, to obtain 600 mg of the title compound as colorless needle crystals.

$^1$H-NMR (400 MHz, $CDCl_3$) δ 3.90 (3H, s), 5.52 (1H, d, J=11.5 Hz), 6.05 (1H, d, J=12.4 Hz), 6.08 (1H, d, J=18.2 Hz), 6.94 (1H, dd, J=12.4, 18.2 Hz), 7.14-7.22 (6H, m), 7.24-7.32 (9H, m), 8.51 (1H, d, J=6.9 Hz).

Production Example 192

6-Fluoro-3-[(E)-2-(pyridin-3-yl)-vinyl]-1-trityl-1H-indazole-5-carboxylic acid methyl ester 600 mg of 6-fluoro-1-trityl-3-vinyl-1H-indazole-5-carboxylic acid methyl ester and 190 μl of 3-bromopyridine were treated in the same manner as described in Example 124, to afford 75 mg of the title compound as a colorless powder.

$^1$H-NMR (400 MHz, $CDCl_3$) δ 3.93 (3H, s), 6.11 (1H, d, J=11.9 Hz), 7.15-7.25 (6H, m), 7.25-7.42 (12H, m), 7.89 (1H, dt, J=1.8, 8.3 Hz), 8.51 (1H, dd, J=1.8, 4.7 Hz), 8.59 (1H, d, J=6.8 Hz), 8.76 (1H, d, J=1.8 Hz).

Example 193

N-[6-Fluoro-3-[(E)-2-(pyridin-3-yl)-vinyl]-1H-indazol-5-yl]-2-(thiophen-2-yl)-acetamide 75 mg of 6-fluoro-3-[(E)-2-(pyridin-3-yl)-vinyl]-1-trityl-1H-indazole-5-carboxylic acid methyl ester was alkaline hydrolyzed in the same manner as described in Example 144, to give 70 mg of 6-fluoro-3-[(E)-2-(pyridin-3-yl)-vinyl]-1-trityl-1H-indazole-5-carboxylic acid as a colorless powder. Then in the same manner as described in Example 174, 30 mg of 6-fluoro-3-[(E)-2-(pyridin-3-yl)-vinyl]-1-trityl-1H-indazol-5-ylamine was obtained. Further, in the same manner as described in Example 175, this compound was subjected to dehydration condensation with 10 mg of 2-thiopheneacetic acid, followed by deprotection, to obtain 8 mg of the title compound as a colorless powder.

$^1$H-NMR (400 MHz, $CD_3OD$) δ 4.02 (2H, s), 7.00 (1H, dd, J=3.5, 4.7 Hz), 7.06 (1H, dd, J=1.0, 3.5 Hz), 7.32 (1H, dd, J=1.0, 4.7 Hz), 7.34 (1H, d, J=11.5 Hz), 7.45 (1H, dd, J=4.7, 8.0 Hz), 7.47 (1H, d, J=16.3 Hz), 7.56 (1H, d, J=16.3 Hz), 8.15 (1H, dt, J=1.8, 8.0 Hz), 8.43 (1H, dd, J=1.8, 4.7 Hz), 8.57 (1H, d, J=6.8 Hz), 8.76 (1H, d, J=1.8 Hz).

Example 194

4-Fluoro-3-[(E)-2-(3-fluorophenyl)-vinyl]-1H-indazole-5-carboxylic acid methyl ester To a solution of 150 mg of 3-bromo-4-fluoro-1-trityl-1H-indazole-5-carboxylic acid methyl ester obtained by Production example 88 in 6 mL of N,N-dimethylformamide were successively added 200 mg of 2-[(E)-2-(3-fluorophenyl)-vinyl]-4,4,5,5-tetramethyl-[1,3,2]dioxaborolane obtained by Production example 137, 24 mg of 2-(di-tert-butylphosphino) biphenyl, 9 mg of palladium acetate (II), 117 mg of potassium fluoride and 0.6 mL of water, and stirred 80° C. for 1.5 hours. The reaction solution was added with 30 mL of ethyl acetate, and the organic layer was washed successively with water, semi-saturated brine and saturated brine and dried over anhydrous magnesium sulfate. The solvent was evaporated, to give 260 mg of a crude coupling compound. Then the crude coupling compound was deblocked in the manner as described in Example 6, to afford 32 mg of the title compound as bright yellow crystals.

$^1$H-NMR (400 MHz, DMSO-$D_6$) δ3.89 (3H, s), 7.15 (1H, dt, J=2.4, 8.4 Hz), 7.42-7.62 (6H, m), 7.84 (1H, dd, J=6.4, 8.8 Hz), 13.81 (1H, s).

Example 195

4-Fluoro-3-[(E)-2-(3-fluorophenyl)-vinyl]-1H-indazole-5-carboxylic acid

From 35 mg of 4-fluoro-3-[(E)-2-(3-fluorophenyl)-vinyl]-1H-indazole-5-carboxylic acid methyl ester, 31 mg of the title compound was obtained as ocher crystals in accordance with the method of Example 144.

$^1$H-NMR (400 MHz, DMSO-$D_6$) δ 7.15 (1H, dt, J=2.4, 8.4 Hz), 7.38-7.60 (6H, m), 7.83 (1H, dd, J=6.4, 8.8 Hz), 13.08 (1H, bs), 13.76 (1H, s).

Example 196

From 4-fluoro-3-[(E)-2-(3-fluorophenyl)-vinyl]-1H-indazole-5-carboxylic acid and various kinds of amine, compounds of Examples 197-202 were obtained in accordance with the method of Example 102.

Example 197

4-Fluoro-3-[(E)-2-(3-fluorophenyl)-vinyl]-1H-indazole-5-carboxylic acid cyclopropylamide MS (ESI) m/z 340 $MH^+$ Example 198

4-Fluoro-3-[(E)-2-(3-fluorophenyl)-vinyl]-1H-indazole-5-carboxylic acid(furan-2-ylmethyl)-amide MS (ESI) m/z 380 $MH^+$ Example 199

4-Fluoro-3-[(E)-2-(3-fluorophenyl)-vinyl]-1H-indazole-5-carboxylic acid(thiophen-2-ylmethyl)-amide MS (ESI) m/z 396 $MH^+$ Example 200

4-Fluoro-3-[(E)-2-(3-fluorophenyl)-vinyl]-1H-indazole-5-carboxylic acid[(1S)-1-hydroxymethyl-2-methyl-propyl]-amide MS (ESI) m/z 386 $MH^+$ Example 201

4-Fluoro-3-[(E)-2-(3-fluorophenyl)-vinyl]-1H-indazole-5-carboxylic acid[(1S)-1-carbamoyl-ethyl]-amide MS (ESI) m/z 763 $2M+Na^+$ Example 202

4-Fluoro-3-[(E)-2-(3-fluorophenyl)-vinyl]-1H-indazole-5-carboxylic acid[(1S)-1-(2-methoxy-ethylcarbamoyl)-ethyl]-amide MS (ESI) m/z 429 $MH^+$ Production Example 203

4-Fluoro-3-[(E)-2-(3-fluorophenyl)-vinyl]-1-trityl-1H-indazole-5-carboxylic acid From 72 mg of 4-fluoro-3-[(E)-2-(3-fluorophenyl)-vinyl]-1H-indazole-5-carboxylic acid methyl ester obtained by Example 194, 45 mg of the title compound was obtained as yellow crystals in accordance with the method of Production example 152.

$^1$H-NMR (400 MHz, DMSO-$D_6$) δ 6.23 (1H, d, J=8.8 Hz), 7.10-7.60 (22H, m), 13.14 (1H, bs).

Production Example 204

4-Fluoro-3-[(E)-2-(3-fluorophenyl)-vinyl]-1-trityl-1H-indazol-5-ylamine

From 45 mg of 4-fluoro-3-[(E)-2-(3-fluorophenyl)-vinyl]-1-trityl-1H-indazole-5-carboxylic acid, 4 mg of the title compound was obtained as a dark brown powder in accordance with the method of Production example 174.

$^1$H-NMR (400 MHz, DMSO-$D_6$) δ4.90 (2H, s), 5.95 (1H, d, J=8.4 Hz), 6.63 (1H, t, J=8.4 Hz), 7.06-7.48 (21H, m).

Example 205

N-{4-Fluoro-3-[(E)-2-(3-fluorophenyl)-vinyl]-1H-indazole-5-carboxylic acid}-2-(thiophen-2-yl)-acetamide From 4 mg 4-fluoro-3-[(E)-2-(3-fluorophenyl)-vinyl]-1-trityl-1H-indazol-5-ylamine and 2-thiopheneacetic acid, 0.83 mg of the title compound was obtained in accordance with the method of Example 183.

MS (ESI) m/z 396 $MH^+$

Production Example 206

4-Fluoro-3-iodo-1H-indazole-5-carbonitrile

To a solution of 161 mg of 4-fluoro-1H-indazole-5-carbonitrile obtained by Production example 85 in 4 mL of N,N-dimethylformamide was added 285 mg of N-iodosuccinimide was added, and stirred at 75° C. for 4 hours. The reaction solution was added with 40 mL of ethyl acetate, then washed successively with semi-saturated aqueous sodium hydrogen carbonate, water, semi-saturated brine and saturated brine, and dried over anhydrous magnesium sulfate. The resultant crude product was purified and separated by silica gel column chromatography (ethyl acetate:toluene=1:9), to afford 273 mg of the title compound as white crystals.

$^1$H-NMR (400 MHz, DMSO-$D_6$) δ7.60 (1H, d, J=8.4 Hz), 7.16 (1H, dd, J=6.0, 8.4 Hz), 14.23 (1H, s).

Production Example 207

4-Fluoro-3-iodo-1-trityl-1H-indazole-5-carbonitrile

From 250 mg of 4-fluoro-3-iodo-1H-indazole-5-carbonitrile, 247 mg of the title compound was obtained as white crystals in accordance with the method of Production example 88.

$^1$H-NMR (400 MHz, DMSO-$D_6$)δ6.34 (1H, d, J=8.8 Hz), 7.08-7.16 (6H, m), 7.30-7.39 (9H, m), 8.47 (1H, dd, J=6.4, 8.8 Hz).

Example 208

4-Fluoro-3-[(E)-2-(thiophen-2-yl)-vinyl]-1H-indazole-5-carbonitrile

In accordance with the method of Example 100, from 235 mg of 4-fluoro-3-iodo-1-trityl-1H-indazole-5-carbonitrile and 98 mg of 2-vinylthiophene, 11 mg of (Z)-compound described in Example 209 was obtained as bright yellow crystal and further 79 mg of the title (E)-compound was obtained as bright yellow crystals.

(E) compound: $^1$H-NMR (400 MHz, DMSO-$D_6$)δ7.12 (1H, dd, J=3.6, 5.2 Hz), 7.14 (1H, d, J=16.4 Hz), 7.38 (1H, d, J=3.6 Hz), 7.54 (1H, d, J=8.8 Hz), 7.56 (1H, d, J=5.2 Hz), 7.70 (1H, d, J=16.4 Hz), 7.71 1H, dd, J=6.0, 8.8 Hz), 13.99 (1H, s).

Example 209

4-Fluoro-3-[(Z)-2-(thiophen-2-yl)-vinyl]-1-trityl-1H-indazole-5-carbonitrile (Z) compound: $^1$H-NMR (400 MHz, DMSO-$D_6$) δ6.71 (1H, d, J=12.0 Hz), 7.07 (1H, dd, J=4.0, 5.2 Hz), 7.10 (1H, d, J=12.0 Hz), 7.51 (1H, d, J=5.2 Hz), 7.57 (1H, d, J=8.8 Hz), 7.59 (1H, d, J=4.0 Hz), 7.71 (1H, dd, J=6.0, 8.8 Hz), 14.09 (1H, s).

Example 210

4-Fluoro-3-[(E)-2-(thiophen-2-yl)-vinyl]-1H-indazole-5-carboxylic acid

A suspension of 25 mg of 4-fluoro-3-[(E)-2-(thiophen-2-yl)-vinyl]-1H-indazole-5-carbonitrile in 2 mL of 4N lithium hydroxide was heated under reflux for 9 hours. After allowing to cool, 2N hydrochloric acid was added to make acidic, and extracted with 15 mL of ethyl acetate. The organic layer was washed with water and saturated brine. After drying over anhydrous magnesium sulfate, and passing through a silica gel pad, the solvent was evaporated, to afford 10 mg of the title compound as a dark brown powder.

$^1$H-NMR (400 MHz, DMSO-$D_6$) δ 7.11 (1H, dd, J=3.2, 4.8 Hz), 7.20 (1H, d, J=16.4 Hz), 7.35 (1H, d, J=3.2 Hz), 7.40 (1H, d, J=8.8 Hz), 7.55 (1H, d, J=4.8 Hz), 7.69 (1H, d, J=16.4 Hz), 7.82 (1H, dd, J=6.8, 8.8 Hz), 13.07 (1H, bs), 13.71 (1H, s).

Example 211

From 4-fluoro-3-[(E)-2-(thiophen-2-yl)-vinyl]-1H-indazole-5-carboxylic acid and various kinds of amine, compounds of Examples 212-213 were obtained in accordance with the method of Example 102.

Example 212

4-Fluoro-3-[(E)-2-(thiophen-2-yl)-vinyl]-1H-indazole-5-carboxylic acid cyclopropylamide MS (ESI) m/z 328 $MH^+$ Example 213

4-Fluoro-3-[(E)-2-(thiophen-2-yl)-vinyl]-1H-indazole-5-carboxylic acid(furan-2-ylmethyl)-amide MS (ESI) m/z 368 $MH^+$ Example 214

4-Methoxy-3-(E)-styryl-1H-indazole-5-carbonitrile 161.5 mg of 3-bromo-4-methoxy-1-trityl-1H-indazole-5-carbonitrile obtained by Production example 99 and 82.3 mg of (E)-2-phenylvinylboronic acid were coupled in the same manner as described in Example 194, followed by deprotection, to afford 35 mg of the title compound as brown crystals.

$^1$H-NMR (400 MHz, $CD_3OD$) δ4.29 (3H, s), 7.28-7.41 (3H, m), 7.31 (1H, d, J=8.8 Hz), 7.47 (1H, d, J=8.8 Hz), 7.56 (1H, d, J=16.8 Hz), 7.56-7.61 (2H, m), 7.61 (1H, d, J=16.8 Hz).

Example 215

4-Methoxy-3-(E)-styryl-1H-indazole-5-carboxylic acid amide 35 mg of 4-methoxy-3-(E)-styryl-1H-indazole-5-carbonitrile was dissolved in a mixed solvent 2 mL concentrated sulfuric acid/1 mL water, and stirred at 110° C. for 1 hour and 15 minutes. After cooling the reaction mixture on ice, water was slowly poured under ice cooling, and the precipitated crystals were collected by filtration, and washed with water. After drying under reduced pressure, 22 mg of the title compound was obtained as brown crude crystals.

$^1$H-NMR (400 MHz, $CD_3OD$) δ4.01 (3H, s), 7.20-7.78 (7H, m), 7.33 (1H, d, J=8.8 Hz), 7.88 (1H, d, J=8.8 Hz).

Example 216

4-methoxy-3-(E)-styryl-1H-indazole-5-carboxylic acid 22 mg of 4-methoxy-3-(E)-styryl-1H-indazole-5-carboxylic acid amide was added to 3 mL of 4N lithium hydroxide aqueous solution, and stirred at 110° C. for 4 hours. After cooling on ice, the reaction solution was neutralized with 2N hydrochloric acid under ice cooling, and the precipitated crystals were collected by filtration and washed with water. This was then dried under reduced pressure, to afford 20 mg of the title compound as brown crude crystals.

$^1$H-NMR (400 MHz, $CD_3OD$) δ 4.0 (3H, s), 7.22-7.75 (7H, m), 7.28 (1H, d, J=8.8 Hz), 7.88 (1H, d, J=8.8 Hz).

MS (ESI) m/z 293 $(M-H)^-$

Example 217

From 4-methoxy-3-(E)-styryl-1H-indazole-5-carboxylic acid and various kinds of amine, compounds of Examples 218-222 were obtained in accordance with the method of Example 102.

Example 218

4-Methoxy-3-styryl-1H-indazole-5-carboxylic acid [(1S)-1-hydroxymethyl-2-metylpropyl]-amide MS (ESI) m/z 380 $MH^+$ Example 219

4-Methoxy-3-styryl-1H-indazole-5-carboxylic acid cyclopropylamide

MS (ESI) m/z 334 $MH^+$

Example 220

4-Methoxy-3-styryl-1H-indazole-5-carboxylic acid (furan-2-ylmethyl)-amide

MS (ESI) m/z 374 $MH^+$

Example 221

4-Methoxy-3-styryl-1H-indazole-5-carboxylic acid [(1S)-2-hydroxy-1-phenylethyl]-amide MS (ESI) m/z 414 $MH^+$ Example 222

4-Methoxy-3-styryl-1H-indazole-5-carboxylic acid [(1S)-1-carbamoylethyl]-amide

MS (ESI) m/z 365 $MH^+$

Example 223

3-[(E)-2-(3-Fluorophenyl)-vinyl]-4-methoxy-1H-indazole-5-carbonitrile 180.3 mg of 3-bromo-4-methoxy-1-trityl-1H-indazole-5-carbonitrile obtained by Production example 99 and 154 mg of 2-[(E)-2-(3-fluorophenyl)-vinyl]-4,4,5,5-tetramethyl-[1,3,2]dioxaborolane obtained by Production example 137 were coupled in accordance with the method of Example 194, followed by deprotection, to afford 30.8 mg of the title compound as brown crystals.

$^1$H-NMR (400 MHz, $CD_3OD$) δ 4.30 (3H, s), 6.99-7.51 (4H, m), 7.31 (1H, d, J=8.8 Hz), 7.48 (1H, d, J=8.8 Hz), 7.57 (1H, d, J=16.4 Hz), 7.61 (1H, d, J=16.4 Hz).

Example 224

3-[(E)-2-(3-Fluorophenyl)-vinyl]-4-methoxy-1H-indazole-5-carboxylic acid amide

From 30.8 mg of 3-[(E)-2-(3-fluorophenyl)-vinyl]-4-methoxy-1H-indazole-5-carbonitrile, 22 mg of the title compound was obtained as brown crude crystals in accordance with the method of Example 215.

$^1$H-NMR (400 MHz, $CD_3OD$) δ 4.00 (3H, s), 7.00-7.05 (1H, m), 7.21-7.43 (3H, m), 7.33 (1H, d, J=8.8 Hz), 7.57 (1H, d, J=16.4 Hz), 7.64 (1H, d, J=16.4 Hz), 7.88 (1H, d, J=8.8 Hz).

Example 225

3-[(E)-2-(3-Fluorophenyl)-vinyl]-4-methoxy-1H-indazole-5-carboxylic acid

From 22 mg of 3-[(E)-2-(3-fluorophenyl)-vinyl]-4-methoxy-1H-indazole-5-carboxylic acid amide, 19 mg of the title compound was obtained as brown crude crystal in accordance with the method of Example 216.

$^1$H-NMR (400 MHz, $CD_3OD$) δ 4.05 (3H, s), 6.99-7.04 (1H, m), 7.22-7.41 (3H, m), 7.55 (1H, d, J=16.4 Hz), 7.69 (1H, d, J=16.4 Hz), 7.77 (1H, d, J=8.6 Hz).

MS (ESI) m/z 311 $(M-H)^-$

Example 226

From 3-[(E)-2-(3-fluorophenyl)-vinyl]-4-methoxy-1H-indazole-5-carboxylic acid and various kinds of amine, compounds of Examples 227-231 were obtained in accordance with the method of Example 102.

Example 227

3-[(E)-2-(3-Fluorophenyl)-vinyl]-4-methoxy-1H-indazole-5-carboxylic acid[(1S)-1-hydroxymethyl-2-methylpropyl]-amide MS (ESI) m/z 398 $MH^+$ Example 228

3-[(E)-2-(3-Fluorophenyl)-vinyl]-4-methoxy-1H-indazole-5-carboxylic acid cyclopropylamide MS (ESI) m/z 352 $MH^+$ Example 229

3-[(E)-2-(3-Fluorophenyl)-vinyl]-4-methoxy-1H-indazole-5-carboxylic acid(furan-2-ylmethyl)-amide MS (ESI) m/z 392 $MH^+$ Example 230

3-[(E)-2-(3-Fluorophenyl)-vinyl]-4-methoxy-1H-indazole-5-carboxylic acid[(1S)-2-hydroxy-1-phenylethyl]-amide MS (ESI) m/z 432 $MH^+$ Example 231

3-[(E)-2-(3-Fluorophenyl)-vinyl]-4-methoxy-1H-indazole-5-carboxylic acid[(1S)-1-carbamoylethyl]-amide MS (ESI) m/z 383 $MH^+$ Example 232

3-[(E)-2-(4-Fluorophenyl)-vinyl]-4-methoxy-1H-indazole-5-carbonitrile

From 420 mg of 3-bromo-4-methoxy-1-trityl-1H-indazole-5-carbonitrile obtained by Production example 99 and 241 mg of (E)-2-(4-fluorophenyl)vinylboronic acid, 66.2 mg of the title compound was obtained as pale yellow crystals in accordance with the method of Example 214.

$^1$H-NMR (400 MHz, DMSO-$D_6$) δ 4.23 (3H, s), 7.24 (2H, t, J=8.8 Hz), 7.37 (1H, d, J=8.6 Hz), 7.47 (1H, d, J=16.4 Hz), 7.55 (1H, d, J=8.6 Hz), 7.57 (1H, d, J=16.4 Hz), 7.72 (2H, dd, J=5.8, 8.8 Hz), 13.68 (1H, s).

Example 233

3-[(E)-2-(4-Fluorophenyl)-vinyl]-4-methoxy-1H-indazole-5-carboxylic acid amide

From 66.2 mg of 3-[(E)-2-(4-fluorophenyl)-vinyl]-4-methoxy-1H-indazole-5-carbonitrile, 61.1 mg of the title compound was obtained as pale yellow crude crystals in accordance with the method of Example 215.

$^1$H-NMR (400 MHz, $CD_3OD$) δ 4.00 (3H, s), 7.08-7.15 (2H, m), 7.32 (1H, d, J=8.6 Hz), 7.53 (1H, d, J=16.4 Hz), 7.58 (1H, d, J=16.4 Hz), 7.58-7.68 (2H, m), 7.87 (1H, d, J=8.6 Hz).

Example 234

3-[(E)-2-(4-Fluorophenyl)-vinyl]-4-methoxy-1H-indazole-5-carboxylic acid

From 61.1 mg of 3-[(E)-2-(4-fluorophenyl)-vinyl]-4-methoxy-1H-indazole-5-carboxylic acid amide, 85.2 mg of the title compound was obtained as pale yellow crude crystal in accordance with the method of Example 216.

$^1$H-NMR (400 MHz, $CD_3OD$) δ 4.04 (3H, s), 7.10-7.16 (2H, m), 7.24 (1H, d, J=8.6 Hz), 7.55 (1H, d, J=16.8 Hz), 7.61 (1H, d, J=16.8 Hz), 7.60-7.65 (2H, m), 7.79 (1H, d, J=8.6 Hz).

MS (ESI) m/z 311 $(M-H)^-$

Example 235

From 3-[(E)-2-(4-Fluorophenyl)-vinyl]-4-methoxy-1H-indazole-5-carboxylic acid and various kinds of amine, compounds of Examples 236-241 were obtained in accordance with the method of Example 102.

Example 236

3-[(E)-2-(4-Fluorophenyl)-vinyl]-4-methoxy-1H-indazole-5-carboxylic acid[(1S)-1-hydroxymethyl-2-methylpropyl]-amide $^1$H-NMR (400 MHz, $CD_3OD$) δ 1.06 (3H, d, J=6.6 Hz), 1.08 (3H, d, J=6.6 Hz), 2.02-2.12 (1H, m), 3.73 (1H, dd, J=4.4, 11.2 Hz), 3.78 (1H, dd, J=5.2, 11.2 Hz), 3.97-4.03 (1H, m), 4.02 (3H, s), 7.11-7.16 (2H, m), 7.34 (1H, d, J=8.8 Hz), 7.54 (1H, d, J=16.6 Hz), 7.59 (1H, d, J=16.6 Hz), 7.63-7.66 (2H, m), 7.84 (1H, d, J=8.8 Hz).

MS (ESI) m/z 398 $MH^+$

Example 237

3-[(E)-2-(4-Fluorophenyl)-vinyl]-4-methoxy-1H-indazole-5-carboxylic acid cyclopropylamide MS (ESI) m/z 352 $MH^+$ Example 238

3-[(E)-2-(4-Fluorophenyl)-vinyl]-4-methoxy-1H-indazole-5-carboxylic acid(furan-2-ylmethyl)-amide $^1$H-NMR (400 MHz, $CD_3OD$) δ 3.89 (3H, s), 4.64 (2H, s), 6.36 (1H, dd, J=0.8, 3.2 Hz), 6.39 (1H, dd, J=1.8, 3.2 Hz), 7.09-7.16 (2H, m), 7.32 (1H, d, J=8.8 Hz), 7.47 (1H, dd, J=0.8, 1.8 Hz), 7.53 (1H, d, J=16.4 Hz), 7.58 (1H, d, J=16.4 Hz), 7.59-7.66 (2H, m), 7.78 (1H, d, J=8.8 Hz).

MS (ESI) m/z 392 $MH^+$

Example 239

3-[(E)-2-(4-Fluorophenyl)-vinyl]-4-methoxy-1H-indazole-5-carboxylic acid[(1S)-2-hydroxy-1-phenylethyl]-amide $^1$H-NMR (400 MHz, $CD_3OD$) δ 3.88 (1H, dd, J=6.6, 11.4 Hz), 3.94 (1H, dd, J=4.8, 11.4 Hz), 3.97 (3H, s), 5.22-5.25 (1H, m), 7.14 (2H, t, J=8.8 Hz), 7.26-7.39 (4H, m), 7.44-7.48 (2H, m) 7.55 (1H, d, J=16.4 Hz), 7.60 (1H, d, J=16.4 Hz), 7.63-7.67 (2H, m), 7.81 (1H, d, J=8.8 Hz).

MS (ESI) m/z 432 $MH^+$

Example 240

3-[(E)-2-(4-Fluorophenyl)-vinyl]-4-methoxy-1H-indazole-5-carboxylic acid[(1S)-1-carbamoylethyl]-amide $^1$H-NMR (400 MHz, $CD_3OD$) δ 1.52 (3H, d, J=7.0 Hz), 4.01 (3H, s), 4.69 (1H, q, J=7.0 Hz), 7.12-7.16 (2H, m), 7.35 (1H, d, J=8.6 Hz), 7.55 (1H, d, J=16.2 Hz), 7.60 (1H, d, J=16.2 Hz), 7.64-7.67 (2H, m), 7.89 (1H, d, J=8.6 Hz).

MS (ESI) m/z. 383 $MH^+$

Example 241

3-[(E)-2-(4-Fluorophenyl)-vinyl]-4-methoxy-1H-indazole-5-carboxylic acid(tetrahydrofuran-2-ylmethyl)-amide MS (ESI) m/z 396 $MH^+$ Example 242

4-Methoxy-3-[(E)-2-(p-tolyl)-vinyl]-1H-indazole-5-carbonitrile

From 160 mg of 3-bromo-4-methoxy-1-trityl-1H-indazole-5-carbonitrile obtained by Production example 99 and 89 mg of (E)-2-(4-methylphenyl)vinylboronic acid, 46.7 mg of the title compound was obtained as colorless crystals in accordance with the method of Example 214.

$^1$H-NMR (400 MHz, $CD_3OD$) δ 2.23 (3H, s), 4.14 (3H, s), 6.09-7.42 (5H, m), 7.06-7.09 (2H, m), 7.15 (1H, d, J=8.4 Hz).

Example 243

4-Methoxy-3-[(E)-2-(p-tolyl)-vinyl]-1H-indazole-5-carboxylic acid

By treating 46.7 mg of 4-methoxy-3-[(E)-2-(p-tolyl)-vinyl]-1H-indazole-5-carbonitrile in the method according to Example 216, 30.8 mg of the title compound was obtained as colorless crude crystals.

$^1$H-NMR (400 MHz, $CD_3OD$) δ 2.37 (3H, s), 4.04 (3H, s), 7.21 (2H, d, J=8.2 Hz), 7.26 (2H, d, J=8.8 Hz), 7.49 (2H, d, J=8.2 Hz), 7.54 (1H, d, J=16.4 Hz), 7.61 (1H, d, J=16.4 Hz), 7.83 (1H, d, J=8.8 Hz).

MS (ESI) m/z 309 $MH^+$

Example 244

From 4-methoxy-3-[(E)-2-(p-tolyl)-vinyl]-1H-indazole-5-carboxylic acid and various kinds of amine, compounds of Examples 245-249 were obtained in accordance with the method of Example 102.

Example 245

4-Methoxy-3-[(E)-2-(p-tolyl)-vinyl]-1H-indazole-5-carboxylic acid[(1S)-1-hydroxymethyl-2-methylpropyl]-amide MS (ESI) m/z 394 $MH^+$ Example 246

4-Methoxy-3-[(E)-2-(p-tolyl)-vinyl]-1H-indazole-5-carboxylic acid cyclopropylamide MS (ESI) m/z 348 $MH^+$ Example 247

4-Methoxy-3-[(E)-2-(p-tolyl)-vinyl]-1H-indazole-5-carboxylic acid(furan-2-ylmethyl)-amide MS (ESI) m/z 388 $MH^+$ Example 248

4-Methoxy-3-[(E)-2-(p-tolyl)-vinyl]-1H-indazole-5-carboxylic acid[(1S)-2-hydroxy-1-phenylethyl]-amide MS (ESI) m/z 428 $MH^+$ Example 249

4-Methoxy-3-[(E)-2-(p-tolyl)-vinyl]-1H-indazole-5-carboxylic acid[(1S)-1-carbamoylethyl]-amide MS (ESI) m/z 379 $MH^+$ Example 250

3-[(E)-2-(4-Chlorophenyl)-vinyl]-4-methoxy-1H-indazole-5-carboxylic acid 160 mg of 3-bromo-4-methoxy-1-trityl-1H-indazole-5-carbonitrile obtained by Production example 99 and 100.3 mg of (E)-2-(4-chlorophenyl)vinylboronic acid were allowed to react in accordance with the method of Example 214, and then alkaline hydrolyzed in accordance with the method of Example 216, to afford 64.8 mg of the title compound as orange crude crystals.

MS (ESI) m/z 327 $(M-H)^-$

Example 251

From 3-[(E)-2-(4-chlorophenyl)-vinyl]-4-methoxy-1H-indazole-5-carboxylic acid and various kinds of amine, compounds of Examples 252-256 were obtained in accordance with the method of Example 102-h.

Example 252

3-[(E)-2-(4-Chlorophenyl)-vinyl]-4-methoxy-1H-indazole-5-carboxylic acid[(1S)-1-hydroxymethyl-2-methylpropyl]-amide MS (ESI) m/z 415 $MH^+$ Example 253

3-[(E)-2-(4-Chlorophenyl)-vinyl]-4-methoxy-1H-indazole-5-carboxylic acid cyclopropylamide MS (ESI) m/z 369 $MH^+$ Example 254

3-[(E)-2-(4-Chlorophenyl)-vinyl]-4-methoxy-1H-indazole-5-carboxylic acid(furan-2-ylmethyl)-amide MS (ESI) m/z 409 $MH^+$ Example 255

3-[(E)-2-(4-Chlorophenyl)-vinyl]-4-methoxy-1H-indazole-5-carboxylic acid[(1S)-2-hydroxy-1-phenylethyl]-amide MS (ESI) m/z 449 $MH^+$ Example 256

3-[(E)-2-(4-Chlorophenyl)-vinyl]-4-methoxy-1H-indazole-5-carboxylic acid[(1S)-1-carbamoylethyl]-amide MS (ESI) m/z 400 $MH^+$ Example 257

3-[(E)-2-(4-Aminophenyl)-vinyl]-4-methoxy-1H-indazole-5-carboxylic acid 180 mg of 3-bromo-4-methoxy-1-trityl-1H-indazole-5-carbonitrile obtained by Production example 99 and 185.5 mg of {4-[(E)-2-(4,4,5,5-tetramethyl-[1,3,2]dioxaborolan-2-yl)-vinyl]-phenyl}-carbamic acid tert-butyl ester obtained by Production example 138 were coupled in accordance with the method of Example 214, followed by alkaline hydrolysis in accordance with the method of Example 216, to afford 30 mg of the title compound as brown crude crystals.

$^1$H-NMR (400 MHz, $CD_3OD$) δ 4.03 (3H, s), 6.72 (2H, d, J=8.6 Hz), 7.19 (1H, d, J=8.6 Hz), 7.36 (2H, d, J=8.6 Hz), 7.41 (1H, d, J=16.6 Hz), 7.46 (1H, d, J=16.6 Hz), 7.73 (1H, d, J=8.6 Hz).

MS (ESI) m/z 308 $(M-H)^-$

Example 258

From 3-[(E)-2-(4-aminophenyl)-vinyl]-4-methoxy-1H-indazole-5-carboxylic acid and various kinds of amine, compounds of Examples 259-263 were obtained in accordance with the method of Example 10.

Example 259

3-[(E)-2-(4-Aminophenyl)-vinyl]-4-methoxy-1H-indazole-5-carboxylic acid[(1S)-1-hydroxymethyl-2-methylpropyl]-amide MS (ESI) m/z 395 $MH^+$ Example 260

3-[(E)-2-(4-Aminophenyl)-vinyl]-4-methoxy-1H-indazole-5-carboxylic acid cyclopropylamide MS (ESI) m/z 349 $MH^+$ Example 261

3-[(E)-2-(4-Aminophenyl)-vinyl]-4-methoxy-1H-indazole-5-carboxylic acid(furan-2-ylmethyl)-amide MS (ESI) m/z 389 $MH^+$ Example 262

3-[(E)-2-(4-Aminophenyl)-vinyl]-4-methoxy-1H-indazole-5-carboxylic acid[(1S)-2-hydroxy-1-phenylethyl]-amide MS (ESI) m/z 429 $MH^+$ Example 263

3-[(E)-2-(4-Aminophenyl)-vinyl]-4-methoxy-1H-indazole-5-carboxylic acid[(1S)-1-carbamoylethyl]-amide MS (ESI) m/z 380 $MH^+$ Example 264

3-[(E)-2-(2-Fluorophenyl)-vinyl]-4-methoxy-1H-indazole-5-carbonitrile 208 mg of 3-bromo-4-methoxy-1-trityl-1H-indazole-5-carbonitrile obtained by Production example 99 and 177 mg of 2-[(E)-2-(2-fluorophenyl)-vinyl]-4,4,5,5-tetramethyl-[1,3,2]dioxaborolane obtained by Production example 139 were coupled in accordance with the method of Example 214, followed by deprotection, to afford 31 mg of the title compound as colorless crystals.

$^1$H-NMR (400 MHz, $CDCl_3$) δ 4.35 (3H, s), 7.44 (1H, d, J=8.8 Hz), 7.05-7.29 (3H, m), 7.19 (1H, d, J=8.8 Hz), 7.60-7.65 (1H, m), 7.65 (1H, d, J=16.6 Hz), 7.78 (1H, d, J=16.6 Hz).

Example 265

3-[(E)-2-(2-Fluorophenyl)-vinyl]-4-methoxy-1H-indazole-5-carboxylic acid

From 31 mg of 3-[(E)-2-(2-fluorophenyl)-vinyl]-4-methoxy-1H-indazole-5-carbonitrile, 20 mg of the title compound was obtained as yellow crude crystals in accordance with the method of Example 216.

$^1$H-NMR (400 MHz, $CD_3OD$) δ 4.03 (3H, s), 7.12-7.17 (1H, m), 7.20-7.24 (1H, m), 7.28-7.34 (1H, m), 7.29 (1H, d, J=8.8 Hz), 7.70-7.75 (1H, m), 7.73 (1H, d, J=15.6 Hz), 7.77 (1H, d, J=15.6 Hz), 7.88 (1H, d, J=8.8 Hz).

Example 266

From 3-[(E)-2-(2-fluorophenyl)-vinyl]-4-methoxy-1H-indazole-5-carboxylic acid and various kinds of amine, compounds of Examples 267-271 were obtained in accordance with the method of Example 102.

Example 267

3-[(E)-2-(2-Fluorophenyl)-vinyl]-4-methoxy-1H-indazole-5-carboxylic acid[(1S)-1-hydroxymethyl-2-methylpropyl]-amide MS (ESI) m/z 398 $MH^+$ Example 268

3-[(E)-2-(2-Fluorophenyl)-vinyl]-4-methoxy-1H-indazole-5-carboxylic acid cyclopropylamide MS (ESI) m/z 352 $MH^+$ Example 269

3-[(E)-2-(2-Fluorophenyl)-vinyl]-4-methoxy-1H-indazole-5-carboxylic acid(furan-2-ylmethyl)-amide MS (ESI) m/z 392 $MH^+$ Example 270

3-[(E)-2-(2-Fluorophenyl)-vinyl]-4-methoxy-1H-indazole-5-carboxylic acid[(1S)-2-hydroxy-1-phenylethyl]-amide MS (ESI) m/z 432 $MH^+$ Example 271

3-[(E)-2-(2-Fluorophenyl)-vinyl]-4-methoxy-1H-indazole-5-carboxylic acid[(1S)-1-carbamoylethyl]-amide MS (ESI) m/z 383 $MH^+$ Production Example 272

4-Methoxy-1H-indazole-5-carboxylic acid amide

By treating 4.7 g of 4-methoxy-1H-indazole-5-carbonitrile obtained by Production example 97 in the same method as described in Example 215, 15 g of a crude product of the title compound was obtained as brown crystals.

$^1$H-NMR (400 MHz, DMSO-$D_6$)δ4.28 (3H, s), 7.14 (1H, d, J=8.8 Hz), 7.44 (1H, bs), 7.60 (1H, bs), 7.80 (1H, d, J=8.8 Hz), 8.43 (1H, s).

Production Example 273

4-Methoxy-1H-indazole-5-carboxylic acid

By treating 15 g of 4-methoxy-1H-indazole-5-carboxylic acid amide in the manner as described in Example 216, 4.5 g of the title compound was obtained as brown crude crystals.

$^1$H-NMR (400 MHz, $CD_3OD$) δ4.31 (3H, s), 7.18 (1H, d, J=8.8 Hz), 7.84 (1H, d, J=8.8 Hz), 8.39 (1H, s).

Production Example 274

4-Methoxy-1H-indazole-5-carboxylic acid ethyl ester 2 g of 4-methoxy-1H-indazole-5-carboxylic acid was added to a mixed solvent of 40 mL ethanol/2.2 mL concentrated sulfuric acid, and stirred at 95° C. for 11 hours. After cooling the reaction solution on ice, water was slowly added under ice cooling, and the precipitated crystals were collected by filtration and washed with water. Thereafter, the crystals were dried under reduced pressure, to afford 1.52 g of the title compound as pale brown crude crystals.

$^1$H-NMR (400 MHz, $CDCl_3$) δ1.41 (3H, t, J=7.0 Hz), 4.26 (3H, s), 4.38 (2H, q, J=7.0 Hz), 7.12 (1H, d, J=8.8 Hz), 7.86 (1H, d, J=8.8 Hz), 8.30 (1H, s).

Production Example 275

3-Iodo-4-methoxy-1H-indazole-5-carboxylic acid ethyl ester

To 15 mL of a solution of 1.33 g of 4-methoxy-1H-indazole-5-carboxylic acid ethyl ester in N,N-dimethylformamide were added 1.95 g of iodine and 0.85 g of potassium hydroxide, stirred at room temperature for 1 hour and 40 minutes, added with another 0.8 g of iodine, and stirred for 3 hours and 20 minutes. Thereafter, 10% sodium hydrogen sulfite aqueous solution was added, extracted twice with ethyl acetate, and the organic layer was washed once with saturated brine, dried over magnesium sulfate, and the solvent was evaporated. The crude product was purified and separated by silica gel column chromatography, to afford 1.68 g of the title compound as colorless crystals.

$^1$H-NMR (400 MHz, $CDCl_3$) δ1.43 (3H, t, J=7.2 Hz), 4.07 (3H, s), 4.42 (2H, q, J=7.2 Hz), 7.24 (1H, d, J=9.0 Hz), 7.92 (1H, d, J=9.0 Hz), 10.36 (1H, bs).

Production Example 276

3-Iodo-4-methoxy-1-trityl-1H-indazole-5-carboxylic acid ethyl ester

From 1.68 g of 3-iodo-4-methoxy-1H-indazole-5-carboxylic acid ethyl ester, 3.21 g of the title compound was obtained as colorless crude crystals in accordance with the method of Production example 94.

$^1$H-NMR (400 MHz, $CDCl_3$) δ 1.37 (3H, t, J=7.2 Hz), 4.05 (3H, s), 4.35 (2H, q, J=7.2 Hz), 6.14 (1H, d, J=9.0 Hz), 7.14-7.17 (5H, m), 7.25-7.30 (10H, m), 7.45 (1H, d, J=9.0 Hz).

Production Example 277

3-[(E)-2-(3-Acetylphenyl)-vinyl]-4-methoxy-1-trityl-1H-indazole-5-carboxylic acid ethyl ester From 560 mg of 3-iodo-4-methoxy-1-trityl-1H-indazole-5-carboxylic acid ethyl ester and 3-acetylstyrene, 150 mg of the title compound was obtained as pale yellow needle crystals in accordance with the method of Production example 181.

$^1$H-NMR (400 MHz, $CDCl_3$) δ 1.38 (3H, t, J=7.5 Hz), 2.63 (3H, s), 4.05 (3H, s), 4.37 (2H, q, J=7.5 Hz), 6.14 (1H, d, J=8.8 Hz), 7.17-7.25 (6H, m), 7.25-7.32 (9H, m), 7.45 (1H, d, J=8.8 Hz), 7.45 (1H, t, J=7.7 Hz), 7.53 (1H, d, J=16.3 Hz), 7.69 (1H, d, J=16.3 Hz), 7.74 (1H, d, J=7.7 Hz), 7.84 (1H, d, J=7.7 Hz), 8.08 (1H, bs).

Example 278

3-[(E)-2-(3-Acetylphenyl)-vinyl]-4-methoxy-1H-indazole-5-carboxylic acid ethyl ester By treating 150 mg of 3-[(E)-2-(3-acetylphenyl)-vinyl]-4-methoxy-1-trityl-1H-indazole-5-carboxylic acid ethyl ester in the similar method as described in Example 16, 70 mg of the title compound was obtained as a colorless powder.

$^1$H-NMR (400 MHz, $CDCl_3$) δ 1.44 (3H, t, J=7.5 Hz), 2.65 (3H, s), 4.05 (3H, s), 4.43 (2H, q, J=7.5 Hz), 7.23 (1H, d, J=8.6 Hz), 7.49 (1H, t, J=7.7 Hz), 7.71 (1H, d, J=16.8 Hz), 7.74 (1H, d, J=16.8 Hz), 7.80 (1H, bd, J=7.7 Hz), 7.89 (1H, bd, J=7.7 Hz), 7.91 (1H, d, J=8.6 Hz), 8.16 (1H, bs).

Example 279

3-[(E)-2-(3-Acetylphenyl)-vinyl]-4-methoxy-1H-indazole-5-carboxylic acid

By treating 70 mg of 3-[(E)-2-(3-acetylphenyl)-vinyl]-4-methoxy-1H-indazole-5-carboxylic acid ethyl ester in the similar method as described in Example 144, 65 mg of the title compound was obtained as a colorless powder.

$^1$H-NMR (400 MHz, DMSO-$d_6$) δ 2.63 (3H, s), 3.96 (3H, s), 7.30 (1H, d, J=8.6 Hz), 7.56 (1H, t, J=7.7 Hz), 7.63 (1H, d, J=16.4 Hz), 7.68 (1H, d, J=16.4 Hz), 7.73 (1H, d, J=8.6 Hz), 7.87 (1H, bd, J=7.7 Hz), 7.93 (1H, bd, J=7.7 Hz), 8.15 (1H, bs), 12.60-12.75 (1H, bs), 13.49 (1H, bs).

Example 280

From 3-[(E)-2-(3-acetylphenyl)-vinyl]-4-methoxy-1H-indazole-5-carboxylic acid and various kinds of amine, compounds of Example 281-287 were obtained in accordance with the method of Example 102.

Example 281

3-[(E)-2-(3-Acetylphenyl)-vinyl]-4-methoxy-1H-indazole-5-carboxylic acid cyclopropylamide MS (ESI) m/z 376 $MH^+$ Example 282

3-[(E)-2-(3-Acetylphenyl)-vinyl]-4-methoxy-1H-indazole-5-carboxylic acid(furan-2-ylmethyl)-amide MS (ESI) m/z 416 $MH^+$ Example 283

3-[(E)-2-(3-Acetylphenyl)-vinyl]-4-methoxy-1H-indazole-5-carboxylic acid[(1S)-1-hydroxymethyl-2-methyl-propyl]-amide MS (ESI) m/z 422 $MH^+$ Example 284

3-[(E)-2-(3-Acetylphenyl)-vinyl]-4-methoxy-1H-indazole-5-carboxylic acid(thiophen-2-ylmethyl)-amide MS (ESI) m/z 432 $MH^+$ Example 285

3-[(E)-2-(3-Acetylphenyl)-vinyl]-4-methoxy-1H-indazole-5-carboxylic acid(1-carbamoyl-2-phenyl-ethyl)-amide MS (ESI) m/z 483 $MH^+$ Example 286

3-[(E)-2-(3-Acetylphenyl)-vinyl]-4-methoxy-1H-indazole-5-carboxylic acid(1-carbamoyl-2-hydroxy-ethyl)-amide MS (ESI) m/z 423 $MH^+$ Example 287

3-[(E)-2-(3-Acetylphenyl)-vinyl]-4-methoxy-1H-indazole-5-carboxylic acid[(1S)-1-carbamoyl-ethyl]-amide MS (ESI) m/z 407 $MH^+$ Production Example 288

3-[(E)-2-(4-Acetylphenyl)-vinyl]-4-methoxy-1-trityl-1H-indazole-5-carboxylic acid ethyl ester By treating 560 mg of 3-iodo-4-methoxy-1-trityl-1H-indazole-5-carboxylic acid ethyl ester obtained by Production example 276 and 4-acetylstyrene in the similar method as described in Production example 181, 100 mg of the title compound was obtained as pale yellow needle crystals.

$^1$H-NMR (400 MHz, $CDCl_3$) δ 1.38 (3H, t, J=7.5 Hz), 2.61 (3H, s), 4.06 (3H, s), 4.38 (2H, q, J=7.5 Hz), 6.14 (1H, d, J=9.3 Hz), 7.18-7.25 (6H, m), 7.25-7.32 (9H, m), 7.45 (1H, d, J=9.3 Hz), 7.49 (1H, d, J=16.4 Hz), 7.60 (2H, d, J=8.3 Hz), 7.75 (1H, d, J=16.4 Hz), 7.84 (2H, d, J=8.3 Hz).

Example 289

3-[(E)-2-(4-Acetylphenyl)-vinyl]-4-methoxy-1H-indazole-5-carboxylic acid ethyl

By treating 100 mg of 3-[(E)-2-(4-acetylphenyl)-vinyl]-4-methoxy-1-trityl-1H-indazole-5-carboxylic acid ethyl ester in the similar method as described in Example 16, 50 mg of the title compound was obtained as a colorless powder.

$^1$H-NMR (400 MHz, $CDCl_3$) δ 1.45 (3H, t, J=7.2 Hz), 2.63 (3H, s), 4.07 (3H, s), 4.43 (2H, q, J=7.2 Hz), 7.24 (1H, d, J=9.1 Hz), 7.67 (2H, d, J=8.5 Hz), 7.70 (1H, d, J=16.2 Hz), 7.79 (1H, d, J=16.2 Hz), 7.92 (1H, bd, J=9.1 Hz), 7.99 (2H, d, J=8.5 Hz).

Example 290

3-[(E)-2-(4-Acetylphenyl)-vinyl]-4-methoxy-1H-indazole-5-carboxylic acid

By treating 50 mg of 3-[(E)-2-(4-acetylphenyl)-vinyl]-4-methoxy-1H-indazole-5-carboxylic acid ethyl ester in the similar method as described in Example 144, 45 mg of the title compound was obtained as a colorless powder.

$^1$H-NMR (400 MHz, DMSO-$d_6$) δ 2.58 (3H, s), 3.96 (3H, s), 7.30 (1H, d, J=8.8 Hz), 7.62 (1H, d, J=16.4 Hz), 7.73 (1H, d, J=16.4 Hz), 7.74 (1H, d, J=8.8 Hz), 7.78 (2H, d, J=8.5 Hz), 7.97 (2H, d, J=8.5 Hz), 12.60-12.75 (1H, bs), 13.54 (1H, bs).

Example 291

From 3-[(E)-2-(4-acetylphenyl)-vinyl]-4-methoxy-1H-indazole-5-carboxylic acid and various kinds of amine, compounds of Examples 292-298 were obtained in accordance with the method of Example 102.

Example 292

3-[(E)-2-(4-Acetylphenyl)-vinyl]-4-methoxy-1H-indazole-5-carboxylic acid cyclopropylamide MS (ESI) m/z 376 $MH^+$ Example 293

3-[(E)-2-4-Acetylphenyl]-vinyl]-4-methoxy-1H-indazole-5-carboxylic acid(furan-2-ylmethyl)-amide MS (ESI) m/z 416 $MH^+$ Example 294

3-[(E)-2-(4-Acetylphenyl)-vinyl]-4-methoxy-1H-indazole-5-carboxylic acid[(1S)-1-hydroxymethyl-2-methyl-propyl]-amide MS (ESI) m/z 422 $MH^+$ Example 295

3-[(E)-2-(4-Acetylphenyl)-vinyl]-4-methoxy-1H-indazole-5-carboxylic acid(thiophen-2-ylmethyl)-amide MS (ESI) m/z 432 $MH^+$ Example 296

3-[(E)-2-(4-Acetylphenyl)-vinyl]-4-methoxy-1H-indazole-5-carboxylic acid(1-carbamoyl-2-phenyl-ethyl)-amide MS (ESI) m/z 483 $MH^+$ Example 297

3-[(E)-2-(4-Acetylphenyl)-vinyl]-4-methoxy-1H-indazole-5-carboxylic acid(1-carbamoyl-2-hydroxy-ethyl)-amide MS (ESI) m/z 423 $MH^+$ Example 298

3-[(E)-2-(4-Acetylphenyl)-vinyl]-4-methoxy-1H-indazole-5-carboxylic acid[(1S)-1-carbamoyl-ethyl]-amide MS (ESI) m/z 407 $MH^+$ Production Example 299

4-Methoxy-3-[(E)-2-(pyridin-4-yl)-vinyl]-1-trityl-1H-indazole-5-carboxylic acid ethyl ester By treating 560 mg of 3-iodo-4-methoxy-1-trityl-1H-indazole-5-carboxylic acid ethyl ester obtained by Production example 276 and 160 μl of 4-vinylpyridine in the similar method as described in Production example 181, 300 mg of the title compound was obtained as a pale yellow oil.

$^1$H-NMR (400 MHz, $CDCl_3$) δ 1.38 (3H, t, J=7.5 Hz), 4.04 (3H, s), 4.38 (2H, q, J=7.5 Hz), 6.15 (1H, d, J=8.8 Hz), 7.17-7.23 (6H, m), 7.26-7.32 (9H, m), 7.17 (2H, d, J=6.0 Hz), 7.18 (1H, d, J=16.4 Hz), 7.46 (1H, d, J=8.8 Hz), 7.82 (1H, d, J=16.4 Hz), 8.57 (2H, d, J=6.0 Hz).

Example 300

4-Methoxy-3-[(E)-2-(pyridin-4-yl)-vinyl]-1H-indazole-5-carboxylic acid ethyl ester By treating 300 mg of 4-methoxy-3-[(E)-2-(pyridin-4-yl)-vinyl]-1-trityl-1H-indazole-5-carboxylic acid ethyl ester in the similar method as described in Example 16, 150 mg of the title compound was obtained as a colorless powder.

$^1$H-NMR (400 MHz, DMSO-$d_6$) δ 1.36 (3H, t, J=7.5 Hz), 3.97 (3H, s), 4.33 (2H, q, J=7.5 Hz), 7.37 (1H, d, J=8.7 Hz), 7.55 (1H, d, J=16.4 Hz), 7.63 (2H, d, J=5.7 Hz), 7.74 (1H, d, J=8.7 Hz), 7.84 (1H, d, J=16.4 Hz), 8.58 (2H, d, J=5.7 Hz).

Example 301

4-Methoxy-3-[(E)-2-(pyridin-4-yl)-vinyl]-1H-indazole-5-carboxylic acid 150 mg of 4-methoxy-3-[(E)-2-(pyridin-4-yl)-vinyl]-1H-indazole-5-carboxylic acid ethyl ester was dissolved in a mixed solvent of 3 mL tetrahydrofuran/1 mL methanol, added with 0.5 mL of 5N sodium hydroxide aqueous solution, and heated at 50° C. for 4 hours. The reaction solution was neutralized with acetic acid, and the solvent distilled off under reduced pressure, to give 500 mg of the crudely produced title compound as a mixture with sodium acetate.

$^1$H-NMR (400 MHz, DMSO-$d_6$) δ 4.01 (3H, s), 7.13 (1H, d, J=8.7 Hz), 7.49 (1H, d, J=16.4 Hz), 7.54 (1H, d, J=8.7 Hz), 7.58 (2H, d, J=6.3 Hz), 7.87 (1H, d, J=16.4 Hz), 8.56 (2H, d, J=6.3 Hz).

Example 302

From 4-methoxy-3-[(E)-2-(pyridin-4-yl)-vinyl]-1H-indazole-5-carboxylic acid and various kinds of amine, compounds of Examples 303-309 were obtained in accordance with the method of Example 102.

Example 303

4-Methoxy-3-[(E)-2-(pyridin-4-yl)-vinyl]-1H-indazole-5-carboxylic acid cyclopropylamide MS (ESI) m/z 335 $MH^+$ Example 304

4-Methoxy-3-[(E)-2-(pyridin-4-yl)-vinyl]-1H-indazole-5-carboxylic acid(furan-2-ylmethyl)-amide MS (ESI) m/z 375 $MH^+$ Example 305

4-Methoxy-3-[(E)-2-(pyridin-4-yl)-vinyl]-1H-indazole-5-carboxylic acid[(1S)-1-hydroxymethyl-2-methyl-propyl]-amide MS (ESI) m/z 381 $MH^+$ Example 306

4-Methoxy-3-[(E)-2-(pyridin-4-yl)-vinyl]-1H-indazole-5-carboxylic acid(thiophen-2-ylmethyl)-amide MS (ESI) m/z 391 $MH^+$ Example 307

4-Methoxy-3-[(E)-2-(pyridin-4-yl)-vinyl]-1H-indazole-5-carboxylic acid(1-carbamoyl-2-phenyl-ethyl)-amide MS (ESI) m/z 442 $MH^+$ Example 308

4-Methoxy-3-[(E)-2-(pyridin-4-yl)-vinyl]-1H-indazole-5-carboxylic acid(1-carbamoyl-2-hydroxy-ethyl)-amide MS (ESI) m/z 382 $MH^+$ Example 309

4-Methoxy-3-[(E)-2-(pyridin-4-yl)-vinyl]-1H-indazole-5-carboxylic acid[(1S)-1-carbamoyl-ethyl]-amide MS (ESI) m/z 366 $MH^+$ Production Example 310

4-Methoxy-3-[(E)-2-(6-methoxypyridin-3-yl)-vinyl]-1-trityl-1H-indazole-5-carboxylic acid ethyl ester By treating 560 mg of 3-iodo-4-methoxy-1-trityl-1H-indazole-5-carboxylic acid ethyl ester obtained by Production example 276 and 500 mg of crudely produced 2-methoxy-5-vinylpyridine in the similar method as described in Production example 181, 70 mg of the title compound was obtained as a colorless powder.

$^1$H-NMR (400 MHz, $CDCl_3$) δ 1.38 (3H, t, J=7.5 Hz), 3.96 (3H, s), 4.03 (3H, s), 4.37 (2H, q, J=7.5 Hz), 6.11 (1H, d, J=8.5 Hz), 6.75 (1H, d, J=8.5 Hz), 7.15-7.24 (6H, m), 7.24-7.36 (10H, m), 7.44 (1H, d, J=8.5 Hz), 7.52 (1H, d, J=16.3 Hz), 7.81 (1H, dd, J=2.2, 8.5 Hz), 8.24 (1H, d, J=2.2 Hz).

Example 311

4-Methoxy-3-[(E)-2-(6-methoxypyridin-3-yl)-vinyl]-1H-indazole-5-carboxylic acid ethyl ester By treating 70 mg of 4-methoxy-3-[(E)-2-(6-methoxypyridin-3-yl)-vinyl]-1-trityl-1H-indazole-5-carboxylic acid ethyl ester in the similar method as described in Example 16, 35 mg of the title compound was obtained as a colorless powder.

$^1$H-NMR (400 MHz, $CD_3OD$) δ 1.42 (3H, t, J=7.5 Hz), 3.94 (3H, s), 4.01 (3H, s), 4.38 (2H, q, J=7.5 Hz), 6.89 (1H, d, J=9.0 Hz), 7.28 (1H, d, J=8.8 Hz), 7.53 (1H, d, J=16.6 Hz), 7.57 (1H, d, J=16.6 Hz), 7.83 (1H, d, J=8.8 Hz), 8.06 (1H, dd, J=2.4, 9.0 Hz), 8.28 (1H, d, J=2.4 Hz).

Example 312

4-Methoxy-3-[(E)-2-(6-methoxypyridin-3-yl)-vinyl]-1H-indazole-5-carboxylic acid

By treating 35 mg of 4-methoxy-3-[(E)-2-(6-methoxypyridin-3-yl)-vinyl]-1H-indazole-5-carboxylic acid ethyl ester in the similar method as described in Example 144, 30 mg of the title compound was obtained as a colorless powder.

$^1$H-NMR (400 MHz, DMSO-$d_6$) δ 3.89 (3H, s), 3.97 (3H, s), 6.89 (1H, d, J=8.7 Hz), 7.28 (1H, d, J=8.7 Hz), 7.51 (1H, d, J=16.4 Hz), 7.54 (1H, d, J=16.4 Hz), 7.73 (1H, d, J=8.7 Hz), 8.09 (1H, dd, J=2.2, 8.7 Hz), 8.39 (1H, d, J=2.2 Hz).

Example 313

From 4-methoxy-3-[(E)-2-(6-methoxypyridin-3-yl)-vinyl]-1H-indazole-5-carboxylic acid and various kinds of amine, compounds of Examples 314-320 were obtained in accordance with the method of Example 102-h.

Example 314

4-Methoxy-3-[(E)-2-(6-methoxypyridin-3-yl)-vinyl]-1H-indazole-5-carboxylic acid cyclopropylamide MS (ESI) m/z 365 $MH^+$ Example 315

4-Methoxy-3-[(E)-2-(6-methoxypyridin-3-yl)-vinyl]-1H-indazole-5-carboxylic acid(furan-2-ylmethyl)-amide MS (ESI) m/z 405 $MH^+$ Example 316

4-Methoxy-3-[(E)-2-(6-methoxypyridin-3-yl)-vinyl]-1H-indazole-5-carboxylic acid[(1S)-1-hydroxymethyl-2-methyl-propyl]-amide MS (ESI) m/z 411 $MH^+$ Example 317

4-Methoxy-3-[(E)-2-(6-methoxypyridin-3-yl)-vinyl]-1H-indazole-5-carboxylic acid(thiophen-2-ylmethyl)-amide MS (ESI) m/z 421 $MH^+$ Example 318

4-Methoxy-3-[(E)-2-(6-methoxypyridin-3-yl)-vinyl]-1H-indazole-5-carboxylic acid (1-carbamoyl-2-phenyl-ethyl)-amide MS (ESI) m/z 472 $MH^+$ Example 319

4-Methoxy-3-[(E)-2-(6-methoxypyridin-3-yl)-vinyl]-1H-indazole-5-carboxylic acid (1-carbamoyl-2-hydroxy-ethyl)-amide MS (ESI) m/z 412 $MH^+$ Example 320

4-Methoxy-3-[(E)-2-(6-methoxypyridin-3-yl)-vinyl]-1H-indazole-5-carboxylic acid[(1S)-1-carbamoyl-ethyl]-amide MS (ESI) m/z 396 $MH^+$ Production Example 321

3-Iodo-4-methoxy-1H-indazole-5-carbonitrile

From 28.4 g of 4-methoxy-1H-indazole-5-carbonitrile obtained by Production example 97, 52.8 g of the title compound was obtained as yellow crude crystal in accordance with the method of Production example 275.

$^1$H-NMR (400 MHz, DMSO-$D_6$) 4.14 (3H, s), 7.42 (1H, d, J=8.6 Hz), 7.56 (1H, d, J=8.6 Hz), 13.96 (1H, s).

Production Example 322

3-Iodo-4-methoxy-1-trityl-1H-indazole-5-carbonitrile

From 52.8 g of 3-iodo-4-methoxy-1H-indazole-5-carbonitrile, 104.5 g of the title compound was obtained as brown crude crystal in accordance with the method of Production example 94.

$^1$H-NMR (400 MHz, $CDCl_3$)δ4.31 (3H, s), 6.13 (1H, d, J=9.0 Hz), 7.00 (1H, d, J=9.0 Hz), 7.10-7.18 (5H, m), 7.22-7.37 (10H, m).

Production Example 323

3-Vinyl-4-methoxy-1-trityl-1H-indazole-5-carbonitrile

By treating 1.02 g of 3-iodo-4-methoxy-1-trityl-1H-indazole-5-carbonitrile in the method of Production example 123, 700 mg of the title compound was obtained as colorless needle crystals.

$^1$H-NMR (400 MHz, $CDCl_3$) δ 4.27 (3H, s), 5.35 (1H, d, J=2.0, 11.0 Hz), 6.05 (1H, d, J=8.7 Hz), 6.08 (1H, dd, J=2.0, 17.9 Hz), 6.96 (1H, d, J=8.7 Hz), 7.12-7.18 (6H, m), 7.14 (1H, d, J=11.0, 17.9 Hz), 7.25-7.34 (9H, m).

Production Example 324

4-Methoxy-3-[(E)-2-(pyridin-3-yl)-vinyl]-1-trityl-1H-indazole-5-carbonitrile 300 mg of 3-vinyl-4-methoxy-1-trityl-1H-indazole-5-carbonitrile and 180 μl of 3-bromopyridine were dissolved in a mixed solvent of 1 mL triethylamine/5 mL acetonitrile, added with 40 mg of tri-p-tolylphosphine and 27 mg of palladium acetate (II), and heated at 110° C. for 24 hours. The reaction solution was added with silica gel, the solvent was evaporated, and the resultant residue was purified by column chromatography (hexane:ethyl acetate=7:3), to afford 120 mg of the title compound as a pale yellow oil.

$^1$H-NMR (400 MHz, $CDCl_3$) δ 4.35 (3H, s), 6.10 (1H, d, J=9.0 Hz), 7.00 (1H, d, J=9.0 Hz), 7.16-7.22 (6H, m), 7.26-7.34 (10H, m), 7.41 (1H, d, J=16.1 Hz), 7.60 (1H, d, J=16.1 Hz), 7.83 (1H, dt, J=2.2, 8.3 Hz), 8.50 (1H, dd, J=2.2, 5.3 Hz), 8.72 (1H, d, J=2.2 Hz).

Example 325

4-Methoxy-3-[(E)-2-(pyridin-3-yl)-vinyl]-1H-indazole-5-carbonitrile

By treating 120 mg of 4-methoxy-3-[(E)-2-(pyridin-3-yl)-vinyl]-1-trityl-1H-indazole-5-carbonitrile in the similar method as described in Example 16, 76 mg of the title compound was obtained as a colorless powder.

$^1$H-NMR (400 MHz, DMSO-$d_6$) δ 4.24 (3H, s), 7.40 (1H, d, J=8.5 Hz), 7.45 (1H, dd, J=4.8, 8.2 Hz), 7.57 (1H, d, J=8.5 Hz), 7.59 (1H, d, J=16.6 Hz), 7.66 (1H, d, J=16.6 Hz), 8.14 (1H, dt, J=1.9, 8.2 Hz), 8.51 (1H, dd, J=1.9, 4.8 Hz), 8.84 (1H, d, J=1.9 Hz), 13.77 (1H, bs).

Example 326

4-Methoxy-3-[(E)-2-(pyridin-3-yl)-vinyl]-1H-indazole-5-carboxylic acid 70 mg of 4-methoxy-3-[(E)-2-(pyridin-3-yl)-vinyl]-1H-indazole-5-carbonitrile was alkaline hydrolyzed in the similar method as described in Example 243, to afford 42 mg of the title compound as a pale yellow powder.

$^1$H-NMR (400 MHz, DMSO-$d_6$) δ 3.97 (3H, s), 7.32 (1H, d, J=8.6 Hz), 7.44 (1H, dd, J=4.5, 7.7 Hz), 7.59 (1H, d, J=16.4 Hz), 7.70 (1H, d, J=16.4 Hz), 7.75 (1H, d, J=8.6 Hz), 8.12 (1H, dt, J=1.8, 7.7 Hz), 8.50 (1H, dd, J=1.8, 4.5 Hz), 8.72 (1H, d, J=1.8 Hz), 13.53 (1H, bs).

Example 327

From 4-methoxy-3-[(E)-2-(pyridin-3-yl)-vinyl]-1H-indazole-5-carboxylic acid and various kinds of amine, compounds of Examples 328-334 were obtained in accordance with the method of Example 102.

Example 328

4-Methoxy-3-[(E)-2-(pyridin-3-yl)-vinyl]-1H-indazole-5-carboxylic acid(furan-2-ylmethyl)-amide MS (ESI) m/z 375 $MH^+$ Example 329

4-Methoxy-3-[(E)-2-(pyridin-3-yl)-vinyl]-1H-indazole-5-carboxylic acid (tetrahydro-furan-2-ylmethyl)-amide MS (ESI) m/z 379 $MH^+$ Example 330

4-Methoxy-3-[(E)-2-(pyridin-3-yl)-vinyl]-1H-indazole-5-carboxylic acid (2-acetylamino-ethyl)-amide MS (ESI) m/z 380 $MH^+$ Example 331

4-Methoxy-3-[(E)-2-(pyridin-3-yl)-vinyl]-1H-indazole-5-carboxylic acid[(1S)-1-hydroxymethyl-2-methyl-propyl]-amide MS (ESI) m/z 381 $MH^+$ Example 332

4-Methoxy-3-[(E)-2-(pyridin-3-yl)-vinyl]-1H-indazole-5-carboxylic acid[(1S)-2-hydroxy-1-phenyl-ethyl]-amide MS (ESI) m/z 415 $MH^+$ Example 333

4-Methoxy-3-[(E)-2-(pyridin-3-yl)-vinyl]-1H-indazole-5-carboxylic acid(thiophen-2-ylmethyl)-amide MS (ESI) m/z 391 $MH^+$ Example 334

4-Methoxy-3-[(E)-2-(pyridin-3-yl)-vinyl]-1H-indazole-5-carboxylic acid cyclopropylamide MS (ESI) m/z 335 $MH^+$ Example 335

4-Methoxy-3-[(E)-2-(thiophen-2-yl)-vinyl]-1H-indazole-5-carbonitrile

2-Vinylthiophene and 500 mg of 3-iodo-4-methoxy-1-trityl-1H-indazole-5-carbonitrile obtained by Production example 322 were reacted in accordance with Example 100, to afford 110 mg of the title compound as a pale yellow powder.

$^1$H-NMR (400 MHz, DMSO-$d_6$) δ 4.21 (3H, s), 7.11 (1H, dd, J=3.7, 5.3 Hz), 7.27 (1H, d, J=16.3 Hz), 7.34 (1H, bd, J=3.7 Hz), 7.38 (1H, d, J=8.5 Hz), 7.54 (1H, bd, J=5.3 Hz), 7.55 (1H, d, J=8.5 Hz), 7.72 (1H, d, J=16.3 Hz).

Example 336

4-Methoxy-3-[(E)-2-(thiophen-2-yl)-vinyl]-1H-indazole-5-carboxylic acid 110 mg of 4-methoxy-3-[(E)-2-(thiophen-2-yl)-vinyl]-1H-indazole-5-carbonitrile was alkaline hydrolyzed in the similar method as described in Example 243, to afford 40 mg of the title compound as a colorless powder.

$^1$H-NMR (400 MHz, DMSO-$d_6$) δ 3.94 (3H, s), 7.11 (1H, dd, J=3.6, 5.1 Hz), 7.31 (1H, d, J=5.1 Hz), 7.32 (1H, d, J=8.6 Hz), 7.35 (1H, d, J=16.1 Hz), 7.52 (1H, bd, J=3.6 Hz), 7.72 (1H, d, J=16.1 Hz), 7.75 (1H, d, J=8.6 Hz).

Example 337

From 4-methoxy-3-[(E)-2-(thiophen-2-yl)-vinyl]-1H-indazole-5-carboxylic acid and various kinds of amine, compounds of Examples 338-342 were obtained in accordance with the method of Example 102.

Example 338

4-Methoxy-3-[(E)-2-(thiophen-2-yl)-vinyl]-1H-indazole-5-carboxylic acid cyclopropylamide MS (ESI) m/z 340 $MH^+$ Example 339

4-Methoxy-3-[(E)-2-(thiophen-2-yl)-vinyl]-1H-indazole-5-carboxylic acid(furan-2-ylmethyl)-amide MS (ESI) m/z 380 $MH^+$ Example 340

4-Methoxy-3-[(E)-2-(thiophen-2-yl)-vinyl]-1H-indazole-5-carboxylic acid[(1S)-1-hydroxymethyl-2-methyl-propyl]-amide MS (ESI) m/z 386 $MH^+$ Example 341

4-Methoxy-3-[(E)-2-(thiophen-2-yl)-vinyl]-1H-indazole-5-carboxylic acid[(1S)-2-hydroxy-1-phenyl-ethyl]-amide MS (ESI) m/z 420 $MH^+$ Example 342

4-Methoxy-3-[(E)-2-(thiophen-2-yl)-vinyl]-1H-indazole-5-carboxylic acid(thiophen-2-ylmethyl)-amide MS (ESI) m/z 396 $MH^+$ Example 343

4-Methoxy-3-[(E)-2-(pyridin-2-yl)-vinyl]-1H-indazole-5-carbonitrile

From 2-vinylpyridine and 500 mg of 3-iodo-4-methoxy-1-trityl-1H-indazole-5-carbonitrile obtained by Production example 322, 110 mg of the title compound was obtained as a colorless powder in accordance with Example 100.

$^1$H-NMR (400 MHz, DMSO-$d_6$) δ 4.23 (3H, s), 7.30 (1H, ddd, J=1.1, 4.6, 7.6 Hz), 7.41 (1H, d, J=8.8 Hz), 7.57 (1H, d, J=8.8 Hz), 7.61 (1H, d, J=7.6 Hz), 7.62 (1H, d, J=16.0 Hz), 7.82 (1H, dt, J=1.8, 7.6 Hz), 8.05 (1H, d, J=16.0 Hz), 8.64 (1H, ddd, J=1.1, 1.8, 4.6 Hz), 13.73-13.85 (1H, bs).

Example 344

4-Methoxy-3-[(E)-2-(pyridin-2-yl)-vinyl]-1H-indazole-5-carboxylic acid 110 mg of 4-methoxy-3-[(E)-2-(pyridin-2-yl)-vinyl]-1H-indazole-5-carbonitrile was alkaline hydrolyzed in the similar method as described in Example 243, to afford 40 mg of the title compound as a pale yellow powder.

$^1$H-NMR (400 MHz, DMSO-$d_6$) δ 3.95 (3H, s), 7.27 (1H, dd, J=5.0, 7.7 Hz), 7.30 (1H, d, J=8.5 Hz), 7.56 (1H, d, J=7.7 Hz), 7.58 (1H, d, J=16.1 Hz), 7.73 (1H, d, J=8.5 Hz), 7.79 (1H, dt, J=1.7, 7.7 Hz), 8.06 (1H, d, J=16.1 Hz), 8.61 (1H, bd, J=5.0 Hz), 13.53 (1H, bs).

Example 345

3-[(E)-2-(4-Fluorophenyl)-vinyl]-4-hydroxy-1H-indazole-5-carboxylic acid ethyl ester To a solution of 5.05 g of 3-iodo-4-methoxy-1-trityl-1H-indazole-5-carboxylic acid ethyl ester obtained by Production example 276 in 70 mL of 1,2-dimethoxyethane were successively added 1.57 g of (E)-2-(4-fluorophenyl)-vinylboronic acid, a solution containing 2.16 g of sodium hydrogen carbonate in 34 mL of water and 496.9 mg of tetrakis(triphenylphosphine)palladium(0), and stirred under nitrogen atmosphere at 110° C. for 21 hours. The reaction solution was cooled to room temperature, poured slowly with saturated aqueous ammonium chloride, extracted with ethyl acetate twice, and the resultant organic layer was washed each once with water and saturated brine, and dried over magnesium sulfate. The solvent was evaporated, to obtain a crude coupling product. The obtained crude product was dissolved in 85 mL of dichloromethane, added with 21.5 mL of a boron tribromide 1M solution in dichloromethane under ice cooling, and stirred under nitrogen atmosphere at room temperature for 19 hours. Thereafter, saturated aqueous ammonium chloride was poured slowly, and extracted twice with a mixed solvent of ethyl acetate:tetrahydrofuran=1:1, and the resultant organic layer was washed once with saturated brine, and dried over magnesium sulfate. The solvent was evaporated, and the obtained crude product was purified and separated by silica gel column chromatography, to afford 608 mg of the title compound as orange crystals.

$^1$H-NMR (400 MHz, DMSO-$D_6$) δ 1.37 (3H, t, J=6.8 Hz), 4.40 (2H, q, J=6.8 Hz), 7.04 (1H, d, J=8.8 Hz), 7.25 (2H, t, J=8.8 Hz), 7.58 (1H, d, J=16.8 Hz), 7.64 (1H, d, J=16.8 Hz), 7.64-7.72 (3H, m), 12.21 (1H, s), 13.47 (1H, s).

Production Example 346

3-[(E)-2-(4-Fluorophenyl)-vinyl]-4-hydroxy-1H-indazole-1,5-dicarboxylic acid 1-tert-butyl ester 5-ethyl ester To a solution of 553 mg of 3-[(E)-2-(4-fluorophenyl)-vinyl]-4-hydroxy-1H-indazole-5-carboxylic acid ethyl ester in 15 mL of tetrahydrofuran were added 257.5 mg of di-tert-butyl dicarbonate and 41.5 mg of 4-(dimethylamino)pyridine, and stirred for 1 hour and 15 minutes under ice cooling. Then the reaction solution was added with water, extracted twice with diethyl ether, and the resultant organic layer was washed each once with water and saturated brine, and dried over magnesium sulfate. The solvent was evaporated, and the crude product was purified and separated by silica gel column chromatography, to afford 431.2 mg of the title compound as colorless crystals.

$^1$H-NMR (400 MHz, $CDCl_3$)δ1.45 (3H, t, J=7.2 Hz), 1.74 (9H, s), 4.46 (2H, q, J=7.2 Hz), 7.05-7.11 (2H, m), 7.58-7.64 (2H, m), 7.61 (1H, d, J=9.0 Hz), 7.65 (1H, d, J=16.2 Hz), 7.87 (1H, d, J=16.2 Hz), 7.94 (1H, bs), 12.15 (1H, s).

Production Example 347

3-[(E)-2-(4-Fluorophenyl)-vinyl]-4-[2-(tetrahydropyran-2-yloxy)-ethoxy]-1H-indazole-1,5-dicarboxylic acid 1-tert-butyl Ester 5-ethyl ester To a solution of 200 mg of 3-[(E)-2-(4-fluorophenyl)-vinyl]-4-hydroxy-1H-indazole-1,5-dicarboxylic acid 1-tert-butyl ester 5-ethyl ester in 13 mL of N,N-dimethylformamide were added 196.5 mg of 2-(2-bromoethoxy)-tetrahydropyran and 306.3 mg of cesium carbonate, stirred for 1 hour and 30 minutes at room temperature, stirred at 50° C. for 17 hours, added with 196.5 mg of 2-(2-bromoethoxy)-tetrahydropyran and 306.3 mg of cesium carbonate, stirred for 3 hours at room temperature and for 2 hours at 50° C., added with 554 mg of 2-(2-bromoethoxy)-tetrahydropyran, and further stirred at 50° C. for 4 hours. Then, the reaction solution was added saturated aqueous ammonium chloride, extracted twice with ethyl acetate, and the resultant organic layer was washed once with saturated brine and dried over magnesium sulfate. The solvent was evaporated, and the crude product was purified and separated by silica gel column chromatography, to afford 147 mg of the title compound as a colorless oil.

$^1$H-NMR (400 MHz, $CDCl_3$) 1.36-1.79 (6H, m), 1.44 (3H, t, J=7.2 Hz), 1.75 (9H, s), 3.40-3.56 (1H,m), 3.74-3.84 (1H, m), 3.85-3.94 (1H, m), 4.09-4.16 (1H, m), 4.28-4.47 (2H, m), 4.43 (2H, q, J=7.2 Hz), 4.57-4.61 (1H, m), 7.02-7.10 (2H, m), 7.60-7.66 (2H, m), 7.70 (1H, d, J=16.4 Hz), 7.81 (1H, d, J=16.4 Hz), 7.86 (1H, d, J=8.8 Hz), 7.99 (1H, d, J=8.8 Hz).

Production Example 348

3-[(E)-2-(4-Fluorophenyl)-vinyl]-4-(2-hydroxy-ethoxy)-1H-indazole-1,5-dicarboxylic acid 1-tert-butyl ester 5-ethyl ester To a solution of 147 mg of 3-[(E)-2-(4-fluorophenyl)-vinyl]-4-[2-(tetrahydropyran-2-yloxy)-ethoxy]-1H-indazole-1,5-dicarboxylic acid 1-tert-butyl ester 5-ethyl ester in 1.5 mL of tetrahydrofuran was added 1.5 mL of 2N hydrochloric acid, and stirred at room temperature for 19 hours. Thereafter, the reaction solution was added with water and extracted twice ethyl acetate, and the resultant organic layer was washed once with saturated brine, and dried over magnesium sulfate. The solvent was evaporated, and the crude product was purified and separated by silica gel column chromatography, to afford 87.1 mg of the title compound as a colorless oil.

$^1$H-NMR (400 MHz, $CDCl_3$) 1.43 (3H, t, J=6.8 Hz), 1.75 (9H, s), 3.42-3.45 (1H, m), 3.96-4.00 (2H, m), 4.24-4.26 (2H, m), 4.43 (2H, q, J=6.8 Hz), 7.05-7.12 (2H, m), 7.57 (1H, d, J=16.4 Hz), 7.57-7.63 (2H, m), 7.80 (1H, d, J=16.2 Hz), 7.93 (1H, d, J=8.8 Hz), 8.08 (1H, d, J=8.8 Hz).

Example 349

3-[(E)-2-(4-Fluorophenyl)-vinyl]-4-(2-hydroxy-ethoxy)-1H-indazole-5-carboxylic acid ethyl ester By treating 87.1 mg of 3-[(E)-2-(4-fluorophenyl)-vinyl]-4-(2-hydroxyethoxy)-1H-indazole-1,5-dicarboxylic acid 1-tert-butyl ester 5-ethyl ester in the similar method as described in Example 16, 31.3 mg of the title compound was obtained as a colorless oil.

$^1$H-NMR (400 MHz, $CDCl_3$) δ1.42 (3H, t, J=6.8 Hz), 3.99 (2H, t, J=4.0 Hz), 4.29 (2H, t, J=4.0 Hz), 4.41 (2H, q, J=6.8 Hz), 7.01-7.10 (2H, m), 7.22 (1H, d, J=8.8 Hz), 7.48-7.58 (2H, m), 7.53 (1H, d, J=16.4 Hz), 7.60 (1H, d, J=16.4 Hz), 7.91 (1H, d, J=8.8 Hz).

MS (ESI) m/z 371 $MH^+$

Example 350

3-[(E)-2-(4-Fluorophenyl)-vinyl]-4-(2-hydroxy-ethoxy)-1H-indazole-5-carboxylic acid To a solution of 31.3 mg of 3-[(E)-2-(4-fluorophenyl)-vinyl]-4-(2-hydroxyethoxy)-1H-indazol-5-carboxylic acid ethyl ester obtained by Example 349 in 0.7 mL of tetrahydrofuran were added 0.3 mL of ethanol and 0.2 mL of 5N sodium hydroxide aqueous solution, and stirred at 70° C. for 1 hour and 20 minutes. After cooling on ice, the solution was neutralized with 2N hydrochloric acid under ice cooling, and the precipitated crystals were collected by filtration, and dried under reduced pressure, to afford 25 mg of the title compound as yellow crude crystals.

$^1$H-NMR (400 MHz, $CD_3OD$) δ3.98 (2H, t, J=4.4 Hz), 4.25 (2H, t, J=4.4 Hz), 7.06-7.14 (2H, m), 7.28 (1H, d, J=8.8 Hz), 7.54 (1H, d, J=16.6 Hz), 7.68-7.74 (2H, m), 7.86 (1H, d, J=16.6 Hz), 7.89 (1H, d, J=8.8 Hz).

ESI-MS: m/z=341 $(M-H)^-$

Example 351

From 3-[(E)-2-(4-fluorophenyl)-vinyl]-4-(2-hydroxy-ethoxy)-1H-indazole-5-carboxylic acid and various kinds of amine, compounds of Examples 352-356 were obtained in accordance with the method of Example 102.

Example 352

3-[(E)-2-(4-Fluorophenyl)-vinyl]-4-(2-hydroxy-ethoxy)-1H-indazole-5-carboxylic acid[(1S)-1-hydroxymethyl-2-methylpropyl]-amide MS (ESI) m/z 428 $MH^+$ Example 353

3-[(E)-2-(4-Fluorophenyl)-vinyl]-4-(2-hydroxy-ethoxy)-1H-indazole-5-carboxylic acid cyclopropylamide MS (ESI) m/z 382 $MH^+$ Example 354

3-[(E)-2-(4-Fluorophenyl)-vinyl]-4-(2-hydroxy-ethoxy)-1H-indazole-5-carboxylic acid(furan-2-ylmethyl)-amide $^1$H-NMR (400 MHz, $CD_3OD$) δ 3.82 (2H, t, J=4.4 Hz), 4.08 (2H, t, J=4.4 Hz), 4.62 (2H, s), 6.35 (1H, dd, J=0.8, 3.6 Hz), 6.38 (1H, dd, J=2.0, 3.6 Hz), 7.06-7.14 (2H, m), 7.33 (1H, d, J=8.8 Hz), 7.46 (1H, dd, J=0.8, 2.0 Hz), 7.53 (1H, d, J=16.6 Hz), 7.64-7.72 (2H, m), 7.74 (1H, d, J=16.6 Hz), 7.85 (1H, d, J=8.8 Hz).

MS (ESI) m/z 422 $MH^+$

Example 355

3-[(E)-2-(4-Fluorophenyl)-vinyl]-4-(2-hydroxy-ethoxy)-1H-indazole-5-carboxylic acid[(1S)-2-hydroxy-1-phenylethyl]-amide MS (ESI) m/z 462 $MH^+$ Example 356

3-[(E)-2-(4-Fluorophenyl)-vinyl]-4-(2-hydroxy-ethoxy)-1H-indazole-5-carboxylic acid[(1S)-1-carbamoylethyl)-amide $^1$H-NMR (400 MHz, $CD_3OD$) δ 1.52 (3H, d, J=6.8 Hz), 3.94-4.06 (2H, m), 4.15-4.25 (2H, m), 4.60-4.67 (1H, m), 7.08-7.16 (2H, m), 7.34 (1H, d, J=8.8 Hz), 7.55 (1H, d, J=16.2 Hz), 7.66-7.74 (2H, m), 7.75 (1H, d, J=16.2 Hz), 7.91 (1H, d, J=8.8 Hz).

MS (ESI) m/z 413 $MH^+$

Example 357

3-[(E)-2-(4-Fluorophenyl)-vinyl]-4-hydroxy-1H-indazole-5-carboxylic acid

By treating 51.6 mg of 3-[(E)-2-(4-fluorophenyl)-vinyl]-4-hydroxy-1H-indazole-5-carboxylic acid ethyl ester obtained by Example 345 in the method according to Example 216, 61.8 mg of the title compound was obtained as brown crude crystals.

MS (ESI) m/z 297 $MH^-$

Example 358

From 3-[(E)-2-(4-Fluorophenyl)-vinyl]-4-hydroxy-1H-indazole-5-carboxylic acid and various kinds of amine, compounds of Examples 359-363 were obtained in accordance with the method of Example 102.

Example 359

3-[(E)-2-(4-Fluorophenyl)-vinyl]-4-hydroxy-1H-indazole-5-carboxylic acid[(1S)-1-hydroxymethyl-2-methylpropyl]-amide MS (ESI) m/z 385 $MH^+$ Example 360

3-[(E)-2-(4-Fluorophenyl)-vinyl]-4-hydroxy-1H-indazole-5-carboxylic acid cyclopropyl amide MS (ESI) m/z 338 $MH^+$ Example 361

3-[(E)-2-(4-Fluorophenyl)-vinyl]-4-hydroxy-1H-indazole-5-carboxylic acid(furan-2-ylmethyl)-amide $^1$H-NMR (400 MHz, $CD_3OD$) δ 4.58 (2H, s), 6.30-6.33 (1H, m), 6.35-6.38 (1H, m), 6.93 (1H, d, J=8.8 Hz), 7.08-7.16 (2H, m), 7.42-7.45 (1H, m), 7.56-7.68 (2H, m), 7.62 (1H, d, J=16.8 Hz), 7.65 (1H, d, J=8.8 Hz), 7.68 (1H, d, J=16.8 Hz).

MS (ESI) m/z 378 $MH^+$

Example 362

3-[(E)-2-(4-Fluorophenyl)-vinyl]-4-hydroxy-1H-indazole-5-carboxylic acid[(1S)-2-hydroxy-1-phenylethyl]-amide MS (ESI) m/z 418 $MH^+$ Example 363

3-[(E)-2-(4-Fluorophenyl)-vinyl]-4-hydroxy-1H-indazole-5-carboxylic acid[(1S)-1-carbamoylethyl]-amide $^1$H-NMR (400 MHz, $CD_3OD$) δ 1.51 (3H, d, J=7.2 Hz), 4.62 (1H, q), 6.96 (1H, d, J=9.2 Hz), 7.05-7.2.0 (2H, m), 7.46-7.72 (4H, m), 7.77 (1H, d, J=9.2 Hz).

MS (ESI) m/z 369 $MH^+$

Production Example 364

Acetic acid 2-(N'-benzyloxycarbonyl-hydrazino)-2-oxo-ethyl ester

To a solution of 2.04 g of hydrazine carboxylic acid benzyl ester in 40 mL of dichloromethane was added 2.57 mL of triethylamine. Under ice cooling, a solution of 1.32 mL of acetoxyacetylchloride in 20 mL of dichloromethane was added dropwise over 25 minutes, and stirred at room temperature for 1 hour. The reaction solution was added with water, extracted with ethyl acetate, and the resultant organic layer was washed with 1N hydrochloric acid, saturated aqueous sodium hydrogen carbonate and saturated brine, and then dried over magnesium sulfate. The solvent was evaporated, and the resulting solid product was washed with diethyl ether and collected by filtration, to give 1.92 g of the title compound as white crystals.

$^1$H-NMR (400 MHz, DMSO-$D_6$) δ 2.09 (3H, s), 4.52 (2H, s), 5.07 (2H, s), 7.26-7.40 (5H, m), 9.25 (1H, bs), 9.95 (1H, bs).

Production Example 365

Acetic acid hydrazinocarbonyl ethyl ester 1.92 g of acetic acid 2-(N'-benzyloxycarbonyl-hydrazino)-2-oxo-ethyl ester was dissolved in 20 mL of ethanol, and added with 900 mg of 10% palladium on carbon. At room temperature, the solution was stirred for 5 hours under 1 atm hydrogen atmosphere, and filtrated through Celite, and the filtrate was evaporated, to afford 0.96 g of the title compound as a pale yellow oil.

$^1$H-NMR (400 MHz, DMSO-$D_6$) δ 2.07 (3H, s), 4.27 (2H, bs), 4.42 (2H, s), 9.20 (1H, bs).

Production Example 366

N'-[2-(tert-Butoxycarbonyl-methyl-amino)-acetyl]-hydrazine carboxylic acid benzyl ester 6.95 g of 2-(tert-butoxycarbonyl-methyl-amino)-acetic acid, 6.1 g of hydrazine carboxylic acid benzyl ester, 6.18 g of 1-hydroxybenzotriazole monohydrate and 19.2 mL of N,N-diisopropylethylamine were dissolved in 120 mL of N,N-dimethylformamide, and 10.6 g of 1-ethyl-3-(3-dimethylaminopropyl)carbodiimide hydrochloride was added under stirring at room temperature. After stirring at room temperature for 17 hours, the reaction solution was added with water and extracted with ethyl acetate, and the resultant organic layer was washed with saturated brine and dried over magnesium sulfate. The solvent was evaporated, followed by purification by silica gel column chromatography (hexane: ethyl acetate=1:1), to obtain 10.9 g of the title compound.

$^1$H-NMR (400 MHz, DMSO-$D_6$) δ1.25-1.46 (9H, m), 2.68-2.86 (3H, m), 3.80 (2H, d, J=16.8 Hz), 5.07 (2H, s), 7.25-7.46 (5H, m), 9.21 (1H, bs), 9.76 (1H, bs).

Production Example 367

Hydrazine carbonylmethyl-methyl-carbamic acid tert-butyl ester

From 10.9 g of N'-[2-(tert-butoxycarbonyl-methyl-amino)-acetyl]-hydrazine carboxylic acid benzyl ester, 6.64 g of the title compound was obtained in accordance with Production example 365.

$^1$H-NMR (400 MHz, DMSO-$D_6$) δ 1.36 (9H, d, J=19.6 Hz), 2.77 (3H, d, J=14.8 Hz), 3.69 (2H, d, J=10.0 Hz), 4.18 (2H, bs), 8.98 (1H, d, J=11.6 Hz).

Production Example 368

3-Iodo-7-fluoro-1-trityl-1H-indazole-5-carbonitrile

By treating 12.8 g of 7-fluoro-1H-indazole-5-carbonitrile obtained by Production example 120 in the similar method as described in Production example 206, followed by treatment in the similar method as describe in Production example 22, 21.2 g of the title compound was obtained as pale brown crystals.

$^1$H-NMR (400 MHz, $CDCl_3$) δ 7.03 (1H, dd, J=10.4, 1.2 Hz), 7.07-7.38 (15H, m), 7.72 (1H, d, J=1.2 Hz).

Example 369

7-Fluoro-3-[(E)-2-(3-fluorophenyl)-vinyl]-1H-indazole-5-carbonitrile

By treating 1.03 g of 3-bromo-7-fluoro-1-trityl-1H-indazole-5-carbonitrile in the similar method as described in Example 100, 348 mg of the title compound was obtained as pale yellow crystals.

$^1$H-NMR (400 MHz, DMSO-$D_6$) δ 7.14 (1H, t, J=9.2 Hz), 7.14-7.47 (1H, m), 7.56-7.71 (4H, m), 7.77 (1H, d, J=10.4 Hz).

Example 370

7-Fluoro-3-[(E)-2-(3-fluorophenyl)-vinyl]-1H-indazole-5-carboximidic acid ethyl ester hydrochloride 4.88 g of 7-fluoro-3-[(E)-2-(3-fluorophenyl)-vinyl]-1H-indazole-5-carbonitrile was dissolved in 100 mL of ethanol, and under stirring and ice cooling, hydrogen chloride was bubbled thereinto for 20 minutes. After stirring at room temperature for 19 hours, the solvent was evaporated, and the generated crystals were washed with diethyl ether, and collected by filtration, to afford 2.86 g of the title compound as pale yellow crystals.

$^1$H-NMR (400 MHz, $CD_3OD$) δ 1.68 (3H, t, J=6.8 Hz), 4.69 (2H, q, J=6.8 Hz), 7.07 (1H, dt, J=1.2, 8.0 Hz), 7.38-7.52 (3H, m), 7.57 (1H, d, J=16.4 Hz), 7.68 (1H, d, J=16.4 Hz), 7.77 (1 h, dd, J=1.2, 7.2 Hz), 8.81 (1H, s).

Example 371

7-fluoro-3-[(E)-2-(3-fluorophenyl)-vinyl]-1H-indazole-5-carboximidic acid ethyl ester hydrochloride, 3 equivalents of commercially available hydrazide or 3 equivalents of hydrazide obtained in Production example 365, and 3 equivalents of triethylamine were dissolved in ethanol, and stirred at 80° C. for 18 hours. After distilling off the solvent, purification by LC-MS was performed to obtain compounds of Examples 372-374.

Example 372

7-Fluoro-3-[(E)-2-(3-fluorophenyl)-vinyl]-5-(5-methyl-4H-[1,2,4]triazol-3-yl)-1H-indazole MS (ESI)m/z 338 $MH^+$ Example 373

(5-{7-Fluoro-3-[(E)-2-(3-fluorophenyl)-vinyl]-1H-indazol-5-yl}-4H-[1,2,4]triazol-3-yl)-methanol MS (ESI)m/z 354 $MH^+$ Example 374

(5-{7-Fluoro-3-[(E)-2-(3-fluorophenyl)-vinyl]-1H-indazole-5-yl}-4H-[1,2,4]triazol-3-ylmethyl)-dimethyl-amine MS (ESI)m/z 381 $MH^+$ Example 375

(5-{7-Fluoro-3-[(E)-2-(3-fluorophenyl)-vinyl]-1H-indazol-5-yl}-4H-[1,2,4]triazol-3-ylmethyl)-methyl-amine 7-Fluoro-3-[(E)-2-(3-fluorophenyl)-vinyl]-1H-indazole-5-carboximidic acid ethyl ester hydrochloride obtained in Example 370, 3 equivalents of hydrazide obtained in Production example 367 and 3 equivalents of triethylamine were dissolved in ethanol, and stirred at 80° C. for 18 hours. After distilling off the solvent, treatment with trifluoroacetic acid and purification by LC-MS were performed to afford the title compound.

MS (ESI)m/z 367 $MH^+$

Example 376

6-Fluoro-3-[(E)-2-(3-fluorophenyl)-vinyl]-1H-indazole-5-carboxymidic acid ethyl ester hydrochloride From 100 mg of 6-fluoro-3-[(E)-2-(3-fluorophenyl)-vinyl]-1H-indazole-5-carbonitrile obtained by Example 100, 120 mg of the title compound was obtained as pale yellow crystals in accordance with the method of Example 370.

$^1$H-NMR (400 MHz, DMSO-$D_6$) δ 1.51 (3H, t, J=6.8 Hz), 4.66 (2H, q, J=6.8 Hz), 7.10-7.22 (1H, m), 7.41-7.48 (1H, m), 7.56 (1H, d, J=8.0 Hz), 7.60-7.69 (4H, m), 8.83 (1H, d, J=6.8 Hz).

Example 377

From 6-fluoro-3-[(E)-2-(3-fluorophenyl)-vinyl]-1H-indazole-5-carboximidic acid ethyl ester hydrochloride compounds of Examples 378-381 were obtained in accordance with the method of Example 371 or 375.

Example 378

6-Fluoro-3-[(E)-2-(3-fluorophenyl)-vinyl]-5-(5-methyl-4H-[1,2,4]triazol-3-yl)-1H-indazole MS (ESI)m/z 338 $MH^+$ Example 379

(5-{6-Fluoro-3-[(E)-2-(3-fluorophenyl)-vinyl]-1H-indazol-5-yl}-4H-[1,2,4]triazol-3-yl)-methanol MS (ESI)m/z 354 $MH^+$ Example 380

(5-{6-Fluoro-3-[(E)-2-(3-fluorophenyl)-vinyl]-1H-indazol-5-yl}-4H-[1,2,4]triazol-3-ylmethyl)-dimethyl-amine MS (ESI)m/z 381 $MH^+$ Example 381

(5-{6-Fluoro-3-[(E)-2-(3-fluorophenyl)-vinyl]-1H-indazol-5-yl}-4H-[1,2,4]triazol-3-ylmethyl)-methyl-amine MS (ESI)m/z 367 $MH^+$ Example 382

7-Fluoro-3-[(E)-2-(4-fluorophenyl)-vinyl]-1H-indazole-5-carbonitrile

From 5.15 g of 3-iodo-7-fluoro-1-trityl-1H-indazole-5-carbonitrile obtained by Production example 368 and 4-fluoro-styrene, 1.68 g of the title compound was obtained in the similar method as described in Example 100.

$^1$H-NMR (400 MHz, DMSO-$D_6$) δ 7.24 (2H, t, J=8.8 Hz), 7.54 (1H, d, J=16.8 Hz), 7.64 (1H, d, J=16.8 Hz), 7.74 (1H, d, J=10.8 Hz), 7.81 (2H, dd, J=8.8, 5.6 Hz), 8.76 (1H, s).

Example 383

7-Fluoro-3-[(E)-2-(4-fluorophenyl)-vinyl]-1H-indazole-5-carboximidic acid ethyl ester hydrochloride From 1.68 g of 7-fluoro-3-[(E)-2-(4-fluorophenyl)-vinyl]-1H-indazole-5-carbonitrile, 1.81 g of the title compound was obtained in accordance with Example 370.

$^1$H-NMR (400 MHz, DMSO-$D_6$) δ 1.52 (3H, t, J=7.2 Hz), 4.64 (2H, q, J=7.2 Hz), 7.25 (2H, t, J=8.8 Hz), 7.54 (1H, d, J=16.8 Hz), 7.82-7.93 (4H, m), 9.20 (1H, s).

Example 384

From 7-fluoro-3-[(E)-2-(4-fluorophenyl)-vinyl]-1H-indazole-5-carboximidic acid ethyl ester hydrochloride, compounds of Examples 385-387 were obtained in accordance with the method of Example 371 or 375.

Example 385

7-Fluoro-3-[(E)-2-(4-fluorophenyl)-vinyl]-5-(5-methyl-4H-[1,2,4]triazol-3-yl)-1H-indazole MS (ESI)m/z 338 $MH^+$ Example 386

(5-{7-Fluoro-3-[(E)-2-(4-fluorophenyl)-vinyl]-1H-indazol-5-yl}-4H-[1,2,4]triazol-3-yl)-methanol MS (ESI)m/z 354 $MH^+$ Example 387

(5-{7-Fluoro-3-[(E)-2-(4-fluorophenyl)-vinyl]-1H-indazol-5-yl}-4H-[1,2,4]triazol-3-ylmethyl)-methyl-amine MS (ESI)m/z 367 $MH^+$ Production Example 388

3-[(E)-2-(3-Fluorophenyl)-vinyl]-4-methoxy-1-trityl-1H-indazole-5-carboxylic acid ethyl ester By coupling 3.21 g of 3-iodo-4-methoxy-1-trityl-1H-indazole-5-carboxylic acid ethyl ester obtained by Production example 276 and 2.3 g of 2-[(E)-2-(3-fluorophenyl)-vinyl]-4,4,5,5-tetramethyl-[1,3,2]dioxaborolane obtained by Production example 137 in accordance with the method of Example 194, 1.72 g of the title compound was obtained as colorless crystals.

$^1$H-NMR (400 MHz, $CDCl_3$) δ1.38 (3H, t, J=7.4 Hz), 4.04 (3H, s), 4.36 (2H, q, J=7.4 Hz), 6.11 (1H, d, J=9.0 Hz), 6.91-6.96 (1H, m), 7.14-7.46 (19H, m), 7.43 (1H, d, J=9.0 Hz), 7.61 (1H, d, J=16.4 Hz).

Production Example 389

3-[(E)-2-(3-Fluorophenyl)-vinyl]-4-methoxy-1-trityl-1H-indazole-5-carboxylic acid By hydrolyzing 1.61 g of 3-[(E)-2-(3-fluorophenyl)-vinyl]-4-methoxy-1-trityl-1H-indazole-5-carboxylic acid ethyl ester in accordance with the method of Example 350, 1.64 g of the title compound was obtained as orange crude crystals.

$^1$H-NMR (400 MHz, $CD_3OD$) δ4.04 (3H, s), 6.19 (1H, d, J=9.2 Hz), 6.97-7.01 (1H, m), 7.17-7.41 (20H, m), 7.66 (1H, d, J=16.4 Hz).

Production Example 390

N'-{3-[(E)-2-(3-Fluorophenyl)-vinyl]-4-methoxy-1-trityl-1H-indazole-5-carbonyl}-hydrazine carboxylic acid tert-butyl ester 94 mg of 3-[(E)-2-(3-fluorophenyl)-vinyl]-4-methoxy-1-trityl-1H-indazole-5-carboxylic acid and 34.4 mg of hydrazine carboxylic acid tert-butyl ester were condensed in the manner as described in Example 127, to afford 126.9 mg of the title compound as pale yellow crude crystals.

$^1$H-NMR (400 MHz, $CDCl_3$) δ1.50 (9H, s), 4.09 (3H, s), 6.22 (1H, d, J=9.0 Hz), 6.75 (1H, bs), 6.92-6.98 (1H, m), 7.15-7.33 (18H, m), 7.40 (1H, d, J=16.2 Hz), 7.50 (1H, d, J=16.2 Hz), 7.63 (1H, d, J=9.0 Hz), 9.40 (1H, bs).

Example 391

3-[(E)-2-(3-Fluorophenyl)-vinyl]-4-methoxy-1H-indazole-5-carboxylic acid hydrazide 113.7 mg of N'-{3-[(E)-2-(3-fluorophenyl)-vinyl]-4-methoxy-1-trityl-1H-indazole-5-carbonyl}-hydrazinecarboxylic acid tert-butyl ester was deprotected in the manner as described in Example 16, to afford 38 mg of the title compound as colorless crude crystals.

$^1$H-NMR (400 MHz, DMSO-$D_6$) δ 3.96 (3H, s), 7.10-7.14 (1H, m), 7.35 (1H, d, J=8.8 Hz), 7.40-7.52 (3H, m), 7.54 (1H, d, J=16.4 Hz), 7.59 (1H, d, J=16.4 Hz), 7.66 (1H, d, J=8.8 Hz), 10.55 (1H, s), 13.49 (1H, bs)

Example 392

3-[(E)-2-(3-Fluorophenyl)-vinyl]-4-methoxy-5-(5-methyl-2H-[1,2,4]triazol-3-yl)-1H-indazole To a suspension of 19 mg of 3-[(E)-2-(3-fluorophenyl)-vinyl]-4-methoxy-1H-indazole-5-carboxylic acid hydrazide in 4 mL of ethanol were added 50 mg of O-methyl acetimidate hydrochloride and 0.19 mL of triethylamine, and stirred in a sealed tube at 150° C. for 17.5 hours. The reaction solution was allowed to cool to room temperature, the solvent was evaporated, and the crude product was purified and separated by silica gel column chromatography, and further purified and separated by LC-MS, to afford 1.17 mg of the title compound as a yellow amorphous.

$^1$H-NMR (400 MHz, $CD_3OD$) δ 2.62 (3H, s), 3.89 (3H, s), 7.02-7.08 (1H, m), 7.37-7.44 (3H, m), 7.47 (1H, d, J=8.8 Hz), 7.62 (1H, d, J=16.4 Hz), 7.67 (1H, d, J=16.4 Hz), 7.89 (1H, d, J=8.8 Hz).

MS (ESI)m/z 392 $MH^+$

Production Example 393

6-Fluoro-3-[(E)-2-(pyridin-3-yl)-vinyl]-1-trityl-1H-indazole-5-carboxylic acid methyl ester In accordance with method of Production example 181, 576 mg of 3-bromo-6-fluoro-1-trityl-1H-indazole-5-carboxylic acid methyl ester obtained by Production example 141 and 235 mg of 3-vinylpyridine were made to react, to afford 312 mg of the title compound as bright yellow crystals.

$^1$H-NMR (400 MHz, DMSO-$D_6$) δ 3.86 (3H, s), 6.01 (1H, d, J=12.4 Hz), 7.16-7.25 (6H, m), 7.32-7.46 (1H, m), 7.76 (1H, d, J=16.8 Hz), 8.21 (1H, d, J=8.4 Hz), 8.49 (1H, dd, J=1.2, 8.8 Hz), 8.77 (1H, d, J=6.8 Hz), 8.88 (1H, d, J=1.2 Hz).

Production Example 394

6-Fluoro-3-[(E)-2-(pyridin-3-yl)-vinyl]-1-trityl-1H-indazole-5-carboxylic acid

From 187 mg of 6-fluoro-3-[(E)-2-(pyridin-3-yl)-vinyl]-1-trityl-1H-indazole-5-carboxylic acid methyl ester, 187 mg of the title compound was obtained as ocher crystals in accordance with the method of Example 144.

$^1$H-NMR (400 MHz, DMSO-$D_6$) δ 5.99 (1H, d, J=12.0 Hz), 7.16-7.25 (6H, m), 7.30-7.46 (11H, m), 7.74 (1H, d, J=16.4 Hz), 8.21 (1H, d, J=8.4 Hz), 8.48 (1H, d, J=4.0 Hz), 8.75 (1H, d, J=7.2 Hz), 8.88 (1H, s), 13.20 (1H, bs).

Production Example 395

6-Fluoro-3-[(E)-2-(pyridin-3-yl)-vinyl]-1-trityl-1H-indazole-5-carboxylic acid hydrazide In accordance with the method as described in Example 127, 110 mg of 6-fluoro-3-[(E)-2-(pyridin-3-yl)-vinyl]-1-trityl-1H-indazole-5-carboxylic acid and 210 mg of hydrazine monohydrate were condensed, to afford 29 mg of the title compound as a yellow powder.

$^1$H-NMR (400 MHz, DMSO-$D_6$) δ 4.50 (2H, s), 6.01 (1H, d, J=11.6 Hz), 7.16-7.26 (6H, m), 7.28-7.46 (10H, m), 7.48 (1H, d, J=16.8 Hz), 7.74 (1H, d, J=16.8 Hz), 8.20 (1H, d, J=7.6 Hz), 8.42 (1H, d, J=7.2 Hz), 8.48 (1H, d, J=4.0 Hz), 8.87 (1H, s), 9.57 (1H, s).

Production Example 396

6-Fluoro-5-(5-methyl-4H-[1,2,4]triazol-3-yl)-3-[(E)-2-(pyridin-3-yl)-vinyl]-1-trityl-1H-indazole To a solution of 28 mg of trityl-1H-indazole-5-carboxylic acid hydrazide in 2 mL of methanol was added 11 mg of S-methyl thioacetimidate hydriodate, and stirred at room temperature for 20 minutes. Then the reaction solution was added with 50 μl of triethylamine, and stirred at 60-75° C. overnight. The reaction solution was added with 15 mL of ethyl acetate, and the organic layer was washed successively with water, saturated aqueous sodium hydrogen carbonate and saturated brine, and dried over anhydrous magnesium sulfate. The solvent was evaporated, and the crude product was purified and separated by silica gel column chromatography (methanol:chloroform=1:49), to afford 16 mg of the title compound as white non-crystalline powder.

$^1$H-NMR (400 MHz, DMSO-$D_6$) δ 2.40 (3H, s), 6.07 (1H, d, J=12.0 Hz), 7.16-7.26 (6H, m), 7.28-7.46 (11H, m), 7.73 (1H, d, J=16.4 Hz), 8.21 (1H, d, J=8.4 Hz), 8.48 (1H, d, J=4.8 Hz), 8.67 (1H, d, J=7.2 Hz), 8.87 (1H, s), 13.80 (1H, bs).

Example 397

6-Fluoro-5-(5-methyl-4H-[1,2,4]triazol-3-yl)-3-[(E)-2-(pyridin-3-yl)-vinyl]-1H-indazole 16 mg of 6-fluoro-5-(5-methyl-4H-[1,2,4]triazol-3-yl)-3-[(E)-2-(pyridin-3-yl)-vinyl]-1-trityl-1H-indazole was deprotected in accordance with Example 16, and then purified and separated by LC-MS, to afford 4.7 mg of the title compound.

MS (ESI) m/z 321 $MH^+$

Example 398

7-Fluoro-5-(5-methyl-4H-[1,2,4]triazol-3-yl)-3-[(E)-2-(pyridin-3-yl)-vinyl]-1H-indazole 7-Fluoro-3-[(E)-2-(pyridin-3-yl)-vinyl]-1-trityl-1H-indazole-5-carbonitrile obtained by Production example 124 was deprotected in the similar method as described in Example 16, followed by reactions in accordance with Examples 370 and 372, and purification and isolation by LC-MS, to afford the title compound.

$^1$H-NMR (400 MHz, DMSO-$D_6$) δ 2.40 (3H, s), 7.41 (1H, dd, J=8.0, 4.8 Hz), 7.52 (1H, d, J=16.4 Hz), 7.74 (1H, d, J=12.4 Hz), 7.81 (1H, d, J=16.4 Hz), 8.23 (1H, d, J=8.0 Hz), 8.47 (1H, d, J=4.8 Hz), 8.53 (1H, s), 8.89 (1H, s).

Example 399

(5-{7-Fluoro-3-[(E)-2-(pyridin-3-yl)-vinyl]-1H-indazol-5-yl}-4H-[1,2,4]triazol-3-ylmethyl)dimethylamine After removing the trityl group from 7-fluoro-3-[(E)-2-(pyridin-3-yl)-vinyl]-1-trityl-1H-indazole-5-carbonitrile obtained by Production example 124 in accordance with the method of Example 16, reactions as described in Examples 370 and 374 as well as separation and purification by LC-MS were followed, to obtain the title compound.

$^1$H-NMR (400 MHz, DMSO-$D_6$) δ 2.25 (6H, s), 3.62 (2H, s), 7.43 (1H, dd, J=8.0, 4.4 Hz), 7.54 (1H, d, J=16.8 Hz), 7.78 (1H, d, J=12.0 Hz), 7.83 (1H, d, J=16.8 Hz), 8.24 (1H, dt, J=8.0, 1.6 Hz), 8.49 (1H, dd, J=4.4, 1.6 Hz), 8.56 (1H, s), 8.90 (1H, d, J=1.6 Hz).

Example 400

4-Methoxy-5-(5-methyl-2H-[1,2,4]triazol-3-yl)-3-[(E)-2-(pyridin-3-yl)-vinyl]-1H-indazole 4-Methoxy-3-[(E)-2-(pyridin-3-yl)-vinyl]-1H-indazole-5-carboxylic acid obtained by Production example 326 was led to hydrazide in accordance with Production examples 390 and 391. A suspension of 30 mg of hydrazide in 5 mL of ethanol was added. 32 mg of s-methyl thioacetimidate hydriodate, and stirred at room temperature for 1 hour. Then the reaction solution was added with 0.069 mL of triethylamine, and allowed to react at 150° C. for 30 minutes under microwave irradiation. The reaction mixture was purified and separated by LC-MS, to obtain 2.04 mg of the title compound and 1.44 mg of 4-methoxy-5-(5-methyl-2H-[1,3,4]oxadiazol-2-yl)-3-[(E)-2-(pyridin-3-yl)-vinyl]-1H-indazole as described in Example 401 below.

$^1$H-NMR (400 MHz, DMSO-$D_6$) 2.60 (3H, s), 3.88 (3H, s), 7.43-7.73 (1H, m), 7.70-7.77 (2H, m), 7.86-7.96 (4H, m), 8.61-8.71 (2H, m), 8.95-8.99 (1H, m).

MS (ESI) m/z 333 $MH^+$

Example 401

4-Methoxy-5-(5-methyl-2H-[1,3,4]oxadiazol-2-yl)-3-[(E)-2-(pyridin-3-yl)-vinyl]-1H-indazole $^1$H-NMR (400 MHz, DMSO-$D_6$) δ2.67 (3H, s), 4.00 (3H, s), 7.09 (1H, d, J=8.4 Hz), 7.48 (1H, d, J=8.8 Hz), 7.90-7.99 (4H, m), 8.66 (1H, bs), 8.76 (1H, d, J=8.4 Hz), 9.01 (1H, d, J=7.6 Hz).

MS (ESI) m/z 334 $MH^+$

Example 402

3-(3-Fluorophenyl)-5-methoxy-1H-pyrazolo[4,3-b]pyridine 35 mg of 3-(3-fluorophenyl)-5-chloro-1-trityl-1H-pyrazolo[4,3-b]pyridine obtained by Production example 37 was dissolved in 2 mL of methanol, added with 20 μl of triethylamine and 15 μl of ethyl chloroformate, and heated at reflux for 16 hours. The reaction solution was allowed to cool to room temperature, the solvent was evaporated, and the residue was dissolved in 3 mL of dichloromethane. After adding 0.5 mL of trifluoroacetic acid and stirring at room temperature for 30 minutes, the reaction solution was partitioned between saturated aqueous sodium hydrogen carbonate and ethyl acetate, extracted with ethyl acetate, and the organic layer was washed with water, and dried over magnesium sulfate. The solvent was evaporated, and the residue was purified by silica gel column chromatography (ethyl acetate:hexane=3:7), to afford 7.25 mg of the title compound as a pale yellow powder.

$^1$H-NMR (400 MHz, $CDCl_3$) δ4.08 (3H, s), 6.88 (1H, d, J=9.1 Hz), 7.08 (1H, dt, J=2.5, 8.1 Hz), 7.46 (1H, dt, J=6.2, 8.1 Hz), 7.71 (1H, d, J=9.1 Hz), 8.29 (1H, bd, J=8.1 Hz), 8.32 (1H, bd, J=11.0 Hz).

Example 403

3-(Naphthalen-2-yl)-1H-pyrazolo[3,4-c]pyridine-5-carboxylic acid

From 40 mg of 3-(naphthalen-2-yl)-1H-pyrazolo[3,4-c]pyridine-5-carbonitrile obtained by Example 75, 33 mg of the title compound was obtained as pale brown crystals in accordance with the method of Example 7.

$^1$H-NMR (400 MHz, DMSO-$D_6$) 7.52-7.63 (2H, m), 7.93-8.23 (4H, m), 8.59 (1H, s), 8.88 (1H, s), 9.20 (1H, s).

Production Example 404

1-Benzyl-3-(naphthalen-2-yl)-1H-pyrazolo[3,4-b]pyridine-5-carbonitrile 900 mg of 2-benzyl-5-(2-naphthyl)-2H-pyrazol-3-ylamine obtained from 3-(naphthalen-2-yl)-3-oxopropionitrile and benzyl hydrazine in the similar method as described in Production example 30 was subjected to the similar reaction as described in Production example 31, to afford 770 mg of the title compound as a pale yellow powder.

$^1$H-NMR (400 MHz, DMSO-d$_6$) δ5.81 (2H, s), 7.25-7.36 (5H, m), 7.54-7.62 (2H, m), 7.94-7.99 (1H, m), 8.04 (1H, d, J=8.7 Hz), 8.13-8.18 (1H, m), 8.19 (1H, dd, J=2.0, 8.7 Hz), 8.70 (1H, d, J=2.0 Hz), 9.03 (1H, d, J=2.0 Hz), 9.53 (1H, d, J=2.0 Hz).

Example 405

3-(Naphthalen-2-yl)-1H-pyrazolo[3,4-b]pyridine-5-carboxylic acid 500 mg of 1-benzyl-3-(naphthalen-2-yl)-1H-pyrazolo[3,4-b]pyridine-5-carbonitrile obtained by Production example 404 was treated in the similar method as described in Example 437, to obtain 230 mg of the title compound as a pale brown powder in which deprotection and hydrolysis had proceeded, as well as 20 mg of 3-(naphthalen-2-yl)-1H-pyrazolo[3,4-b]pyridine-5-carbonitrile described in Example 406 as a pale brown powder.

$^1$H-NMR (400 MHz, DMSO-d$_6$) δ7.55-7.60 (2H, m), 8.08 (1H, d, J=8.5 Hz), 8.14-8.19 (1H, m), 8.18 (1H, dd, J=1.5, 8.5 Hz), 8.59 (1H, s), 9.09 (1H, d, J=1.5 Hz), 9.12 (1H, d, J=1.5 Hz), 13.25-13.40 (1H, bs), 14.25 (1H, bs).

Example 406

3-(Naphthalen-2-yl)-1H-pyrazolo[3,4-b]pyridine-5-carbonitrile $^1$H-NMR (400 MHz, DMSO-d$_6$) δ7.55 (1H, bt, J=8.4 Hz), 7.58 (1H, bt, J=8.4 Hz), 7.96 (1H, bd, J=8.4 Hz), 8.05 (1H, d, J=8.4 Hz), 8.15 (1H, bd, J=8.4 Hz), 8.23 (1H, dd, J=2.1, 8.4 Hz), 8.69 (1H, d, J=2.1 Hz), 8.93 (1H, d, J=2.1 Hz), 9.47 (1H, d, J=2.1 Hz), 14.35-14.60 (1H, bs)

Production Example 407

N-(2-Methyl-pyridin-3-yl)-acetamide

Under nitrogen atmosphere, 47.6 g of 2-chloro-3-nitropyridine was dissolved in 500 mL of tetrahydrofuran, and 150 mL of 2M methylzinc chloride in tetrahydrofuran and 6.9 g of tetrakis(triphenylphosphine)palladium(0) were added, and the reaction solution was stirred at 70° C. for 2 hours. The reaction solution was poured into cold water, extracted with ethyl acetate, washed with water, and dried over anhydrous magnesium sulfate. The solvent was evaporated, and the residue was subjected to column chromatography (n-hexane: ethyl acetate=3:1) to obtain 35.4 g of 2-methyl-3-nitropyridine as a colorless oil. Then 35.4 g of 2-methyl-3-nitropyridine was dissolved in a mixed solution of 300 mL methanol/5 mL triethylamine, added with 5 g of 10% palladium on carbon, and stirred for 6 hours under hydrogen atmosphere and at normal temperature and pressure. The reaction solution was filtered thorough Celite, the solvent was evaporated, and 33.0 g of crudely produced 2-methyl-3-aminopyridine was obtained as a pale brown oil. Next, to 100 mL of a solution of 65 g of crude 3-amino-2-methylpyridine in dichloromethane were added 60 mL of pyridine and 71 mL of acetic anhydride at room temperature and stirred for 3 hours. The reaction solution was added with about 150 mL of silica gel powder, the solvent was evaporated, and the residue was purified by silica gel column chromatography (ethyl acetate: methanol=100:3), to afford 74 g of the title compound as colorless crystals.

$^1$H-NMR (400 MHz, CDCl$_3$) δ2.25 (3H, s), 2.53 (3H, s), 7.00 (1H, bs), 7.18 (1H, dd, J=4.6, 8.0 Hz), 8.23 (1H, d, J=8.0 Hz), 8.30 (1H, d, J=4.6 Hz).

Production Example 408

1-Pyrazolo[4,3-b]pyridin-1-yl-ethanone

To a solution of 74 g of N-(2-methyl-pyridin-3-yl)-acetamide obtained by Production example 407 in toluene were added 106 mL of isoamyl sulfite, 140 mL of acetic anhydride and 57.6 g of potassium acetate at room temperature, and the reaction solution was heated at 80° C. for 2 hours. The reaction solution was partitioned into water and ethyl acetate, and the organic layer was extracted and dried over magnesium sulfate. The solvent was evaporated, and the residue was purified by silica gel column chromatography (ethyl acetate: hexane=1:5), to afford 20 g of the title compound as colorless crystals.

$^1$H-NMR (400 MHz, CDCl$_3$) δ2.83 (3H, s), 7.48 (1H, dd, J=4.7, 8.3 Hz), 8.37 (1H, s), 8.72 (1H, bd, J=8.3 Hz), 8.73 (1H, d, J=4.7 Hz).

Production Example 409

1H-Pyrazolo[4,3-b]pyridine 20 g of 1-pyrazolo[4,3-b]pyridin-1-yl-ethanone obtained by Production example 408 was dissolved in a mixed solution of 20 mL methanol/80 mL tetrahydrofuran, added with 10 mL of 2N sodium hydroxide aqueous solution at room temperature and stirred for 0.5 hours. The reaction solution was neutralized by adding 2 mL of 5N hydrochloric acid, then added with about 50 mL of silica gel powder, and the solvent was evaporated. The residue was purified by silica gel column chromatography (ethyl acetate:methanol=100:2), to afford 14.6 g of the title compound as pale yellow cubic crystals.

$^1$H-NMR (400 MHz, CDCl$_3$) δ7.35 (1H, dd, J=4.3, 8.6 Hz), 7.89 (1H, d, J=8.6 Hz), 8.36 (1H, bs), 8.64 (1H, dd, J=1.5, 4.3 Hz).

Production Example 410

3-Bromo-1H-pyrazolo[4,3-b]pyridine 750 mg of N-bromosuccinimide was reacted on 0.5 g of 1H-pyrazolo[4,3-b]pyridine in the similar method as described in Production example 87, to afford 570 mg of the title compound as a colorless powder.

$^1$H-NMR (400 MHz, DMSO-d$_6$) δ7.43 (1H, dd, J=4.3, 8.6 Hz), 8.07 (1H, dd, J=1.4, 8.6 Hz), 8.59 (1H, dd, J=1.4, 4.3 Hz), 13.68 (1H, bs).

Production Example 411

3-Bromo-1-trityl-1H-pyrazolo[4,3-b]pyridine

By treating 570 mg of 3-bromo-1H-pyrazolo[4,3-b]pyridine obtained by Production example 410 in the similar method as described in Production example 22, 860 mg of the title compound was obtained as a colorless powder.

$^1$H-NMR (400 MHz, DMSO-d$_6$) δ6.73 (1H, d, J=8.8 Hz), 7.14-7.19 (6H, m), 7.20 (1H, dd, J=4.1, 8.8 Hz), 7.28-7.38 (9H, m), 8.51 (1H, dd, J=4.1 Hz).

Production Example 412

3-Bromo-1-trityl-1H-pyrazolo[4,3-b]pyridine 4-oxide

By treating 110 mg of 3-bromo-1-trityl-1H-pyrazolo[4,3-b]pyridine in the similar method as described in Production example 4, 70 mg of the title compound was obtained as a colorless powder.

$^1$H-NMR (400 MHz, $CDCl_3$) δ6.25 (1H, d, J=8.8 Hz), 7.06 (1H, dd, J=6.4, 8.8 Hz), 7.12-7.17 (6H, m), 7.28-7.38 (9H, m), 8.08 (1H, d, J=6.4 Hz).

Production Example 413

3-Bromo-1-trityl-1H-pyrazolo[4,3-b]pyridine-5-carbonitrile

By treating 300 mg of 3-bromo-1-trityl-1H-pyrazolo[4,3-b]pyridine 4-oxide in the same manner as described in Production example 5, 240 mg of the title compound was obtained as a colorless powder.

$^1$H-NMR (400 MHz, $CDCl_3$) δ6.65 (1H, d, J=9.0 Hz), 7.14-7.18 (6H, m), 7.27 (1H, d, J=9.0 Hz), 7.29-7.35 (9H, m).

Production Example 414

3-[(E)-2-(3-Fluorophenyl)-vinyl]-1-trityl-1H-pyrazolo[4,3-b]pyridine-5-carbonitrile By treating 180 mg of 3-bromo-1-trityl-1H-pyrazolo[4,3-b]pyridine-5-carbonitrile obtained by Production example 413 in the similar method as described in Example 194, 180 mg of a crude product of the title compound as a colorless oil.

$^1$H-NMR (400 MHz, $CDCl_3$) δ6.66 (1H, d, J=8.5 Hz), 6.95-7.01 (1H, m), 7.13-7.22 (7H, m), 7.23-7.40 (12H, m), 7.26 (1H, d, J=8.5 Hz), 7.40 (1H, d, J=16.6 Hz), 8.19 (1H, d, J=16.6 Hz).

Example 415

3-[(E)-2-(3-Fluorophenyl)-vinyl]-1H-pyrazolo[4,3-b]-pyridine-5-carbonitrile

By treating 180 mg of the crude 3-[(E)-2-(3-fluorophenyl)-vinyl]-1-trityl-1H-pyrazolo[4,3-b]pyridine-5-carbonitrile obtained by Production example 414 in the similar method as described in Example 16, 60 mg of the title compound was obtained as a pale yellow powder.

$^1$H-NMR (400 MHz, $CDCl_3$) δ7.00-7.06 (1H, m), 7.35-7.40 (2H, m), 7.40-7.45 (1H, m), 7.47 (1H, d, J=16.9 Hz), 7.72 (1H, d, J=8.5 Hz), 7.95 (1H, d, J=8.5 Hz), 8.25 (1H, d, J=16.9 Hz).

Example 416

3-[(E)-2-(3-Fluorophenyl)-vinyl]-1H-pyrazolo[4,3-b]-pyridine-5-carboxylic acid

By treating 60 mg of 3-[(E)-2-(3-fluorophenyl)-vinyl]-1H-pyrazolo[4,3-b]pyridine-5-carbonitrile in the similar method as described in Example 7, 36 mg of the title compound was obtained as a colorless powder.

$^1$H-NMR (400 MHz, DMSO-$d_6$) δ7.14 (1H, bt, 8.5 Hz), 7.44 (1H, dt, 6.2, 7.7 Hz), 7.50 (1H, bd, 7.7 Hz), 7.57 (1H, bd, 8.5 Hz), 7.61 (1H, d, J=16.6 Hz), 8.09 (1H, d, J=8.8 Hz), 8.14 (1H, d, J=8.8 Hz), 8.19 (1H, d, J=16.6 Hz), 13.07 (1H, bs), 13.68 (1H, bs).

Production Example 417

3-Iodo-1H-pyrazolo[4,3-b]pyridine

In the similar method as described in Production example 206, 9.5 g of N-iodosuccinimide was reacted on 5 g of 1H-pyrazolo[4,3-b]pyridine, to afford 5.9 g of the title compound as a colorless powder.

$^1$H-NMR (400 MHz, DMSO-$d_6$) δ7.43 (1H, dd, J=4.2, 8.2 Hz), 8.00 (1H, dd, J=1.3, 8.2 Hz), 8.53 (1H, dd, J=1.3, 4.2 Hz), 13.64-13.83 (1H, bs).

Production Example 418

3-Iodo-1-trityl-1H-pyrazolo[4,3-b]pyridine

By treating 5.9 g of 3-iodo-1H-pyrazolo[4,3-b]pyridine obtained by Production example 417 in the similar method as described in Production example 22, 10.7 g of the title compound was obtained as a colorless powder.

$^1$H-NMR (400 MHz, DMSO-$d_6$) δ6.56 (1H, dd, J=1.2, 8.7 Hz), 6.96 (1H, dd, J=4.3, 8.7 Hz), 7.15-7.22 (6H, m), 7.25-7.35 (9H, m), 8.53 (1H, dd, J=1.2, 4.3 Hz).

Production Example 419

3-(Naphthalen-2-yl)-1-trityl-1H-pyrazolo[4,3-b]pyridine

By treating 731 mg of 3-iodo-1-trityl-1H-pyrazolo[4,3-b]pyridine obtained by Example 418 and 340 mg of 2-naphthalene boronic acid in the manner as described in Production example 194, 210 mg of the title compound was obtained as a colorless powder.

The instrumental data coincided with that of Production example 13.

Example 420

5-Chloro-3-naphthalen-2-yl-1H-pyrazolo[4,3-b]pyridine

After treating 210 mg of 3-(naphthalen-2-yl)-1-trityl-1H-pyrazolo[4,3-b]pyridine obtained by Production example 419 in the similar method as described in Production example 4, 2 mL of residue solution in toluene was added at room temperature with 190 μl of phosphorus oxychloride, and treated in the similar method as described in Production example 28, to afford 60 mg of the title compound as a pale yellow powder.

$^1$H-NMR (400 MHz, $CDCl_3$) δ7.38 (1H, d, J=8.9 Hz), 7.48-7.55 (2H, m), 7.83 (1H, d, J=8.9 Hz), 7.85-7.90 (1H, m), 7.97 (1H, d, J=8.9 Hz), 8.01-8.06 (1H, m), 8.52 (1H, dd, J=1.8, 8.9 Hz), 9.08 (1H, d, J=1.8 Hz).

Production Example 421

5-Chloro-3-(naphthalen-2-yl)-1-trityl-1H-pyrazolo[4,3-b]pyridine

By treating 170 mg 5-chloro-3-(naphthalen-2-yl)-1H-pyrazolo[4,3-b]pyridine obtained by Example 420 in the similar method as described in Production example 22, 340 mg of the title compound was obtained as a colorless powder.

$^{1}$H-NMR (400 MHz, $CDCl_3$) δ6.56 (1H, d, J=8.7 Hz), 6.94 (1H, d, J=8.7 Hz), 7.22-7.28 (6H, m), 7.28-7.36 (9H, m), 7.44-7.52 (2H, m), 7.81-7.85 (1H, m), 7.87 (1H, d, J=8.7 Hz), 7.97-8.03 (1H, m), 8.38 (1H, dd, J=2.0, 8.7 Hz), 9.08 (1H, d, J=2.0 Hz).

Production Example 422

3-(Naphthalen-2-yl)-1-trityl-1H-pyrazolo[4,3-b]pyridin-5-ylamine 280 mg of 5-chloro-3-(naphthalen-2-yl)-1-trityl-1H-pyrazolo[4,3-b]pyridine was dissolved in 8 mL of toluene, added with 73 mg sodium t-butoxide, 180 μl of benzophenone imine, 100 mg of 2,2'-bis(diphenylphosphino)-1,1'-binaphthyl and 56 mg of tris(dibenzylidene acetone)bispalladium, and stirred at 100° C. for 1.5 hours. The reaction solution was allowed to cool to room temperature, the solvent evaporated, and the residue was added with 5 mL of tetrahydrofuran and 0.3 mL of 5N hydrochloric acid and stirred at room temperature for 1 hour. The resultant reaction solution was added with aqueous sodium hydrogen carbonate, extracted with ethyl acetate, and the organic layer was washed with water and dried over magnesium sulfate. The solvent was evaporated, and the residue was purified by silica gel column chromatography (ethyl acetate:hexane=1:3), to afford 220 mg of the title compound as a colorless powder.

$^{1}$H-NMR (400 MHz, $CDCl_3$) δ4.47-4.63 (2H, bs), 6.25 (1H, d, J=9.1 Hz), 6.43 (1H, d, J=9.1 Hz), 7.24-7.33 (15H, m), 7.39-7.48 (2H, m), 7.78-7.82 (1H, m), 7.83 (1H, d, J=8.8 Hz), 7.92-7.96 (1H, m), 8.36 (1H, dd, J=1.6, 8.8 Hz), 9.06 (1H, d, J=1.6 Hz).

Production Example 423

Cyclopropane carboxylic acid[3-(naphthalen-2-yl)-1-trityl-1H-pyrazolo[4,3-b]pyridin-5-yl]amide 20 mg of 3-(naphthalen-2-yl)-1-trityl-1H-pyrazolo[4,3-b]pyridin-5-ylamine was dissolved in 3 mL of toluene, and added with 20 μl of triethylamine and 10 μl of cyclopropanecarbonyl chloride at room temperature and stirred all day and night. The reaction solution was added with saturated aqueous sodium hydrogen carbonate, extracted with sodium acetate, and dried over anhydrous magnesium sulfate. The solvent was evaporated, and the residue was purified by silica gel column chromatography (ethyl acetate:hexane=1:4), to afford 20 mg of the title compound as a colorless powder.

$^{1}$H-NMR (400 MHz, $CDCl_3$) δ0.88-0.95 (2H, m), 1.03-1.12 (2H, m), 1.57-1.65 (1H, m), 6.64 (1H, d, J=9.4 Hz), 7.23-7.33 (15H, m), 7.42-7.51 (2H, m), 7.80-7.86 (1H, m), 7.86 (1H, d, J=8.4 Hz), 7.92-7.98 (1H, m), 7.96 (1H, d, J=9.4 Hz), 8.35 (1H, dd, J=1.8, 8.4 Hz), 8.45 (1H, bs), 9.01 (1H, d, J=1.8 Hz).

Example 424

Cyclopropane carboxylic acid[3-(naphthalen-2-yl)-1H-pyrazolo[4,3-b]pyridin-5-yl]amide By deprotecting 20 mg of cyclopropane carboxylic acid (3-naphthalen-2-yl-1-trityl-1H-pyrazolo[4,3-b]pyridin-5-yl) amide obtained by Production example 423 in the similar method as described in Example 16, 9.1 mg of the title compound was obtained as a colorless powder.

$^{1}$H-NMR (400 MHz, $CD_3OD$) δ0.89-0.95 (2H, m), 1.00-1.15 (2H, m), 1.96-2.04 (1H, m), 7.45-7.54 (2H, m), 7.84-7.90 (1H, m), 7.93 (1H, d, J=8.9 Hz), 7.97 (1H, d, J=9.2 Hz), 7.97-8.03 (1H, m), 8.25 (1H, d, J=9.2 Hz), 8.49 (1H, dd, J=1.9, 8.9 Hz), 9.11 (1H, s).

Production Example 425

2-Iodo-4-methyl-5-nitropyridine

To a solution of 1.0 g of 2-amino-4-methyl-5-nitropyridine in 10 mL of diiodomethane was added 1.8 mL of isopentyl sulfite at room temperature, stirred at this temperature for 30 minutes, and after raising the temperature to 80° C., the solution was stirred for 2 hours. The diiodomethane was evaporated, and the crude product was purified and separated by silica gel column chromatography (ethyl acetate:n-hexane=1:20), to afford 897 mg of the title compound as colorless crystals.

$^{1}$H-NMR (400 MHz, $CDCl_3$) δ2.58 (3H, s), 7.77 (1H, s), 8.90 (1H, s).

Production Example 426

6-Iodo-4-methylpyridin-3-ylamine

To a solution of 1.76 g of 2-iodo-4-methyl-5-nitropyridine in 7.0 mL of concentrated hydrochloric acid and 7.0 mL of diethyl ether was added 6.32 g of tin chloride (II) at room temperature, and stirred at 100° C. for 4 hours. After cooling the solution to room temperature, 5N sodium hydroxide aqueous solution was added to make the solution alkaline. Then the solution was diluted with dichloromethane and the insoluble substances were filtered off through Celite. The organic layer of the filtrate was dried over anhydrous magnesium sulfate, and the solvent was evaporated, to afford 897 mg of the title compound as orange-brown crystals.

$^{1}$H-NMR (400 MHz, $CDCl_3$) δ2.10 (3H, s), 3.61 (2H, bs), 7.33 (1H, s), 7.80 (1H, s).

Production Example 427

N-(6-Iodo-4-methylpyridin-3-yl)acetamide

By treating 1.55 g of 6-iodo-4-methylpyridin-3-ylamine obtained by Production example 426 in the similar method as described in Production example 176, 1.68 g of the title compound was obtained as colorless crystals.

$^{1}$H-NMR (400 MHz, $CDCl_3$) δ2.21 (3H, s), 2.22 (3H, s), 6.89 (1H, bs), 7.56 (1H, s), 8.62 (1H, s).

Production Example 428

1-(5-Iodo-pyrazolo[3,4-c]pyridin-1-yl)ethanone

By treating 1.68 g of N-(6-iodo-4-methylpyridin-3-yl)acetamide in the similar method as described in Production example 408, 1.58 g of the title compound was obtained as colorless crystals.

$^{1}$H-NMR (400 MHz, $CDCl_3$) δ2.80 (3H, s), 8.10 (2H, d, J=0.8 Hz), 9.56 (1H, t, J=0.8 Hz).

Production Example 429

1H-Pyrazolo[3,4-c]pyridine-5-carbonitrile

A suspension of 6.40 g of 1-(5-iodo-pyrazolo[3,4-c]pyridin-1-yl)ethanone obtained by Production example 428, 5.24 g of zinc cyanide and 2.58 g of tetrakis(triphenylphosphine) palladium(0) in 70 mL of N,N-dimethylformamide was stirred at 40° C. for 2 days. The suspension was diluted with ethyl acetate, and the insoluble substances were filtered through Celite. The filtrate was washed successively with saturated ammonium chloride and saturated brine, and then dried over anhydrous magnesium sulfate. The solvent was evaporated, and the crude product was purified and separated by silica gel column chromatography (ethyl acetate:n-hexane=1:10-1:1), to afford 2.78 g of the title compound as colorless crystals.

$^1$H-NMR (400 MHz, $CD_3OD$) δ8.34 (1H, d, J=0.8 Hz), 8.38 (1H, d, J=0.8 Hz), 9.09 (1H, t, J=0.8 Hz).

Production Example 430

3-Iodo-1H-pyrazolo[3,4-c]pyridine-5-carbonitrile

From 2.78 g of 1H-pyrazolo[3,4-c]pyridine-5-carbonitrile, 5.89 g of the title compound (N,N-dimethylformamide still remaining) was obtained as colorless crystals in accordance with the method of Production example 206.

$^1$H-NMR (400 MHz, $CD_3OD$) δ8.08 (1H, d, J=0.8 Hz), 9.05 (1H, t, J=0.8 Hz).

Production example 431

3-Iodo-1-trityl-1H-pyrazolo[3,4-c]pyridine-5-carbonitrile

To a solution of 5.8 g of 3-iodo-1H-pyrazolo[3,4-c]pyridine-5-carbonitrile in 70 mL of dichloromethane were added 13.1 mL of diisopropylethylamine, 2.4 g of tetra-n-butylammonium iodide and 12.0 g of trityl chloride at room temperature, and stirred at this temperature for a day. The solution was evaporated, diluted with ethyl acetate, washed successively with saturated ammonium chloride and saturated brine, and dried over anhydrous magnesium sulfate. The solvent was evaporated, and the crude product was purified and separated by silica gel column chromatography (ethyl acetate:n-hexane=1:10), to afford 5.2 g of the title compound as colorless crystals.

$^1$H-NMR (400 MHz, $CDCl_3$) δ7.10-7.15 (6H, m), 7.27-7.36 (9H, m), 7.60 (1H, d, J=1.2 Hz), 7.84 (1H, d, J=1.2 Hz).

Production Example 432

3-[(E)-2-(3-Fluorophenyl)-vinyl]-1-trityl-1H-pyrazolo[3,4-c]pyridine-5-carbonitrile From 1.0 g of 3-iodo-1-trityl-1H-pyrazolo[3,4-c]pyridine-5-carbonitrile, 326 mg of the title compound was obtained as colorless crystals in accordance with the method of Example 194.

$^1$H-NMR (400 MHz, $CDCl_3$) δ6.98-7.04 (1H, m), 7.15-7.36 (20H, m), 7.73 (1H, d, J=1.2 Hz), 8.30 (1H, d, J=1.2 Hz).

Example 433

3-[(E)-2-(3-Fluorophenyl)-vinyl]-1H-pyrazolo[3,4-c]pyridine-5-carboxylic acid

From 87 mg of 3-[(E)-2-(3-fluorophenyl)-vinyl]-1-trityl-1H-pyrazolo[3,4-c]pyridine-5-carbonitrile obtained by Production example 432, the trityl group was deprotected in accordance with Example 16, followed by treatment in accordance with the method of Example 7, to thereby afford 55 mg of the title compound as pale yellow crystals.

$^1$H-NMR (400 MHz, DMSO-$D_6$) δ7.11 (1H, td, J=8.0, 2.0 Hz), 7.42 (1H, dd, J=14.4, 8.0 Hz), 7.57 (1H, d, J=8.0 Hz), 7.58 (1H, d, 16.4 Hz), 7.69 (1H, d, J=10.4 Hz), 7.79 (1H, d, J=14.4 Hz), 8.89 (1H, d, J=1.2 Hz), 9.07 (1H, s).

Production Example 434

2-Benzyl-5-(naphthalen-2-yl)-4-nitroso-2H-pyrazol-3-ylamine 600 mg of 2-benzyl-5-(2-naphthyl)-2H-pyrazol-3-ylamine obtained as an intermediate of Production example 404 was dissolved in a mixed solvent of 15 mL ethanol/0.5 mL concentrated hydrochloric acid, and 340 μl of isoamyl sulfite was added dropwise under ice cooling. The reaction solution was partitioned between saturated aqueous sodium hydrogen carbonate and ethyl acetate, and the organic layer was extracted and washed with water. The organic layer was dried over magnesium sulfate, the solvent was evaporated, and the residue was purified by silica gel column chromatography (ethyl acetate:hexane=3:7), to afford 440 mg of the title compound as red-brown needle crystals.

$^1$H-NMR (400 MHz, DMSO-$d_6$) δ5.24 (2H, s), 7.26-7.31 (3H, m), 7.33-7.38 (2H, m), 7.51-7.58 (2H, m), 7.92-7.96 (1H, m), 7.97-8.01 (1H, m), 7.99 (1H, d, J=8.8 Hz), 8.26 (1H, dd, J=1.6, 8.8 Hz), 8.57 (2H, bs), 8.88 (1H, s).

Production Example 435

2-Benzyl-5-(naphthalen-2-yl)-2H-pyrazole-3,4-diamine 200 mg of 2-benzyl-5-(naphthalen-2-yl)-4-nitroso-2H-pyrazol-3-ylamine obtained by Production example 434 was dissolved in a mixed solvent of methanol/tetrahydrofuran, added with 100 mg of palladium-carbon, and stirred for 2 hours under hydrogen atmosphere at normal temperature and normal pressure. The reaction solution was filtered through Celite, and the solvent was evaporated, to afford 190 mg of the title compound as yellow-brown needle crystals.

$^1$H-NMR (400 MHz, DMSO-$d_6$) δ3.45 (2H, bs), 4.77 (2H, bs), 5.16 (2H, s), 7.19 (2H, d, J=7.1 Hz), 7.22 (1H, t, J=7.1 Hz), 7.30 (2H, t, J=7.1 Hz), 7.41 (1H, bt, J=7.9 Hz), 7.45 (1H, bt, J=7.9 Hz), 7.82 (1H, d, J=8.8 Hz), 7.83 (1H, d, J=7.9 Hz), 7.86 (1H, d, J=7.9 Hz), 8.05 (1H, dd, J=1.6, 8.8 Hz), 8.38 (1H, dd, J=1.6 Hz).

Production Example 436

1-Benzyl-3-(naphthalen-2-yl)-1H-pyrazolo[3,4-b]pyrazine 190 mg of 2-benzyl-5-(naphthalen-2-yl)-2H-pyrazole-3,4-diamine was dissolved in 10 mL of methanol, added with 100 μl of 40% glyoxal aqueous solution, and stirred at room temperature for 5 hours. The reaction solution was partitioned between water and ethyl acetate, and the organic layer was extracted and washed with water. The organic layer was dried over magnesium sulfate, the solvent was evaporated, and the residue was purified by silica gel column chromatography (ethyl acetate:hexane=1:5), to afford 180 mg of the title compound as a pale yellow powder.

$^1$H-NMR (400 MHz, $CDCl_3$) δ5.80 (2H, s), 7.26-7.36 (3H, m), 7.42-7.47 (2H, m), 7.48-7.55 (2H, m), 7.85-7.90 (1H, m), 8.02 (1H, d, J=8.4 Hz), 7.99-8.04 (1H, m), 8.53 (1H, d, J=2.1 Hz), 8.55 (1H, dd, J=1.7, 8.4 Hz), 8.70 (1H, d, J=2.1 Hz), 9.08 (1H, s).

Example 437

3-Naphthalen-2-yl-1H-pyrazolo[3,4-b]pyrazine

A mixture of 50 mg of 1-benzyl-3-(naphthalen-2-yl)-1H-pyrazolo[3,4-b]pyrazine obtained by Production example 436 and 1.0 g of pyridine hydrochloride was heated at 200° C. for 24 hours. The reaction solution was allowed to cool to room temperature, partitioned between water and ethylacetate, extracted with ethyl acetate, and the organic layer was washed with water and dried over magnesium sulfate. The solvent was evaporated, and the residue was purified by silica gel column chromatography (ethyl acetate:hexane=3:7), to afford 21 mg of the title compound as a pale yellow powder.

$^1$H-NMR (400 MHz, DMSO-$d_6$) δ7.52-7.59 (2H, m), 7.93-7.98 (1H, m), 8.02-8.07 (1H, m), 8.06 (1H, d, J=9.0 Hz), 8.50 (1H, dd, J=1.4, 9.0 Hz), 8.67 (1H, d, J=2.0 Hz), 8.78 (1H, d, J=2.0 Hz), 9.06 (1H, s), 14.27 (1H, bs).

Production Example 438

N-[2-Benzyl-5-(naphthalen-2-yl)-4-nitroso-2H-pyrazole-3-ylamino]-maronamic acid ethyl ester 200 mg of 2-benzyl-5-(naphthalen-2-yl)-4-nitroso-2H-pyrazol-3-ylamine obtained by Production example 434 was dissolved in 10 mL of tetrahydrofuran, added with 300 μl of triethylamine and 270 μl of ethyl chlorocarbonylethyl acetate, and stirred at room temperature all day and night. The reaction solution was partitioned between water and ethyl acetate, and the organic layer was extracted and washed with water. The organic layer was dried over magnesium sulfate, the solvent was evaporated, and the residue was purified by silica gel column chromatography (ethyl acetate:hexane=3:7), to afford 2100 mg of the title compound as green needle crystals.

$^1$H-NMR (400 MHz, DMSO-$d_6$) δ1.19 (3H, t, J=7.3 Hz), 3.61 (2H, s), 4.14 (2H, q, J=7.3 Hz), 5.32 (2H, s), 7.27-7.38 (5H, m), 7.53-7.61 (2H, m), 7.95-8.00 (1H, m), 8.02-8.06 (1H, m), 8.03 (1H, d, J=8.7 Hz), 8.17 (1H, dd, J=1.4, 8.7 Hz), 8.72 (1H, bs), 11.02 (1H, bs).

Production Example 439

1-Benzyl-3-(naphthalen-2-yl)-1H-pyrazolo[3,4-b]pyrazine-5-carboxylic acid 50 mg of N-[2-benzyl-5-(naphthalen-2-yl)-4-nitroso-2H-pyrazol-3-ylamino]-maronamic acid ethyl ester obtained by Production example 438 was dissolved in 5 mL of tetrahydrofuran, added with 30 mg of a sodium methoxide (28%) solution in methanol, and stirred at 50° C. for 10 minutes. The reaction solution was partitioned between diluted hydrochloric acid and ethyl acetate, and the organic layer was extracted and washed with water. The organic layer was dried over magnesium sulfate, the solvent was evaporated, and the residue was purified by silica gel column chromatography (ethyl acetate:hexane=1:1), to afford 22 mg of the title compound as a pale yellow powder.

$^1$H-NMR (400 MHz, DMSO-$d_6$) δ5.38 (2H, s), 7.24-7.31 (3H, m), 7.31-7.36 (2H, m), 7.50-7.56 (2H, m), 7.90-7.95 (1H, m), 7.99-8.04 (1H, m), 8.02 (1H, d, J=8.8 Hz), 8.21 (1H, bs), 8.39 (1H, dd, J=1.4, 8.8 Hz), 8.91 (1H, d, J=1.4 Hz).

Production Example 440

1-Benzyl-3-(naphthalen-2-yl)-1H-pyrazolo[3,4-b]pyrazine-5-carboxylic acid methyl ester 20 mg of 1-benzyl-3-(naphthalen-2-yl)-1H-pyrazolo[3,4-b]pyrazine-5-carboxylic acid was dissolved in 5 mL of N,N-dimethylformamide, added with 10 mg of potassium carbonate and 20 μl methyl iodide, and stirred at room temperature for 3 hours. The reaction solution was partitioned between water and ethyl acetate, and the organic layer was extracted and washed with water. The organic layer was dried over magnesium sulfate, the solvent was evaporated, and the residue was purified by silica gel column chromatography (ethyl acetate:hexane=1:10), to afford 20 mg the title compound as a colorless powder.

$^1$H-NMR (400 MHz, $CDCl_3$) δ4.07 (3H, s), 5.65 (2H, s), 7.25-7.36 (3H, m), 7.40-7.44 (2H, m), 7.45-7.52 (2H, m), 7.82-7.87 (1H, m), 7.93 (1H, d, J=8.5 Hz), 7.96-8.01 (1H, m), 8.27 (1H, s). 8.48 (1H, dd, J=1.5, 8.5 Hz), 8.97 (1H, s)

Example 441

3-Naphthalen-2-yl-1H-pyrazolo[3,4-b]pyrazine-5-carboxylic acid

By treating 150 mg of 1-benzyl-3-(naphthalen-2-yl)-1H-pyrazolo[3,4-b]pyrazine-5-carboxylic acid methyl ester obtained by Production example 440 in the similar method as described in Example 437, 54 mg of the title compound was obtained as a pale brown powder.

$^1$H-NMR (400 MHz, $CD_3OD$) δ7.52-7.58 (2H, m), 7.88-7.93 (1H, m), 7.93-7.99 (1H, m), 7.98 (1H, s), 8.00 (1H, d, J=9.1 Hz), 8.24 (1H, d, J=9.1 Hz), 8.72 (1H, bs).

Example 442

3-(3-Fluorophenyl)-1H-pyrazolo[4,3-b]pyridine-5-carboxylic acid obtained by Example 7 and various kinds of amine were condensed in the similar method as described in Example 44, to afford the compounds of Examples 443-446.

Example 443

3-(3-Fluorophenyl)-1H-pyrazolo[4,3-b]pyridine-5-carboxylic acid carbamoylmethyl-amide MS (ESI)m/z 314 $MH^+$ Example 444

3-(3-Fluorophenyl)-1H-pyrazolo[4,3-b]pyridine-5-carboxylic acid(1-carbamoyl-ethyl)-amide $^1$H-NMR (400 MHz, DMSO-$d_6$) δ1.44 (3H, d, J=7.5 Hz), 4.99 (1H, dq, J=7.5 Hz), 7.28 (1H, dt, J=2.4, 7.9 Hz), 7.27 (1H, bs), 7.59 (1H, dt, J=6.0, 7.9 Hz), 7.64 (1H, bs), 8.13 (1H, bd, J=9.0 Hz), 8.25 (1H, bd, J=9.0 Hz), 8.29 (1H, dd, J=2.4, 10.5 Hz), 8.39 (1H, bd, J=7.9 Hz), 8.83 (1H, d, J=7.5 Hz).

MS (ESI)m/z 328 $MH^+$

Example 445

3-(3-Fluorophenyl)-1H-pyrazolo[4,3-b]pyridine-5-carboxylic acid(1-carbamoyl-2-hydroxy-ethyl)-amide $^1$H-NMR (400 MHz, $CD_3OD$) δ3.95 (1H, dd, J=4.7, 11.2 Hz), 4.05 (1H, dd, J=4.4, 11.2 Hz), 4.66 (1H, bt, J=4.7 Hz), 7.14 (1H, dt, J=2.6, 8.6 Hz), 7.56 (1H, dt, J=6.0, 8.0 Hz), 8.16 (1H, d, J=8.8 Hz), 8.22 (1H, d, J=8.8 Hz), 8.23 (1H, bd, J=10.5 Hz), 8.47 (1H, bd, J=8.6 Hz).

MS (ESI)m/z 344 $MH^+$

Example 446

3-(3-Fluorophenyl)-1H-pyrazolo[4,3-b]pyridine-5-carboxylic acid(1-carbamoyl-2-phenyl-ethyl)-amide $^1$H-NMR (400 MHz, DMSO-$d_6$) δ 3.15 (1H, dd, J=8.4, 13.9 Hz), 3.22 (1H, dd, J=5.5, 13.9 Hz), 4.66 (1H, dt, J=5.5, 8.4 Hz), 7.16 (1H, bt, J=7.4 Hz), 7.23 (2H, bt, J=7.4 Hz), 7.23 (1H, bs), 7.30 (1H, dt, J=2.8, 7.9 Hz), 7.38 (2H, d, J=7.4 Hz), 7.60 (1H, dt, J=6.2, 7.9 Hz), 7.66 (1H, bs), 8.04 (1H, bd, J=9.0 Hz), 8.20 (1H, bd, J=9.0 Hz), 8.29 (1H, bd, J=10.5 Hz), 8.36 (1H, bd, J=7.9 Hz), 8.63 (1H, d, J=8.4 Hz).

MS (ESI)m/z 404 $MH^+$

Example 447

3-(Naphthalen-2-yl)-1H-pyrazolo[3,4-c]pyridine-5-carboxylic acid obtained by Example 403 and various kinds of amine were condensed in the similar method as described in Example 44, to afford the compounds of Examples 448-451.

Example 448

3-(Naphthalen-2-yl)-1H-pyrazolo[3,4-c]pyridine-5-carboxylic acid cyclopropylamide MS (ESI)m/z 329 $MH^+$ Example 449

3-(Naphthalen-2-yl)-1H-pyrazolo[3,4-c]pyridine-5-carboxylic acid(furan-2-ylmethyl)amide MS (ESI)m/z 369 $MH^+$ Example 450

3-(Naphthalen-2-yl)-1H-pyrazolo[3,4-c]pyridine-5-carboxylic acid[(1S)-1-hydroxymethyl-2-methylpropyl]amide MS (ESI)m/z 375 $MH^+$ Example 451

3-(Naphthalen-2-yl)-1H-pyrazolo[3,4-c]pyridine-5-carboxylic acid[(1S)-2-hydroxy-1-phenylethyl]amide MS (ESI)m/z 409 $MH^+$ Example 452

3-[(E)-2-(3-Fluorophenyl)-vinyl]-1H-pyrazolo[4,3-b]pyridine-5-carboxylic acid obtained by Example 416 and various kinds of amine were condensed in the similar method as described in Example 44, to afford the compounds of Examples 453-463.

Example 453

3-[(E)-2-(3-Fluorophenyl)-vinyl]-1H-pyrazolo[4,3-b]-pyridine-5-carboxylic acid cyclopropylamide MS (ESI)m/z 323 $MH^+$ Example 454

3-[(E)-2-(3-Fluorophenyl)-vinyl]]-1H-pyrazolo[4,3-b]-pyridine-5-carboxylic acid(furan-2-ylmethyl)-amide MS (ESI)m/z 363 $MH^+$ Example 455

3-[(E)-2-(3-Fluorophenyl)-vinyl]-1H-pyrazolo[4,3-b]-pyridine-5-carboxylic acid(tetrahydrofuran-2-ylmethyl)-amide MS (ESI)m/z 367 $MH^+$ Example 456

3-[(E)-2-(3-Fluorophenyl)-vinyl]-1H-pyrazolo[4,3-b]-pyridine-5-carboxylic acid(2-acetylamino-ethyl)-amide MS (ESI)m/z 368 $MH^+$ Example 457

3-[(E)-2-(3-Fluorophenyl)-vinyl]-1H-pyrazolo[4,3-b]-pyridine-5-carboxylic acid(1-hydroxymethyl-2-methyl-propyl)-amide MS (ESI)m/z 369 $MH^+$ Example 458

3-[(E)-2-(3-Fluorophenyl)-vinyl]-1H-pyrazolo[4,3-b]-pyridine-5-carboxylic acid(2-hydroxy-1-phenyl-ethyl)-amide MS (ESI)m/z 403 $MH^+$ Example 459

3-[(E)-2-(3-Fluorophenyl)-vinyl]-1H-pyrazolo[4,3-b]-pyridine-5-carboxylic acid(pyridin-3-ylmethyl)-amide MS (ESI)m/z 374 $MH^+$ Example 460

3-[(E)-2-(3-Fluorophenyl)-vinyl]-1H-pyrazolo[4,3-b]-pyridine-5-carboxylic acid(thiophen-2-ylmethyl)-amide MS (ESI)m/z 379 $MH^+$ Example 461

3-[(E)-2-(3-Fluorophenyl)-vinyl]-1H-pyrazolo[4,3-b]-pyridine-5-carboxylic acid(1-carbamoyl-2-phenyl-ethyl)-amide MS (ESI)m/z 430 $MH^+$ Example 462

3-[(E)-2-(3-Fluorophenyl)-vinyl]-1H-pyrazolo[4,3-b]-pyridine-5-carboxylic acid (1-carbamoyl-2-hydroxy-ethyl)-amide MS (ESI)m/z 370 $MH^+$ Example 463

3-[(E)-2-(3-Fluorophenyl)-vinyl]-1H-pyrazolo[4,3-b]-pyridine-5-carboxylic acid (1-carbamoyl-ethyl)-amide MS (ESI)m/z 354 $MH^+$ Example 464

3-[(E)-2-(3-Fluorophenyl)-vinyl]-1H-pyrazolo[3,4-c]-pyridine-5-carboxylic acid obtained by Example 433 and various kinds of amine were condensed in the similar method as described in Example 44, to afford the compounds of Examples 465-469.

Example 465

3-[(E)-2-(3-Fluorophenyl)-vinyl]-1H-pyrazolo[3,4-c]-pyridine-5-carboxylic acid cyclopropylamide MS (ESI)m/z 323 $MH^+$ Example 466

3-[(E)-2-(3-Fluorophenyl)-vinyl]]-1H-pyrazolo[3,4-c]-pyridine-5-carboxylic acid (furan-2-ylmethyl) amide MS (ESI)m/z 363 $MH^+$ Example 467

3-[(E)-2-(3-Fluorophenyl)-vinyl]-1H-pyrazolo[3,4-c]-pyridine-5-carboxylic acid [(1S)-1-hydroxymethyl-2-methylpropyl]]amide MS (ESI)m/z 369 $MH^+$ Example 468

3-[(E)-2-(3-Fluorophenyl)-vinyl]-1H-pyrazolo[3,4-c]-pyridine-5-carboxylic acid [(1S)-2-hydroxy-1-phenylethyl]amide MS (ESI)m/z 403 $MH^+$ Example 469

3-[(E)-2-(3-Fluorophenyl)-vinyl]-1H-pyrazolo[3,4-c]-pyridine-5-carboxylic acid [(1S)-1-carbamoyl-ethyl]amide MS (ESI)m/z 354 $MH^+$ Example 470

3-(Naphthalen-2-yl)-1H-pyrazolo[3,4-b]pyridine-5-carboxylic acid obtained by Example 405 and various kinds of amine were condensed in the similar method as described in Example 44, to afford the compounds of Examples 471-477.

Example 471

3-(Naphthalen-2-yl)-1H-pyrazolo[3,4-b]pyridine-5-carboxylic acid cyclopropylamide MS (ESI)m/z 329 $MH^+$ Example 472

3-(Naphthalen-2-yl)-1H-pyrazolo[3,4-b]pyridine-5-carboxylic acid (furan-2-ylmethyl)-amide MS (ESI)m/z 369 $MH^+$ Example 473

3-(Naphthalen-2-yl)-1H-pyrazolo[3,4-b]pyridine-5-carboxylic acid (tetrahydrofuran-2-ylmethyl)-amide MS (ESI)m/z 373 $MH^+$ Example 474

3-(Naphthalen-2-yl)-1H-pyrazolo[3,4-b]pyridine-5-carboxylic acid (2-acetylamino-ethyl)-amide MS (ESI)m/z 374 $MH^+$ Example 475

3-(Naphthalen-2-yl)-1H-pyrazolo[3,4-b]pyridine-5-carboxylic acid (pyridin-3-ylmethyl)-amide MS (ESI)m/z 380 $MH^+$ Example 476

3-(Naphthalen-2-yl)-1H-pyrazolo[3,4-b]pyridine-5-carboxylic acid (1-hydroxymethyl-2-methyl-propyl)-amide MS (ESI)m/z 375 $MH^+$ Example 477

3-(Naphthalen-2-yl)-1H-pyrazolo[3,4-b]pyridine-5-carboxylic acid (thiophen-2-ylmethyl)-amide MS (ESI)m/z 385 $MH^+$ Example 478

Furan-2-carboxylic acid [3-(naphthalen-2-yl)-1H-pyrazolo[4,3-b]pyridin-5-yl]amide 20 mg of 3-(naphthalen-2-yl)-1-trityl-1H-pyrazolo[4,3-b]pyridin-5-ylamine obtained by Production example 422 and furan-2-carboxylic acid chloride were allowed to react in the similar method as described in Production example 423, followed by deprotection in the similar method as described in Example 16, to afford 10.3 mg of the title compound as pale brown crystals.

$^1$H-NMR (400 MHz, $CD_3OD$) δ 6.69 (1H, dd, J=1.9, 3.5 Hz), 7.39 (1H, dd, J=0.8, 3.5 Hz), 7.46-7.54 (2H, m), 7.81 (1H, dd, J=0.8, 1.9 Hz), 7.86-7.90 (1H, m), 7.95 (1H, d, J=8.5 Hz), 8.02-8.05 (1H, m), 8.05 (1H, d, J=9.5 Hz), 8.34 (1H, d, J=9.5 Hz), 8.47 (1H, dd, J=1.5, 8.5 Hz), 9.10 (1H, s).

Example 479

N-[3-(Naphthalen-2-yl)-1H-pyrazolo[4,3-b]pyridin-5-yl]acetamide

From 20 mg of 3-(naphthalen-2-yl)-1-trityl-1H-pyrazolo[4,3-b]pyridin-5-ylamine and acetyl chloride, 9.4 mg of the title compound was obtained as colorless crystals in the similar method as described in Example 478.

$^1$H-NMR (400 MHz, $CD_3OD$) δ2.24 (3H, bs), 7.45-7.53 (2H, m), 7.85-7.89 (1H, m), 7.93 (1H, d, J=8.7 Hz), 7.96-8.00 (1H, m), 7.98 (1H, d, J=9.1 Hz), 8.27 (1H, bd, J=9.1 Hz), 8.48 (1H, dd, J=1.6, 8.7 Hz), 9.10 (1H, s).

Example 480

N-[3-(Naphthalen-2-yl)-1H-pyrazolo[4,3-b]pyridin-5-yl]-2-(thiophen-2-yl)acetamide From 20 mg of 3-(naphthalen-2-yl)-1-trityl-1H-pyrazolo[4,3-b]pyridin-5-ylamine and 2-thiopheneacetic acid chloride, 11.6 mg of the title compound was obtained as colorless crystals in the similar method as described in Example 478.

$^1$H-NMR (400 MHz, $CD_3OD$) δ4.06(2H, s), 6.99 (1H, dd, J=3.6, 5.1 Hz), 7.07 (1H, dd, J=1.2, 3.6 Hz), 7.31 (1H, dd, J=1.2, 5.1 Hz), 7.46-7.54 (2H, m), 7.86-7.90 (1H, m), 7.94 (1H, d, J=8.5 Hz), 7.97-8.03 (1H, m), 7.99 (1H, d, J=9.1 Hz), 8.28 (1H, d, J=9.1 Hz), 8.49 (1H, dd, J=1.7, 8.5 Hz), 9.11 (1H, s)

Example 481

3-(Naphthalen-2-yl)-1H-pyrazolo[4,3-b]pyridin-5-ylamine 15 mg of 3-(naphthalen-2-yl)-1-trityl-1H-pyrazolo[4,3-b]pyridin-5-ylamine obtained by Production example 422 was deprotected in the similar method as described in Example 16, to afford 7.1 mg of the title compound as pale brown crystals.

$^1$H-NMR (400 MHz, $CD_3OD$) δ6.79 (1H, d, J=9.1 Hz), 7.44-7.52 (2H, m), 7.74 (1H, d, J=9.1 Hz), 7.84-7.88 (1H, m), 7.93 (1H, d, J=8.7 Hz), 7.93-7.97 (1H, m), 8.32 (1H, d, J=8.7 Hz), 8.86 (1H, bs).

Production Example 482

3-[(E)-2-(3-Fluorophenyl)-vinyl]-1-trityl-1H-pyrazolo[4,3-b]pyridine 1.95 g of 3-iodo-1-trityl-1H-pyrazolo[4,3-b]pyridine obtained by Production example 418 and 1.0 g of 2-[(E)-2-(3-fluorophenyl)-vinyl]-4,4,5,5-tetramethyl[1, 3,2]dioxaborolane obtained by Production example 137 were allowed to react in the manner as described in Example 194, to afford 730 mg of the title compound as a colorless powder.

$^1$H-NMR (400 MHz, $CDCl_3$) δ 6.62 (1H, dd, J=1.0, 9.0 Hz), 6.92 (1H, dd, J=4.5, 9.0 Hz), 7.04 (2H, t, J=8.7 Hz), 7.21-7.32 (15H, m), 7.38 (1H, d, J=16.7 Hz), 7.57 (2H, dd, J=5.2, 8.7 Hz), 8.15 (1H, d, J=16.7 Hz), 8.53 (1H, dd, J=1.0, 4.5 Hz)

Production Example 483

3-[(E)-2-(3-Fluorophenyl)-vinyl]-1-trityl-1H-pyrazolo[4,3-b]pyridine-4-oxide 470 mg of 3-[(E)-2-(3-fluorophenyl)-vinyl]-1-trityl-1H-pyrazolo[4,3-b]pyridine obtained by Production example 482 and 216 mg of m-chloroperbenzoic acid were allowed to react in the manner as described in Production example 4, to afford 210 mg of the title compound as a colorless oil.

$^1$H-NMR (400 MHz, $CDCl_3$) δ 6.21 (1H, d, J=8.7 Hz), 6.76 (1H, dd, J=6.0, 8.7 Hz), 7.02 (2H, t, J=8.8 Hz), 7.16-7.23 (6H, m), 7.28-7.35 (9H, m), 7.46 (1H, d, J=16.5 Hz), 7.53 (2H, dd, J=5.6, 8.8 Hz), 8.03 (1H, d, J=16.5 Hz), 8.06 (1H, dd, J=6.0 Hz).

Example 484

5-Chloro-3-[(E)-2-(3-fluorophenyl)-vinyl]-1H-pyrazolo[4,3-b]pyridine 210 mg of 3-[(E)-2-(3-fluorophenyl)-vinyl]-1-trityl-1H-pyrazolo[4,3-b]pyridine-4-oxide obtained by Production example 483 was dissolved in 5 mL of toluene, added with 240 μl of phosphorus oxychloride at room temperature and stirred for 4 days. The reaction solution was added with aqueous sodium hydrogen carbonate, extracted with ethyl acetate and washed with water, and dried over magnesium sulfate. The solvent was evaporated, and the residue was purified by silica gel column chromatography (n-hexane: ethyl acetate=3:1), to afford 75 mg of the title compound as a colorless powder.

$^1$H-NMR (400 MHz, $CDCl_3$) δ 7.08 (2H, t, J=8.7 Hz), 7.36 (1H, d, J=8.9 Hz), 7.37 (1H, d, J=16.4 Hz), 7.62 (2H, dd, J=6.0, 8.7 Hz), 7.80 (1H, d, J=8.9 Hz), 8.10 (1H, d, J=16.4 Hz).

Production Example 485

3-[(E)-2-(3-Fluorophenyl)-vinyl]-1-trityl-1H-pyrazolo[4,3-b]pyridin-5-ylamine 60 mg of 5-chloro-3-[(2E)-2-(3-fluorophenyl)vinyl]-1-trityl-1H-pyrazolo[4,3-b]pyridine which is obtained by tritylating 5-chloro-3-[(E)-2-(3-fluorophenyl)-vinyl]-1H-pyrazolo

[4,3-b]pyridine obtained by Example 484 in accordance with Production example 22 was treated with benzophenoneimine in the similar method as described in Production example 422, to afford 40 mg of the title compound as a pale yellow oil.

$^1$H-NMR (400 MHz, $CDCl_3$) δ 4.53 (2H, bs), 6.21 (1H, d, J=9.0 Hz), 6.40 (1H, d, J=9.0 Hz), 7.02 (2H, t, J=8.6 Hz), 7.19-7.25 (6H, m), 7.25-7.32 (10H, m), 7.53 (2H, dd, J=5.0, 8.6 Hz), 7.98 (1H, d, J=16.5 Hz).

Production Example 486

3-(3-Fluorophenyl)-1-trityl-1H-pyrazolo[4,3-b]pyridin-5-ylamine 1.1 g of 3-(3-fluorophenyl)-5-chloro-1-trityl-1H-pyrazolo[4,3-b]pyridine obtained by Production example 37 was treated with benzophenoneimine in the similar method as described in Production example 422, to afford 690 mg of the title compound as pale yellow crystals.

$^1$H-NMR (400 MHz, $CDCl_3$) δ 4.40-4.65 (2H, bs), 6.22 (1H, d, J=9.0 Hz), 6.40 (1H, d, J=9.0 Hz), 7.18-7.25 (6H, m), 7.26-7.32 (9H, m), 7.35 (1H, dt, J=6.2, 8.2 Hz), 8.15 (1H, bd, J=11.2 Hz), 8.18 (1H, d, J=8.2 Hz).

Example 487

3-(3-Fluorophenyl)-1H-pyrazolo[4,3-b]pyridin-5-ylamine 3-(3-Fluorophenyl)-1-trityl-1H-pyrazolo[4,3-b]pyridin-5-ylamine was treated with trifluoroacetic acid in the similar method as described in Example 16 and so on, followed by purification by LC-MS, to give the title compound.

MS (ESI) m/z 229 $MH^+$

Example 488

Each 25 mg of 3-(3-fluorophenyl)-1-trityl-1H-pyrazolo[4,3-b]pyridin-5-ylamine obtained by Production example 486 was put into several test tubes, added with 0.5 mL of tetrahydrofuran, further added with 0.07 mmol of various kinds of acid chloride and 0.07 mmol of triethylamine, and left at room temperature all day and night. The reaction solution was added with 2 mL of water, extracted with 4 mL of ethyl acetate, and the solvent was distilled of by blowing nitrogen thereto. The resultant residue was added with 0.5 mL of 70% trifluoroacetic acid solution in dichloromethane, sonicated at room temperature for 15 minutes, and the solvent was distilled off by blowing nitrogen thereto. The residue was dissolved in 0.25 mL of N,N-dimethylformamide, and purified by LC-MS, to afford the compounds of Examples 489-492.

Example 489

Cyclopropane carboxylic acid [3-(3-fluorophenyl)-1H-pyrazolo[4,3-b]pyridin-5-yl]-amide MS (ESI) m/z 297 $MH^+$ Example 490

Furan-2-carboxylic acid [3-(3-fluorophenyl)-1H-pyrazolo[4,3-b]pyridin-5-yl]-amide MS (ESI) m/z 323 $MH^+$ Example 491

N-[3-(3-Fluorophenyl)-1H-pyrazolo[4,3-b]pyridin-5-yl]-acetamide

MS (ESI) m/z 271 $MH^+$

Example 492

N-[3-(3-Fluorophenyl)-1H-pyrazolo[4,3-b]pyridine-5-yl]-2-(thiophen-2-yl)-acetamide MS (ESI) m/z 353 $MH^+$ Example 493

3-[(E)-2-(3-Fluorophenyl)vinyl]-1-trityl-1H-pyrazolo[4,3-b]pyridin-5-ylamine obtained by Production example 485 was reacted with various kinds of acid chloride in the similar method as described in Example 488, followed by deprotection and LC-MS purification, to afford the compounds of Examples 494-497.

Example 494

Cyclopropane carboxylic acid {3-[(E)-2-(4-fluorophenyl)-vinyl]-1H-pyrazolo[4,3-b]pyridin-5-yl}-amide MS (ESI) m/z 323 $MH^+$ Example 495

Furan-2-carboxylic acid {3-[(E)-2-(4-fluorophenyl)-vinyl]-1H-pyrazolo[4,3-b]pyridin-5-yl}-amide MS (ESI) m/z 349 $MH^+$ Example 496

N-{3-[(E)-2-(4-Fluorophenyl)-vinyl]-1H-pyrazolo[4,3-b]pyridin-5-yl}-acetamide

MS (ESI) m/z 297 $MH^+$

Example 497

N-{3-[(E)-2-(4-Fluorophenyl)-vinyl]-1H-pyrazolo[4,3-b]pyridin-5-yl}-2-(thiophen-2-yl)-acetamide MS (ESI) m/z 379 $MH^+$ Production Example 498

3-(3-Fluorophenyl)-1-trityl-1H-pyrazolo[4,3-b]pyridine-5-carbonitrile 13.3 g of 3-(3-fluorophenyl)-1-trityl-1H-pyrazolo[4,3-b]pyridine-4-oxide obtained by Production example 36 was cyanized in accordance with Production example 5, to afford 11.9 g of the title compound as a colorless powder.

$^1$H-NMR (400 MHz, DMSO-$d_6$) δ6.90 (1H, d, J=9.0 Hz), 7.20-7.25 (6H, m), 7.31 (1H, dt, J=2.8, 8.6 Hz), 7.34-7.43 (9H, m), 7.61 (1H, dt, J=6.0, 8.0 Hz), 7.77 (1H, d, J=9.0 Hz), 8.03 (1H, ddd, J=1.6, 2.8, 10.4 Hz), 8.16 (1H, d, J=8.0 Hz).

Production Example 499

Ethyl 3-(3-fluorophenyl)-1-trityl-1H-pyrazolo[4,3-b]pyridine-5-carboxyimidate

Under nitrogen atmosphere, 100 mg of metal sodium was added to 10 mL of dry methanol, and upon complete consumption of the metal, 480 mg of 3-(3-fluorophenyl)-1-trityl-1H-pyrazolo[4,3-b]pyridine-5-carbonitrile obtained by Production example 498 and 5 mL of dry tetrahydrofuran were added and stirred at room temperature for 2 days. The product was collected by filtration, and washed with diethyl ether, to afford 440 mg of the title compound as a colorless powder.

$^1$H-NMR (400 MHz, DMSO-$d_6$) δ 3.89 (3H, s), 6.88 (1H, d, J=8.8 Hz), 7.18-7.23 (6H, m), 7.26 (1H, dt, J=3.0, 8.0 Hz), 7.32-7.40 (9H, m), 7.58 (1H, dt, J=5.5, 8.0 Hz), 7.63 (1H, d, J=8.8 Hz), 8.08 (1H, bd, J=10.5 Hz), 8.29 (1H, bd, J=8.0 Hz), 9.27 (1H, s).

Production Example 500

3-(3-Fluorophenyl)-5-(5-methyl-1H-[1,2,4]triazol-3-yl)-1-trityl-1H-pyrazolo[4,3-b]pyridine 100 mg of ethyl[3-(3-fluorophenyl)-1-trityl-1H-pyrazolo[4,3-b]pyridine-5-carboxyimidate obtained by Production example 499 and 44 mg of acetohydrazide were dissolved in 3 mL of pyridine, and heated at 130° C. for 2.5 days. The reaction solution was added with silica gel, the solvent was evaporated, and the resultant residue was purified by silica gel column chromatography (ethyl acetate:hexane=4:6), to afford 60 mg of the title compound as a colorless powder.

$^1$H-NMR (400 MHz, DMSO-$d_6$) δ 2.50 (3H, s), 6.72 (1H, d, J=8.7 Hz), 7.02 (1H, dt, J=2.9, 8.1 Hz), 7.18-7.25 (6H, m), 7.27-7.32 (9H, m), 7.37 (1H, dt, J=5.8, 8.1 Hz), 7.80 (1H, d, J=8.7 Hz), 8.13 (1H, bd, J=10.4 Hz), 8.23 (1H, bd, J=8.1 Hz).

Example 501

3-(3-Fluorophenyl)-5-(5-methyl-2H-[1,2,4]triazol-3-yl)-1H-pyrazolo[4,3-b]pyridine 30 mg of 3-(3-fluorophenyl)-5-(5-methyl-1H-[1,2,4]triazol-3-yl)-1-trityl-1H-pyrazolo[4,3-b]pyridine was deprotected in the similar method as described in Production example 16, and the resultant residue was purified by LC-MS, to afford 16 mg of the title compound as a colorless powder.

$^1$H-NMR (400 MHz, DMSO-$d_6$) δ 2.46 (3H, s), 7.24 (1H, bt, J=8.4 Hz), 7.57 (1H, bdt, J=6.7, 8.4 Hz), 8.13 (1H, d, J=8.7 Hz), 8.19 (1H, d, J=8.7 Hz), 8.40 (1H, bd, J=10.4 Hz), 8.51 (1H, bd, J=8.4 Hz), 13.70 (1H, bs), 13.80-14.00 (1H, bs).

MS (ESI) m/z 295 $MH^+$

Production Example 502

{5-[3-(3-Fluorophenyl)-1-trityl-1H-pyrazolo[4,3-b]pyridin-5-yl]-2H-[1,2,4]triazol-3-ylmethyl}methyl carbamic acid Tert-Butyl Ester 100 mg of ethyl[3-(3-fluorophenyl)-1-trityl-1H-pyrazolo[4,3-b]pyridine-5-carboxyimidate obtained by Production example 499 and 80 mg of hydrazinocarbonylmethyl-methylcarbamic acid tert-butyl ester produced by Production example 367 were dissolved in a mixed solvent of 3 mL methanol-3 mL pyridine, and heated at 110° C. for 3 days. The reaction solution was added with silica gel, the solvent was evaporated, and the residue was purified by silica gel column chromatography (n-hexane:ethyl acetate=2:1), to afford 74 mg of the title compound as a colorless oil.

$^1$H-NMR (400 MHz, $CDCl_3$) δ 1.50 (9H, s), 2.97 (3H, s), 4.60 (2H, bs), 6.73 (1H, bd, J=8.8 Hz), 7.06 (1H, dt, J=7.6 Hz), 7.20-7.28 (6H, m), 7.28-7.35 (9H, m), 7.42 (1H, dt, J=5.8, 7.6 Hz), 7.84 (1H, bd, J=8.8 Hz), 8.17 (1H, d, J=10.8 Hz), 8.22-8.32 (1H, m).

Example 503

{5-[3-(3-Fluorophenyl)-1H-pyrazolo[4,3-b]pyridin-5-yl]-1H-[1,2,4]triazol-3-ylmethyl}-methylamine 30 mg of {5-[3-(3-fluorophenyl)-1-trityl-1H-pyrazolo[4,3-b]pyridin-5-yl]-2H-[1,2,4]triazol-3-ylmethyl}methylcarbamic acid tert-butyl ester was deprotected in the similar method as described in Production example 16, and the resultant residue was purified by LC-MS, to obtain 15 mg of the title compound as a colorless powder.

MS (ESI) m/z 324 $MH^+$

Production Example 504

(2-Chlorothiophen-3-yl)methanol

To a solution of 3.0 g thiophene-2-methanol in 26 mL of dimethylformamide was added 3.5 g of N-chlorosuccinimide at room temperature, and stirred at this temperature for a day. Adding 10 mL of 10% sodium thiosulfate, and the resultant solution was diluted with ethyl acetate. The organic layer was washed successively with saturated aqueous ammonium chloride and saturated brine, dried over anhydrous magnesium sulfate, and the solvent was evaporated, to afford 3.0 g of the title compound as a colorless oil.

$^1$H-NMR (400 MHz, $CDCl_3$) δ 4.64 (2H, d, J=6.0 Hz), 7.01 (1H, d, J=6.0 Hz), 7.09 (1H, d, J=6.0 Hz).

Production Example 505

(5-Bromo-2-chlorothiophen-3-yl)methanol

To a solution of 3.0 g of (2-chlorothiophen-3-yl)methanol in 60 mL of dimethylformamide was added 3.59 g of N-bromosuccinimide at room temperature, and stirred at this temperature for 2 hours. Adding 10 mL of 10% sodium thiosulfate, and the resultant solution was diluted with ethyl acetate. The organic layer was washed successively with saturated aqueous ammonium chloride and saturated brine, dried over anhydrous magnesium sulfate, and the solvent was evaporated, to afford 3.7 g of the title compound as a colorless oil.

$^1$H-NMR (400 MHz, $CDCl_3$) δ 4.58 (2H, d, J=6.0 Hz), 7.01 (1H, s).

Production Example 506

5-Chloro-4-hydroxymethylthiophene-2-carbonitrile

To a solution of 25.0 g (5-bromo-2-chlorothiophen-3-yl)methanol in 330 mL of dimethylformamide, 25.8 g of zinc cyanide (I) and 12.7 g tetrakis(triphenylphosphine)palladium (0) were added at room temperature, and stirred at 100° C. for 4 hours. Diluting with ethyl acetate, the organic layer was washed successively with saturated aqueous ammonium chloride and saturated brine, dried over anhydrous magnesium sulfate, and the solvent was evaporated. The crude product was purified and separated by silica gel column chromatography (ethyl acetate:n-hexane=1:10-1:5), to afford 16.0 g of the title compound as colorless crystals.

$^1$H-NMR (400 MHz, $CDCl_3$) δ 4.65 (2H, s), 7.57 (1H, s).

Production Example 507

5-Chloro-4-formylthiophene-2-carbonitrile

To a solution of 3.0 g of 5-chloro-4-hydroxymethylthiophene-2-carbonitrile in 34 mL of dichloromethane was added 8.06 g of Dess-Martin reagent at room temperature, and stirred at this temperature for a day. After diluting with dichloromethane, washing successively with aqueous sodium hydrogen carbonate and saturated brine, and drying over anhydrous magnesium sulfate, the solvent was evaporated, to afford 4.5 g of a crude product of the title compound as colorless crystals.

$^1$H-NMR (400 MHz, $CDCl_3$) δ 7.86 (1H, s), 10.00 (1H, s).

Production Example 508

Acetic acid (2-chloro-5-cyanothiophen-3-ylmethylene)hydrazide

To a suspension of 4.5 g of 5-chloro-4-formylthiophene-2-carbonitrile in ethanol was added 2.56 g of acetylhydrazide at room temperature, and heated at reflux for 2 hours. After cooling to room temperature, the crystals were collected by filtration, washed with ethanol, to afford 2.53 g of the title compound (diastereomic mixture of E form:Z form=5:2) as pale yellow crystals.

(E) compound: $^1$H-NMR (400 MHz, DMSO-$D_6$) δ 2.18 (3H, s), 7.97 (1H, s), 8.22 (1H, s), 11.39 (1H, bs).

(Z) compound: $^1$H-NMR (400 MHz, DMSO-$D_6$) δ 1.95 (3H, s), 8.09 (1H, s), 8.20 (1H, s), 11.55 (1H, bs).

Production Example 509

1-Acetyl-1H-thieno[2,3-c]pyrazole-5-carbonitrile

To a solution of 2.53 g of acetic acid (2-chloro-5-cyanothiophen-3-ylmethylene)hydrazide in 22 mL of diphenyl ether were added copper powder and potassium acetate at room temperature, and stirred at 200° C. for 6 hours. Following filtration through Celite, the filtrate was washed successively with saturated aqueous ammonium chloride and saturated brine, dried over anhydrous magnesium sulfate, and the solvent was evaporated. The crude product was purified and separated by silica gel column chromatography (ethyl acetate:n-hexane=1:10-1:5), to afford 215 mg of the title compound as colorless crystals.

$^1$H-NMR (400 MHz, DMSO-$D_6$) δ 2.72 (3H, s), 8.17 (1H, s), 8.40 (1H, s).

Production Example 510

1H-Thieno[2,3-c]pyrazole-5-carbonitrile

To a suspension of 215 mg of 1-acetyl-1H-thieno[2,3-c]pyrazole-5-carbonitrile in 8 mL of ethanol, 1 mL of 5N sodium hydroxide aqueous solution was added at room temperature, and stirred at this temperature for 10 minutes. Then the solution was neutralized with 5N hydrochloric acid, extracted with ethyl acetate, and the organic layer was washed with saturated brine, dried over anhydrous magnesium sulfate, and the solvent was evaporated, to afford 168 mg of the title compound as colorless crystals.

$^1$H-NMR (400 MHz, DMSO-$D_6$) δ 8.07 (1H, s), 8.34 (1H, s).

Production Example 511

3-Bromo-1H-thieno[2,3-c]pyrazole-5-carbonitrile

To a solution of 168 mg of 1H-thieno[2,3-c]pyrazole 5-carbonitrile in 5 mL of dimethylformamide was added 200 mg of N-bromosuccinimide at room temperature and stirred at this temperature for 2 hours. After adding 1 mL of 10% sodium thiosulfate aqueous solution, the solution was diluted with ethyl acetate. The organic layer was washed successively with saturated aqueous ammonium chloride and saturated brine, dried over anhydrous magnesium sulfate, and the solvent was evaporated. This afforded 3.7 g of the title compound as a colorless oil. The crude product was purified and separated by silica gel column chromatography (ethyl acetate:n-hexane=1:10), to afford 220 mg of the title compound as colorless crystals.

$^1$H-NMR (400 MHz, $CDCl_3$) δ 8.00 (1H, s)

Example 512

5-Iodo-3-(naphthalen-2-yl)-1H-thieno[2,3-c]pyrazole

To a solution of 70 mg of 3-naphthalene-2-yl-1H-thieno[2,3-c]pyrazole obtained by Example 78 in 3.0 mL of N,N-dimethylformamide was added 63 mg of N-iodosuccinimide at room temperature, and stirred at 40° C. for a day. Then the solution was added with 1.0 mL of 10% sodium thiosulfate aqueous solution, and extracted with ethyl acetate. The organic layer was washed successively with saturated aqueous ammonium chloride and saturated brine, dried over anhydrous magnesium sulfate, and the solvent was evaporated. The crude product was purified and separated by silica gel column chromatography (ethyl acetate:n-hexane=1:3), to afford 75 mg of the title compound as colorless crystals.

$^1$H-NMR (400 MHz, DMSO-$D_6$) δ7.49-7.57 (2H, m), 7.90-7.94 (1H, m), 7.98-8.07 (3H, m), 8.01 (1H, s), 8.43 (1H, s).

Production Example 513

5-Iodo-3-(naphthalen-2-yl)-1-trityl-1H-thieno[2,3-c]-pyrazole

To a solution of 75 mg of 5-iodo-3-(naphthalen-2-yl)-1H-thieno[2,3-c]pyrazole in 1 m L of N,N-dimethylformamide 1 was added 12 mg of sodium hydride at room temperature, stirred for 15 minutes, then added with 56 mg of trityl chloride, and stirred at this temperature for a day. The solution was added with water and diluted with ethyl acetate, and the organic layer was washed successively with saturated aqueous ammonium chloride and saturated brine, dried over anhydrous magnesium sulfate, and the solvent was evaporated. The residue was purified and separated by silica gel column chromatography (ethyl acetate:n-hexane=1:30), to afford 93 mg of the title compound as colorless crystals.

$^1$H-NMR (400 MHz, $CDCl_3$) δ 7.25-7.38 (15H, m), 7.43-7.50 (2H, m), 7.57 (1H, s), 7.80-7.89 (3H, m), 8.03 (1H, dd, J=8.4, 2.0 Hz), 8.25 (1H, d, J=0.8 Hz).

Example 514

3-(Naphthalen-2-yl)-1H-thieno[2,3-c]pyrazole-5-carbonitrile

To a solution of a crude product which was obtained by treating 93 mg of 5-iodo-3-(naphthalen-2-yl)-1-trityl-1H- thieno[2,3-c]pyrazole obtained by Production example 513 in the manner as described in Production example 506 (purification by silica gel column is not executed) in 2 mL of dichloromethane, 1 mL of trifluoroacetic acid was added at room temperature and stirred at this temperature for 30 minutes. The reaction solution was poured into aqueous sodium hydrogen carbonate, extracted with ethyl acetate, and the organic layer was washed with saturated brine, dried over anhydrous magnesium sulfate, and the solvent was evaporated. The crude product was purified and separated by silica gel column chromatography (ethyl acetate:n-hexane=1:3), to afford 33 mg of the title compound as colorless crystals.

$^1$H-NMR (400 MHz, DMSO-$D_6$) δ 7.53-7.61 (2H, m), 7.94-7.97 (1H, m), 8.01-8.11 (2H, m), 8.05 (1H, s), 8.53 (1H, d, J=0.8 Hz), 8.70 (1H, s).

Example 515

3-(Naphthalen-2-yl)-1H-thieno[2,3-c]pyrazole-5-carboxylic acid

To a solution of 33 mg of 3-(naphthalen-2-yl)-1H-thieno[2,3-c]pyrazole-5-carbonitrile in 1.0 mL of acetic acid and 0.3 mL of water was added 0.3 mL of concentrated sulfuric acid at room temperature and stirred at 110° C. for a day. After cooling the solution to room temperature, 10 mL of ice water was added, and the precipitated crystals were collected by filtration and washed with water, to afford 33 mg of the title compound as pale brown crystals.

$^1$H-NMR (400 MHz, DMSO-$D_6$) δ 7.50-7.60 (2H, m), 7.91-8.15 (4H, m), 8.34 (1H, s), 8.54 (1H, s).

Production Example 516

3-(Naphthalen-2-yl)-1-trityl-1H-thieno[2,3-c]pyrazole-5-carboxylic acid

By treating 56 mg of 3-(naphthalen-2-yl)-1H-thieno[2,3-c]pyrazole-5-carboxylic acid in the manner as described in Production example 513, 61 mg of the title compound was obtained as pale brown crystals.

$^1$H-NMR (400 MHz, DMSO-$D_6$) δ 7.22-7.27 (6H, m), 7.39-7.45 (9H, m), 7.50-7.57 (2H, m), 7.90-7.93 (1H, m), 7.96 (1H, d, J=9.2 Hz), 8.03 (1H, dd, J=9.2, 1.6 Hz), 8.14-8.18 (1H, m), 8.28 (1H, s), 8.53 (1H, s).

Production Example 517

3-(Naphthalen-2-yl)-1-trityl-1H-thieno[2,3-c]pyrazole-5-carbonitrile

By treating 310 mg of 5-iodo-3-(naphthalen-2-yl)-1-trityl-1H-thieno[2,3-c]-pyrazole obtained by Production example 513 in the manner as described in Production example 506, 167 mg of the title compound was obtained as colorless crystals.

$^1$H-NMR (400 MHz, $CDCl_3$) δ 7.25-7.42 (15H, m), 7.47-7.54 (2H, m), 7.83-7.92 (3H, m), 7.90 (1H, s), 8.02 (1H, dd, J=8.4, 2.0 Hz), 8.28 (1H, d, J=0.8 Hz).

Production Example 518 c-[3-(Naphthalen-2-yl)-1-trityl-1H-thieno[2,3-c]pyrazol-5-yl]methylamine

Under nitrogen atmosphere, a suspension of 51.2 mg of lithium aluminum hydride in 1.0 mL of tetrahydrofuran was added with 180 mg of aluminum chloride at 0° C., and stirred at room temperature for 20 minutes. A solution of 167 mg of 3-(naphthalen-2-yl)-1-trityl-1H-thieno[2,3-c]pyrazole-5-carbonitrile in 2.0 mL of tetrahydrofuran was added and stirred at this temperature for 3 hours. Under ice cooling, 10 mL of Rochelle salt aqueous solution was slowly added, followed by filtration through Celite. The filtrate was diluted with ethyl acetate, washed with saturated brine, dried over anhydrous magnesium sulfate, and then the solvent was evaporated. The crude product was purified and separated by NH silica gel column chromatography (ethyl acetate:n-hexane=1:1), to afford 86 mg of the title compound as colorless crystals.

$^1$H-NMR (400 MHz, $CDCl_3$) δ 3.91 (2H, s), 7.17 (1H, t, J=1.2 Hz), 7.27-7.35 (15H, m), 7.45 (2H, ttd, 6.8, 6.8, 1.6 Hz), 7.81 (1H, dd, J=8.4, 1.6 Hz), 7.84 (1H, d, J=8.4 Hz), 7.87 (1H, dd, J=8.4, 1.6 Hz), 8.07 (1H, dd, J=8.4, 1.6 Hz), 8.29 (1H, d, J=1.2 Hz).

Example 519

3-(Naphthalen-2-yl)-1-trityl-1H-thieno[2,3-c]-pyrazol-5-carboxylic acid obtained by Production example 516 and various kinds of amine were dehydration-condensed in accordance with Example 44, deprotected in accordance with the deprotection condition of Example 183 and purified by LC-MS, to afford the compounds of Examples 520-523.

Example 520

3-(Naphthalen-2-yl)-1H-thieno[2,3-c]pyrazol-5-carboxylic acid cyclopropylamide

MS (ESI) m/z 334 $MH^+$

Example 521

3-(Naphthalen-2-yl)-1H-thieno[2,3-c]pyrazol-5-carboxylic acid (furan-2-ylmethyl) amide MS (ESI) m/z 374 $MH^+$ Example 522

3-(Naphthalen-2-yl)-1H-thieno[2,3-c]pyrazol-5-carboxylic acid (2-hydroxy-1-phenylethyl) amide MS (ESI) m/z 414 $MH^+$ Example 523

3-(Naphthalen-2-yl)-1H-thieno[2,3-c]pyrazol-5-carboxylic acid (1-carbamoylethyl) amide MS (ESI) m/z 365 $MH^+$ Example 524 c-[3-(Naphthalen-2-yl)-1-trityl-1H-thieno[2,3-c]-pyrazol-5-yl]methylamine obtained by Production example 518 and various kinds of carboxylic acid were amidated in accordance with Example 183, deprotected and purified by LC-MS, to afford the compounds of Examples 525-532.

Example 525

N-[3-(Naphthalen-2-yl)-1H-thieno[2,3-c]pyrazol-5-ylmethyl]acetamide

MS (ESI) m/z 322 $MH^+$

Example 526

Cyclopropane carboxylic acid [3-(naphthalen-2-yl)-1H-thieno[2,3-c]pyrazol-5-ylmethyl]amide MS (ESI) m/z 348 $MH^+$ Example 527

Thiophene-2-carboxylic acid [3-(naphthalen-2-yl)-1H-thieno[2,3-c]pyrazol-5-ylmethyl]amide MS (ESI) m/z 390 $MH^+$ Example 528

Furan-2-carboxylic acid [3-(naphthalen-2-yl)-1H-thieno[2,3-c]pyrazol-5-ylmethyl]amide MS (ESI) m/z 374 $MH^+$ Example 529

(2S)-5-Oxopyrrolidine-2-carboxylic acid [3-(naphthalen-2-yl)-1H-thieno[2,3-c]pyrazol-5-ylmethyl] amide MS (ESI) m/z 391 $MH^+$ Example 530

2-Methoxy-N-[3-(naphthalen-2-yl)-1H-thieno[2,3-c] pyrazol-5-ylmethyl]benzamide

MS (ESI) m/z 414 $MH^+$

Example 531

3-Methoxy-N-[3-(naphthalen-2-yl)-1H-thieno[2,3-c] pyrazol-5-ylmethyl]benzamide

MS (ESI) m/z 414 $MH^+$

Example 532

Pyridine-2-carboxylic acid[3-(naphthalen-2-yl)-1H-thieno[2,3-c]pyrazol-5-ylmethyl]amide MS (ESI) m/z 385 $MH^+$ Production Example 533

2,2-Dimethyl-N-(pyridin-4-yl)-propionamide

To a solution of 20.0 g of 4-aminopyridine in 100 mL of dichloromethane, 32.6 mL of triethylamine was added at 0° C., followed by 27.5 mL of pivaloyl chloride, and stirred at this temperature for 1 hour. The organic layer was washed successively with water and saturated brine, dried over anhydrous magnesium sulfate, and the solvent was evaporated, and the precipitated crystals were collected by filtration, and washed with a mixed solvent of diethyl ether and n-hexane. The filtrate was diluted with ethanol, and treated with 5 N sodium hydroxide at room temperature, thereby hydrolyzing coexisting dipivaloyl compounds into monopivaloyl compounds. Following neutralization with 5N hydrochloric acid, and extraction with ethyl acetate, the organic layer was washed with saturated brine, dried over anhydrous magnesium sulfate, and the solvent was evaporated, the precipitated crystals were collected by filtration, and washed with a mixed solvent of diethyl ether and n-hexane. This was then combined with the previously obtained crystals, to afford 25.1 g of the title compound as colorless crystals.

$^1$H-NMR (400 MHz, $CDCl_3$) δ 1.32 (9H, s), 7.47 (1H, bs), 7.49 (2H, dd, J=4.8, 1.6 Hz), 8.48 (2H, dd, J=4.8, 1.6 Hz).

Production Example 534

2,2-Dimethyl-N-(3-methylpyridin-4-yl)propionamide

From 20.0 g of 2,2-dimethyl-N-(pyridin-4-yl)-propionamide, 19.9 g of the title compound was obtained as pale yellow oil in the manner as described in the document (*J. Org. Chem*., 1983, 48, 3401.).

$^1$H-NMR (400 MHz, $CDCl_3$) δ 1.35 (9H, s), 7.40 (1H, bs), 8.17 (1H, d, J=5.6 Hz), 8.34 (1H, s), 8.39 (1H, d, J=5.6 Hz).

Production Example 535

N-(3-Methylpyridin-4-yl)acetamide

To 17.5 g of 2,2-dimethyl-N-(3-methylpyridin-4-yl)propionamide, 70 mL of 5N hydrochloric acid aqueous solution was added and stirred at 90° C. for a day. Under ice cooling, the solution was neutralized with 5N sodium hydroxide aqueous solution, and the solvent was evaporated. The crystals were washed with a mixed solution of dichloromethane: methanol=10:1, and the solvent of filtrate was evaporated. To a solution of the resultant crude product in 100 mL of pyridine, 17.2 mL of acetic anhydride was added at room temperature and stirred at this temperature for 6 hours. The solvent was evaporated, and the residue was purified and separated by NH silica gel column chromatography (ethyl acetate:n-hexane=1:1), to afford 12.1 g of the title compound as colorless crystals.

$^1$H-NMR (400 MHz, $CDCl_3$) δ 2.25 (3H, s), 2.25 (3H, s), 7.10 (1H, bs), 8.12 (1H, d, J=5.6 Hz), 8.35 (1H, s), 8.39 (1H, d, J=5.6 Hz).

Production Example 536

1-Pyrazolo[4,3-c]pyridin-1-yl-ethanone

By treating 12.1 g of N-(3-methylpyridin-4-yl)acetamide in the manner as described in Production example 408, 6.44 g of the title compound was obtained as colorless crystals.

$^1$H-NMR (400 MHz, $CDCl_3$) δ 2.81 (3H, s), 8.25 (1H, d, J=0.8 Hz), 8.28 (1H, dt, J=6.0, 0.8 Hz), 8.66 (1H, d, J=6.0 Hz), 9.13 (1H, d, J=0.8 Hz)

Production Example 537

1H-Pyrazolo[4,3-c]pyridine

To a solution of 6.44 g of 1-pyrazolo[4,3-c]pyridin-1-yl-ethanone in 120 mL of ethanol, 10 mL of 5N sodium hydroxide aqueous solution was added at room temperature and stirred at this temperature for 30 minutes. After neutralization with 5N hydrochloric acid, the solvent was evaporated, the residue was washed with ethyl acetate, and the solvent of filtrate was evaporated, to afford 3.88 g of the title compound as pale yellow crystals.

$^1$H-NMR (400 MHz, $CDCl_3$) δ 7.43 (1H, dt, J=6.0, 0.8 Hz), 8.24 (1H, d, J=0.8 Hz), 8.46 (1H, d, J=6.0 Hz), 9.17 (1H, d, J=0.8 Hz).

Production Example 538

3-Bromo-1H-pyrazolo[4,3-c]pyridine

To a solution of 3.85 g of 1H-pyrazolo[4,3-c]pyridine in 50 mL of N,N-dimethylformamide was added 6.04 g of N-bromosuccinimide at room temperature and stirred at this temperature for 2 hours. Adding 10 mL of 10% sodium thiosulfate aqueous solution, the solution was diluted with ethyl acetate. The organic layer was washed successively with saturated aqueous ammonium chloride and saturated brine, dried over anhydrous magnesium sulfate, and the solvent was evaporated, to afford 4.69 g of the title compound as pale red-brown crystals.

$^1$H-NMR (400 MHz, DMSO-$D_6$) δ 7.58 (1H, d, J=2.0 Hz), 8.42 (1H, d, J=2.0 Hz), 8.95 (1H, s), 13.81 (1H, bs).

Production Example 539

3-Bromo-1-trityl-1H-pyrazolo[4,3-c]pyridine

To a solution of 4.69 g of 3-bromo-1H-pyrazolo[4,3-c]pyridine in 72 mL of dimethylformamide was added 1.42 g of sodium hydride at room temperature and stirred for 15 minutes, and then added with 6.6 g of trityl chloride and stirred at this temperature for a day. The solution was diluted with dichloromethane, and the organic layer was washed successively with saturated aqueous ammonium chloride and saturated brine, dried over anhydrous magnesium sulfate, and the solvent was evaporated. The precipitated crystals were washed with ethyl acetate, the filtrate was evaporated, and the residue was purified and separated by silica gel column chromatography (ethyl acetate:n-hexane=1:10-1:3), an the resultant product was combined with the above crystals, to afford 5.28 g of the title compound as colorless crystals.

$^1$H-NMR (400 MHz, DMSO-$D_6$) δ6.22 (1H, dd, J=6.4, 1.2 Hz), 7.13-7.40 (15H, m), 8.15 (1H, d, J=6.4 Hz), 8.93 (1H, d, J=1.2 Hz).

Production Example 540

3-(3-Fluorophenyl)-1-trityl-1H-pyrazolo[4,3-c]pyridine

A solution of 500 mg of 3-bromo-1-trityl-1H-pyrazolo[4,3-c]pyridine, 131 mg of 3-fluorophenylboronic acid, tetrakis(triphenylphosphine)palladium(0) and 537 mg of barium hydroxide octahydrate in a mixed solution of 18 mL of dimethoxyethane and 3 mL of water was stirred at 80° C. for 2 hours. The solution was diluted with ethyl acetate and water, followed by filtration through Celite. The organic layer of filtrate was washed with saturated brine, dried over anhydrous magnesium sulfate, and the solvent was evaporated. The crude product was purified and separated by silica gel column chromatography (ethyl acetate:n-hexane=1:10-1:3-dichloromethane:n-hexane=1:2-1:1-dichloromethane:methanol 100:1), to afford 399 mg of the title compound as colorless crystals.

$^1$H-NMR (400 MHz, $CDCl_3$) δ 6.20 (1H, dt, J=6.0, 0.8 Hz), 7.08 (1H, td, J=8.0, 0.8 Hz), 7.17-7.32 (15H, m), 7.43 (1H, td, J=8.0, 6.0 Hz), 7.61 (1H, ddd, J=10.0, 2.0, 1.6 Hz), 7.73 (1H, dt, J=8.0, 1.2 Hz), 8.05 (1H, d, 6.4 Hz), 9.35 (1H, d, J=0.8 Hz).

Example 541

3-(3-Fluorophenyl)-1H-pyrazolo[4,3-c]pyridine

To a solution of 12 mg of 3-(3-fluorophenyl)-1-trityl-1H-pyrazolo[4,3-c]pyridine in 2 mL of dichloromethane was added 1 mL of trifluoroacetic acid at room temperature and stirred at this temperature for 10 minutes. The reaction solution was poured into aqueous sodium hydrogen carbonate, extracted with ethyl acetate, and the organic layer was washed with saturated brine, dried over anhydrous magnesium sulfate, and the solvent was evaporated. The crude product was purified and separated by silica gel column chromatography (ethyl acetate:n-hexane=1:10-1:3), to afford 4 mg of the title compound as colorless crystals.

$^1$H-NMR (400 MHz, $CD_3OD$) δ 7.21 (1H, tdd, J=8.0, 2.4, 0.8 Hz), 7.57 (1H, td, J=8.0, 6.0 Hz), 7.60 (1H, dd, J=6.0, 1.2 Hz), 7.75 (1H, ddd, J=10.4, 2.8, 1.6 Hz), 7.86 (1H, dt, J=8.0, 1.2 Hz), 8.37 (1H, d, 6.0 Hz), 9.33 (1H, d, J=0.8 Hz)

Production Example 542

3-(3-Fluorophenyl)-1-trityl-1H-pyrazolo[4,3-c]pyridin-5-ol

By treating 380 mg of 3-(3-fluorophenyl)-1-trityl-1H-pyrazolo[4,3-c]pyridine obtained by Production example 540 in the manner as described in Production example 4, 341 mg of the title compound was obtained as colorless crystals.

$^1$H-NMR (400 MHz, $CDCl_3$) δ 6.14 (1H, d, J=8.0 Hz), 7.09 (1H, td, J=8.0, 0.8 Hz), 7.16-7.34 (15H, m), 7.42 (1H, td, J=8.0, 6.0 Hz), 7.48 (1H, dt, J=10.0, 1.6 Hz), 7.55 (1H, dd, J=8.0, 0.8 Hz), 7.74 (1H, dd, 8.0, 1.6 Hz), 8.96 (1H, d, J=0.8 Hz).

Production Example 543

3-(3-Fluorophenyl)-1-trityl-1,5-dihydropyrazolo[4,3-c]-pyridin-4-one

A solution of 340 mg of 3-(3-fluorophenyl)-1-trityl-1H-pyrazolo[4,3-c]pyridine-5-ol in acetic anhydride was stirred at 80° C. for a day and at 100° C. for 12 hours. Excess acetic anhydride was distilled off under reduced pressure, and a solution of residue in 5 mL of ethanol was added with 1 mL of 5N sodium hydroxide aqueous solution at room temperature and stirred for 1 hour. The solution was diluted with ethyl acetate, washed successively with saturated aqueous sodium hydrogen carbonate and saturated brine, dried over anhydrous magnesium sulfate, and the solvent was evaporated. The resultant crude product was purified and separated by silica gel column chromatography (ethyl acetate:n-hexane=1:3-1:0), to give 195 mg of the title compound as colorless crystals, as well as 45 mg of 3-(3-fluorophenyl)-1,5-dihydropyrazolo[4,3-c]pyridin-4-one described in Example 544 described below in which detritylation partially proceeded as colorless crystals.

$^1$H-NMR (400 MHz, DMSO-$D_6$) δ 5.23 (1H, d, J=7.2 Hz), 6.92 (1H, dd, J=7.2, 6.0 Hz), 7.10-7.42 (17H, m), 8.01 (1H, dt, J=7.6, 1.2 Hz), 8.22 (1H, ddd, J=11.2, 2.4, 1.2 Hz), 11.19 (1H, d, J=6.0 Hz).

Example 544

3-(3-Fluorophenyl)-1,5-dihydropyrazolo[4,3-c]pyridin-4-one $^1$H-NMR (400 MHz, DMSO-$D_6$) δ 6.45 (1H, d, J=7.2 Hz), 7.17 (2H, m), 7.45 (1H, td, J=8.0, 2.4 Hz), 8.19 (1H, d, J=8.0 Hz), 8.37 (1H, ddd, J=7.6, 2.4, 1.2 Hz), 11.04 (1H, d, J=4.8 Hz).

Example 545

3-(3-Fluorophenyl)-5-(2-methoxyethyl)-1,5-dihydropyrazolo[4,3-c]pyridin-4-one

To a solution of 10 mg of 3-(3-fluorophenyl)-1-trityl-1,5-dihydropyrazolo[4,3-c]pyridin-4-one obtained by Production example 543 in 0.5 mL of dimethylformamide was added 2 mg of sodium hydride at room temperature, stirred for 5 minutes, then added with 25 μl 2-bromoethylmethylether (in 1.0 M dimethylformamide), and stirred at this temperature for a day. After adding aqueous ammonium chloride, the solution was extracted with ethyl acetate, and the organic layer was concentrated. The residue was dissolved in dichloromethane, added with 0.5 mL of trifluoroacetic acid at room temperature and stirred for 10 minutes. Following concentration, separation and purification by LC-MS were performed, to afford 0.89 mg of the title compound as colorless crystals.

MS (ESI) m/z 288 $MH^+$

Example 546

3-(3-Fluorophenyl)-4-oxo-1,4-dihydropyrazolo[4,3-c]pyridine-5-carboxylic acid ethylamide To a solution of 10 mg of 3-(3-fluorophenyl)-1-trityl-1,5-dihydropyrazolo[4,3-c]pyridin-4-one obtained by Production example 543 in 0.5 mL of chloroform was added 25 μl of ethyl isocyanate (in 1.0 M chloroform) at room temperature, and stirred at the same temperature for a day. At the same temperature, 0.5 mL of trifluoroacetic acid was added and stirred for 10 minutes. Following concentration, the residue was separated and purified by LC-MS, to afford 1.57 mg of the title compound as colorless crystals.

MS (ESI) m/z 301 $MH^+$

Example 547

3-(3-Fluorophenyl)-4-oxo-1,4-dihydropyrazolo[4,3-c]pyridine 5-carboxylic acid benzylamide From 10 mg of 3-(3-fluorophenyl)-1-trityl-1,5-dihydropyrazolo[4,3-c]pyridin-4-one obtained by Production example 543 and 25 μl of benzyl isocyanate (in 1.0 M chloroform), 1.16 mg of the title compound was obtained as colorless crystals in accordance with Example 546.

MS (ESI) m/z 363 $MH^+$

Production Example 548

5-Bromo-2-chloro-4-methylpyrimidine 5 g of 5-bromo-2,4-dichloropyrimidine was dissolved in 70 mL of tetrahydrofuran, and under stirring at room temperature, 15.8 g of trimethyl aluminum in 15% n-hexane and 1.77 g of tetrakis(triphenyl)phosphine were added, and stirred at 80° C., under nitrogen atmosphere for 7 hours. Under ice cooling, 70 mL of water was added little by little, followed by 46 g of potassium sodium tartrate tetrahydrate, and stirred at room temperature for 1 hour. Then the solution was extracted twice with ethyl acetate, and the resultant organic layer was washed with saturated brine. After drying over magnesium sulfate, the solvent was evaporated, and purification and isolation by silica gel column chromatography (ethyl acetate:n-hexane=1:8) were followed, to obtain 1.6 g of the title compound as a pale yellow syrup.

$^1$H-NMR (400 MHz, $CDCl_3$) δ 2.63 (3H, s), 8.57 (1H, s)

Production Example 549

2-Chloro-4-methylpyridin-5-ylamine 308 mg of 5-bromo-2-chloro-4-methylpyridine was dissolved in 6 mL of toluene, added with 680 mg cesium carbonate, 0.3 mL of benzophenoneimine, 42 mg of 2,2'-bis (diphenylphosphino)-1,1'-binaphtyl and 46 mg of tris (dibenzylideneacetone)bis palladium, and stirred under nitrogen atmosphere at 110° C. for 15 hours. The reaction solution was allowed to cool to room temperature, then added with saturated brine, extracted with ethylacetate, dried over magnesium sulfate, and then the solvent was evaporated. The residue was added with 10 mL of tetrahydrofuran and 10 mL of 5N hydrochloric acid, and stirred at room temperature for 1 hour. The reaction solution was added with aqueous sodium hydrogen carbonate, extracted with ethyl acetate, and the organic layer was washed with saturated brine, and dried over magnesium sulfate. The solvent was evaporated, and the residue was purified by silica gel column chromatography (ethyl acetate:hexane=1:1), to afford 56 mg of the title compound.

$^1$H-NMR (400 MHz, $CDCl_3$) δ 2.40 (3H, s), 3.67 (2H, brs), 7.96 (1H, s)

Production Example 550

N-(2-Chloro-4-methylpyrimidin-5-yl)-acetamide 1.36 g of 2-chloro-4-methylpyrimidin-5-ylamine was dissolved in 20 mL of dichloromethane, and under stirring on ice, 1.53 mL of pyridine, 2.7 mL of acetic anhydride and 1.16 g of 4-dimethylaminopyridine were added. After stirring at room temperature for 1 hour, water was added, extracted with ethyl acetate, and the resultant organic layer was washed with saturated brine and dried over magnesium sulfate. After evaporating the solvent, the residue was purified by silica gel column chromatography (ethyl acetate:hexane=2:1), to afford 178 mg of the title compound as a brown oil.

$^1$H-NMR (400 MHz, $CDCl_3$) δ 2.26 (3H, s), 2.50 (3H, s), 7.07 (1H, brs), 9.01 (1H, s)

Production Example 551

1-(5-Chloro-pyrazolo[4,3-d]pyrimidin-1-yl)-ethanone

From 110 mg of N-(2-chloro-4-methylpyrimidin-5-yl)-acetamide, 27 mg of the title compound was obtained in the manner as described in Production example 408.

$^1$H-NMR (400 MHz, $CDCl_3$) δ 2.83 (3H, s), 8.33 (1H, s), 9.71 (1H, s)

Production Example 552

5-Chloro-1H-pyrazolo[4,3-d]pyrimidine 27 mg of 1-(5-chloro-pyrazolo[4,3-d]pyrimidin-1-yl)-ethanone was dissolved in 1.5 mL of acetonitrile, added with 1.5 mL of 5N sodium hydroxide aqueous solution, and stirred for 2 hours. After adding 2N hydrochloric acid to the reaction solution to render it acidic, the solution was extracted with ethyl acetate, and the resultant organic layer was washed with saturated brine, then dried over magnesium sulfate, and the solvent was evaporated, to afford 16 mg of the title compound.

$^1$H-NMR (400 MHz, $CDCl_3$) δ 8.32 (1H, s), 9.14 (1H, s)

Production Example 553

5-Chloro-3-iodo-1-trityl-1H-pyrazolo[4,3-d]pyrimidine

From 58 mg of 5-chloro-1H-pyrazolo[4,3-d]pyrimidine, 160 mg of the title compound was obtained in the manner as described in Production example 206, followed by the manner as described in Production example 22.

$^1$H-NMR (400 MHz, $CDCl_3$) δ 7.11-7.36 (16H, m)

Production Example 554

5-Chloro-3-[(E)-2-(4-fluorophenyl)-vinyl]-1-trityl-1H-pyrazolo[4,3-d]pyrimidine From 43 mg of 5-chloro-3-iodo-1-trityl-1H-pyrazolo[4,3-d]pyrimidine, 29 mg of the title compound was obtained in accordance with Production example 181.

$^1$H-NMR (400 MHz, $CDCl_3$) δ 7.05 (2H, t, J=8.8 Hz), 7.10-7.37 (17H, m), 7.52-7.58 (2H, m), 8.01 (1H, d, J=16.8 Hz)

Example 555

5-Chloro-3-[(E)-2-(4-fluorophenyl)-vinyl]-1H-pyrazolo[4,3-d]pyrimidine

From 15 mg of 5-chloro-3-[(E)-2-(4-fluorophenyl)-vinyl]-1-trityl-1H-pyrazolo[4,3-d]pyrimidine obtained by Production example 554, 0.61 mg of the title compound was obtained in accordance with Production example 16.

$^1$H-NMR (400 MHz, $CD_3OD$) δ 7.14 (2H, t, J=8.8 Hz), 7.39 (1H, d, J=16.8 Hz), 7.66 (2H, dd, J=8.8, 5.2 Hz), 8.04 (1H, d, J=16.8 Hz), 9.13 (1H, s)

Production Example 556

6-Fluoro-3-iodo-1H-indazole-5-carbonitrile

From 6.01 g of 6-fluoro-1H-indazole-5-carbonitrile obtained by Production example 82, 11.6 g of the title compound was obtained as pale brown crystal in accordance with the method of Production example 206.

$^1$H-NMR (400 MHz, $CDCl_3$) δ 7.30 (1H, d, J=8.8 Hz), 7.88 (1H, d, J=8.8 Hz), 10.8 (1H, brs)

Production Example 557

6-Fluoro-3-iodo-1-trityl-1H-indazole-5-carbonitrile

From 11.6 g of 6-fluoro-3-iodo-1H-indazole-5-carbonitrile obtained by Production example 556, 14.9 g of the title compound was obtained as pale brown crystal in accordance with the method of Production example 22.

$^1$H-NMR (400 MHz, $CDCl_3$) δ 6.07 (1H, d, J=10.4 Hz), 7.10-7.17 (6H, m), 7.25-7.33 (9H, m), 7.78 (1H, d, J=6.0 Hz)

Example 558

6-Fluoro-3-{(E)-2-(4-fluorophenyl)-vinyl}-1H-indazole-5-carbonitrile

By treating 4 g of 6-fluoro-3-iodo-1-trityl-1H-indazole-5-carbonitrile obtained by Production example 557 in the similar method as described in Example 100, 1.37 g of the title compound was obtained as pale brown crystals.

$^1$H-NMR (400 MHz, DMSO-$D_6$) δ 7.24 (2H, t, J=8.8 Hz), 7.49 (1H, d, J=16.8 Hz), 7.62 (1H, d, J=16.8 Hz), 7.63 (1H, d, J=9.6 Hz), 7.79 (2H, dd, J=8.8, 5.6 Hz), 8.95 (1H, d, J=6.0 Hz)

Example 559

6-Fluoro-3-{(E)-2-(4-fluorophenyl)-vinyl}-1H-indazole-5-carboxymidic acid ethyl ester hydrochloride From 1.37 of 6-fluoro-3-[(E)-2-(4-fluorophenyl)-vinyl]-1H-indazole-5-carbonitrile obtained by Example 558, 1.78 g of the title compound was obtained as pale yellow crystals in accordance with Example 370.

$^1$H-NMR (400 MHz, DMSO-$D_6$) δ 1.49 (3H, t, J=7.2 Hz) 4.66 (2H, q, J=7.2 Hz) 7.25 (2H, t, J=8.8 Hz), 7.54 (1H, d, J=16.8 Hz), 7.62 (1H, d, J=9.6 Hz), 7.68 (1H, d, J=16.8 Hz), 7.77-7.84 (2H, m), 8.85 (1H, d, J=6.4 Hz)

Production Example 560

N-Formyl-N-methylhydrazine 5 g of Methylhydrazine was dissolved in 50 mL of tetrahydrofuran, and under stirring at room temperature, 8.8 mL of ethyl formate was added and stirred for 14 hours. By evaporating the solvent, 8.42 g of a crudely purified product of the title compound as a pale yellow syrup.

$^1$H-NMR (400 MHz, DMSO-$D_6$) δ 2.91 (3H, s), 4.80 (2H, brs), 8.01 (1H, s)

Production Example 561

N-Acetyl-N-methylhydrazine 5.2 g of methylhydrazine was dissolved in 50 mL of tetrahydrofuran, and under stirring on ice, 10.6 mL of acetic anhydride was added and stirred at room temperature for 7 hours. By distilling off the solvent under reduced pressure, 17.8 g of a crudely purified product of the title compound as a colorless syrup.

$^1$H-NMR (400 MHz, DMSO-$D_6$) δ 2.01 (3H, s), 2.97 (3H, s), 4.71 (2H, brs)

Example 562

In accordance with the method described in Example 371 or 375, from 7-fluoro-3-[(E)-2-(4-fluorophenyl)-vinyl]-1H-indazole-5-carboxymidic acid ethyl ester hydrochloride obtained by Example 383 and 6-fluoro-3-{(E)-2-(4-fluorophenyl)-vinyl}-1H-indazole-5-carboxymidic acid ethyl ester hydrochloride obtained by Example 559, the compounds of Examples 563-598 were produced. Hydrazines used in Examples 563-591, 597, 598 were produced in accordance with Production examples 366-367 unless they were commercially available. In Examples 592 and 594, N-formyl-N-methylhydrazine produced by Production example 560 was used, and in Example 593 N-acetyl-N-methylhydrazine produced by Production example 561 was used.

Example 563

1-(5-{6-Fluoro-3-[(E)-2-(4-fluorophenyl)-vinyl]-1H-indazol-5-yl}-4H-[1,2,4]triazol-3-yl)-ethanol MS (ESI) m/z 368 $MH^+$ Example 564

3-(5-{6-Fluoro-3-[(E)-2-(4-fluorophenyl)-vinyl]-1H-indazol-5-yl}-4H-[1,2,4]triazol-3-yl)-propan-1-ol MS (ESI) m/z 382 $MH^+$ Example 565

1-(5-{7-Fluoro-3-[(E)-2-(4-fluorophenyl)-vinyl]-1H-indazol-5-yl}-4H-[1,2,4]triazol-3-yl)-ethanol MS (ESI) m/z 368 $MH^+$ Example 566

3-(5-{7-Fluoro-3-[(E)-2-(4-fluorophenyl)-vinyl]-1H-indazol-5-yl}-4H-[1,2,4]triazol-3-yl)-propan-1-ol MS (ESI) m/z 382 $MH^+$ Example 567

6-Fluoro-3-[(E)-2-(4-fluorophenyl)-vinyl]-5-(4H-[1,2,4]triazol-3-yl)-1H-indazole MS (ESI) m/z 324 $MH^+$ Example 568

7-Fluoro-3-[(E)-2-(4-fluorophenyl)-vinyl]-5-(4H-[1,2,4]triazol-3-yl)-1H-indazole MS (ESI) m/z 324 $MH^+$ Example 569

6-Fluoro-3-{(E)-2-(4-fluorophenyl)-vinyl}-5-(5-methyl-4H-[1,2,4]triazol-3-yl)-1H-indazole MS (ESI) m/z 338 $MH^+$ Example 570

(5-{6-Fluoro-3-[(E)-2-(4-fluorophenyl)-vinyl]-1H-indazol-5-yl}-4H-[1,2,4]triazol-3-yl)-methanol MS (ESI) m/z 354 $MH^+$ Example 571

(5-{6-Fluoro-3-[(E)-2-(4-fluorophenyl)-vinyl]-1H-indazol-5-yl}-4H-[1,2,4]triazol-3-ylmethyl)-methyl-amine MS (ESI) m/z 367 $MH^+$ Example 572

(5-{7-Fluoro-3-[(E)-2-(4-fluorophenyl)-vinyl]-1H-indazol-5-yl}-4H-[1,2,4]triazol-3-ylmethyl)-dimethyl-amine MS (ESI) m/z 381 $MH^+$ Example 573

C-(5-{7-Fluoro-3-[(E)-2-(4-fluorophenyl)-vinyl]-1H-indazol-5-yl}-4H-[1,2,4]triazol-3-yl)-methylamine MS (ESI) m/z 353 $MH^+$ Example 574

(1S)-1-(5-{7-Fluoro-3-[(E)-2-(4-fluorophenyl)-vinyl]-1H-indazol-5-yl}-4H-[1,2.,4]triazol-3-yl)-2-methyl-propylamine MS (ESI) m/z 395 $MH^+$ Example 575

(5-{6-Fluoro-3-[(E)-2-(4-fluorophenyl)-vinyl]-1H-indazol-5-yl}-4H-[1,2,4]triazol-3-ylmethyl)-dimethyl-amine MS (ESI) m/z 381 $MH^+$ Example 576

C-(5-{6-Fluoro-3-[(E)-2-(4-fluorophenyl)-vinyl]-1H-indazol-5-yl}-4H-[1,2,4]triazol-3-yl)-methylamine MS (ESI) m/z 353 $MH^+$ Example 577

(1S)-1-(5-{6-Fluoro-3-[(E)-2-(4-fluorophenyl)-vinyl]-1H-indazol-5-yl}-4H-[1,2,4]triazol-3-yl)-2-methyl-propylamine MS (ESI) m/z 395 $MH^+$ Example 578

2-(5-{7-Fluoro-3-[(E)-2-(4-fluorophenyl)-vinyl]-1H-indazol-5-yl}-4H-[1,2,4]triazol-3-yl)-propan-2-ol MS (ESI) m/z 382 $MH^+$ Example 579

2-(5-{6-Fluoro-3-[(E)-2-(4-fluorophenyl)-vinyl]-1H-indazol-5-yl}-4H-[1,2,4]triazol-3-yl)-propan-2-ol MS (ESI) m/z 382 $MH^+$ Example 580

1-(5-{6-Fluoro-3-[(E)-2-(4-fluorophenyl)-vinyl]-1H-indazol-5-yl}-4H-[1,2,4]triazol-3-yl)-1-methyl-ethylamine MS (ESI) m/z 382 $MH^+$ Example 581

1-(5-{7-Fluoro-3-[(E)-2-(4-fluorophenyl)-vinyl]-1H-indazole 5-yl}-4H-[1,2,4]triazole-3-yl)-1-methyl-ethylamine MS (ESI) m/z 382 $MH^+$ Example 582

[(1S)-1-(5-{6-Fluoro-3-[(E)-2-(4-fluorophenyl)-vinyl]-1H-indazol-5-yl}-4H-[1,2,4]triazol-3-yl)-2-methyl-propyl]-methyl-amine MS (ESI) m/z 409 $MH^+$ Example 583

1-(5-{6-Fluoro-3-[(E)-2-(4-fluorophenyl)-vinyl]-1H-indazol-5-yl}-4H-[1,2,4]triazol-3-yl)-cyclopropylamine MS (ESI) m/z 379 $MH^+$ Example 584

1-(5-{7-Fluoro-3-[(E)-2-(4-fluorophenyl)-vinyl]-1H-indazol-5-yl}-4H-[1,2,4]triazol-3-yl)-cyclopropylamine MS (ESI) m/z 379 $MH^+$ Example 585

6-Fluoro-3-[(E)-2-(4-fluorophenyl)-vinyl]-5-[5-(thiophen-2-yl)methyl-4H-[1,2,4]triazol-3-yl]-1H-indazole MS (ESI) m/z 379 $MH^+$ Example 586

5-(5-Benzyl-4H-[1,2,4]triazol-3-yl)-6-fluoro-3-[(E)-2-(4-fluorophenyl)-vinyl]-1H-indazole MS (ESI) m/z 379 $MH^+$ Example 587

(1S)-1-(5-{6-Fluoro-3-[(E)-2-(4-fluorophenyl)-vinyl]-1H-indazol-5-yl}-4H-[1,2,4]triazol-3-yl)-2-phenyl-ethylamine MS (ESI) m/z 443 $MH^+$ Example 588

[2-(5-{6-Fluoro-3-[(E)-2-(4-fluorophenyl)-vinyl]-1H-indazol-5-yl}-4H-[1,2,4]triazol-3-yl)-ethyl]-dimethyl-ethylamine MS (ESI) m/z 395 $MH^+$ Example 589

[2-(5-{7-Fluoro-3-[(E)-2-(4-fluorophenyl)-vinyl]-1H-indazol-5-yl}-4H-[1,2,4]triazol-3-yl)-ethyl]-dimethyl-ethylamine MS (ESI) m/z 395 $MH^+$ Example 590

5-[5-(Azetidin-3-yl)-4H-[1,2,4]triazol-3-yl]-6-fluoro-3-[(E)-2-(4-fluorophenyl)-vinyl]-1H-indazole MS (ESI) m/z 379 $MH^+$ Example 591

5-[5-(Azetidine-3-yl)-4H-[1,2,4]triazol-3-yl]-7-fluoro-3-[( E)-2-(4-fluorophenyl)-vinyl]-1H-indazole MS (ESI) m/z 379 $MH^+$ Example 592

6-Fluoro-3-[(E)-2-(4-fluorophenyl)-vinyl]-5-(1-methyl-1H-[1,2,4]triazol-3-yl)-1H-indazole MS (ESI) m/z 338 $MH^+$ Example 593

5-(1,5-Dimethyl-1H-[1,2,4]triazol-3-yl)-6-fluoro-3-[(E)-2-(4-fluorophenyl)-vinyl]-1H-indazole MS (ESI) m/z 352 $MH^+$ Example 594

7-Fluoro-3-[(E)-2-(4-fluorophenyl)-vinyl]-5-(1-methyl-1H-[1,2,4]triazol-3-yl)-1H-indazole MS (ESI) m/z 338 $MH^+$ Example 595

2-(5-{6-Fluoro-3-[(E)-2-(4-fluorophenyl)-vinyl]-1H-indazol-5-yl}-4H-[1,2,4]triazol-3-yl)-acetamide After reacting 15 mg of 6-fluoro-3-{(E)-2-(4-fluorophenyl)vinyl}-1H-indazole-5-carboxymidic acid ethyl ester hydrochloride obtained by Example 559 and 18 mg of hydrazinocarbonylacetic acid ethyl ester in accordance with Example 371, the reaction solution was stirred at 70° C. for 10 hours in 5 mL of 2N ammonia-ethanol solution. After distilling off the solvent, purification by LC-MS was conducted, to give 4.62 mg of the title compound.

MS (ESI) m/z 381 $MH^+$

Example 596

2-(5-{7-Fluoro-3-[(E)-2-(4-fluorophenyl)-vinyl]-1H-indazol-5-yl}-4H-[1,2,4]triazol-3-yl)-acetamide From 15 mg of 7-fluoro-3-[(E)-2-(4-fluorophenyl)-vinyl]-1H-indazole-5-carboxymidic acid ethyl ester hydrochloride obtained by Example 383, 1.42 mg of the title compound was obtained in accordance with Example 595.

MS (ESI) m/z 381 $MH^+$

Example 597

[1-(5-{6-Fluoro-3-[(E)-2-(4-fluorophenyl)-vinyl]-1H-indazol-5-yl}-[1,3,4]oxadiazol-2-yl)-1-methyl-ethyl]-methyl-amine 15 mg of 6-fluoro-3-{(E)-2-(4-fluorophenyl)-vinyl}-1H-indazole-5-carboxymidic acid ethyl ester hydrochloride produced by Example 559 and 19 mg of (1-hydrazinocarbonyl-1-methyl-ethyl)-methyl-carbamic acid tert-butyl ester were dissolved in 1 mL of pyridine, and stirred at 110° C. for 12 hours. After allowing to cool to room temperature, water was added and extracted twice with ethyl acetate, and then the solvent was distilled off. The resultant residue was added with 1 mL of 4N hydrochloric acid-ethyl acetate solution, stirred at room temperature for 4 hours, then the solvent distilled off, followed by purification by LC-MS, to give 0.36 mg of the title compound.

MS (ESI) m/z 396 $MH^+$

Example 598

(S)-1-(5-{7-Fluoro-3-[(E)-2-(4-fluorophenyl)-vinyl]-1H-indazol-5-yl}-[1,3,4]oxadiazol-2-yl)-2-methyl-propylamine 15 mg of 7-fluoro-3-[(E)-2-(4-fluorophenyl)-vinyl]-1H-indazole-5-carboxymidic acid ethyl ester hydrochloride obtained by Example 383 and 19 mg of ((1S)-1-hydrazinocarbonyl-2-methyl-propyl)-carbamic acid tert-butyl ester were dissolved in 1 mL of 1,4-dioxane, and stirred at 85° C. for 12 hours. After distilling off the solvent, 1 mL of 4N hydrochloric acid-ethyl acetate solution was added and stirred at room temperature for 3 hours. After distilling off the solvent, purification by LC-MS was conducted, to give 6.05 mg of the title compound.

MS (ESI) m/z 396 $MH^+$

Example 599

6-Fluoro-3-[(E)-2-(4-fluorophenyl)-vinyl]-1H-indazole-5-car boxamidine hydrochloride 400 mg of 6-fluoro-3-{(E)-2-(4-fluorophenyl)-vinyl}-1H-indazole-5-carboxymidic acid ethyl ester hydrochloride produced by Example 559 was dissolved in 20 mL of 2N ammonia-ethanol solution, and stirred at 50° C. for 6 hours. After allowing to cool to room temperature, was added saturated brine, extracted with a mixed solvent of ethyl acetate:tetrahydrofuran=1:1, dried over magnesium sulfate, and evaporated. After adding 4N hydrochloric acid-ethyl acetate solution to the residue, the solvent was evaporated, and the resultant solid was washed with diethyl ether, followed by filtration, to afford 351 mg of the title compound as pale yellow crystals.

MS (ESI) m/z 299 $MH^+$

Example 600

6-Fluoro-3-[(E)-2-(4-fluorophenyl)-vinyl]-5-(pyrimidin-2-yl)-1H-indazole 36 mg of 6-fluoro-3-[(E)-2-(4-fluorophenyl)-vinyl]-1H-indazole-5-carboxamidine hydrochloride obtained by Example 599 and 15 μl of 3-dimethylaminopropenal were dissolved in 1 mL of pyridine, and stirred at 120° C. for 7 hours. After distilling off the solvent, purification by LC-MS was conducted, to give 0.61 mg of the title compound.

MS (ESI)m/z 335 $MH^+$

Example 601

6-Fluoro-3-[(E)-2-(4-fluorophenyl)-vinyl]-5-(4-methyl-pyrimidin-2-yl)-1H-indazole From 20 mg of 6-fluoro-3-[(E)-2-(4-fluorophenyl)-vinyl]-1H-indazole-5-carboxamidine hydrochloride obtained by Example 599 and 14 mg of 4-dimethylamino-3-buthene-2-on, 1.94 mg of the title compound was obtained in accordance with Example 600.

$^1$H-NMR (400 MHz, $CD_3OD$) δ 2.66 (3H, s), 7.12 (2H, t, J=8.8 Hz), 7.36 (1H, d, J=10.8 Hz), 7.39 (1H, d, J=4.8 Hz), 7.42 (1H, d, J=16.4 Hz), 7.57 (1H, d, J=16.4 Hz), 7.67 (1H, dd, J=8.8, 5.2 Hz), 8.62 (1H, d, J=6.8 Hz), 8.75 (1H, d, J=4.8 Hz)

Example 602

6-Fluoro-3-[(E)-2-(4-fluorophenyl)-vinyl]-5-(5-methyl-pyrimidin-2-yl)-1H-indazole From 20 mg of 6-fluoro-3-[(E)-2-(4-fluorophenyl)-vinyl]-1H-indazole-5-carboxamidine hydrochloride obtained by Example 599 and 14 mg of (E)-3-dimethylamino-2-buthenal, 8.43 mg of the title compound was obtained in accordance with Example 600.

$^1$H-NMR (400 MHz, $CD_3OD$) δ 2.43 (3H, s), 7.12 (2H, t, J=8.8 Hz), 7.35 (1H, d, J=11.2 Hz), 7.40 (1H, d, J=16.8 Hz), 7.56 (1H, d, J=16.8 Hz), 7.67 (1H, dd, J=8.8, 5.2 Hz), 8.64 (1H, d, J=6.8 Hz), 8.78 (2H, s)

Example 603

7-Fluoro-3-[(E)-2-(4-fluorophenyl)-vinyl]-5-(1H-imidazol-2-yl)-1H-indazole

After suspending 108 mg of 7-fluoro-3-[(E)-2-(4-fluorophenyl)-vinyl]-1H-indazole-5-car boxymidic acid ethyl ester hydrochloride obtained by Example 383 in 2 mL of ethanol, 206 μl of triethylamine and 50 μl of aminoacetoaldehyde ethylacetal were added, and stirred at 70° C. for 5 hours. After cooling to room temperature, water was added, extracted with ethyl acetate, and the resultant layer was washed with saturated brine and dried over anhydrous sodium sulfate. After evaporating the solvent, the resultant crude product was dissolved in 5 mL of tetrahydrofuran, added with 5 mL of 5N hydrochloric acid and stirred at room temperature overnight. After neutralization by adding saturated sodium hydrogen carbonate, the reaction mixture was extracted with ethylacetate, and washed with water and saturated brine. The organic layer was dried over magnesium sulfate, and the solvent was evaporated. The resultant crude product was purified by preparative TLC, to obtain 36.5 mg of the title compound as yellow crystals.

MS (ESI) m/z 323 $MH^+$

Production Example 604

5-(1-Dimethylsulfamoyl-1H-imidazol-2-yl)-7-fluoro-3-[(E)-2-(4-fluorophenyl)-vinyl]-indazole-1-sulfonic acid dimethylamide 36.5 mg of 7-fluoro-3-[(E)-2-(4-fluorophenyl)-vinyl]-5-(1H-imidazol-2-yl)-1H-indazole obtained by Example 603 was dissolved in N,N-dimethylformamide, and added with 14 mg of sodium hydride (containing 60%) under ice cooling and stirred for 10 minutes. Adding dropwise with 30.3 μl of N,N-dimethylsulfamoyl chloride, the solution was warmed to room temperature and stirred overnight. After stopping the reaction by adding water, the solution was extracted with ethyl acetate, and the organic layer was washed with water and saturated brine. After drying the organic layer over magnesium sulfate, the solvent was evaporated. The crude product was purified by preparative TLC, to afford 14.2 mg of the title compound.

$^1$H-NMR (400 MHz, $CDCl_3$) δ 2.60 (6H, s), 3.17 (6H, s), 7.09 (2H, t, J=8.4 Hz), 7.17 (1H, d, J=1.6 Hz), 7.24 (1H, d, J=16.8 Hz), 7.51 (1H, d, J=1.6 Hz), 7.53-7.59 (2H, m), 7.60 (1H, d, J=16.8 Hz), 7.68 (1H, dd, J=11.6, 1.2 Hz), 8.26 (1H, d, J=1.6 Hz

Example 605

(2-{7-Fluoro-3-[(E)-2-(4-fluorophenyl)-vinyl]-1H-indazol-5-yl}-3H-imidazol-4-yl)-methanol 14.2 mg of 5-(1-dimethylsulfamoyl-1H-imidazol-2-yl)-7-fluoro-3-[(E)-2-(4-fluorophenyl)-vinyl]-indazole-1-sulofonic acid dimethylamide obtained by Production example 604 was dissolved in 1 mL of tetrahydrofuran, added at −78° C. with 20.1 μl of 1.58 M n-butyllithium in hexane, stirred at this temperature for 10 minutes, then added with 5 μl of benzylchloromethylether, warmed to room temperature, and stirred for 20 minutes. After stopping the reaction by adding water, the solution extracted with ethylacetate, and the organic layer was washed with water and saturated brine and then dried over anhydrous magnesium sulfate. After evaporating the solvent, the resultant crude product was dissolved in 2 mL of aqueous hydrogen bromide, and stirred at 60° C. overnight. After cooling to room temperature, the reaction solution was neutralized with saturated aqueous sodium hydrogen carbonate and extracted with ethyl acetate. The organic layer was washed with water and saturated brine, and then dried over anhydrous magnesium sulfate. After evaporating the solvent, purification by LC-MS was conducted, to obtain 0.58 mg of the title compound.

MS (ESI) m/z 353 $MH^+$

Example 606

6-Fluoro-3-[(E)-2-(4-fluorophenyl)-vinyl]-5-(1H-imidazol-2-yl)-1H-indazole

By treating 108 mg of 6-fluoro-3-[(E)-2-(4-fluorophenyl)-vinyl]-1H-indazole-5-carboxymidic acid ethyl ester hydrochloride obtained by Example 559 in the similar method as described in Example 603, 34.4 mg of the title compound was obtained as white crystals.

MS (ESI) m/z 323 $MH^+$

Production Example 607

5-(1-Dimethylsulfamoyl-1H-imidazol-2-yl)-6-fluoro-3-[(E)-2-(4-fluorophenyl)-vinyl]-indazole-1-sulfonic acid dimethylamide 34.4 mg of 6-fluoro-3-[(E)-2-(4-fluorophenyl)-vinyl]-5-(1H-imidazol-2-yl)-1H-indazole obtained by Example 606 was treated in the similar method as described in Production example 604, to afford 29.5 mg of the title compound.

$^1$H-NMR (400 MHz, $CDCl_3$) δ2.71 (6H, s), 3.03 (6H, s), 7.06-7.12 (2H, m), 7.24 (1H, d, J=2.0 Hz), 7.50 (1H, d, J=1.2 Hz), 7.53-7.63 (3H, m), 7.69 (1H, d, J=16.4 Hz

Example 608

(2-{6-Fluoro-3-[(E)-2-(4-fluorophenyl)-vinyl]-1H-indazol-5-yl}-3H-imidazol-4-yl)-methanol 29.5 mg of 5-(1-dimethylsulfamoyl-1H-imidazol-2-yl)-6-fluoro-3-[(E)-2-(4-fluorophenyl)-vinyl]-indazole-1-sulfonic acid dimethylamide obtained by Production example 607 was treated in the similar method as described in Example 605, to afford 0.54 mg of the title compound.

MS (ESI) m/z 353 $MH^+$

Example 609

5-{7-Fluoro-3-[(E)-2-(4-fluorophenyl)-vinyl]-1H-indazol-5-yl}-4H-[1,2,4]triazol-3-ol 20 mg of 7-fluoro-3-[(E)-2-(4-fluorophenyl)-vinyl]-1H-indazole-5-carboxymidic acid ethyl ester hydrochloride obtained by Example 383 was dissolved in 3 mL of pyridine, added with 6.1 mg of semicarbazide hydrochloride and refluxed for 8 hours. After cooling to room temperature, the solvent was distilled off under reduced pressure, followed by purification by LC-MS, to afford 1.66 mg of the title compound.

$^1$H-NMR (400 MHz, $CD_3OD$) δ 7.15 (2H, t, J=8.8 Hz), 7.41 (1H, d, J=16.8 Hz), 7.62 (1H, d, J=16.8 Hz), 7.66 (1H, d, J=12.4 Hz), 7.70 (1H, dd, J=6.0, 8.8 Hz), 8.32 (1H, s)

MS (ESI) m/z 340 $MH^+$

Example 610

5-{7-Fluoro-3-[(E)-2-(4-fluorophenyl)-vinyl]-1H-indazol-5-yl}-4H-[1,2,4]triazol-3-ylamine 20 mg of 7-fluoro-3-[(E)-2-(4-fluorophenyl)-vinyl]-1H-indazole-5-carboxymidic acid ethyl ester hydrochloride obtained by Example 383 was dissolved in 3 mL of pyridine, added with 6.1 mg of aminoguanidine hydrochloride, and refluxed for 8 hours. After cooling to room temperature, the solvent was evaporated, followed by purification by LC-MS, to afford 0.72 mg of the title compound.

$^1$H-NMR (400 MHz, $CD_3OD$) δ 7.15 (2H, t, J=8.8 Hz), 7.43 (1H, d, J=16.8 Hz), 7.61 (1H, d, J=16.4 Hz), 7.67-7.73 (3H, m), 8.44 (1H, d, J=1.2 Hz)

MS (ESI) m/z 339 $MH^+$

Example 611

4-Amino-5-{7-fluoro-3-[(E)-2-(4-fluorophenyl)-vinyl]-1H-indazol-5-yl}-2,4-dihydro-[1,2,4]triazol-3-one 20 mg of 7-fluoro-3-[(E)-2-(4-fluorophenyl)-vinyl]-1H-indazole-5-carboxymidic acid ethyl ester hydrochloride obtained by Example 383 was dissolved in 5 mL of ethanol, added with 5.5 mg of carbohydrazide and refluxed overnight. The solvent was evaporated, followed by purification by LC-MS, to afford 1.47 mg of the title compound.

$^1$H-NMR (400 MHz, DMSO-$D_6$) δ 5.49 (2H, s), 7.24 (2H, t, J=8.8 Hz), 7.53 (2H, s), 7.72-7.80 (3H, m), 8.68 (1H, s), 11.9 (1H, s)

MS (ESI) m/z 355 $MH^+$

Example 612

5-{6-Fluoro-3-[(E)-2-(4-fluorophenyl)-vinyl]-1H-indazol-5-yl}-4H-[1,2,4]triazol-3-ylamine 20 mg 6-fluoro-3-[(E)-2-(4-fluorophenyl)-vinyl]-1H-indazole-5-carboxymidic acid ethyl ester hydrochloride obtained by Example 559 was treated in accordance with Example 610, to afford 0.64 mg of the title compound.

$^1$H-NMR (400 MHz, $CD_3OD$) δ 7.14 (2H, t, J=8.8 Hz), 7.41 (1H, d, J=17.2 Hz), 7.44 (1H, d, J=10.8 Hz), 7.58 (1H, d, J=16.8), 7.69 (1H, dd, J=5.4, 8.4 Hz), 8.62 (1H, d, J=6.4 Hz)

MS (ESI) m/z 339 $MH^+$

Example 613

5-{6-Fluoro-3-[(E)-2-(4-fluorophenyl)-vinyl]-1H-indazol-5-yl}-4H-[1,2,4]triazol-3-ol 20 mg of 6-fluoro-3-[(E)-2-(4-fluorophenyl)-vinyl]-1H-indazole-5-carboxymidic acid ethyl ester hydrochloride obtained by Example 559 was treated in accordance with Example 609, followed by purification by preparative TLC, to afford 1.55 mg of the title compound as white crystals.

$^1$H-NMR (400 MHz, DMSO-$D_6$) δ 7.24 (2H, t, J=8.8 Hz), 7.47-7.54 (3H, m), 7.76-7.80 (2H, m), 8.48 (1H, d, J=6.4 Hz)

MS (ESI) m/z 340 $MH^+$

Example 614

4-Amino-5-{6-fluoro-3-[(E)-2-(4-fluorophenyl)-vinyl]-1H-indazol-5-yl}-2,4-dihydro-[1,2,4]triazol-3-one 20 mg of 6-fluoro-3-[(E)-2-(4-fluorophenyl)-vinyl]-1H-indazole-5-carboxymidic acid ethyl ester hydrochloride obtained by Example 559 was treated in the similar method as described in Example 611, followed by purification by preparative TLC, to afford 2.19 mg of the title compound as white crystals.

$^1$H-NMR (400 MHz, DMSO-$D_6$) δ 5.27 (2H, s), 7.24 (2H, t, J=8.7 Hz), 7.47 (1H, d, J=10.8 Hz), 7.52 (2H, s), 7.77-7.80 (2H, m), 8.43 (1H, d, J=6.0 Hz)

MS (ESI) m/z 355 $MH^+$

Example 615

5-(1H-Benzimidazol-2-yl)-6-fluoro-3-[(E)-2-(4-fluorophenyl)vinyl]-1H-indazole

To a solution of 10 mg of 6-fluoro-3-[(E)-2-(4-fluorophenyl)-vinyl]-1H-indazole-5-carboxydimic acid ethyl ester hydrochloride obtained by Example 559 in 0.5 mL of acetic acid was added 85 μl of phenylene diamine (in 1 molar acetic acid) at room temperature and stirred at 120° C. for a day. Following addition of water and extraction with ethyl acetate, the organic layer was concentrated. The residue was separated and purified by LC-MS, to afford 10.08 mg of the title compound as colorless crystals.

MS (ESI)m/z 373 $MH^+$

Example 616

The compounds of Examples 617-623 were synthesized from 6-fluoro-3-[(E)-2-(4-fluorophenyl)vinyl]-1H-indazole-5-carboxydimic acid ethyl ester hydrochloride and commercially available substituted phenylene diamine in accordance with the method of Example 615.

Example 617

6-Fluoro-3-[(E)-2-(4-fluorophenyl)-vinyl]-5-(7-methyl-1H-benzimidazol-2-yl)-1H-indazole MS (ESI)m/z 387 $MH^+$ Example 618

6-Fluoro-3-[(E)-2-(4-fluorophenyl)-vinyl]-5-(6-methyl-1H-benzimidazol-2-yl)-1H-indazole MS (ESI)m/z 387 $MH^+$ Example 619

5-(6-Chloro-1H-benzimidazol-2-yl)-6-fluoro-3-[(E)-2-(4-fluorophenyl)-vinyl]-1H-indazole MS (ESI)m/z 407 M+

Example 620

6-Fluoro-5-(6-fluoro-1H-benzimidazol-2-yl)-3-[(E)-2-(4-fluorophenyl)-vinyl]-1H-indazole MS (ESI)m/z 391 $MH^+$ Example 621

6-Fluoro-3-[(E)-2-(4-fluorophenyl)-vinyl]-5-(6-nitro-1H-benzimidazol-2-yl)-1H-indazole MS (ESI)m/z 418 $MH^+$ Example 622

5-(5,6-Dichloro-1H-benzimidazol-2-yl)-6-fluoro-3-[(E)-2-(4-fluorophenyl)-vinyl]-1H-indazole MS (ESI)m/z 441 M+

Example 623

5-(5-Chloro-6-fluoro-1H-benzimidazol-2-yl)-6-fluoro-3-[(E)-2-(4-fluorophenyl)-vinyl]-1H-indazole MS (ESI)m/z 425 M+

Production Example 624

5-Bromo-1H-indazole-3-carboxylic acid

A mixture of 15 g of 5-bromoisatine, 34 mL of water and 2.79 g of sodium hydroxide was stirred at 50° C. for 5 minutes, and then under stirring on ice, added with a solution containing 4.58 g of sodium sulfite in 16 mL of water. The reaction mixture was added dropwise under cooling on ice to a mixed solution of 6.72 mL concentrated sulfuric acid/133 mL water in such a speed that did not cause the temperature of the reaction solution to exceed 4° C. After stirring for 15 minutes under ice cooling, a solution containing 30.2 g of tin chloride (II) in 56 mL of concentrated hydrochloric acid was added dropwise in such a speed that did not cause the temperature of the reaction solution to exceed 4° C., followed by 1-hour stirring on ice. Then the reaction mixture was added with water and extracted with a mixed solvent of ethyl acetate:tetrahydrofuran=1:1, and the resultant organic layer was washed with saturated brine, and dried over magnesium sulfate. The solvent was evaporated, and the generated crystals were washed with diethyl ether and filtered, to obtain 4.64 g of the title compound as pale yellow crystals.

$^1$H-NMR (400 MHz, DMSO-$D_6$) δ 7.54 (1H, dd, J=8.8, 2.0 Hz), 7.63 (1H, d, J=8.8 Hz), 8.19 (1H, d, J=2.0 Hz)

Production Example 625

5-Bromo-1H-indazole-3-carboxylic acid ethyl ester 3 g of 5-bromo-1H-indazole-3-carboxylic acid was dissolved in 60 mL of ethanol, added with 0.6 mL of concentrated sulfuric acid, and heated under reflux for 8 hours. After allowing to cool to room temperature, addition of water and extraction with ethyl acetate were conducted, and the resultant organic layer was washed with saturated aqueous sodium hydrogen carbonate and saturated brine, dried over magnesium sulfate, and the solvent was evaporated, to afford 2.7 g of the title compound as yellow crystals.

$^1$H-NMR (400 MHz, $CDCl_3$) δ 1.50 (3H, t, J=7.2 Hz), 4.54 (2H, q, J=7.2 Hz), 7.54 (2H, d, J=1.2 Hz), 8.37 (1H, t, J=1.2 Hz)

Production Example 626

5-Bromo-1-trityl-1H-indazole-3-carboxylic acid 2.19 g of 5-bromo-1H-indazole-3-carboxylic acid ethyl ester was dissolved in 40 mL of dimethylformamide, added with 391 mg of 60% sodium hydride (oil-based) and 2.38 g of trityl chloride, and stirred at room temperature for 1 hour. After adding a saturated aqueous ammonium chloride, the reaction solution was extracted with ethyl acetate, and the resultant organic layer was washed with saturated brine, dried over magnesium sulfate, and the solvent was evaporated. The resultant residue was dissolved in a solution of 20 mL of ethanol, 20 mL of tetrahydrofuran and 15 mL of 5N sodium hydroxide aqueous, and stirred at 60° C. for 2 hours. After allowing to cool to room temperature, the reaction solution was neutralized by adding 1N hydrochloric acid, extracted with a mixed solvent of ethyl acetate:tetrahydrofuran=1:1, and the resultant organic layer was washed with saturated brine and dried over magnesium sulfate. After evaporated the solvent, the generated crystals were washed with diethyl ether and filtered to afford 3.3 g of the title compound as pale yellow crystals.

MS (ESI) m/z 481, 483 $(M-H)^-$

Production Example 627

5-Bromo-1-trityl-1H-indazole-3-carboxylic acid phenylamide

From 1 g of 5-bromo-1-trityl-1H-indazole-3-carboxylic acid and 0.23 mL of aniline, 755 mg of the title compound was obtained as pale yellow crystal in accordance with Example 127.

$^1$H-NMR (400 MHz, $CDCl_3$) δ 6.28 (1H, d, J=8.8 Hz), 6.65-6.70 (1H, m), 6.75 (1H, t, J=6.8 Hz), 7.06-7.39 (17H, m), 7.56 (2H, d, J=8.8 Hz), 8.55 (1H, brs), 8.62 (1 h, d, J=2.0 Hz)

Production Example 628

5-Amino-1-trityl-1H-indazole-3-carboxylic acid phenylamide

From 318 mg of 5-bromo-1-trityl-1H-indazole-3-carboxylic acid phenylamide, 258 mg of the title compound was obtained in accordance with Production example 422.

$^1$H-NMR (400 MHz, $CDCl_3$) δ 6.20 (1H, d, J=8.8 Hz), 6.47 (1H, dd, J=8.8, 2.4 Hz), 7.02-7.82 (21H, m), 8.59 (1H, brs)

Production Example 629

3-Phenylcarbamoyl-1-trityl-1H-indazole-5-carboxylic acid 470 mg of 5-bromo-1-trityl-1H-indazole-3-carboxylic acid phenylamide obtained by Production example 627 was dissolved in 8.4 mL of tetrahydrofuran, and added with 1.58 mL of 1.6 M n-butyllithium hexane solution under stirring at −70°. After stirring at −70° for 15 minutes, dry ice-ethanol bath was removed, and carbon dioxide was blown into the reaction for 25 minutes. After adding a saturated aqueous ammonium chloride, the reaction solution was extracted with ethyl acetate, and the resultant organic layer was washed with saturated brine and dried over magnesium sulfate. The solvent was evaporated, and the generated crystals were washed with a mixed solvent of hexane:diethyl ether=2:1 and filtered, to afford 230 mg of the title compound as pale yellow crystals.

$^1$H-NMR (400 MHz, $CDCl_3$) δ 6.46 (1H, d, J=9.2 Hz), 6.98-7.45 (18H, m), 7.54-7.64 (2H, m), 7.73 (1H, dd, J=8.8, 1.6 Hz), 8.58 (1H, s), 9.25 (1H, s)

Example 630

5-Amino-1-trityl-1H-indazole-3-carboxylic acid phenylamide produced by Production example 628 and various kinds of carboxylic acid were treated in the similar method as described in Example 183, to afford the compounds of Examples 631-635.

Example 631

5-Acetylamino-1H-indazole-3-carboxylic acid phenylamide

MS (ESI) m/z 295 $MH^+$

Example 632

5-Cyclopropane carbonylamino-1H-indazole-3-carboxylic Acid phenylamide

MS (ESI) m/z 321 $MH^+$

Example 633

5-[((2S)-5-Oxopyrrolidine-2-carbonyl)-amino]-1H-indazole-3-carboxylic acid phenylamide MS (ESI) m/z 364 $MH^+$ Example 634

5-[(Furan-2-carbonyl)-amino]-1H-indazole-3-carboxylic acid phenylamide

MS (ESI) m/z 347 $MH^+$

Example 635

5-[2-(Thiophen-2-yl)-acetylamino]-1H-indazole-3-carboxylic acid phenylamide

MS (ESI) m/z 377 $MH^+$

Example 636

5-Methanesulfonylamino-1H-indazole-3-carboxylic acid phenylamide 10 mg of 5-amino-1-trityl-1H-indazole-3-carboxylic acid phenylamide obtained by Production example 628 was dissolved in dichloromethane, added with 6 μl triethylamine and 4 mg of methanesulfonyl chloride, and stirred at room temperature for 3 hours. Following addition of water and extraction with ethyl acetate, the residue obtained by evaporating the solvent was added with 0.5 mL of dichloromethane and 0.5 mL of trifluoroacetic acid, and stirred at room temperature for 1 hour. After evaporating the solvent, purification by LC-MS was conducted, to afford 0.22 mg of the title compound.

MS (ESI) m/z 331 $MH^+$

Example 637

3-Phenylcarbamoyl-1-trityl-1H-indazole-5-carboxylic acid produced by Production example 629 and various kinds of amine were amidated in the similar method as described in Example 44, followed by deprotection in accordance with the deprotection condition of Example 183, and purification by LC-MS, to afford the compounds of Examples 638-640.

Example 638

3-Phenylcarbamoyl-1H-indazole-5-carboxylic acid [(1S)-1-hydroxymethyl-2-methylpropyl]-amide MS (ESI)m/z 367 $MH^+$ Example 639

3-Phenylcarbamoyl-1H-indazole-5-carboxylic acid [(1S)-2-hydroxy-1-phenylethyl]-amide MS (ESI)m/z 401 $MH^+$ Example 640

3-Phenylcarbamoyl-1H-indazole-5-carboxylic acid[(1S)-1-carbamoylethyl]-amide

MS (ESI)m/z 352 $MH^+$

Example 641

3-Phenylcarbamoyl-1H-indazole-5-carboxylic acid 10 mg of 3-phenylcarbamoyl-1-trityl-1H-indazole-5-carboxylic acid produced by Production example 629 was dissolved in 0.5 mL of dichloromethane and 0.5 mL of trifluoroacetic acid, and stirred at room temperature for 3 hours, followed by purification by LC-MS, to afford 0.72 mg of the title compound.

MS (ESI)m/z 282 $MH^+$

Production Example 642

6-Fluoro-3-[(E)-2-(2-fluorophenyl)-vinyl]-5-nitro-1-trityl-1H-indazole

From 2.0 g 3-bromo-6-fluoro-5-nitro-1-trityl-1H-indazole obtained by Production example 180 and 1.46 g of 2-fluorostyrene, 1.15 g of the title compound was obtained as bright yellow crystals in accordance with the method of Example 181.

$^1$H-NMR (400 MHz, DMSO-$D_6$) δ 6.13 (1H, d, J=12.8 Hz), 7.17-7.45 (18H, m), 7.54 (1H, d, J=16.8 Hz), 7.81 (1H, d, J=16.8 Hz), 8.01 (1H, t, J=7.6 Hz), 9.15 (1H, d, J=7.2 Hz)

Production Example 643

6-Fluoro-3-[(E)-2-(2-fluorophenyl)-vinyl]-1-trityl-1H-indazol-5-ylamine

From 1.14 g of 6-fluoro-3-[(E)-2-(2-fluorophenyl)-vinyl]-5-nitro-1-trityl-1H-indazole obtained by Production example 642, 1.07 g of the title compound was obtained as bright yellow crystals in accordance with the method of Example 182.

$^1$H-NMR (400 MHz, DMSO-$D_6$) δ 5.09 (2H, br s), 5.92 (1H, d, J=12.4 Hz), 7.16-7.38 (20H, m), 7.41 (1H, d, J=16.8 Hz), 7.87 (1H, t, J=7.6 Hz

Production Example 644

6-Fluoro-3-[(E)-2-(3-fluorophenyl)-vinyl]-5-nitro-1-trityl-1H-indazole

In accordance with the method of Example 181, from 1.5 g of 3-bromo-6-fluoro-5-nitro-1-trityl-1H-indazole obtained by Production example 180 and 730 mg of 3-fluorostyrene, 872 mg of the title compound was obtained as bright yellow crystals.

$^1$H-NMR (400 MHz, DMSO-$D_6$) δ 6.12 (1H, d, J=12.8 Hz), 7.15 (1H, dt, J=2.0, 8.8 Hz), 7.20-7.45 (16H, m), 7.48 (1H, d, J=16.4 Hz), 7.54 (1H, d, J=8.0 Hz), 7.69 (1H, d, J=10.8 Hz), 7.77 (1H, d, J=16.4 Hz), 9.19 (1H, d, J=7.2 Hz)

Production Example 645

6-Fluoro-3-[(E)-2-(3-fluorophenyl)-vinyl]-1-trityl-1H-indazol-5-ylamine

In accordance with the method of Example 182, from 870 mg of 6-fluoro-3-[(E)-2-(3-fluorophenyl)-vinyl]-5-nitro-1- trityl-1H-indazole obtained by Production example 644, 707 mg of the title compound was obtained as bright yellow crystals. The instrumental data coincided with that of Production example 174.

Production Example 646

6-Fluoro-5-nitro-3-[(E)-2-(pyridin-3-yl)-vinyl]-1-trityl-1H-indazole

In accordance with the method of Example 181, from 1.0 g of 3-bromo-6-fluoro-5-nitro-1-trityl-1H-indazole obtained by Production example 180 and 314 mg of 3-vinylpyridine, 588 mg of the title compound was obtained as bright yellow crystals.

$^1$H-NMR (400 MHz, DMSO-$D_6$) δ 6.14 (1H, d, J=12.8 Hz), 7.10-7.45 (16H, m), 7.50 (1H, d, J=16.8 Hz), 7.81 (1H, d, J=16.8 Hz), 8.01 (1H, d, J=8.0 Hz), 8.50 (1H, dd, J=2.0, 4.8 Hz), 8.90 (1H, d, J=2.0 Hz), 9.19 (1H, d, J=7.2 Hz)

Production Example 647

6-Fluoro-3-[(E)-2-(pyridin-3-yl)-vinyl]-1-trityl-1H-indazol-5-ylamine

In accordance with the method of Example 182, from 587 mg of 6-fluoro-5-nitro-3-[(E)-2-(pyridin-3-yl)-vinyl]-1-trityl-1 h-indazole obtained by Production example 646, 465 mg of the title compound was obtained as bright yellow crystals.

$^1$H-NMR (400 MHz, DMSO-$D_6$) δ 4.99 (2H, br s), 5.90 (1H, d, J=12.4 Hz), 7.13-7.45 (18H, m), 7.46 (1H, d, J=16.8 Hz), 8.11 (1H, d, J=7.6 Hz), 8.43 (1H, d, J=2.0, 4.4 Hz), 8.75 (1H, d, J=2.0 Hz)

Production Example 648

6-Fluoro-5-nitro-3-[(E)-2-(thiophen-2-yl)-vinyl]-1-trityl-1H-indazole

In accordance with the method of Example 181, from 2.0 g of 3-bromo-6-fluoro-5-nitro-1-trityl-1H-indazole obtained by Production example 180 and 1.10 g of 2-vinylthiophene, 684 mg of the title compound was obtained as yellow crystals.

$^1$H-NMR (400 MHz, DMSO-$D_6$) δ 6.14 (1H, d, J=12.4 Hz), 7.11 (1H, dd, J=3,6, 4.8 Hz), 7.17-7.45 (17H, m), 7.57 (1H, d, J=4.8 Hz), 7.67 (1H, d, J=16.4 Hz), 9.15 (1H, d, J=7.2 Hz

Production Example 649

6-Fluoro-3-[(E)-2-(thiophen-2-yl)-vinyl]-1-trityl-1H-indazol-5-ylamine

In accordance with the method of Example 182, from 647 mg of 6-fluoro-5-nitro-3-[(E)-2-(thiophen-2-yl)-vinyl]-1-trityl-1H-indazole obtained by Production example 648, 623 mg of the title compound was obtained as bright yellow crystals.

$^1$H-NMR (400 MHz, DMSO-$D_6$) δ 5.00 (2H, br s), 5.90 (1H, d, J=12.0 Hz), 7.01 (1H, d, J=16.4 Hz), 7.08 (1H, dd, J=3.6, 5.2 Hz), 7.16-7.44 (18H, m), 7.49 (1H, d, J=5.2 Hz

Production Example 650

1-(tert-Butoxycarbonyl-methyl-amino)-cyclopropane carboxylic acid ethyl ester

To a solution of 500 mg of 1-tert-butoxycarbonylamino-cyclopropane carboxylic acid ethyl ester which was obtained from 1,1-cyclopropane dicarboxylic acid diethyl ester in accordance with the method described in the document (Journal of Medicinal Chemistry, 31, 2004 (1988)) in 5 mL of dimethylformamide, 0.2 mL of methyl iodide and 88 mg of 60% sodium hydride were added and stirred at room temperature for 1 hour. After adding water, the reaction solution was extracted with diethyl ether. The organic layer was washed with water and saturated brine, and dried over anhydrous magnesium sulfate. The residue obtained by evaporating the solvent was purified by silica gel column chromatography (ethyl acetate:n-hexane=1:19), to afford 59 mg of the title compound as a pale yellow oil.

$^1$H-NMR (400 MHz, DMSO-$D_6$) δ 1.17 (3H, t, J=7.2 Hz), 1.22 (2H, br s), 1.36, 1.40 (11H, each s), 2.76, 2.81 (3H, each s), 4.09 (2H, q, J=7.2 Hz Production Example 651

1-(tert-Butoxycarbonyl-methyl-amino)-cyclopropane carboxylic acid

To a solution of 48 mg of 1-(tert-butoxycarbonyl-methyl-amino)-cyclopropane carboxylic acid ethyl ester in 0.4 mL of methanol, 0.1 mL of 5N sodium hydroxide aqueous solution was added and stirred at room temperature overnight. After adding water, the reaction solution was washed with diethyl ether. The aqueous layer was added with 0.7 mL of 1N hydrochloric acid, and extracted with ethyl acetate. The organic layer was washed with saturated brine, and dried over anhydrous magnesium sulfate. The solvent was evaporated, to afford 36 mg of the title compound as white crystals.

$^1$H-NMR (400 MHz, DMSO-$D_6$) δ 1.18-1.46 (4H, m), 1.36, 1.39 (9H, each s), 2.76, 2.80 (3H, each s), 12.50 (1H, br s Production Example 652

1-(tert-Butyl-dimethyl-silanyloxymethyl)-cyclopropane carboxylic acid ethyl ester To a solution of 700 mg of 1-hydroxymethyl-cyclopropane carboxylic acid ethyl ester obtained from 1,1-cyclopropane dicarboxylic acid diethyl ester in accordance with the method described in the document (Tetrahedron Letters, 40, 5467 (1988)) in 7 mL of N,N-dimethylformamide, 430 mg of imidazole and 916 mg of tert-butyldimethylchlorosilane were added and stirred at room temperature overnight. After adding n-hexane to the reaction solution, the organic layer was washed successively with water, 1N hydrochloric acid, water, saturated aqueous sodium hydrogen carbonate and saturated brine. The organic layer was dried over anhydrous magnesium sulfate. The solvent was evaporated, to afford 1.13 g of the title compound as a colorless oil.

$^1$H-NMR (400 MHz, DMSO-$D_6$) δ 0.03 (6H, s), 0.85 (11H, S), 1.13 (2H, dd, J=4.0, 6.8 Hz), 1.17 (3H, t, J=7.2 Hz 3.74 (2H, s), 4.05 (2H, q, J=7.2 Hz

Production Example 653

1-(tert-Butyl-dimethyl-silanyloxymethyl)-cyclopropane carboxylic acid 1.10 g of 1-(tert-butyl-dimethyl-silanyloxymethyl)-cyclopropane carboxylic acid ethyl ester was hydrolyzed in the manner as described in Production method 651, to afford 781 mg of the title compound as a colorless oil.

$^1$H-NMR (400 MHz, DMSO-$D_6$) δ 0.03 (6H, s), 0.81 (2H, dd, J=3.6, 6.8 Hz), 0.85 (9H, S), 0.99 (2H, dd, J=3.6, 6.8 Hz 3.74 (2H, s), 12.18 (1H, br s

Production Example 654

(2S, 4R)-4-(tert-Butyl-dimethyl-silanyloxy)-pyrrolidine-2-carboxylic acid methyl ester To a solution of 2.5 g of 4-(tert-butyl-dimethyl-silanyloxy)-pyrrolidine-1,2-dicarboxylic acid 1-benzylester 2-methyl ester obtained from trans-4-hydroxy-L-proline in accordance with the method of JP-A 62-155279 in 25 mL of methanol was added 250 mg of 20% palladium hydroxide, and stirred overnight at normal pressure under nitrogen atmosphere. After filtering out the catalyst, the solvent was evaporated, to afford 1.64 g of the title compound as a colorless oil.

$^1$H-NMR (400 MHz, DMSO-$D_6$) δ 1.78-1.93 (2H, m), 2.60 (1H, dd, J=2.4, 11.2 Hz), 3.03 (1H, dd, J=5.2, 11.2 Hz), 3.61 (3H, s), 3.79 (1H, t, J=8.0 Hz), 4.32-4.39 (1H, m)

Production Example 655

(2S, 4R)-4-(tert-butyl-dimethyl-silanyloxy)-1-methyl-pyrrolidine-2-carboxylic acid methyl ester To a solution of 800 mg of (2S, 4R)-4-(tert-butyl-dimethyl-silanyloxy)-pyrrolidine-2-carboxylic acid methyl ester in 8 mL of methanol, 0.35 mL of 37% formalin and 80 mg of 10% palladium on carbon were added, and stirred at 4 atm. Hydrogen pressure for 10 hours. After filtering out the catalyst, the solvent was evaporated, and the residue was separated and purified by silica gel column chromatography (ethyl acetate: n-hexane=1:6), to afford 489 mg of the title compound as a colorless oil.

$^1$H-NMR (400 MHz, DMSO-$D_6$) δ 1.80-1.90 (1H, ddd, 4.0, 8.0, 12.0 Hz), 2.08 (1H, td, J=4.0, 12.0 Hz), 2.20 (1H, dd, J=5.6, 9.2 Hz), 2.27 (3H, s), 3.15-3.24 (2H, m), 3.62 (3H, s), 4.32-4.39 (1H, m)

Production Example 656

(2S, 4R)-4-(tert-Butyl-dimethyl-silanyloxy)-1-methyl-pyrrolidine-2-carboxylic acid From 488 mg of (2S,4R)-4-(tert-butyl-dimethyl-silanyloxy)-methyl-pyrrolidine-2-carboxylic acid methyl ester, 625 mg of the title compound was obtained as white non-crystalline powder in the method as described in Production method 651.

$^1$H-NMR (400 MHz, DMSO-$D_6$) δ 1.80-1.90 (1H, ddd, 4.0, 8.0, 12.0 Hz), 2.08 (1H, td, J=4.0, 12.0 Hz), 2.20 (1H, dd, J=5.6, 9.2 Hz), 2.27 (3H, s), 3.15-3.24 (2H, m), 3.62 (3H, s), 4.32-4.39 (1H, m Production Example 657

(2S, 4R)-1-Acetyl 4-(tert-butyl-dimethyl-silanyloxy)-pyrrolidine-2-carboxylic acid To a solution of 800 mg of (2S, 4R)-4-(tert-butyl-dimethyl-silanyloxy)-pyrrolidine-2-carboxylic acid methyl ester obtained by Production example 654 in 10 mL of pyridine, 0.35 mL of acetic anhydride was added and stirred at room temperature for 1.5 hours. After adding ethyl acetate to the reaction solution, the organic layer was washed successively with water, 1N hydrochloric acid, water, saturated aqueous sodium hydrogen carbonate and saturated brine. After drying the organic layer over anhydrous magnesium sulfate, the solvent was evaporated, to obtain crude (2S, 4R)-1-acetyl-4-(tert-butyl-dimethyl-silanyloxy)-pyrrolidine-2-carboxylic acid methyl ester. Then this ester was hydrolyzed in the manner as described in Production example 651, to afford 337 mg of the title compound as pale red crystals.

$^1$H-NMR (400 MHz, DMSO-$D_6$) δ 0.07 (6H, s), 0.85 (9H, s), 1.92-2.13 (2H, m), 1,95 (3H, s), 3.70 (1H, dd, J=5.2, 10.8 Hz), 4.20 (1H, t, J=8.0 Hz), 4.46-4.53 (1H, m), 12.45 (1H, br s )

Example 658

Various kinds of amine obtained by Production example 182, Production example 643, Production example 645, Production example 647 and Production example 649, and various kinds of carboxylic acid obtained by Production example 651, Production example 653, Production example 656 and Production example 657 or commercially available carboxylic acid were amidated in the manner as described in Example 183, followed by deprotection (deprotection of compounds having a tert-butyldimethylsilyl group was conducted using 95% trifluoroacetic acid) and purification by LC-MC, to afford the compounds of Examples 659-688.

Example 659

Cyclopropane Carboxylic acid {6-fluoro-3-[(E)-2-(2-fluorophenyl)-vinyl]-1H-indazol-5-yl}-amide MS (ESI) m/z 340 $MH^+$ Example 660

N-{6-Fluoro-3-[(E)-2-(2-fluorophenyl)-vinyl]-1H-indazol-5-yl}-acetamide

MS (ESI) m/z 314 $MH^+$

Example 661

N-{6-Fluoro-3-[(E)-2-(2-fluorophenyl)-vinyl]-1H-indazol-5-yl}-3-hydroxy-2,2-dimethyl-propionamide MS (ESI) m/z 372 $MH^+$ Example 662

N-{6-Fluoro-3-[(E)-2-(2-fluorophenyl)-vinyl]-1H-indazol-5-yl}-3-hydroxy-3-methyl-butylamide MS (ESI) m/z 372 $MH^+$ Example 663

N-{6-Fluoro-3-[(E)-2-(2-fluorophenyl)-vinyl]-1H-indazol-5-yl}-3-hydroxy-propionamide MS (ESI) m/z 344 $MH^+$ Example 664

N-{6-Fluoro-3-[(E)-2-(4-fluorophenyl)-vinyl]-1H-indazol-5-yl}-3-hydroxy-3-methyl-butylamide MS (ESI) m/z 372 $MH^+$ Example 665

N-{6-Fluoro-3-[(E)-2-(4-fluorophenyl)-vinyl]-1H-indazol-5-yl}-3-hydroxy-propionamide MS (ESI) m/z 344 $MH^+$ Example 666

N-{6-Fluoro-3-[(E)-2-(4-fluorophenyl)-vinyl]-1H-indazol-5-yl}-3-hydroxy-butylamide MS (ESI) m/z 358 $MH^+$ Example 667

N-{6-Fluoro-3-[(E)-2-(4-fluorophenyl)-vinyl]-1H-indazol-5-yl}-(3R)-3-hydroxy-3-phenyl-propionamide MS (ESI) m/z 420 $MH^+$ Example 668

Cyclopropane-1,1-dicarboxylic acid amide {6-fluoro-3-[(E)-2-(4-fluorophenyl)-vinyl]-1H-indazol-5-yl}-amide MS (ESI) m/z 383 $MH^+$ Example 669

N-{6-Fluoro-3-[(E)-2-(pyridine-3-yl)-vinyl]-1H-indazol-5-yl}-3-hydroxy-2,2-dimethyl-propionamide MS (ESI) m/z 355 $MH^+$ Example 670

N-{6-Fluoro-3-[(E)-2-(pyridin-3-yl)-vinyl]-1H-indazol-5-yl}-3-hydroxy-3-methyl-butylamide MS (ESI) m/z 355 $MH^+$ Example 671

1-Hydroxy-cyclopropane carboxylic acid {6-fluoro-3-[(E)-2-(pyridin-3-yl)-vinyl]-1H-indazol-5-yl}-amide MS (ESI) m/z 339 $MH^+$ Example 672

Cyclopropane-1,1-dicarboxylic acid amide {6-fluoro-3-[(E)-2-(pyridin-3-yl)-vinyl]-1H-indazol-5-yl}-amide MS (ESI) m/z 366 $MH^+$ Example 673

Cyclopropane Carboxylic acid {6-fluoro-3-[(E)-2-(pyridin-3-yl)-vinyl]-1H-indazol-5-yl}-amide MS (ESI) m/z 323 $MH^+$ Example 674

N-{6-Fluoro-3-[(E)-2-(pyridin-3-yl)-vinyl]-1H-indazol-5-yl}-acetamide

MS (ESI) m/z 297 $MH^+$

Example 675 cis-2-Hydroxy-cyclopentane carboxylic acid {6-fluoro-3-[(E)-2-(4-fluorophenyl)-vinyl]-1H-indazol-5-yl}-amide MS (ESI) m/z 384 $MH^+$ Example 676

1-Hydroxy-cyclopropane carboxylic acid {6-fluoro-3-[(E)-2-(4-fluorophenyl)-vinyl]-1H-indazol-5-yl}-amide MS (ESI) m/z 356 $MH^+$ Example 677

(2S, 4R)-4-Hydroxy-pyrrolidine-2-carboxylic acid {6-fluoro-3-[(E)-2-(4-fluorophenyl)-vinyl]-1H-indazol-5-yl}-amide MS (ESI) m/z 385 $MH^+$ Example 678

1-Hydroxymethyl-cyclopropane carboxylic acid {6-fluoro-3-[(E)-2-(4-fluorophenyl)-vinyl]-1H-indazol-5-yl}-amide MS (ESI) m/z 320 $MH^+$ Example 679

1-Hydroxymethyl-cyclopropane carboxylic acid {6-fluoro-3-[(E)-2-(3-fluorophenyl)-vinyl]-1H-indazol-5-yl}-amide MS (ESI) m/z 370 $MH^+$ Example 680

1-Hydroxymethyl-cyclopropane carboxylic acid {6-fluoro-3-[(E)-2-(thiophen-2-yl)-vinyl]-1H-indazol-5-yl}-amide MS (ESI) m/z 358 $MH^+$ Example 681

1-Methylamino-cyclopropane carboxylic acid {6-fluoro-3-[(E)-2-(4-fluorophenyl)-vinyl]-1H-indazol-5-yl}-amide MS (ESI) m/z 369 $MH^+$ Example 682

1-Methylamino-cyclopropane carboxylic acid {6-fluoro-3-[(E)-2-(3-fluorophenyl)-vinyl]-1H-indazol-5-yl}-amide MS (ESI) m/z 369 $MH^+$ Example 683

1-Methylamino-cyclopropane carboxylic acid {6-fluoro-3-[(E)-2-(thiophen-2-yl)-vinyl]-1H-indazol-5-yl}-amide MS (ESI) m/z 357 $MH^+$ Example 684

1-Hydroxy-cyclopropane carboxylic acid {6-fluoro-3-[(E)-2-(3-fluorophenyl)-vinyl]-1H-indazol-5-yl}-amide MS (ESI) m/z 356 $MH^+$ Example 685

1-Hydroxy-cyclopropane carboxylic acid {6-fluoro-3-[(E)-2-(thiophen-2-yl)-vinyl]-1H-indazol-5-yl}-amide MS (ESI) m/z 344 $MH^+$ Example 686

2-Cyclopropyl-N-{6-fluoro-3-[(E)-2-(4-fluorophenyl)-vinyl]-1H-indazol-5-yl}-acetamide MS (ESI) m/z 354 $MH^+$ Example 687

(2S, 4R)-4-Hydroxy-1-methyl-pyrrolidine-2-carboxylic acid {6-fluoro-3-[(E)-2-(4-fluorophenyl)-vinyl]-1H-indazol-5-yl}-amide MS (ESI) m/z 399 $MH^+$ Example 688

(2S, 4R)-1-Acetyl-4-hydroxy-pyrrolidine-2-carboxylic acid {6-fluoro-3-[(E)-2-(4-fluorophenyl)-vinyl]-1H-indazol-5-yl}-amide MS (ESI) m/z 427 $MH^+$ Production Example 689

1-(6-Fluoro-5-nitro-1H-indazole-1-yl)-ethanone

A mixed solution of 10 g of N-(5-fluoro-2-methyl-4-nitrophenyl)-acetamide obtained by Production example 177, 40 mL of glacial acetic acid and 13.4 mL of acetic anhydride was added dropwise with 10.1 mL of isoamyl nitrite while heating to 80° C., and after completion of the dropping, the mixture was stirred at 90° C. for 3 hours. The solvent was evaporated, and the precipitated crystals were collected by filtration, to afford 1.71 g of the title compound as bright yellow crystals.

$^1$H-NMR (400 MHz, DMSO-$D_6$) δ 2.76 (3H, s), 8.27 (1H, d, J=11.6 Hz), 8.68 (1H, s), 8.88 (1H, d, J=7.6 Hz)

Production Example 690

6-Fluoro-5-nitro-1H-indazole 1.6 g of 1-(6-fluoro-5-nitro-1H-indazole-1-yl)-ethanone was hydrolyzed in accordance with the method of Production example 409, to afford 1.26 g of the title compound as pale red crystals. The instrumental data coincided with that of Production example 179.

Example 691

6-Fluoro-3-[(E)-2-(4-fluorophenyl)-vinyl]-1-trityl-1H-indazol-5-ylamine synthesized by Production example 182 and various kinds of carboxylic acid were treated in the similar method as described in Example 183, to afford the compounds of Examples 692-730.

Example 692

2-Amino-N-{6-fluoro-3-[(E)-2-(4-fluorophenyl)-vinyl]-1H-indazol-5-yl}-3-methyl-butylamide MS (ESI) m/z 371 $MH^+$ Example 693

N-{6-Fluoro-3-[(E)-2-(4-fluorophenyl)-vinyl]-1H-indazol-5-yl}-3-methyl-2-methylamino-butylamide MS (ESI) m/z 385 $MH^+$ Example 694

N-{6-Fluoro-3-[(E)-2-(4-fluorophenyl)-vinyl]-1H-indazol-5-yl}-benzamide

MS (ESI) m/z 376 $MH^+$

Example 695

Pyridine-2-carboxylic acid {6-fluoro-3-[(E)-2-(4-fluorophenyl)-vinyl]-1H-indazol-5-yl}-amide MS (ESI) m/z 377 MH+

Example 696

N-{6-Fluoro-3-[(E)-2-(4-fluorophenyl)-vinyl]-1H-indazol-5-yl}-nicotinamide

MS (ESI) m/z 377 MH+

Example 697

N-{6-Fluoro-3-[(E)-2-(4-fluorophenyl)-vinyl]-1H-indazol-5-yl}-isonicotinamide

MS (ESI) m/z 377 MH+

Example 698

Pyrimidine-5-carboxylic acid {6-fluoro-3-[(E)-2-(4-florophenyl)-vinyl]-1H-indazol-5-yl}-amide MS (ESI) m/z 378 MH+

Example 699

Pyrazine-2-carboxylic acid {6-fluoro-3-[(E)-2-(4-fluorophenyl)-vinyl]-1H-indazol-5-yl}-amide MS (ESI) m/z 378 MH+

Example 700

Thiophene-2-carboxylic acid {6-fluoro-3-[(E)-2-(4-fluorophenyl)-vinyl]-1H-indazol-5-yl}-amide MS (ESI) m/z 382 MH+

Example 701

1-Methyl-1H-pyrrole-2-carboxylic acid {6-fluoro-3-[(E)-2-(4-fluorophenyl)-vinyl]-1H-indazol-5-yl}-amide MS (ESI) m/z 379 MH+

Example 702

1H-Pyrrole-2-carboxylic acid {6-fluoro-3-[(E)-2-(4-fluorophenyl)-vinyl]-1H-indazol-5-yl}-amide MS (ESI) m/z 365 MH+

Example 703

5-Methyl-isoxazole-4-carboxylic acid {6-fluoro-3-[(E)-2-(4-fluorophenyl)-vinyl]-1H-indazole-5-yl}-amide MS (ESI) m/z 381 MH+

Example 704

3,5-Dimethyl-isoxazole-4-carboxylic acid {6-fluoro-3-[(E)-2-(4-fluorophenyl)-vinyl]-1H-indazol-5-yl}-amide MS (ESI) m/z 395 MH+

Example 705

N-{6-Fluoro-3-[(E)-2-(4-fluorophenyl)-vinyl]-1H-indazol-5-yl}-2,6-dimethoxy-nicotinamide MS (ESI) m/z 437 MH+

Example 706

6-Hydroxy-pyridine-2-carboxylic acid {6-fluoro-3-[(E)-2-(4-fluorophenyl)-vinyl]-1H-indazol-5-yl}-amide MS (ESI) m/z 393 MH+

Example 707

N-{6-Fluoro-3-[(E)-2-(4-fluorophenyl)-vinyl]-1H-indazol-5-yl}-2-methoxy-nicotinamide MS (ESI) m/z 407 MH+

Example 708

N-{6-Fluoro-3-[(E)-2-(4-fluorophenyl)-vinyl]-1H-indazol-5-yl}-2-hydroxy-nicotinamide MS (ESI) m/z 393 MH+

Example 709

N-{6-Fluoro-3-[(E)-2-(4-fluorophenyl)-vinyl]-1H-indazol-5-yl}-6-hydroxy-nicotinamide MS (ESI) m/z 393 MH+

Example 710

Cyclobutane Carboxylic Acid {6-fluoro-3-[(E)-2-(4-fluorophenyl)-vinyl]-1H-indazole-5-yl}-amide MS (ESI) m/z 354 MH+

Example 711

1-Cyano-cyclopropane carboxylic acid {6-fluoro-3-[(E)-2-(4-fluorophenyl)-vinyl]-1H-indazol-5-yl}-amide MS (ESI) m/z 365 MH+

Example 712

N-{6-Fluoro-3-[(E)-2-(4-fluorophenyl)-vinyl]-1H-indazol-5-yl}-2,2-dimethyl-propioneamide MS (ESI) m/z 356 MH+

Example 713

1-Methyl-cyclopropane carboxylic acid {6-fluoro-3-[(E)-2-(4-fluorophenyl)-vinyl]-1H-indazol-5-yl}-amide MS (ESI) m/z 354 $MH^+$ Example 714

2-Methyl-cyclopropane carboxylic acid {6-fluoro-3-[(E)-2-(4-fluorophenyl)-vinyl]-1H-indazol-5-yl}-amide MS (ESI) m/z 354 $MH^+$ Example 715

Thiazole-5-carboxylic acid {6-fluoro-3-[(E)-2-(4-fluorophenyl)-vinyl]-1H-indazol-5-yl}-amide MS (ESI) m/z 383 $MH^+$ Example 716

2-Ethyl-N-{6-fluoro-3-[(E)-2-(4-fluorophenyl)-vinyl]-1H-indazol-5-yl}-butylamide MS (ESI) m/z 370 $MH^+$ Example 717

2,2-Difluoro-N-{6-fluoro-3-[(E)-2-(4-fluorophenyl)-vinyl]-1H-indazol-5-yl}-acetamide MS (ESI) m/z 350 $MH^+$ Example 718

Thiophene-3-carboxylic acid {6-fluoro-3-[(E)-2-(4-fluorophenyl)-vinyl]-1H-indazol-5-yl}-amide MS (ESI) m/z 382 $MH^+$ Example 719

N-{6-Fluoro-3-[(E)-2-(4-fluorophenyl)-vinyl]-1H-indazol-5-yl)-2-(pyridin-2-yl}-acetamide MS (ESI) m/z 391 $MH^+$ Example 720

N-{6-Fluoro-3-[(E)-2-(4-fluorophenyl)-vinyl]-1H-indazol-5-yl}-2-(pyridin-3-yl)-acetamide MS (ESI) m/z 391 $MH^+$ Example 721

N-{6-Fluoro-3-[(E)-2-(4-fluorophenyl)-vinyl]-1H-indazol-5-yl}-2-(pyridin-4-yl)-acetamide MS (ESI) m/z 391 $MH^+$ Example 722

N-{6-Fluoro-3-[(E)-2-(4-fluorophenyl)-vinyl]-1H-indazol-5-yl}-2-(thiophen-3-yl)-acetamide MS (ESI) m/z 396 $MH^+$ Example 723

2-Benzo[1,3]dioxol-5-yl-N-{6-fluoro-3-[(E)-2-(4-fluorophenyl)-vinyl]-1H-indazol-5-yl}-acetamide MS (ESI) m/z 434 $MH^+$ Example 724

2-Amino-N-{6-fluoro-3-[(E)-2-(4-fluorophenyl)-vinyl]-1H-indazol-5-yl}-acetamide

MS (ESI) m/z 329 $MH^+$

Example 725

N-{6-Fluoro-3-[(E)-2-(4-fluorophenyl)-vinyl]-1H-indazol-5-yl}-2-methylamino-acetamide MS (ESI) m/z 343 $MH^+$ Example 726

2-Dimethylamino-N-{6-fluoro-3-[(E)-2-(4-fluorophenyl)-vinyl]-1H-indazol-5-yl}-acetamide MS (ESI) m/z 357 $MH^+$ Example 727

2-Acetoylamino-N-{6-fluoro-3-[(E)-2-(4-fluorophenyl)-vinyl]-1H-indazol-5-yl}-acetamide MS (ESI) m/z 371 $MH^+$ Example 728

N-{6-Fluoro-3-[(E)-2-(4-fluorophenyl)-vinyl]-1H-indazol-5-yl}-2-methoxy-acetamide MS (ESI) m/z 344 $MH^+$ Example 729

2-Cyano-N-{6-fluoro-3-[(E)-2-(4-fluorophenyl)-vinyl]-1H-indazol-5-yl}-acetamide

MS (ESI) m/z 339 $MH^+$

Example 730

Furan-2-carboxylic acid {6-fluoro-3-[(E)-2-(4-fluorophenyl)-vinyl]-1H-indazol-5-yl}-amide MS (ESI) m/z 366 $MH^+$ Production Example 731

5-Formylfuran-2-carboxylic acid benzyl ester 500 mg of 5-formylfuran-2-carboxylic acid was dissolved in 10 mL of tetrahydrofuran, added with 990 μl of triethylamine, cooled to 0° C., and then added with 374 μl of ethyl chloroformate. After stirring at this temperature for 30 minutes, 406 μl of benzylalcohol was added and stirred at room temperature overnight. Adding water to stop the reaction, the solution was extracted with ethyl acetate. The organic phase was washed with water and saturated brine, and dried over anhydrous magnesium sulfate. The solvent was evaporated, and purified by silica gel column chromatography, to afford 508 mg of the title compound as white crystals.

$^1$H-NMR (400 MHz, DMSO-$D_6$) δ 5.38 (2H, s), 7.31-7.49 (5H, m), 7.54 (1H, dd, J=1.2, 3.6 Hz), 7.63 (1H, dd, J=1.2, 3.6 Hz)

Production Example 732

Furan-2,5-dicarboxylic acid monobenzyl ester 490 mg of 5-formylfuran-2-carboxylic acid benzyl ester was dissolved in 10 mL of acetonitrile, and added with a solution containing 413 mg of sulfamic acid in 5 mL of water. After cooling to 0° C., a solution containing 202 mg of sodium chlorite and 232 mg of potassium dihydrogen phosphate in 5 mL of water was added dropwise. After cooling at this temperature for 30 minutes, sodium thiosulfate aqueous solution was added at 0° C. to stop the reaction, and extracted with a mixture of tetrahydrofuran and ethyl acetate. The organic phase was washed with water and saturated brine, and dried over anhydrous magnesium sulfate. The solvent was distilled off to afford 520 mg of the title compound as white crystals.

$^1$H-NMR (400 MHz, DMSO-$D_6$) δ 5.36 (2H, s), 7.32-7.48 (7H, m )

Production Example 733

5-Carbamoylfuran-2-carboxylic acid benzyl ester 170 mg of furan-2,5-dicarboxylic acid monobenzyl ester was dissolved in 5 mL of tetrahydrofuran, and added with 144 μl of triethylamine. After cooling to 0° C., 72.3 μl of ethyl chloroformate was added dropwise and stirred at this temperature for 30 minutes. 1 mL of concentrated ammonia water was added and stirred at room temperature for 10 minutes, and then aqueous ammonium chloride was added to stop the reaction. After extracting the aqueous phase with ethyl acetate, the organic phase was washed with water and saturated brine, and dried over anhydrous magnesium sulfate. The solvent was evaporated, to afford 185 mg of the title compound as white crystals.

$^1$H-NMR (400 MHz, DMSO-$D_6$) δ 5.35 (2H, s), 7.25 (1H, d, J=1.2 Hz), 7.35-7.47 (6H, m), 7.67 (1H, bs), 8.04 (1H, bs)

Production Example 734

5-Methylcarbamoylfuran-2-carboxylic acid benzyl ester 170 mg of furan-2,5-dicarboxylic acid monobenzyl ester obtained by Production example 732 was dissolved in 15 mL of N,N-dimethylformamide, and this solution was added with 470 μl of diisopropylethylamine, 127 mg of hydroxybenzotriazole, and 414 μl of 2.0M methylamine in tetrahydrofuran, and stirred room temperature for 10 minutes. After adding 265 mg of 1-ethyl-3-(3-dimethylaminopropyl)carbodiimide hydrochloride and stirring overnight, ice was added to stop the reaction. The aqueous phase was extracted with ethyl acetate, and the organic phase was washed with water and saturated brine and dried over anhydrous magnesium sulfate. The solvent was distilled off, to afford 128 mg of the title compound as pale yellow crystals.

$^1$H-NMR (400 MHz, DMSO-$D_6$) δ 2.76 (3H, d, J=4.8 Hz), 5.36 (2H, s), 7-0.20 (1H, d, J=3.6 Hz), 7.31-7.47 (6H, m), 8.57 (1H, d, J=4.8 Hz)

Production Example 735

5-Dimethylcarbamoylfuran-2-carboxylic acid benzyl ester

In accordance with Production example 734, from 170 mg of furan-2,5-dicarboxylic acid monobenzyl ester obtained by Production example 732 and 414 μl of 2.0 M dimethyl amine in tetrahydrofuran, 139 mg of the title compound was obtained as a yellow oil.

$^1$H-NMR (400 MHz, DMSO-$D_6$) δ 2.98 (3H, bs), 3.18 (3H, bs), 5.35 (2H, s), 7.12 (1H, dd, J=0.8, 4.0 Hz), 7.31-7.47 (6H, m )

Production Example 736

5-Carbamoylfuran-2-carboxylic acid 90 mg of 5-carbamoylfuran-2-carboxylic acid benzyl ester obtained by Production example 733 was suspended in 2 mL of ethanol, added with 9 mg of palladium carbon, and stirred overnight at room temperature under hydrogen atmosphere. The insoluble substances were filtered, and the filtrate was evaporated, and the resultant white solid was washed with 500 μl of diethyl ether, to afford 48 mg of the title compound.

$^1$H-NMR (400 MHz, DMSO-$D_6$) δ 7.12-7.17 (2H, m), 7.54 (1H, bs), 7.89 (1H, bs)

Production Example 737

5-Methylcarbamoylfuran-2-carboxylic acid

In accordance with the method of Production example 736, from 60 mg of 5-methylcarbamoylfuran-2-carboxylic acid benzyl ester obtained by Production example 734, 48 mg of the title compound was obtained.

$^1$H-NMR (400 MHz, DMSO-$D_6$) δ 2.75 (3H, d, J=4.8 Hz), 7.03 (1H, bs), 7.07 (1H, bs), 8.39 (1H, bs )

Production Example 738

5-Dimethylcarbamoylfuran-2-carboxylic acid

In accordance with the method of Production example 736, from 56 mg of 5-dimethylcarbamoylfuran-2-carboxylic acid benzyl ester obtained by Production example 735, 34 mg of the title compound was obtained.

$^1$H-NMR (400 MHz, DMSO-$D_6$) δ 2.99 (3H, bs), 3.20 (3H, bs), 7.06 (1H, d, J=3.6 Hz), 7.20 (1H, d, J=3.6 Hz)

Example 739

In accordance with the method of Example 183, from amines obtained by Production example 182 and Production example 649 and carboxylic acids obtained by Production examples 736-738, the compounds of Examples 740-745 were obtained.

Example 740

Furan-2,5-dicarboxylic acid 2-amide 5-{6-fluoro-3-[(E)-2-(4-fluorophenyl)-vinyl]-1H-indazol-5-yl}-amide MS (ESI) m/z 409 $MH^+$ Example 741

Furan-2,5-dicarboxylic Acid 2-({6-fluoro-3-[(E)-2-(4-fluorophenyl)-vinyl]-1H-indazol-5-yl}-amide) 5-methylamide MS (ESI) m/z 423 $MH^+$ Example 742

Furan-2,5-dicarboxylic Acid 2-dimethylamide 5-{6-fluoro-3-[(E)-2-(4-fluorophenyl)-vinyl]-1H-indazol-5-yl}-amide MS (ESI) m/z 437 $MH^+$ Example 743

Furan-2,5-dicarboxylic Acid 2-amide 5-{6-fluoro-3-[(E)-2-(thiophen-2-yl)-vinyl]-1H-indazol-5-yl}-amide MS (ESI) m/z 397 $MH^+$ Example 744

Furan-2,5-dicarboxylic acid 2-{6-fluoro-3-[(E)-2-(thiophen-2-yl)-vinyl]-1H-indazol-5-yl}-amide 5-methylamide MS (ESI) m/z 411 $MH^+$ Example 745

Furan-2,5-dicarboxylic acid 2-dimethylamide 5-{6-fluoro-3-[(E)-2-(thiophen-2-yl)-vinyl]-1H-indazol-5-yl}-amide MS (ESI) m/z 425 $MH^+$ Production Example 746

6-Fluoro-3-iodo-5-nitro-1H-indazole

In accordance with the method of Production example 206, from 5.57 g of 6-fluoro-5-nitro-1H-indazole obtained by Production example 179 and 7.97 g of N-iodosuccinimide, 9.24 g of the title compound was obtained as yellow crystals.

$^1$H-NMR (400 MHz, DMSO-$D_6$) δ 7.78 (1H, d, J=11.6 Hz), 8.29 (1H, d, J=6.8 Hz), 14.16 (1H, br s)

Production Example 747

6-Fluoro-3-iodo-5-nitro-1-trityl-1H-indazole 4.0 g of 6-fluoro-3-iodo-5-nitro-1H-indazole obtained by Production example 746 was dissolved in 150 mL of N,N-dimethylformamide, added with 782 mg of sodium hydride (containing 60%) at 0° C. and stirred at this temperature for 10 minutes. After adding 4.35 g of trityl chloride and stirring at room temperature for 5 hours and 30 minutes, ice was added to stop the reaction. The solid precipitated by adding water was collected via glass filter, and washed with water and 50% diethyl ether in hexane. The solvent was evaporated, to afford 5.9 g of the title compound as yellow crystals.

$^1$H-NMR (400 MHz, DMSO-$D_6$) δ 6.18 (1H, d, J=12.8 Hz), 7.16-7.19 (6H, m), 7.35-7.40 (9H, m), 8.28 (1H, d, J=7.2 Hz)

Production Example 748

3-[(E)-2-(Benzo[1,3]dioxol-5-yl)-vinyl]-6-fluoro-5-nitro-1-trityl-1 h-indazole

Under nitrogen atmosphere, 1 g of 6-fluoro-3-iodo-5-nitro-1-trityl-1H-indazole was dissolved in 10 mL of acetonitrile, added successively with 1.35 g of 5-vinyl-benzo[1,3]dioxole, 81.7 mg of palladium acetate (II), 162 mg of 2-(di-tert-butylphosphino)biphenyl and 2 mL of triethylamine, and stirred at 100° C. for 5 hours. After cooling to room temperature, 5 g of silica gel was added, and the solvent was evaporated, and purified by silica gel column chromatography, to obtain 468 mg of the crude product as yellow crystal. This crude product was washed with 50% diethylether solution in hexane, and the solvent was evaporated, to afford 143 mg of the title compound as yellow crystals.

$^1$H-NMR (400 MHz, DMSO-$D_6$) δ 6.06 (2H, s), 6.09 (1H, d, J=12.8 Hz), 6.93 (1H, d, J=8.4 Hz), 7.13 (1H, d, J=8.4 Hz), 7.02-7.23 (6H, m), 7.35-7.39 (10H, m), 7.51 (1H, s), 7.56 (1H, d, J=16.4), 9.14 (1H, d, J=7.2 Hz)

Production Example 749

3-[(E)-2-(Benzo[1,3]dioxol-5-yl)-vinyl]-6-fluoro-1-trityl-1H-indazole-5-ylamine 123 mg of 3-[(E)-2-(benzo[1,3]dioxol-5-yl)-vinyl]-6-fluoro-5-nitro-1-trityl-1H-indazole was treated in the similar method as described in Production example 182, to afford 95 mg of the title compound as a yellow solid.

$^1$H-NMR (400 MHz, $CDCl_3$) δ 5.97 (2H, s), 6.03 (1H, d, J=12.0 Hz), 6.78 (1H, d, J=8.0 Hz), 6.94 (1H, dd, J=1.2, 8.0 Hz), 7.07 (1H, d, J=0.8 Hz), 7.16-7.33 (16H, m)

Example 750

In accordance with Example 183, from 3-[(E)-2-benzo[1,3]dioxol-5-yl-vinyl]-6-fluoro-1-trityl-1H-indazol-5-ylamine obtained by Production example 749 and various kinds of carboxylic acid, the compounds of Examples 751-756 were obtained.

Example 751

N-{3-[(E)-2-(Benzo[1,3]dioxol-5-yl)-vinyl]-6-fluoro-1H-indazol-5-yl}-acetamide

MS (ESI) m/z 340 $MH^+$

Example 752

Cyclopropane carboxylic acid {3-[(E)-2-(benzo[1,3] dioxol-5-yl)-vinyl]-6-fluoro-1H-indazol-5-yl}-amide MS (ESI) m/z 366 $MH^+$ Example 753

Furan-2-carboxylic acid {3-[(E)-2-(benzo[1,3]dioxol-5-yl)-vinyl]-6-fluoro-1H-indazol-5-yl}-amide MS (ESI) m/z 392 $MH^+$ Example 754

N-{3-[(E)-2-(Benzo[1,3]dioxol-5-yl)-vinyl]-6-fluoro-1H-indazol-5-yl}-2-(thiophen-2-yl)-acetamide MS (ESI) m/z 422 $MH^+$ Example 755

1-Hydroxy-cyclopropane carboxylic acid {3-[(E)-2-(benzo[1,3]-dioxol-5-yl)-vinyl]-6-fluoro-1H-indazol-5-yl}-amide MS (ESI) m/z 382 $MH^+$ Example 756

(2S,4R)-4-Hydroxypyrrolidine-2-carboxylic acid {3-[(E)-2-(benzo[1,3]dioxol-5-yl)-vinyl]-6-fluoro-1H-indazol-5-yl}-amide MS (ESI) m/z 411 $MH^+$ Production Example 757

1-Aminomethyl-cyclopropane carboxylic acid

To a solution of 500 mg of 1-cyanocyclopropane carboxylic acid in 50 mL acetic acid was added 50 mg of platinum dioxide, stirred at room temperature for 4 hours under 4 atm. hydrogen atmosphere, and then the platinum dioxide was filtered off. The solvent was evaporated, to afford 518 mg of the title compound as a yellow oil.

$^1$H-NMR (400 MHz, DMSO-$D_6$) δ 0.58-0.64 (2H, m), 0.93 (2H, dd, J=3.6, 6.4 Hz), 2.78 (2H, s).

Example 758

1-Aminomethyl-cyclopropane Carboxylic acid {6-fluoro-3-[(E)-2-(4-fluorophenyl)-vinyl]-1H-indazol-5-yl}-amide 518 mg of 1-aminomethyl-cyclopropane carboxylic acid obtained by Production example 757 was dissolved in a mixed solvent of 9 mL 1,4-dioxane/4.5 mL water, added with 4.5 mL of 1N sodium hydroxide aqueous solution, stirred for 10 minutes under ice cooling, added with 1.08 g of tert-butyl dicarbonate under ice cooling, and further stirred at room temperature for 21 hours. Then the solvent was evaporated, added with saturated aqueous ammonium chloride under ice cooling, extracted twice with ethyl acetate, and the organic layer was washed with water and dried over anhydrous magnesium sulfate. The solvent was evaporated, to afford 1-(tert-butoxycarbonylaminomethyl)-cyclopropane carboxylic acid as a colorless oil.

To a solution of 200 mg 6-fluoro-3-[(E)-2-(4-fluorophenyl)-vinyl]-1-trityl-1H-indazol-5-ylamine obtained by Production example 182 in 3 mL of N,N-dimethylformamide were successively added 126 mg of 1-(tert-butoxycarbonylaminomethyl)-cyclopropane carboxylic acid, 151 mg of diisopropylethylamine, 89.4 mg of 1-hydroxybenztriazole monohydrate and 112 mg of 1-ethyl-3-(3-dimethylaminopropyl)carbodiimide hydrochloride (=WSC—HCl), stirred at room temperature for 46 hours, then added with aqueous ammonium chloride, extracted twice with ethyl acetate, an the organic layer was washed successively with water and saturated brine and dried over anhydrous magnesium sulfate. The solvent was evaporated, and the resultant crude product was purified and separated by silica gel column chromatography, to afford (1-{6-fluoro-3-[(E)-2-(4-fluorophenyl)-vinyl]-1-trityl-1H-indazol-5-yl carbamoyl}-cyclopropylmethyl)-carbamic acid tert-butyl ester. This was then dissolved in 2 mL of dichloromethane, several drops of triisopropylsilane was added followed by 2 mL of trifluoroacetic acid, and stirred at room temperature for 4.5 hours. Thereafter, saturated aqueous sodium hydrogen carbonate was added, extracted twice with ethyl acetate, and the organic layer was washed with saturated brine and dried over anhydrous magnesium sulfate. The solvent was evaporated, and the resultant crude product was purified and separated by LC-MS, to afford 46.64 mg of the title compound.

$^1$H-NMR (400 MHz, $CD_3OD$) δ1.24 (2H, dd, J=5.2, 6.8 Hz), 1.60 (2H, dd, J=5.2, 6.8 Hz), 3.19 (2H, s), 7.08-7.18 (2H, m), 7.31 (1H, d, J=10.4 Hz), 7.35 (1H, d, J=16.8 Hz), 7.46 (1H, d, J=16.8 Hz), 7.60-7.68 (2H, m), 8.14 (1H, d, J=6.8 Hz).

MS (ESI) m/z 369 $MH^+$

Example 759

1-(Acetylamino-methyl)-cyclopropane carboxylic acid {6-fluoro-3-[(E)-2-(4-fluorophenyl)-vinyl]-1H-indazol-5-yl}-amide To a solution of 10 mg of 1-aminomethyl-cyclopropane carboxylic acid {6-fluoro-3-[(E)-2-(4-fluorophenyl)-vinyl]-1H-indazol-5-yl}-amide obtained by Example 758 in 0.3 mL of N,N-dimethylformamide was added 2.9 mg of acetic anhydride, and stirred at room temperature for 38 hours under nitrogen atmosphere, and separated and purified by LC-MS, to afford 3.66 mg of the title compound.

$^1$H-NMR (400 MHz, $CD_3OD$) δ0.98 (2H, dd, J=4.4, 7.2 Hz), 1.32 (2H, dd, J=4.4, 7.2 Hz), 2.03 (3H, s), 3.60 (2H, s), 7.06-7.16 (2H, m), 7.30 (1H, d, J=10.0 Hz), 7.35 (1H, d, J=16.8 Hz), 7.46 (1H, d, J=16.8 Hz), 7.60-7.69 (2H, m), 8.30 (1H, d, J=7.2 Hz).

MS (ESI) m/z 411 $MH^+$

Production Example 760

3-[(E)-2-(4-Fluorophenyl)-vinyl]-4-[3-(tetrahydropyran-2-yl oxy)-propoxy]-1H-indazole-1,5-dicarboxylic acid 1-tert-butyl Ester 5-ethyl ester In accordance with the method of Production example 347, from 200 mg of 3-[(E)-2-(4-fluorophenyl)-vinyl]-4-hydroxy-1H-indazole-1,5-dicarboxylic acid 1-tert-butyl ester 5-ethyl ester obtained by Production example 346 and 1.05 g of 2-(3-bromopropoxy)-tetrahydropyran, 267 mg of the title compound was obtained as a colorless oil.

$^1$H-NMR (400 MHz, $CDCl_3$) δ1.23-2.33 (8H, m), 1.44 (3H, t, J=6.8 Hz), 1.75 (9H, s), 3.36-3.44 (1H,m), 3.52-3.60 (1H,m), 3.68-3.76 (1H, m), 3.85-3.91 (1H, m), 4.18-4.29 (2H, m), 4.43 (2H, q, J=6.8 Hz), 4.49 (1H, t, J=4.0 Hz), 7.05-7.12 (2H, m), 7.52-7.62 (3H, m), 7.80 (1H, d, J=16.4 Hz), 7.87 (1H, d, J=8.8 Hz), 7.99 (1H, d, J=8.8 Hz).

Example 761

3-[(E)-2-(4-Fluorophenyl)-vinyl]-4-(3-hydroxypropoxy)-1H-indazole-5-carboxylic acid In accordance with the methods of Example 16 and Example 350, from 267 mg of 3-[(E)-2-(4-fluorophenyl)-vinyl]-4-[3-(tetrahydropyran-2-yl oxy)-propoxy]-1H-indazole-1,5-dicarboxylic acid 1-tert-butyl ester 5-ethyl ester obtained by Production example 760, 83.1 mg of the title compound was obtained as flesh color crude crystals.

$^1$H-NMR (400 MHz, $CD_3OD$) 2.06-2.18 (2H, m), 3.82 (2H, t, J=6.0 Hz), 4.26 (2H, t, J=6.4 Hz), 7.10-7.17 (2H, m), 7.25 (1H, d, J=8.4 Hz), 7.54 (1H, d, J=16.0 Hz), 7.59-7.67 (2H, m), 7.63 (1H, d, J=16.0 Hz), 7.84 (1H, d, J=8.4 Hz).

MS (ESI) m/z 355 $(M-H)^-$

Production Example 762

4-(2-Carbamoylethoxy)-3-[(E)-2-(4-fluorophenyl)-vinyl]-1H-indazole-1,5-dicarboxylic acid 1-tert-butyl ester 5-ethyl ester In accordance with the method of Production example 347, from 120 mg of 3-[(E)-2-(4-fluorophenyl)-vinyl]-4-hydroxy-1H-indazole-1,5-dicarboxylic acid 1-tert-butyl ester 5-ethyl ester obtained by Production example 346 and 427.1 mg of 3-bromopropionamide, 110 mg of the title compound was obtained as colorless crystals.

$^1$H-NMR (400 MHz, $CDCl_3$) δ1.45 (3H, t, J=7.2 Hz), 1.75 (9H, s), 2.84 (2H, t, J=5.6 Hz), 4.37 (2H, t, J=5.6 Hz), 4.42 (2H, q, J=7.2 Hz), 7.06-7.15 (2H, m), 7.50 (1H, d, J=16.4 Hz), 7.58-7.66 (2H, m), 7.80 (1H, d, J=16.4 Hz), 7.94 (1H, d, J=8.8 Hz), 8.07 (1H, d, J=8.8 Hz).

Example 763

4-(2-Carbamoylethoxy)-3-[(E)-2-(4-fluorophenyl)-vinyl]-1H-indazole-5-carboxylic acid ethyl ester In accordance with the method of Example 16, from 110 mg of 4-(2-carbamoylethoxy)-3-[(E)-2-(4-fluorophenyl)-vinyl]-1H-indazole-1,5-dicarboxylic acid 1-tert-butyl ester 5-ethyl ester obtained by Production example 762, 78 mg of the title compound was obtained as colorless crude crystals.

$^1$H-NMR (400 MHz, $CD_3OD$) δ1.42 (3H, t, J=6.8 Hz), 2.83 (2H, t, J=6.0 Hz), 4.39 (2H, t, J=6.0 Hz), 4.40 (2H, q, J=6.8 Hz), 7.09-7.18 (2H, m), 7.28 (1H, d, J=8.8 Hz), 7.53 (1H, d, J=16.4 Hz), 7.62 (1H, d, J=16.4 Hz), 7.66-7.74 (2H, m), 7.85 (1H, d, J=8.8 Hz).

MS (ESI) m/z 396 $(M-H)^-$

Example 764

4-(2-Carbamoylethoxy)-3-[(E)-2-(4-fluorophenyl)-vinyl]-1H-indazole-5-carboxylic acid 85.3 mg of 4-(2-carbamoylethoxy)-3-[(E)-2-(4-fluorophenyl)-vinyl]-1H-indazole-5-carboxylic acid ethyl ester obtained by Example 763 was dissolved in 3 mL of concentrated sulfuric acid, stirred at 35° C. for 16 hours, and then added with ice under ice cooling. The precipitated crystals were collected by filtration, washed with water, and then dried under reduced pressure, to afford 43.7 mg of the title compound as yellow crude crystals.

$^1$H-NMR (400 MHz, $CD_3OD$) δ2.85 (2H, t, J=6.0 Hz), 4.41 (2H, t, J=6.0 Hz), 7.06-7.18 (2H, m), 7.28 (1H, d, J=8.8 Hz), 7.44-7.76 (2H, m), 7.51 (1H, d, J=16.4 Hz), 7.60 (1H, d, J=16.4 Hz), 7.92 (1H, d, J=8.8 Hz).

MS (ESI) m/z 370 $MH^+$

Production Example 765

4-(2-Bromoethoxy)-3-[(E)-2-(4-fluorophenyl)-vinyl]-1H-indazole-1,5-dicarboxylic acid 1-tert-butyl ester 5-ethyl ester In accordance with the method of Production example 347, from 3.34 g of 3-[(E)-2-(4-fluorophenyl)-vinyl]-4-hydroxy-1H-indazole-1,5-dicarboxylic acid 1-tert-butyl ester 5-ethyl ester obtained by Production example 346 and 14.7 g of 1,2-dibromoethane, 3.20 g of the title compound was obtained as a colorless foam.

$^1$H-NMR (400 MHz, $CDCl_3$) δ1.44 (3H, t, J=7.2 Hz), 1.75 (9H, s), 3.78 (2H, t, J=5.6 Hz), 4.42 (2H, q, J=7.2 Hz), 4.46 (2H, t, J=5.6 Hz), 7.04-7.13 (2H, m), 7.56-7.68 (2H, m), 7.64 (1H, d, J=16.4 Hz), 7.81 (1H, d, J=16.4 Hz), 7.91 (1H, d, J=8.8 Hz), 8.03 (1H, d, J=8.8 Hz).

Example 766

3-[(E)-2-(4-Fluorophenyl)-vinyl]-4-[2-(morpholin-4-yl)ethoxy]-1H-indazole-5-carboxylic acid ethyl ester 100 mg of 4-(2-bromoethoxy)-3-[(E)-2-(4-fluorophenyl)-vinyl]-1H-indazole-1,5-dicarboxylic acid 1-tert-butyl ester 5-ethyl ester obtained by Production example 765 was dissolved in 1 mL of N,N-dimethylformamide, added with 40.8 mg of morpholine, and stirred at room temperature for 14 hours and 30 minutes, followed by stirring at 50° C. for 3 hours and further at 80° C. for 1 hour. Then adding water and extracting twice with ethyl acetate, the organic layer was washed successively with water and saturated brine and dried over anhydrous magnesium sulfate. The solvent was evaporated, to afford 81.9 mg of the title compound.

$^1$H-NMR (400 MHz, $CD_3OD$) δ1.41 (3H, t, J=7.2 Hz), 2.45 (4H, bs), 2.86 (2H, t, J=6.0 Hz), 3.45-3.70 (4H, m), 4.27 (2H, t, J=6.0 Hz), 4.39 (2H, q, J=7.2 Hz), 7.07-7.18 (2H, m), 7.27 (1H, d, J=8.4 Hz), 7.52 (1H, d, J=16.8 Hz), 7.58-7.70 (3H, m), 7.83 (1H, d, J=8.4 Hz).

Example 767

3-[(E)-2-(4-Fluorophenyl)-vinyl]-4-[2-(morpholin-4-yl)ethoxy]-1H-indazole-5-carboxylic acid In accordance with the method of Example 350, from 81.9 mg of 3-[(E)-2-(4-fluorophenyl)-vinyl]-4-[2-(morpholin-4-yl)ethoxy]-1H-indazole-5-carboxylic acid ethyl ester obtained by Example 766, 64.1 mg of the title compound was obtained.

MS (ESI) m/z 412 $MH^+$

Example 768

3-[(E)-2-(4-Fluorophenyl)-vinyl]-4-methoxy-1H-indazole-5-carboxylic acid [(1H-pyrrol-2-yl)-methyl]-amide To a solution of 1H-pyrrole-2-carboaldehyde in 31.5 mL of methanol, 8.1 g ammonium acetate and 462 mg of sodium cyano borohydride were added, and under nitrogen atmosphere stirred at room temperature for 27 hours. Then, concentrated hydrochloric acid was added until pH decreased to not more than 2, and the solvent was evaporated. After dissolving the residue in water, the solution was extracted twice with diethyl ether. Then, the aqueous phase was added with potassium hydroxide until pH reached to not less than 10, extracted twice with ethyl acetate, and dried over anhydrous magnesium sulfate. The solvent was evaporated, followed by purification and separation by NH silica gel column chromatography, to afford 475 mg of C-(1H-pyrrol-2-yl)-methylamine as a brown oil.

In accordance with the method of Example 102, from 10 mg of 3-[(E)-2-(4-fluorophenyl)-vinyl]-4-methoxy-1H-indazole-5-carboxylic acid obtained by Example 234 and 9.2 mg of C-(1H-pyrrol-2-yl)-methylamine, 0.98 mg of the title compound was obtained.

$^1$H-NMR (400 MHz, $CD_3OD$) δ3.84 (3H, s), 4.58 (2H, s), 6.03 (1H, dd, J=2.8, 5.6 Hz), 6.09-6.13 (1H, m), 6.67-6.72 (1H, m), 7.06-7.18 (2H, m), 7.32 (1H, d, J=8.4 Hz), 7.52 (1H, d, J=16.4 Hz), 7.56 (1H, d, J=16.4 Hz), 7.56-7.66 (2H, m), 7.82 (1H, d, J=8.4 Hz).

MS (ESI) m/z 391 $MH^+$

Production Example 769

[Oxazol-2-yl-(toluene-4-sulfonyl)-methyl]-carbamic acid tert-butyl ester 300 mg of oxazole 2-carboaldehyde was dissolved in a mixed solvent of 3 mL of methanol and 6 mL of water, added successively with 363 mg of tert-butyl carbamate, 552 mg of sodium p-toluenesulfonate and 0.76 mL of formic acid and stirred at room temperature for 16 hours and 30 minutes. The precipitated crystals were collected by filtration, washed with water, and dried under reduced pressure, to afford 247 mg of the title compound as colorless crystals.

$^1$H-NMR (400 MHz, DMSO-$D_6$) δ1.23 (9H, s), 2.40 (3H, s), 6.12 (1H, d, J=10.0 Hz), 7.35 (1H, s), 7.46 (2H, d, J=7.6 Hz), 7.71 (2H, d, J=7.6 Hz), 8.28 (1H, s), 8.86 (1H, d, J=10.0 Hz).

Production Example 770

Oxazole-2-ylmethyl-carbamic acid tert-butyl ester

To 4 mL of tetrahydrofuran was added 51.4 mg of sodium borohydride, and added with 240 mg of [oxazole-2-yl-(toluene-4-sulfonyl)-methyl]-carbamic acid tert-butyl ester obtained by Production example 769 over 13 minutes at room temperature under stirring. Thereafter, the solution was stirred for another 2 hours and 30 minutes under room temperature, added with saturated aqueous ammonium chloride under ice cooling, and stirred for another 30 minutes under ice cooling. Thereafter, water was added, extracted twice with diethyl ether and dried over anhydrous magnesium sulfate. The solvent was evaporated, followed by purification and separation by silica gel column chromatography, to afford 72.3 mg of the title compound as colorless crystals.

$^1$H-NMR (400 MHz, DMSO-$D_6$) δ1.39 (9H, s), 4.44 (1H, d, J=5.6 Hz), 7.51 (1H, s), 7.61 (1H, t, J=5.6 Hz), 8.38 (1H, s).

Example 771

3-[(E)-2-(4-Fluorophenyl)-vinyl]-4-methoxy-1H-indazole-5-carboxylic acid (oxazol-2-ylmethyl)-amide In accordance with the method of Example 16, from 36 mg oxazol-2-ylmethyl-carbamic acid tert-butyl ester obtained by Production example 770, C-(oxazol-2-yl)-methylamine was obtained as transparent oil. From this and 10 mg of 3-[(E)-2-(4-fluorophenyl)-vinyl]-4-methoxy-1H-indazole-5-carboxylic acid obtained by Example 234, 3.82 mg of the title compound was obtained in accordance with the method of Example 102.

$^1$H-NMR (400 MHz, $CD_3OD$) δ4.00 (3H, s), 4.78 (2H, s), 7.09-7.19 (2H, m), 7.16 (1H, d, J=0.8 Hz), 7.43 (1H, d, J=8.8 Hz), 7.55 (1H, d, J=16.4 Hz), 7.60 (1H, d, J=16.4 Hz), 7.59-7.68 (2H, m), 7.85 (1H, d, J=8.8 Hz), 7.90 (1H, d, J=0.8 Hz).

MS (ESI) m/z 393 $MH^+$

Production Example 772

Acetic Acid 5-(tert-butoxycarbonylamino-methyl)-furan-2-ylmethyl ester

In accordance with the methods of Production example 769 and Production example 77.0, from 1 g of acetic acid 5-formyl-furan-2-ylmethyl ester, 443 mg of the title compound was obtained as a colorless oil.

$^1$H-NMR (400 MHz, DMSO-$D_6$) δ1.36 (9H, s), 2.00 (3H, s), 4.07 (2H, d, J=5.2 Hz), 4.95 (2H, s), 6.13 (1H, d, J=2.8 Hz), 6.40 (1H, d, J=2.8 Hz), 7.32 (1H, bs).

Production Example 773

(5-Hydroxymethyl-furan-2-ylmethyl)-carbamic acid tert-butyl ester 416 mg of acetic acid 5-(tert-butoxycarbonylamino-methyl)-furan-2-yl methyl ester was dissolved in a mixed solvent of 8 mL of methanol and 8 mL of water, added with 639 mg of potassium carbonate, and stirred at room temperature for 30 minutes. Then, the solution was added with saturated aqueous ammonium chloride, extracted twice with ethyl acetate, the organic layer washed with saturated brine, and dried over anhydrous magnesium sulfate. The solvent was evaporated, to afford 363 mg of the title compound as a colorless oil.

$^1$H-NMR (400 MHz, DMSO-$D_6$) δ 1.36 (9H, s), 4.05 (2H, d, J=5.6 Hz), 4.30 (2H, d, J=5.6 Hz), 5.13 (1H, t, J=5.6 Hz), 6.06 (1H, d, J=2.8 Hz), 6.15 (1H, d, J=2.8 Hz), 7.28 (1H, t, J=5.6 Hz).

Production Example 774

(5-Azidomethyl-furan-2-ylmethyl)-carbamic acid tert-butyl ester 99.4 mg of (5-hydroxymethyl-furan-2-ylmethyl)-carbamic acid tert-butyl ester was added to 4.5 mL of toluene, added successively with 83.7 mg of 1,8-diazabicyclo[5,4,0]undec-7-ene and 151.6 mg of diphenylphosphoryl azide, and stirred at room temperature under nitrogen atmosphere for 1 hour and 45 minutes. Then the solvent was evaporated, followed by purification and separation by silica gel column chromatography, to afford 88.6 mg of the title compound as a colorless oil.

$^1$H-NMR (400 MHz, DMSO-$D_6$) δ 1.36 (9H, s), 4.07 (2H, d, J=5.2 Hz), 4.39 (2H, s), 6.14 (1H, t, J=2.8 Hz), 6.38 (1H, d, J=2.8 Hz), 7.32 (1H, t, J=5.2 Hz).

Production Example 775

(5-Aminomethyl-furan-2-ylmethyl)-carbamic acid tert-butyl ester

To a solution of 88.6 mg of (5-azidomethyl-furan-2-ylmethyl)-carbamic acid tert-butyl ester in 3 mL of ethanol was added 30 mg of Lindlar catalyst, stirred at room temperature under hydrogen atmosphere for 15 hours, the catalyst filtered off, and the solvent was evaporated, to afford 81 mg of the title compound as a colorless oil.

$^1$H-NMR (400 MHz, $CD_3OD$) δ 1.43 (9H, s), 3.71 (2H, s), 4.15 (2H, s), 6.05-6.20 (2H, m).

MS (ESI) m/z 225 $(M-H)^-$

Example 776

3-[(E)-2-(4-Fluorophenyl)-vinyl]-4-methoxy-1H-indazole-5-carboxylic acid (5-aminomethyl-furan-2-ylmethyl)-amide In accordance with the methods of Example 102 and Example 16, from 19 mg (5-aminomethyl-furan-2-ylmethyl)-carbamic acid tert-butyl ester obtained by Production example 775 and 17.5 mg of 3-[(E)-2-(4-fluorophenyl)-vinyl]-4-methoxy-1H-indazole-5-carboxylic acid obtained by Example 234, 4.26 mg of the title compound was obtained.

$^1$H-NMR (400 MHz, $CD_3OD$) δ 3.92 (3H, s), 4.15 (2H, s), 4.65 (2H, s), 6.40 (1H, d, J=3.6 Hz), 6.51 (1H, d, J=3.6 Hz), 7.08-7.18 (2H, m), 7.34 (1H, d, J=8.4 Hz), 7.53 (1H, d, J=16.4 Hz), 7.58 (1H, d, J=16.4 Hz), 7.58-7.66 (2H, m), 7.81 (1H, d, J=8.4 Hz)

MS (ESI) m/z 421 $MH^+$

Example 777

3-[(E)-2-(4-Fluorophenyl)-vinyl]-4-methoxy-1H-indazole-5-carboxylic acid (5-methylaminomethyl-furan-2-ylmethyl)-amide To a solution of 15 mg of acetic acid 5-(tert-butoxycarbonylamino-methyl)-furan-2-ylmethylester obtained by Production example 772 in 0.5 mL of N,N-dimethylformamide were added 31.8 mg of iodomethane and 2.5 mg of sodium hydride under ice cooling, and stirred for another 2 hours under ice cooling. Then saturated aqueous ammonium chloride was added under ice cooling, extracted twice with diethyl ether, the organic layer washed with water, and dried over anhydrous magnesium sulfate. The solvent was evaporated, to afford acetic acid 5-[(tert-butoxycarbonyl-methyl-amino)-methyl]-furan-2-ylmethylester. This was then subjected to the reactions similar to those described in Production example 773, Production example 774 and Production example 775, to afford (5-aminomethyl-furan-2-ylmethyl)-methyl-carbamic acid tert-butyl ester.

This was then reacted with 3-[(E)-2-(4-fluorophenyl)-vinyl]-4-methoxy-1H-indazole-5-carboxylic acid obtained by Example 234 in accordance with the methods of Example 102 and Example 16, followed by separation and purification by LC-MS, to afford 0.58 mg of the title compound.

$^1$H-NMR (400 MHz, $CD_3OD$) δ 2.70 (3H, s), 3.93 (3H, s), 4.24 (2H, s), 4.66 (2H, s), 6.43 (1H, d, J=3.2 Hz), 6.60 (1H, d, J=3.2 Hz), 7.10-7.18 (2H, m), 7.35 (1H, d, J=8.8 Hz), 7.53 (1H, d, J=16.4 Hz), 7.59 (1H, d, J=16.4 Hz), 7.60-7.68 (2H, m), 7.81 (1H, d, J=8.8 Hz).

MS (ESI) m/z 435 $MH^+$

Example 778

3-[(E)-2-(4-Fluorophenyl)-vinyl]-4-methoxy-1H-indazole-5-carboxylic acid (5-dimethylaminomethyl-furan-2-ylmethyl)-amide 10 mg of 3-[(E)-2-(4-fluorophenyl)-vinyl]-4-methoxy-1H-indazole-5-carboxylic acid (5-aminomethyl-furan-2-ylmethyl)-amide obtained by Example 776 was dissolved in a mixed solvent of 0.25 mL methanol/0.25 mL tetrahydrofuran, added with 7.2 mg of 37% formaldehyde aqueous solution, 6 μl of acetic acid, and 3.8 mg of sodium cyanoborohydride, and stirred at room temperature under nitrogen atmosphere for 18 hours. Then the solvent was evaporated, followed by separation and purification by LC-MS, to afford 0.60 mg of the title compound.

$^1$H-NMR (400 MHz, $CD_3OD$) δ 2.87 (6H, s), 3.94 (3H, s), 4.38 (2H, s), 4.67 (2H, bs), 6.47 (1H, d, J=2.8 Hz), 6.69 (1H, d, J=2.8 Hz), 7.10-7.20 (2H, m), 7.35 (1H, d, J=8.8 Hz), 7.53 (1H, d, J=16.8 Hz), 7.59 (1H, d, J=16.8 Hz), 7.60-7.68 (2H, m), 7.80 (1H, d, J=8.8 Hz).

MS (ESI) m/z 450 $MH^+$

Example 779

3-[(E)-2-(4-Fluorophenyl)-vinyl]-4-methoxy-1H-indazole-5-carboxylic acid (5-hydroxymethyl-furan-2-ylmethyl)-amide In accordance with the method of Example 16, from acetic acid 5-(tert-butoxycarbonylamino-methyl)-furan-2-ylmethyl ester obtained by Production example 772, acetic acid 5-aminomethyl-furan-2-ylmethyl ester was obtained.

This compound and 17.5 mg of 3-[(E)-2-(4-fluorophenyl)-vinyl]-4-methoxy-1H-indazole-5-carboxylic acid obtained by Example 234 were amidated in accordance with Example 102, followed by hydrolysis of acetate in accordance with the method of Production example 773. Then the resultant product was separated and purified by LC-MS, to afford 1.95 mg of the title compound.

$^1$H-NMR (400 MHz, $CD_3OD$) δ 3.91 (3H, s), 4.49 (2H, s), 4.63 (2H, s), 6.27 (1H, d, J=. 3.2 Hz), 6.31 (1H, d, J=3.2 Hz), 7.08-7.18 (2H, m), 7.33 (1H, d, J=8.8 Hz), 7.53 (1H, d, J=16.4 Hz), 7.58 (1H, d, J=16.4 Hz), 7.59-7.67 (2H, m), 7.79 (1H, d, J=8.8 Hz).

MS (ESI) m/z 422 $MH^+$

Example 780

(S)-({3-[(E)-2-(4-Fluorophenyl)-vinyl]-4-methoxy-1H-indazole-5-carbonyl}-amino)-phenyl-acetic acid In accordance with the methods of Example 102 and Example 16, from 40 mg of 3-[(E)-2-(4-fluorophenyl)-vinyl]-4-methoxy-1H-indazole-5-carboxylic acid obtained by Example 234 and (S)-amino-phenyl-acetic acid tert-butyl ester, 110 mg of the title compound was obtained as a yellow oil.

MS (ESI) m/z 446 $MH^+$

Example 781

From carboxylic acids obtained by Example 761, Example 764, Example 234 and Example 780 and various kinds of amine, the compounds of Examples 782-794 were obtained in accordance with the method of Example 102.

Example 782

3-[(E)-2-(4-Fluorophenyl)-vinyl]-4-(3-hydroxypropoxy)-1H-indazole-5-carboxylic acid [(1S)-1-hydroxymethyl-2-methyl-propyl]-amide MS (ESI) m/z 443 $MH^+$ Example 783

3-[(E)-2-(4-Fluorophenyl)-vinyl]-4-(3-hydroxypropoxy)-1H-indazole-5-carboxylic acid cyclopropylamide MS (ESI) m/z 396 $MH^+$ Example 784

3-[(E)-2-(4-Fluorophenyl)-vinyl]-4-(3-hydroxypropoxy)-1H-indazole-5-carboxylic acid (furan-2-ylmethyl)-amide MS (ESI) m/z 436 $MH^+$ Example 785

3-[(E)-2-(4-Fluorophenyl)-vinyl]-4-(3-hydroxypropoxy)-1H-indazole-5-carboxylic acid [(15)-2-hydroxy-1-phenyl-ethyl]-amide MS (ESI) m/z 477 $MH^+$ Example 786

3-[(E)-2-(4-Fluorophenyl)-vinyl]-4-(3-hydroxypropoxy)-1H-indazole-5-carboxylic acid [(1S)-1-carbamoyl-ethyl]-amide MS (ESI) m/z 427 $MH^+$ Example 787

4-(2-Carbamoylethoxy)-3-[(E)-2-(4-fluorophenyl)-vinyl]-1H-indazole-5-carboxylic acid [(1S)-1-hydroxymethyl-2-methyl-propyl]-amide MS (ESI) m/z 456 $MH^+$ Example 788

4-(2-Carbamoylethoxy)-3-[(E)-2-(4-fluorophenyl)-vinyl]-1H-indazole-5-carboxylic acid cyclopropylamide MS (ESI) m/z 409 $MH^+$ Example 789

4-(2-Carbamoylethoxy)-3-[(E)-2-(4-fluorophenyl)-vinyl]-1H-indazole-5-carboxylic acid (furan-2-ylmethyl)-amide MS (ESI) m/z 449 $MH^+$ Example 790

4-(2-Carbamoylethoxy)-3-[(E)-2-(4-fluorophenyl)-vinyl]-1H-indazole-5-carboxylic acid [(1S)-2-hydroxy-1-phenyl-ethyl]-amide MS (ESI) m/z 490 $MH^+$ Example 791

4-(2-Carbamoylethoxy)-3-[(E)-2-(4-fluorophenyl)-vinyl]-1H-indazole-5-carboxylic acid [(1S)-1-carbamoyl-ethyl]-amide MS (ESI) m/z 440 $MH^+$ Example 792

3-[(E)-2-(4-Fluorophenyl)-vinyl]-4-methoxy-1H-indazole-5-carboxlic acid cyclopropylmethyl-amide MS (ESI) m/z 366 $MH^+$ Example 793

3-[(E)-2-(4-Fluorophenyl)-vinyl]-4-methoxy-1H-indazole-5-carboxylic acid [(3R)-2-oxo-tetrahydro-furan-3-yl]-amide MS (ESI) m/z 396 $MH^+$ Example 794

3-[(E)-2-(4-Fluorophenyl)-vinyl]-4-methoxy-1H-indazole-5-carboxylic acid [(S)-cyclopropylcarbamoyl-phenyl-methyl]-amide MS (ESI) m/z 486 $MH^+$ Example 795

To a solution of either carboxylic acid obtained by Example 767, Example 234 and Example 780 in 1.5 mL of tetrahydrofuran were successively added 6 equivalents of triethylamine and 2.5 equivalents of ethyl chloroformate under ice cooling, and stirred under ice cooling for 1 hour. Then an excess amount of various kinds of amine was added and stirred at room temperature overnight. The solvent was distilled off, and the resultant residue was separated and purified by LC-MS, to afford the compounds of Examples 796-799.

Example 796

3-[(E)-2-(4-Fluorophenyl)-vinyl]-4-[2-(morpholin-4-yl)ethoxy]-1H-indazole-5-carboxylic Acid Amide MS (ESI) m/z 411 $MH^+$ Example 797

3-[(E)-2-(4-Fluorophenyl)-vinyl]-4-[2-(morpholin-4-yl)-ethoxy]-1H-indazole-5-carboxylic acid methylamide MS (ESI) m/z 425 $MH^+$ Example 798

3-[(E)-2-(4-Fluorophenyl)-vinyl]-4-methoxy-1H-indazole-5-carboxylic acid methylamide MS (ESI) m/z 326 $MH^+$ Example 799

3-[2-(4-Fluorophenyl)-vinyl]-4-methoxy-1H-indazole-5-carboxylic acid [(S)-dimethylcarbamoyl-phenyl-methyl]-amide MS (ESI) m/z 474 $MH^+$ Production Example 800

1-Benzyloxymethyl-cyclopropylamine

The title compound was prepared in accordance with the known method (*J. Org. Chem*. 2002, 67, 3965.).

Production Example 801

1-(2-Benzyloxy-ethyl)-cyclopropylamine

The title compound was prepared in accordance with the known method (*J. Org. Chem*. 2002, 67, 3965.).

Production Example 802

1-Azido-2-methyl-propan-2-ol 3.6 g of isobutylene oxide was dissolved in 100 mL of water, added with 18.2 g of cetyltrimethyl ammonium bromide and 16.3 g of sodium azide, and stirred at 30° C. overnight. The solution was extracted with 50% tetrahydrofuran solution in ethyl acetate, the organic phase was washed with water and saturated brine, and dried over anhydrous magnesium sulfate. The solvent was evaporated, followed by purification by silica gel column chromatography, and the solvent was evaporated at room temperature, to afford 6.44 g of the title compound as a mixture with ethyl acetate.

$^1$H-NMR (400 MHz, $CDCl_3$) 1.26 (6H, s), 2.04 (2H, s)

Production Example 803

1-Amino-2-methyl-propan-2-ol 3.22 g of 1-azido-2-methyl-propan-2-ol obtained by Production example 802 was dissolved in 50 mL of ethanol, added with 30 mg of palladium carbon, and stirred overnight at room temperature under hydrogen atmosphere. The insoluble substances were filtered off through Celite, and the solvent was evaporated, to afford 1.5 g of the title compound as a colorless oil substance.

$^1$H-NMR (400 MHz, DMSO-$D_6$) 1.16 (6H, s), 2.71 (2H, dd, J=6, 11.6 Hz)

Production Example 804

1-Amino-3-methyl-buthan-3-ol hydrochloride

To 3 g of 3-hydroxy-3-methylbutyronitrile, 10 mL of ethanol, 5 mL of concentrated hydrochloric acid and 100 mg of platinum dioxide were added, and under 5-atom hydrogen atmosphere, the solution was stirred at room temperature for 5 hours. The insoluble substances were filtered off through Celite, and the solvent evaporated, to afford 3.5 g of the title compound as a dark brown solid.

$^1$H-NMR (400 MHz, DMSO-$D_6$) δ1.12 (6H, s), 1.65 (2H, t, J=8.0 Hz), 2.82-2.87 (2H, m)

Production Example 805

2-Amino-N,N-dimethyl-acetamide 10 g of glycine ethyl ester hydrochloride was suspended in 200 mL of dichloromethane, added with 22 mL of triethylamine, cooled to 0° C., and added with 11.3 mL of benzylchloroformate. The suspension was allowed to warm to room temperature, stirred for 4 days, and added with water to stop the reaction. Extracting with ethyl acetate, the organic layer was washed with water and saturated brine, and dried over anhydrous magnesium sulfate. The solvent was evaporated, and 12.2 g of the resultant white crystal was suspended in 200 mL of ethanol, added with 100 mL of 1N sodium hydroxide aqueous solution, and stirred overnight at room temperature. The organic solvent was evaporated, and the residual aqueous phase was washed twice with 100 mL of ether. The aqueous phase was made to pH 2 by using 5N hydrochloric acid, and extracted with ethyl acetate. The organic phase was washed with water and saturated brine, dried over anhydrous magnesium sulfate, and the solvent was evaporated, to afford 4.82 g of white crystals. 497 mg of this white crystals were dissolved in 20 mL of DMF, added with 1.62 mL of diisopropylethylamine, 1.4 mL of dimethyl amine in 2.0 M tetrahydrofuran and 437 mg of hydroxybenzotriazole, and stirred at room temperature for 10 minutes. After cooling to 0° C., 912 mg of WSC hydrochloride was added and stirred overnight at room temperature. Water was added to stop the reaction, the solution was extracted with ethyl acetate, and the organic phase washed with water and saturated brine and dried over anhydrous magnesium sulfate. The solvent was evaporated, followed by purification by silica gel column chromatography, to afford 402 mg of a colorless oil substance. This was then dissolved in 5 mL of ethanol, added with 40 mg of palladium carbon, and stirred overnight at room temperature under hydrogen atmosphere. The insoluble substances were filtered off through Celite, and the filtrate was evaporated, to afford 113 mg of the title compound.

$^1$H-NMR (400 MHz, $CD_3OD$) 2.95 (3H, s), 2.97 (3H, s), 3.44 (2H, s)

Production Example 806

The compounds of Production example 807 to Production example 811 were prepared in accordance with method of Production example 805.

Production Example 807

3-Amino-N-methyl-propionamide $^1$H-NMR (400 MHz, $CD_3OD$) δ2.39 (2H, t, J=6.8 Hz), 2.71 (3H, s), 3.46 (2H, t, J=6.4 Hz)

Production Example 808

3-Amino-N,N-dimethyl-propionamide $^1$H-NMR (400 MHz, $CD_3OD$) δ 2.60 (2H, t, J=6.8 Hz), 2.93 (3H, s), 3.03 (3H, s), 3.47 (2H, t, J=6.8 Hz)

Production Example 809

4-Amino-butylamide $^1$H-NMR (400 MHz, $CD_3OD$) δ1.80 (2H, quint, J=7.2 Hz), 2.24 (2H, t, J=7.2 Hz), 3.25 (2H, t, J=7.2 Hz)

Production Example 810

4-Amino-N-methyl-butylamide $^1$H-NMR (400 MHz, $CD_3OD$) δ1.79 (2H, quint, J=7.2 Hz), 2.21 (2H, t, J=7.2 Hz), 2.71 (3H, s), 3.23 (2H, t, J=7.2 Hz)

Production Example 811

4-Amino-N,N-dimethyl-butylamide $^1$H-NMR (400 MHz, $CD_3OD$) 1.79 (2H, quint, J=7.2 Hz), 2.41 (2H, t, J=7.2 Hz), 2.92 (3H, s), 3.05 (3H, s), 3.25 (2H, t, J=7.2 Hz)

Example 812

In accordance with the method of Example 102, from 3-[(E)-2-(4-fluorophenyl)-vinyl]-4-methoxy-1H-indazole-5-ca rboxylic acid obtained by Example 234 or commercially available amine, or various kinds of amine obtained by Production example 800, 801, 803, 804, 805, 807-811, the compounds of Examples 813-887 were obtained.

Example 813

3-[(E)-2-(4-Fluorophenyl)-vinyl]-4-methoxy-1H-indazole-5-carboxylic acid (1-benzyloxymethyl-cyclopropyl)-amide MS (ESI) m/z 472 $MH^+$ Example 814

3-[(E)-2-(4-Fluorophenyl)-vinyl]-4-methoxy-1H-indazole-5-carboxylic acid [1-(2-benzyloxyethyl)-cyclopropyl]-amide MS (ESI) m/z 486 $MH^+$ Example 815

3-[(E)-2-(4-Fluorophenyl)-vinyl]-4-methoxy-1H-indazole-5-carboxylic acid (1-hydroxymethyl-cyclopentyl)-amide MS (ESI) m/z 410 $MH^+$ Example 816

3-[(E)-2-(4-Fluorophenyl)-vinyl]-4-methoxy-1H-indazole-5-carboxylic acid (2-hydroxy-1,1-dimethyl-ethyl)-amide MS (ESI) m/z 384 $MH^+$ Example 817

3-[(E)-2-(4-Fluorophenyl)-vinyl]-4-methoxy-1H-indazole-5-carboxylic acid [(1R)-1-hydroxymethyl-2-methyl-propyl]-amide MS (ESI) m/z 398 $MH^+$ Example 818

3-[(E)-2-(4-Fluorophenyl)-vinyl]-4-methoxy-1H-indazole-5-carboxylic acid [(1R)-2-hydroxy-1-phenyl-ethyl]-amide MS (ESI) m/z 432 $MH^+$ Example 819

3-[(E)-2-(4-Fluorophenyl)-vinyl]-4-methoxy-1H-indazole-5-carboxylic acid [2-hydroxy-1-(pyridin-3-yl)-ethyl]-amide MS (ESI) m/z 433 $MH^+$ Example 820

3-[(E)-2-(4-Fluorophenyl)-vinyl]-4-methoxy-1H-indazole-5-carboxylic acid (2-hydroxyethyl)-amide MS (ESI) m/z 356 $MH^+$ Example 821

3-[(E)-2-(4-Fluorophenyl)-vinyl]-4-methoxy-1H-indazole-5-carboxylic acid (2-hydroxy-2-methyl-propyl)-amide MS (ESI) m/z 384 $MH^+$ Example 822

3-[(E)-2-(4-Fluorophenyl)-vinyl]-4-methoxy-1H-indazole-5-carboxylic acid (3-hydroxy-3-methyl-butyl)-amide MS (ESI) m/z 398 $MH^+$ Example 823

3-[(E)-2-(4-Fluorophenyl)-vinyl]-4-methoxy-1H-indazole-5-carboxylic acid [(2S)-2-hydroxy-2-phenyl-ethyl]-amide MS (ESI) m/z 432 $MH^+$ Example 824

3-[(E)-2-(4-fluorophenyl)-vinyl]-4-methoxy-1H-indazole-5-carboxylic acid [(2R)-2-hydroxy-2-phenyl-ethyl]-amide MS (ESI) m/z 432 $MH^+$ Example 825

3-[(E)-2-(4-Fluorophenyl)-vinyl]-4-methoxy-1H-indazole-5-carboxylic acid [(2S)-2-hydroxypropyl]-amide MS (ESI) m/z 370 $MH^+$ Example 826

3-[(E)-2-(4-Fluorophenyl)-vinyl]-4-methoxy-1H-indazole-5-carboxylic acid [(2R)-2-hydroxypropyl]-amide MS (ESI) m/z 370 $MH^+$ Example 827

3-[(E)-2-(4-Fluorophenyl)-vinyl]-4-methoxy-1H-indazole-5-carboxylic acid (3-amino-propyl)-amide MS (ESI) m/z 369 $MH^+$ Example 828

3-[(E)-2-(4-Fluorophenyl)-vinyl]-4-methoxy-1H-indazole-5-carboxylic acid (3-methylamino-propyl)-amide MS (ESI) m/z 383 $MH^+$ Example 829

3-[(E)-2-(4-Fluorophenyl)-vinyl]-4-methoxy-1H-indazole-5-carboxylic acid (3-ethylamino-propyl)-amide MS (ESI) m/z 397 $MH^+$ Example 830

3-[(E)-2-(4-Fluorophenyl)-vinyl]-4-methoxy-1H-indazole-5-carboxylic acid (3-dimethylamino-propyl)-amide MS (ESI) m/z 397 $MH^+$ Example 831

3-[(E)-2-(4-Fluorophenyl)-vinyl]-4-methoxy-1H-indazole-5-carboxylic acid [3-(2-oxo-pyrrolidin-1-yl)-propyl]-amide MS (ESI) m/z 437 $MH^+$ Example 832

3-[(E)-2-(4-Fluorophenyl)-vinyl]-4-methoxy-1H-indazole-5-carboxylic acid [3-(morpholin-4-yl)-propyl]-amide MS (ESI) m/z 439 $MH^+$ Example 833

3-[(E)-2-(4-Fluorophenyl)-vinyl]-4-methoxy-1H-indazole-5-carboxylic acid [3-(1H-imidazol-1-yl)-propyl]-amide MS (ESI) m/z 420 $MH^+$ Example 834

3-[(E)-2-(4-Fluorophenyl)-vinyl]-4-methoxy-1H-indazole-5-carboxylic acid [2-(1H-imidazol-4-yl)-ethyl]-amide MS (ESI) m/z 406 $MH^+$ Example 835

3-[(E)-2-(4-Fluorophenyl)-vinyl]-4-methoxy-1H-indazole-5-carboxylic acid (4-amino-cyclohexyl)-amide MS (ESI) m/z 409 $MH^+$ Example 836

3-[(E)-2-(4-Fluorophenyl)-vinyl]-4-methoxy-1H-indazole-5-carboxylic acid [(3R)-pyrrolidin-3-yl]-amide MS (ESI) m/z 381 $MH^+$ Example 837

3-[(E)-2-(4-fluorophenyl)-vinyl]-4-methoxy-1H-indazole-5-carboxylic acid [(3S)-pyrrolidin-3-yl]-amide MS (ESI) m/z 381 $MH^+$ Example 838

3-[(E)-2-(4-Fluorophenyl)-vinyl]-4-methoxy-1H-indazole-5-carboxylic acid (piperidin-4-ylmethyl)-amide MS (ESI) m/z 409 $MH^+$ Example 839

3-[(E)-2-(4-Fluorophenyl)-vinyl]-4-methoxy-1H-indazole-5-carboxylic acid (piperidin-4-yl)-amide MS (ESI) m/z 395 $MH^+$ Example 840

3-[(E)-2-(4-Fluorophenyl)-vinyl]-4-methoxy-1H-indazole-5-carboxylic acid carbamoylmethyl-amide MS (ESI) m/z 369 $MH^+$ Example 841

3-[(E)-2-(4-Fluorophenyl)-vinyl]-4-methoxy-1H-indazole-5-carboxylic acid methylcarbamoylmethyl-amide MS (ESI) m/z 383 $MH^+$ Example 842

3-[(E)-2-(4-Fluorophenyl)-vinyl]-4-methoxy-1H-indazole-5-carboxylic acid dimethylcarbamoylm-ethyl-amide MS (ESI) m/z 397 $MH^+$ Example 843

3-[(E)-2-(4-Fluorophenyl)-vinyl]-4-methoxy-1H-indazole-5-carboxylic acid (2-carbamoyl-ethyl)-amide MS (ESI) m/z 383 $MH^+$ Example 845

3-[(E)-2-(4-Fluorophenyl)-vinyl]-4-methoxy-1H-indazole-5-carboxylic acid (2-methylcarbamoyl-ethyl)-amide MS (ESI) m/z 397 $MH^+$ Example 846

3-[(E)-2-(4-Fluorophenyl)-vinyl]-4-methoxy-1H-indazole-5-carboxylic acid (2-dimethylcarbamoyl-ethyl)-amide MS (ESI) m/z 411 $MH^+$ Example 847

3-[(E)-2-(4-Fluorophenyl)-vinyl]-4-methoxy-1H-indazole-5-carboxylic acid (3-carbamoyl-propyl)-amide MS (ESI) m/z 397 $MH^+$ Example 848

3-[(E)-2-(4-Fluorophenyl)-vinyl]-4-methoxy-1H-indazole-5-carboxylic acid (3-methylcarbamoyl-propyl)-amide MS (ESI) m/z 411 $MH^+$ Example 849

3-[(E)-2-(4-Fluorophenyl)-vinyl]-4-methoxy-1H-indazole-5-carboxylic acid (3-dimethylcarbamoyl-propyl)-amide MS (ESI) m/z 425 $MH^+$ Example 850

3-[(E)-2-(4-Fluorophenyl)-vinyl]-4-methoxy-1H-indazole-5-carboxylic acid [(1S)-1-methylcarbam-oyl-ethyl]-amide MS (ESI) m/z 397 $MH^+$ Example 851

3-[(E)-2-(4-Fluorophenyl)-vinyl]-4-methoxy-1H-indazole-5-carboxylic acid (2-oxo-azepan-3-yl)-amide MS (ESI) m/z 423 $MH^+$ Example 852

3-[(E)-2-(4-Fluorophenyl)-vinyl]-4-methoxy-1H-indazole-5-carboxylic acid (pyridin-2-ylmethyl)-amide MS (ESI) m/z 403 $MH^+$ Example 853

3-[(E)-2-(4-Fluorophenyl)-vinyl]-4-methoxy-1H-indazole-5-carboxylic acid (pyridin-3-ylmethyl)-amide MS (ESI) m/z 403 $MH^+$ Example 854

3-[(E)-2-(4-Fluorophenyl)-vinyl]-4-methoxy-1H-indazole-5-carboxylic acid (pyridin-4-ylmethyl)-amide MS (ESI) m/z 403 $MH^+$ Example 855

3-[(E)-2-(4-Fluorophenyl)-vinyl]-4-methoxy-1H-indazole-5-carboxylic acid benzylamide MS (ESI) m/z 402 $MH^+$ Example 856

3-[(E)-2-(4-Fluorophenyl)-vinyl]-4-methoxy-1H-indazole-5-carboxylic acid [2-(pyridin-2-yl)ethyl]-amide MS (ESI) m/z 417 $MH^+$ Example 857

3-[(E)-2-(4-Fluorophenyl)-vinyl]-4-methoxy-1H-indazole-5-carboxylic acid [2-(pyridin-3-yl)ethyl]-amide MS (ESI) m/z 417 $MH^+$ Example 858

3-[(E)-2-(4-Fluorophenyl)-vinyl]-4-methoxy-1H-indazole-5-carboxylic acid [2-(pyridin-4-yl)ethyl]-amide MS (ESI) m/z 417 $MH^+$ Example 859

3-[(E)-2-(4-Fluorophenyl)-vinyl]-4-methoxy-1H-indazole-5-carboxylic acid (pyrazin-2-ylmethyl)-amide MS (ESI) m/z 404 $MH^+$ Example 860

3-[(E)-2-(4-Fluorophenyl)-vinyl]-4-methoxy-1H-indazole-5-carboxylic acid [2-(thiophen-2-yl)-ethyl]-amide MS (ESI) m/z 422 $MH^+$ Example 861

3-[(E)-2-(4-Fluorophenyl)-vinyl]-4-methoxy-1H-indazole-5-carboxylic acid (thiophen-2-ylmethyl)-amide MS (ESI) m/z 408 $MH^+$ Example 862

3-[(E)-2-(4-Fluorophenyl)-vinyl]-4-methoxy-1H-indazole-5-carboxylic acid cyclobutylamide MS (ESI) m/z 366 $MH^+$ Example 863

3-[(E)-2-(4-Fluorophenyl)-vinyl]-4-methoxy-1H-indazole-5-carboxylic acid cyclopentylamide MS (ESI) m/z 380 $MH^+$ Example 864

3-[(E)-2-(4-Fluorophenyl)-vinyl]-4-methoxy-1H-indazole-5-carboxylic acid allylamide MS (ESI) m/z 352 $MH^+$ Example 865

3-[(E)-2-(4-Fluorophenyl)-vinyl]-4-methoxy-1H-indazole-5-carboxylic acid propan-2-ynylamide MS (ESI) m/z 352 $MH^+$ Example 866

3-[(E)-2-(4-Fluorophenyl)-vinyl]-4-methoxy-1H-indazole-5-carboxylic acid cyanomethyl-amide MS (ESI) m/z 351 $MH^+$ Example 867

3-[(E)-2-(4-Fluorophenyl)-vinyl]-4-methoxy-1H-indazole-5-carboxylic acid (thiophen-3-ylmethyl)-amide MS (ESI) m/z 408 $MH^+$ Example 868

3-[(E)-2-(4-Fluorophenyl)-vinyl]-4-methoxy-1H-indazole-5-carboxylic acid (5-methyl-furan-2-ylmethyl)-amide MS (ESI) m/z 406 $MH^+$ Example 869

3-[(E)-2-(4-Fluorophenyl)-vinyl]-4-methoxy-1H-indazole-5-carboxylic acid 2-fluoro-benzylamide MS (ESI) m/z 420 $MH^+$ Example 870

3-[(E)-2-(4-Fluorophenyl)-vinyl]-4-methoxy-1H-indazole-5-carboxylic acid 3-fluoro-benzylamide MS (ESI) m/z 420 $MH^+$ Example 871

3-[(E)-2-(4-Fluorophenyl)-vinyl]-4-methoxy-1H-indazole-5-carboxylic acid 4-fluoro-benzylamide MS (ESI) m/z 420 $MH^+$ Example 872

3-[(E)-2-(4-Fluorophenyl)-vinyl]-4-methoxy-1H-indazole-5-carboxylic acid 2-methoxy-benzylamide MS (ESI) m/z 432 $MH^+$ Example 873

3-[(E)-2-(4-Fluorophenyl)-vinyl]-4-methoxy-1H-indazole-5-carboxylic acid 3-methoxy-benzylamide MS (ESI) m/z 432 $MH^+$ Example 874

3-[(E)-2-(4-Fluorophenyl)-vinyl]-4-methoxy-1H-indazole-5-carboxylic acid 4-methoxy-benzylamide MS (ESI) m/z 432 $MH^+$ Example 875

3-[(E)-2-(4-Fluorophenyl)-vinyl]-4-methoxy-1H-indazole-5-carboxylic acid 3,4-dimethoxy-benzylamide MS (ESI) m/z 462 $MH^+$ Example 876

3-[(E)-2-(4-Fluorophenyl)-vinyl]-4-methoxy-1H-indazole-5-carboxylic acid 2,4-dimethoxy-benzylamide MS (ESI) m/z 462 $MH^+$ Example 877

3-[(E)-2-(4-Fluorophenyl)-vinyl]-4-methoxy-1H-indazole-5-carboxylic acid 3,5-dimethoxy-benzylamide MS (ESI) m/z 462 $MH^+$ Example 878

3-[(E)-2-(4-Fluorophenyl)-vinyl]-4-methoxy-1H-indazole-5-carboxylic acid (benzo[1,3]dioxol-5-ylmethyl)-amide MS (ESI) m/z 446 $MH^+$ Example 879

3-[(E)-2-(4-Fluorophenyl)-vinyl]-4-methoxy-1H-indazole-5-carboxylic acid 3,4,5-trimethoxy-benzylamide MS (ESI) m/z 492 $MH^+$ Example 880

3-[(E)-2-(4-Fluorophenyl)-vinyl]-4-methoxy-1H-indazole-5-carboxylic acid 2,4,6-trimethoxy-benzylamide MS (ESI) m/z 492 $MH^+$ Example 881

3-[(E)-2-(4-Fluorophenyl)-vinyl]-4-methoxy-1H-indazole-5-carboxylic acid 2-trifluoromethyl-benzylamide MS (ESI) m/z 470 $MH^+$ Example 882

3-[(E)-2-(4-Fluorophenyl)-vinyl]-4-methoxy-1H-indazole-5-carboxylic acid 3-trifluoromethyl-benzylamide MS (ESI) m/z 470 $MH^+$ Example 883

3-[(E)-2-(4-Fluorophenyl)-vinyl]-4-methoxy-1H-indazole-5-carboxylic acid 4-trifluoromethyl-benzylamide MS (ESI) m/z 470 $MH^+$ Example 884

3-[(E)-2-(4-Fluorophenyl)-vinyl]-4-methoxy-1H-indazole-5-carboxylic acid 3-chloro-benzylamide MS (ESI) m/z 436 $MH^+$ Example 885

3-[(E)-2-(4-Fluorophenyl)-vinyl]-4-methoxy-1H-indazole-5-carboxylic acid 4-methanesulfonyl-benzylamide MS (ESI) m/z 480 $MH^+$ Example 886

3-[(E)-2-(4-Fluorophenyl)-vinyl]-4-methoxy-1H-indazole-5-carboxylic acid (2-cyano-ethyl)-amide MS (ESI) m/z 365 $MH^+$ Example 887

3-[(E)-2-(4-Fluorophenyl)-vinyl]-4-methoxy-1H-indazole-5-carboxylic acid (4-amino-2H-pyrazol-3-ylmethyl)-amide MS (ESI) m/z 407 $MH^+$ Example 888

3-[(E)-2-(4-Fluorophenyl)-vinyl]-4-methoxy-1H-indazole-5-carboxylic acid [1-(2-hydroxyethyl)-cyclopropyl]-amide 20 mg of 3-[(E)-2-(4-fluorophenyl)-vinyl]-4-methoxy-1H-indazole-5-carboxylic acid (1-benzyloxyethyl-cyclopropyl)-amide obtained by Example 814 was dissolved in 1 mL of dichloromethane, added with 6.4 μl of trimethylsilyliodide at 0° C. under nitrogen atmosphere, and stirred at this temperature for 2 hours. The reaction solution was added with methanol to stop the reaction, and the solvent was concentrated, followed by purification by LC-MS, to afford 1.7 mg of the title compound.

MS (ESI) m/z 396 $MH^+$

Production Example 889

3-Iodo-4-methoxy-1H-indazole-5-carboxylic acid

In accordance with the method of Example 216, from 14.5 g of 3-iodo-4-methoxy-1H-indazole-5-carbonitrile obtained by Production example 321, 5.4 g of the title compound was obtained as beige crude crystals.

$^1$H-NMR (400 MHz, $CD_3OD$) δ4.04 (3H, s), 7.31 (1H, d, J=8.8 Hz), 7.89 (1H, d, J=8.8 Hz).

Production Example 890

3-Iodo-4-methoxy-1-trityl-1H-indazole-5-carboxylic acid methyl ester 3.1 g of crude 3-iodo-4-methoxy-1H-indazole-5-carboxylic acid obtained by Production example 889 was esterified in methanol in the manner as described in Production example 274, and further tritylated in the manner as described in Production example 94, to afford 2.0 g of the title compound as a colorless powder.

$^1$H-NMR (400 MHz, DMSO-$d_6$) 3.80 (3H, s), 3.94 (3H, s), 6.22 (1H, d, J=8.9 Hz), 7.10-7.15 (6H, m), 7.28-7.37 (9H, m), 7.42 (1H, d, J=8.9 Hz).

Example 891

4-Methoxy-3-[(E)-2-(pyridin-2-yl)-vinyl]-1H-indazole-5-carboxylic acid methyl ester 550 mg of 3-iodo-4-methoxy-1-trityl-1H-indazole-5-carboxylic acid methyl ester obtained by Production example 890 and 160 mg of 2-vinylpyridine were reacted in the similar method as described in Production example 181, followed by deprotection in the similar method as described in Example 16, to afford 150 mg of the title compound as a colorless powder.

$^1$H-NMR (400 MHz, DMSO-$d_6$) δ 3.87 (3H, s), 3.95 (3H, s), 7.29 (1H, dd, J=4.8, 7.7 Hz), 7.36 (1H, d, J=9.2 Hz), 7.60 (1H, d, J=7.7 Hz), 7.61 (1H, d, J=15.9 Hz), 7.74 (1H, d, J=9.2 Hz), 7.81 (1H, dt, J=1.9, 7.7 Hz), 8.08 (1H, d, J=15.9 Hz), 8.63 (1H, dd, J=1.9, 4.8 Hz), 13.61 (1H, bs).

Example 892

4-Methoxy-3-[(E)-2-(pyridin-2-yl)-vinyl]-1H-indazole-5-carboxylic acid 150 mg of 4-methoxy-3-[(E)-2-(pyridin-2-yl)-vinyl]-1H-indazole-5-carboxylic acid methyl ester was treated in the similar method as described in Example 144, to afford 120 mg of the title compound as a pale yellow powder.

$^1$H-NMR (400 MHz, DMSO-$d_6$) δ 3.96 (3H, s), 7.29 (1H, dd, J=4.8, 7.7 Hz), 7.33 (1H, d, J=8.6 Hz), 7.59 (1H, d, J=7.7 Hz), 7.61 (1H, d, J=16.0 Hz), 7.75 (1H, d, J=8.6 Hz), 7.81 (1H, dt, J=1.7, 7.7 Hz), 8.09 (1H, d, J=16.0 Hz), 8.63 (1H, bd, J=4.8 Hz), 12.65-12.80 (1H, bs), 13.55 (1H, bs).

Example 893

In the similar method as described in Example 44, 4-methoxy-3-[(E)-2-(pyridin-2-yl)-vinyl]-1H-indazole-5-carboxylic acid obtained by Production example 892 and various kinds of amine were condensed, followed by purification by LC-MS, to afford the compounds of Examples 894-898.

Example 894

4-Methoxy-3-[(E)-2-(pyridin-2-yl)-vinyl]-1H-indazole-5-carboxylic acid cyclopropylamide MS (ESI) m/z 335 $MH^+$ Example 895

4-Methoxy-3-[(E)-2-(pyridin-2-yl)-vinyl]-1H-indazole-5-carboxylic acid (furan-2-ylmethyl)-amide MS (ESI) m/z 375 $MH^+$ Example 896

4-Methoxy-3-[(E)-2-(pyridin-2-yl)-vinyl]-1H-indazole-5-carboxlic acid (thiophen-2-ylmethyl)-amide MS (ESI) m/z 391 $MH^+$ Example 897

4-Methoxy-3-[(E)-2-(pyridin-2-yl)-vinyl]-1H-indazole-5-carboxylic acid (1-carbamoyl-2-phenylethyl)-amide MS (ESI) m/z 442 $MH^+$ Example 898

4-Methoxy-3-[(E)-2-(pyridin-2-yl)-vinyl]-1H-indazole-5-carboxylic acid (1-hydroxymethyl-2-methylpropyl)-amide MS (ESI) m/z 381 $MH^+$ Example 899

3-[(E)-2-(6-Hydroxy-pyridin-2-yl)-vinyl]-4-methoxy-1H-indazole-5-carboxylic acid methyl ester 550 mg of 3-iodo-4-methoxy-1-trityl-1H-indazole-5-carboxylic acid methyl ester obtained by Production example 890 and 270 mg of 2-tert-butoxy-5-vinylpyridine were reacted in the similar method as described in Production example 181, followed by deprotection in the similar method as described in Example 16, to afford 120 mg of the title compound as a yellow powder.

$^1$H-NMR (400 MHz, DMSO-$d_6$) δ 3.87 (3H, s), 3.94 (3H, s), 6.50 (1H, bd, J=9.1 Hz), 6.58 (1H, bd, J=7.0 Hz), 7.30 (1H, d, J=16.1 Hz), 7.35 (1H, d, J=9.1 Hz), 7.46 (1H, dd, J=7.0, 9.1 Hz), 7.74 (1H, d, J=9.1 Hz), 7.83 (1H, d, J=16.1 Hz).

Example 900

3-[(E)-2-(6-Hydroxy-pyridin-2-yl)-vinyl]-4-methoxy-1H-indazole-5-carboxylic acid 120 mg of 3-[(E)-2-(6-hydroxy-pyridin-2-yl)-vinyl]-4-methoxy-1H-indazole-5-carboxylic acid methyl ester obtained by Example 899 was treated in the similar method as described in Example 144, to afford 95 mg of the title compound as a yellow powder.

$^1$H-NMR (400 MHz, DMSO-$d_6$) δ 3.95 (3H, s), 6.35 (1H, d, J=9.2 Hz), 6.64 (1H, bd, J=7.1 Hz), 7.33 (1H, d, J=16.8 Hz), 7.34 (1H, d, J=8.8 Hz), 7.51 (1H, dd, J=7.1, 9.2 Hz), 7.75 (1H, d, J=8.8 Hz), 7.84 (1H, d, J=16.8 Hz).

Example 901

3-[(E)-2-(6-Hydroxy-pyridin-2-yl)-vinyl]-4-methoxy-1H-indazole-5-carboxylic acid and various kinds of amine were condensed in the similar method as described in Example 44, followed by purification by LC-MS, to afford the compounds of Examples 902-906.

Example 902

3-[(E)-2-(6-Hydroxy-pyridin-2-yl)-vinyl]-4-methoxy-1H-indazole-5-carboxylic acid cyclopropylamide MS (ESI) m/z 351 $MH^+$ Example 903

3-[[(E)-2-(6-Hydroxy-pyridin-2-yl)-vinyl]-4-methoxy-1H-indazole-5-carboxylic acid (furan-2-ylmethyl)-amide MS (ESI) m/z 391 $MH^+$ Example 904

3-[(E)-2-(6-Hydroxy-pyridin-2-yl)-vinyl]-4-methoxy-1H-indazole-5-carboxylic acid (thiophene-2-ylmethyl)-amide MS (ESI) m/z 407 $MH^+$ Example 905

3-[(E)-2-(6-Hydroxy-pyridin-2-yl)-vinyl]-4-methoxy-1H-indazole-5-carboxylic acid (1-carbamoyl-2-phenylethyl)-amide MS (ESI) m/z 458 $MH^+$ Example 906

3-[(E)-2-(6-Hydroxy-pyridin-2-yl)-vinyl]-4-methoxy-1H-indazole-5-carboxylic acid (1-hydroxymethyl-2-methyl-propyl)-amide MS (ESI) m/z 397 $MH^+$ Example 907

3-[(E)-2-(6-Acetylpyridin-3-yl)-vinyl]-4-methoxy-1H-indazole-5-carboxylic acid methyl ester 400 mg of 3-iodo-4-methoxy-1-trityl-1H-indazole-5-carboxylic acid methyl ester obtained by Production example 890 and 160 mg of 1-(5-vinylpyridin-2-yl)ethanone were reacted in the similar method as described in Production example 181, followed by deprotection in the similar method as described in Example 16, to afford 50 mg of the title compound as an orange powder.

$^1$H-NMR (400 MHz, DMSO-$d_6$) δ 2.66 (3H, s), 3.87 (3H, s), 3.99 (3H, s), 7.37 (1H, d, J=8.8 Hz), 7.69 (1H, d, J=16.8 Hz), 7.74 (1H, d, J=8.8 Hz), 7.84 (1H, d, J=16.8 Hz), 7.99 (1H, d, J=8.2 Hz), 8.32 (1H, dd, J=2.2, 8.2 Hz), 8.98 (1H, d, J=2.2 Hz), 13.70 (1H, bs).

Example 908

3-[(E)-2-(6-Acetylpyridin-3-yl)-vinyl]-4-methoxy-1H-indazole-5-carboxylic acid 50 mg of 3-[(E)-2-(6-acetylpyridin-3-yl)-vinyl]-4-methoxy-1H-indazole-5-carboxylic acid methyl ester was treated in the similar method as described in Example 144, to afford 50 mg of the title compound as an orange powder.

$^1$H-NMR (400 MHz, DMSO-$d_6$) δ 2.66 (3H, s), 3.99 (3H, s), 7.33 (1H, d, J=8.7 Hz), 7.69 (1H, d, J=16.6 Hz), 7.55 (1H, d, J=8.7 Hz), 7.84 (1H, d, J=16.6 Hz), 7.99 (1H, d, J=8.1 Hz), 8.30 (1H, dd, J=2.1, 8.1 Hz), 8.98 (1H, d, J=2.1 Hz), 13.63 (1H, bs).

Example 909

3-[(E)-2-(6-Acetylpyridin-3-yl)-vinyl]-4-methoxy-1H-indazole-5-carboxylic acid and various kinds of amine were condensed in the similar method as described in Example 44, followed by purification by LC-MS, to afford the compounds of Examples 910-916.

Example 910

3-[(E)-2-(6-Acetylpyridin-3-yl)-vinyl]-4-methoxy-1H-indazole-5-carboxylic acid cyclopropylamide MS (ESI) m/z 377 $MH^+$ Example 911

3-[(E)-2-(6-Acetylpyridin-3-yl)-vinyl]-4-methoxy-1H-indazole-5-carboxylic acid (furan-2-ylmethyl)-amide MS (ESI) m/z 417 $MH^+$ Example 912

3-[(E)-2-(6-Acetylpyridin-3-yl)-vinyl]-4-methoxy-1H-indazole-5-carboxylic acid (thiophen-2-ylmethyl)-amide MS (ESI) m/z 433 $MH^+$ Example 913

3-[(E)-2-(6-Acetylpyridin-3-yl)-vinyl]-4-methoxy-1H-indazole-5-carboxylic acid (1-carbamoyl-2-phenylethyl)-amide MS (ESI) m/z 484 $MH^+$ Example 914

3-[(E)-2-(6-Acetylpyridin-3-yl)-vinyl]-4-methoxy-1H-indazole-5-carboxylic acid (1-hydroxymethyl-2-methyl-propyl)-amide MS (ESI) m/z 423 $MH^+$ Example 915

3-[(E)-2-(6-Acetylpyridin-3-yl)-vinyl]-4-methoxy-1H-indazole-5-carboxylic acid (2-hydroxy-propyl)-amide MS (ESI) m/z 395 $MH^+$ Example 916

3-[(E)-2-(6-Acetylpyridin-3-yl)-vinyl]-4-methoxy-1H-indazole-5-carboxylic acid (2-acetylaminoethyl)-amide MS (ESI) m/z 422 $MH^+$ Example 917

3-[(E)-2-(Benzo[1,3]dioxol-5-yl)-vinyl]-4-methoxy-1H-indazole-5-carboxylic acid methyl ester 400 mg of 3-iodo-4-methoxy-1-trityl-1H-indazole-5-carboxylic acid methyl ester obtained by Production example 890 and 160 mg of 5-vinylbenzo[1,3]dioxole were reacted in the similar method as described in Production example 181, followed by deprotection in the similar method as described in Example 16, to afford 150 mg of the title compound as a colorless powder.

$^1$H-NMR (400 MHz, $CDCl_3$) δ 3.97 (3H, s), 4.04 (3H, s), 6.01 (2H, s), 6.83 (1H, d, J=7.9 Hz), 7.03 (1H, dd, J=1.6, 7.9 Hz), 7.15 (1H, d, J=1.6 Hz), 7.21 (1H, d, J=8.9 Hz), 7.48 (1H, d, J=16.6 Hz), 7.58 (1H, d, J=16.6 Hz), 7.90 (1H, d, J=8.9 Hz).

Example 918

3-[(E)-2-(Benzo[1,3]dioxol-5-yl)-vinyl]-4-methoxy-1H-indazole-5-carboxylic acid 150 mg of 3-(E)-2-(benzo[1,3]dioxole-5-yl)-vinyl]-4-methoxy-1H-indazole-5-carboxylic acid methyl ester was treated in the similar method as described in Example 144, to afford 130 mg of the title compound as a pale yellow powder.

$^1$H-NMR (400 MHz, DMSO-$d_6$) δ 3.94 (3H, s), 6.06 (2H, s), 6.94 (1H, d, J=8.0 Hz), 7.09 (1H, dd, J=1.6, 8.0 Hz), 7.27 (1H, d, J=8.8 Hz), 7.27 (1H, d, J=1.6 Hz), 7.40 (1H, d, J=16.0 Hz), 7.47 (1H, d, J=16.0 Hz), 7.72 (1H, d, J=8.8 Hz), 12.65 (1H, bs), 13.25 (1H, bs).

Example 919

3-[(E)-2-(Benzo[1,3]dioxol-5-yl)-vinyl]-4-methoxy-1H-indazole-5-carboxylic acid and various kinds of amine were condensed in the similar method as described in Example 44, followed by purification by LC-MS, to afford the compounds of Examples 920-930.

Example 920

3-[(E)-2-(Benzo[1,3]dioxol-5-yl)-vinyl]-4-methoxy-1H-indazole-5-carboxylic acid cyclopropylamide MS (ESI) m/z 378 $MH^+$ Example 921

3-[(E)-2-(Benzo[1,3]dioxol-5-yl)-vinyl]-4-methoxy-1H-indazole-5-carboxylic acid (furan-2-ylmethyl)-amide $^1$H-NMR (400 MHz, $CDCl_3$) δ 3.90 (3H, s), 4.74 (2H, d, J=6.0 Hz), 6.01 (2H, s), 6.34 (1H, d, J=3.9 Hz), 6.38 (1H, d, J=3.9 Hz), 6.83 (1H, d, J=8.0 Hz), 7.03 (1H, dd, J=1.6, 8.0 Hz), 7.15 (1H, d, J=1.6 Hz), 7.30 (1H, d, J=9.0 Hz), 7.37 (1H, d, J=16.4 Hz), 7.42 (1H, s), 7.57 (1H, d, J=16.4 Hz), 8.16 (1H, d, J=9.0 Hz), 8.18 (1H, bt, J=6.0 Hz).

MS (ESI) m/z 418 $MH^+$

Example 922

3-[(E)-2-(Benzo[1,3]dioxol-5-yl)-vinyl]-4-methoxy-1H-indazole-5-carboxylic acid (thiophen-2-ylmethyl)-amide MS (ESI) m/z 434 $MH^+$ Example 923

3-[(E)-2-(Benzo[1,3]dioxol-5-yl)-vinyl]-4-methoxy-1H-indazole-5-carboxylic acid (1-carbamoyl-2-phenylethyl)-amide MS (ESI) m/z 485 $MH^+$ Example 924

3-[(E)-2-(Benzo[1,3]dioxol-5-yl)-vinyl]-4-methoxy-1H-indazole-5-carboxylic acid (1-hydroxymethyl-2-methyl-propyl)-amide MS (ESI) m/z 424 $MH^+$ Example 925

3-[(E)-2-(Benzo[1,3]dioxol-5-yl)-vinyl]-4-methoxy-1H-indazole-5-carboxylic acid (2-hydroxy-propyl)-amide MS (ESI) m/z 396 $MH^+$ Example 926

3-[(E)-2-(Benzo[1,3]dioxol-5-yl)-vinyl]-4-methoxy-1H-indazole-5-carboxylic acid (2-acetylaminoethyl)-amide MS (ESI) m/z 423 $MH^+$ Example 927

3-[(E)-2-(Benzo[1,3]dioxol-5-yl)-vinyl]-4-methoxy-1H-indazole-5-carboxylic acid (pyrazin-2-ylmethyl)-amide MS (ESI) m/z 430 $MH^+$ Example 928

3-[(E)-2-(Benzo[1,3]dioxol-5-yl)-vinyl]-4-methoxy-1H-indazole-5-carboxylic acid cyclopropylmethyl-amide MS (ESI) m/z 392 $MH^+$ Example 929

3-[(E)-2-(Benzo[1,3]dioxol-5-yl)-vinyl]-4-methoxy-1H-indazole-5-carboxylic acid benzylamide MS (ESI) m/z 428 $MH^+$ Example 930

3-[(E)-2-(Benzo[1,3]dioxol-5-yl)-vinyl]-4-methoxy-1H-indazole-5-carboxylic acid (pyridin-3-ylmethyl)-amide MS (ESI) m/z 429 $MH^+$ Example 931

4-Methoxy-3-[(E)-2-(pyrazin-2-yl)-vinyl]-1H-indazole-5-carboxylic acid ethyl ester 1.12 g of 3-iodo-4-methoxy-1-trityl-1H-indazole-5-carboxylic acid ethyl ester obtained by Production example 276 and 160 mg of 2-vinylpyrazine were reacted in the similar method as described in Production example 181, followed by deprotection in the similar method as described in Example 16, to afford 440 mg of the title compound as a pale yellow powder.

$^1H$-NMR (400 MHz, $CDCl_3$) δ 1.46 (3H, t, J=7.2 Hz), 4.08 (3H, s), 4.45 (2H, q, J=7.2 Hz), 7.26 (1H, d, J=8.8 Hz), 7.77 (1H, d, J=16.0 Hz), 7.90 (1H, d, J=8.8 Hz), 8.30 (1H, d, J=16.0 Hz), 8.45 (1H, d, J=2.4 Hz), 8.61 (1H, dd, J=1.6, 2.4 Hz), 8.71 (1H, d, J=1.6 Hz).

Example 932

4-Methoxy-3-[(E)-2-(pyrazin-2-yl)-vinyl]-1H-indazole-5-carboxylic acid 440 mg of 4-methoxy-3-[(E)-2-(pyrazin-2-yl)-vinyl]-1H-indazole-5-carboxylic acid ethyl ester was treated in the similar method as described in Example 144, to afford 340 mg of the title compound as a yellow powder.

$^1H$-NMR (400 MHz, DMSO-$d_6$) δ 3.97 (3H, s), 7.35 (1H, d, J=8.8 Hz), 7.68 (1H, d, J=16.0 Hz), 7.76 (1H, d, J=8.8 Hz), 8.20 (1H, d, J=16.0 Hz), 8.53 (1H, d, J=2.4 Hz), 8.69 (1H, dd, J=1.2, 2.4 Hz), 8.85 (1H, d, J=1.2 Hz), 12.70-12.90 (1H, bs), 13.67 (1H, bs).

Example 933

4-Methoxy-3-[(E)-2-(pyrazin-2-yl)-vinyl]-1H-indazole-5-carboxylic acid and various kinds of amine were condensed in the similar method as described in Example 44, followed by purification by LC-MS, to afford the compounds of Examples 934-940.

Example 934

4-Methoxy-3-[(E)-2-(pyrazin-2-yl)-vinyl]-1H-indazole-5-carboxylic acid (pyrazin-2-ylmethyl)-amide MS (ESI) m/z 388 $MH^+$ Example 935

4-Methoxy-3-[(E)-2-(pyrazin-2-yl)-vinyl]-1H-indazole-5-carboxylic acid (furan-3-ylmethyl)-amide MS (ESI) m/z 376 $MH^+$ Example 936

4-Methoxy-3-[(E)-2-(pyrazin-2-yl)-vinyl]-1H-indazole-5-carboxylic acid cyclopropylmethyl-amide MS (ESI) m/z 350 $MH^+$ Example 937

4-Methoxy-3-[(E)-2-(pyrazin-2-yl)-vinyl]-1H-indazole-5-carboxylic acid (thiophen-3-ylmethyl)-amide MS (ESI) m/z 392 $MH^+$ Example 938

4-Methoxy-3-[(E)-2-(pyrazin-2-yl)-vinyl]-1H-indazole-5-carboxylic acid cyclopropylamide MS (ESI) m/z 336 $MH^+$ Example 939

4-Methoxy-3-[(E)-2-(pyrazin-2-yl)-vinyl]-1H-indazole-5-carboxylic acid benzylamide MS (ESI) m/z 386 $MH^+$ Example 940

4-Methoxy-3-[(E)-2-(pyrazin-2-yl)-vinyl]-1H-indazole-5-carboxylic acid (pyridin-3-ylmethyl)-amide MS (ESI) m/z 387 $MH^+$ Example 941

3-[(E)-2-(3-Fluoro-4-methoxyphenyl)-vinyl]-4-methoxy-1H-indazole-5-carboxylic acid ethyl ester 550 mg of 3-iodo-4-methoxy-1-trityl-1H-indazole-5-carboxylic acid ethyl ester obtained by Production example 276 and 300 mg of 3-fluoro-4-methoxystyrene were reacted in the similar method as described in Production example 181, followed by deprotection in the similar method as described in Example 16, to afford 170 mg of the title compound as a colorless powder.

$^1H$-NMR (400 MHz, $CDCl_3$) δ 1.46 (3H, t, J=7.2 Hz), 3.93 (3H, s), 4.04 (3H, s), 4.44 (2H, q, J=7.2 Hz), 6.97 (1H, t, J=8.6 Hz), 7.21 (1H, d, J=8.8 Hz), 7.25-7.30 (1H, m), 7.36 (1H, dd, J=2.2, 12.6 Hz), 7.52 (1H, d, J=16.4 Hz), 7.56 (1H, d, J=16.4 Hz), 7.90 (1H, d, J=8.8 Hz).

Example 942

3-[(E)-2-(3-Fluoro-4-methoxyphenyl)-vinyl]-4-methoxy-1H-indazole-5-carboxylic acid 170 mg of 3-[(E)-2-(3-fluoro-4-methoxyphenyl)-vinyl]-4-methoxy-1H-indazole-5-carboxylic acid ethyl ester was treated in the similar method as described in Example 144, to afford 150 mg of the title compound as a pale yellow powder.

$^1H$-NMR (400 MHz, DMSO-$d_6$) δ 3.88 (3H, s), 3.96 (3H, s), 7.20 (1H, t, J=8.8 Hz), 7.29 (1H, d, J=8.8 Hz), 7.42 (1H, bd, J=8.8 Hz), 7.46 (1H, d, J=16.1 Hz)., 7.50 (1H, d, J=16.1 Hz), 7.55 (1H, dd, J=2.2, 12.8 Hz), 7.74 (1H, d, J=8.8 Hz), 12.60 (1H, bs), 13.42 (1H, s).

Example 943

3-[(E)-2-(3-fluoro-4-methoxyphenyl)-vinyl]-4-methoxy-1H-indazole-5-carboxylic acid and various kinds of amine were condensed in the similar method as described in Example 44, followed by purification by LC-MS, to afford the compounds of Examples 944-953.

Example 944

3-[(E)-2-(3-Fluoro-4-methoxyphenyl)-vinyl]-4-methoxy-1H-indazole-5-carboxylic acid (pyrazin-2-ylmethyl) amide MS (ESI) m/z 434 $MH^+$ Example 945

3-[(E)-2-(3-Fluoro-4-methoxyphenyl)-vinyl]-4-methoxy-1H-indazole-5-carboxylic acid (furan-2-ylmethyl) amide MS (ESI) m/z 422 $MH^+$ Example 946

3-[(E)-2-(3-Fluoro-4-methoxyphenyl)-vinyl]-4-methoxy-1H-indazole-5-carboxylic acid cyclopropylmethyl amide MS (ESI) m/z 396 $MH^+$ Example 947

3-[(E)-2-(3-Fluoro-4-methoxyphenyl)-vinyl]-4-methoxy-1H-indazole-5-carboxylic acid (thiophen-2-ylmethyl) amide MS (ESI) m/z 438 $MH^+$ Example 948

3-[(E)-2-(3-Fluoro-4-methoxyphenyl)-vinyl]-4-methoxy-1H-indazole-5-carboxylic acid cyclopropylamide MS (ESI) m/z 382 $MH^+$ Example 949

3-[(E)-2-(3-Fluoro-4-methoxyphenyl)-vinyl]-4-methoxy-1H-indazole-5-carboxylic acid benzylamide MS (ESI) m/z 432 $MH^+$ Example 950

3-[(E)-2-(3-Fluoro-4-methoxyphenyl)-vinyl]-4-methoxy-1H-indazole-5-carboxylic acid (pyridin-3-ylmethyl) amide MS (ESI) m/z 433 $MH^+$ Example 951

3-[(E)-2-(3-Fluoro-4-methoxyphenyl)-vinyl]-4-methoxy-1H-indazole-5-carboxylic Acid (pyridin-2-ylmethyl) amide MS (ESI) m/z 433 $MH^+$ Example 952

3-[(E)-2-(3-Fluoro-4-methoxyphenyl)-vinyl]-4-methoxy-1H-indazole-5-carboxylic acid (thiophen-3-ylmethyl) amide MS (ESI) m/z 438 $MH^+$ Example 953

3-[(E)-2-(3-Fluoro-4-methoxyphenyl)-vinyl]-4-methoxy-1H-indazole-5-carboxylic acid (oxazol-2-ylmethyl) amide MS (ESI) m/z 423 $MH^+$ Example 954

3-[(E)-2-(4-Fluoro-3-methoxyphenyl)-vinyl]-4-methoxy-1H-indazole-5-carboxylic acid ethyl ester 550 mg of 3-iodo-4-methoxy-1-trityl-1H-indazole-5-carboxylic acid ethyl ester obtained by Production example 276 and 300 mg of 4-fluoro-3-methoxystyrene were reacted in the similar method as described in Production example 181, followed by deprotection in the similar method as described in Example 16, to afford 160 mg of the title compound as a colorless powder.

$^1$H-NMR (400 MHz, $CDCl_3$) δ 1.45 (3H, t, J=7.2 Hz), 3.94 (3H, s), 4.06 (3H, s), 4.45 (2H, q, J=7.2 Hz), 7.06-7.17 (2H, m), 7.19 (1H, dd, J=1.6, 8.0 Hz), 7.23 (1H, d, J=8.8 Hz), 7.57 (1H, d, J=16.4 Hz), 7.61 (1H, d, J=16.4 Hz), 7.91 (1H, d, J=8.8 Hz).

Example 955

3-[(E)-2-(4-Fluoro-3-methoxyphenyl)-vinyl]-4-methoxy-1H-indazole-5-carboxylic acid 160 mg of 3-[(E)-2-(4-fluoro-3-methoxyphenyl)-vinyl]-4-methoxy-1H-indazole-5-carboxylic acid ethyl ester was treated in the similar method as described in Example 144, to afford 140 mg of the title compound as a colorless powder.

$^1$H-NMR (400 MHz, DMSO-$d_6$) δ 3.93 (3H, s), 3.96 (3H, s), 7.22-7.28 (2H, m), 7.30 (1H, d, J=8.4 Hz), 7.42 (1H, dd, J=1.6, 7.6 Hz), 7.54 (1H, d, J=16.3 Hz), 7.55 (1H, d, J=16.3 Hz), 7.74 (1H, d, J=8.4 Hz), 12.60-12.80 (1H, bs), 13.46 (1H, bs).

Example 956

3-[(E)-2-(4-Fluoro-3-methoxyphenyl)-vinyl]-4-methoxy-1H-indazole-5-carboxylic acid and various kinds of amine were condensed in the similar method as described in Example 44, followed by purification by LC-MS, to afford the compounds of Examples 957-966.

Example 957

3-[(E)-2-(4-Fluoro-3-methoxyphenyl)-vinyl]-4-methoxy-1H-indazole-5-carboxylic acid (pyrazin-2-ylmethyl) amide MS (ESI) m/z 434 $MH^+$ Example 958

3-[(E)-2-(4-Fluoro-3-methoxyphenyl)-vinyl]-4-methoxy-1H-indazole-5-carboxylic acid (furan-2-ylmethyl) amide MS (ESI) m/z 422 $MH^+$ Example 959

3-[(E)-2-(4-Fluoro-3-methoxyphenyl)-vinyl]-4-methoxy-1H-indazole-5-carboxylic acid cyclopropylmethyl amide MS (ESI) m/z 396 $MH^+$ Example 960

3-[(E)-2-(4-Fluoro-3-methoxyphenyl)-vinyl]-4-methoxy-1H-indazole-5-carboxylic acid (thiophen-2-ylmethyl) amide MS (ESI) m/z 438 $MH^+$ Example 961

3-[(E)-2-(4-Fluoro-3-methoxyphenyl)-vinyl]-4-methoxy-1H-indazole-5-carboxylic acid cyclopropylamide MS (ESI) m/z 382 $MH^+$ Example 962

3-[(E)-2-(4-Fluoro-3-methoxyphenyl)-vinyl]-4-methoxy-1H-indazole-5-carboxylic acid benzylamide MS (ESI) m/z 432 $MH^+$ Example 963

3-[(E)-2-(4-Fluoro-3-methoxyphenyl)-vinyl]-4-methoxy-1H-indazole-5-carboxylic acid (pyridin-3-ylmethyl) amide MS (ESI) m/z 433 $MH^+$ Example 964

3-[(E)-2-(4-Fluoro-3-methoxyphenyl)-vinyl]-4-methoxy-1H-indazole-5-carboxylic acid (pyridin-2-ylmethyl) amide MS (ESI) m/z 433 $MH^+$ Example 965

3-[(E)-2-(4-Fluoro-3-methoxyphenyl)-vinyl]-4-methoxy-1H-indazole-5-carboxylic acid (thiophen-3-ylmethyl) amide MS (ESI) m/z 438 $MH^+$ Example 966

3-[(E)-2-(4-Fluoro-3-methoxyphenyl)-vinyl]-4-methoxy-1H-indazole-5-carboxylic acid (oxazol-2-ylmethyl) amide MS (ESI) m/z 423 $MH^+$ Example 967

3-[(E)-2-(3,4-Difluorophenyl)-vinyl]-4-methoxy-1H-indazole-5-carboxylic acid ethyl ester 410 mg of 3-iodo-4-methoxy-1-trityl-1H-indazole-5-carboxylic acid ethyl ester obtained by Production example 276 and 300 mg of 3,4-difluorostyrene were reacted in the similar method as described in Production example 181, followed by deprotection in the similar method as described in Example 16, to afford 110 mg of the title compound as a colorless powder.

$^1$H-NMR (400 MHz, $CDCl_3$) δ 1.45 (3H, t, J=7.2 Hz), 4.05 (3H, s), 4.46 (2H, q, J=7.2 Hz), 7.17 (1H, dt, J=8.1, 9.8 Hz), 7.23 (1H, d, J=9.0 Hz), 7.26-7.31 (1H, m), 7.40 (1H, ddd, J=2.1, 8.1, 11.4 Hz), 7.56 (1H, d, J=16.4 Hz), 7.58 (1H, d, J=16.4 Hz), 7.92 (1H, d, J=9.0 Hz).

Example 968

3-[(E)-2-(3,4-Difluorophenyl)-vinyl]-4-methoxy-1H-indazole-5-carboxylic acid 110 mg of 3-[(E)-2-(3,4-difluorophenyl)-vinyl]-4-methoxy-1H-indazole-5-carboxylic acid ethyl ester was treated in the similar method as described in Example 144, to afford 100 mg of the title compound as a colorless powder.

$^1$H-NMR (400 MHz, DMSO-$d_6$) δ 3.97 (3H, s), 7.31 (1H, d, J=8.8 Hz), 7.46 (1H, dt, J=8.4, 10.4 Hz), 7.49-7.55 (1H, m), 7.54 (1H, d, J=16.4 Hz), 7.57 (1H, d, J=16.4 Hz), 7.75 (1H, d, J=8.8 Hz), 7.77 (1H, ddd, J=1.9, 8.4, 12.1 Hz), 12.75 (1H, bs), 13.51 (1H, bs).

Example 969

3-[(E)-2-(3,4-Difluorophenyl)-vinyl]-4-methoxy-1H-indazole-5-carboxylic acid and various kinds of amine were condensed in the similar method as described in Example 44, followed by purification by LC-MS, to afford the compounds of Examples 970-979.

Example 970

3-[(E)-2-(3,4-Difluorophenyl)-vinyl]-4-methoxy-1H-indazole-5-carboxylic acid (pyrazin-2-ylmethyl) amide MS (ESI) m/z 422 $MH^+$ Example 971

3-[(E)-2-(3,4-Difluorophenyl)-vinyl]-4-methoxy-1H-indazole-5-carboxylic acid (furan-2-ylmethyl) amide MS (ESI) m/z 410 $MH^+$ Example 972

3-[(E)-2-(3,4-Difluorophenyl)-vinyl]-4-methoxy-1H-indazole-5-carboxylic acid cyclopropylmethyl amide MS (ESI) m/z 384 $MH^+$ Example 973

3-[(E)-2-(3,4-Difluorophenyl)-vinyl]-4-methoxy-1H-indazole-5-carboxylic acid (thiophen-2-ylmethyl) amide MS (ESI) m/z 426 $MH^+$ Example 974

3-[(E)-2-(3,4-Difluorophenyl)-vinyl]-4-methoxy-1H-indazole-5-carboxylic acid cyclopropylamide MS (ESI) m/z 370 $MH^+$ Example 975

3-[(E)-2-(3,4-Difluorophenyl)-vinyl]-4-methoxy-1H-indazole-5-carboxylic acid benzylamide MS (ESI) m/z 420 $MH^+$ Example 976

3-[(E)-2-(3,4-Difluorophenyl)-vinyl]-4-methoxy-1H-indazole-5-carboxylic acid (pyridin-3-ylmethyl) amide MS (ESI) m/z 421 $MH^+$ Example 977

3-[(E)-2-(3,4-Difluorophenyl)-vinyl]-4-methoxy-1H-indazole-5-carboxylic acid (pyridin-2-ylmethyl) amide MS (ESI) m/z 421 $MH^+$ Example 978

3-[(E)-2-(3,4-Difluorophenyl)-vinyl]-4-methoxy-1H-indazole-5-carboxylic acid (thiophen-3-ylmethyl) amide MS (ESI) m/z 426 $MH^+$ Example 979

3-[(E)-2-(3,4-Difluorophenyl)-vinyl]-4-methoxy-1H-indazole-5-carboxylic acid (oxazol-2-ylmethyl) amide MS (ESI) m/z 411 $MH^+$ Example 980

3-[(E)-2-(2,4-Difluorophenyl)-vinyl]-4-methoxy-1H-indazole-5-carboxylic acid ethyl ester 410 mg of 3-iodo-4-methoxy-1-trityl-1H-indazole-5-carboxylic acid ethyl ester obtained by Production example 276 and 300 mg of 2,4-difluorostyrene were reacted in the similar method as described in Production example 181, followed by deprotection in the similar method as described in Example 16, to afford 50 mg of the title compound as a colorless powder.

$^1$H-NMR (400 MHz, $CDCl_3$) δ 1.46 (3H, t, J=7.2 Hz), 4.05 (3H, s), 4.43 (2H, q, J=7.2 Hz), 6.87 (1H, ddd, J=2.6, 8.4, 11.2 Hz), 6.93 (1H, dt, J=2.7, 8.4 Hz), 7.24 (1H, d, J=8.8 Hz), 7.62 (1H, dt, J=6.4, 8.4 Hz), 7.70 (1H, d, J=16.4 Hz), 7.75 (1H, d, J=16.4 Hz), 7.92 (1H, d, J=8.8 Hz).

Example 981

3-[(E)-2-(2,4-Difluorophenyl)-vinyl]-4-methoxy-1H-indazole-5-carboxylic acid 50 mg of 3-[(E)-2-(2,4-difluorophenyl)-vinyl]-4-methoxy-1H-indazole-5-carboxylic acid ethyl ester was treated in the similar method as described in Example 144, to afford 40 mg of the title compound as a colorless powder.

$^1$H-NMR (400 MHz, DMSO-$d_6$) δ 3.95 (3H, s), 7.17 (1H, dt, J=2.4, 8.8 Hz), 7.30-7.38 (1H, m), 7.32 (1H, d, J=8.8 Hz), 7.61 (1H, d, J=16.4 Hz), 7.67 (1H, d, J=16.4 Hz), 7.75 (1H, d, J=8.8 Hz), 7.88 (1H, dt, J=6.8, 8.8 Hz), 12.68-12.82 (1H, bs), 13.52 (1H, bs).

Example 982

3-[(E)-2-(2,4-Difluorophenyl)-vinyl]-4-methoxy-1H-indazole-5-carboxylic acid and various kinds of amine were condensed in the similar method as described in Example 44, followed by purification by LC-MS, to afford the compounds of Examples 983-992.

Example 983

3-[(E)-2-(2,4-Difluorophenyl)-vinyl]-4-methoxy-1H-indazole-5-carboxylic acid (pyrazin-2-ylmethyl) amide MS (ESI) m/z 422 $MH^+$ Example 984

3-[(E)-2-(2,4-Difluorophenyl)-vinyl]-4-methoxy-1H-indazole-5-carboxylic acid (furan-2-ylmethyl)amide MS (ESI) m/z 410 $MH^+$ Example 985

3-[(E)-2-(2,4-Difluorophenyl)-vinyl]-4-methoxy-1H-indazole-5-carboxylic acid cyclopropylmethyl amide MS (ESI) m/z 384 $MH^+$ Example 986

3-[(E)-2-(2,4-Difluorophenyl)-vinyl]-4-methoxy-1H-indazole-5-carboxylic acid (thiophen-2-ylmethyl) amide MS (ESI) m/z 426 $MH^+$ Example 987

3-[(E)-2-(2,4-Difluorophenyl)-vinyl]-4-methoxy-1H-indazole-5-carboxylic acid cyclopropylamide MS (ESI) m/z 370 $MH^+$ Example 988

3-[(E)-2-(2,4-Difluorophenyl)-vinyl]-4-methoxy-1H-indazole-5-carboxylic acid benzylamide MS (ESI) m/z 420 $MH^+$ Example 989

3-[(E)-2-(2,4-Difluorophenyl)-vinyl]-4-methoxy-1H-indazole-5-carboxylic acid (pyridin-3-ylmethyl) amide MS (ESI) m/z 421 $MH^+$ Example 990

3-[(E)-2-(2,4-Difluorophenyl)-vinyl]-4-methoxy-1H-indazole-5-carboxylic acid (pyridin-2-ylmethyl) amide MS (ESI) m/z 421 $MH^+$ Example 991

3-[(E)-2-(2,4-Difluorophenyl)-vinyl]-4-methoxy-1H-indazole-5-carboxylic acid (thiophen-3-ylmethyl) amide MS (ESI) m/z 426 $MH^+$ Example 992

3-[(E)-2-(2,4-Difluorophenyl)-vinyl]-4-methoxy-1H-indazole-5-carboxylic acid (oxazol-2-ylmethyl) amide MS (ESI) m/z 411 $MH^+$ Production Example 993

6-Fluoro-3-[(E)-2-(4-fluoro-3-methoxyphenyl)-vinyl]-5-nitro-1-trityl-1H-indazole 505 mg of 6-fluoro-3-iodo-5-nitro-1-trityl-1H-indazole obtained by Production example 747 and 304 mg of 3-methoxy-4-fluorostyrene were reacted in the similar method as described in Production example 181, to afford 145 mg of the title compound as a yellow powder.

$^1$H-NMR (400 MHz, DMSO-$d_6$) δ 3.93 (3H, s), 6.16 (1H, d, J=12.4 Hz), 7.21-7.30 (6H, m), 7.30-7.45 (11H, m), 7.46 (1H, d, J=16.4 Hz), 7.57 (1H, d, J=2.0, 8.4 Hz), 7.62 (1H, d, J=16.4 Hz), 9.12 (1H, d, J=7.6 Hz).

Production Example 994

6-Fluoro-3-[(E)-2-(4-fluoro-3-methoxyphenyl)-vinyl]-1-trityl-1H-indazol-5-ylamine 145 mg of 6-fluoro-3-[(E)-2-(4-fluoro-3-methoxyphenyl)-vinyl]-5-nitro-1-trityl-1H-indazole obtained by Production example 993 was reduced in the similar method as described in Production example 182, to afford 130 mg of the title compound as a pale brown oil.

$^1$H-NMR (400 MHz, $CDCl_3$) δ 3.93 (3H, s), 6.16 (1H, d, J=11.9 Hz), 7.00-7.26 (2H, m), 7.14 (1H, dd, J=2.0, 8.1 Hz), 7.20-7.35 (18H, m).

Example 995

In the similar method as described in Example 183, from 6-fluoro-3-[(E)-2-(4-fluoro-3-methoxyphenyl)-vinyl]-1-trityl-1H-indazol-5-ylamine and various kinds of carboxylic acid, the compounds of Examples 996-1004 were obtained.

Example 996

Cyclopropane carboxylic acid {6-fluoro-3-[(E)-2-(4-fluoro-3-methoxyphenyl)-vinyl]-1H-indazol-5-yl}amide MS (ESI) m/z 370 $MH^+$ Example 997

1-Hydroxycyclopropane carboxylic acid {6-fluoro-3-[(E)-2-(4-fluoro-3-methoxyphenyl)-vinyl]-1H-indazol-5-yl}amide MS (ESI) m/z 386 $MH^+$ Example 998

1-Acetyl piperidine-4-carboxylic acid {6-fluoro-3-[(E)-2-(4-fluoro-3-methoxyphenyl)-vinyl]-1H-indazol-5-yl}amide MS (ESI) m/z 455 $MH^+$ Example 999

Tetrahydrofuran-3-carboxylic acid {6-fluoro-3-[(E)-2-(4-fluoro-3-methoxyphenyl)-vinyl]-1H-indazol-5-yl}amide MS (ESI) m/z 400 $MH^+$ Example 1000

1-Methylaminocyclopropane carboxylic acid {6-fluoro-3-[(E)-2-(4-fluoro-3-methoxyphenyl)-vinyl]-1H-indazol-5-yl}amide MS (ESI) m/z 399 $MH^+$ Example 1001

N-{6-Fluoro-3-[(E)-2-(4-fluoro-3-methoxyphenyl)-vinyl]-1H-indazol-5-yl}-2-(thiophen-2-yl)acetamide MS (ESI) m/z 426 $MH^+$ Example 1002

Furan-2-carboxylic acid {6-fluoro-3-[(E)-2-(4-fluoro-3-methoxyphenyl)-vinyl]-1H-indazol-5-yl}amide MS (ESI) m/z 396 $MH^+$ Example 1003

2-Cyclopropyl-N-{6-fluoro-3-[(E)-2-(4-fluoro-3-methoxyphenyl)-vinyl]-1H-indazol-5-yl}acetamide MS (ESI) m/z 384 $MH^+$ Example 1004

(2S,4R)-4-hydroxypyrrolidine-2-carboxylic acid {6-fluoro-3-[(E)-2-(4-fluoro-3-methoxyphenyl)-vinyl]-1H-indazol-5-yl}amide MS (ESI) m/z 415 $MH^+$ Production Example 1005

6-Fluoro-3-[(E)-2-(3-fluoro-4-methoxyphenyl)-vinyl]-5-nitro-1-trityl-1H-indazole 505 mg of 6-fluoro-3-iodo-5-nitro-1-trityl-1H-indazole obtained by Production example 747 and 304 mg of 4-methoxy-3-fluorostyrene were reacted in the similar method as described in Production example 181, to afford 160 mg of the title compound as a yellow powder.

$^1$H-NMR (400 MHz, DMSO-$d_6$) δ 3.87 (3H, s), 6.11 (1H, d, J=12.4 Hz), 7.18 (1H, t, J=8.8 Hz), 7.18-7.27 (6H, m), 7.31-7.44 (11H, m), 7.60 (1H, d, J=16.4 Hz), 7.75 (1H, d, J=2.0, 13.2 Hz), 9.15 (1H, d, J=7.6 Hz).

Production Example 1006

6-Fluoro-3-[(E)-2-(3-fluoro-4-methoxyphenyl)-vinyl]-1-trityl-1H-indazol-5-ylamine 160 mg of 6-fluoro-3-[(E)-2-(3-fluoro-4-methoxyphenyl)-vinyl]-5-nitro-1-trityl-1H-indazole obtained by Production example 1005 was reduced in the similar method as described in Production example 182, to afford 140 mg of the title compound as a pale brown oil.

$^1$H-NMR (400 MHz, $CDCl_3$) δ 3.89 (3H, s), 6.15 (1H, d, J=12.6 Hz), 6.92 (1H, t, J=8.8 Hz), 7.15-7.38 (20H, m).

Example 1007

In the similar method as described in Example 183, from 6-fluoro-3-[(E)-2-(3-fluoro-4-methoxyphenyl)-vinyl]-1-trityl-1H-indazol-5-ylamine and various kinds of carboxylic acid, the compounds of Examples 1008-1016 were obtained.

Example 1008

Cyclopropane carboxylic acid {6-fluoro-3-[(E)-2-(3-fluoro-4-methoxyphenyl)-vinyl]-1H-indazol-5-yl}amide MS (ESI) m/z 370 $MH^+$ Example 1009

1-Hydroxycyclopropane carboxylic acid {6-fluoro-3-[(E)-2-(3-fluoro-4-methoxyphenyl)-vinyl]-1H-indazol-5-yl}amide MS (ESI) m/z 386 $MH^+$ Example 1010

1-Acetyl piperidine-4-carboxylic acid {6-fluoro-3-[(E)-2-(3-fluoro-4-methoxyphenyl)-vinyl]-1H-indazol-5-yl}amide MS (ESI) m/z 455 $MH^+$ Example 1011

Tetrahydrofuran-3-carboxylic acid {6-fluoro-3-[(E)-2-(3-fluoro-4-methoxyphenyl)-vinyl]-1H-indazol-5-yl}amide MS (ESI) m/z 400 $MH^+$ Example 1012

1-Methylaminocyclopropane carboxylic acid {6-fluoro-3-[(E)-2-(3-fluoro-4-methoxyphenyl)-vinyl]-1H-indazol-5-yl}amide MS (ESI) m/z 399 $MH^+$ Example 1013

N-{6-Fluoro-3-[(E)-2-(3-fluoro-4-methoxyphenyl)-vinyl]-1H-indazol-5-yl}-2-(thiophen-2-yl)acetamide MS (ESI) m/z 426 $MH^+$ Example 1014

Furan-2-carboxylic acid {6-fluoro-3-[(E)-2-(3-fluoro-4-methoxyphenyl)-vinyl]-1H-indazol-5-yl}amide MS (ESI) m/z 396 $MH^+$ Example 1015

2-Cyclopropyl-N-{6-fluoro-3-[(E)-2-(3-fluoro-4-methoxyphenyl)-vinyl]-1H-indazol-5-yl}acetamide MS (ESI) m/z 384 $MH^+$ Example 1016

(2S,4R)-4-Hydroxypyrrolidine-2-carboxylic acid {6-fluoro-3-[(E)-2-(3-fluoro-4-methoxyphenyl)-vinyl]-1H-indazol-5-yl}amide MS (ESI) m/z 415 $MH^+$ Example 1017

96 pieces of polystyrene labeled with TRANSTEM™ (SynPhase Polystyrene D-Seriese, Trityl™) were prepared and left in 130 mL of a solution of 20 mL acetyl chloride in dichloromethane for 3 hours. After removing the solution, the resin pieces were washed three times with dichloromethane, dried under reduced pressure, and the resin was heated at 80° C. for 4 hours in 100 mL of solution of 4.7 g of 3-iodo-4-methoxy-1H-indazole-5-carboxylic acid methyl ester produced as intermediate of Production example 890 and 2.2 mL of diisopropylethylamine in N-methylpyrrolidone. After removing the solution, the resin was washed successively with N-methylpyrrolidone, ethanol, water, methanol and tetrahydrofuran, and dried under reduced pressure.

The resultant resin pieces were divided into several groups each consisting of 10 pieces in accordance with the label, and each resin piece was added to 10 mL of previously-prepared several kinds of 0.5 M styrene compound in a mixed solution of N-methylpyrrolidone-triethylamine (7.5:2.5). To each reaction solution were added 150 mg of 0.5M 2-(di-tert-butylphosphino)biphenyl and 110 mg of palladium acetate (II), and heated at 100° C. for 8 hours. After removing the solution, the resin was washed in the manner as described in the above operation, and dried under reduced pressure.

The resultant resin was heated at reflux for 12 hours in a mixed solution of ethanol (2 mL), dioxane (0.7 mL), 5N sodium hydroxide aqueous solution (2 mL), washed in the similar method as described in the above operation, and dried under reduced pressure.

Then the resin pieces were divided into several groups in accordance with the label, and each resin piece was added with 15 mL of a previously-prepared different 0.5 M amine in N-methylpyrrolidone. To each container, 1.15 g of 1-hydroxybenzotriazole monohydrate, 1.2 mL of 1-ethyl-3-(3-dimethylaminopropyl)carbodiimide (=WSC) and 2.0 mL of diisopropylethylamine were successively added, sonicated for 1 hour, and then left overnight at room temperature. After removing the solution, the resin was washed in the manner as described in the above operation, and dried under reduced pressure. In accordance with the label of resin, they were arranged in a 96-well pin plate.

The resin was immersed in a mixed solution of 0.5 mL trifluoroacetic acid/0.1 mL triisopropylsilane/0.5 mL dichloromethane prepared in advance in 96-well plate, and after conducting sonication for 10 minutes, they were left for 30 minutes. This operation was repeated twice, and then the resin was washed with 1 mL of N,N-dimethylformamide. Next, nitrogen was blown into the acid-treated wells, and the resultant residues were dissolved in N,N-dimethylformamide solution obtained during washing operation, followed by purification and separation by LC-MS, to afford the compounds of Examples 1018-1029.

Example 1018

4-Methoxy-3-[(E)-2-(4-methoxy-phenyl)-vinyl]-1H-indazole-5-carboxylic acid (pyrazin-2-ylmethyl)-amide MS (ESI) m/z 416 $MH^+$ Example 1019

4-Methoxy-3-[(E)-2-(4-methoxy-phenyl)-vinyl]-1H-indazole-5-carboxylic acid (furan-2-ylmethyl)-amide MS (ESI) m/z 404 $MH^+$ Example 1020

4-Methoxy-3-[(E)-2-(4-methoxy-phenyl)-vinyl]-1H-indazole-5-carboxylic acid (thiophen-2-ylmethyl)-amide MS (ESI) m/z 420 $MH^+$ Example 1021

4-Methoxy-3-[(E)-2-(4-methoxy-phenyl)-vinyl]-1H-indazole-5-carboxylic acid benzylamide MS (ESI) m/z 414 $MH^+$ Example 1022

4-Methoxy-3-[(E)-2-(4-methoxy-phenyl)-vinyl]-1H-indazole-5-carboxylic acid (pyridin-3-ylmethyl)-amide MS (ESI) m/z 415 $MH^+$ Example 1023

3-[(E)-2-(3,4-Dimethoxy-phenyl)-vinyl]-4-methoxy-1H-indazole-5-carboxylic acid (pyrazin-2-ylmethyl)-amide MS (ESI) m/z 446 $MH^+$ Example 1024

3-[(E)-2-(3,4-Dimethoxy-phenyl)-vinyl]-4-methoxy-1H-indazole-5-carboxylic acid (furan-3-ylmethyl)-amide MS (ESI) m/z 434 $MH^+$ Example 1025

3-[(E)-2-(3,4-Dimethoxy-phenyl)-vinyl]-4-methoxy-1H-indazole-5-carboxylic acid cyclopropylmethyl-amide MS (ESI) m/z 408 $MH^+$ Example 1026

3-[(E)-2-(3,4-Dimethoxy-phenyl)-vinyl]-4-methoxy-1H-indazole-5-carboxylic acid (thiophen-2-ylmethyl)-amide MS (ESI) m/z 450 $MH^+$ Example 1027

3-[(E)-2-(3,4-Dimethoxy-phenyl)-vinyl]-4-methoxy-1H-indazole-5-carboxylic acid cyclopropylamide MS (ESI) m/z 394 $MH^+$ Example 1028

3-[(E)-2-(3,4-Dimethoxy-phenyl)-vinyl]-4-methoxy-1H-indazole-5-carboxylic acid benzylamide MS (ESI) m/z 444 $MH^+$ Example 1029

3-[(E)-2-(3,4-Dimethoxy-phenyl)-vinyl]-4-methoxy-1H-indazole-5-carboxylic acid (pyridin-3-ylmethyl)-amide MS (ESI) m/z 445 $MH^+$ Example 1030

6-Fluoro-3-[(E)-2-(4-fluorophenyl)-vinyl]-1-trityl-1H-indazol-5-ylamine obtained by Production example 182 and various kinds of carboxylic acid were treated in the similar method as described in Example 183, to afford the compounds of Examples 1031-1053.

Example 1031

3-Oxo-cyclopentane carboxylic acid {6-fluoro-3-[(E)-2-(4-fluorophenyl)-vinyl]-1H-indazol-5-yl}-amide MS (ESI) m/z 382 $MH^+$ Example 1032

1-(4-Methoxy-phenyl)-cyclopentane carboxylic acid {6-fluoro-3-[(E)-2-(4-fluorophenyl)-vinyl]-1H-indazol-5-yl}-amide MS (ESI) m/z 474 $MH^+$ Example 1033

2,2-Dimethyl-5-oxo-tetrahydrofuran-3-carboxylic acid {6-fluoro-3-[(E)-2-(4-fluorophenyl)-vinyl]-1H-indazol-5-yl}-amide MS (ESI) m/z 412 $MH^+$ Example 1034

(4S)-2-Oxo-thiazolidine-4-carboxylic acid {6-fluoro-3-[(E)-2-(4-fluorophenyl)-vinyl]-1H-indazol-5-yl}-amide MS (ESI) m/z 401 $MH^+$ Example 1035

5-Oxo-tetrahydrofuran-2-carboxylic acid {6-fluoro-3-[(E)-2-(4-fluorophenyl)-vinyl]-1H-indazol-5-yl}-amide MS (ESI) m/z 384 $MH^+$ Example 1036

(2S)-Pyrrolidine-2-carboxylic acid {6-fluoro-3-[(E)-2-(4-fluorophenyl)-vinyl]-1H-indazol-5-yl}-amide MS (ESI) m/z 369 $MH^+$ Example 1037

(2R)-Pyrrolidine-2-carboxylic acid {6-fluoro-3-[(E)-2-(4-fluorophenyl)-vinyl]-1H-indazol-5-yl}-amide MS (ESI) m/z 369 $MH^+$ Example 1038

(4S)-Thiazolidine-4-carboxylic acid {6-fluoro-3-[(E)-2-(4-fluorophenyl)-vinyl]-1H-indazol-5-yl}-amide MS (ESI) m/z 387 $MH^+$ Example 1039

1-Amino-cyclopentane carboxylic acid {6-fluoro-3-[(E)-2-(4-fluorophenyl)-vinyl]-1H-indazol-5-yl}-amide MS (ESI) m/z 383 $MH^+$ Example 1040

Tetrahydrofuran-2-carboxylic acid {6-fluoro-3-[(E)-2-(4-fluorophenyl)-vinyl]-1H-indazol-5-yl}-amide MS (ESI) m/z 370 $MH^+$ Example 1041

Tetrahydrofuran-3-carboxylic acid {6-fluoro-3-[(E)-2-(4-fluorophenyl)-vinyl]-1H-indazol-5-yl}-amide MS (ESI) m/z 370 $MH^+$ Example 1042

(2R)-2-Amino-N-{6-fluoro-3-[(E)-2-(4-fluorophenyl)-vinyl]-1H-indazol-5-yl}-2-(thiophen-2-yl)-acetamide MS (ESI) m/z 411 $MH^+$ Example 1043

5-Oxo-1-(thiophen-2-ylmethyl)-pyrrolidine-3-carboxylic acid {6-fluoro-3-[(E)-2-(4-fluorophenyl)-vinyl]-1H-indazol-5-yl}-amide MS (ESI) m/z 479 $MH^+$ Example 1044

1-(Furan-2-ylmethyl)-5-oxo-pyrrolidine-3-carboxylic acid {6-fluoro-3-[(E)-2-(4-fluorophenyl)-vinyl]-1H-indazole-5-yl }-amide MS (ESI) m/z 463 $MH^+$ Example 1045

Piperidine-3-carboxylic acid {6-fluoro-3-[(E)-2-(4-fluorophenyl)-vinyl]-1H-indazol-5-yl}-amide MS (ESI) m/z 383 $MH^+$ Example 1046

Piperidine-4-carboxylic acid {6-fluoro-3-[(E)-2-(4-fluorophenyl)-vinyl]-1H-indazol-5-yl}-amide MS (ESI) m/z 383 $MH^+$ Example 1047

Piperidine-2-carboxylic acid {6-fluoro-3-[(E)-2-(4-fluorophenyl)-vinyl]-1H-indazol-5-yl}-amide MS (ESI) m/z 383 $MH^+$ Example 1048

1-Acetyl-piperidine-4-carboxylic acid {6-fluoro-3-[(E)-2-(4-fluorophenyl)-vinyl]-1H-indazol-5-yl}-amide MS (ESI) m/z 425 $MH^+$ Example 1049

1-Amino-cyclopropane carboxylic acid {6-fluoro-3-[(E)-2-(4-fluorophenyl)-vinyl]-1H-indazol-5-yl}-amide MS (ESI) m/z 355 $MH^+$ Example 1050

2-Oxo-imidazolidine-4-carboxylic acid {6-fluoro-3-[(E)-2-(4-fluorophenyl)-vinyl]-1H-indazol-5-yl}-amide MS (ESI) m/z 384 $MH^+$ Example 1051

N-{6-Fluoro-3-[(E)-2-(4-fluorophenyl)-vinyl]-1H-indazol-5-yl}-2-(morpholin-4-yl)-acetamide MS (ESI) m/z 399 $MH^+$ Example 1052

(2S)-1-Methyl-pyrrolidine-2-carboxylic acid {6-fluoro-3-[(E)-2-(4-fluorophenyl)-vinyl]-1H-indazol-5-yl}-amide MS (ESI) m/z 383 $MH^+$ Example 1053

2-Amino-N-[6-fluoro-3-[(E)-2-(4-fluorophenyl)-vinyl]-1H-indazol-5-yl)-2-(pyridin-3-yl)-acetamide MS (ESI) m/z 406 $MH^+$ Example 1054

1-Ethyl-3- {6-fluoro-3-[(E)-2-(4-fluorophenyl)-vinyl]-1H-indazol-5-yl }-urea 10 mg of 6-fluoro-3-[(E)-2-(4-fluorophenyl)-vinyl]-1-trityl- 1H-indazol-5-ylamine obtained by Production example 182 and 3 μl of ethyl isocyanate was dissolved in 5 mL of chloroform, and heated at reflux for 2 hours. The reaction solution was allowed to cool to room temperature, added with 0.5 mL of trifluoroacetic acid, stirred at room temperature for 30 minutes, and the reaction mixture was purified and separated by LC-MS, to afford 0.67 mg of the title compound as pale yellow powder.

MS (ESI) m/z 343 $MH^+$

Example 1055

6-Fluoro-3-[(E)-2-(4-fluorophenyl)-vinyl]-1-trityl-1H-indazol-5-ylamine obtained by Production example 182 and various kinds of isocyanate were treated in the similar method as described in Example 1054, to afford the compounds of Examples 1056-1060.

Example 1056

1-{(6-Fluoro-3-[(E)-2-(4-fluorophenyl)-vinyl]-1H-indazol-5-yl}-3-propyl-urea

MS (ESI) m/z 357 $MH^+$

Example 1057

1-{6-Fluoro-3-[(E)-2-(4-fluorophenyl)-vinyl]-1H-indazole-5-yl}-3-isopropyl-urea

MS (ESI) m/z 357 $MH^+$

Example 1058

1-tert-Butyl-3-{6-fluoro-3-[(E)-2-(4-fluorophenyl)-vinyl]-1H-indazol-5-yl}-urea

MS (ESI) m/z 371 $MH^+$

Example 1059

1-Cyclohexyl-3-{6-fluoro-3-[(E)-2-(4-fluorophenyl)-vinyl]-1H-indazol-5-yl}-urea

MS (ESI) m/z 397 $MH^+$

Example 1060

1-{6-Fluoro-3-[(E)-2-(4-fluorophenyl)-vinyl]-1H-indazol-5-yl}-3-phenyl-urea

MS (ESI) m/z 391 $MH^+$

Example 1061

3-Vinyl-4-methoxy-1-trityl-1H-indazole-5-carbonitrile obtained by Production example 323 and various kinds of aryl halide were subjected to Heck reaction in accordance with Production example 324, and deprotected in accordance with Example 16, followed by separation and purification by LC-MS, to afford the compounds of Examples 1062-1065.

Example 1062

4-Methoxy-3-[(E)-2-(4-trifluoromethyl-phenyl)-vinyl]-1H-indazole-5-carbonitrile

MS (ESI) m/z 344 $MH^+$

Example 1063

4-Methoxy-3-[(E)-2-(3-trifluoromethyl-phenyl)-vinyl]-1H-indazole-5-carbonitrile

MS (ESI) m/z 344 $MH^+$

Example 1064

3-[(E)-2-(5-Hydroxymethyl-pyridin-3-yl)-vinyl]-4-methoxy-1H-indazole-5-carbonitrile MS (ESI) m/z 307 $MH^+$ Example 1065

4-Methoxy-3-[(E)-2-(2-trifluoromethyl-phenyl)-vinyl]-1H-indazole-5-carbonitrile

MS (ESI) m/z 344 $MH^+$

Production Example 1066

4-Methoxy-1-trityl-3-vinyl-1H-indazole-5-carboxylic acid ethyl ester

In accordance with Production example 123, from 2.80 g of 3-iodo-4-methoxy-1-trityl-1H-indazole-5-carboxylic acid ethyl ester obtained by Production example 276, 1.87 g of the title compound was obtained as ocher crystals.

$^1$H-NMR (400 MHz, $CDCl_3$) δ 1.37 (3H, t, J=6.8 Hz), 4.00 (3H, s), 4.35 (3H, q, J=6.8 Hz), 5.36 (1H, d, J=16.0 Hz), 6.07-6.14 (2H, m), 7.18-7.23 (17H, m)

Production Example 1067

4-Methoxy-1-trityl-3-vinyl-1H-indazole-5-carboxylic acid

In accordance with Production example 350, from 1.87 g of 4-methoxy-1-trityl-3-vinyl-1H-indazole-5-carboxylic acid ethyl ester, 1.07 g of the title compound was obtained as white crystals.

$^1$H-NMR (400 MHz, DMSO-$D_6$) δ 3.89 (3H, s), 5.37 (1H, d, J=11.2 Hz), 5.91 (1H, d, J=17.6 Hz), 6.07 (1H, d, 8.8 Hz), 7.08-7.15 (7H, m), 7.26-7.35 (10H, m)

Production Example 1068

4-Methoxy-1-trityl-3-vinyl-1H-indazole-5-carboxylic acid cyclopropylamide

In accordance with Production example 127, from 400 mg of 4-methoxy-1-trityl-3-vinyl-1H-indazole-5-carboxylic acid and cyclopropylamine, 464 mg of the title compound was obtained as white crystals.

$^1$H-NMR (400 MHz, DMSO-$D_6$) δ 0.48-0.52 (2H, m), 0.63-0.66 (2H, m), 2.79-2.82 (1H, m), 3.84 (3H, s), 5.37 (1H, d, J=11.2 Hz), 5.92 (1H, d, J=17.6 Hz), 6.07 (1H, d, J=8.8 Hz), 7.04 (1H, d, J=8.8 Hz), 7.08-7.16 (6H, m), 7.28-7.36 (10H, m), 8.26 (1H, d, J=4.8 Hz)

Production Example 1069

4-Methoxy-1-trityl-3-vinyl-1H-indazole-5-carboxylic acid [(1S)-(2-hydroxy-1-phenyl-ethyl)]-amide In accordance with Production example 127, from 310 mg of 4-methoxy-1-trityl-3-vinyl-1H-indazole-5-carboxylic acid obtained by Production example 1067 and (2S)-2-amino-2-phenyl-ethanol, 270 mg of the title compound was obtained as white crystals.

$^1$H-NMR (400 MHz, DMSO-$D_6$) δ 3.60-3.63 (2H, m), 3.81 (3H, s), 4.92 (1H, t, J=6.8 Hz), 5.10 (1H, br s), 5,37 (1H, d, J=11.2 Hz), 5.92 (1H, d, J=17.6 Hz), 6.08 (1H, d, J=8.8 Hz), 7.08-7.36 (22H, m), 8.65 (1H, d, J=8.4 Hz)

Production Example 1070

4-Methoxy-1-trityl-3-vinyl-1H-indazole-5-carboxylic acid (furan-2-ylmethyl)-amide In accordance with Production example 127, from 542 mg of 4-methoxy-1-trityl-3-vinyl-1H-indazole-5-carboxylic acid obtained by Production example 1067 and furan-2-ylmethylamine, 329 mg of the title compound was obtained as white crystals.

$^1$H-NMR (400 MHz, $CDCl_3$) δ 3.84 (3H, s), 4.65 (2H, d, J=5.2 Hz), 5.37 (1H, d, J=11.2 Hz), 6.07 (1H, d, 17.6 Hz), 6.18 (1H, d, J=8.8 Hz), 6.30 (1H, d, J=16.8 Hz.), 7.06-7.27 (18H, m), 7.63 (1H, d, J=9.6 Hz), 8.05 (1H, br s)

Production Example 1071

3-Bromo-7-fluoro-1H-indazole-5-carboxylic acid

In accordance with Production example 7, from 10.00 g of 3-bromo-7-fluoro-1-trityl-1H-indazole-5-carbonitrile obtained by Production example 122, 3.80 g of the title compound was obtained as ocher crystals.

$^1$H-NMR (400 MHz, DMSO-$D_6$) δ 7.25-7.39 (1H, br s), 7.75 (1H, d, J=11.6 Hz), 8.03 (1H, s)

Production Example 1072

7-Fluoro-1-trityl-3-vinyl-1H-indazole-5-carboxylic acid

From 3.80 g of 3-bromo-7-fluoro-1H-indazole-5-carboxylic acid, an ester compound was obtained in accordance with Production example 274, then the ester was tritylated in accordance with Production example 22, and a vinyl group was introduced in accordance with Production example 123. Further, by hydrolyzing the ester in accordance with Production example 350, 410 mg of the title compound was obtained as white crystals.

$^1$H-NMR (400 MHz, $CDCl_3$) δ 5.53 (1H, d, J=11.2 Hz), 6.19 (1H, d, J=17.6 Hz), 7.10-7.38 (16H, m), 7.45 (1H, d, J=11.2 Hz), 8.53 (1H, s)

Production Example 1073

7-Fluoro-1-trityl-3-vinyl-1H-indazole-5-carboxylic acid cyclopropylamide

In accordance with Production example 127, from 120 mg of 7-fluoro-1-trityl-3-vinyl-1H-indazole-5-carboxylic acid and cyclopropylamine, 73 mg of the title compound was obtained as white crystals.

$^1$H-NMR (400 MHz, $CDCl_3$) δ 0.58-0.62 (2H, m), 0.84-0.91 (2H, m), 2.81-2.94 (1H, m), 5.51 (1H, d, J=11.2 Hz), 6.04 (1H, d, J=18.0 Hz), 6.21 (1H, br s), 6.93 (1H, dd, J=18.0, 18.0 Hz), 7.10-7.16 (6H, m), 7.22-7.32 (10H, m), 8.09 (1H, s)

Example 1074

Vinyl compounds obtained by Production examples 1068-1070 and 1073 and various kinds of aryl halide were subjected to Heck reaction in accordance with Production example 324, and deprotected in accordance with Example 16, followed by separation and purification by LC-MS, to afford the compounds of Examples 1075-1125.

Example 1075

3-[(E)-2-(2-Hydroxymethyl-phenyl)-vinyl]-4-methoxy-1H-indazole-5-carboxylic acid cyclopropylamide MS (ESI) m/z 364 $MH^+$

Example 1076

3-[(E)-2-(3-Hydroxymethyl-phenyl)-vinyl]-4-methoxy-1H-indazole-5-carboxylic acid cyclopropylamide MS (ESI) m/z 364 $MH^+$

Example 1077

7-Fluoro-3-[(E)-2-(4-trifluoromethyl-phenyl)-vinyl]-1H-indazole-5-carboxylic acid [(1S)-(2-hydroxy-1-phenyl-ethyl)]-amide MS (ESI) m/z 470 $MH^+$

Example 1078

4-Methoxy-3-[(E)-2-(2-methoxy-phenyl)-vinyl]-1H-indazole-5-carboxylic acid cyclopropylamide MS (ESI) m/z 364 $MH^+$

Example 1079

4-Methoxy-3-[(E)-2-(3-methoxy-phenyl)-vinyl]-1H-indazole-5-carboxylic acid cyclopropylamide MS (ESI) m/z 364 $MH^+$

Example 1080

4-Methoxy-3-[(E)-2-(4-methoxy-phenyl)-vinyl]-1H-indazole-5-carboxylic acid cyclopropylamide MS (ESI) m/z 364 $MH^+$

Example 1081

3-[(E)-2-(4-Hydroxymethyl-phenyl)-vinyl]-4-methoxy-1H-indazole-5-carboxylic acid cyclopropylamide MS (ESI) m/z 364 $MH^+$

Example 1082

3-{(E)-2-[4-(2-Hydroxyethyl)-phenyl]-vinyl}-4-methoxy-1H-indazole-5-carboxylic acid cyclopropylamide MS (ESI) m/z 378 $MH^+$

Example 1083

3-[(E)-2-(4-Cyanomethyl-phenyl)-vinyl]-4-methoxy-1H-indazole-5-carboxylic acid cyclopropylamide MS (ESI) m/z 373 $MH^+$

Example 1084

3-[(E)-2-(4-Acetylaminophenyl)-vinyl]-4-methoxy-1H-indazole-5-carboxylic acid [(1S)-(2-hydroxy-1-phenyl-ethyl)]-amide MS (ESI) m/z 471 $MH^+$

Example 1085

3-[(E)-2-(4-Dimethylamino-phenyl)-vinyl]-4-methoxy-1H-indazole-5-carboxylic acid [(1S)-(2-hydroxy-1-phenyl-ethyl)]-amide MS (ESI) m/z 457 $MH^+$

Example 1086

3-[(E)-2-(3-Dimethylamino-phenyl)-vinyl]-4-methoxy-1H-indazole-5-carboxylic acid [(1S)-(2-hydroxy-1-phenyl-ethyl)]-amide MS (ESI) m/z 457 $MH^+$

Example 1087

4-Methoxy-3-[(E)-2-(2-methoxy-phenyl)-vinyl]-1H-indazole-5-carboxylic acid [(1S)-(2-hydroxy-1-phenyl-ethyl)]-amide MS (ESI) m/z 444 $MH^+$ Example 1088

4-Methoxy-3-[(E)-2-(3-methoxy-phenyl)-vinyl]-1H-indazole-5-carboxylic acid [(1S)-(2-hydroxy-1-phenyl-ethyl)]-amide MS (ESI) m/z 444 $MH^+$ Example 1089

4-Methoxy-3-[(E)-2-(4-methoxy-phenyl)-vinyl]-1H-indazole-5-carboxylic acid [(1S)-(2-hydroxy-1-phenyl-ethyl)]-amide MS (ESI) m/z 444 $MH^+$ Example 1090

3-[(E)-2-(3-Hydroxymethyl-phenyl)-vinyl]-4-methoxy-1H-indazole-5-carboxylic acid [(1S)-(2-hydroxy-1-phenyl-ethyl)]-amide MS (ESI) m/z 444 $MH^+$ Example 1091

4-Methoxy-3-[(E)-2-(3-methoxymethyl-phenyl)-vinyl]-1H-indazole-5-carboxylic acid [(1S)-(2-hydroxy-1-phenyl-ethyl)]-amide MS (ESI) m/z 458 $MH^+$ Example 1092

3-[(E)-2-(3-Aminomethyl-phenyl)-vinyl]-4-methoxy-1H-indazole-5-carboxylic acid [(1S)-(2-hydroxy-1-phenyl-ethyl)]-amide MS (ESI) m/z 443 $MH^+$ Example 1093

3-{(E)-2-[3-(Acetylamino-methyl)-phenyl]-vinyl}-4-methoxy-1H-indazole-5-carboxylic acid [(1S)-(2-hydroxy-1-phenyl-ethyl)]-amide MS (ESI) m/z 485 $MH^+$ Example 1094

3-[(E)-2-(4-Hydroxymethyl-phenyl)-vinyl]-4-methoxy-1H-indazole-5-carboxylic acid [(1S)-(2-hydroxy-1-phenyl-ethyl)]-amide MS (ESI) m/z 444 $MH^+$ Example 1095

4-Methoxy-3-[(E)-2-(4-methoxymethyl-phenyl)-vinyl]-1H-indazole-5-carboxylic acid[(1S)-(2-hydroxy-1-phenyl-ethyl)]-amide MS (ESI) m/z 458 $MH^+$ Example 1096

3-[(E)-2-(4-Aminomethyl-phenyl)-vinyl]-4-methoxy-1H-indazole-5-carboxylic acid[(1S)-(2-hydroxy-1-phenyl-ethyl)]-amide MS (ESI) m/z 443 $MH^+$ Example 1097

3-{(E)-2-[4-(Acetylamino-methyl)-phenyl]-vinyl}-4-methoxy-1H-indazole-5-carboxylic acid[(1S)-(2-hydroxy-1-phenyl-ethyl)]-amide MS (ESI) m/z 485 $MH^+$ Example 1098

4-Methoxy-3-[(E)-2-(thiophen-3-yl)-vinyl]-1H-indazole-5-carboxylic acid cyclopropylamide MS (ESI) m/z 340 $MH^+$ Example 1099

4-Methoxy-3-[(E)-2-(thiophen-3-yl)-vinyl]-1H-indazole-5-carboxylic acid[(1S)-(2-hydroxy-1-phenyl-ethyl)]-amide MS (ESI) m/z 420 $MH^+$ Example 1100

4-Methoxy-3-[(E)-2-(thiophen-3-yl)-vinyl]-1H-indazole-5-carboxylic acid(furan-2-ylmethyl)-amide MS (ESI) m/z 380 $MH^+$ Example 1101

4-Methoxy-3-[(E)-2-(3-methyl-thiophen-2-yl)-vinyl]-1H-indazole-5-carboxylic acid cyclopropylamide MS (ESI) m/z 354 $MH^+$ Example 1102

4-Methoxy-3-[(E)-2-(3-methyl-thiophen-2-yl)-vinyl]-1H-indazole-5-carboxylic acid[(1S)-(2-hydroxy-1-phenyl-ethyl)]-amide MS (ESI) m/z 434 $MH^+$ Example 1103

4-Methoxy-3-[(E)-2-(3-methyl-thiophen-2-yl)-vinyl]-1H-indazole-5-carboxylic acid(furan-2-ylmethyl)-amide MS (ESI) m/z 394 $MH^+$ Example 1104

3-[(E)-2-(5-Acetyl-thiophen-2-yl)-vinyl]-4-methoxy-1H-indazole-5-carboxylic acid cyclopropylamide MS (ESI) m/z 382 $MH^+$ Example 1105

3-[(E)-2-(5-Acetyl-thiophen-2-yl)-vinyl]-4-methoxy-1H-indazole-5-carboxylic acid[(1S)-(2-hydroxy-1-phenyl-ethyl)]-amide MS (ESI) m/z 462 $MH^+$ Example 1106

3-[(E)-2-(5-Acetyl-thiophen-2-yl)-vinyl]-4-methoxy-1H-indazole-5-carboxylic acid(furan-2-ylmethyl)-amide MS (ESI) m/z 422 $MH^+$ Example 1107

3-[(E)-2-(Furan-3-yl)-vinyl]-4-methoxy-1H-indazole-5-carboxylic acid cyclopropylamide MS (ESI) m/z 324 $MH^+$ Example 1108

3-[(E)-2-(Furan-3-yl)-vinyl]-4-methoxy-1H-indazole-5-carboxylic acid[(1S)-(2-hydroxy-1-phenyl-ethyl)]-amide MS (ESI) m/z 404 $MH^+$ Example 1109

3-[(E)-2-(Furan-3-yl)-vinyl]-4-methoxy-1H-indazole-5-carboxylic acid (furan-2-ylmethyl)-amide MS (ESI) m/z 364 $MH^+$ Example 1110

4-Methoxy-3-[(E)-2-(thiazol-2-yl)-vinyl]-1H-indazole-5-carboxylic acid cyclopropylamide MS (ESI) m/z 341 $MH^+$ Example 1111

4-Methoxy-3-[(E)-2-(thiazol-2-yl)-vinyl]-1H-indazole-5-carboxylic acid(furan-2-ylmethyl)-amide MS (ESI) m/z 381 $MH^+$ Example 1112

3-[(E)-2-(6-Fluoro-pyridin-3-yl)-vinyl]-4-methoxy-1H-indazole-5-carboxylic acid cyclopropylamide MS (ESI) m/z 353 $MH^+$ Example 1113

3-[(E)-2-(6-Fluoro-pyridin-3-yl)-vinyl]-4-methoxy-1H-indazole-5-carboxylic acid[(1S)-(2-hydroxy-1-phenyl-ethyl)]-amide MS (ESI) m/z 433 $MH^+$ Example 1114

3-[(E)-2-(6-Fluoro-pyridin-3-yl)-vinyl]-4-methoxy-1H-indazole-5-carboxylic acid (furan-2-ylmethyl)-amide MS (ESI) m/z 393 $MH^+$ Example 1115

Cyclopropane carboxylic acid{7-fluoro-3-[(E)-2-(2-fluorophenyl)-vinyl]-1H-indazol-5-yl}-amide MS (ESI) m/z 340 $MH^+$ Example 1116

Cyclopropane carboxylic acid{7-fluoro-3-[(E)-2-(3-fluorophenyl)-vinyl]-1H-indazol-5-yl}-amide MS (ESI) m/z 340 $MH^+$ Example 1117

Cyclopropane carboxylic acid{7-fluoro-3-[(E)-2-(4-fluorophenyl)-vinyl]-1H-indazole-5-yl }-amide MS (ESI) m/z 340 $MH^+$ Example 1118

Cyclopropane carboxylic acid{7-fluoro-3-[(E)-styryl]-1H-indazol-5-yl}-amide

MS (ESI) m/z 322 $MH^+$

Example 1119

Cyclopropane carboxylic acid{7-fluoro-3-((E)-2-(thiophen-2-yl)-vinyl]-1H-indazol-5-yl}-amide MS (ESI) m/z 328 $MH^+$ Example 1120

Cyclopropane carboxylic acid{7-fluoro-3-[(E)-2-(thiophen-3-yl)-vinyl]-1H-indazol-5-yl}-amide MS (ESI) m/z 328 $MH^+$ Example 1121

Cyclopropane carboxylic acid{7-fluoro-3-[(E)-2-(pyridin-2-yl)-vinyl]-1H-indazol-5-yl)-amide MS (ESI) m/z 323 $MH^+$ Example 1122

Cyclopropane carboxylic acid{7-fluoro-3-[(E)-2-(pyridin-3-yl)-vinyl]-1H-indazol-5-yl}-amide MS (ESI) m/z 323 $MH^+$ Example 1123

Cyclopropane carboxylic acid{7-fluoro-3-[(E)-2-(pyridin-4-yl)-vinyl]-1H-indazol-5-yl}-amide MS (ESI) m/z 323 $MH^+$ Example 1124

Cyclopropane carboxylic acid{7-fluoro-3-[(E)-2-(6-methoxy-pyridin-2-yl)-vinyl]-1H-indazol-5-yl}-amide MS (ESI) m/z 353 $MH^+$ Example 1125

Cyclopropane carboxylic acid{7-fluoro-3-[(E)-2-(6-methoxy-pyridin-3-yl)-vinyl]-1H-indazol-5-yl}-amide MS (ESI) m/z 353 $MH^+$ Production Example 1126

3-Iodo-1-trityl-1H-pyrazolo[3,4-c]pyridine-5-carboxylic acid

To a suspension of 3.0 g of 3-iodo-1-trityl-1H-pyrazolo[3,4-c]pyridine-5-carbonitrile obtained by Production example 431 in 20 mL of ethanol was added 20 mL of 4N lithium hydroxide aqueous solution at room temperature, and heated at reflux for a day. After cooling to room temperature, the solution was neutralized with 5N hydrochloric acid aqueous solution, and the precipitated crystals were collected by filtration. The crystals were washed successively with water and diethyl ether, to afford 3.0 g of the title compound as colorless crystals.

$^1$H-NMR (400 MHz, $CDCl_3$) δ 7.14-7.18 (6H, m), 7.33-7.39 (9H, m), 7.57 (1H, d, J=1.2 Hz), 8.07 (1H, d, J=1.2 Hz).

Production Example 1127

(3-Iodo-1-trityl-1H-pyrazolo[3,4-c]pyridin-5-yl)carbamic acid tert-butyl ester

To a suspension of 1.0 g of 3-iodo-1-trityl-1H-pyrazolo[3,4-c]pyridine-5-carboxylic acid in tert-butanol were added 0.57 g of diphenylphosphoryl azide and 0.31 mL of triethylamine at room temperature, and heated at reflux for 6 hours. The solution was diluted with ethyl acetate, the organic layer was washed successively with water and saturated brine, and dried over anhydrous magnesium sulfate. The solvent was evaporated, and the crude product was purified and separated by silica gel column chromatography (ethyl acetate:n-hexane=1:10), to afford 455 mg of the title compound as colorless crystals.

$^1$H-NMR (400 MHz, $CDCl_3$) δ 1.53 (9H, s), 7.07 (1H, bs), 7.15-7.19 (6H, m), 7.21 (1H, d, J=1.2 Hz), 7.25-7.29 (9H, m), 7.84 (1H, bs).

Production Example 1128

{3-[(E)-2-(4-Fluorophenyl)vinyl]-1-trityl-1H-pyrazolo[3,4-c]pyridin-5-yl}carbamic acid tert-butyl ester To a solution of 400 mg of (3-iodo-1-trityl-1H-pyrazolo[3,4-c]pyridin-5-yl)carbamic acid tert-butyl ester and 162 mg of 4-fluorostyrene in 2.0 mL of N,N-dimethylformamide were added 15 mg of palladium acetate, 40 mg of 2-(di-tert-butylphosphino)biphenyl and 0.46 mL of triethylamine at room temperature, and stirred at 80° C. for 6 hours. After diluting with ethyl acetate, the organic layer was washed successively with saturated aqueous ammonium chloride and saturated brine, and dried over anhydrous magnesium sulfate. The solvent was evaporated, and the crude product was purified and separated by silica gel column chromatography (ethyl acetate:n-hexane=1:10-dichloromethane:n-hexane=1:1-ethyl acetate:n-hexane=1:3). The resultant crystals were washed with diethyl ether, to afford 270 mg of the title compound as colorless crystals.

$^1$H-NMR (400 MHz, $CDCl_3$) δ 1.55 (9H, s), 7.04 (2H, t, J=8.4 Hz), 7.08 (1H, bs), 7.20-7.30 (m, 16H), 7.31 (1H, d, J=1.6 Hz), 7.37 (1H, d, J=16.4 Hz), 7.51 (2H, dd, J=8.4, 5.6 Hz), 8.32 (1H, bs)

Example 1129

3-[(E)-2-(4-Fluorophenyl)vinyl]-1H-pyrazolo[3,4-c]pyridin-5-ylamine

To a solution of 10 mg of 13-[(E)-2-(4-fluorophenyl)vinyl]-1-trityl-1H-pyrazolo[3,4-c]pyridin-5-yl}carbamic acid tert-butyl ester in 0.5 mL of dichloromethane was added 0.2 mL of trifluoroacetic acid at room temperature, and stirred at this temperature for 10 minutes. Following concentration by nitrogen blowing, the residue was separated and purified by LC-MS, to afford the title compound.

MS (ESI)m/z 255 $MH^+$

Example 1130

N-{3-[(E)-2-(4-Fluorophenyl)vinyl]-1H-pyrazolo[3,4-c]-pyridin-5-yl}acetamide

To a solution of 10 mg of {3-[(E)-2-(4-fluorophenyl)vinyl]-1-trityl-1H-pyrazolo[3,4-c]pyridin-5-yl}carbamic acid tert-butyl ester obtained by Production example 1128 in 0.2 mL of dichloromethane were successively added 7 μl of diisopropylethylamine at room temperature and 3 μl of acetyl chloride, and stirred at this temperature for a day. To this reaction solution was added 0.1 mL of trifluoroacetic acid at this temperature and stirred for 10 minutes. Following concentration by nitrogen blowing, the residue was separated and purified by LC-MS, to afford the title compound.

MS (ESI)m/z 297 $MH^+$

Example 1131

The compounds of Examples 1132 and 1133 were synthesized from {3-[(E)-2-(4-fluorophenyl)vinyl]-1-trityl-1H-pyrazolo[3,4-c]pyridin-5-yl}carbamic acid tert-butyl ester and commercially available acid chloride in accordance with the procedure of Example 1130.

Example 1132

Cyclopropane Carboxylic acid{3-[(E)-2-(4-fluorophenyl)-vinyl]-1H-pyrazolo[3,4-c]pyridin-5-yl}amide MS (ESI)m/z 323 $MH^+$ Example 1133

Furan-2-carboxylic acid{3-[(E)-2-(4-fluorophenyl)-vinyl]-1H-pyrazolo[3,4-c]pyridin-5-yl}amide MS (ESI)m/z 349 $MH^+$ Example 1134

In accordance with the method of Example 598, 7-fluoro-3-[(E)-2-(4-fluorophenyl)-vinyl]-1H-indazole-5-carboxymidic acid ethyl ester hydrochloride obtained by Example 383 or 6-fluoro-3-{(E)-2-(4-fluoro-phenyl)-vinyl}-1H-indazole-5-carboxymidic acid ethyl ester hydrochloride obtained by Example 559 and various kinds of hydrazide, the compounds of Examples 1135-1138 were obtained.

Example 1135

(5-{6-Fluoro-3-[(E)-2-(4-fluorophenyl)-vinyl]-1H-indazol-5-yl}-[1,3,4]oxadiazol-2-ylmethyl)-methyl-amine MS (ESI)m/z 368 $MH^+$ Example 1136

1-(5-{6-Fluoro-3-[(E)-2-(4-fluorophenyl)-vinyl]-1H-indazol-5-yl}-[1,3,4]oxadiazol-2-yl)-cyclopropylamine MS (ESI)m/z 380 $MH^+$ Example 1137

(5-{7-Fluoro-3-[(E)-2-(4-fluorophenyl)-vinyl]-1H-indazol-5-yl}-[1,3,4]oxadiazol-2-ylmethyl)-methyl-amine MS (ESI)m/z 368 $MH^+$ Example 1138

1-(5-{7-Fluoro-3-[(E)-2-(4-fluorophenyl)-vinyl]-1H-indazol-5-yl}-[1,3,4]oxadiazol-2-yl)-cyclopropylamine MS (ESI)m/z 380 $MH^+$ Production Example 1139

Piperidin-1-yl-acetic acid hydrazide 3.86 g of piperidin-1-yl-acetic acid ethyl ester was dissolved in 40 mL of ethanol, added with 3.39 mL of hydrazine monohydrate, and stirred at 70° C. for 5 hours. After allowing the solution to cool to room temperature, the solvent was evaporated, to afford 3.8 g of the title compound as pale yellow crystals.

$^1$H-NMR (400 MHz, $CDCl_3$) δ 1.38-1.48 (2H, m), 1.51-1.63 (4H, m), 2.42 (4H, brs), 3.02 (2H, s), 3.84 (2H, brs), 8.22 (1H, brs)

Production Example 1140

Pyridin-3-yl-acetic acid hydrazide

In accordance with Production example 1139, from 5.37 g of pyridin-3-yl-acetic acid ethyl ester, 6.0 g of the title compound was obtained as pale yellow crystals.

$^1$H-NMR (400 MHz, DMSO-$d_6$) δ 4.22 (2H, brs), 7.32 (1H, ddd, J=7.6, 4.8, 0.8 Hz), 7.64-7.68 (1H, m), 8.42-8.46 (2H, m), 9.29 (1H, brs)

Example 1141

In accordance with the method of Example 371 or 375, from 7-fluoro-3-[(E)-2-(4-fluorophenyl)-vinyl]-1H-indazole-5-carboxymidic acid ethyl ester hydrochloride obtained by Example 383, and hydrazide obtained by Production example 1140 or various kinds of hydrazide synthesized in accordance with Production examples 366-367, the compounds of Examples 1142-1145 were obtained.

Example 1142

7-Fluoro-3-[(E)-2-(4-fluorophenyl)-vinyl]-5-[5-(piperidin-4-yl)-4H-[1,2,4]triazol-3-yl]-1H-indazole MS (ESI)m/z 407 $MH^+$ Example 1143

7-Fluoro-3-[(E)-2-(4-fluorophenyl)-vinyl]-5-[5-(pyridine-3-yl)methyl-4H-[1,2,4]triazol-3-yl]-1H-indazole MS (ESI)m/z 415 $MH^+$ Example 1144

1-(5-[7-Fluoro-3-[(E)-2-(4-fluorophenyl)-vinyl]-1H-indazol-5-yl]-4H-[1,2,4]triazol-3-yl)-cyclopentylamine MS (ESI)m/z 407 $MH^+$ Example 1145

7-Fluoro-3-[(E)-2-(4-fluorophenyl)-vinyl]-5-[5-(piperidin-4-yl)methyl-4H-[1,2,4]triazol-3-yl]-1H-indazole MS (ESI)m/z 421 $MH^+$ Example 1146

7-Fluoro-3-[(E)-2-(4-fluorophenyl)-vinyl]-5-[5-(piperidin-1-yl)methyl-4H-[1,2,4]triazol-3yl]-1H-indazole 13 mg piperidin-1-yl-acetic acid hydrazide produced by Production example 1139 and 15 mg of 7-fluoro-3-{(E)-2-(4-fluorophenyl)-vinyl}-1H-indazole-5-carboxymidic acid ethyl ester hydrochloride obtained by Example 383 were dissolved in 1 mL of butanol, and added with 30 μl of triethylamine. After stirring at 105° C. for 8 hours, the solution was purification by LC-MS, to afford 2.08 mg of the title compound.

Example 1147

[(1S)-1-(5-{7-Fluoro-3-[(E)-2-(4-fluorophenyl)-vinyl]-1H-indazol-5-yl}-4H-[1,2,4]triazol-3-yl)-2-methyl-propyl]-methyl-amine 20.2 mg of [(1S)-1-hydrazinocarbonyl-2-methyl-propyl]-methylcarbamic acid tert-butyl ester and 15 mg of 7-fluoro-3-{(E)-2-(4-fluorophenyl)-vinyl}-1H-indazole-5-car boxymidic acid ethyl ester hydrochloride obtained by Example 383 were reacted in accordance with Example 1146, the solvent was distilled off, treated with 1 mL of 4N hydrogen chloride-ethyl acetate for 3 hours, and then purified by LC-MS, to afford 5.31 mg of the title compound.

MS (ESI)m/z 409 $MH^+$

Production Example 1148

N-Methyl-hydrazine carboxylic acid tert-butyl ester 10 mL of methyl hydrazine was dissolved in 90 mL of ethanol, and under stirring at ice-cooling, a solution of 41 g of di-tert-butyldicarbonate in 90 mL of ethanol was added dropwise over 45 minutes. After stirring at room temperature for 7 hours, the solvent was evaporated, to afford 24.7 g of the title compound as a colorless oil.

$^1$H-NMR (400 MHz, $CDCl_3$) δ 1.47 (9H, s), 3.05 (3H, s), 4.05 (2H, brs)

Production Example 1149

N'-benzyloxycarbonyl-N-methyl-hydrazine carboxylic acid tert-butyl ester 13.5 g of N-methyl-hydrazine carboxylic acid tert-butyl ester was dissolved in 90 mL of chloroform, added with 90 mL of 1N sodium hydroxide aqueous solution and 28 mL of benzyl chloroformate, and stirred at room temperature for 6 days. Adding water, extracting with chloroform, and the resultant organic layer was washed with saturated brine and dried over magnesium sulfate. The solvent was evaporated, followed by purification by silica gel column chromatography (ethyl acetate:hexane=1:4), to afford 17.7 g of the title compound as a colorless oil.

$^1$H-NMR (400 MHz, $CDCl_3$) δ 1.42 (9H, s), 3.14 (3H, brs), 5.17 (2H, s), 7.28-7.42 (5H, m)

Production Example 1150

N'-Methyl-hydrazine carboxylic acid benzyl ester hydrochloride 17.7 g of N'-benzyloxycarbonyl-N-methyl-hydrazine carboxylic acid tert-butyl ester was dissolved in 20 mL of ethyl acetate, added with 70 mL 4N hydrogen chloride-ethyl acetate solution, and stirred at room temperature for 4 hours. The solvent was evaporated, and the resulting crystals were washed with diethyl ether and filtered, to afford 11.4 g of the title compound as white crystals.

$^1$H-NMR (400 MHz, DMSO-$d_6$) δ2.72 (3H, s), 5.19 (2H, s), 7.32-7.44 (5H, m)

Production Example 1151

Methyl-(N-methyl-hydrazinocarbonylmethyl)-carbamic acid tert-butyl ester 2.1 g of (tert-butoxycarbonyl-methyl-amino)-acetic acid was dissolved in 150 mL of tetrahydrofuran, and 4.64 mL of triethylamine and 1.51 mL of isobutyl chloroformate were added under stirring at ice-cooling. After stirring at room temperature for 10 minutes, N'-methyl-hydrazine carboxylic acid benzyl ester hydrochloride was added and stirred at room temperature for 50 minutes. The reaction solution was added with water, extracted with ethyl acetate, and the resultant organic layer was washed with saturated brine and dried over magnesium sulfate. The solvent was evaporated, followed by purification by silica gel column chromatography (ethyl acetate:n-hexane=1:1), to afford 3.2 g of N'-[2-(tert-butoxycarbonyl-methyl-amino)-acetyl]-N'-methyl-hydrazine carboxylic acid benzyl ester. Subsequently, by conducting catalytic hydrogen reduction in accordance with Production example 365, 1.9 g of the title compound was obtained.

MS (ESI)m/z 240 $MNa^+$

Example 1152

(5-{7-Fluoro-3-[(E)-2-(4-fluoro-phenyl)-vinyl]-1H-indazol-5-yl}-2-methyl-2H-[1,2,4]triazol-3-ylm-ethyl)-methylamine In accordance with Example 1147, from methyl-(N-methyl-hydrazinocarbonylmethyl)-carbamic acid tert-butyl ester and 7-fluoro-3-{(E)-2-(4-fluoro-phenyl)-vinyl}-1H-indazole-5-carboxymidic acid ethyl ester hydrochloride obtained by Example 383, the title compound was obtained.

MS (ESI)m/z 381 $MH^+$

Example 1153

5-(4,5-Dihydro-1H-imidazol-2-yl)-6-fluoro-3-[(E)-2-(4-fluorophenyl)vinyl]-1H-indazole To a suspension of 10 mg of 6-fluoro-3-[(E)-2-(4-fluorophenyl)vinyl]-1H-indazole-5-carboxydimic acid ethyl ester hydrochloride obtained by Example 559 in 0.5 mL of ethanol was added 30 μl (1 mole in ethanol) of ethylenediamine at room temperature, and heated under reflux for 2 days. After filtering out the insoluble substances, the residue was separated and purified by LC-MS, to afford the title compound.

MS (ESI)m/z 325 $MH^+$

Example 1154

In accordance with the procedure of Example 1153, from 6-fluoro-3-[(E)-2-(4-fluorophenyl)vinyl]-1H-indazole-5-carboxydimic acid ethyl ester hydrochloride obtained by Example 559 or 7-fluoro-3-[(E)-2-(4-fluorophenyl)vinyl]-1H-indazole-5-carboxydimic acid ethyl ester hydrochloride obtained by Example 383, and commercially available substituted ethylenediamine or substituted 1,3-diaminopropane, the compounds of Examples 1155-1165 were synthesized.

Example 1155

6-Fluoro-3-[(E)-2-(4-fluorophenyl)vinyl]-5-(1-methyl-4,5-dihydro-1H-imidazol-2-yl)-1H-indazole MS (ESI)m/z 339 $MH^+$ Example 1156

6-Fluoro-3-[(E)-2-(4-fluorophenyl)vinyl]-5-(5-methyl-4,5-dihydro-1H-imidazol-2-yl)-1H-indazole MS (ESI)m/z 339 $MH^+$ Example 1157

6-Fluoro-3-[(E)-2-(4-fluorophenyl)vinyl]-5-(1,4,5,6-tetrahydropyrimidin-2-yl)-1H-indazole MS (ESI)m/z 439 M+

Example 1158

6-Fluoro-3-[(E)-2-(4-fluorophenyl)vinyl]-5-(1-methyl-1,4,5,6-tetrahydropyrimidin-2-yl)-1H-indazole MS (ESI)m/z 353 $MH^+$ Example 1159

2-{6-Fluoro-3-[(E)-2-(4-fluorophenyl)vinyl]-1H-indazole-5-yl}-1,4,5,6-tetrahydropyrimidin-5-ol MS (ESI)m/z 355 $MH^+$ Example 1160

5-(4,5-Dihydro-1H-imidazol-2-yl)-7-fluoro-3-[(E)-2-(4-fluorophenyl)vinyl]-1H-indazole MS (ESI)m/z 325 $MH^+$ Example 1161

7-Fluoro-3-[(E)-2-(4-fluorophenyl)vinyl]-5-(1-methyl-4,5-dihydro-1H-imidazol-2-yl)-1H-indazole MS (ESI)m/z 339 $MH^+$ Example 1162

7-Fluoro-3-[(E)-2-(4-fluorophenyl)vinyl]-5-(5-methyl-4,5-dihydro-1H-imidazol-2-yl)-1H-indazole MS (ESI)m/z 339 $MH^+$ Example 1163

7-Fluoro-3-[(E)-2-(4-fluorophenyl)vinyl]-5-(1,4,5,6-tetrahydropyrimidin-2-yl)-1H-indazole MS (ESI)m/z 339 $MH^+$ Example 1164

7-Fluoro-3-[(E)-2-(4-fluorophenyl)vinyl]-5-(1-methyl-1,4,5,6-tetrahydropyrimidin-2-yl)-1H-indazole MS (ESI)m/z 353 $MH^+$ Example 1165

2-{7-Fluoro-3-[(E)-2-(4-fluorophenyl)vinyl]-1H-indazol-5-yl}-1,4,5,6-tetrahydropyrimidin-5-ol MS (ESI)m/z 355 $MH^+$ Example 1166

3-[(E)-2-(4-Fluorophenyl)-vinyl]-4-methoxy-1H-indazole-5-carboxylic acid (2-oxopropyl) amide 100 mg of 3-[(E)-2-(4-fluorophenyl)-vinyl]-4-methoxy-1H-indazole-5-carboxylic acid (2-hydroxylpropyl) amide obtained by Example 825 and 300 μl of triethylamine were dissolved in a mixed solvent of 4 mL dichloromethane/1 mL dimethyl sulfoxide, added with 1 mL of a solution of 260 mg of pyridine sulfur trioxide complex in dimethyl sulfoxide under ice cooling, and the reaction solution was heated at 40° C. for 3 hours. The reaction solution was diluted with water, extracted with ethyl acetate, washed with water, and then dried over magnesium sulfate. The solvent was evaporated, and the residue was purified by silica gel column chromatography (ethyl acetate:methanol=100:3), and then crystallized from ethyl acetate and diisopropyl ether, to afford 80 mg of the title compound as a colorless powder.

$^1$H-NMR (400 MHz, DMSO-$d_6$) δ 2.18 (3H, s), 3.98 (3H, s), 4.22 (2H, d, J=5.5 Hz), 7.25 (2H, t, J=8.8 Hz), 7.35 (1H, d, J=8.4 Hz), 7.51 (1H, d, J=16.4 Hz), 7.51 (1H, d, J=16.4 Hz), 7.57 (1H, d, J=16.4 Hz), 7.72 (2H, dd, J=5.6, 8.8 Hz), 7.73 (1H, d, J=8.4 Hz), 8.64 (1H, bt, J=5.5 Hz), 13.48 (1H, bs)

Example 1167

3-[(E)-2-(4-Fluorophenyl)-vinyl]-4-methoxy-1H-indazole-5-carboxylic acid[2-hydroxy-3-(morpholin-4-yl)propyl]amide 100 mg of 3-[(E)-2-(4-fluorophenyl)-vinyl]-4-methoxy-1H-indazole-5-carboxylic acid obtained by Example 234 and 130 mg of 1-amino-3-(morpholine-4-yl)propane-2-ol were condensed in the similar method as described in Example 44, to afford 66 mg of the title compound as colorless needle crystals.

$^1$H-NMR (400 MHz, $CD_3OD$) δ 2.51 (2H, d, J=6.4 Hz), 2.53-2.62 (4H, m), 3.44 (1H, dd, J=6.8, 13.6 Hz), 3.68 (1H, dd, J=4.4, 13.6 Hz), 3.71 (4H, t, J=4.6 Hz), 4.00 (3H, s), 4.00-4.07 (1H, m), 7.14 (2H, t, J=8.8 Hz), 7.34 (1H, d, J=8.8 Hz), 7.54 (1H, d, J=16.4 Hz), 7.59 (1H, d, J=16.4 Hz), 7.64 (2H, dd, J=5.6, 8.8 Hz), 7.87 (1H, d, J=8.8. Hz).

Example 1168

3-[(E)-2-(2,3-Dihydrobenzofuran-5-yl)-vinyl]-4-methoxy-1H-indazole-5-carboxylic acid ethyl ester 410 mg of 3-iodo-4-methoxy-1-trityl-1H-indazole-5-carboxylic acid ethyl ester obtained by Production example 276 and 300 mg of 5-vinyl-2,3-dihydrobenzofuran were reacted in the similar method as described in Production example 181, followed by deprotection in the similar method as described in Example 16, to afford 50 mg of the title compound as a colorless powder.

$^1$H-NMR (400 MHz, $CDCl_3$) δ 1.44 (3H, t, J=7.2 Hz), 3.26 (2H, t, J=8.7 Hz), 4.05 (3H, s), 4.42 (2H, q, J=7.2 Hz), 4.62 (2H, t, J=8.7 Hz), 6.81 (1H, d, J=8.4 Hz), 7.21 (1H, d, J=8.6 Hz), 7.36 (1H, bd, J=8.4 Hz), 7.48 (1H, bs), 7.50 (1H, d, J=16.4 Hz), 7.62 (1H, d, J=16.4 Hz), 7.91 (1H, d, J=8.6 Hz).

Example 1169

3-[(E)-2-(2,3-Dihydrobenzofuran-5-yl)-vinyl]-4-methoxy-1H-indazole-5-carboxylic acid 50 mg of 3-[(E)-2-(2,3-dihydrobenzofuran-5-yl)-vinyl]-4-methoxy-1H-indazole-5-carboxylic acid ethyl ester was treated in the similar method as described in Example 144, to afford 35 mg of the title compound as a colorless powder.

$^1$H-NMR (400 MHz, $CD_3OD$) δ 3.25 (2H, t, J=8.8 Hz), 4.02 (3H, s), 4.58 (2H, t, J=8.8 Hz), 6.75 (1H, d, J=8.4 Hz), 7.27 (1H, d, J=8.6 Hz), 7.34 (1H, dd, J=1.6, 8.4 Hz), 7.47 (1H, d, J=16.4 Hz), 7.51 (1H, bs), 7.52 (1H, d, J=16.4 Hz), 7.88 (1H, d, J=8.6 Hz).

Example 1170

4-Methoxy-3-[(E)-2-(4-methoxyphenyl)-vinyl]-1H-indazole-5-carboxylic acid ethyl ester 470 mg of 3-iodo-4-methoxy-1-trityl-1H-indazole-5-carboxylic acid ethyl ester obtained by Production example 276 and 300 mg of 4-methoxystyrene were reacted in the similar method as described in Production example 181, followed by deprotection in the similar method as described in Example 16, to afford 130 mg of the title compound as a pale yellow oil.

$^1$H-NMR (400 MHz, $CDCl_3$) δ 1.45 (3H, t, J=7.2 Hz), 3.85 (3H, s), 4.05 (3H, s), 4.43 (2H, q, J=7.2 Hz), 6.93 (2H, d, J=8.8 Hz), 7.20 (1H, d, J=8.8 Hz), 7.54 (2H, d, J=8.8 Hz), 7.54 (1H, d, J=16.4 Hz), 7.62 (1H, d, J=16.4 Hz), 7.89 (1H, d, J=8.8 Hz).

Example 1171

4-Methoxy-3-[(E)-2-(4-methoxyphenyl)-vinyl]-1H-indazole-5-carboxylic acid 50 mg of 4-methoxy-3-[(E)-2-(4-methoxyphenyl)-vinyl]-1H-indazole-5-carboxylic acid ethyl ester was treated in the similar method as described in Example 144, to afford 40 mg of the title compound as a colorless powder.

$^1$H-NMR (400 MHz, DMSO-$d_6$) δ 3.80 (3H, s), 3.96 (3H, s), 6.99 (2H, d, J=8.6 Hz), 7.29 (1H, d, J=8.6 Hz), 7.44 (1H, d, J=16.4 Hz), 7.51 (1H, d, J=16.4 Hz), 7.59 (2H, d, J=8.6 Hz), 7.74 (1H, d, J=8.6 Hz), 13.38 (1H, bs).

Example 1172

3-[(E)-2-(3,4-Dimethoxyphenyl)-vinyl]-4-methoxy-1H-indazole-5-carboxylic acid ethyl ester 470 mg of 3-iodo-4-methoxy-1-trityl-1H-indazole-5-carboxylic acid ethyl ester obtained by Production example 276 and 300 mg of 3,4-dimethoxystyrene were reacted in the similar method as described in Production example 181, followed by deprotection in the similar method as described in Example 16, to afford 120 mg of the title compound as a pale yellow powder.

$^1$H-NMR (400 MHz, $CDCl_3$) δ 1.45 (3H, t, J=7.2 Hz), 3.93 (3H, s), 3.96 (3H, s), 4.05 (3H, s), 4.44 (2H, q, J=7.2 Hz), 6.90 (1H, d, J=8.8 Hz), 7.15 (1H, dd, J=1.6, 8.8 Hz), 7.16 (1H, bs), 7.22 (1H, d, J=8.8 Hz), 7.53 (1H, d, J=16.4 Hz), 7.62 (1H, d, J=16.4 Hz), 7.91 (1H, d, J=8.8 Hz).

Example 1173

3-[(E)-2-(3,4-Dimethoxyphenyl)-vinyl]-4-methoxy-1H-indazole-5-carboxylic acid 50 mg of 3-[(E)-2-(3,4-dimethoxyphenyl)-vinyl]-4-methoxy-1H-indazole-5-carboxylic acid ethyl ester was treated in the similar method as described in Example 144, to afford 40 mg of the title compound as a colorless powder.

$^1$H-NMR (400 MHz, DMSO-$d_6$) δ 3.79 (3H, s), 3.85 (3H, s), 3.96 (3H, s), 7.00 (1H, d, J=8.4 Hz), 7.17 (1H, dd, J=2.0, 8.4 Hz), 7.23 (1H, d, J=2.0 Hz), 7.29 (1H, d, J=8.4 Hz), 7.45 (1H, d, J=16.4 Hz), 7.51 (1H, d, J=16.4 Hz), 7.74 (1H, d, J=8.6 Hz), 13.39 (1H, bs).

Example 1174

After condensing various kinds of carboxylic acid obtained by Example 942, 955, 968, 1169, 1171 and 1173, and various kinds of amine in the similar method as described in Example 44, purification by LC-MS was conducted, to afford the compounds of Examples 1175-1195.

Example 1175

4-Methoxy-3-[(E)-2-(4-methoxyphenyl)-vinyl]-1H-indazole-5-carboxylic acid cyclopropylmethyl amide MS (ESI) m/z 378 $MH^+$ Example 1176

4-Methoxy-3-[(E)-2-(4-methoxyphenyl)-vinyl]-1H-indazole-5-carboxylic acid (oxazol-2-ylmethyl) amide MS (ESI) m/z 405 $MH^+$ Example 1177

3-[(E)-2-(4-Methoxyphenyl)-vinyl]-4-methoxy-1H-indazole-5-carboxylic acid cyanomethylamide MS (ESI) m/z 363 $MH^+$ Example 1178

3-[(E)-2-(4-Methoxyphenyl)-vinyl]-4-methoxy-1H-indazole-5-carboxylic acid allylamide MS (ESI) m/z 364 $MH^+$ Example 1179

4-Methoxy-3-[(E)-2-(3,4-dimethoxyphenyl)-vinyl]-1H-indazole-5-carboxylic acid (oxazol-2-ylmethyl) amide MS (ESI) m/z 435 $MH^+$ Example 1180

3-[(E)-2-(3,4-Dimethoxyphenyl)-vinyl]-4-methoxy-1H-indazole-5-carboxylic acid cyanomethylamide MS (ESI) m/z 393 $MH^+$ Example 1181

3-[(E)-2-(3,4-Dimethoxyphenyl)-vinyl]-4-methoxy-1H-indazole-5-carboxylic acid allylamide MS (ESI) m/z 394 $MH^+$ Example 1182

3-[(E)-2-(2,3-Dihydrobenzofuran-5-yl)-vinyl]-4-methoxy-1H-indazole-5-carboxylic acid(furan-2-ylmethyl)amide MS (ESI) m/z 416 $MH^+$ Example 1183

3-[(E)-2-(2,3-Dihydrobenzofuran-5-yl)-vinyl]-4-methoxy-1H-indazole-5-carboxylic acid cyclopropylmethyl amide MS (ESI) m/z 390 $MH^+$ Example 1184

3-[(E)-2-(2,3-Dihydrobenzofuran-5-yl)-vinyl]-4-methoxy-1H-indazole-5-carboxylic acid(thiophen-2-ylmethyl)amide MS (ESI) m/z 432 $MH^+$ Example 1185

3-[(E)-2-(2,3-Dihydrobenzofuran-5-yl)-vinyl]-4-methoxy-1H-indazole-5-carboxylic acid cyclopropylamide MS (ESI) m/z 376 $MH^+$ Example 1186

3-[(E)-2-(2,3-Dihydrobenzofuran-5-yl)-vinyl]-4-methoxy-1H-indazole-5-carboxylic acid(pyridin-3-ylmethyl)amide MS (ESI) m/z 427 $MH^+$ Example 1187

3-[(E)-2-(2,3-Dihydrobenzofuran-5-yl)-vinyl]-4-methoxy-1H-indazole-5-carboxylic acid(oxazol-2-ylmethyl)amide MS (ESI) m/z 417 $MH^+$ Example 1188

3-[(E)-2-(2,3-Dihydrobenzofuran-5-yl)-vinyl]-4-methoxy-1H-indazole-5-carboxylic acid cyanomethylamide MS (ESI) m/z 375 $MH^+$ Example 1189

3-[(E)-2-(2,3-Dihydrobenzofuran-5-yl)-vinyl]-4-methoxy-1H-indazole-5-carboxylic acid allylamide MS (ESI) m/z 376 $MH^+$ Example 1190

3-[(E)-2-(4-Fluoro-3-methoxyphenyl)-vinyl]-4-methoxy-1H-indazole-5-carboxylic acid cyanomethylamide MS (ESI) m/z 381 $MH^+$ Example 1191

3-[(E)-2-(4-Fluoro-3-methoxyphenyl)-vinyl]-4-methoxy-1H-indazole-5-carboxylic acid allylamide MS (ESI) m/z 382 $MH^+$ Example 1192

3-[(E)-2-(3-Fluoro-4-methoxyphenyl)-vinyl]-4-methoxy-1H-indazole-5-carboxylic acid cyanomethylamide MS (ESI) m/z 381 $MH^+$ Example 1193

3-[(E)-2-(3-Fluoro-4-methoxyphenyl)-vinyl]-4-methoxy-1H-indazole-5-carboxylic acid allylamide MS (ESI) m/z 382 $MH^+$ Example 1194

3-[(E)-2-(3,4-Difluorophenyl)-vinyl]-4-methoxy-1H-indazole-5-carboxylic acid cyanomethylamide MS (ESI) m/z 369 $MH^+$ Example 1195

3-[(E)-2-(3,4-Difluorophenyl)-vinyl]-4-methoxy-1H-indazole-5-carboxylic acid allylamide MS (ESI) m/z 370 $MH^+$ Production Example 1196

Acetic acid 5-(morpholin-4-yl)methyl-furan-2-ylmethyl ester

Under nitrogen atmosphere, to a solution of 2.0 g of 5-acetoxymethyl-2-furanaldehyde and 1.1 mL of morpholine in 35 mL of 1,2-dichloroethane was added 4.0 g of sodium triacetoxy borohydride at room temperature, and stirred at this temperature for 3 hours. The reaction solution was diluted with dichloromethane, washed successively with saturated aqueous sodium hydrogen carbonate and saturated brine, and then dried over anhydrous magnesium sulfate. The solvent was evaporated, and the residue was purified and separated by silica gel column chromatography, to afford 2.3 g of the title compound as a colorless oil.

$^1$H-NMR (400 MHz, $CDCl_3$) δ 2.08 (3H, s), 2.49 (4H, m), 3.53 (2H, s), 3.73 (4H, m), 5.02 (2H, s), 6.19 (1H, d, J=3.2 Hz), 6.34 (1H, d, J=3.2 Hz).

Production Example 1197

[5-(Morpholin-4-yl)methyl-furan-2-yl]-methanol

In accordance with the method of Production example 773, from 2.2 g of acetic acid 5-(morpholin-4-yl)methyl-furan-2-ylmethyl ester, 1.4 g of the title compound was obtained as colorless crystals.

$^1$H-NMR (400 MHz, $CDCl_3$) δ2.48 (4H, m), 3.52 (2H, s), 3.72 (4H, m), 4.59 (2H, s), 6.17 (1H, d, J=3.2 Hz), 6.23 (1H, d, J=3.2 Hz).

Production Example 1198

4-(5-Azidomethyl-furan-2-ylmethyl)-morpholine

In accordance with the method of Production example 774, from 11.0 g of [5-(morpholin-4-yl)methyl-furan-2-yl]-methanol, 1.07 g of the title compound was obtained as a colorless oil.

$^1$H-NMR (400 MHz, $CDCl_3$) δ2.48 (4H, m), 3.54 (2H, s), 3.73 (4H, m), 4.29 (2H, s), 6.20 (1H, d, J=3.2 Hz), 6.30 (1H, d, J=3.2 Hz).

Production Example 1199

C-[5-(Morpholin-4-yl)methyl-furan-2-yl]-methylamine

In accordance with the method of Production example 775, from 1.07 g of 4-(5-azidomethyl-furan-2-ylmethyl)-morpholine, 900 mg of the title compound was obtained as colorless oil.

$^1$H-NMR (400 MHz, $CDCl_3$) δ2.48 (4H, m), 3.50 (2H, s), 3.74 (4H, m), 3.80 (2H, s), 6.06 (1H, d, J=3.2 Hz), 6.13 (1H, d, J=3.2 Hz).

Production Example 1200

Acetic acid 5-(4-methyl-piperazin-1-ylmethyl)-furan-2-ylmethyl ester

In accordance with the method of Production example 1196, from 1.44 mL of 1-methylpiperazine, 2.1 g of the title compound was obtained as a pale yellow oil.

$^1$H-NMR (400 MHz, $CDCl_3$) δ2.08 (3H, s), 2.29 (3H, s), 2.49 (8H, m), 3.55 (2H, s), 5.02 (2H, s), 6.18 (1H, d, J=3.2 Hz), 6.33 (1H, d, J=3.2 Hz).

Production Example 1201

[5-(4-Methyl-piperazin-1-ylmethyl)-furan-2-yl]-methanol

In accordance with the method of Production example 773, from 2.1 g of acetic acid 5-(4-methyl-piperazin-1-ylmethyl)-furan-2-ylmethyl ester, 1.26 g of the title compound was obtained as a colorless oil.

$^1$H-NMR (400 MHz, $CDCl_3$) δ2.29 (3H, s), 2.51 (8H, bs), 3.54 (2H, s), 4.57 (2H, s), 6.16 (1H, d, J=3.2 Hz), 6.22 (1H, d, J=3.2 Hz).

Production Example 1202

1-(5-Azidomethyl-furan-2-ylmethyl)-4-methyl-piperazine

In accordance with the method of Production example 774, from 1.26 g of [5-(4-methyl-piperazin-1-ylmethyl)-furan-2-yl]-methanol, 1.0 g of the title compound was obtained as a colorless oil.

$^1$H-NMR (400 MHz, $CDCl_3$) δ2.29 (3H, s), 2.49 (8H, bs), 3.55 (2H, s), 4.28 (2H, s), 6.19 (1H, d, J=3.2 Hz), 6.29 (1H, d, J=3.2 Hz).

Production Example 1203

C-[5-(4-Methyl-piperazin-1-ylmethyl)-furan-2-yl]-methylamine

In accordance with the method of Production example 775, from 1.0 g of 1-(5-azidomethyl-furan-2-ylmethyl)-4-methyl-piperazine, 920 mg of the title compound was obtained as a colorless oil.

$^1$H-NMR (400 MHz, $CDCl_3$) δ2.28 (3H, s), 2.49 (8H, bs), 3.52 (2H, s), 3.79 (2H, s), 6.05 (1H, d, J=3.2 Hz), 6.12 (1H, d, J=3.2 Hz).

Example 1204

3-[(E)-2-(4-Fluorophenyl)-vinyl]-4-methoxy-1H-indazole-5-carboxylic acid obtained by Example 234 and amine obtained by Production example 1199 and 1203 were condensed in accordance with the method of Example 44, followed by purification by LC-MS, to afford the compounds of Examples 1205-1206.

Example 1205

3-[(E)-2-(4-Fluorophenyl)-vinyl]-4-methoxy-1H-indazole-5-carboxylic acid[5-(4-methylpiperazin-1-ylmethyl)-furan-2-ylmethyl)-amide MS (ESI) m/z 505 $MH^+$

Example 1206

3-[(E)-2-(4-Fluorophenyl)-vinyl]-4-methoxy-1H-indazole-5-carboxylic acid[5-(morpholin-4-ylmethyl)-furan-2-ylmethyl]-amide MS (ESI) m/z 492 $MH^+$ Example 1207

{3-[(E)-2-(4-Fluorophenyl)-vinyl]-4-methoxy-1H-indazole-5-carbonyl}-aminoacetic acid tert-butyl ester 3-[(E)-2-(4-Fluorophenyl)-vinyl]-4-methoxy-1H-indazole-5-carboxylic acid obtained by Example 234 and 258 mg of glycine ter-butyl ester hydrochloride were dissolved in 20 mL of N,N-dimethylformamide, and 0.871 mL of diisopropylethylamine and 235 mg of 1-hydroxybenzotriazole were added, and stirred at room temperature for 10 minutes. After cooling to 0° C., 491 mg of WSC hydrochloride was added, and stirred overnight at room temperature. After adding ice water to stop the reaction, the solution was extracted with ethyl acetate. The organic phase was washed with water and saturated brine and dried over anhydrous magnesium sulfate. The solvent was evaporated, to afford 547 mg of the title compound as pale green crystals.

$^1$H-NMR (400 MHz, DMSO-$D_6$) δ 1.45 (9H, s), 3.98 (5H, s), 7.25 (2H, t, J=8.8 Hz), 7.34 (1H, d, J=8.4 Hz), 7.51 (1H, d, J=16.4 Hz), 7.57 (1H, d, J=16.4 Hz), 7.68-7.72 (3H, m), 8.63 (1H, t, J=6.0 Hz

Example 1208

{3-[(E)-2-(4-Fluorophenyl)-vinyl]-4-methoxy-1H-indazole-5-carbonyl}-aminoacetic acid 472 mg of {3-[(E)-2-(4-fluorophenyl)-vinyl]-4-methoxy-1H-indazole-5-carbonyl}-aminoacetic acid tert-butyl ester was dissolved in 5 mL of dichloromethane, 2.5 mL of trifluoroacetic acid was added, and stirred overnight at room temperature. The reaction solution was added with water, and extracted with a mixed solution of ethyl acetate:tetrahydrofuran=1:1. The organic layer was washed with saturated brine, and dried over anhydrous magnesium sulfate. The solvent was evaporated, to give 384 mg of the title compound as a pale yellow solid.

$^1$H-NMR (400 MHz, DMSO-$D_6$) δ 3.98 (3H, s), 4.02 (2H, d, J=6.0 Hz), 7.25 (2H, t, J=8.4 Hz), 7.34 (1H, d, J=8.4 Hz), 7.51 (1H, d, J=16.0 Hz), 7.57 (1H, d, J=16.0 Hz), 7.70-7.72 (3H, m), 8.62 (1H, t, J=5.6 Hz

Example 1209

In accordance with the method of Example 102, from {3-[(E)-2-(4-fluorophenyl)-vinyl]-4-methoxy-1H-indazole-5-carbonyl}-aminoacetic acid obtained by Example 1208 and various kinds of amine, the compounds of Examples 1210-1224 were obtained.

Example 1210

3-[(E)-2-(4-Fluorophenyl)-vinyl]-4-methoxy-1H-indazole-5-carboxylic acid[(cyclohexyl-methyl-carbamoyl)-methyl]-amide MS (ESI) m/z 465 $MH^+$ Example 1211

3-[(E)-2-(4-Fluorophenyl)-vinyl]-4-methoxy-1H-indazole-5-carboxylic acid (benzylcarbamoyl-methyl)-amide MS (ESI) m/z 459 $MH^+$ Example 1212

3-[(E)-2-(4-Fluorophenyl)-vinyl]-4-methoxy-1H-indazole-5-carboxylic acid[2-oxo-2-(pyrrolidin-1-yl)-ethyl]-amide MS (ESI) m/z 423 $MH^+$ Example 1213

3-[(E)-2-(4-Fluorophenyl)-vinyl]-4-methoxy-1H-indazole-5-carboxylic acid[2-oxo-2-(piperidin-1-yl)-ethyl]-amide MS (ESI) m/z 437 $MH^+$ Example 1214

3-[(E)-2-(4-Fluorophenyl)-vinyl]-4-methoxy-1H-indazole-5-carboxylic acid[2-(morpholin-4-yl)-2-oxo-ethyl]-amide MS (ESI) m/z 439 $MH^+$ Example 1215

4-[2-({3-[(E)-2-(4-Fluorophenyl)-vinyl]-4-methoxy-1H-indazole-5-carbonyl}-amino)-acetyl]-piperazine-1-carboxylic acid tert-butyl ester MS (ESI) m/z 538 $MH^+$ Example 1216

3-[(E)-2-(4-Fluorophenyl)-vinyl]-4-methoxy-1H-indazole-5-carboxylic acid[2-(4-methyl-piperazin-1-yl)-2-oxo-ethyl]-amide MS (ESI) m/z 452 $MH^+$ Example 1217

3-[(E)-2-(4-fluorophenyl)-vinyl]-4-methoxy-1H-indazole-5-carboxylic acid diethylcarbamoylmethyl-amide MS (ESI) m/z 425 $MH^+$ Example 1218

3-[(E)-2-(4-Fluorophenyl)-vinyl]-4-methoxy-1H-indazole-5-carboxylic acid cyclohexylcarbamoylmethyl-amide MS (ESI) m/z 451 $MH^+$ Example 1219

3-[(E)-2-(4-Fluorophenyl)-vinyl]-4-methoxy-1H-indazole-5-carboxylic acid cyclopentylcarbamoylmethyl-amide MS (ESI) m/z 437 $MH^+$ Example 1220

3-[(E)-2-(4-Fluorophenyl)-vinyl]-4-methoxy-1H-indazole-5-carboxylic acid cyclobutylcarbamoylm-ethyl-amide MS (ESI) m/z 423 $MH^+$ Example 1221

3-[(E)-2-(4-Fluorophenyl)-vinyl]-4-methoxy-1H-indazole-5-carboxylic acid cyclopropylcarbamoylm-ethyl-amide MS (ESI) m/z 409 $MH^+$ Example 1222

3-[(E)-2-(4-Fluorophenyl)-vinyl]-4-methoxy-1H-indazole-5-carboxylic acid ethylcarbamoylmethyl-amide MS (ESI) m/z 397 $MH^+$ Example 1223

3-[(E)-2-(4-Fluorophenyl)-vinyl]-4-methoxy-1H-indazole-5-carboxylic acid propylcarbamoylmethyl-amide MS (ESI) m/z 411 $MH^+$ Example 1224

3-[(E)-2-(4-Fluorophenyl)-vinyl]-4-methoxy-1H-indazole-5-carboxylic acid butylcarbamoylmethyl-amide MS (ESI) m/z 425 $MH^+$ Example 1225

3-[(E)-2-(4-Fluorophenyl)-vinyl]-4-methoxy-1H-indazole-5-carboxylic acid[2-oxo-2-(piperazin-1-yl)-ethyl]-amide 4-[2-({3-[(E)-2-(4-Fluorophenyl)-vinyl]-4-methoxy-1H-indazole-5-carbonyl}-amino)-acetyl]-piperazine-1-carboxylic acid tert-butyl ester obtained by Example 1215 was dissolved in 1 mL of dichloromethane, added with 1 mL of trifluoroacetic acid, and stirred at room temperature for 2 hours. The solvent was evaporated, followed by purification by LC-MS, to afford the title compound.

MS (ESI) m/z 438 $MH^+$

Example 1226

3-[(E)-2-(4-Fluorophenyl)-vinyl]-4-methoxy-1H-indazole-5-carboxylic acid(3-hydroxyisoxazol-5-ylmethyl)-amide In accordance with the method of Example 102, 3-[(E)-2-(4-fluorophenyl)-vinyl]-4-methoxyl 1H-indazole-5-carboxylic acid obtained by Example 234 and 5-aminomethyl-isooxazol-3-ol, the title compound was obtained.

MS (ESI) m/z 409 $MH^+$

Production Example 1227

1-Methanesulfonyloxymethyl-cyclopropane carboxylic acid ethyl ester

In accordance with the method described in the document (Tetrahedron Letters, 40, 5467 (1988)), a solution of 720 mg of 1-hydroxymethyl-cyclopropane carboxylic acid ethyl ester obtained from 1,1-cyclopropane dicarboxylic acid diethyl ester in 10 mL of dichloromethane was added with 1.05 mL of triethylamine and 0.5 mL of methanesulfonyl chloride under ice cooling, and stirred at this temperature for 2 hours. After adding water, the reaction solution was extracted with ethyl acetate. The organic layer was washed successively with 1N hydrochloric acid, saturated brine, saturated aqueous sodium hydrogen carbonate and saturated brine. The organic layer was dried over anhydrous magnesium sulfate. The solvent was evaporated, to afford 1.04 g of the title compound as a pale yellow oil.

$^1$H-NMR (400 MHz, DMSO-$D_6$) δ 1.11 (2H, dd, J=4.0, 6.8 Hz), 1.18 (3H, t, J=7.2 Hz), 1.24 (2H, dd, J=4.0, 6.8 Hz), 3.18 (3H, s), 4.09 (2H, q, J=7.2 Hz), 4.32 (2H, s)

Production Example 1228

1-Dimethylaminomethyl-cyclopropane carboxylic acid ethyl ester

To a solution of 222 mg of 1-methanesulfonyloxymethyl-cyclopropane carboxylic acid ethyl ester in 5 mL of tetrahydrofuran was added 3 mL of 2M dimethyl amine in tetrahydrofuran, and stirred at room temperature for 3 days. The solvent was distilled off, and the residue was added with 2 mL of 1N hydrochloric acid, and washed with diethyl ether. The aqueous layer was added with 10% potassium carbonate aqueous solution, and extracted with ethyl acetate. The extracted layer was washed with saturated brine, and dried over anhydrous magnesium sulfate. The solvent was evaporated, to afford 56 mg of the title compound as a pale yellow oil.

$^1$H-NMR (400 MHz, DMSO-$D_6$) δ 0.79 (2H, dd, J=3.6, 6.8 Hz), 1.07 (2H, dd, J=3.6, 6.8 Hz), 1.16 (3H, t, J=7.2 Hz), 2.13 (6H, s), 2.46 (2H, s) 4.03 (2H, q, J=7.2 Hz)

Production Example 1229

1-Dimethylaminomethyl-cyclopropane carboxylic acid

To a solution of 222 mg of 1-dimethylaminomethyl-cyclopropane carboxylic acid ethyl ester in 0.4 mL of ethanol was added 0.1 mL of 5N sodium hydroxide aqueous solution, and stirred overnight at room temperature. The reaction solution was added with 0.5 mL of 1N hydrochloric acid, and the solvent and water were evaporated, to give 78 mg of a mixture of the title compound and sodium chloride as a white powder.

$^1$H-NMR (400 MHz, $D_2O$) δ 0.83 (2H, br s), 1.20 (2H, br s), 2.86 (6H, s), 3.16 (2H, s)

Production Example 1230

1-[(tert-Butoxycarbonyl-methyl-amino)-methyl]-cyclopropane carboxylic acid ethyl ester To a solution of 222 mg of 1-methanesulfonyloxymethyl-cyclopropane carboxylic acid ethyl ester obtained by Production example 1227 in 2 mL of tetrahydrofuran was added 3 mL of 2M methylamine in tetrahydrofuran, and stirred at room temperature for 2 days. The reaction solution was added with 1.5 mL of 2N hydrochloric acid, and then washed with diethyl ether. The aqueous layer was added with 10% potassium carbonate aqueous solution, the water distilled off, and extracted with ethyl acetate. The extracted layer was added with 114 mg of di-tert-butyldicarbonate, and stirred for 1 hour. The reaction solution was washed successively with water and saturated brine, and dried over anhydrous magnesium sulfate. The solvent was evaporated, to afford 105 mg of the title compound as a colorless oil.

$^1$H-NMR (400 MHz, DMSO-$D_6$) δ 0.91 (2H, br s), 1.11 (2H,br s), 1.16 (3H, t, J=7.2 Hz), 1.39 (9H, s), 2.80 (3H, br s), 3.50 (2H, s), 4.05 (2H, q, J=7.2 Hz

Production Example 1231

1-[(tert-Butoxycarbonyl-methyl-amino)-methyl]-cyclopropane carboxylic acid

In accordance with the method of Production example 651, from 105 mg of 1-[(tert-butoxycarbonyl-methyl-amino)-methyl]-cyclopropane carboxylic acid ethyl ester, 50 mg of the title compound was obtained as a colorless oil.

$^1$H-NMR (400 MHz, DMSO-$D_6$) δ 0.85 (2H, br s), 1.09 (2H,br s), 1.38 (9H, s), 2.78, 2.82 (3H, each s), 3.48 (2H, s), 12.30 (1H, br s)

Example 1232

Various kinds of amine obtained by Production examples 182, 643, 645 and 649, and various kinds of carboxylic acid obtained by Production examples 1229 and 1231 were amidated in the manner described in Example 183, deblocked, and purified by LC-MS [1%-100% gradient], to afford the compounds of Examples 1233-1240.

Example 1233

1-Dimethylaminomethyl-cyclopropane carboxylic acid{6-fluoro-3-[(E)-2-(4-fluorophenyl)-vinyl]-1H-indazol-5-yl}-amide MS (ESI) m/z 397 $MH^+$ Example 1234

1-Dimethylaminomethyl-cyclopropane Carboxylic acid{6-fluoro-3-[(E)-2-(3-fluorophenyl)-vinyl]-1H-indazol-5-yl}-amide MS (ESI) m/z 397 $MH^+$ Example 1235

1-Dimethylaminomethyl-cyclopropane carboxylic acid{6-fluoro-3-[(E)-2-(2-fluorophenyl)-vinyl]-1H-indazol-5-yl}-amide MS (ESI) m/z 397 $MH^+$ Example 1236

1-Dimethylaminomethyl-cyclopropane carboxylic acid{6-fluoro-3-[(E)-2-(thiophen-2-yl)-vinyl]-1H-indazol-5-yl}-amide MS (ESI) m/z 385 $MH^+$ Example 1237

1-Methylaminomethyl-cyclopropane carboxylic acid{6-fluoro-3-[(E)-2-(4-fluorophenyl)-vinyl]-1H-indazol-5-yl}-amide MS (ESI) m/z 383 $MH^+$ Example 1238

1-Methylaminomethyl-cyclopropane carboxylic acid{6-fluoro-3-[(E)-2-(3-fluorophenyl)-vinyl]-1H-indazol-5-yl}-amide MS (ESI) m/z 383 $MH^+$ Example 1239

1-Methylaminomethyl-cyclopropane carboxylic acid{6-fluoro-3-[(E)-2-(2-fluorophenyl)-vinyl]-1H-indazol-5-yl}-amide MS (ESI) m/z 383 $MH^+$ Example 1240

1-Methylaminomethyl-cyclopropane carboxylic acid{6-fluoro-3-[(E)-2-(thiophen-2-yl)-vinyl]-1H-indazol-5-yl}-amide MS (ESI) m/z 371 $MH^+$ Production Example 1241

6-Fluoro-3-[(E)-2-(3,4-difluorophenyl)-vinyl]-5-nitro-1-trityl-1H-indazole 600 mg of 6-fluoro-3-iodo-5-nitro-1-trityl-1H-indazole obtained by Production example 747 and 305 mg of 1,2-difluoro-4-vinylbenzene was dissolved in 10 mL of 1,4-dioxane. The resultant solution was added with 56 mg of bis(tri-tert-butylphosphine)palladium(0) and 408 μl of diisopropylethylamine, and refluxed overnight under nitrogen atmosphere. After cooling to room temperature, the reaction mixture was added with silica gel, and the solvent was evaporated, followed by purification by silica gel column chromatography, to afford 513 mg of the title compound as yellow crystals.

$^1$H-NMR (400 MHz, DMSO-$D_6$) δ 6.13 (1H, d, J=12.4 Hz), 7.22 (6H, d, J=7.6 Hz), 7.34-7.49 (11H, m), 7.53 (1H, d, J=8.4 Hz), 7.71 (1H, d, J=16.8 Hz), 7.95 (1H, t, J=10.4 Hz), 9.16 (1H, d, J=7.2 Hz)

Production Example 1242

6-Fluoro-3-[(E)-2-(3,4-difluorophenyl)-vinyl]-1-trityl-1H-indazol-5-ylamine

In accordance with the method of Production example 182, from 513 mg of 6-fluoro-3-[(E)-2-(3,4-difluorophenyl)-vinyl]-5-nitro-1-trityl-1H-indazole, 150 mg of the title compound was obtained as yellow crystals.

$^1$H-NMR (400 MHz, DMSO-$D_6$) δ 4.98 (2H, bs), 5.91 (1H, d, J=11.6 Hz), 7.18-7.45 (20H, m), 7.83 (1H, dd, J=8.4, 14.0 Hz

Example 1243

6-Fluoro-3-[(E)-2-(3,4-difluorophenyl)-vinyl]-1-trityl-1H-indazol-5-ylamine obtained by Production example 1242 and various kinds of carboxylic acid were treated in the similar method as described in Example 183, to afford the compounds of Examples 1244-1256.

Example 1244

Cyclopropane carboxylic acid{3-[(E)-2-(3,4-difluorophenyl)-vinyl]-6-fluoro-1H-indazol-5-yl}-amide MS (ESI) m/z 358 $MH^+$ Example 1245

1-Hydroxycyclopropane carboxylic acid{3-[(E)-2-(3,4-difluorophenyl)-vinyl]-6-fluoro-1H-indazol-5-yl}-amide MS (ESI) m/z 374 $MH^+$ Example 1246

1-Acetyl-piperidine-4-carboxylic acid{3-[(E)-2-(3,4-difluorophenyl)-vinyl]-6-fluoro-1H-indazol-5-yl}-amide MS (ESI) m/z 443 $MH^+$ Example 1247

Tetrahydrofuran-3-carboxylic acid{3-[(E)-2-(3,4-difluorophenyl)-vinyl]-6-fluoro-1H-indazol-5-yl}-amide MS (ESI) m/z 388 $MH^+$ Example 1248

1-Methylaminocyclopropane Carboxylic acid{3-[(E)-2-(3,4-difluorophenyl)-vinyl]-6-fluoro-1H-indazole-5-yl}-amide MS (ESI) m/z 387 $MH^+$ Example 1249

N-{3-[(E)-2-(3,4-difluorophenyl)-vinyl]-6-fluoro-1H-indazol-5-yl}-2-(thiophen-2-yl)-acetamide MS (ESI) m/z 414 $MH^+$ Example 1250

Furan-2-carboxylic acid{3-[(E)-2-(3,4-difluorophenyl)-vinyl]-6-fluoro-1H-indazol-5-yl}-amide MS (ESI) m/z 384 $MH^+$ Example 1251

2-Cyclopropyl-N-{3-[(E)-2-(3,4-difluorophenyl)-vinyl]-6-fluoro-1H-indazol-5-yl}-acetamide MS (ESI) m/z 372 $MH^+$ Example 1252

(2S, 4R)-4-Hydroxy-pyrrolidine-2-carboxylic acid{3-[(E)-2-(3,4-difluorophenyl)-vinyl]-6-fluoro-1H-indazol-5-yl}-amide MS (ESI) m/z 403 $MH^+$ Example 1253

N-{3-[(E)-2-(3,4-Difluorophenyl)-vinyl]-6-fluoro-1H-indazol-5-yl}-2-(morpholin-4-yl)-acetamide MS (ESI) m/z 417 $MH^+$ Example 1254

Piperidine-4-carboxylic acid{3-[(E)-2-(3,4-difluorophenyl)-vinyl]-6-fluoro-1H-indazol-5-yl}-amide MS (ESI) m/z 401 $MH^+$ Example 1255

(2S)-1-Methyl-pyrrolidine-2-carboxylic acid{3-[(E)-2-(3,4-difluorophenyl)-vinyl]-6-fluoro-1H-indazol-5-yl}-amide MS (ESI) m/z 401 $MH^+$ Example 1256

(2S)-2-Amino-N-{3-[(E)-2-(3,4-difluorophenyl)-vinyl]-6-fluoro-1H-indazol-5-yl}-2-(thiophen-2-yl)-acetamide MS (ESI) m/z 429 $MH^+$ Example 1257

6-Fluoro-3-[(E)-2-(4-fluorophenyl)-vinyl]-1-trityl-1H-indazol-5-ylamine synthesized by Production example 182 and various kinds of carboxylic acid were treated in the similar method as described in Example 183, to afford the compounds of Examples 1258-1260.

Example 1258

N-{6-Fluoro-3-[(E)-2-(4-fluorophenyl)-vinyl]-1H-indazol-5-yl}-2-methoxy-2-(thiophen-2-yl)-acetamide MS (ESI) m/z 426 $MH^+$ Example 1259

Azetidine-3-carboxylic acid{6-fluoro-3-[(E)-2-(4-fluorophenyl)-vinyl]-1H-indazol-5-yl}-amide MS (ESI) m/z 355 $MH^+$ Example 1260

N-{6-Fluoro-3-[(E)-2-(4-fluorophenyl)-vinyl]-1H-indazol-5-yl}-2-(piperazin-1-yl)-acetamide MS (ESI) m/z 398 $MH^+$ Production Example 1261

4-Bromo-5-fluoro-2-methylphenylamine

To a solution of 49.0 g of 5-fluoro-o-toluidine in 600 mL of dichloromethane was added 69.7 g of N-bromosuccinimide at 0° C., and stirred at this temperature for an hour. Then sodium thiosulfate aqueous solution was added, and the reaction solution was evaporated and diluted with ethyl acetate. The organic layer was washed successively with water and saturated brine and dried over anhydrous magnesium sulfate. Then the solvent was evaporated, and the precipitated crystals were washed with diethyl ether:n-hexane=1:10, to afford 81.6 g of the title compound as colorless crystals.

$^1$H-NMR (400 MHz, $CDCl_3$) δ 2.09 (3H, s), 3.69 (2H, bs), 6.44 (1H, d, J=10.4 Hz), 7.14 (1H, dd, J=7.6, 0.8 Hz).

Production Example 1262

N-(4-Bromo-5-fluoro-2-methylphenyl)acetamide 73.6 mL of acetic anhydride was added with 80.0 g of 4-bromo-5-fluoro-2-methylphenylamine at room temperature, and stirred at this temperature for 10 minutes. Excess acetic anhydride was distilled off under reduced pressure, and the precipitated crystals were washed with water, to afford 77.6 g of the title compound as colorless crystal.

$^1$H-NMR (400 MHz, $CDCl_3$) δ 2.21 (6H, s), 6.92 (1H, bs), 7.32 (1H, d, J=7.6 Hz), 7.90 (1H, d, J=10.4 Hz).

Production Example 1263

1-(5-Bromo-6-fluoro-indazol-1-yl)ethanone

To a solution of 77.0 g of N-(4-bromo-5-fluoro-2-methylphenyl)acetamide in 930 mL of toluene were added 93.0 mL of acetic anhydride and 37.0 g of potassium acetate at room temperature, and the resultant solution was heated at 90° C., slowly added dropwise with 67.0 mL of isoamyl nitrite, and stirred at this temperature for 3 hours. After diluting with ethyl acetate, washing successively with water and saturated brine, and drying over anhydrous magnesium sulfate, the solvent was evaporated. The precipitated crystals were washed with diethyl ether:n-hexane=1:10, the filtrate concentrated and purified and separated by silica gel column chromatography (ethyl acetate:n-hexane=0:100-1:5) and finally combined with the previous crystals, to afford 22.5 g of the title compound as pale brown crystals.

$^1$H-NMR (400 MHz, $CDCl_3$) δ 2.78 (3H, s), 7.93 (1H, d, J=6.4 Hz), 8.05 (1H, d, J=0.8 Hz), 8.23 (1H, dd, J=4.8, 0.8 Hz).

Production Example 1264

5-Bromo-6-fluoro-1H-indazole

To a solution of 22.5 g of 1-(5-bromo-6-fluoro-indazol-1-yl)ethanone in 250 mL of ethanol was added 20.0 mL of 5N sodium hydroxide aqueous solution at room temperature, and stirred at this temperature for 5 minutes. After neutralizing in 5N hydrochloric acid aqueous solution, the solution was diluted with ethyl acetate. The organic layer was successively washed with water and saturated brine, dried over anhydrous magnesium sulfate, and then the solvent was evaporated. The residue was purified and separated by silica gel column chromatography (ethyl acetate:n-hexane=1:3), to afford 16.7 g of the title compound as pale brown crystals.

$^1$H-NMR (400 MHz, $CDCl_3$) δ 7.24-7.27 (1H, m), 7.94-7.97 (1H, m), 8.01 (1H, d, J=0.8 Hz)-, 10.26 (1H, bs).

Production Example 1265

5-Bromo-6-fluoro-3-iodo-1H-indazole

To a solution of 10.0 g of 5-bromo-6-fluoro-1H-indazole in 150 mL of N,N-dimethylformamide was added 10.5 g of N-iodosuccinimide at room temperature, and stirred at 70° C. for 2 days. Then the solution was diluted with ethyl acetate, washed successively with aqueous ammonium chloride and saturated brine, dried over anhydrous magnesium sulfate, and the solvent was evaporated. The crystals precipitated by adding diethyl ether to the residue were collected by filtration. The filtrate was further concentrated and purified and separated by silica gel column chromatographsy (ethyl acetate:n-hexane=1:10-1:5) and combined with the previous crystals, to afford 14.5 g of the title compound as colorless crystals.

$^1$H-NMR (400 MHz, DMSO-$d_6$) δ 7.61 (1H, d, J=9.2 Hz), 7.75 (1H, d, J=6.4 Hz), 13.75 (1H, bs).

Production Example 1266

5-Bromo-6-fluoro-3-iodo-1-trityl-1H-indazole

To a solution of 3.0 g of 5-bromo-6-fluoro-3-iodo-1H-indazole in N,N-dimethylformamide in 150 mL was added 0.42 g of sodium hydride at room temperature, and the resultant solution was stirred for 15 minutes, added with 2.45 g of trityl-chloride, and stirred at this temperature for 1 hour. After adding water and diluting with ethyl acetate, washing successively with aqueous ammonium chloride and saturated brine and drying over anhydrous magnesium sulfate, the solvent was evaporated. The residue was purified and separated by silica gel column chromatography (ethyl acetate:n-hexane=1:30-1:5), and the resultant product was added with n-hexane. Then the precipitated crystals were washed with diethyl ether:n-hexane=1:10, to afford 3.79 g of the title compound as colorless crystals.

$^1$H-NMR (400 MHz, $CDCl_3$) δ 6.07 (1H, d, J=9.2 Hz), 7.14-7.20 (6H, m), 7.26-7.31 (9H, m), 7.64 (1H, d, J=6.4 Hz).

Production Example 1267

5-Bromo-6-fluoro-3-[(E)-2-(4-fluorophenyl)vinyl]-1-trityl-1H-indazole

A solution of 3.0 g of 5-bromo-6-fluoro-3-iodo-1-trityl-1H-indazole, 628 mg of 4-fluorostyrene, 115 mg of palladium acetate, 307 mg of 2-(di-ter-butylphosphino)biphenyl and 3.60 mL of triethylamine in N,N-dimethylformamide was stirred at 70° C. for a day. After diluting with ethyl acetate, washing successively with aqueous ammonium chloride and saturated brine, and drying over anhydrous magnesium sulfate, the solvent was evaporated. The residue was purified and separated by silica gel column chromatography (ethyl acetate:n-hexane=1:100), to afford 2.2 g of the title compound as colorless crystals.

$^1$H-NMR (400 MHz, $CDCl_3$) δ 6.14 (1H, d, J=10.0 Hz), 7.06 (2H, t, J=8.8 Hz), 7.18-7.24 (17H, m), 7.51 (2H, dd, J=8.8, 6.4 Hz), 8.13 (1H, d, J=6.8 Hz).

Production Example 1268

1-{5-(1-Acetyl-1H-pyrazol-4-yl)-6-fluoro-3-[(E)-2-(4-fluorophenyl)vinyl]-1H-indazol-1-yl}ethanone A solution of 40 mg of 5-bromo-6-fluoro-3-[(E)-2-(4-fluorophenyl)vinyl]-1-trityl-1H-indazole, 29.4 mg of 1-tritylpyrazole-4-boronic acid, 4 mg of tetrakis(triphenylphosphine)palladium(0) and 32.8 mg of barium hydroxide octahydrate in a mixture of dimethoxyethane:water=0.6 mL:0.1 mL was stirred at 80° C. for a day. The solution was diluted with ethyl acetate and water, and the organic layer was washed with saturated brine and dried over anhydrous magnesium sulfate. Then the solvent was evaporated. A solution of the crude product in 1 mL of dichloromethane was added with 0.2 mL of trifluoroacetic acid at room temperature, and stirred at this temperature for 1 hour. The reaction solution was poured to aqueous sodium hydrogen carbonate, and extracted with ethyl acetate. The organic layer was washed with saturated brine, dried over anhydrous magnesium sulfate, and the then the solvent was evaporated. A solution of the crude product in 1 mL of tetrahydrofuran and 0.5 mL of diisopropylethylamine was added with 0.1 mL of acetic anhydride at room temperature and stirred at this temperature for a day. The reaction solution was evaporated, and the residue was purified and separated by silica gel column chromatography (ethyl acetate:n-hexane=1:3-1:1), to afford 13 mg of the title compound as colorless crystals.

$^1$H-NMR (400 MHz, $CDCl_3$) δ 2.78 (3H, s), 2.82 (3H, s), 7.14 (2H, t, J=8.8 Hz), 7.26 (1H, d, J=16.4 Hz), 7.61-7.66 (3H, m), 8.05 (1H, d, J=6.8 Hz), 8.14 (1H, s), 8.29 (1H, d, J=11.2 Hz), 8.67 (1H, s).

Example 1269

6-Fluoro-3-[(E)-2-(4-fluorophenyl)vinyl]-5-(1H-pyrazolo-4-yl)-1H-indazole

To a solution of 13 mg of 1-{5-(1-acetyl-1H-pyrazol-4-yl)-6-fluoro-3-[(E)-2-(4-fluorophenyl)vinyl]-1H-indazol-1-yl}ethanone in 1 mL of ethanol was added 0.2 mL of 5N sodium hydroxide aqueous solution at room temperature, and stirred at this temperature for 10 minutes. The solution was neutralized with 5N hydrochloric acid aqueous solution and diluted with ethyl acetate. After washing the organic layer with saturated brine and drying over anhydrous magnesium sulfate, the solvent was evaporated. The residue was purified and separated by silica gel column chromatography (ethyl acetate:n-hexane=1:3-1:1), to afford 7.09 mg of the title compound as colorless crystal.

MS (ESI)m/z 323 $MH^+$

Example 1270

The compounds of Examples 1271 and 1272 were obtained according to the method of Example 1146 from 6-fluoro-3-[(E)-2-(4-fluorophenyl)-vinyl]-1H-indazole-5-carboxymidic acid ethyl ester hydrochloride obtained in Example 559 and the hydrazides obtained in Production Examples 1139 and 1140.

Example 1271

6-Fluoro-3-[(E)-2-(4-fluorophenyl)-vinyl]-5-[5-(piperidin-1-yl)-4H-[1,2,4]triazol-3-yl]-1H-indazole MS (ESI)m/z 421 $MH^+$ Example 1272

6-Fluoro-3-[(E)-2-(4-fluorophenyl)-vinyl]-5-[5-(pyridin-3-yl)methyl-4H-[1,2,4]triazol-3-yl]-1H-indazole MS (ESI)m/z 415 $MH^+$ Example 1273

The compounds of Examples 1274 and 1275 were obtained according to the method of Example 1147 from 6-fluoro-3-[(E)-2-(4-fluorophenyl)-vinyl]-1H-indazole-5-carboxymidic acid ethyl ester hydrochloride obtained in Example 559 and the hydrazides synthesized according to Production Examples 366 and 367.

Example 1274

6-Fluoro-3-[(E)-2-(4-fluorophenyl)-vinyl]-5-[5-(piperidin-4-yl)-4H-[1,2,4]triazol-3-yl]-1H-indazole MS (ESI)m/z 407 $MH^+$ Example 1275

6-Fluoro-3-[(E)-2-(4-fluorophenyl)-vinyl]-5-[5-(piperidin-4-yl)methyl-4H-[1,2,4]triazol-3-yl]-1H-indazole MS (ESI)m/z 421 $MH^+$ Production Example 1276

2-Chloro-N-{6-fluoro-3-[(E)-2-(4-fluorophenyl)-vinyl]-1-trityl-1H-indazol-5-yl}-acetamide 400 mg of 6-fluoro-3-[(E)-2-(4-fluorophenyl)-vinyl]-1-trityl-1H-indazol-5-ylamine synthesized in Production Example 182 was dissolved in 20 ml of chloroform, 20 ml of a saturated aqueous solution of sodium hydrogen carbonate and 124 μl of chloroacetyl chloride were added thereto at 0° C., and then the resulting mixture was stirred at room temperature overnight. The organic layer was washed with water and saturated brine, dried over anhydrous magnesium sulfate, and then the solvent was evaporated, to give 495 mg of the title compound as a yellow solid.

$^1$H-NMR (400 MHz, DMSO-$D_6$) δ 4.35 (2H, s), 6.05 (1H, d, J=12.0 Hz), 7.19-7.23 (8H, m), 7.28-7.39 (10H, m), 7.44 (1H, d, J=16.8 Hz), 7.75 (2H, dd, J=5.6, 9.2 Hz), 8.49 (1H, d, J=7.6 Hz)

Example 1277

To a suspension of 10 mg of 2-chloro-N-{6-fluoro-3-[(E)-2-(4-fluorophenyl)-vinyl]-1-trityl-1H-indazol-5-yl}-acetamide obtained in Production Example 1276 in 1 ml of acetonitrile was added a previously prepared solutions of various amines in 85 μl of 1.0M N,N-dimethylformamide, followed by stirring at 60° C. for 5 hours. The solvent was removed by nitrogen stream and the obtained solids were dissolved in 1 ml of dichloromethane, then 1 ml of trifluoroacetic acid was added thereto and the solutions were stirred for 2 hours at room temperature. The solvent was evaporated by nitrogen stream and the obtained crude products were purified by LC-MS, to give the compounds of Examples 1278 to 1287.

Example 1278

N-{6-Fluoro-3-[(E)-2-(4-fluorophenyl)-vinyl]-1H-indazol-5-yl}-2-(4-methyl-piperazin-1-yl)-acetamide MS (ESI) m/z 412 $MH^+$ Example 1279

2-(Azetidin-1-yl)-N-{6-fluoro-3-[(E)-2-(4-fluorophenyl)-vinyl]-1H-indazol-5-yl}-acetamide MS (ESI) m/z 369 $MH^+$ Example 1280

N-{6-Fluoro-3-[(E)-2-(4-fluorophenyl)-vinyl]-1H-indazol-5-yl}-2-(pyrrolidin-1-yl)-acetamide MS (ESI) m/z 383 $MH^+$ Example 1281

N-{6-Fluoro-3-[(E)-2-(4-fluorophenyl)-vinyl]-1H-indazol-5-yl}-2-(piperidin-1-yl)-acetamide MS (ESI) m/z 397 $MH^+$ Example 1282

2-Cyclopropylamino-N-{6-fluoro-3-[(E)-2-(4-fluorophenyl)-vinyl]-1H-indazol-5-yl}-acetamide MS (ESI) m/z 369 $MH^+$ Example 1283

N-{6-Fluoro-3-[(E)-2-(4-fluorophenyl)-vinyl]-1H-indazol-5-yl}-2-(imidazol-1-yl)-acetamide MS (ESI) m/z 380 $MH^+$ Example 1284

2-Benzylamino-N-{6-fluoro-3-[(E)-2-(4-fluorophenyl)-vinyl]-1H-indazol-5-yl}-acetamide MS (ESI) m/z 419 $MH^+$ Example 1285

N-{6-Fluoro-3-[(E)-2-(4-fluorophenyl)-vinyl]-1H-indazol-5-yl}-2-(pyridin-2-ylamino)-acetamide MS (ESI) m/z 406 $MH^+$ Example 1286

N-{6-Fluoro-3-[(E)-2-(4-fluorophenyl)-vinyl]-1H-indazol-5-yl}-2-(pyridin-3-ylamino)-acetamide MS (ESI) m/z 406 $MH^+$ Example 1287

N-{6-Fluoro-3-[(E)-2-(4-fluorophenyl)-vinyl]-1H-indazol-5-yl}-2-(pyridin-4-yl amino)-acetamide MS (ESI) m/z 406 $MH^+$ Production Example 1288

1-Hydroxymethyl-cyclopropane carboxylic acid{6-fluoro-3-[(E)-2-(4-fluorophenyl)-vinyl]-1-trityl-1H-indazol-5-yl}-amide 513 mg of 6-fluoro-3-[(E)-2-(4-fluorophenyl)-vinyl]-1-trityl-1H-indazol-5-yl-amine obtained in Production Example 182 and 345 mg of 1-(tert-butyl-dimethyl-silanyloxymethyl)-cyclopropane carboxylic acid obtained in Production Example 653 were amidated according to the method of Production Example 183. Next, the tert-butyl-dimethyl-silyl group was removed by treatment with 2 ml of a 1M solution of tetra-n-butyl ammonium fluoride in tetrahydrofuran. Next, the crystals obtained by treatment with 0.5 ml of a 5N aqueous solution of sodium hydroxide were recrystallized using ethyl acetate-diisopropyl ether, to give 400 mg of the title compound as pale yellow crystals.

$^1$H-NMR (400 MHz, DMSO-$D_6$) δ 0.76 (2H, dd, J=3.6, 6.8 Hz), 1.07 (2H, dd, J=3.6, 6.8 Hz), 3.61 (2H, d, J=5.2 Hz), 5.74 (1H, t, J=5.2 Hz), 6.05 (1H, d, J=12.0 Hz), 7.16-7.24 (8H, m), 7.26-7.44 (11H, m), 7.73 (2H, dd, J=5.6, 8.8 Hz), 8.68 (1H, d, J=7.6 Hz), 9.80 (1H, s)

Production Example 1289

1-{6-Fluoro-3-[(E)-2-(4-fluorophenyl)-vinyl]-1-trityl-1H-indazol-5-ylcarbamoyl}-cyclopropyl methyl methanesulfonate 100 mg of 1-hydroxymethyl-cyclopropane carboxylic acid {6-fluoro-3-[(E)-2-(4-fluorophenyl)-vinyl]-1-trityl-1H-indazol-5-yl}-amide was mesylated according to the method of Production Example 1227, to give 98 mg of the title compound as pale yellow crystals.

$^1$H-NMR (400 MHz, DMSO-$D_6$) δ 1.07 (2H, dd, J=4.4, 6.8 Hz), 1.33 (2H, dd, J=3.6, 6.8 Hz), 3.18 (3H, s), 4.44 (2H, s), 6.04 (1H, d, J=11.6 Hz), 7.16-7.24 (8H, m), 7.28-7.40 (10H, m), 7.44 (1H, d, J=16.8 Hz), 7.76 (2H, dd, J=5.6, 8.8 Hz), 8.20 (1H, d, J=7.2 Hz), 9.16 (1H, s)

Example 1290

A solution of 1-[(6-fluoro-3-[(E)-2-(4-fluorophenyl)-vinyl]-1-trityl-1H-indazol-5-yl-carbamoyl]-cyclopropyl methyl methanesulfonate in N-methyl-2-pyrrolidone was dispensed in test tubes, and 5 equivalents of various amines were added thereto, followed by stirring at room temperature for 4 days. After adding 0.1N hydrochloric acid to the reaction mixture, it was extracted with ethyl acetate and the solvent was evaporated. Then, the residue was deprotected under deprotecting conditions according to Example 183, and purified by LC-MS (1% to 100% gradient), to give the compounds of Examples 1291 to 1296.

Example 1291

1-(Morpholin-4-yl)methyl-cyclopropane carboxylic acid{6-fluoro-3-[(E)-2-(4-fluorophenyl)-vinyl]-1H-indazol-5-yl}-amide MS (ESI) m/z 439 $MH^+$ Example 1292

1-(Piperidin-1-yl)methyl-cyclopropane carboxylic acid{6-fluoro-3-[(E)-2-(4-fluorophenyl)-vinyl]-1H-indazol-5-yl}-amide MS (ESI) m/z 437 $MH^+$ Example 1293

1-(Pyrrolidin-1-yl)methyl-cyclopropane carboxylic acid{6-fluoro-3-[(E)-2-(4-fluorophenyl)-vinyl]-1H-indazol-5-yl}-amide MS (ESI) m/z 423 $MH^+$ Example 1294

1-(4-Hydroxy-piperidin-1-yl)methyl-cyclopropane carboxylic acid{6-fluoro-3-[(E)-2-(4-fluorophenyl)-vinyl]-1H-indazol-5-yl}-amide MS (ESI) m/z 453 $MH^+$ Example 1295

1-(4-Methyl-piperazin-1-yl)methyl-cyclopropane carboxylic acid{6-fluoro-3-[(E)-2-(4-fluorophenyl)-vinyl]-1H-indazol-5-yl}-amide MS (ESI) m/z 452 $MH^+$ Example 1296

1-(4-Acetyl-piperazin-1-yl)methyl-cyclopropane carboxylic acid{6-fluoro-3-[(E)-2-(4-fluorophenyl)-vinyl]-1H-indazol-5-yl}-amide MS (ESI) m/z 480 $MH^+$ Production Example 1297

(2S,4S)-4-(tert-Butyl-dimethyl-silyloxy)-pyrrolidin-1,2-dicarboxylic acid 1-tert-butyl ester 2-methyl ester 4.97 g of commercially available 1-tert-butyl 2-methyl (2S, 4S)-4-hydroxy-pyrrolidin-1,2-dicarboxylic acid 1-tert-butyl ester 2-methyl ester was silyl etherified according to the method of Production Example 652, to give 5.37 g of the title compound as a colorless oil.

$^1$H-NMR (400 MHz, DMSO-$D_6$) δ 0.01, 0.03 (6H, each s), 0.82, 0.84 (9H, each s), 1.34, 1.40 (9H, each s), 1.85-1.92 (1H,m), 2.26-2.42 (1H, m), 3.07-3.14 (1H, m), 3.48-3.57 (1H, m), 3.59, 3.62 (3H, each s), 4.24-4.33 (1H, m), 4.36-4.44(1H, m)

Production Example 1298

(2S, 4S)-4-(tert-Butyl-dimethyl-silyloxy)-pyrrolidin-1,2-dicarboxylic acid 1-tert-butyl ester 1.07 g of (2S,4S)-4-(tert-butyl-dimethyl-silyloxy)-pyrrolidin-1,2-dicarboxylic acid 1-tert-butyl ester 2-methyl ester was hydrolyzed according to the method of Production Example 651, to give 352 mg of the title compound as white crystals.

$^1$H-NMR (400 MHz, DMSO-$D_6$) δ 0.03 (6H, s), 0.83 (9H, s), 1.34, 1.40 (9H, each s), 1.80-1.88 (1H,m), 2.28-2.42 (1H, m), 3.03-3.10 (1H, m), 3.49-3.58 (1H, m), 4.10-4.19 (1H, m), 4.33-4.44 (1H, m), 12.38 (1H, br s)

Production Example 1299

1-Acetyl-cyclopropane carboxylic acid 426 mg of 1-acetyl-cyclopropane carboxylic acid methyl ester obtained from methyl acetoacetate using a known method (Synthetic Commun., 26, 525 (1996)) was hydrolyzed according to the method of Production Example 651, to give 337 mg of the title compound as a colorless oil.

$^1$H-NMR (400 MHz, DMSO-$D_6$) 51.28-1.35 (4H, m), 2.36 (3H, s), 12.88 (1H, br s)

Example 1300

6-Fluoro-3-[(E)-2-(4-fluorophenyl)-vinyl]-1-trityl-1H-indazol-5-yl-amine obtained in Production Example 182 and the two carboxylic acids obtained in Production Examples 1298 and 1299 were amidated and deprotected according to the method of Example 183, and then the products were purified by LC-MS (1% to 100% gradient), to give the compounds of Examples 1301 and 1302.

Example 1301

(2S, 4S)-4-Hydroxy-pyrrolidine-2-carboxylic acid{6-fluoro-3-[(E)-2-(4-fluorophenyl)-vinyl]-1H-indazol-5-yl}-amide MS (ESI) m/z 385 $MH^+$ Example 1302

1-Acetyl-cyclopropane carboxylic acid{6-fluoro-3-[(E)-2-(4-fluorophenyl)-vinyl]-1H-indazol-5-yl}-amide MS (ESI) m/z 382 $MH^+$ Production Example 1303

Amino-phenyl acetonitrile

To a 0.3 ml aqueous solution of 46 mg of sodium cyanide and 55 mg of ammonium chloride was added a solution of 100 mg of benzaldehyde in 0.3 ml of methanol, and the resulting mixture was stirred at room temperature for 5 hours. After adding aqueous solution of ammonium chloride to the reaction mixture, it was extracted with ethyl acetate twice. The organic layer was washed successively with a saturated aqueous solution of ammonium chloride and saturated brine, dried over anhydrous magnesium sulfate, and the solvent was evaporated. Then, the crude product was purified and separated by LC-MS, to give 44.2 mg of the title compound as colorless crystals.

$^1$H-NMR (400 MHz, $CD_3OD$) δ5.80 (1H, s), 7.52-7.59 (3H, m), 7.61-7.67 (2H, m).

Production Example 1304

Amino-pyridin-2-yl-acetonitrile 2.3 mg of the title compound was obtained from 100.7 mg of 2-pyridinecarboxaldehyde according to the method of Production Example 1303.

$^1$H-NMR (400 MHz, $CD_3OD$) δ5.92 (1H, s), 7.55 (1H, dd, J=4.4, 7.6 Hz), 7.70 (1H, d, J=7.6 Hz), 7.99 (1H, ddd, J=1.6, 7.6, 7.6 Hz), 8.71 (1H, d, J=4.4 Hz).

Production Example 1305

3-Bromo-piperidin-2-one

Based on a method disclosed in the literature (J. Med. Chem., 1988, Vol. 31, p. 422), 10.2 g of a crude compound containing the title compound was obtained in the form of a yellow solid from 10 g of piperidin-2-one. This mixture was purified by silica gel chromatography, to give 2.0 g of the title compound as a yellow solid.

$^1$H-NMR (400 MHz, DMSO-$D_6$) δ 1.67-1.74 (1H, m), 1.84-1.95 (1H, m), 2.05-2.12 (1H, m), 2.23-2.31 (1H, m), 3.19 (2H, m), 4.59 (1H, t, J=4.8 Hz), 7.77 (1H, bs)

Production Example 1306

3-Azido-piperidin-2-one

To a solution of 2.0 g of 3-bromopiperidin-2-one in 30 ml of N,N-dimethylformamide was added 5.9 g of sodium azide, followed by stirring at 60° C. overnight. After cooling down to room temperature, water was added to the reaction mixture and then the mixture was extracted with ethyl acetate. The organic layer was washed with water and saturated brine, dried over anhydrous magnesium sulfate and the solvent was evaporated, to give 890 mg of the title compound as a yellow oil.

$^1$H-NMR (400 MHz, DMSO-$D_6$) δ 1.49-1.58 (1H, m), 1.60-1.75 (2H, m), 1.93-2.00 (1H, m), 3.09-3.12 (2H, m), 4.13 (1H, dd, J=6.0, 9.6 Hz), 7.82 (1H, bs)

Production Example 1307

3-Amino-piperidin-2-one

To a solution of 890 mg of 3-azido-piperidin-2-one in 10 ml of ethanol was added 89 mg of 10% palladium on carbon, followed by stirring in a hydrogen atmosphere at room temperature overnight. The catalyst was filtered off through Celite and the filtrate was evaporated, to give 700 mg of the title compound as a yellow oil.

$^1$H-NMR (400 MHz, DMSO-$D_6$) δ 1.38-1.48 (1H, m), 1.58-1.83 (2H, m), 1.92-1.97 (1H, m), 2.50 (1H, t, J=3.6 Hz), 3.08-3.12 (2H, m), 7.40 (1H, bs)

Example 1308

3-[(E)-2-(4-Fluorophenyl)-vinyl]-4-methoxy-1H-indazol-5-carboxylic acid obtained in Example 234 was condensed according to a similar method as in Example 44 with the amines obtained in Production Examples 1303, 1304 or 1307, or with commercially available amines, and then purified by LC-MS, to give the compounds of Examples 1309 to 1316.

Example 1309

3-[(E)-2-(4-Fluorophenyl)-vinyl]-4-methoxy-1H-indazol-5-carboxylic acid(cyano-phenyl-methyl)-amide MS (ESI) m/z 427 $MH^+$ Example 1310

3-[(E)-2-(4-Fluorophenyl)-vinyl]-4-methoxy-1H-indazol-5-carboxylic acid[cyano-(pyridin-2-yl)-methyl]-amide MS (ESI) m/z 428 $MH^+$ Example 1311

3-[(E)-2-(4-Fluorophenyl)-vinyl]-4-methoxy-1H-indazol-5-carboxylic acid[(ethyl-methyl-carbamoyl)-methyl]-amide MS (ESI) m/z 411 $MH^+$ Example 1312

3-[(E)-2-(4-Fluorophenyl)-vinyl]-4-methoxy-1H-indazol-5-carboxylic acid[(isopropyl-methyl-carbamoyl)-methyl]-amide MS (ESI) m/z 425 $MH^+$ Example 1313

3-[(E)-2-(4-Fluorophenyl)-vinyl]-4-methoxy-1H-indazol-5-carboxylic acid[(isobutyl-methyl-carbamoyl)-methyl]-amide MS (ESI) m/z 439 $MH^+$ Example 1314

3-[(E)-2-(4-Fluorophenyl)-vinyl]-4-methoxy-1H-indazol-5-carboxylic acid[(cyanomethyl-methyl-carbamoyl)-methyl]-amide MS (ESI) m/z 422 $MH^+$ Example 1315

3-[(E)-2-(4-Fluorophenyl)-vinyl]-4-methoxy-1H-indazol-5-carboxylic acid[2-(azetidin-1-yl)-2-oxo-ethyl]-amide MS (ESI) m/z 409 $MH^+$ Example 1316

3-[(E)-2-(4-Fluorophenyl)-vinyl]-4-methoxy-1H-indazol-5-carboxylic acid (2-oxo-piperidin-3-yl)-amide MS (ESI) m/z 409 $MH^+$ Example 1317

1-({3-[(E)-2-(4-Fluorophenyl)-vinyl]-4-methoxy-1H-indazol-5-carbonyl}-amino)-cyclopropane carboxylic acid methyl ester 536 mg of the title compound was obtained as a brown solid according to the method of Example 1207 from 400 mg of 3-[(E)-2-(4-fluorophenyl)-vinyl]-4-methoxy-1H-indazol-5-carboxylic acid obtained in Example 234 and 233 mg of 1-aminocyclopropane carboxylic acid methyl ester hydrochloride.

$^1$H-NMR (400 MHz, DMSO-$D_6$) δ 1.22 (2H, dd, J=4.0, 7.2 Hz), 1.47 (2H, dd, J=4.8, 8.0), 3.64 (3H, s), 3.96 (3H, s), 7.25 (2H, t, J=8.8 Hz), 7.31 (1H, d, J=8.8 Hz), 7.51 (1H, d, J=16.4 Hz), 7.52 (1H, d, J=8.4 Hz), 7.57 (1H, d, J=16.4 Hz), 7.70 (1H, dd, J=5.2, 8.8 Hz), 8.83 (1H, s)

Example 1318

1-({3-[(E)-2-(4-Fluorophenyl)-vinyl]-4-methoxy-1H-indazol-5-carbonyl}-amino)-cyclopropane carboxylic acid To a mixed solution of 200 mg of 1-({3-[(E)-2-(4-fluorophenyl)-vinyl]-4-methoxy-1H-indazol-5-carbonyl}-amino)-cyclopropane carboxylic acid methyl ester obtained in Example 1317 in 5 ml of tetrahydrofuran and 2 ml of methanol was added 2 ml of a 1N sodium hydroxide aqueous solution, followed by stirring at room temperature overnight. The reaction mixture was diluted with water and the aqueous layer was washed with diethyl ether. The aqueous layer was adjusted to pH 2 by adding 1N hydrochloric acid, and the precipitated solid was collected by filtration with glass filter. The solid was washed with water and was dried under reduced pressure, to give 151 mg of the title compound as a brown solid.

$^1$H-NMR (400 MHz, DMSO-$D_6$) δ 1.17 (2H, dd, J=4.4,7.6 Hz), 1.43 (2H, dd, J=4.8, 7.6 Hz), 3.96 (3H, s), 7.25 (2H, t, J=8.8 Hz), 7.30 (1H, d, J=8.4 Hz), 7.51 (1H, d, J=16.8 Hz), 7.54 (1H, d, J=8.8 Hz), 7.56 (1H, d, J=16.4 Hz), 7.70 (1H, dd, J=5.6,8.8 Hz), 8.73 (1H, s)

Example 1319

The compounds of Examples 1320 to 1332 were obtained according to the method of Example 102 from various amines and 1-({3-[(E)-2-(4-fluorophenyl)-vinyl]-4-methoxy-1H-indazol-5-carbonyl}-amino)-cyclopropane carboxylic acid obtained in Example 1318.

Example 1320

3-[(E)-2-(4-Fluorophenyl)-vinyl]-4-methoxy-1H-indazol-5-carboxylic acid (1-carbamoyl-cyclopropyl)-amide MS (ESI) m/z 395 $MH^+$ Example 1321

3-[(E)-2-(4-Fluorophenyl)-vinyl]-4-methoxy-1H-indazol-5-carboxylic acid(1-methylcarbamoyl-cyclopropyl)-amide MS (ESI) m/z 409 $MH^+$ Example 1322

3-[(E)-2-(4-Fluorophenyl)-vinyl]-4-methoxy-1H-indazol-5-carboxylic acid (1-dimethylcarbamoyl-cyclopropyl)-amide MS (ESI) m/z 423 $MH^+$ Example 1323

3-[(E)-2-(4-Fluorophenyl)-vinyl]-4-methoxy-1H-indazol-5-carboxylic acid[1-(ethyl-methyl-carbamoyl)-cyclopropyl]-amide MS (ESI) m/z 437 $MH^+$ Example 1324

3-[(E)-2-(4-Fluorophenyl)-vinyl]-4-methoxy-1H-indazol-5-carboxylic acid[1-(isopropyl-methylcarbamoyl)-cyclopropyl]-amide MS (ESI) m/z 451 $MH^+$ Example 1325

3-[(E)-2-(4-Fluorophenyl)-vinyl]-4-methoxy-1H-indazol-5-carboxylic acid[1-(isobutyl-methylcarbamoyl)-cyclopropyl]-amide MS (ESI) m/z 465 $MH^+$ Example 1326

3-[(E)-2-(4-fluorophenyl)-vinyl]-4-methoxy-1H-indazol-5-carboxylic acid (1-diethylcarbamoyl-cyclopropyl)-amide MS (ESI) m/z 451 $MH^+$ Example 1327

3-[(E)-2-(4-Fluorophenyl)-vinyl]-4-methoxy-1H-indazol-5-carboxylic acid {1-[(azetidin-1-yl)carbonyl]-cyclopropyl}-amide MS (ESI) m/z 435 $MH^+$ Example 1328

3-[(E)-2-(4-Fluorophenyl)-vinyl]-4-methoxy-1H-indazol-5-carboxylic acid {1-[(pyrrolidin-1-yl)carbonyl]-cyclopropyl}-amide MS (ESI) m/z 449 $MH^+$ Example 1329

3-[(E)-2-(4-Fluorophenyl)-vinyl]-4-methoxy-1H-indazol-5-carboxylic acid {1-[(piperidin-1-yl)carbonyl]-cyclopropyl}-amide MS (ESI) m/z 463 $MH^+$ Example 1330

3-[(E)-2-(4-Fluorophenyl)-vinyl]-4-methoxy-1H-indazol-5-carboxylic acid {1-[(morpholin-4-yl)carbonyl]-cyclopropyl}-amide MS (ESI) m/z 465 $MH^+$ Example 1331

3-[(E)-2-(4-Fluorophenyl)-vinyl]-4-methoxy-1H-indazol-5-carboxylic acid (trans-2-hydroxy-cyclopentyl)-amide MS (ESI) m/z 396 $MH^+$ Example 1332

3-[(E)-2-(4-Fluorophenyl)-vinyl]-4-methoxy-1H-indazol-5-carboxylic acid (trans-2-hydroxy-cyclohexyl)-amide MS (ESI) m/z 410 $MH^+$ Example 1333

3-[(E)-2-(2,3-Dihydrobenzo[1,4]dioxin-6-yl)-vinyl]-4-methoxy-1H-indazol-5-carboxylic acid ethyl ester 590 mg of the 3-iodo-4-methoxy-1-trityl-1H-indazol-5-carboxylic acid ethyl ester obtained in Production Example 276 and 250 mg of 6-vinyl-2,3-dihydrobenzo[1,4]dioxine were reacted according to a similar method as in Production Example 181, and then the product was deprotected according to a similar method as in Example 16, to give 150 mg of the title compound as a pale yellow oil.

$^1H$-NMR (400 MHz, $CDCl_3$) δ 1.46 (3H, t, J=7.2 Hz), 4.04 (3H, s), 4.30 (4H, s), 4.43 (2H, q, J=7.2 Hz), 6.88 (1H, d, J=8.8 Hz), 7.10 (1H, dd, J=2.0, 8.8 Hz), 7.13 (1H, d, J=2.0 Hz), 7.20 (1H, d, J=8.8 Hz), 7.51 (1H, d, J=16.4 Hz), 7.55 (1H, d, J=16.4 Hz), 7.90 (1H, d, J=8.8 Hz).

Example 1334

3-[(E)-2-(2,3-Dihydrobenzo[1,4]dioxin-6-yl)-vinyl]-4-methoxy-1H-indazol-5-carboxylic acid 150 mg of 3-[(E)-2-(2,3-dihydrobenzo[1,4]dioxin-6-yl)-vinyl]-4-methoxy-1H-indazol-5-carboxylic acid ethyl ester was treated according to a similar method as in Example 144, to give 140 mg of the title compound as a colorless powder.

$^1H$-NMR (400 MHz, DMSO-$d_6$) δ 3.95 (3H, s), 4.27 (4H, s), 6.90 (1H, d, J=8.8 Hz), 7.12 (1H, s), 7.13 (1H, dd, J=2.0, 8.8 Hz), 7.29 (1H, d, J=8.8 Hz), 7.40 (1H, d, J=16.4 Hz), 7.44 (1H, d, J=16.4 Hz), 7.73 (1H, d, J=8.8 Hz), 13.39 (1H, bs).

Example 1335

3-[(E)-2-(Benzofuran-5-yl)-vinyl]-4-methoxy-1H-indazol-5-carboxylic acid ethyl ester 590 mg of 3-iodo-4-methoxy-1-trityl-1H-indazol-5-carboxylic acid ethyl ester obtained in Production Example 276 and 430 mg of crude 5-vinylbenzofuran were reacted according to a similar method as in Production Example 181, and then the product was deprotected according to a similar method as in Example 16, to give 125 mg of the title compound as a colorless oil.

$^1H$-NMR (400 MHz, $CDCl_3$) δ 1.45 (3H, t, J=7.2 Hz), 4.07 (3H, s), 4.44 (2H, q, J=7.2 Hz), 6.80 (1H, d, J=2.0 Hz), 7.21 (1H, d, J=8.8 Hz), 7.52 (1H, d, J=8.4 Hz), 7.59 (1H, dd, J=2.0, 8.4 Hz), 7.64 (1H, d, J=2.0 Hz), 7.66 (1H, d, J=16.6 Hz), 7.76 (1H, d, J=16.6 Hz), 7.80 (1H, d, J=2.0 Hz), 7.90 (1H, d, J=8.8 Hz).

Example 1336

3-[(E)-2-(Benzofuran-5-yl)-vinyl]-4-methoxy-1H-indazol-5-carboxylic acid 125 mg of 3-[(E)-2-(benzofuran-5-yl)vinyl]-4-methoxy-1H-indazol-5-carboxylic acid ethyl ester was treated according to a similar method as in Example 144, to give 120 mg of the title compound as a colorless powder.

$^1H$-NMR (400 MHz, DMSO-$d_6$) δ 4.00 (3H, s), 7.00 (1H, d, J=2.0 Hz), 7.30 (1H, d, J=8.6 Hz), 7.58 (1H, d, J=16.4 Hz), 7.64 (1H, d, J=8.3 Hz), 7.65 (1H, d, J=8.3 Hz), 7.67 (1H, d, J=16.4 Hz), 7.74 (1H, d, J=8.6 Hz), 7.12 (1H, bs), 8.02 (1H, d, J=2.0 Hz), 13.41 (1H, bs).

Example 1337

3-[(E)-2-(3-Acetyl-4-fluorophenyl)-vinyl]-4-methoxy-1H-indazol-5-carboxylic acid ethyl ester 580 mg of 3-iodo-4-methoxy-1-trityl-1H-indazol-5-carboxylic acid ethyl ester obtained in Production Example 276 and 210 mg of 1-(2-fluoro-5-vinylphenyl)ethanone were reacted according to a similar method as in Production Example 181, and then the product was deprotected according to a similar method as in Example 16, to give 120 mg of the title compound as a colorless powder.

$^1H$-NMR (400 MHz, $CDCl_3$) δ 1.45 (3H, t, J=7.2 Hz), 2.69 (3H, d, J=4.8 Hz), 4.05 (3H, s), 4.44 (2H, q, J=7.2 Hz), 7.17 (1H, dd, J=8.8, 10.8 Hz), 7.23 (1H, d, J=8.8 Hz), 7.63 (1H, d, J=16.4 Hz), 7.65 (1H, d, J=16.4 Hz), 7.70 (1H, ddd, J=2.4, 4.8, 8.8 Hz), 7.91 (1H, d, J=8.8 Hz), 8.08 (1H, dd, J=2.4, 7.2 Hz).

Example 1338

3-[(E)-2-(3-Acetyl-4-fluorophenyl)-vinyl]-4-methoxy-1H-indazol-5-carboxylic acid 120 mg of 3-[(E)-2-(3-acetyl-4-fluorophenyl)-vinyl]-4-methoxy-1H-indazol-5-carboxylic acid ethyl ester was treated according to a similar method as in Example 144, to give 110 mg of the title compound as a colorless powder.

$^1H$-NMR (400 MHz, DMSO-$d_6$) δ 2.63 (3H, d, J=4.0 Hz), 3.96 (3H, s), 7.32 (1H, bd, J=8.8 Hz), 7.41 (1H, dd, J=8.7, 10.6 Hz), 7.59 (1H, d, J=16.4 Hz), 7.62 (1H, d, J=16.4 Hz), 7.75 (1H, bd, J=8.8 Hz), 7.95-8.01 (1H, m), 8.02 (1H, bd, J=7.2 Hz), 13.52 (1H, bs)

Example 1339

The compounds of Examples 1340 to 1363 were obtained by condensation of the carboxylic acids obtained in Examples 1334, 1336 and 1338 with various amines followed by LC-MS purification, according to a similar method as in Example 44.

Example 1340

3-[(E)-2-(2,3-Dihydrobenzo[1,4]dioxin-6-yl)-vinyl]-4-methoxy-1H-indazol-5-carboxylic acid(pyrazin-2-ylmethyl)amide MS (ESI) m/z 444 $MH^+$ Example 1341

3-[(E)-2-(2,3-Dihydrobenzo[1,4]dioxin-6-yl)-vinyl]-4-methoxy-1H-indazol-5-carboxylic acid(furan-2-ylmethyl)amide MS (ESI) m/z 432 $MH^+$ Example 1342

3-[(E)-2-(2,3-Dihydrobenzo[1,4]dioxin-6-yl)-vinyl]-4-methoxy-1H-indazol-5-carboxylic acid cyclopropylmethylamide MS (ESI) m/z 406 $MH^+$ Example 1343

3-[(E)-2-(2,3-Dihydrobenzo[1,4]dioxin-6-yl)-vinyl]-4-methoxy-1H-indazol-5-carboxylic acid(thiophen-2-ylmethyl)amide MS (ESI) m/z 448 $MH^+$ Example 1344

3-[(E)-2-(2,3-Dihydrobenzo[1,4]dioxin-6-yl)-vinyl]-4-methoxy-1H-indazol-5-carboxylic acid cyclopropylamide MS (ESI) m/z 392 $MH^+$ Example 1345

3-[(E)-2-(2,3-Dihydrobenzo[1,4]dioxin-6-yl)-vinyl]-4-methoxy-1H-indazol-5-carboxylic acid(pyridin-3-ylmethyl)amide MS (ESI) m/z 443 $MH^+$ Example 1346

3-[(E)-2-(2,3-Dihydrobenzo[1,4]dioxin-6-yl)-vinyl]-4-methoxy-1H-indazol-5-carboxylic acid cyanomethylamide MS (ESI) m/z 391 $MH^+$ Example 1347

3-[(E)-2-(2,3-Dihydrobenzo[1,4]dioxin-6-yl)-vinyl]-4-methoxy-1H-indazol-5-carboxylic acid(2-hydroxypropyl)amide MS (ESI) m/z 410 $MH^+$ Example 1348

3-[(E)-2-(3-Acetyl-4-fluorophenyl)-vinyl]-4-methoxy-1H-indazol-5-carboxylic acid(pyrazin-2-ylmethyl)amide MS (ESI) m/z 446 $MH^+$ Example 1349

3-[(E)-2-(3-Acetyl-4-fluorophenyl)-vinyl]-4-methoxy-1H-indazol-5-carboxylic acid(furan-2-ylmethyl) amide MS (ESI) m/z 434 $MH^+$ Example 1350

3-[(E)-2-(3-Acetyl-4-fluorophenyl)-vinyl]-4-methoxy-1H-indazol-5-carboxylic Acid cyclopropylmethylamide MS (ESI) m/z 408 $MH^+$ Example 1351

3-[(E)-2-(3-Acetyl-4-fluorophenyl)-vinyl]-4-methoxy-1H-indazol-5-carboxylic acid(thiophen-2-ylmethyl)amide MS (ESI) m/z 450 $MH^+$ Example 1352

3-[(E)-2-(3-Acetyl-4-fluorophenyl)-vinyl]-4-methoxy-1H-indazol-5-carboxylic acid cyclopropylamide MS (ESI) m/z 394 $MH^+$ Example 1353

3-[(E)-2-(3-Acetyl-4-fluorophenyl)-vinyl]-4-methoxy-1H-indazol-5-carboxylic acid (pyridin-3-ylmethyl)amide MS (ESI) m/z 445 $MH^+$ Example 1354

3-[(E)-2-(3-Acetyl-4-fluorophenyl)-vinyl]-4-methoxy-1H-indazol-5-carboxylic acid cyanomethylamide MS (ESI) m/z 393 $MH^+$ Example 1355

3-[(E)-2-(3-Acetyl-4-fluorophenyl)-vinyl]-4-methoxy-1H-indazol-5-carboxylic acid(2-hydroxypropyl) amide MS (ESI) m/z 412 $MH^+$ Example 1356

3-[(E)-2-(Benzofuran-5-yl)-vinyl]-4-methoxy-1H-indazol-5-carboxylic acid(pyrazin-2-ylmethyl)amide MS (ESI) m/z 426 $MH^+$ Example 1357

3-[(E)-2-(Benzofuran-5-yl)-vinyl]-4-methoxy-1H-indazol-5-carboxylic acid(furan-2-ylmethyl)amide MS (ESI) m/z 414 $MH^+$ Example 1358

3-[(E)-2-(Benzofuran-5-yl)-vinyl]-4-methoxy-1H-indazol-5-carboxylic acid cyclopropylmethylamide MS (ESI) m/z 388 $MH^+$ Example 1359

3-[(E)-2-(Benzofuran-5-yl)-vinyl]-4-methoxy-1H-indazol-5-carboxylic acid(thiophen-2-ylmethyl) amide MS (ESI) m/z 430 $MH^+$ Example 1360

3-[(E)-2-(Benzofuran-5-yl)-vinyl]-4-methoxy-1H-indazol-5-carboxylic acid cyclopropylamide MS (ESI) m/z 374 $MH^+$ Example 1361

3-[(E)-2-(Benzofuran-5-yl)-vinyl]-4-methoxy-1H-indazol-5-carboxylic acid(pyridin-3-ylmethyl)amide MS (ESI) m/z 425 $MH^+$ Example 1362

3-[(E)-2-(Benzofuran-5-yl)-vinyl]-4-methoxy-1H-indazol-5-carboxylic acid cyanomethylamide MS (ESI) m/z 373 $MH^+$ Example 1363

3-[(E)-2-(Benzofuran-5-yl)-vinyl]-4-methoxy-1H-indazol-5-carboxylic acid(2-hydroxypropyl)amide MS (ESI) m/z 392 $MH^+$ The compounds (I) to (III) according to the present invention or a salt thereof exhibited an excellent action in tests for determining JNK inhibitory action. For example, the inhibitory actions on JNK 3 were as follows.

Test Example 1

Measurement of JNK 3 Inhibition

Human JNK 3 was expressed as a fusion protein (GST-JNK 3) with glutathione S-transferase (GST) in *Escherichia coli* and was purified using glutathione Sepharose 4B beads. The amino acid sequence 1-169 of c-Jun was prepared as a fusion protein (GST-c-Jun) with GST in *Escherichia coli*, was purified using glutathione Sepharose 4B beads and was used as a substrate. A test compound was solved in 100% dimethyl sulfoxide into 10 mM and was then further diluted with 10% aqueous dimethyl sulfoxide solution to yield a dilution series. In 96-well OPTI plate (available from ParkinElmer Life Sciences), 20 μl of diluted compound, 30 μl of substrate solution (1.2 μg GST-c-Jun, 0.2 μCi [$\gamma$-$^{33}$P]ATP, 25 mM HEPES pH=7.5, 10 mM MgAcetate, 3.33 μM ATP) and 50 μl of enzyme solution (0.04 μg GST-JNK3, 25 mM HEPES pH=7.5, 10 mM MgAcetate) were mixed per 1-well, made up to 100 μl, and allowed to react for 30 minutes. After terminating the reaction by adding 100 μl of a reaction terminator (80 mM ATP, 50 mg/ml glutathione SPA beads (available from Amersham Pharmacia Biotech)), the reaction mixture was shaken for 30 minutes. The mixture was centrifuged at room temperature at 1000×g for 5 minutes, and the emission intensity thereof was determined on a TopCount™ illuminator (available from available from ParkinElmer Life Sciences). The activity is expressed by the 50% inhibitory concentration on the enzymatic activity of JNK, i.e., $IC_{50}$ (nM).

Results

The compounds (I) to (III) according to the present invention or a salt thereof exhibited an excellent JNK3 inhibitory action. The following shows examples of $IC_{50}$ values.

| Example No. | JNK3 inhibitory activity |
|---|---|
| 56 | 234 nM |
| 106 | 195 nM |
| 128 | 117 nM |
| 136 | 167 nM |
| 213 | 117 nM |
| 353 | 148 nM |
| 392 | 403 nM |
| 466 | 578 nM |
| 472 | 505 nM |
| 495 | 118 nM |
| 522 | 146 nM |
| 571 | 63 nM |
| 573 | 66 nM |
| 603 | 117 nM |
| 786 | 175 nM |
| 790 | 70 nM |
| 992 | 107 nM |
| 1003 | 122 nM |
| 1056 | 132 nM |

Test Example 2

Measurement of ERK2 Inhibition

A plate for ELISA was coated for 1 hour with 1 μg/well myelin basic protein (available from Upstate Biotech) serving as a reaction substrate. Following washing operation with PBS-Tween, blocking with 1% BSA-PBS was conducted for 3 hours. After washing with PBS-Tween, 25 μl of a reaction solution (20 mM MOPS, 25 mM β-glycerophosphoric acid, 5 mM EGTA, 1 mM orthovanadic acid, 1 mM dithiothreitol), 5 μl of a dilution sample of compound from dilution series which was prepared using 1% DMSO-1% BSA solution, 10 μl of 0.5 μg/ml ERK2 (available from Upstate Bioech), 10 μl of 500 μM ATP were added to made up to 50 μl, and allowed to react at room temperature for 30 minutes. 100 μl of 200 mM EDTA (pH 8.0) was added to stop the reaction, which was then washed with PBS-Tween. This was then added with mouse anti-phospho-myelin basic protein antibody (available from Usptate Biotech), allowed to react for 1 hour, and washed with PBS-Tween, thereafter added with anti-mouse IgG antibody combined with horseradish peroxidase (available from ICN), allowed to react for 1 hour, and washed with PBS-Tween. Subsequently 100 μl of a TMB peroxidase substrate solution (available from KPL) was added, coloring reaction was allowed for 10 minutes, and then measurement at OD 450 nm was conducted. The activity is represented by the concentration at which ERK2 enzyme activity was inhibited to 50%, namely by $IC_{50}$(nM)

Results

The compounds of the present invention exhibited an excellent selectivity.

| | JNK3 inhibitory activity | ERK2 inhibitory activity |
|---|---|---|
| Example 103 | 55 nM | 22100 nM |
| Reference example 1 | 92 nM | 710 nM |

The compound of Reference example 1, 3-[(E)-2-(3-fluorophenyl)-vinyl]-1H-indazole-5-carboxylic acid (furan-2-ylmethyl)-amide was synthesized while referring to WO02-10137(A2).

MS (ESI) m/z 362 $MH^+$

The compounds according to the present invention had an excellent JNK3 inhibitory action as described above, and hence desired results were obtained also in the following tests.

Test example 3

Cell Death Induced by Low $K^+$ Exposure in Primary Culture of Mouse Cerebellar Granular Neurons Cerebellum was removed from an ICR mouse (CHARLES RIVER JAPAN, INC.) of 7-8 days old, and cerebellar granular neurons were isolated by means of enzyme treatment and physical treatment. The cerebellar granular neurons were seeded in a 96-well plate so that the density was $3\times10^5$-$4\times10^5$ cells/$cm^2$, and cultured for about 1 week in a culture medium A (Basal medium Eagle+10% FBS, 20 mM $K^+$). Then the medium was changed from the culture medium A to a culture medium B in which $K^+$ concentration was low, namely Basal medium Eagle. A test compound was dissolved in 100% DMSO to concentration of 10 mM, diluted with the culture medium B into an objective concentration, and added at the time of medium replacement. After 24 hours from medium replacement, survival of cerebellar granular cells was determined by MTT assay.

Test example 4

Cell Death Induced by $MPP^+$ in Primary Culture of Rat Mesencephalic Dopaminergic Neurons Ventral mesencephalon was removed from 14-day fetal Wistar rat (CHARLES RIVER JAPAN, INC.), and mesencephalic neurons were isolated by means of enzyme treatment and physical treatment. The mesencephalic neurons were seeded in a 48-well or 96-well plate so that the density was $2\times10^5$ cells/$cm^2$, and cultured for about 1 week in a culture medium (DMEM+10% FBS). To this medium, a solution of test compound dissolved in 100% DMSO to 10 mM and diluted with the culture medium into ×22 concentration of objective concentration was added in an amount of 1/22 of the medium volume, and next 660 μM $MPP^+$ was added in an amount of 1/22 of the medium volume. After 48 hours from addition of $MPP^+$, the cells were fixed by paraformaldehyde, and immunostained using anti-tyrosine hydroxylase antibody. Then surviving cells was counted under microscope, and quantified by using an image analyzer (ANAX50, Kyusyu Matsushita Electric Co., Ltd.)

Test example 5

Cell Death Induced by Amyloid β (Aβ) in Primary Culture of Rat Cerebral Cortex and Hippocampus Neurons Cerebral cortex and hippocampus were removed from 17-day fetal Wistar rat (CHARLES RIVER JAPAN, INC.), and neurons of each site were isolated by means of enzyme treatment and physical treatment. Each neurons were seeded in a 96-well plate so that the density was $2\times10^5$ cells/$cm^2$, and cultured for 4 days in a culture medium A (Neurobasal™ mediuM+B27 supplement). To this medium, a solution of test compound dissolved in 100% DMSO to 10 mM and diluted into an objective concentration with the culture medium B (D/F medium+N2 supplement) was added, and then an appropriate concentration of Aβ1-40 was added in an amount of 1/10 of the medium volume. After 48 hours from addition of Aβ1-40, cell injury was quantitatively measured by LDH assay.

Test example 6

Protective Effect Against Dopaminergic Neuron Degeneration in MPTP-Treated Mouse To a group consisting of 5 male C57BL/6 mice (Japane SLC) in 8-10 weeks old, 40 mg/kg of MPTP hydrochloride (Sigma) dissolved in saline was subcutaneously administered. After 3 days, contents of dopamine and its metabolites (DOPAC and HVA) in striatum were measured by HPLC. For determination of drug effect, a drug was orally or intrapenetorially administered twice a day including 1 hour before treating of MPTP. The recovery rate of dopamine content owing to administration of drug was determined in accordance with the following formula.

Recovery rate (%)=100×[(striatal dopamine content in MPTP-untreated mouse)−(striatal dopamine content of drug-administered group in MPTP-treated mouse)/(striatal dopamine content in MPTP-untreated mouse)−(striatal dopamine content of control group in MPTP-treated mouse)]

Test example 7

LPS Induced Tumor Necrosis Factor α (TNF-α) Production

A group consisting of 5 male C57BL/6 mice (Japane SLC) in 7-12 weeks old was sensitized by intravenously administering 2 mg of BCG vaccine (Japan BCG). After 1 to 2 weeks, 0.3 mg/kg of lipopolysaccharoid (LPS; Sigma) was intravenously administered, and after 1 hour plasma was obtained by collecting blood from cerebral hemorrhage. TNF-α produced in plasma was measured by using a commercially available ELISA kit (Biosource) For determination of drug effect, a drug was orally or intrapenetorially administered 1 hour before treating of LPS. The suppression rate of TNF-α production owing to drug was determined in accordance with the following formula.

Suppression rate (%)=100×[1−(plasma TNF-α concentration of drug-administered group)/(plasma TNF-α concentration of control group)]

Test example 8

Analysis Using Insulin-Resistant Model Mouse (db/db-mouse, ob/ob Mouse)

A db/db mouse or an ob/ob mouse was administered with a test compound once a day for 7 days, and blood glucose was measured in fasting state and non-fasting state. Also after single administration and final administration, glucose tolerance test with 2 g glucose/kg was conducted. Furthermore, organs were extracted during autopsy, and a variety of phosphorylation of c-jun or IRS-1 in different organs were analyzed.

Structural formulae for compounds of the above Production examples and Examples are shown below.

Production Example 1

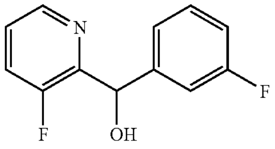

Production Example 2

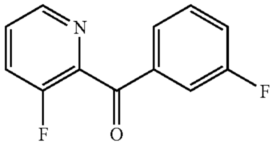

Production Example 3

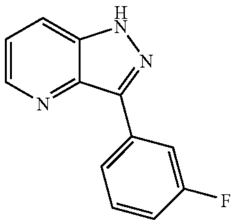

Production Example 4

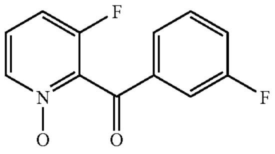

-continued

Production Example 5

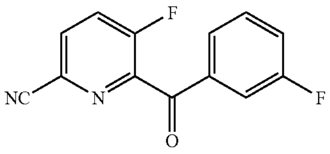

Production Example 6

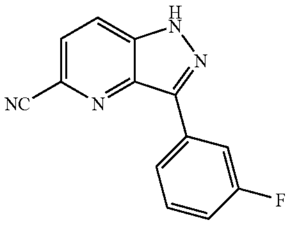

Example 7

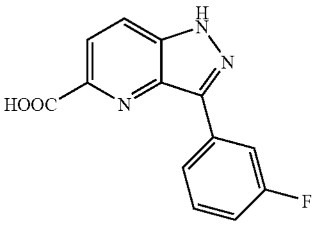

Production Example 8

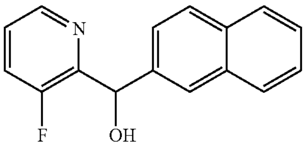

Production Example 9

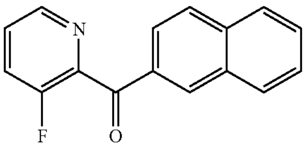

Example 10

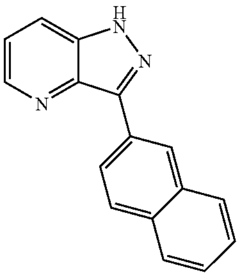

Production Example 11

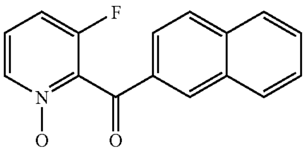

-continued
Production Example 12
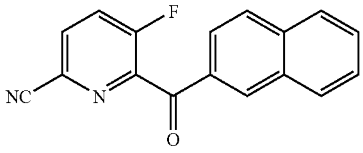
Production Example 13
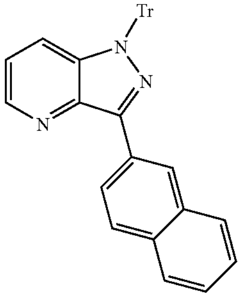
Production Example 14
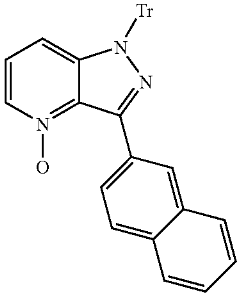
Production Example 15
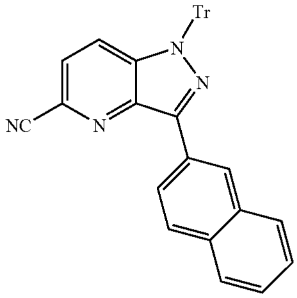
Example 16
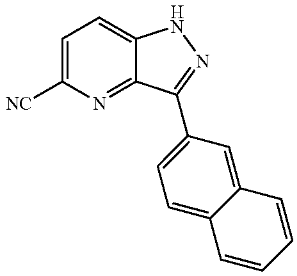
-continued
Example 17
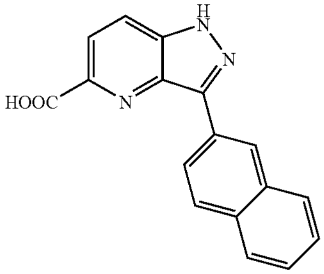
Production Example 18
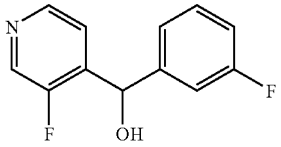
Production Example 19
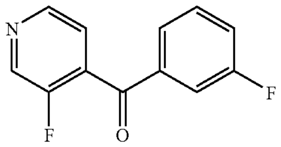
Production Example 20
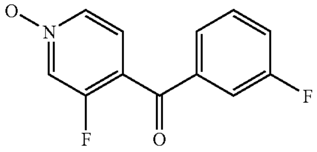
Example 21
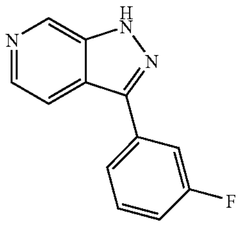
Production Example 22
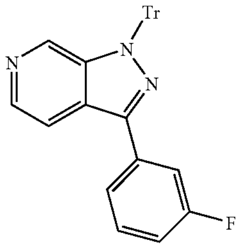

-continued
Production Example 23
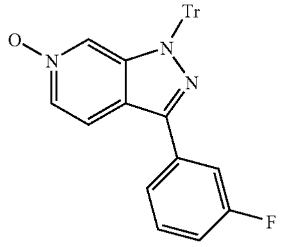
Production Example 24
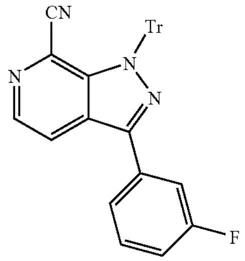
Production Example 25
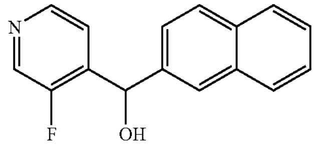
Production Example 26
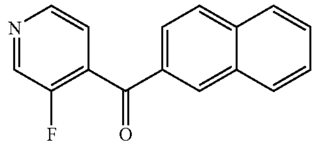
Production Example 27
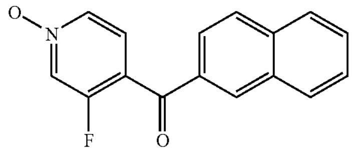
Production Example 28
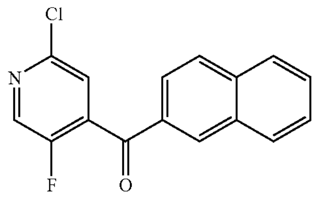
-continued
Production Example 29
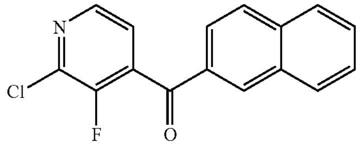
Production Example 30
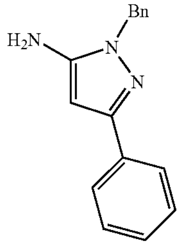
Production Example 31
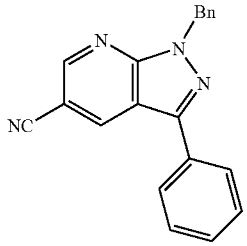
Production Example 32
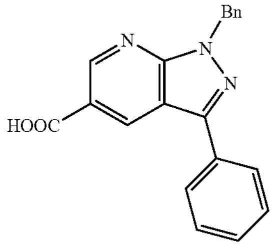
Production Example 33
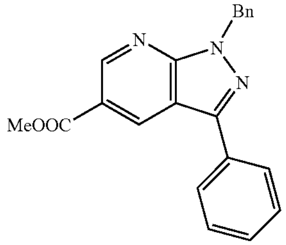
Example 34
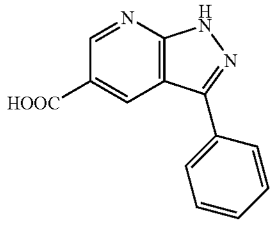

-continued
Production Example 35
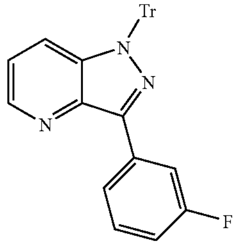
Production Example 36
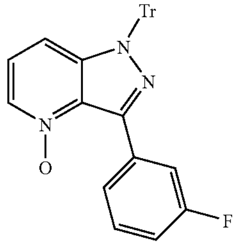
Production Example 37
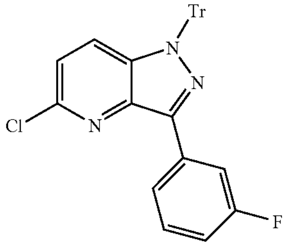
Example 38
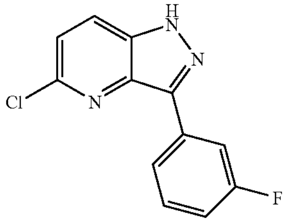
Example 39
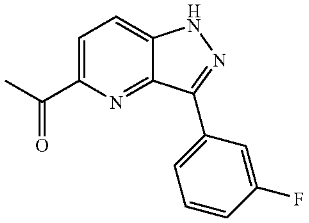
-continued
Production Example 40
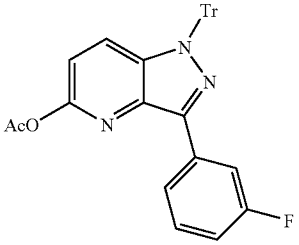
Production Example 41
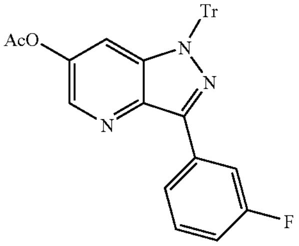
Example 42
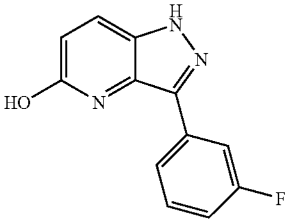
Example 43
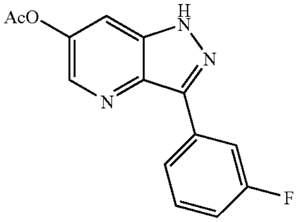
Example 45
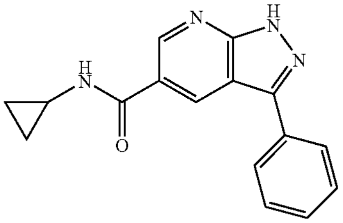
Example 46
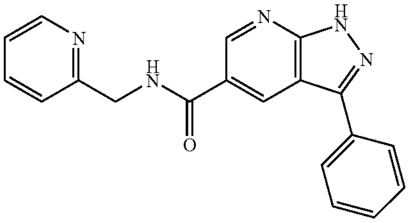
Example 47
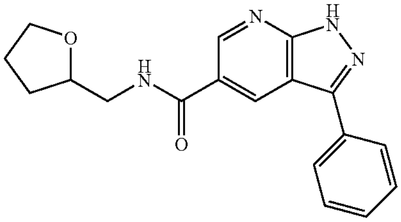

-continued
Example 48
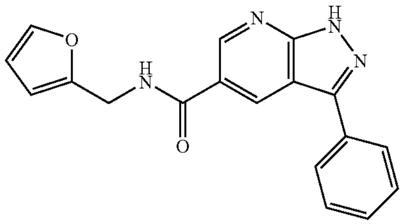
Example 49
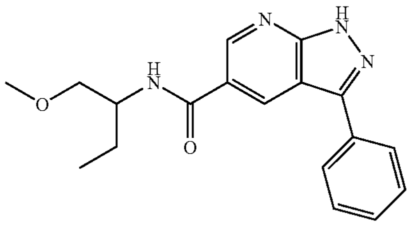
Example 50
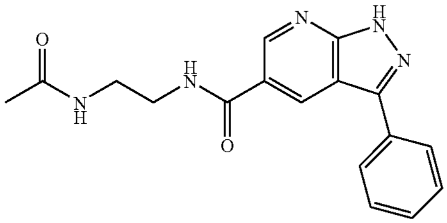
Example 51
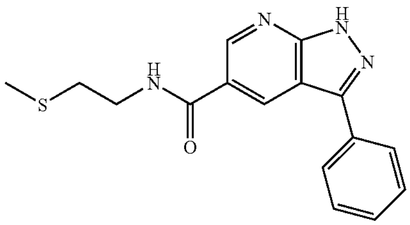
Example 52
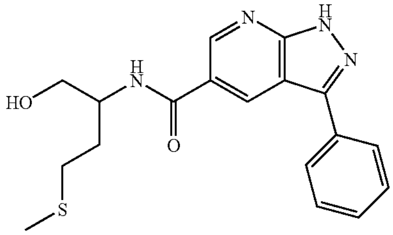
-continued
Example 53
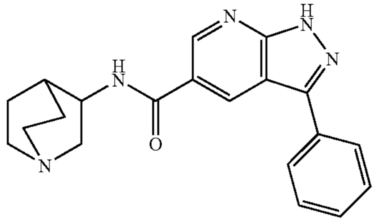
Example 54
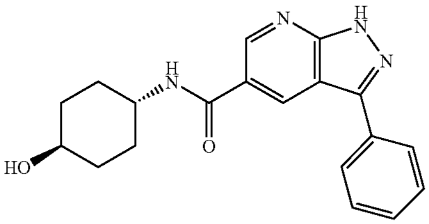
Example 56
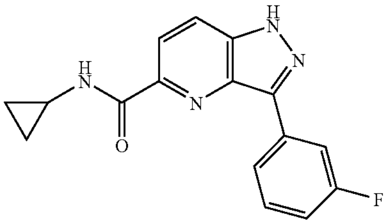
Example 57
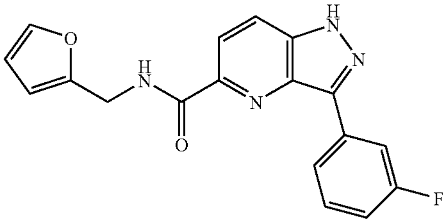
Example 58
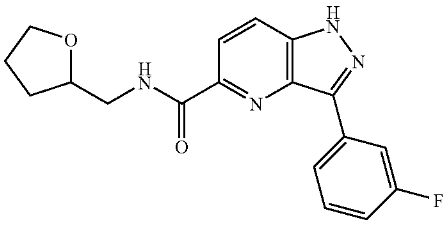
Example 59
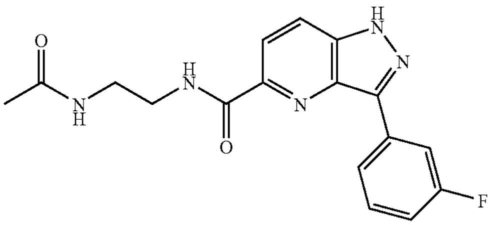

-continued
Example 60
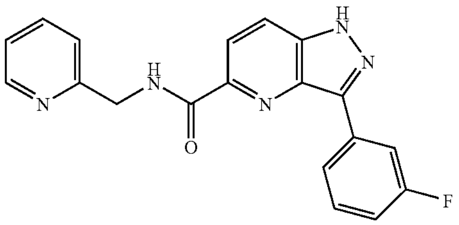
Example 61
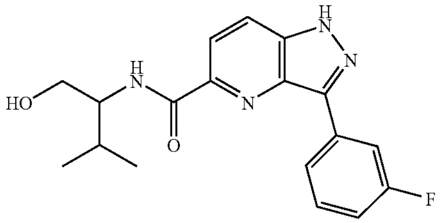
Example 62
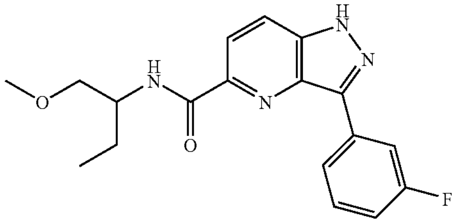
Example 64
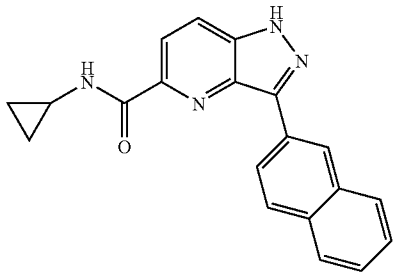
Example 65
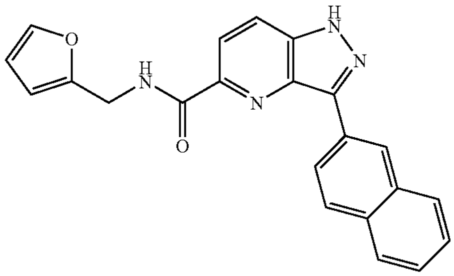
Example 66
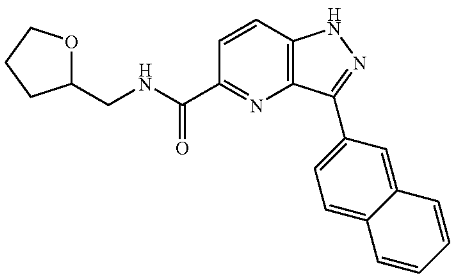
-continued
Example 67
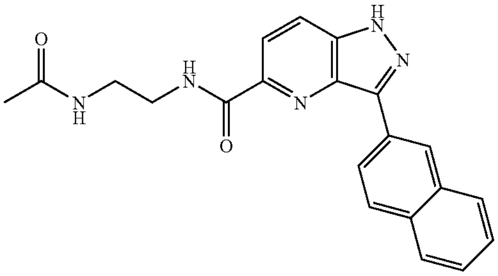
Example 68
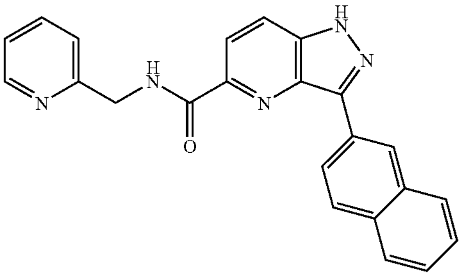
Example 69
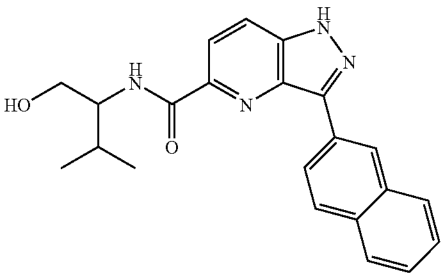
Example 70
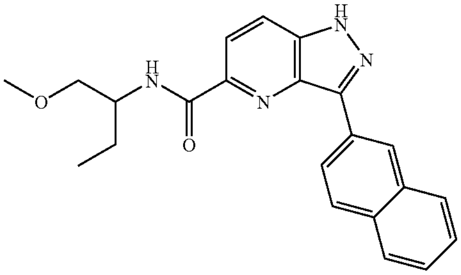
Production Example 71
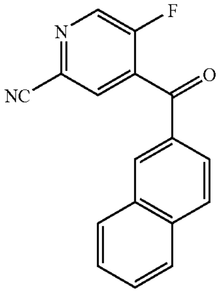

-continued
Production Example 72
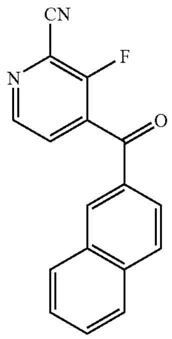
Example 73
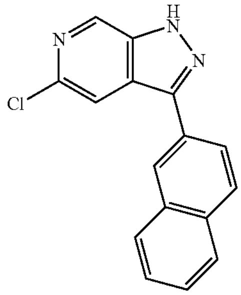
Production Example 74
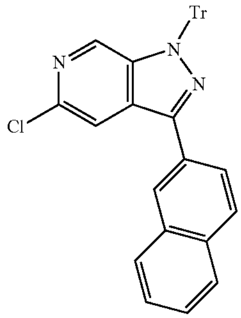
Example 75
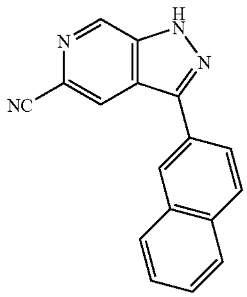
Production Example 76
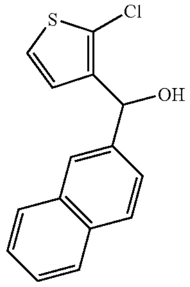
-continued
Production Example 77
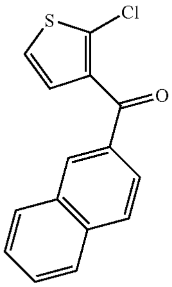
Example 78
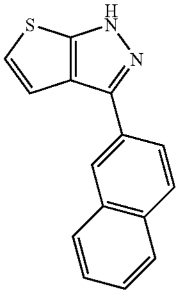
Production Example 79
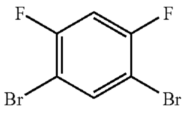
Production Example 80
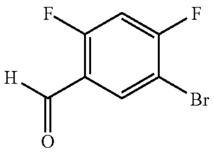
Production Example 81
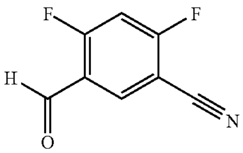
Production Example 82
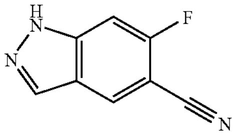
Production Example 83
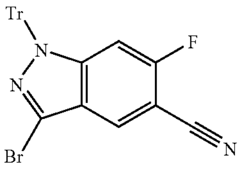
Production Example 84
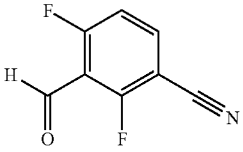

-continued
Production Example 85
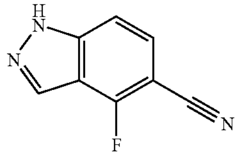
Production Example 86
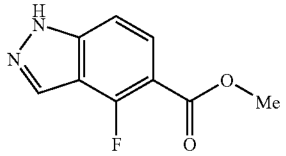
Production Example 87
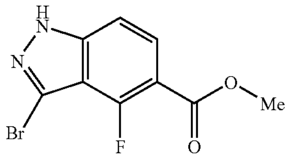
Production Example 88
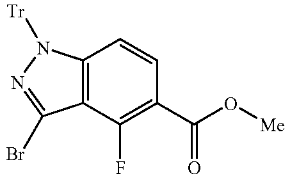
Production Example 89
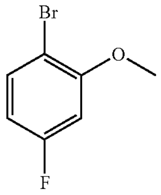
Production Example 90
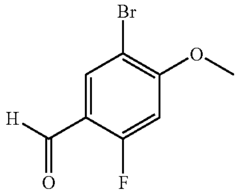
Production Example 91
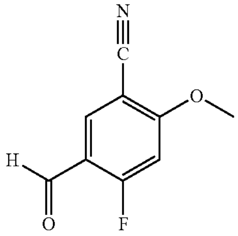
-continued
Production Example 92
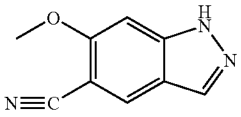
Production Example 93
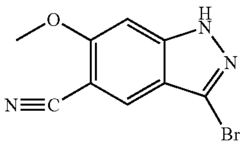
Production Example 94
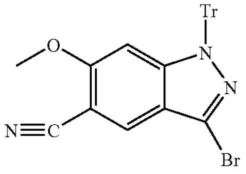
Production Example 95
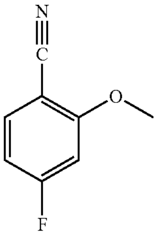
Production Example 96
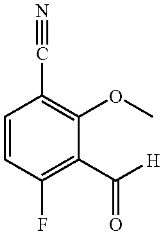
Production Example 97
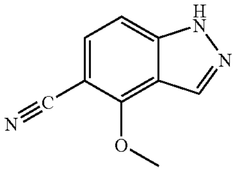
Production Example 98
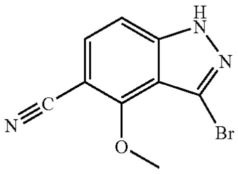
Production Example 99
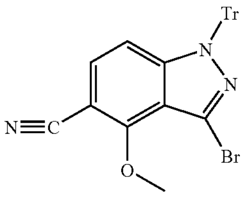

-continued
Example 100
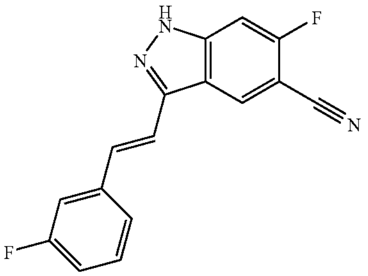
Example 101
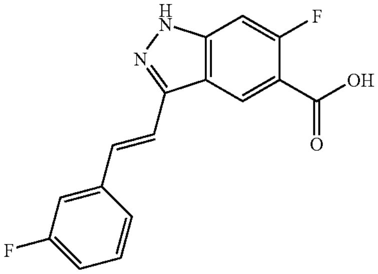
Example 102
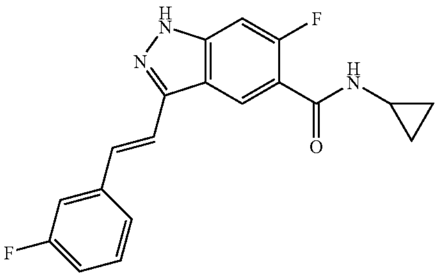
Example 103
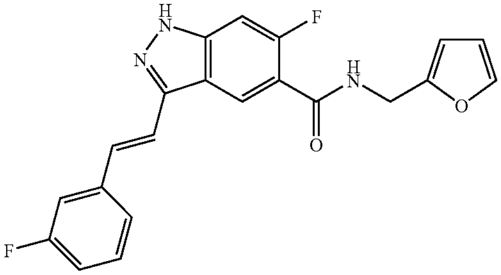
Example 104
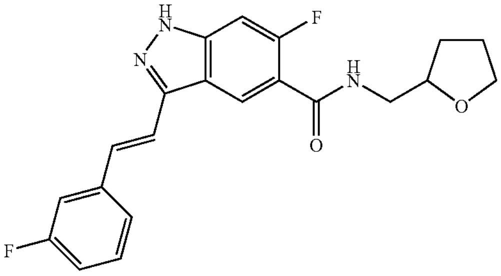
-continued
Example 105
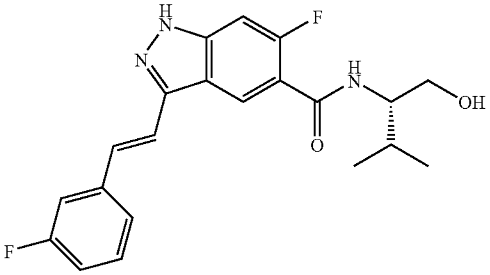
Example 106
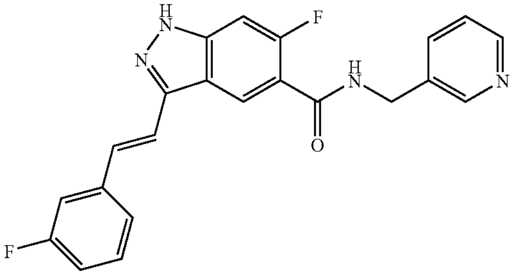
Example 107
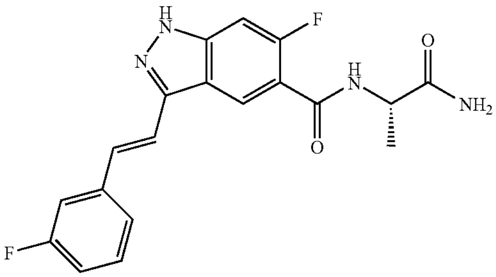
Production Example 108
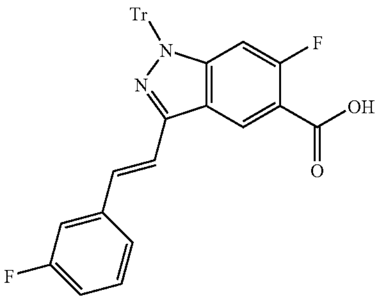

-continued
Production Example 109
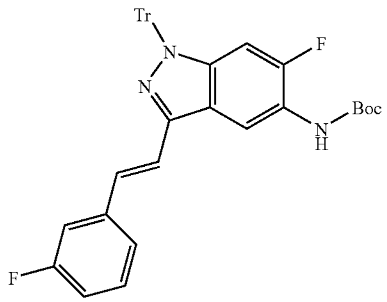
Example 110
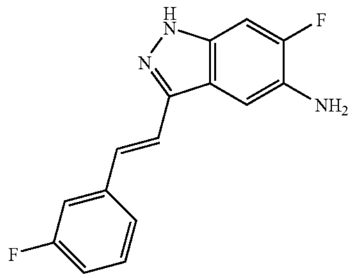
Example 111
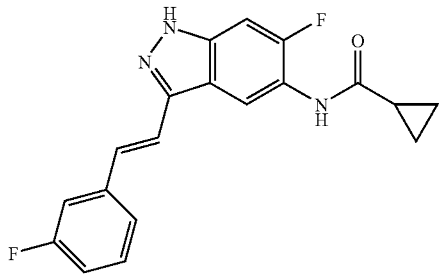
Example 112
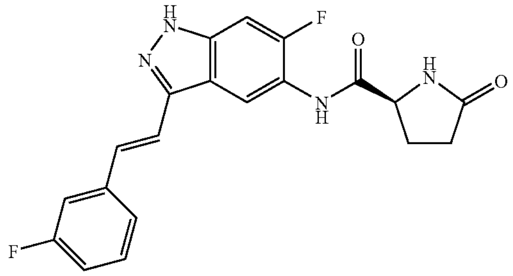
Example 113
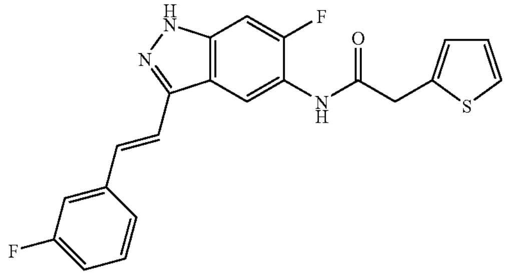
-continued
Example 114
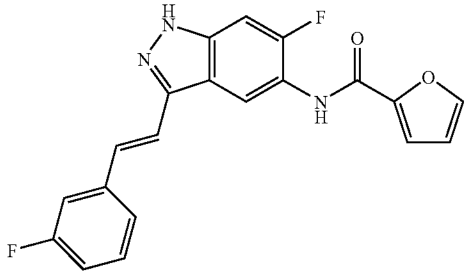
Example 115
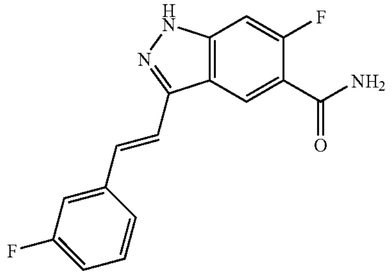
Production Example 116
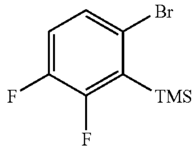
Production Example 117
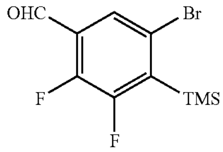
Production Example 118
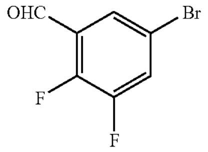
Production Example 119
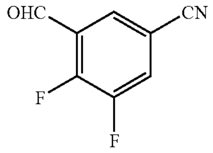
Production Example 120
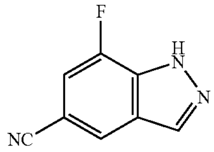

-continued
Production Example 121
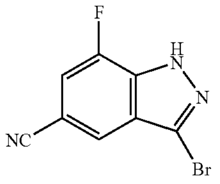
Production Example 122
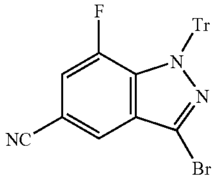
Production Example 123
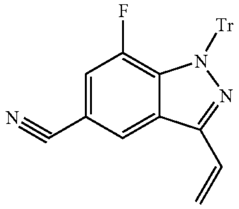
Production Example 124
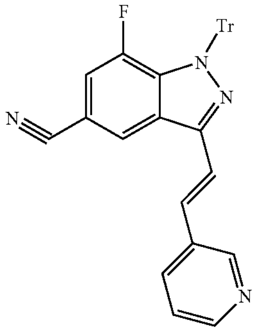
Production Example 125
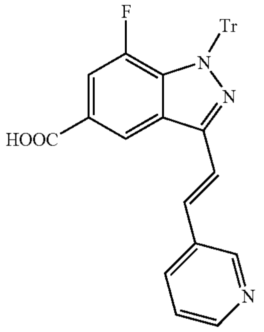
Example 126
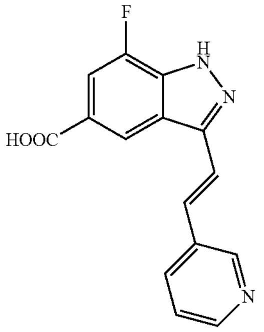
-continued
Example 127
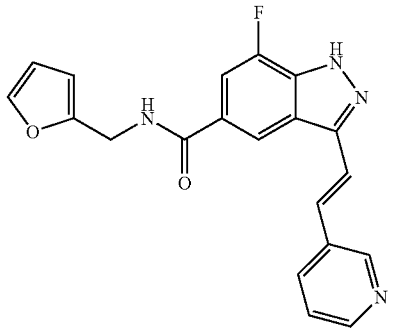
Example 128
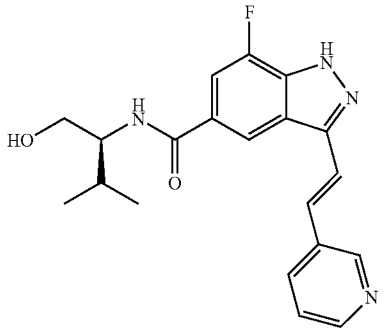
Example 129
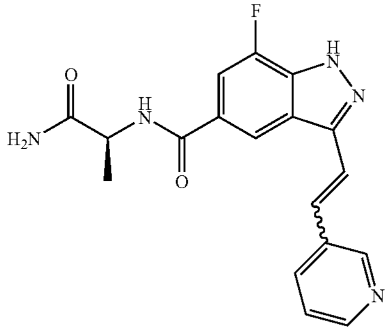
Example 131
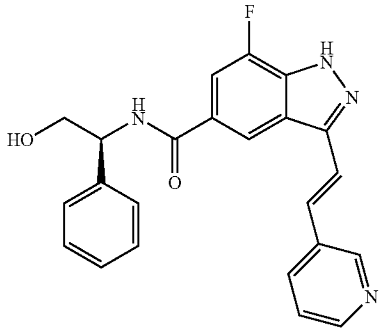

-continued
Example 132
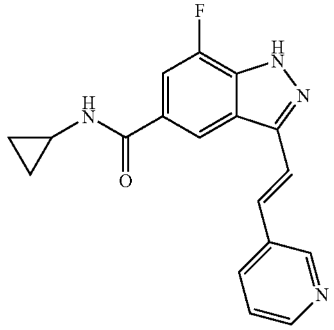
Production Example 133
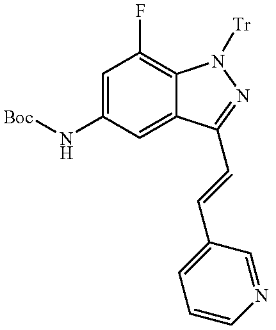
Example 134
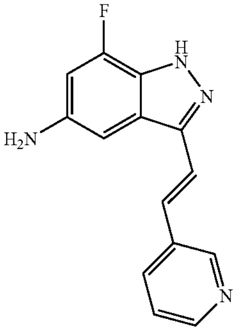
Production Example 135
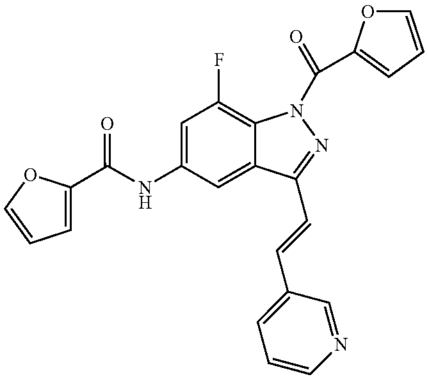
-continued
Example 136
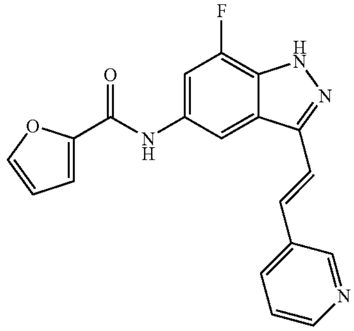
Production Example 137
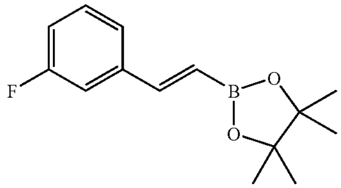
Production Example 138
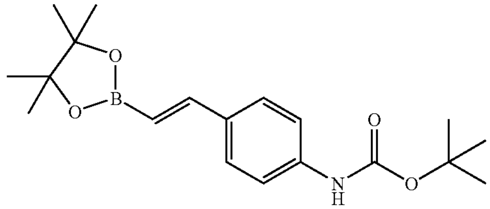
Production Example 139
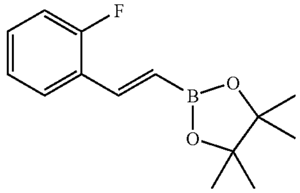
Production Example 140
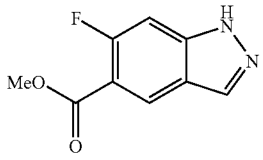
Production Example 141
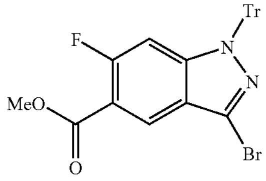

-continued
Example 142
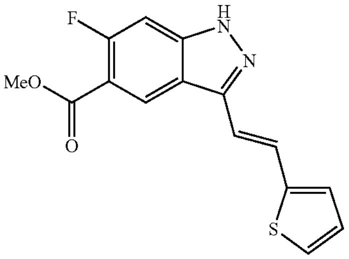
Example 143
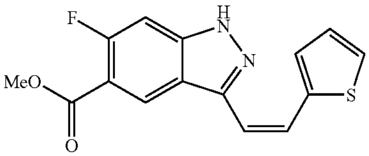
Example 144
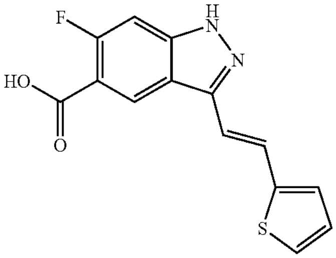
Example 146
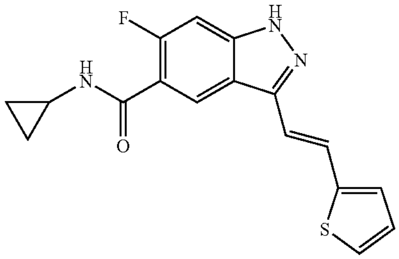
Example 147
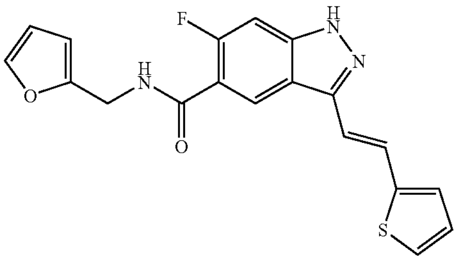
Example 148
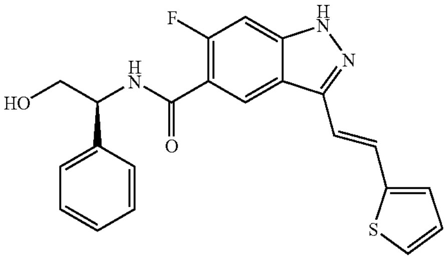
-continued
Example 149
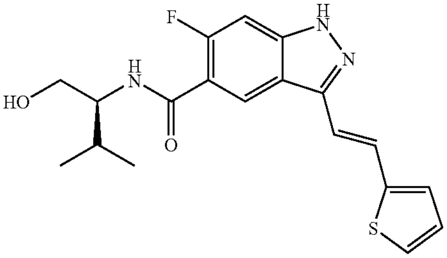
Example 150
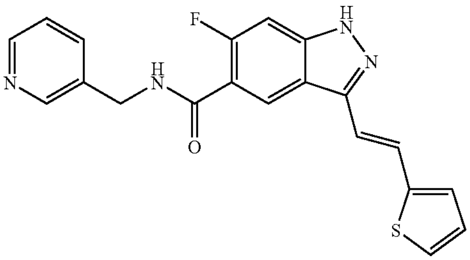
Example 151
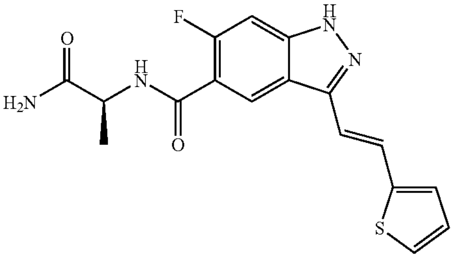
Production Example 152
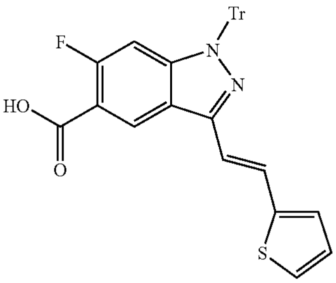
Production Example 153
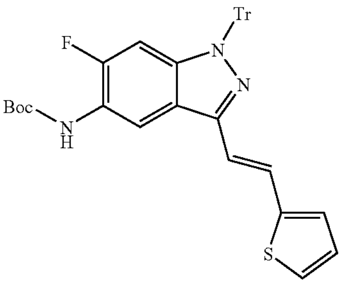

-continued
Example 154
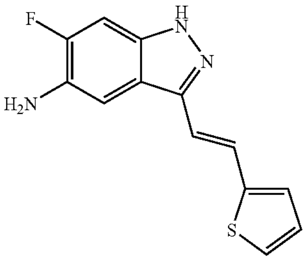
Example 156
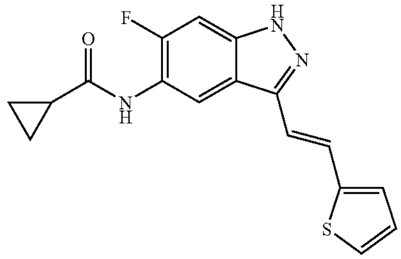
Example 157
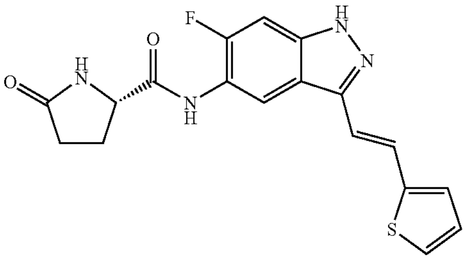
Example 158
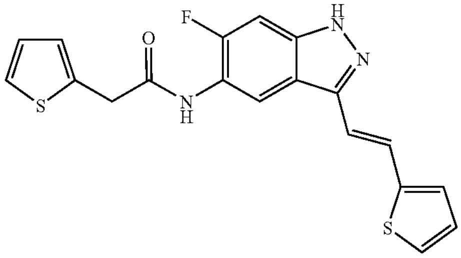
Example 159
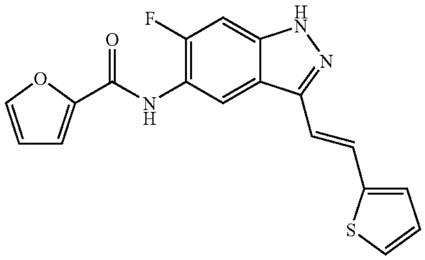
-continued
Example 160
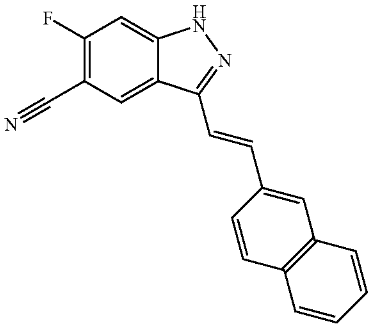
Example 161
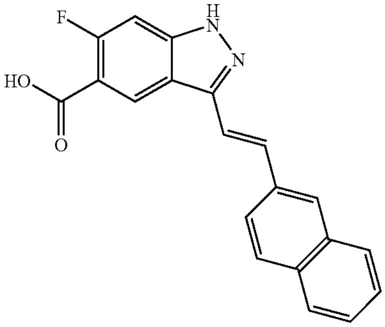
Example 163
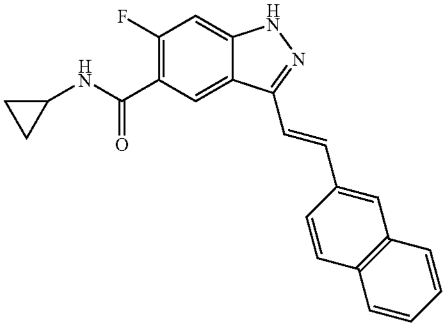
Example 164
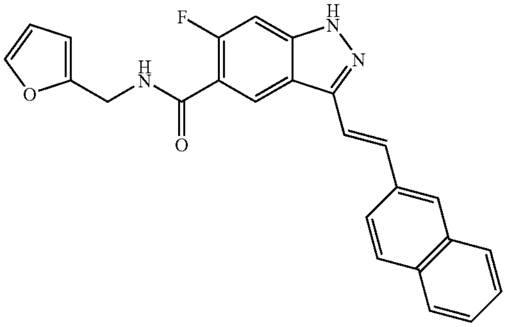

-continued
Example 165
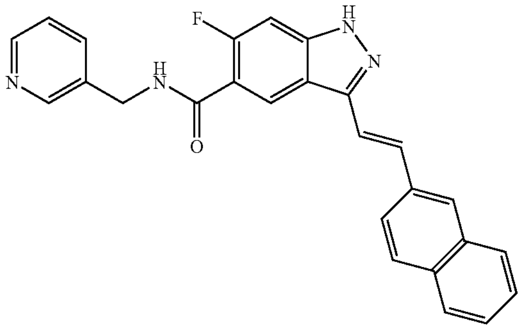
Example 166
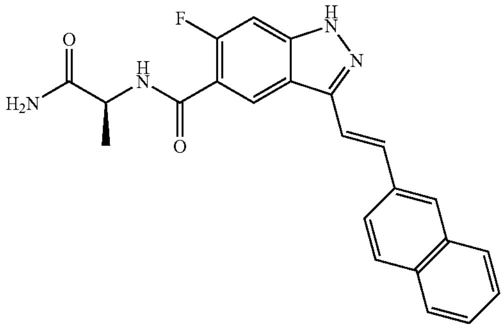
Production Example 167
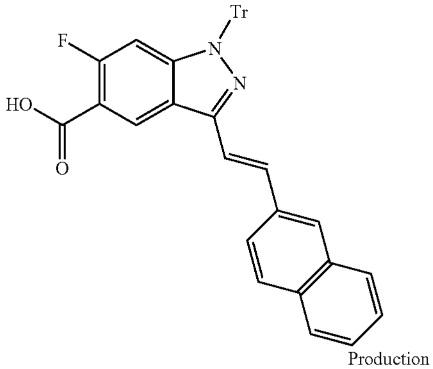
Production Example 168
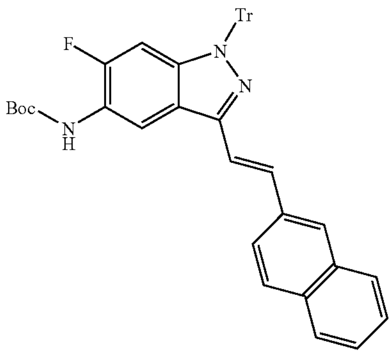
-continued
Example 169
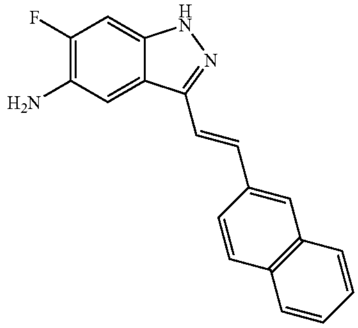
Example 171
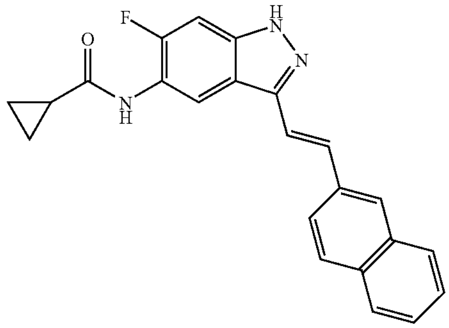
Example 172
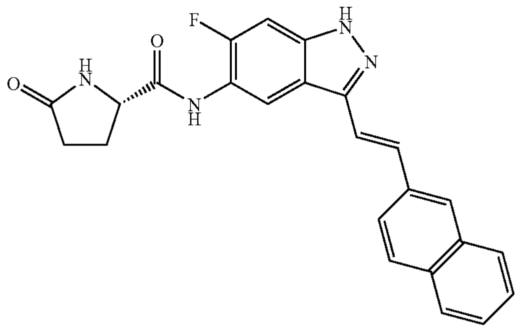
Example 173
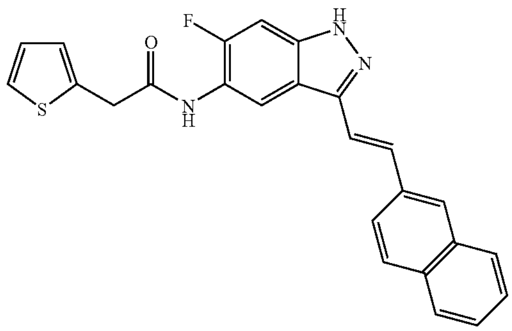

-continued
Production Example 174
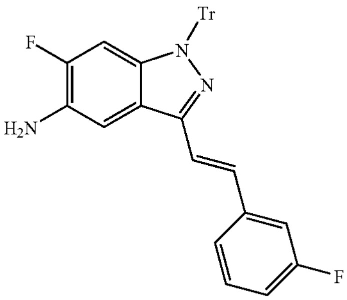
Example 175
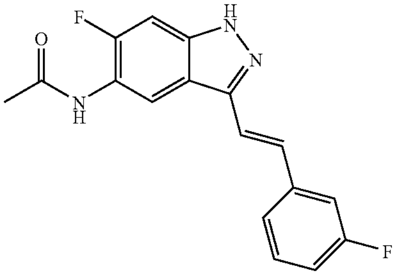
Production Example 176
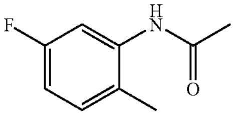
Production Example 177
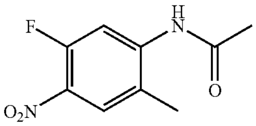
Production Example 178
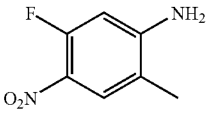
Production Example 179
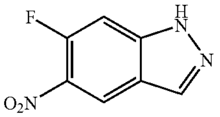
-continued
Production Example 180
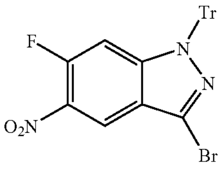
Production Example 181
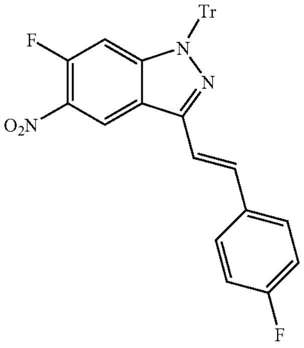
Production Example 182
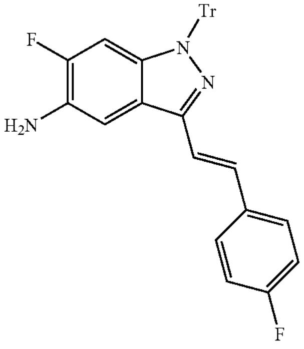
Example 184
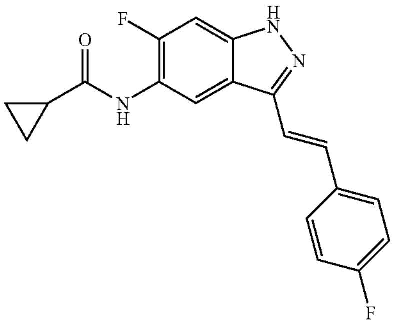

-continued
Example 185
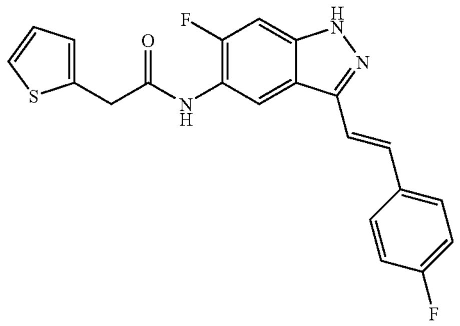
Example 186
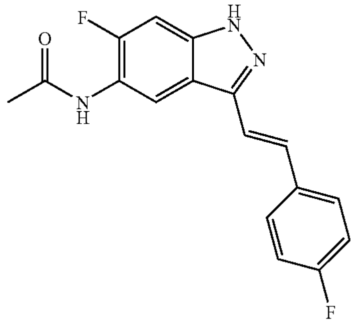
Example 187
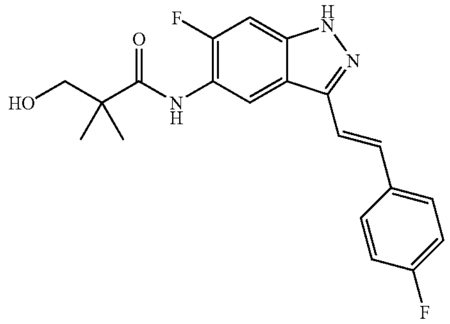
Example 188
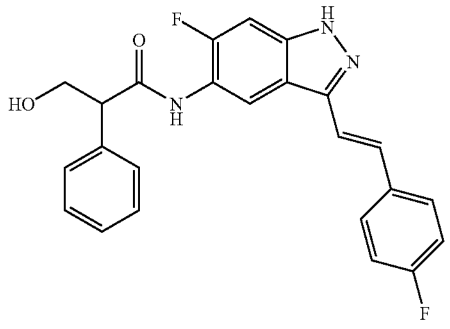
-continued
Example 189
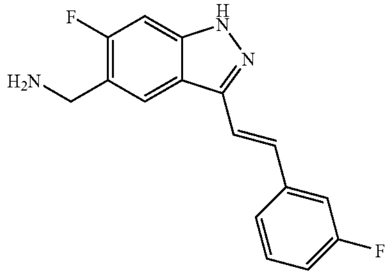
Example 190
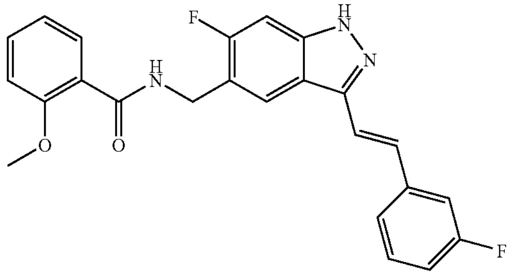
Production Example 191
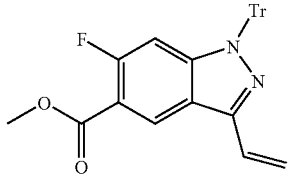
Production Example 192
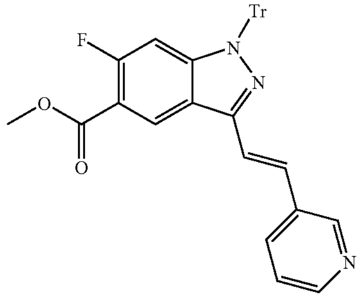

-continued
Example 193
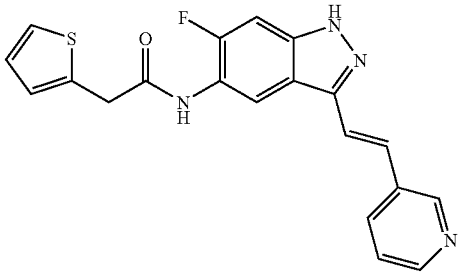
Example 194
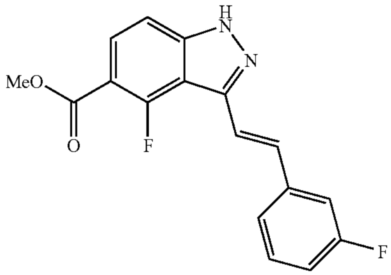
Example 195
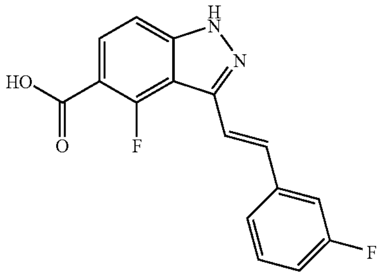
Example 197
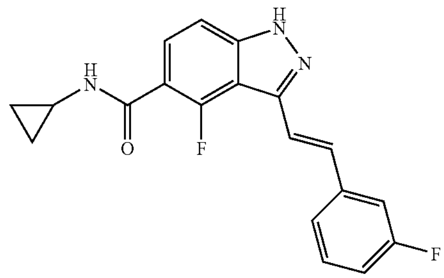
Example 198
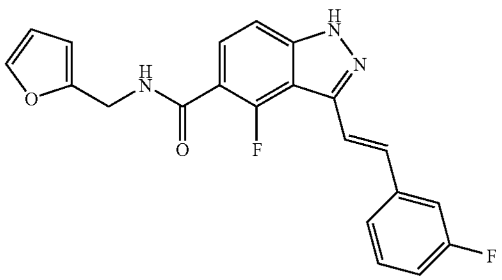
-continued
Example 199
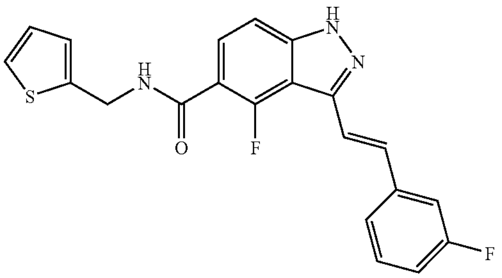
Example 200
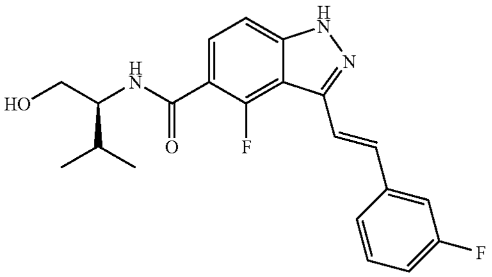
Example 201
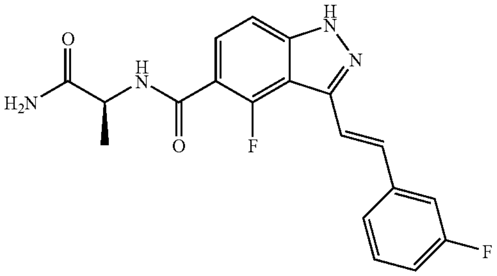
Example 202
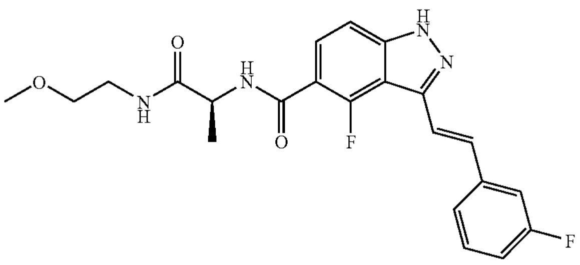

-continued
Production Example 203
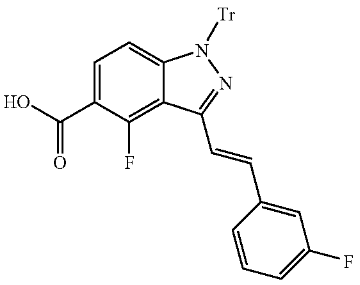
Production Example 204
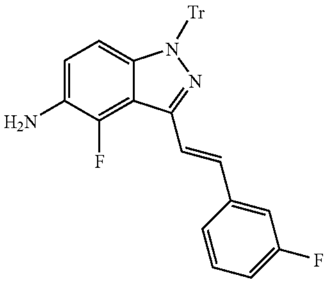
Example 205
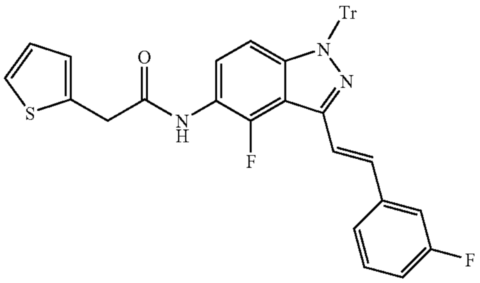
Production Example 206
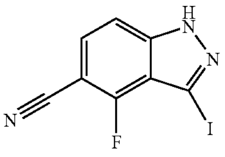
Production Example 207
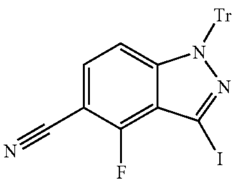
-continued
Example 208
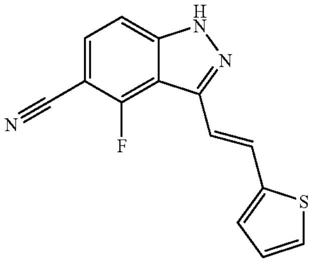
Example 209
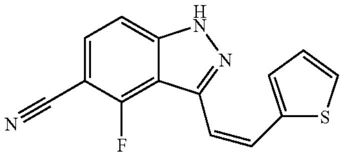
Example 210
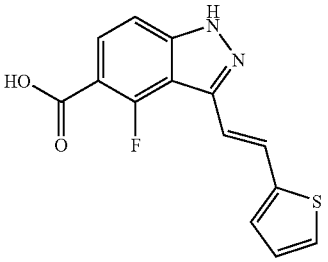
Example 212
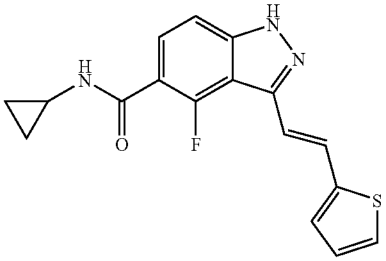
Example 213
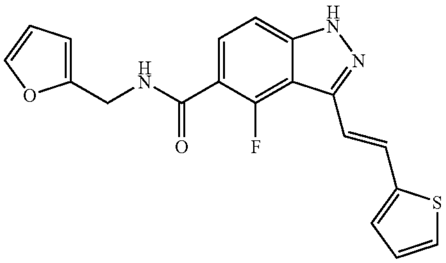
Example 214
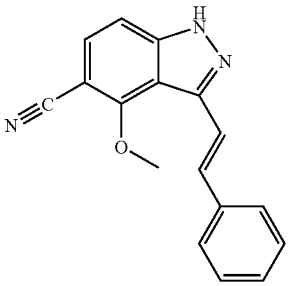

-continued
Example 215
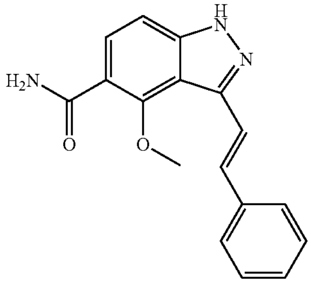
Example 216
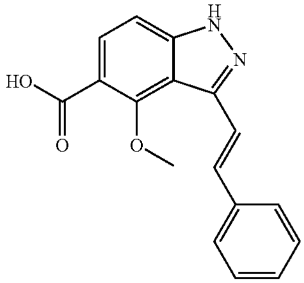
Example 218
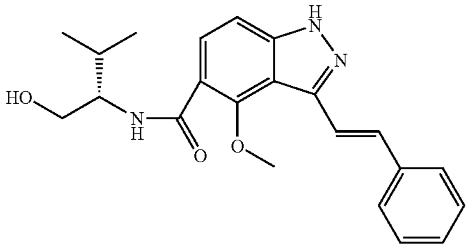
Example 219
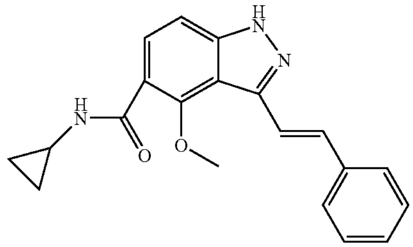
Example 220
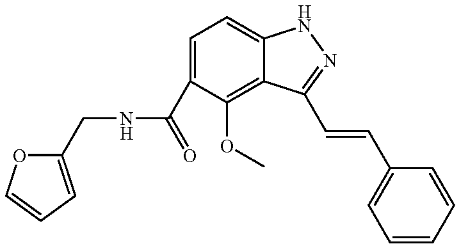
-continued
Example 221
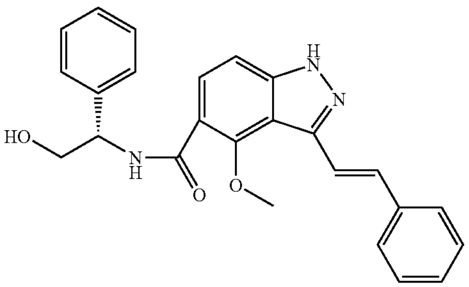
Example 222
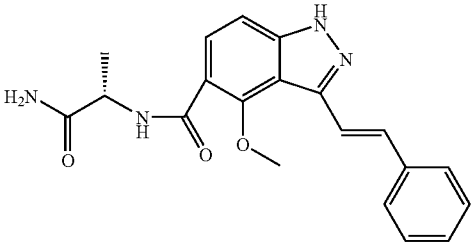
Example 223
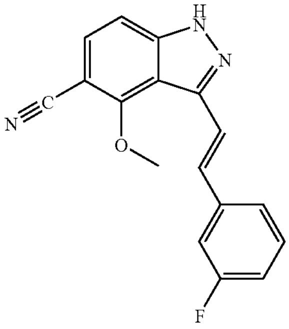
Example 224
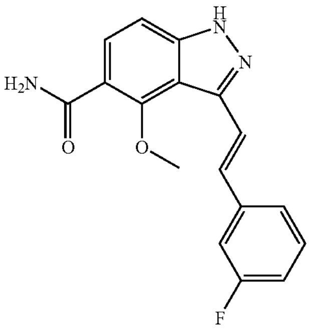

-continued
Example 225
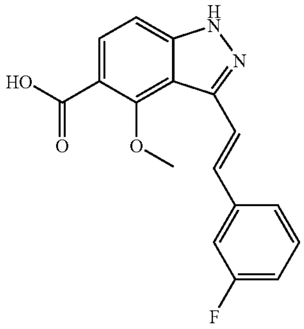
Example 227
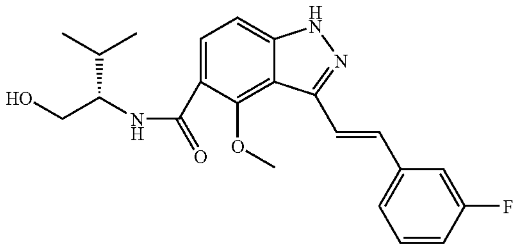
Example 228
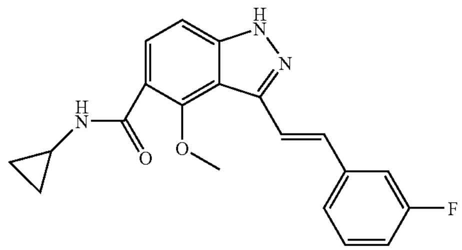
Example 229
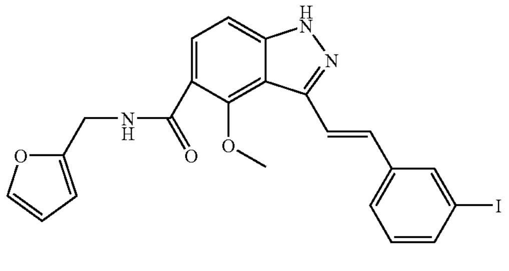
-continued
Example 230
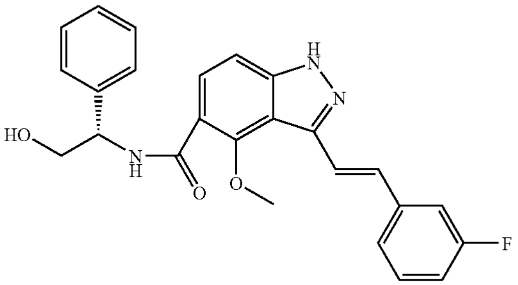
Example 231
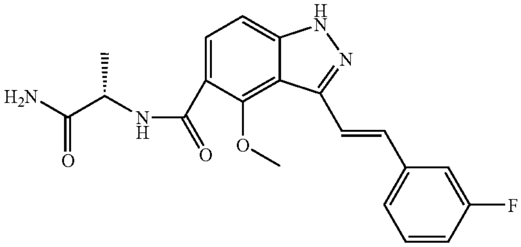
Example 232
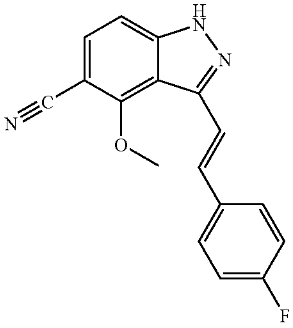
Example 233
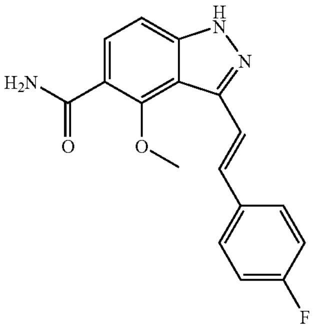
Example 234
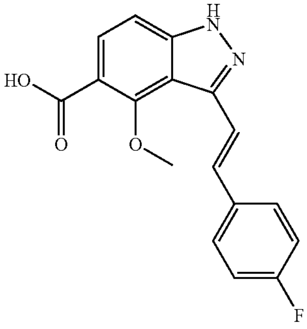

-continued
Example 236
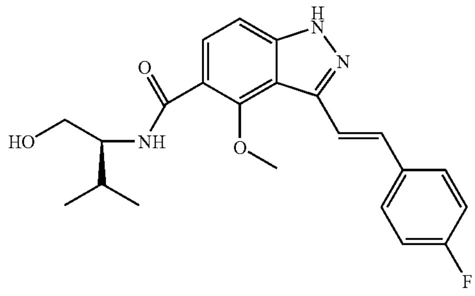
Example 237
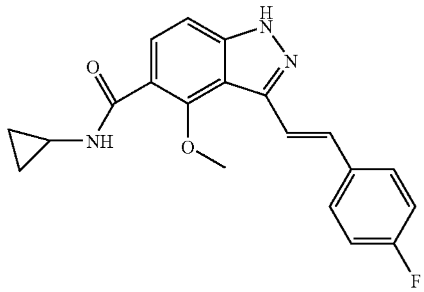
Example 238
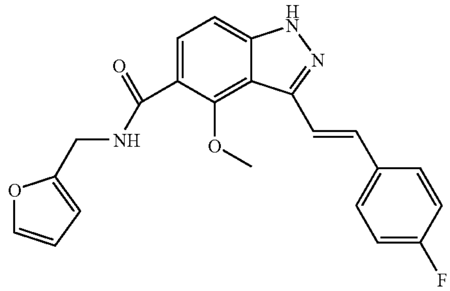
Example 239
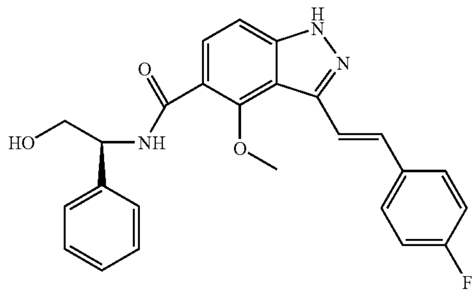
-continued
Example 240
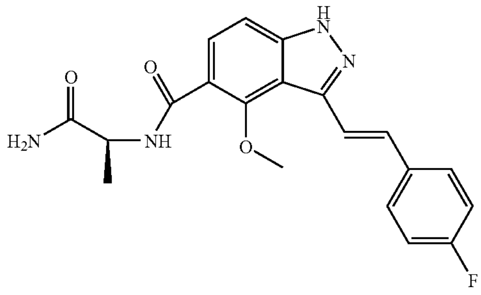
Example 241
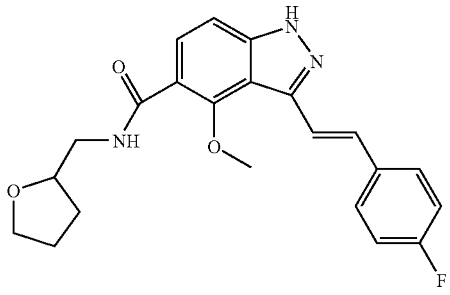
Example 242
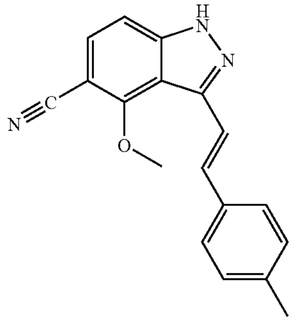
Example 243
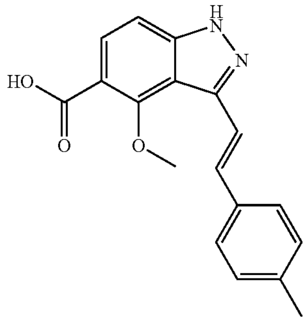

-continued
Example 245
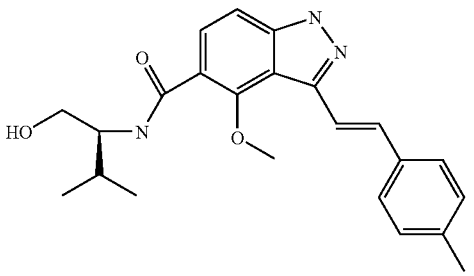
Example 246
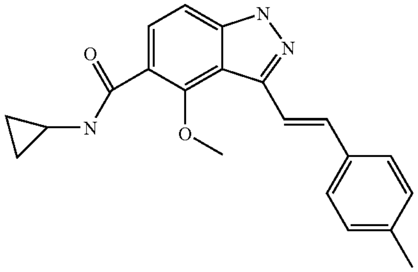
Example 247
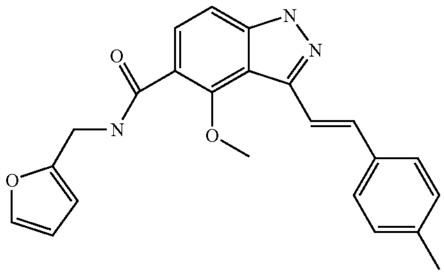
Example 248
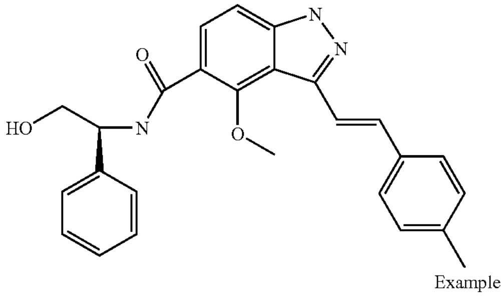
Example 249
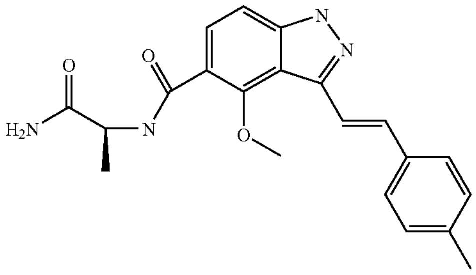
-continued
Example 250
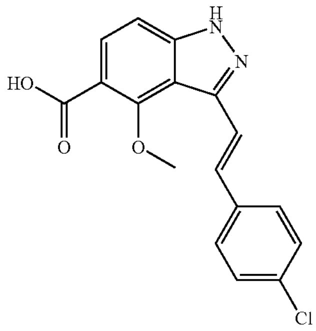
Example 252
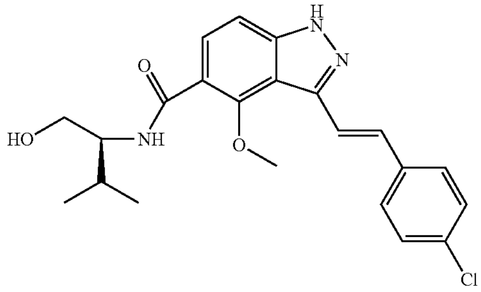
Example 253
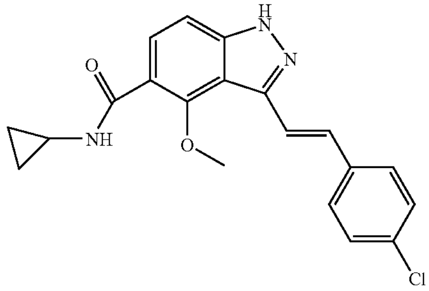
Example 254
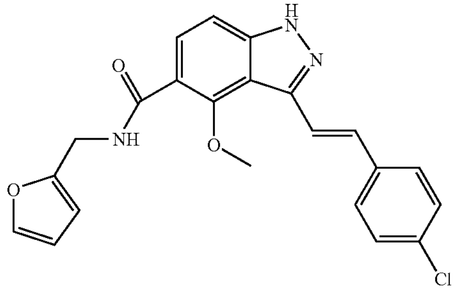

-continued
Example 255
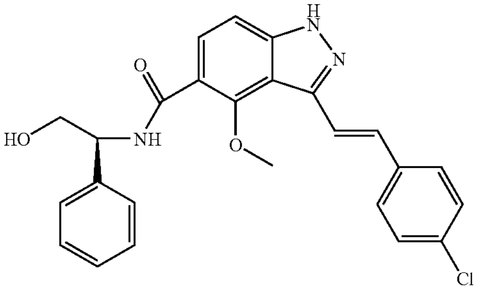
Example 256
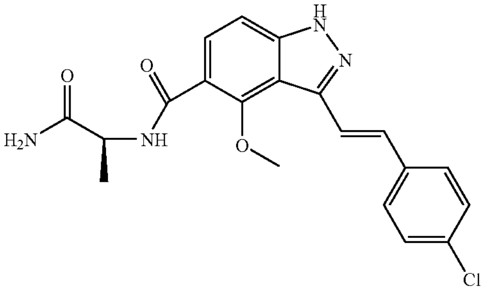
Example 257
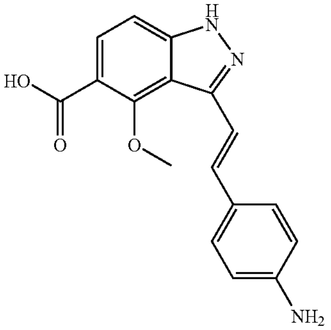
Example 259
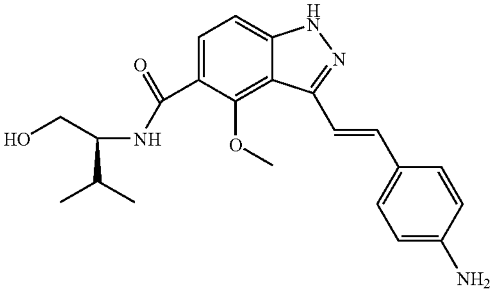
Example 260
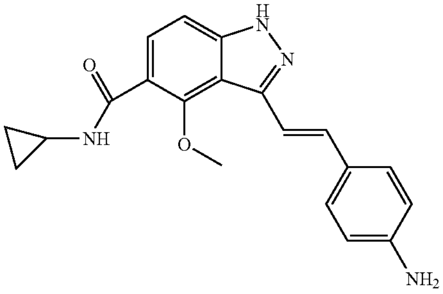
-continued
Example 261
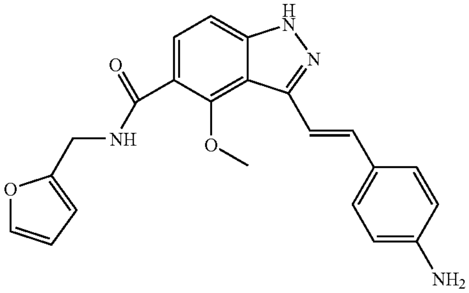
Example 262
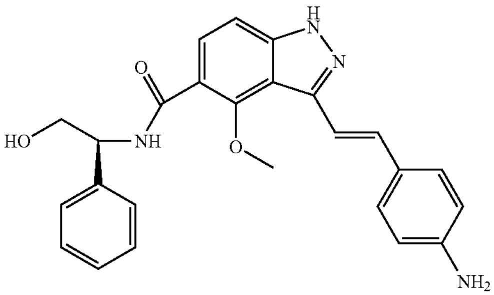
Example 263
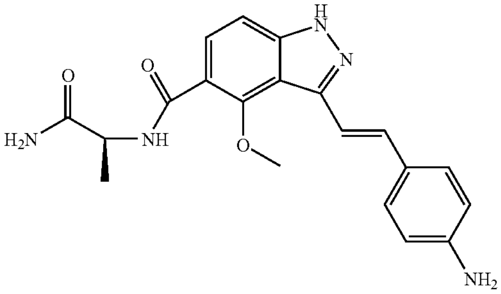
Example 264
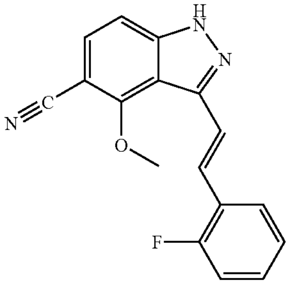
Example 265
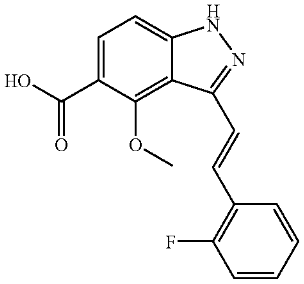

-continued
Example 267
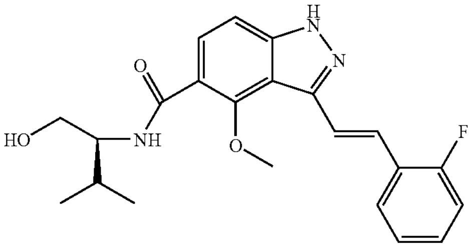
Example 268
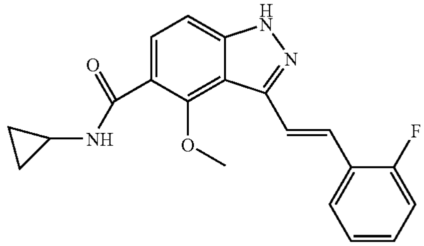
Example 269
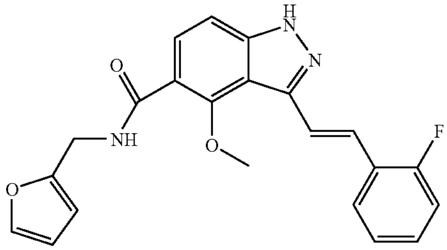
Example 270
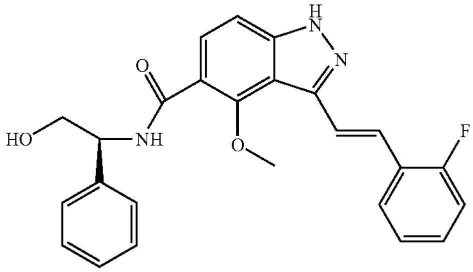
Example 271
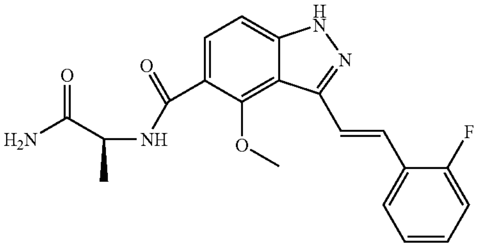
-continued
Production Example 272
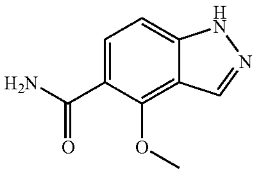
Production Example 273
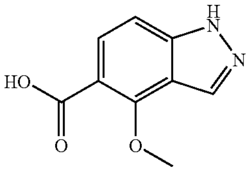
Production Example 274
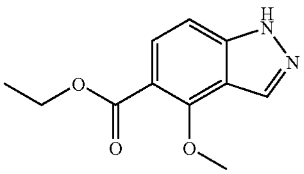
Production Example 275
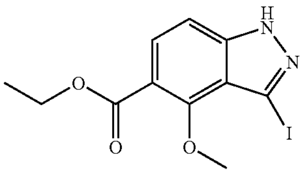
Production Example 276
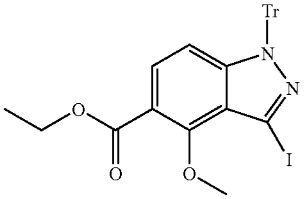
Production Example 277
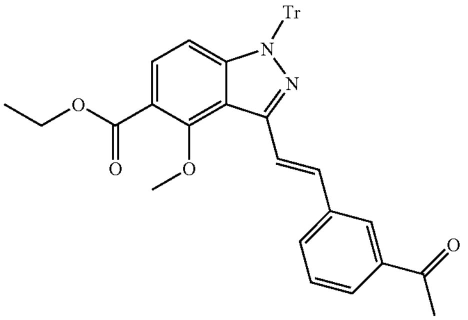

-continued
Example 278
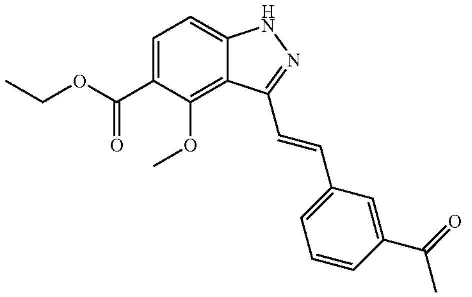
Example 279
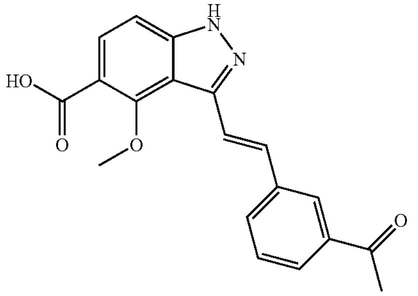
Example 281
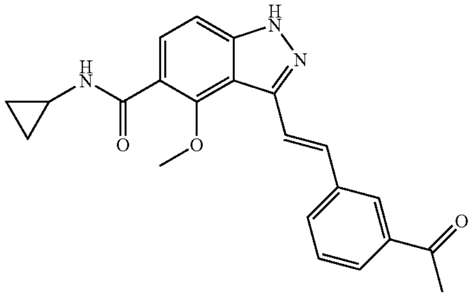
Example 282
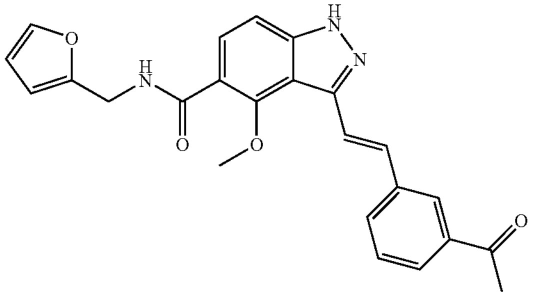
-continued
Example 283
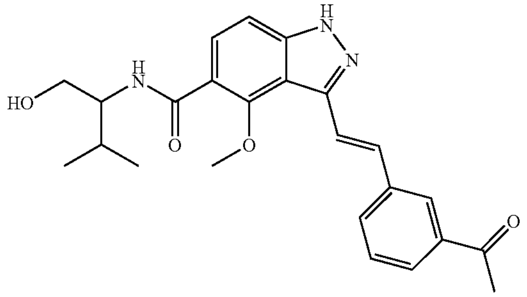
Example 284
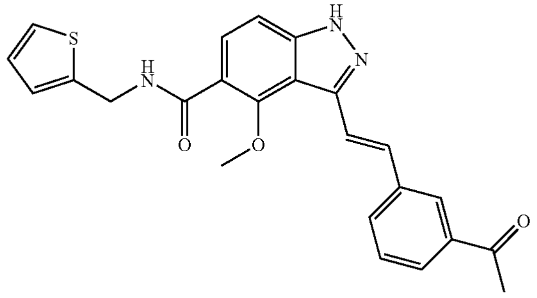
Example 285
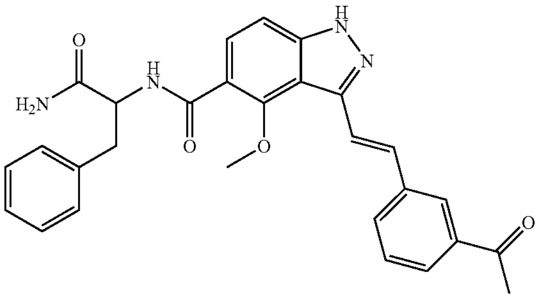
Example 286
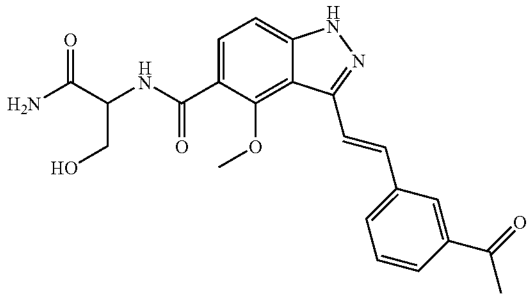

-continued
Example 287
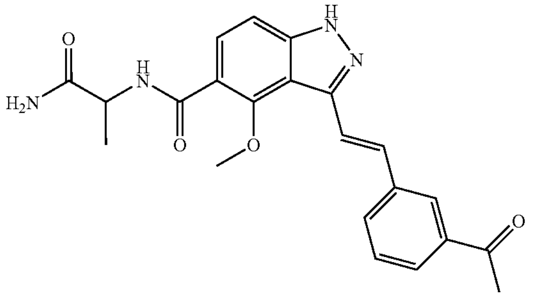
Production Example 288
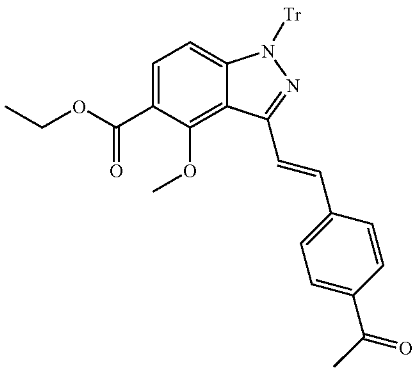
Example 289
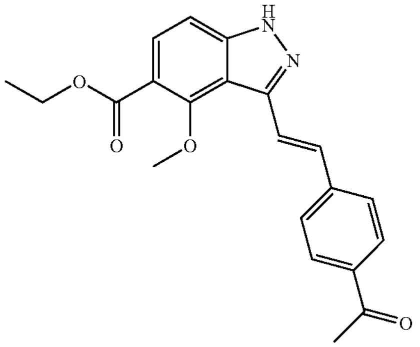
-continued
Example 290
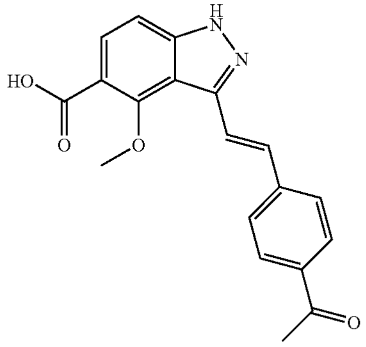
Example 292
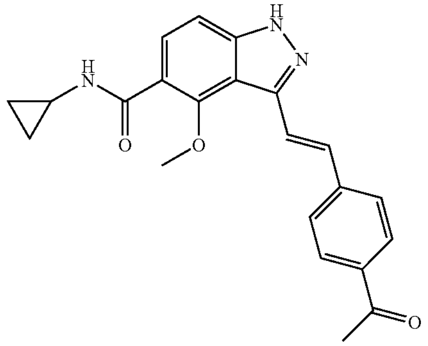
Example 293
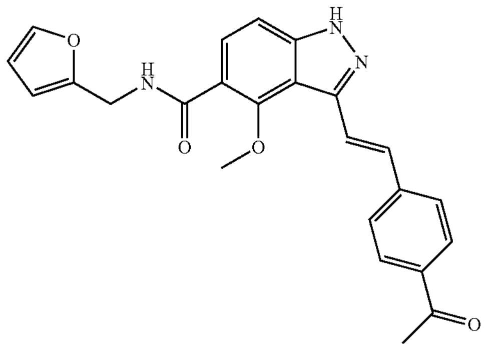
Example 294
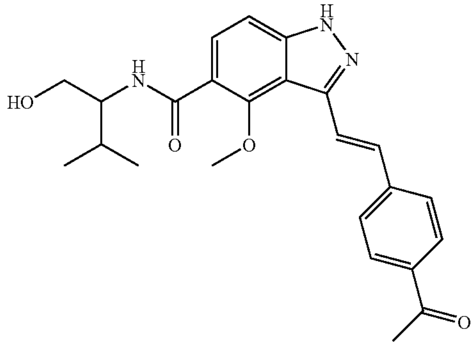

-continued
Example 295
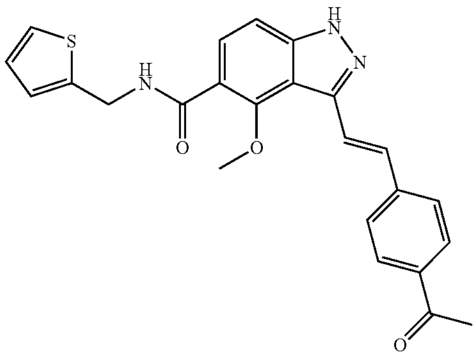
Example 296
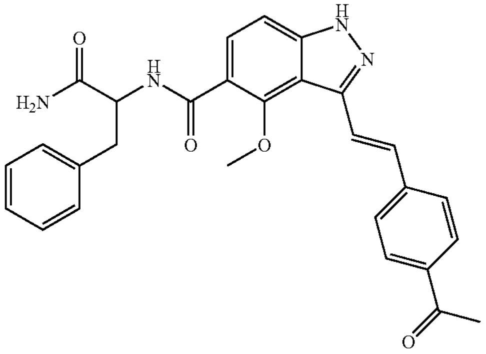
Example 297
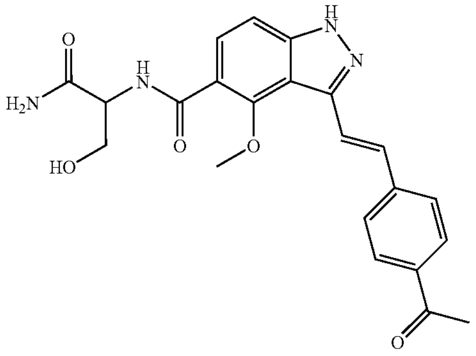
Example 298
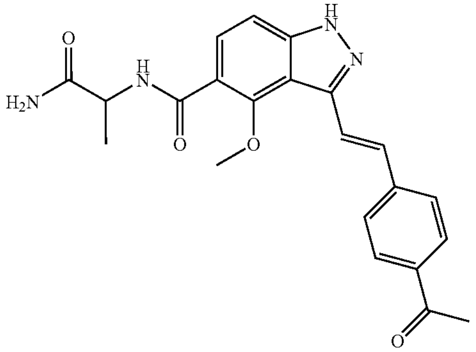
-continued
Production Example 299
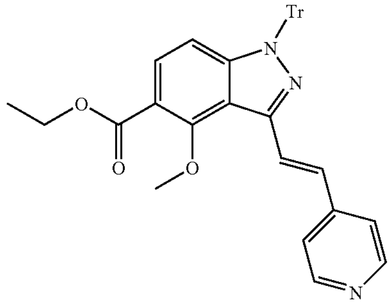
Example 300
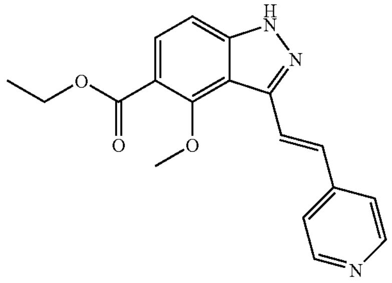
Example 301
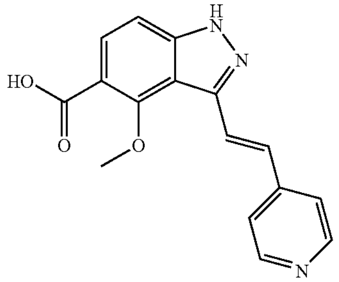
Example 303
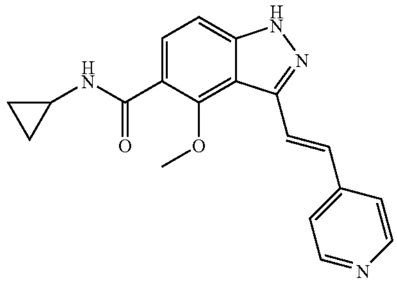
Example 304
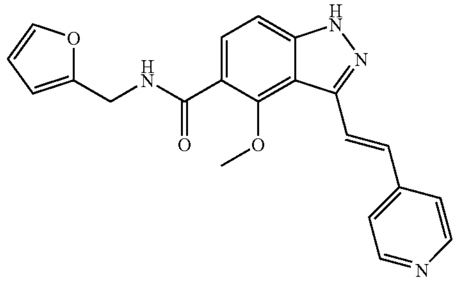

-continued
Example 305
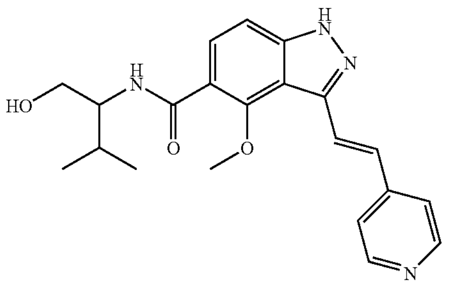
Example 306
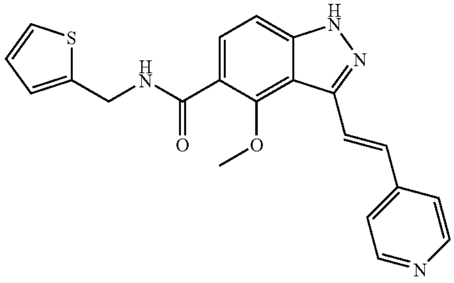
Example 307
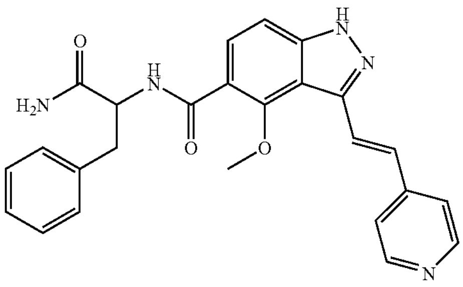
Example 308
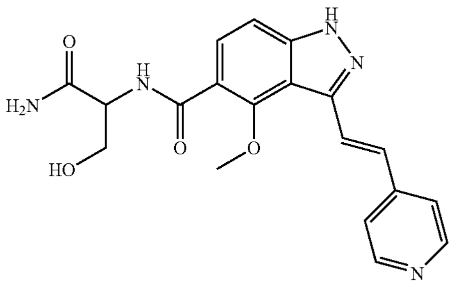
Example 309
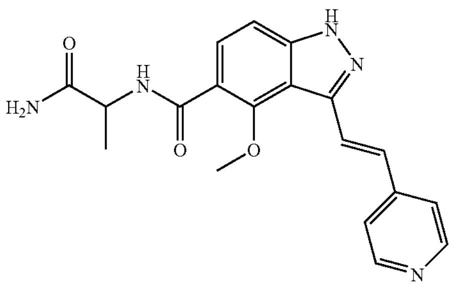
-continued
Production Example 310
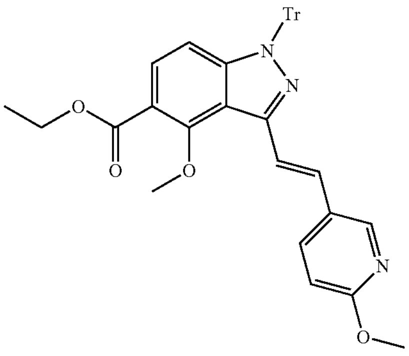
Example 311
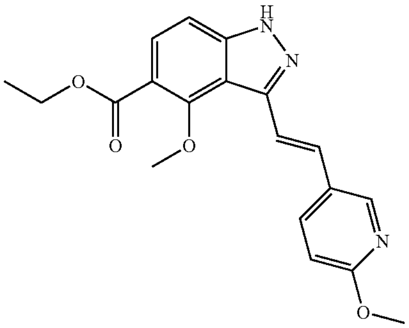
Example 312
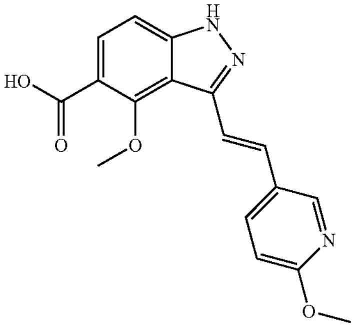
Example 314
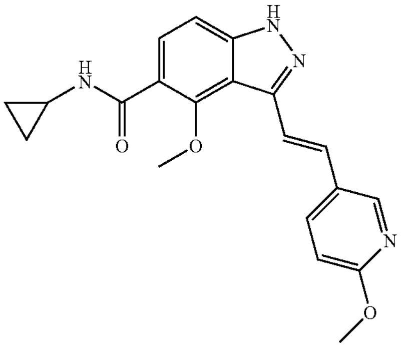

-continued
Example 315
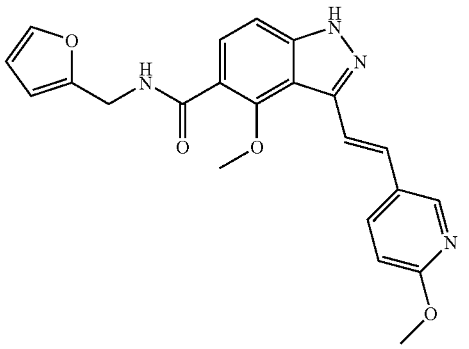
Example 316
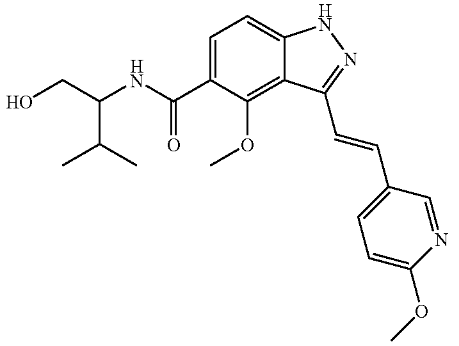
Example 317
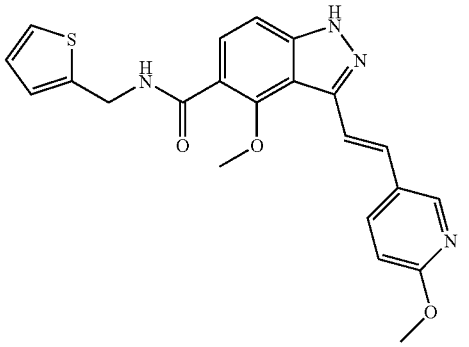
Example 318
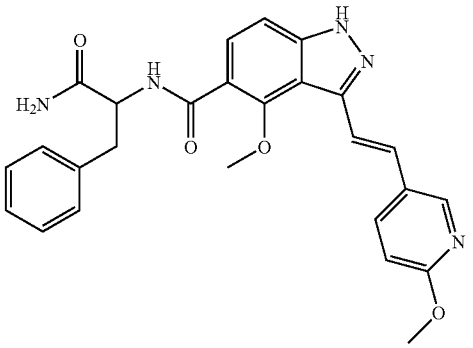
-continued
Example 319
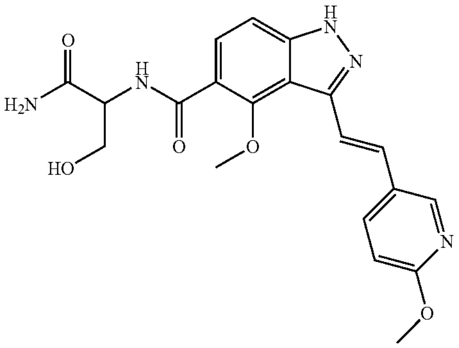
Example 320
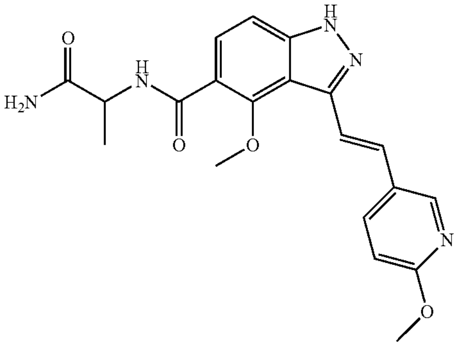
Production Example 321
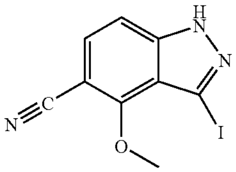
Production Example 322
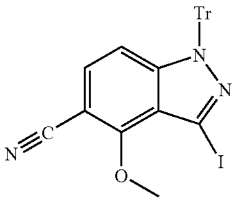
Production Example 323
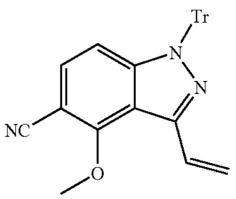

-continued
Production Example 324
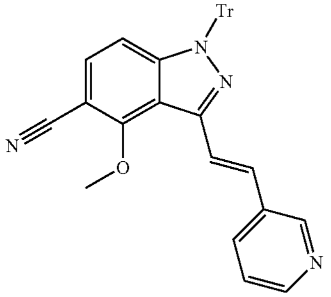
Example 325
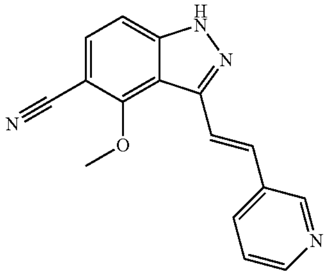
Example 326
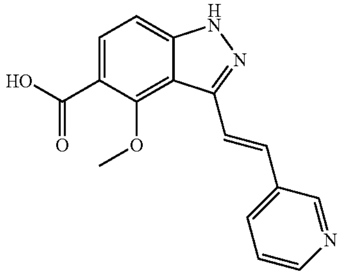
Example 328
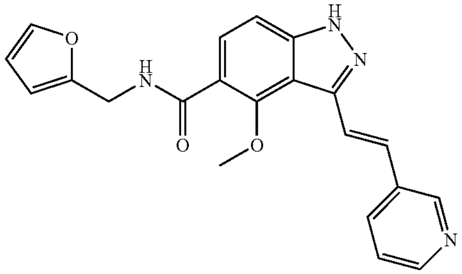
Example 329
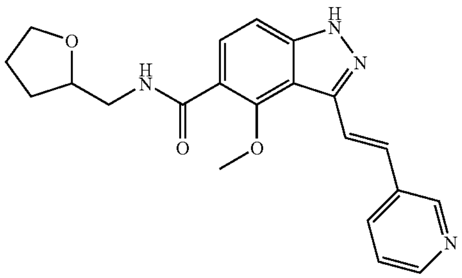
-continued
Example 330
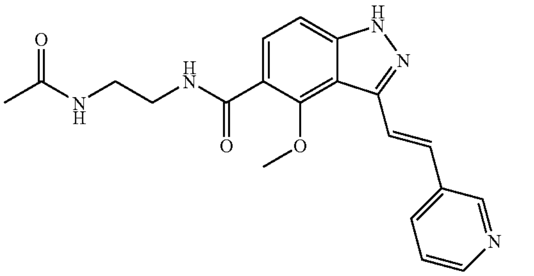
Example 331
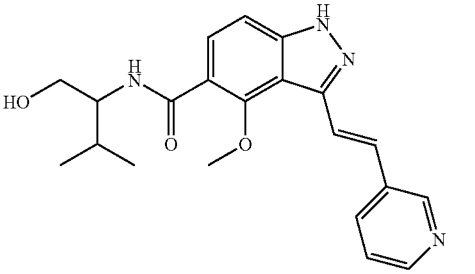
Example 332
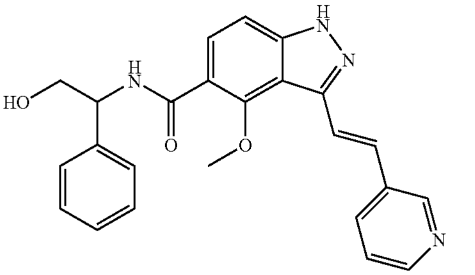
Example 333
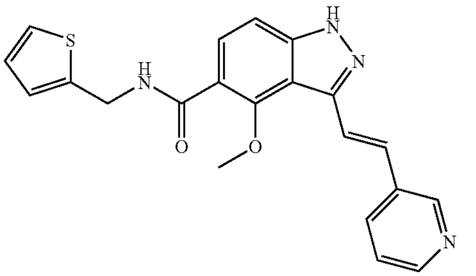

-continued
Example 334
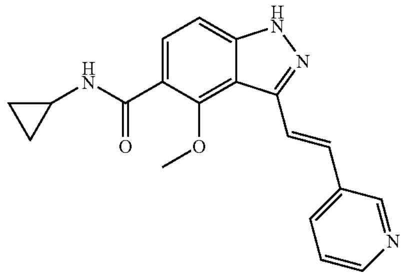
Example 335
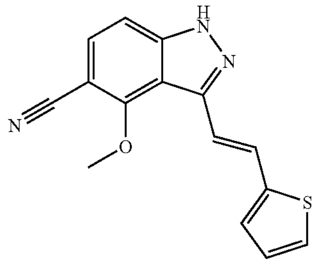
Example 336
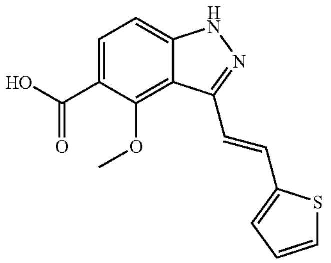
Example 338
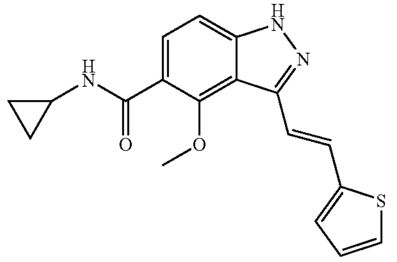
Example 339
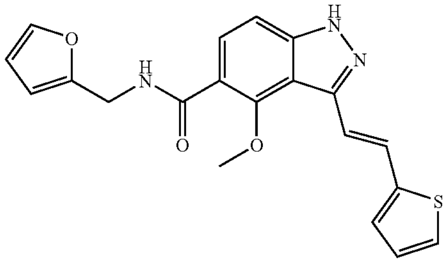
-continued
Example 340
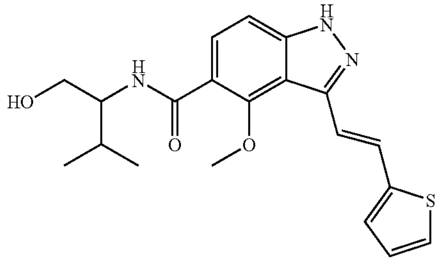
Example 341
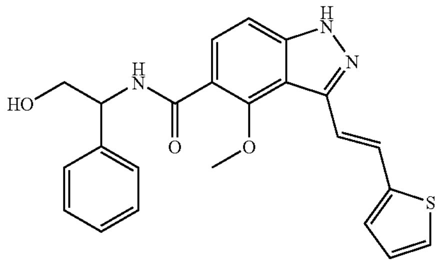
Example 342
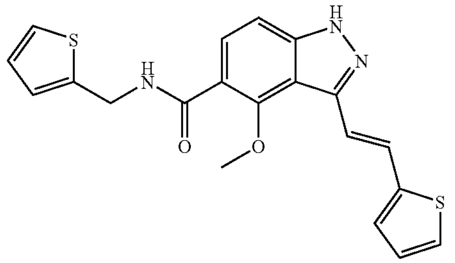
Example 343
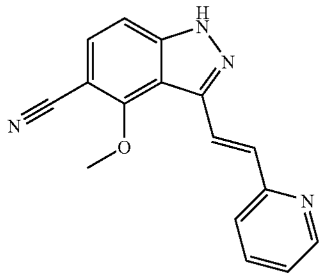

-continued
Example 344
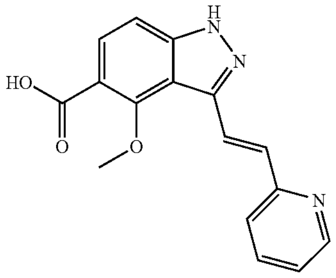
Example 345
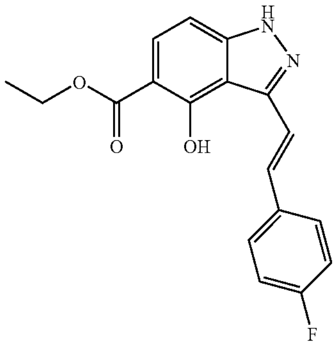
Production Example 346
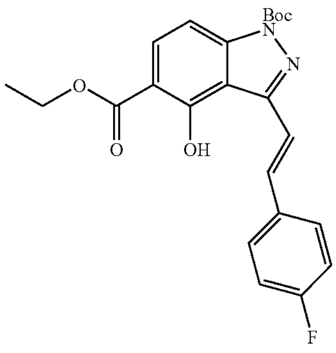
-continued
Production Example 347
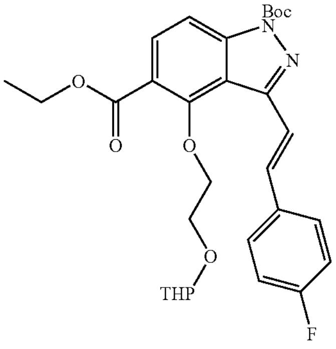
Production Example 348
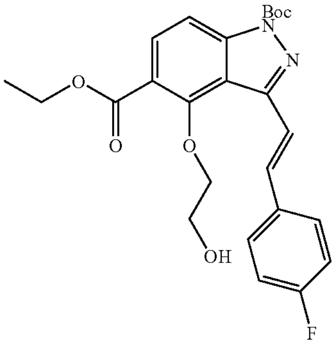
Example 349
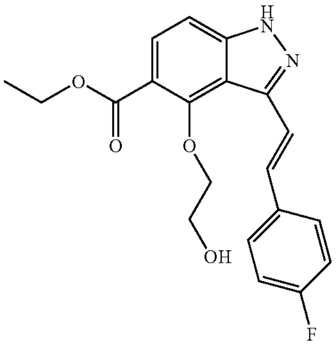
Example 350
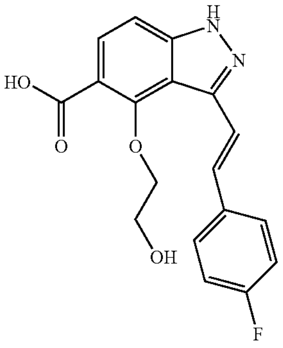

-continued
Example 352
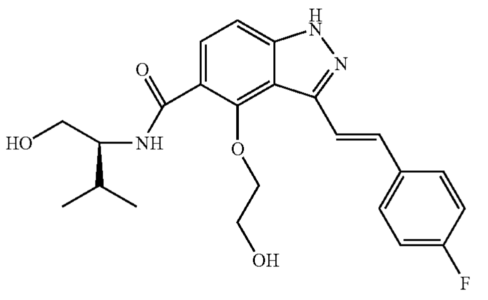
Example 353
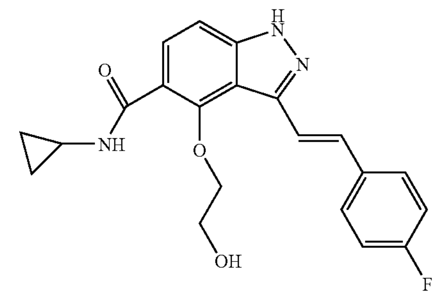
Example 354
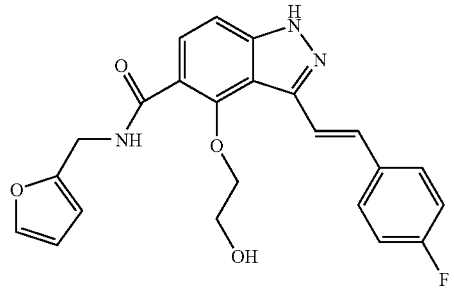
Example 355
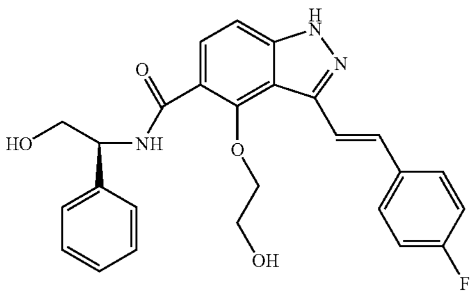
Example 356
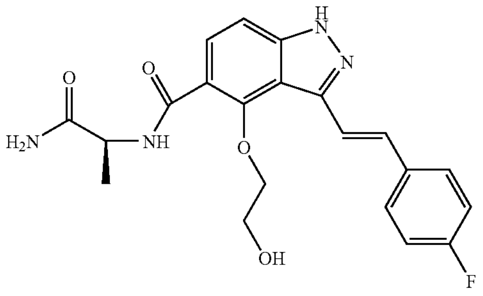
-continued
Example 357
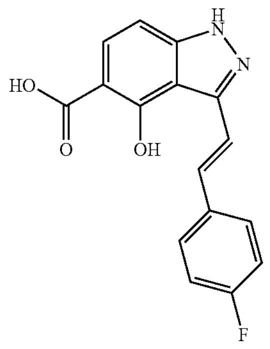
Example 359
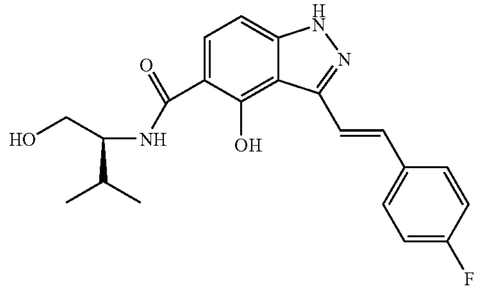
Example 360
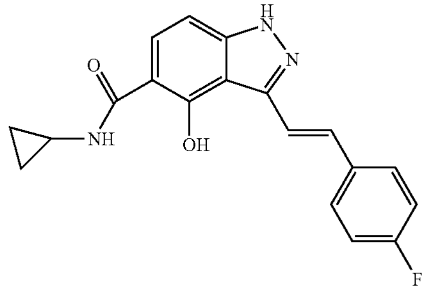
Example 361
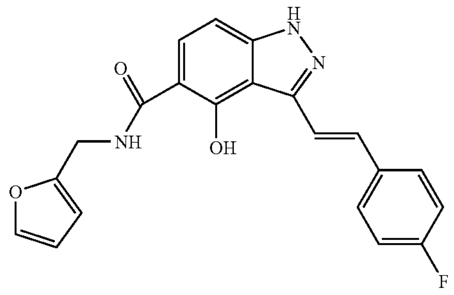

-continued
Example 362
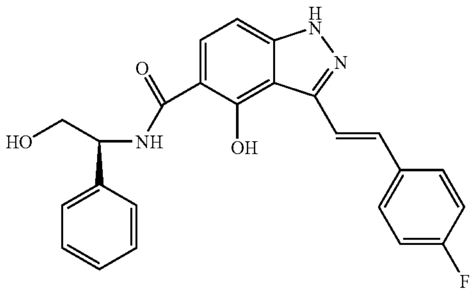
Example 363
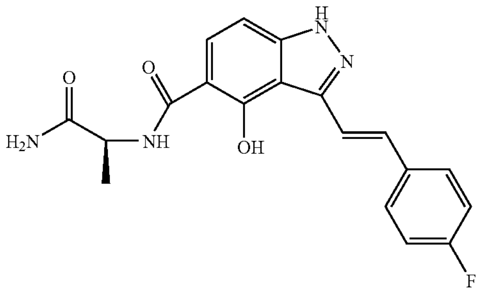
Production Example 364
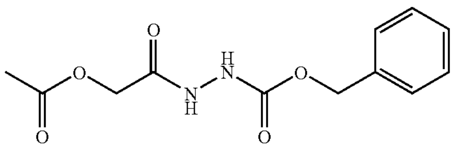
Production Example 365
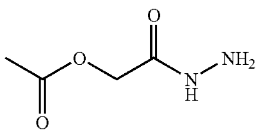
Production Example 366
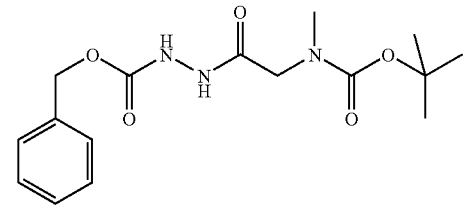
-continued
Production Example 367
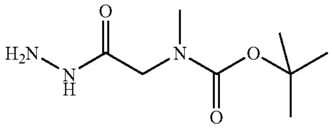
Production Example 368
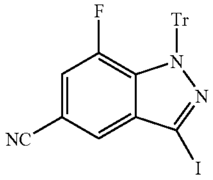
Example 369
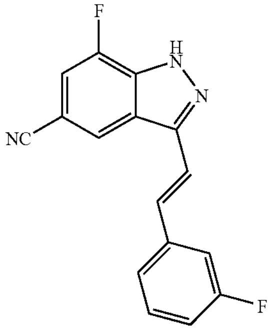
Example 370
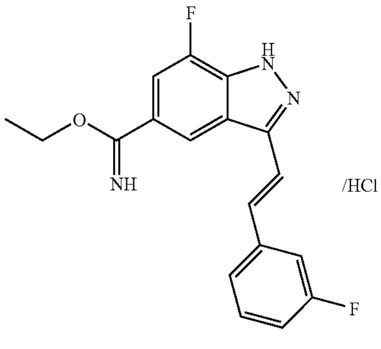
/HCl
Example 372
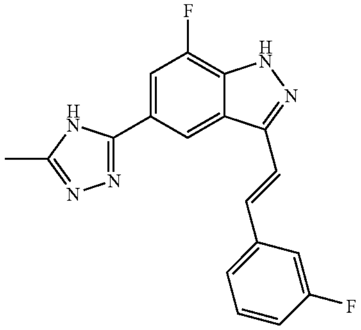

-continued
Example 373
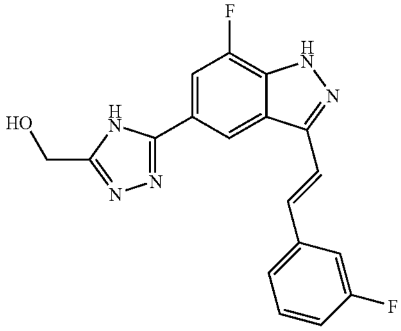
Example 374
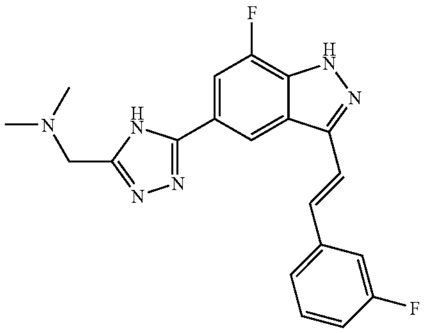
Example 375
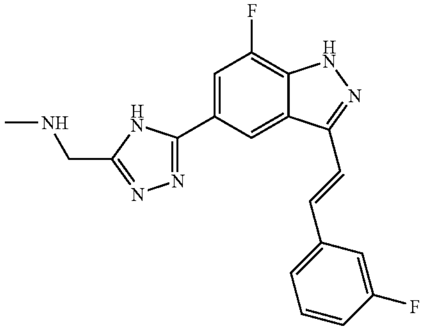
Example 376
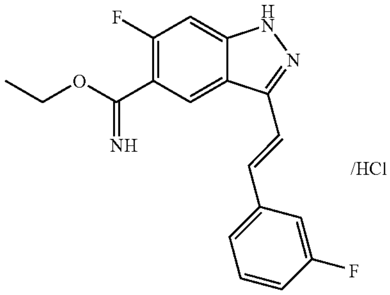
/HCl
-continued
Example 378
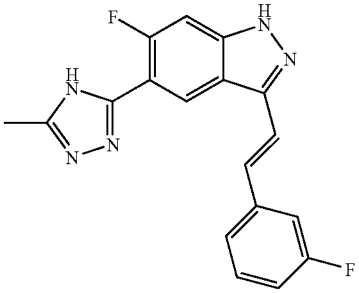
Example 379
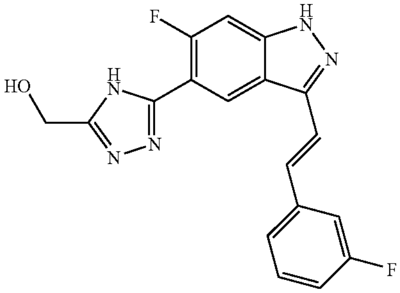
Example 380
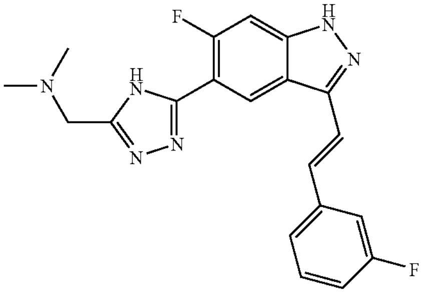
Example 381
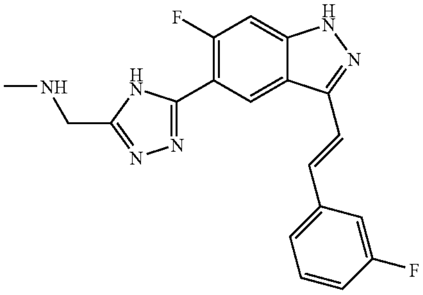

-continued
Example 382
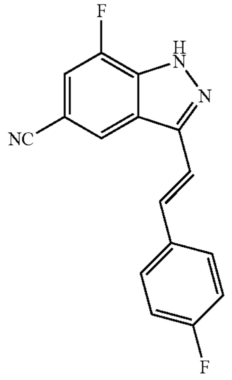
Example 383
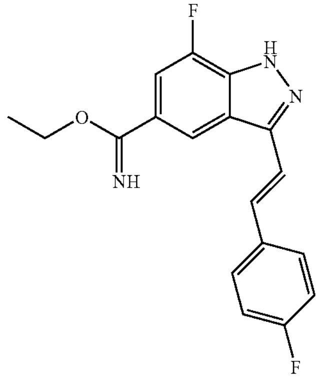
/HCl
Example 385
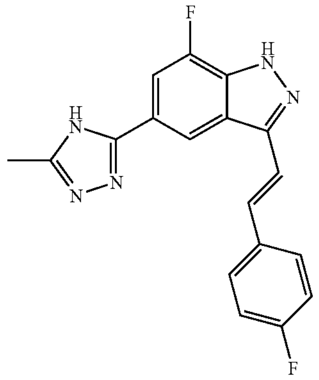
Example 386
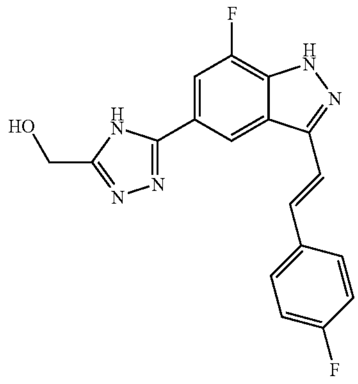
-continued
Example 387
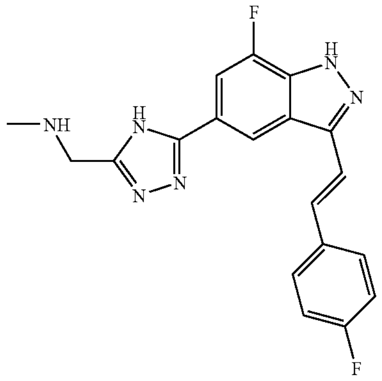
Production Example 388
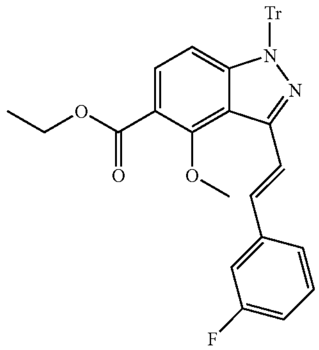
Production Example 389
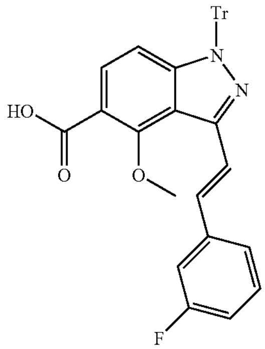
Production Example 390
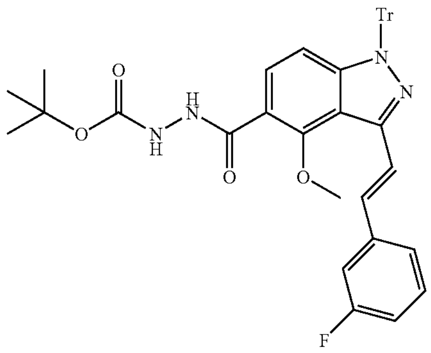

-continued
Example 391
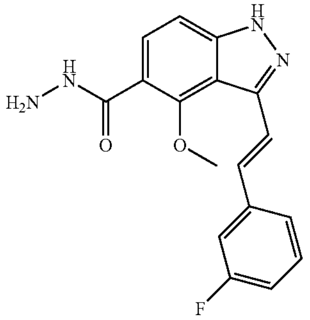
Example 392
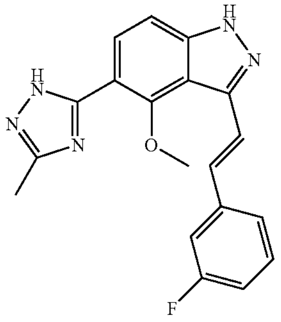
Production Example 393
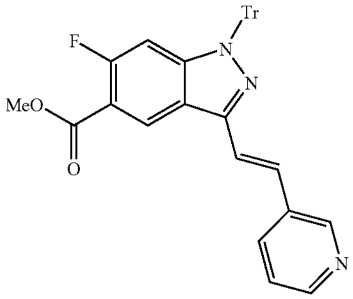
Production Example 394
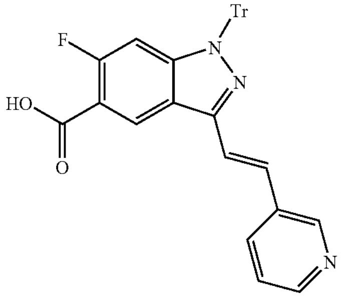
-continued
Production Example 395
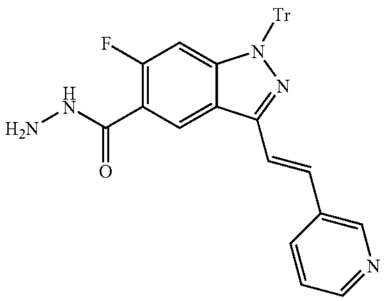
Production Example 396
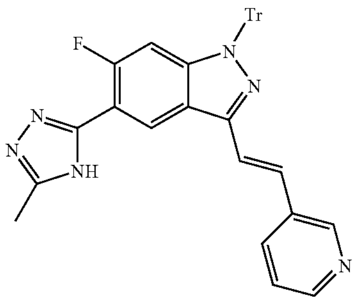
Example 397
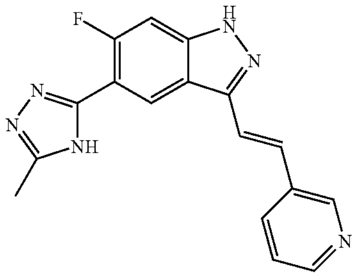
Example 398
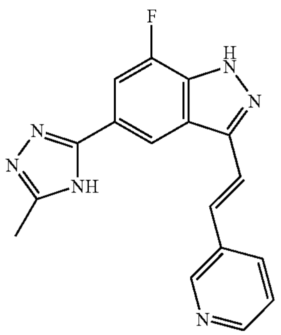

-continued
Example 399
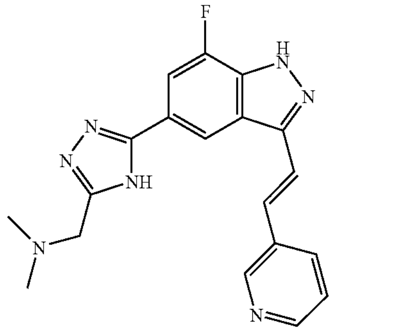
Example 400
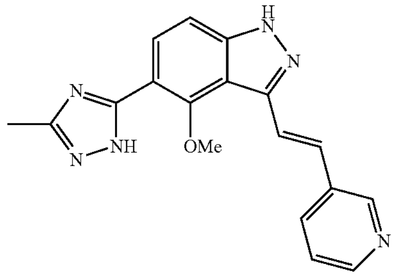
Example 401
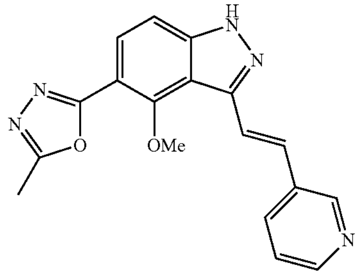
Example 402
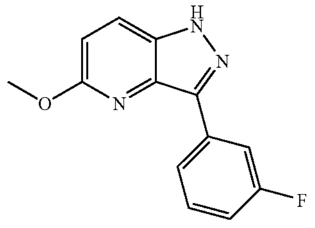
Example 403
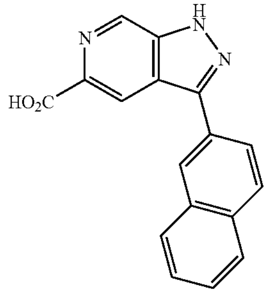
-continued
Production Example 404
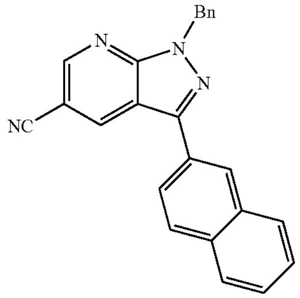
Example 405
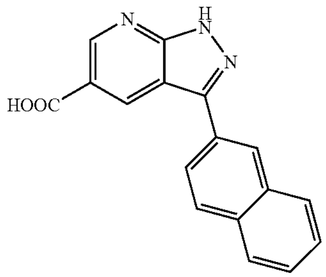
Example 406
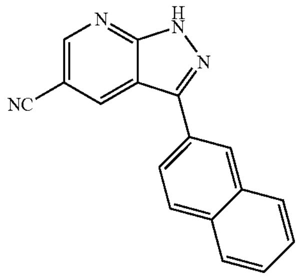
Production Example 407
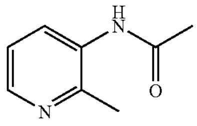
Production Example 408
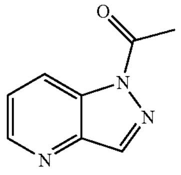
Production Example 409
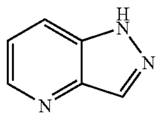
Production Example 410
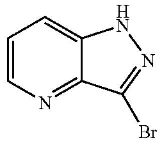

-continued
Production Example 411
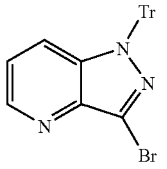
Production Example 412
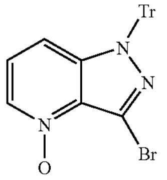
Production Example 413
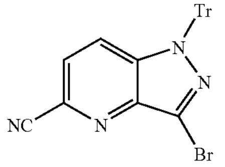
Production Example 414
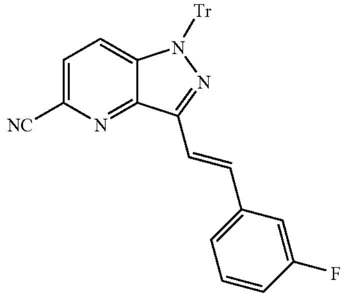
Example 415
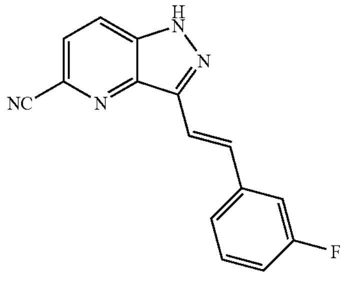
-continued
Example 416
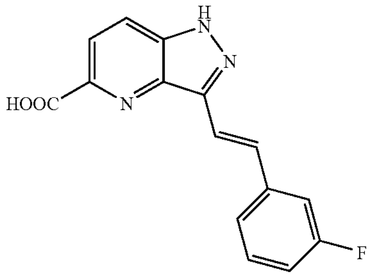
Production Example 417
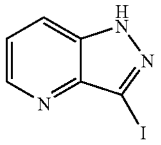
Production Example 418
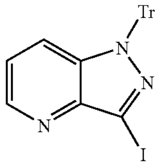
Production Example 419
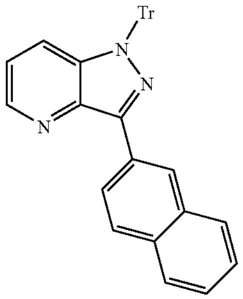
Example 420
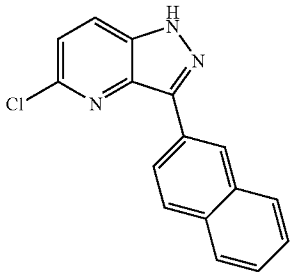
Production Example 421
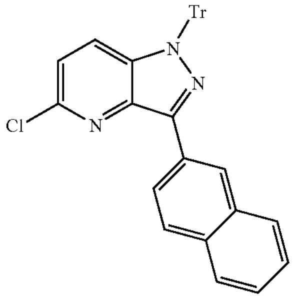

-continued
Production Example 422
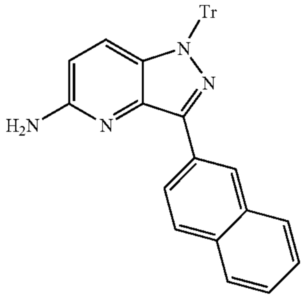
Production Example 423
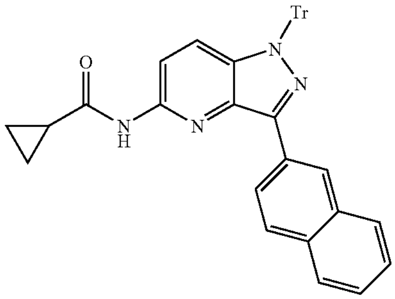
Example 424
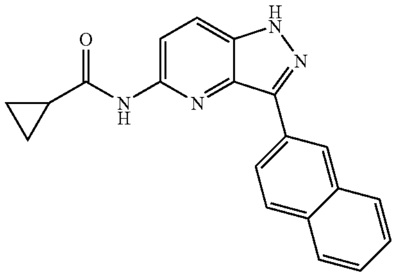
Production Example 425
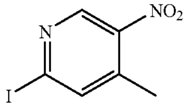
Production Example 426
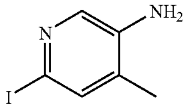
Production Example 427
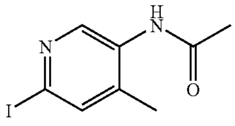
Production Example 428
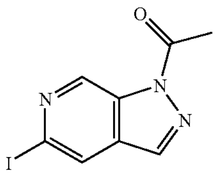
-continued
Production Example 429
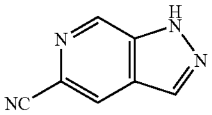
Production Example 430
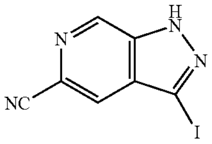
Production Example 431
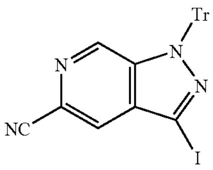
Production Example 432
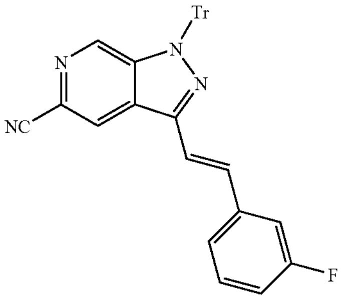
Example 433
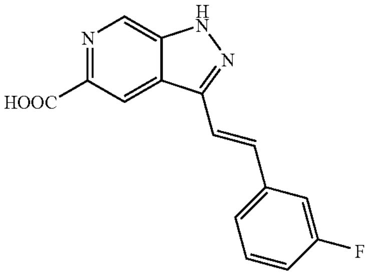
Production Example 434
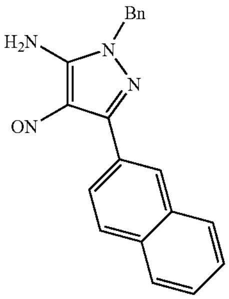

-continued
Production Example 435
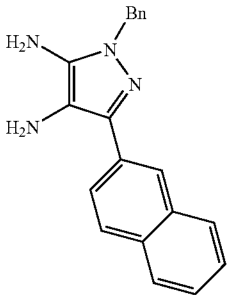
Production Example 436
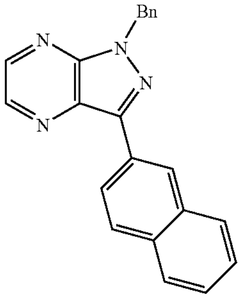
Example 437
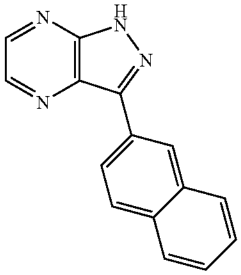
Production Example 438
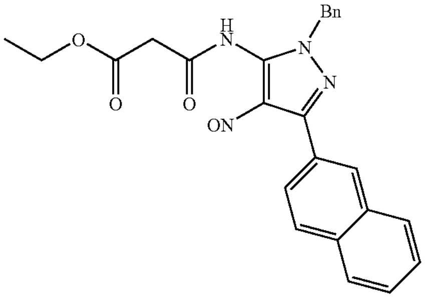
-continued
Production Example 439
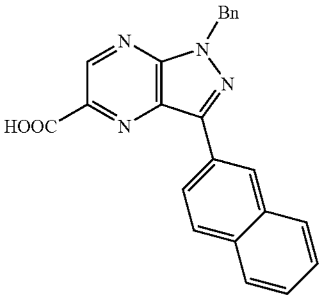
Production Example 440
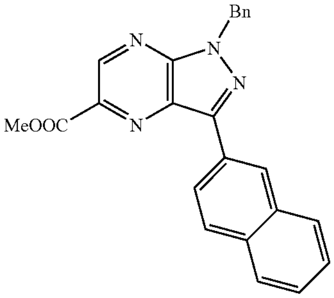
Example 441
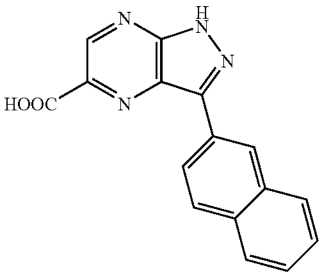
Example 443
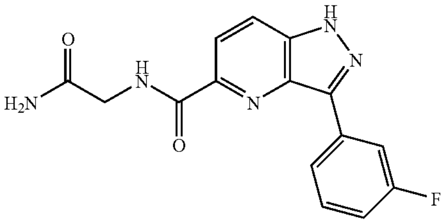
Example 444
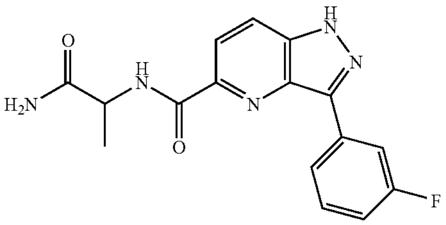
Example 445
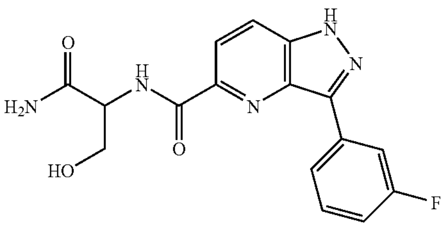

-continued
Example 446
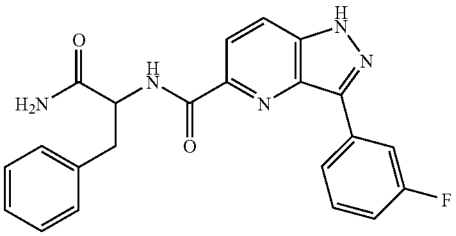
Example 448
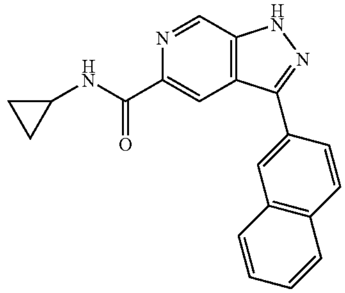
Example 449
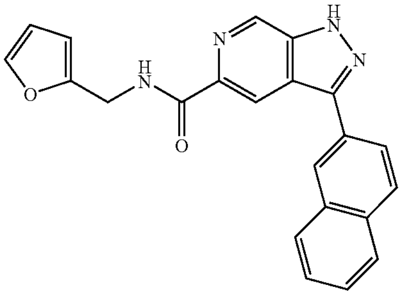
Example 450
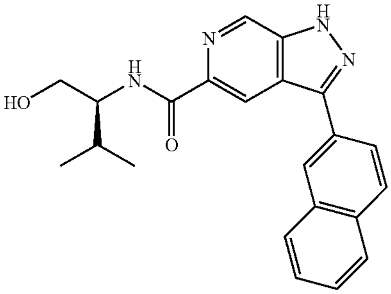
-continued
Example 451
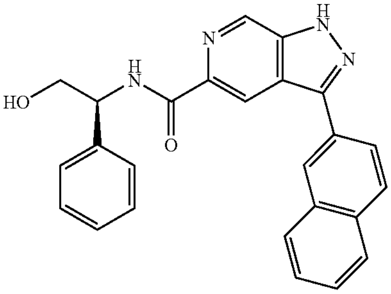
Example 453
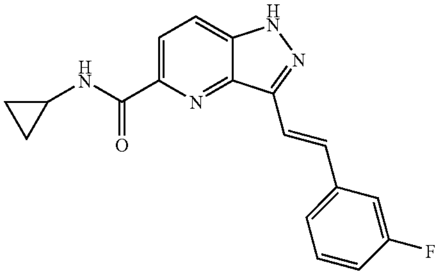
Example 454
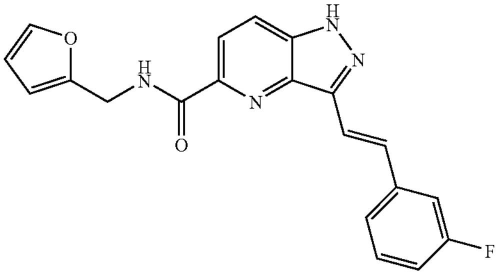
Example 455
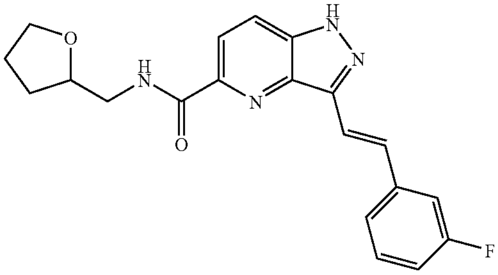
Example 456
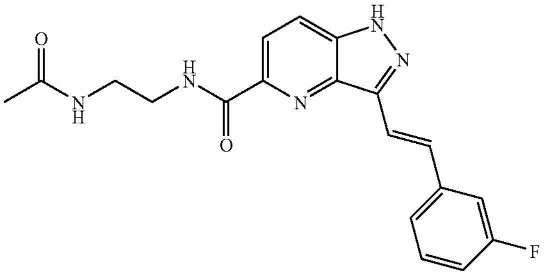

-continued
Example 457
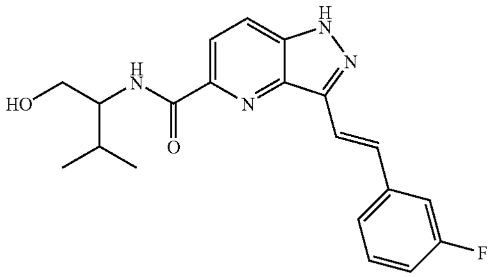
Example 458
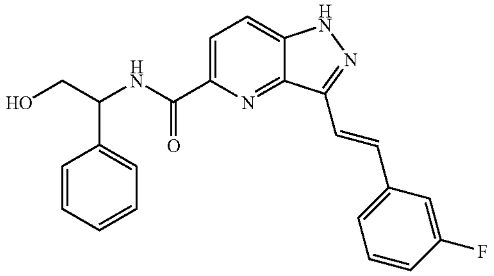
Example 459
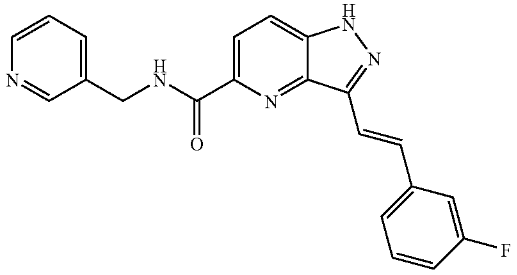
Example 460
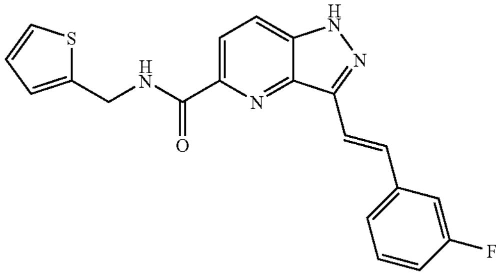
-continued
Example 461
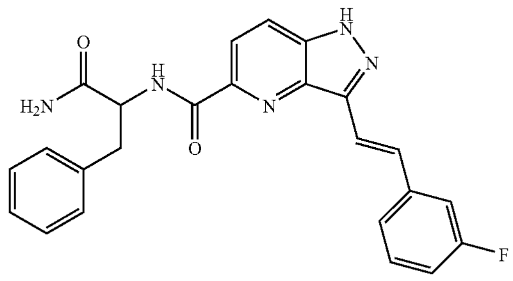
Example 462
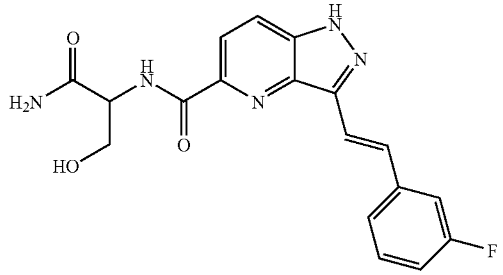
Example 463
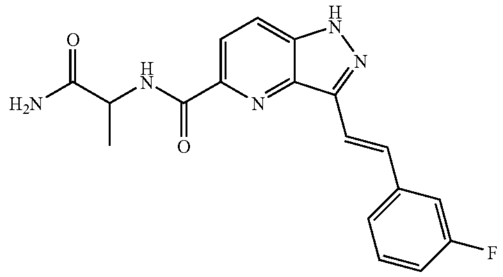
Example 465
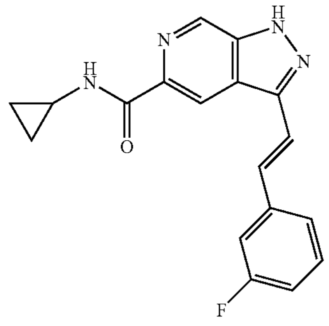
Example 466
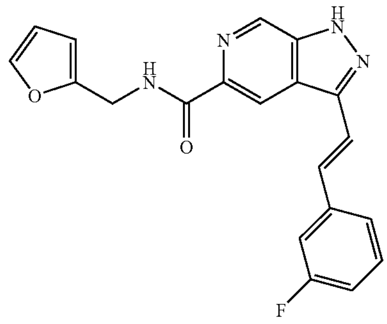

-continued
Example 467
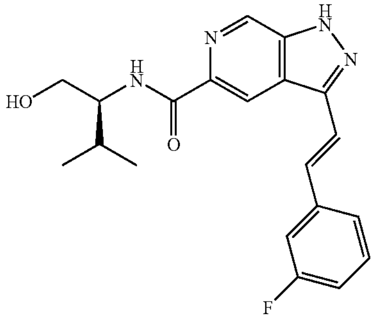
Example 468
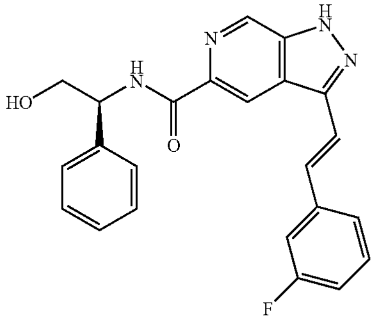
Example 469
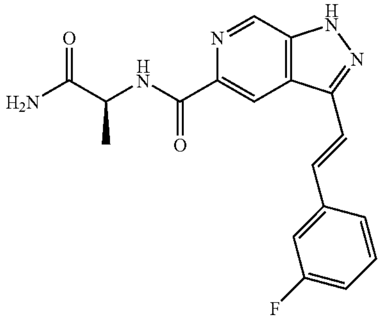
Example 471
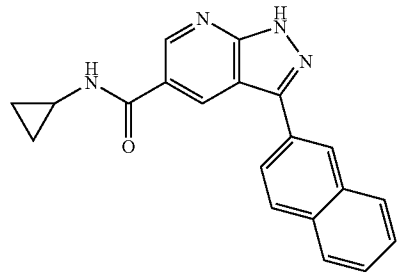
Example 472
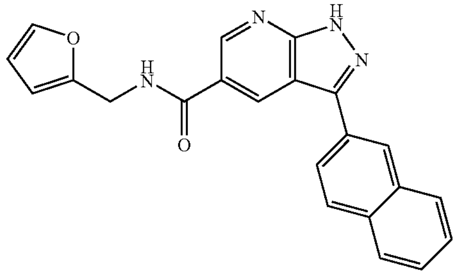
-continued
Example 473
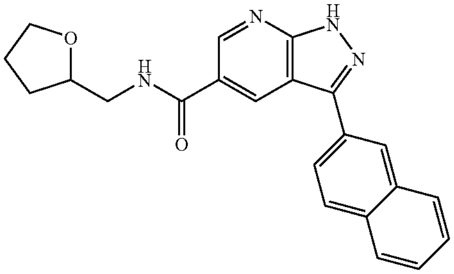
Example 474
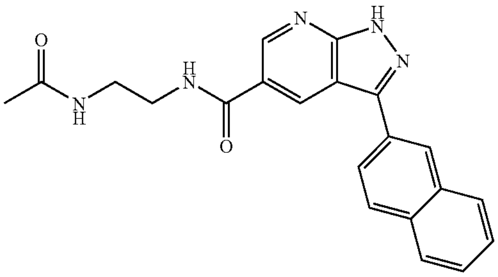
Example 475
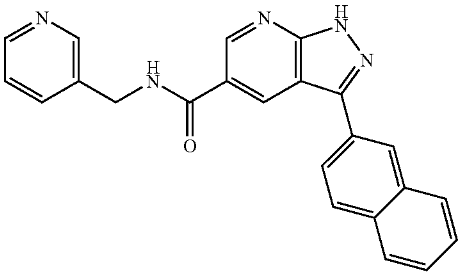
Example 476
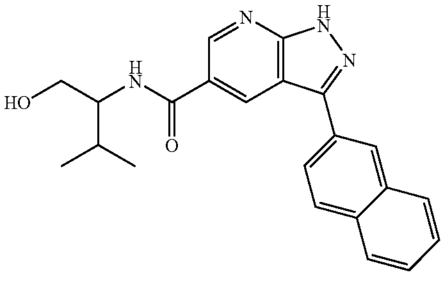
Example 477
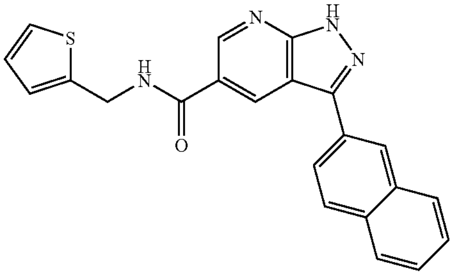

-continued
Example 478
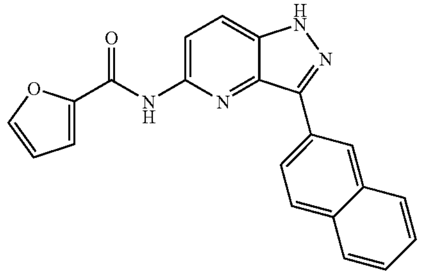
Example 479
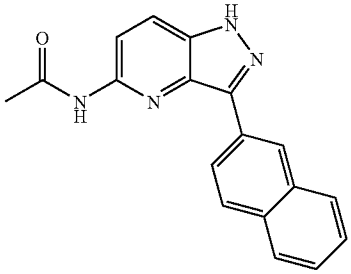
Example 480
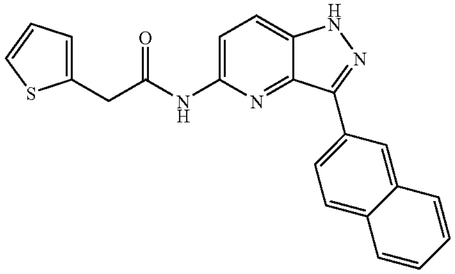
Example 481
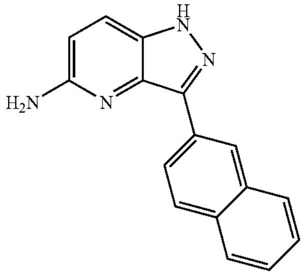
-continued
Production Example 482
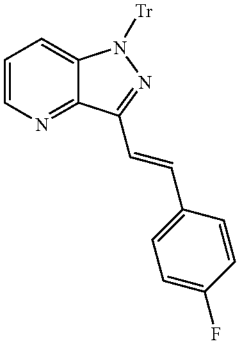
Production Example 483
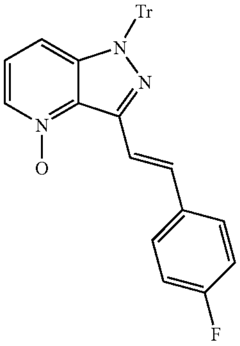
Example 484
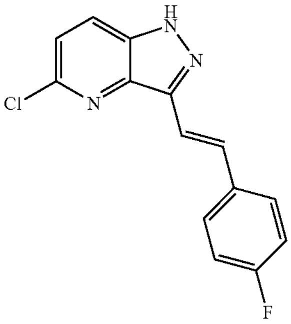
Production Example 485
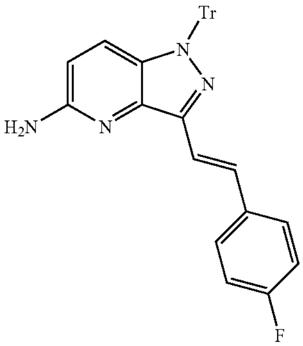
Production Example 486
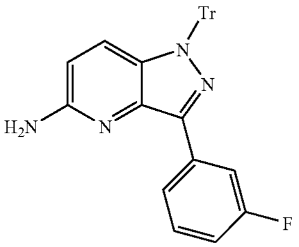

-continued
Example 487
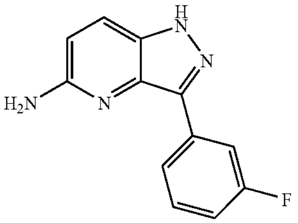
Example 489
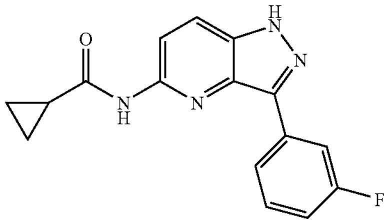
Example 490
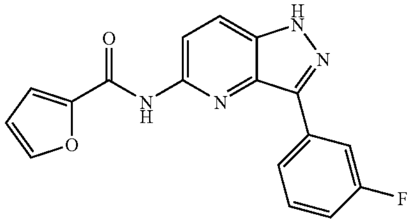
Example 491
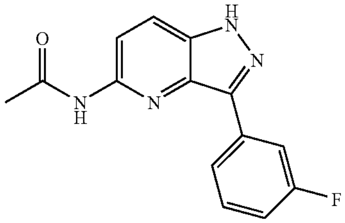
Example 492
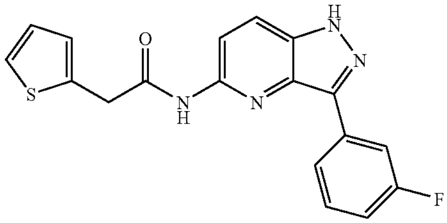
-continued
Example 494
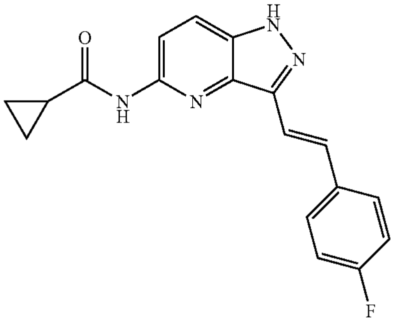
Example 495
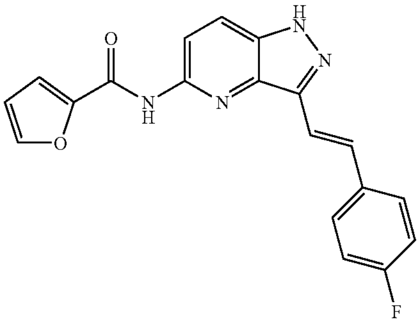
Example 496
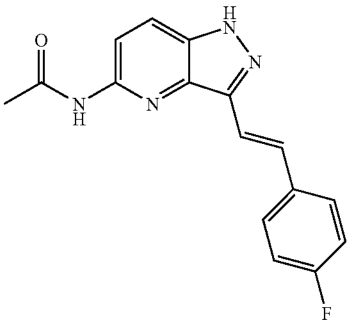
Example 497
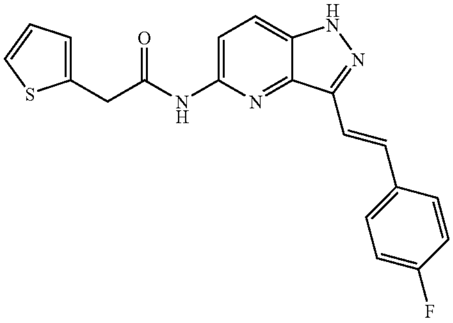
Production Example 498
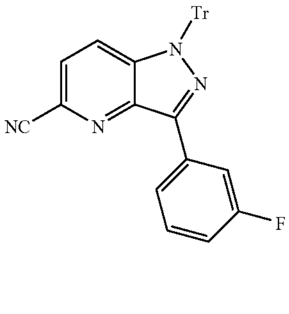

-continued
Production Example 499
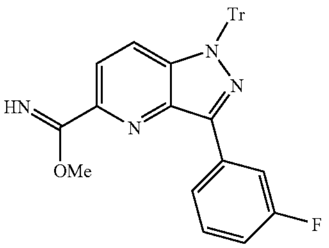
Production Example 500
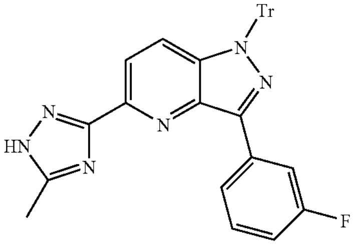
Example 501
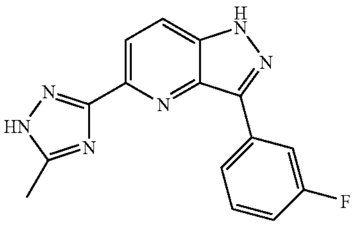
Production Example 502
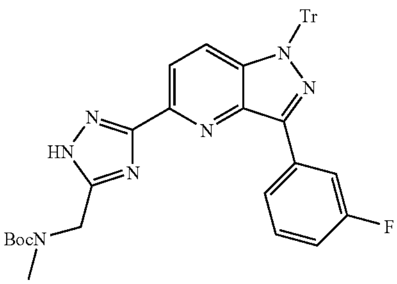
-continued
Example 503
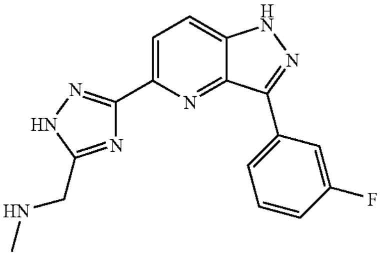
Production Example 504
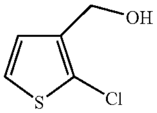
Production Example 505
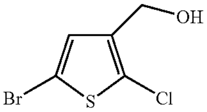
Production Example 506
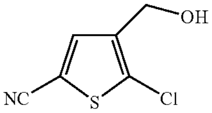
Production Example 507
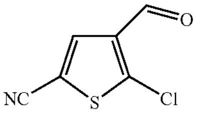
Production Example 508
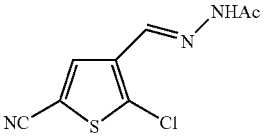
Production Example 509
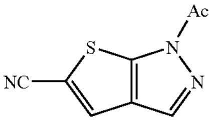
Production Example 510
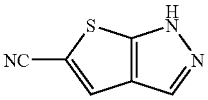
Production Example 511
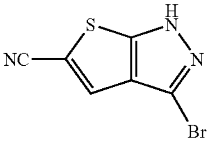
Example 512
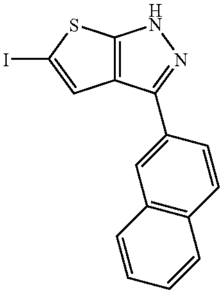

-continued
Production Example 513
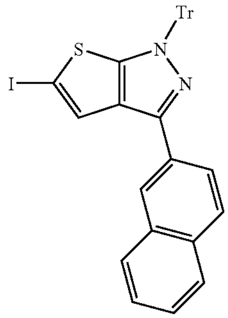
Example 514
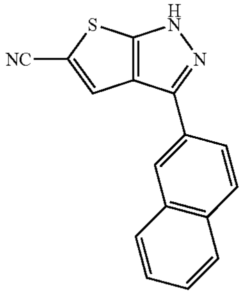
Example 515
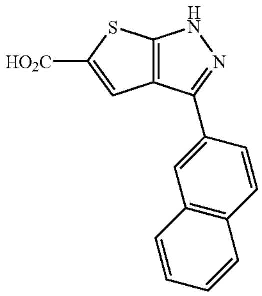
Production Example 516
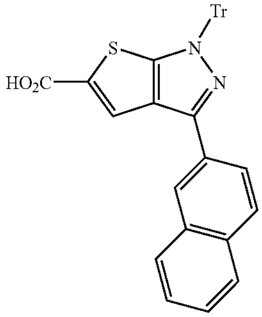
-continued
Production Example 517
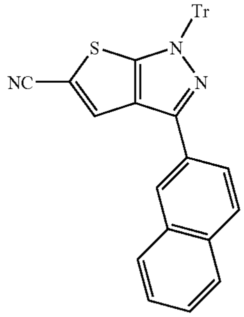
Production Example 518
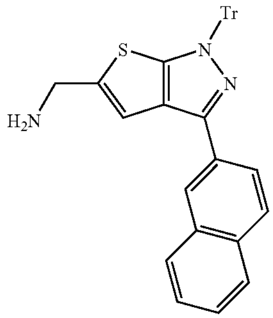
Example 520
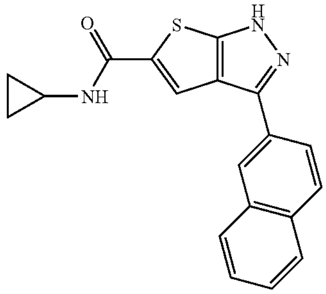
Example 520
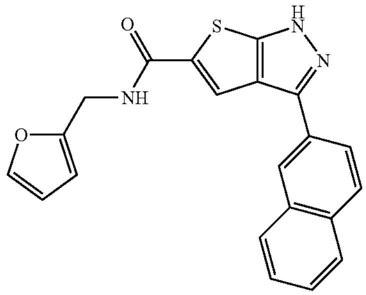

-continued
Example 522
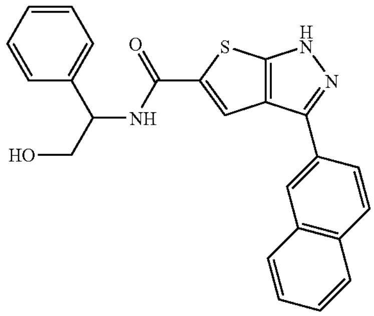
Example 523
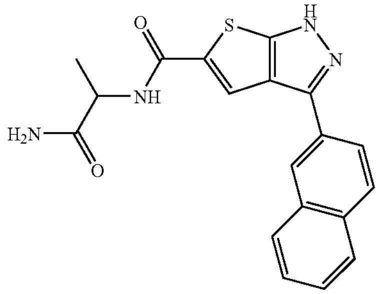
Example 525
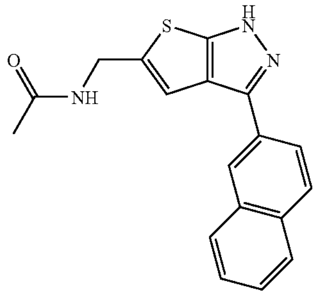
Example 526
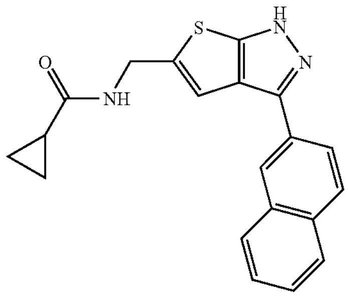
-continued
Example 527
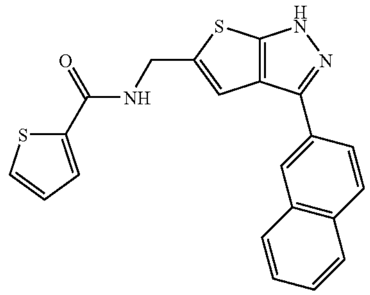
Example 528
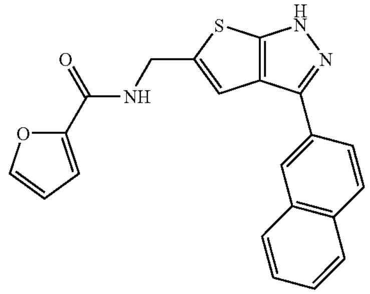
Example 529
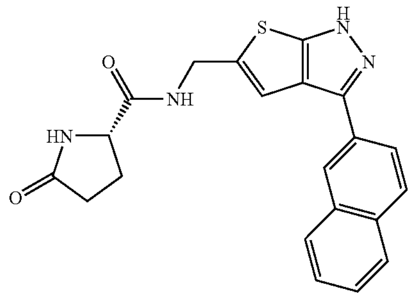
Example 530
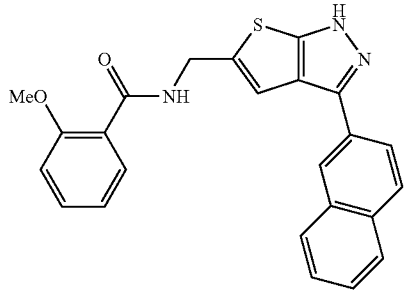

-continued
Example 531
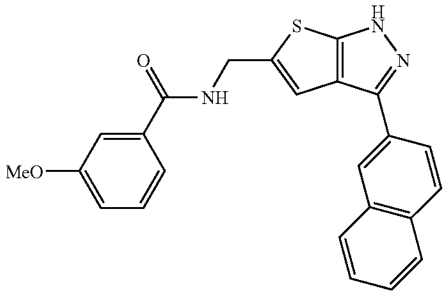
Example 532
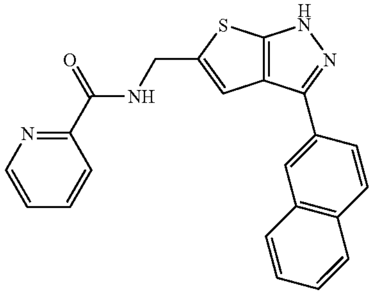
Production Example 533
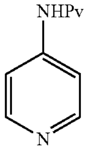
Production Example 534
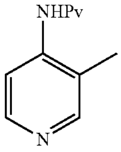
Production Example 535
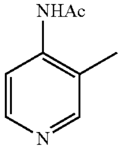
Production Example 536
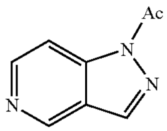
Production Example 537
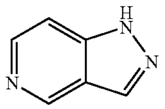
-continued
Production Example 538
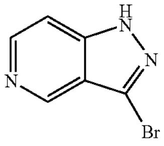
Production Example 539
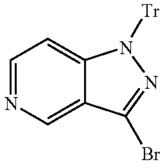
Production Example 540
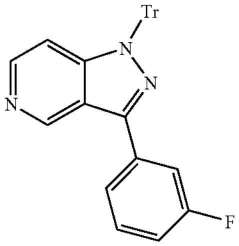
Example 541
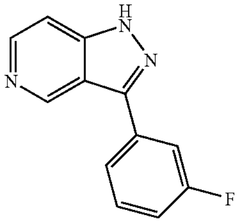
Production Example 542
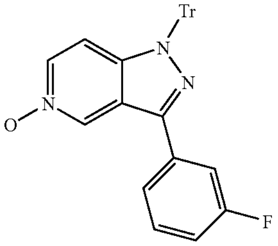
Production Example 543
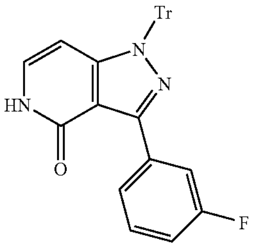
Example 544
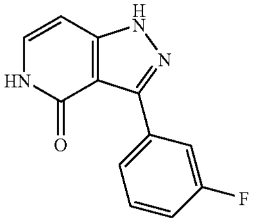

-continued
Example 545
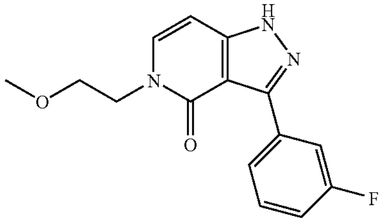
Example 546
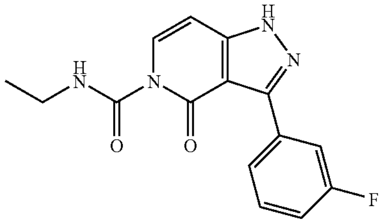
Example 547
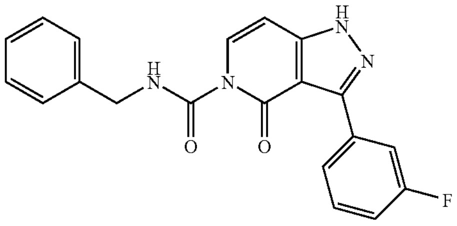
Production Example 548
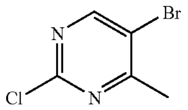
Production Example 549
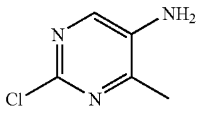
Production Example 550
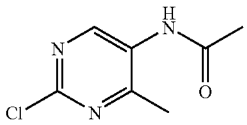
-continued
Production Example 551
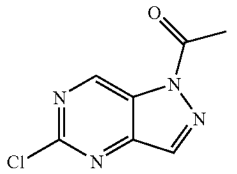
Production Example 552
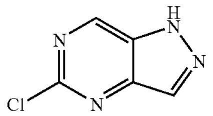
Production Example 553
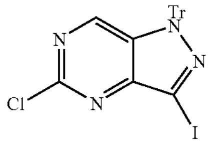
Production Example 554
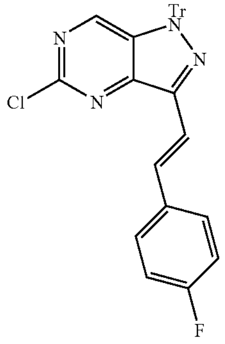
Example 555
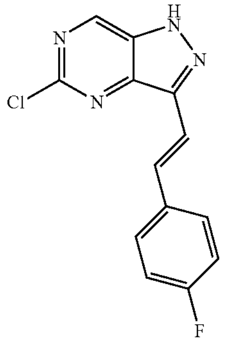
Production Example 556
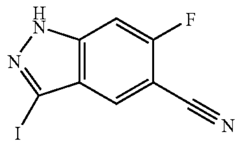
Production Example 557
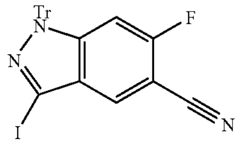

-continued
Example 558
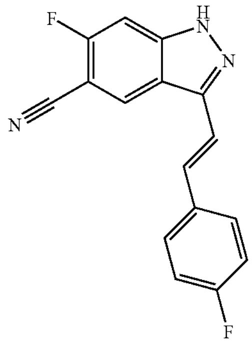
Example 559
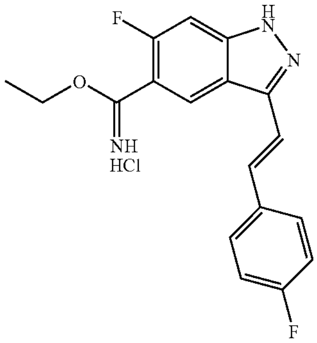
Production Example 560
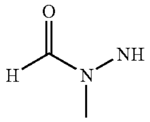
Production Example 561
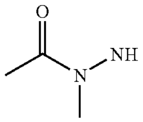
Example 563
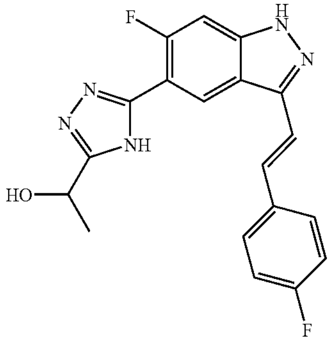
-continued
Example 564
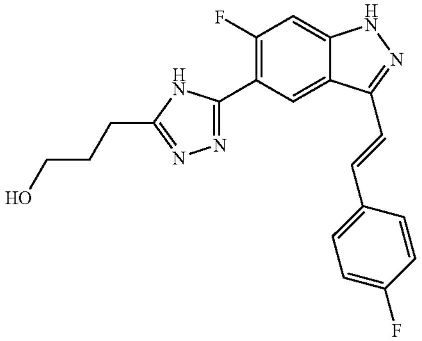
Example 565
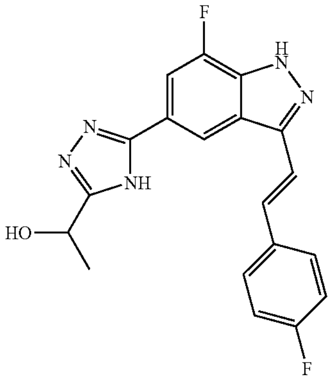
Example 566
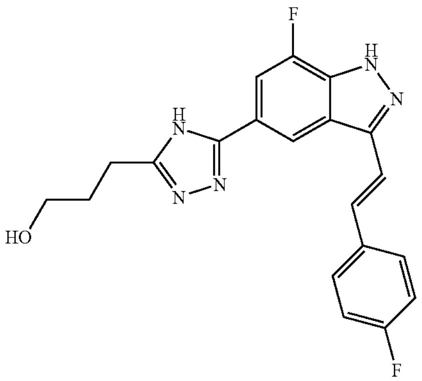

-continued
Example 567
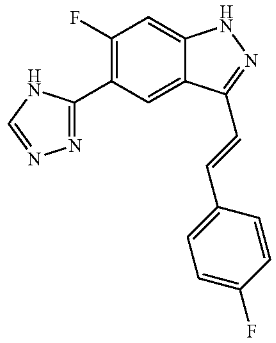
Example 568
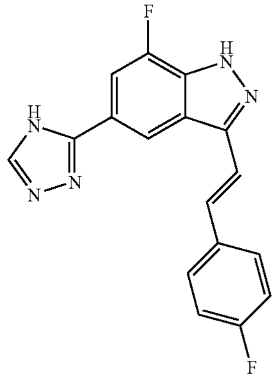
Example 569
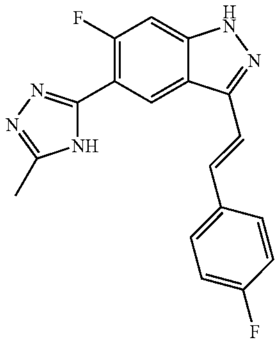
-continued
Example 570
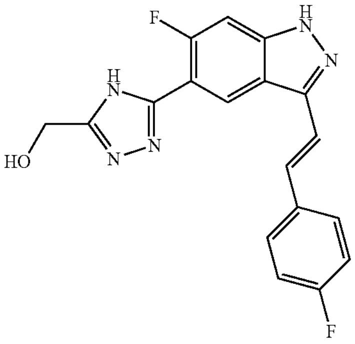
Example 571
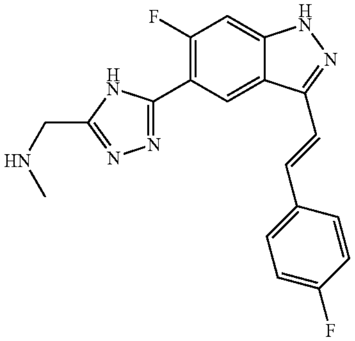
Example 572
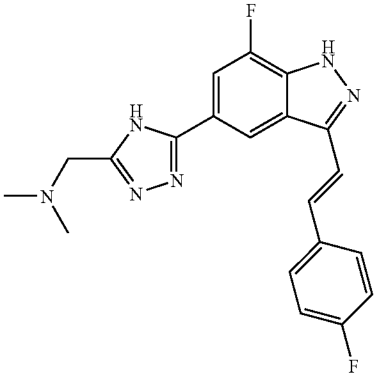
Example 573
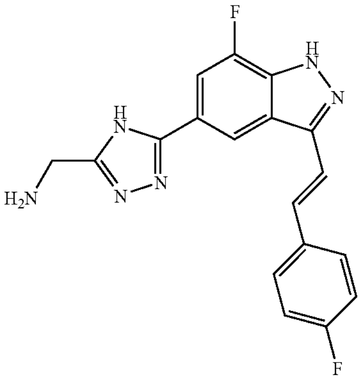

-continued
Example 574
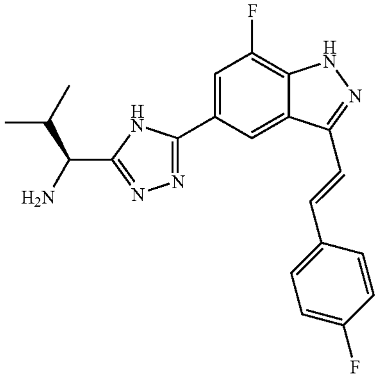
Example 575
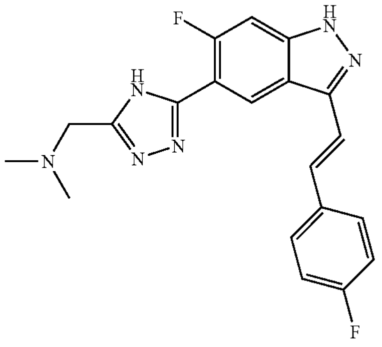
Example 576
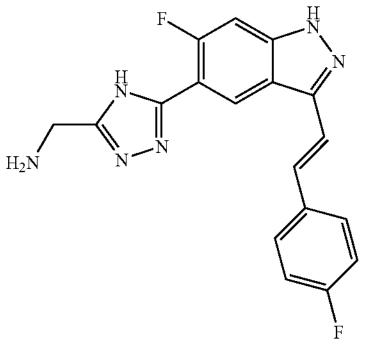
-continued
Example 577
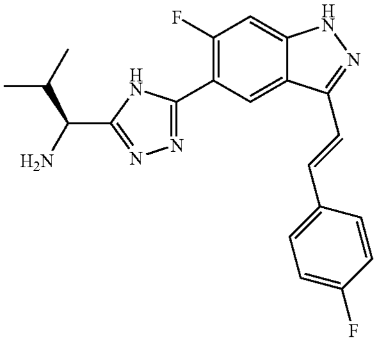
Example 578
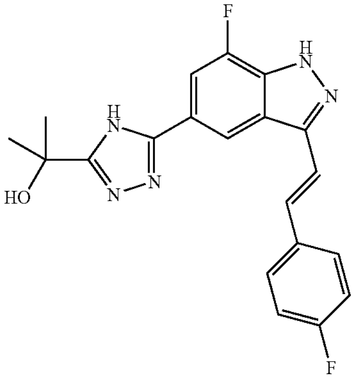
Example 579
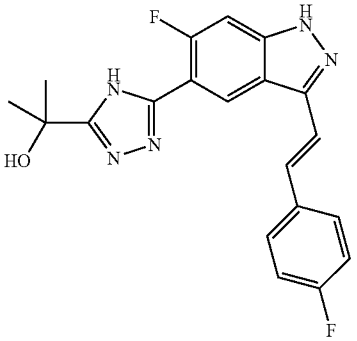
Example 580
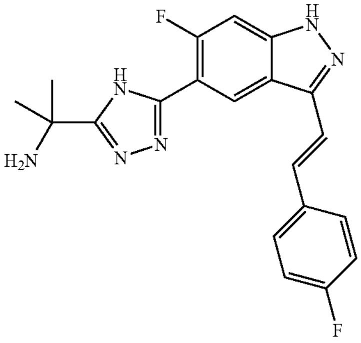

-continued
Example 581
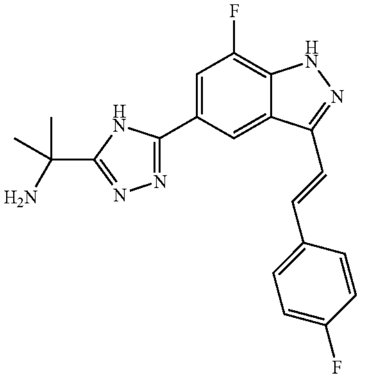
Example 582
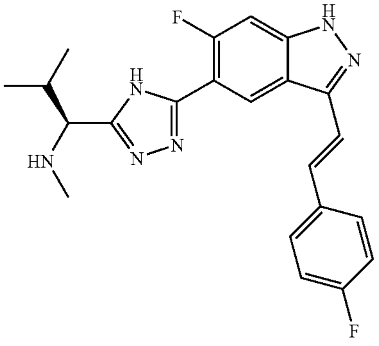
Example 583
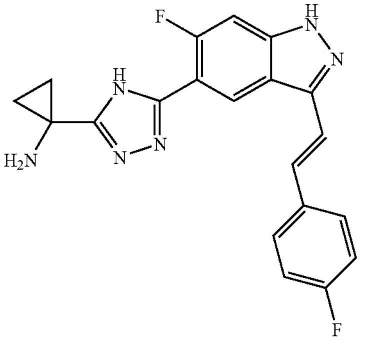
-continued
Example 584
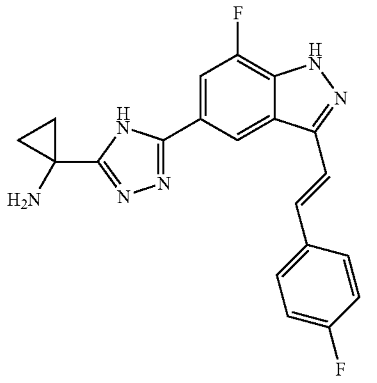
Example 585
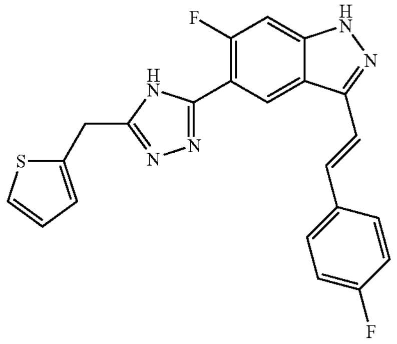
Example 586
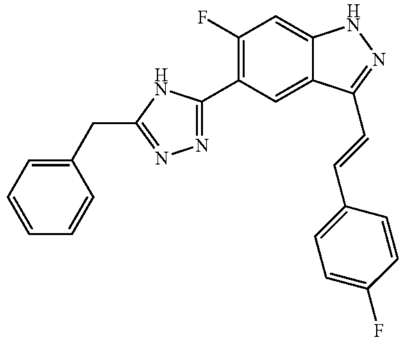

-continued

Example 587

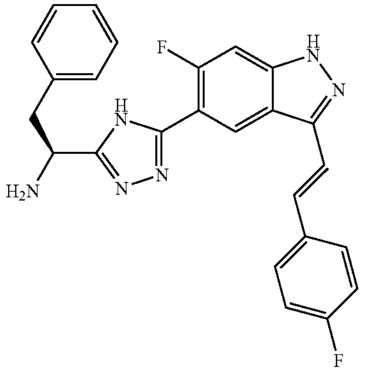

Example 588

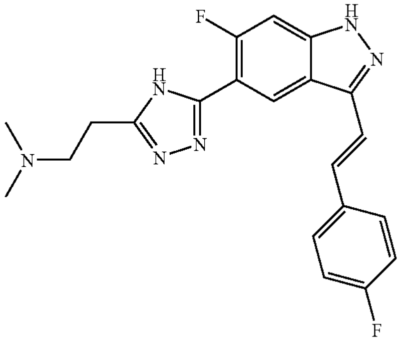

Example 589

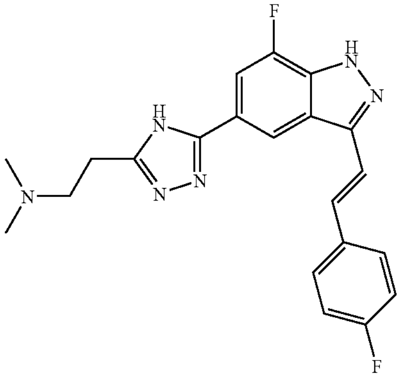

Example 590

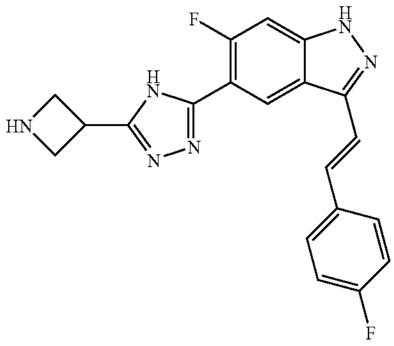

-continued

Example 591

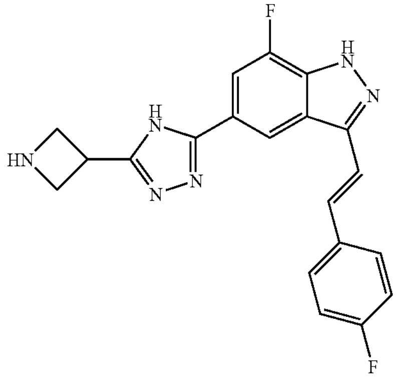

The invention claimed is:

1. A compound represented by the formula (III), a salt thereof or a hydrate thereof:

(III)

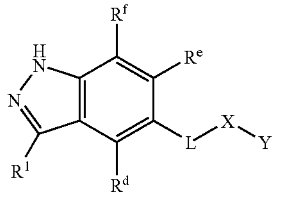

wherein $R^1$ designates a group represented by the formula —$CR^b$═$CR^c$—Ar wherein $R^b$ and $R^c$ each independently designate a hydrogen atom, halogen atom, hydroxyl group, an optionally substituted $C_{1-6}$ alkyl group, an optionally substituted $C_{2-6}$ alkenyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group; Ar designates an optionally substituted $C_{6-14}$ aryl group or an optionally substituted 5- to 14-membered heteroaryl group;

$R^d$ and $R^f$ each designates a hydrogen atom and $R^e$ designates a halogen atom, hydroxyl group, cyano group, nitro group, carboxyl group, an optionally substituted $C_{1-6}$ alkyl group, an optionally substituted $C_{1-6}$ alkoxy group, an optionally substituted $C_{2-7}$ acyl group, —CO—$NR^{2a}R^{2b}$, —$NR^{2b}$CO—$R^{2a}$ or —$NR^{2a}R^{2b}$ wherein $R^{2a}$ and $R^{2b}$ each independently designate a hydrogen atom or an optionally substituted $C_{1-6}$ alkyl group;

L designates a single bond, an optionally substituted $C_{1-6}$ alkylene group, an optionally substituted $C_{2-6}$ alkenylene group or an optionally substituted $C_{2-6}$ alkynylene group;

X designates a single bond, or a group represented by —$NR^7$—, —O—, —CO—, —S—, —SO—, —$SO_2$—, —CO—$NR^8$-Z-, —C(O)O—, —$NR^8$—CO-Z-, —$NR^8$—C(O)O—, —$NR^8$—S—, —$NR^8$—SO—, —$NR^8$—$SO_2$-Z-, —$NR^9$—CO—$NR^{10}$—, —$NR^9$—CS—$NR^{10}$—, —$S(O)_m$—$NR^{11}$-Z—, —C(=$NR^{12}$)—$NR^{13}$—, —OC(O)—, —OC(O)—$NR^{14}$— or —$CH_2$—$NR^8$—$COR^7$— wherein $R^7$, $R^8$, $R^9$, $R^{10}$, $R^{11}$, $R^{12}$, $R^{13}$ and $R^{14}$ each independently designate a hydrogen atom, halogen atom, hydroxyl group, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{2-6}$ alkenyloxy group, an optionally substituted $C_{1-6}$ alkylthio group, an optionally substituted $C_{2-6}$ alkenylthio group, an optionally substituted $C_{3-8}$ cycloalkyl group, an optionally substituted $C_{3-8}$ cycloalkenyl group, an optionally substituted 4- to 14-membered non-aromatic heterocyclic group, an optionally substituted $C_{6-14}$ aryl group or an optionally substituted 5- to 14-membered heteroaryl group, Z designates a single bond or an optionally substituted $C_{1-6}$ alkylene group, and m designates 0, 1 or 2; and Y designates any one group selected from the group consisting of a halogen atom, nitro group, hydroxyl group, cyano group, carboxyl group or an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{3-8}$ cycloalkenyl group, an optionally substituted 4- to 14-membered non-aromatic heterocyclic group, an optionally substituted $C_{6-14}$ aryl group, an optionally substituted 5- to 14-membered heteroaryl group, an optionally substituted amino group and a group represented by the formula —W—$R^{15}$ wherein W designates CO or $SO_2$; and $R^{15}$ designates an optionally substituted $C_{1-6}$ alkyl group, an optionally substituted amino group, an optionally substituted $C_{6-14}$ aryl group or an optionally substituted 5- to 14-membered heteroaryl group.

2. The compound according to claim 1, a salt thereof or a hydrate thereof, wherein $R^e$ is a halogen atom or an optionally substituted $C_{1-6}$ alkoxy group.

3. The compound according to claim 1, a salt thereof or a hydrate thereof, wherein L and X are a single bond, and Y is a 5- to 6-membered heteroaryl group, and Y is a group optionally substituted with 1 to 3 group(s) selected from the group consisting of (1) (a) $C_{1-6}$ alkyl groups, (b) $C_{1-6}$ alkenyl groups, (c) $C_{1-6}$ alkynyl groups, (d) $C_{1-6}$ alkoxy groups, (e) $C_{2-7}$ acyl groups, (f) amide group, (g) amino group, (h) $C_{3-8}$ cycloalkyl groups, (i) $C_{3-8}$ cycloalkenyl groups, (j) $C_{6-14}$ aryl groups, (k) 5- to 14-membered heteroaryl groups, (l) $C_{6-14}$ aryloxy groups, and (m) 4- to 14-membered non-aromatic heterocyclic groups, each optionally substituted, (2) halogen atom, (3) hydroxyl group, (4) nitro group, (5) cyano group, and (6) carboxyl group.

4. A pharmaceutical composition comprising the compound according to claim 1, a salt thereof or a hydrate thereof, and a pharmaceutically acceptable carrier.

5. A c-Jun amino-terminal kinase (JNKs) inhibitor comprising the compound according to claim 1, a salt thereof or a hydrate thereof.

6. A c-Jun amino-terminal kinase 1 (JNK 1), c-Jun amino-terminal kinase 2 (JNK 2) and/or c-Jun amino-terminal kinase 3 (JNK 3) inhibitor, comprising the compound according to claim 1, a salt thereof or a hydrate thereof.

* * * * *